United States Patent
Wilson et al.

(10) Patent No.: US 9,233,979 B2
(45) Date of Patent: Jan. 12, 2016

(54) COMPOUNDS THAT ARE ERK INHIBITORS

(71) Applicant: Merck Sharp & Dohme Corp., Rahway, NJ (US)

(72) Inventors: Kevin J. Wilson, Boston, MA (US); David J. Witter, Norfolk, MA (US); Phieng Siliphaivanh, Newton, MA (US); Kathryn Lipford, Boston, MA (US); David Sloman, Brookline, MA (US); Danielle Falcone, Brookline, MA (US); Brendan O'Boyle, Pittsburgh, PA (US); Umar Faruk Mansoor, Framington, MA (US); Jongwon Lim, Lexington, MA (US); Joey L. Methot, Westwood, MA (US); Christopher Boyce, Flemington, NJ (US); Lei Chen, Basking Ridge, NJ (US); Matthew H. Daniels, Somerville, MA (US); Salem Fevrier, Cranford, NJ (US); Xianhai Huang, Warren, NJ (US); Ravi Kurukulasuriya, Niantic, CT (US); Ling Tong, Warren, NJ (US); Wei Zhou, Scotch Plains, NJ (US); Joseph Kozlowski, Princeton, NJ (US); Milana M. Maletic, Summit, NJ (US); Bidhan A. Shinkre, Bangalore (IN); Jayanth Thiruvellore Thatai, Bangalore (IN); Raman Kumar Bakshi, Bangalore (IN); Ganesh Babu Karunakaran, Bangalore (IN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/431,462

(22) PCT Filed: Sep. 26, 2013

(86) PCT No.: PCT/US2013/061878
§ 371 (c)(1),
(2) Date: Mar. 26, 2015

(87) PCT Pub. No.: WO2014/052563
PCT Pub. Date: Apr. 3, 2014

(65) Prior Publication Data
US 2015/0266895 A1    Sep. 24, 2015

Related U.S. Application Data

(60) Provisional application No. 61/707,081, filed on Sep. 28, 2012.

(51) Int. Cl.
| | | |
|---|---|---|
| *C07D 401/14* | (2006.01) | |
| *A61K 31/437* | (2006.01) | |
| *C07D 498/18* | (2006.01) | |
| *C07D 471/04* | (2006.01) | |
| *A61K 31/5377* | (2006.01) | |
| *A61K 31/496* | (2006.01) | |
| *C07D 471/14* | (2006.01) | |
| *A61K 31/4375* | (2006.01) | |
| *C07D 498/14* | (2006.01) | |
| *A61K 31/553* | (2006.01) | |
| *C07D 519/00* | (2006.01) | |
| *A61K 45/06* | (2006.01) | |

(52) U.S. Cl.
CPC ............ *C07D 498/18* (2013.01); *A61K 31/437* (2013.01); *A61K 31/4375* (2013.01); *A61K 31/496* (2013.01); *A61K 31/5377* (2013.01); *A61K 31/553* (2013.01); *A61K 45/06* (2013.01); *C07D 471/04* (2013.01); *C07D 471/14* (2013.01); *C07D 498/14* (2013.01); *C07D 519/00* (2013.01)

(58) Field of Classification Search
CPC ............................ C07D 401/41; A61K 31/437
USPC ........................................... 546/119; 514/303
See application file for complete search history.

(56) References Cited

U.S. PATENT DOCUMENTS

| | | | |
|---|---|---|---|
| 6,706,711 | B2 | 3/2004 | Hale |
| 7,348,339 | B2 | 3/2008 | Bailey et al. |
| 7,485,643 | B2 | 2/2009 | Wallace et al. |
| 7,566,784 | B2 | 7/2009 | Borzilleri et al. |
| 9,023,865 | B2 * | 5/2015 | Lim et al. ..................... 514/303 |
| 2006/0142572 | A1 | 6/2006 | Martinez-Botella et al. |
| 2009/0163488 | A1 | 6/2009 | Oguro et al. |
| 2010/0273776 | A1 | 10/2010 | Lindquist et al. |
| 2011/0189192 | A1 | 8/2011 | Cooper et al. |
| 2011/0251199 | A1 | 10/2011 | De Morin et al. |
| 2012/0214823 | A1 | 8/2012 | Zhu et al. |

FOREIGN PATENT DOCUMENTS

| | | |
|---|---|---|
| WO | 2012000595 A1 | 1/2012 |
| WO | 2012058127 A2 | 5/2012 |

* cited by examiner

*Primary Examiner* — Niloofar Rahmani
(74) *Attorney, Agent, or Firm* — Richard S. Parr; Laura M. Ginkel

(57) ABSTRACT

Disclosed are the ERK inhibitors of formula (1): and the pharmaceutically acceptable salts thereof. Also disclosed are methods of treating cancer using the compounds of formula (1).

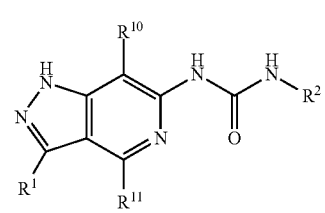

16 Claims, No Drawings

COMPOUNDS THAT ARE ERK INHIBITORS

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (ERK2 activity), which small-molecules would be useful for treating a broad spectrum of cancers, such as, for example, melanoma, pancreatic cancer, thryroid cancer, colorectal cancer, lung cancer, breast cancer, and ovarian cancer. Such a contribution is provided by this invention.

SUMMARY OF THE INVENTION

This invention provides compounds that inhibit the activity of ERK2.

Thus, this invention provides compounds that are ERK inhibitors (i.e., ERK2 inhibitors), said compounds being of the formula (1):

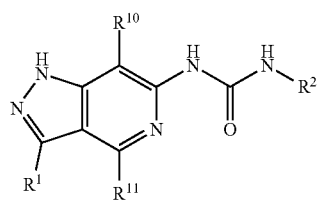

(1)

or a pharmaceutically acceptable salt, ester, solvate or prodrug thereof, wherein $R^1$, $R^2$, $R^{10}$ and $R^{11}$ are defined below.

This invention provides: (1) compounds of formula (1); (2) compounds of formula (1) in pure or isolated form; (3) pharmaceutically acceptable salts of the compounds of formula (1); (4) solvates of the compounds of formula (1); (5) compounds of formula (1) wherein from one to all of the hydrogens are deuterium; (6) compounds of formula (1) wherein at least one H is deuterium; (7) compounds of formula (1) wherein 1 to 5H are deuterium; (8) compounds of formula (1) wherein 1 to 2H are deuterium; and (9) compounds of formula (1) wherein one H is deuterium.

This invention provides the final compounds of Examples 1-458.

This invention also provides the final compounds of Examples 1 to 60.

This invention also provides the final compounds of Examples 61 to 458.

This invention also provides a pharmaceutical composition comprising an effective amount of at least one (e.g., 1) compound of formula (1) and a pharmaceutically acceptable carrier. This invention also provides a pharmaceutical composition comprising an effective amount of at least one (e.g., 1) compound of formula (1) and an effective amount of at least one (e.g., 1) other pharmaceutically active ingredient (such as, for example, a chemotherapeutic agent), and a pharmaceutically acceptable carrier.

This invention also provides a method of inhibiting ERK (i.e., inhibiting the activity of ERK2) in a patient in need of such treatment comprising administering to said patient an effective amount of at least one (e.g., 1) compound of formula (1).

This invention also provides a method for treating cancer in a patient in need of such treatment, said method comprising administering to said patient an effective amount of at least one (e.g., 1) compound of formula (1). This invention also provides a method for treating cancer in a patient in need of such treatment, said method comprising administering to said patient an effective amount of at least one (e.g., 1) compound of formula (1), in combination with an effective amount of at least one chemotherapeutic agent. The methods of this invention include the administration of a pharmaceutical composition comprising at least one (e.g., 1) compound of this invention and a pharmaceutically acceptable carrier. This invention also provides any of the above methods of treating cancer wherein the cancer is colorectal. This invention also provides any of the above methods of treating cancer wherein the cancer is melanoma.

The methods of treating cancers described herein can optionally include the administration of an effective amount of radiation (i.e., the methods of treating cancers described herein optionally include the administration of radiation therapy).

DETAILED DESCRIPTION OF THE INVENTION

All patents, publications and pending patent applications identified herein are hereby incorporated by reference.

As described herein, unless otherwise indicated, the use of a drug or compound in a specified period is per treatment cycle. For example, once a day means once per day of each day of the treatment cycle, and once a week means one time per week during the treatment cycle.

The following abbreviations have the following meanings unless defined otherwise: DCM is dichloromethane; DIBAL-H is diisobutylaluminum hydride; DIEA is diisopropylethylamine; DMA is dimethylacetamide; DMF is dimethylformamide; DMSO is dimethyl sulfoxide; EtOAc is ethyl acetate; NBS is N-bromosuccinimide; RT is room temperature; Selectfluor® is 1-chloromethyl-4-fluoro-1,4-diazonia-bicyclo[2.2.2]octane bis(tetrafluoroborate); SFC is Supercritcal fluid chromatography; TEA is triethylamine; TFA is trifluoroacetic acid; THF is tetrahydrofuran; TRC1 is triphenyl methane chloride; TRT is trityl or triphenylmethane; MeOH is methanol; Cy is cyclohexyl;

As used herein, unless otherwise specified, the terms below have the meaning indicated.

The term "composition" is intended to encompass a product comprising the specified ingredients in the specified amounts, as well as any product which results, directly or indirectly, from combination of the specified ingredients in the specified amounts.

The term "anti-cancer agent" means a drug (medicament or pharmaceutically active ingredient) for treating cancer.

The term "antineoplastic agent" means a drug (medicament or pharmaceutically active ingredient) for treating cancer (i.e., a chemotherapeutic agent).

The term "at least one" means one or more than one. In one example "at least one" means 1-4, and in another example 1-3, and in another example 1-2, and in another example 1. The meaning of "at least one" with reference to the number of compounds of this invention is independent of the meaning with reference to the number of chemotherapeutic agents.

The term "chemotherapeutic agent" means a drug (medicament or pharmaceutically active ingredient) for treating cancer (i.e., antineoplastic agent); The term "compound" with reference to the antineoplastic agents, includes the agents that are antibodies.

The term "consecutively" means one following the other.

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of this invention) is that amount which results in the reduction in ERK (ERK2) activity and phosphorylation. The reduction in ERK activity may be determined by the analysis of pharmacodynamic markers such as phosphorylated RSK1,2 using techniques well known in the art.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The term "one or more" has the same meaning as "at least one".

The term "patient" means an animal, such as a mammal (e.g., a human being, and preferably a human being).

The term sequentially represents (1) administration of one component of the method ((a) compound of the invention, or (b) chemotherapeutic agent, signal transduction inhibitor and/or radiation therapy) followed by administration of the other component or components. After administration of one component, the next component can be administered substantially immediately after the first component, or the next component can be administered after an effective time period after the first component. The effective time period is the amount of time given for realization of maximum benefit from the administration of the first component.

The term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like; "hydrate" is a solvate wherein the solvent molecule is $H_2O$.

The term "fused" with reference to, for example, two fused rings, means that the two rings have two atoms in common.

The term "monocyclic", as used to describe a ring, means the ring is a single ring (i.e., the ring is not a fused ring). Thus, for example, a "monocyclic heteroaryl ring" means a single heteroaryl ring. A bridged monocyclic ring means a monocyclic ring wherein two atoms in the ring are connected by a bridge. Thus, for example, a "bridged monocyclic heterocycloalkyl ring" means a monocyclic heterocycloalkyl ring wherein two atoms in the ring are connected by a bridge.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, unless otherwise specified, the terms below have the meanings indicated, and unless otherwise specified, the definitions of each term (i.e., moiety or substituent) apply when that term is used individually or as a component of another term (e.g., the definition of heteroaryl is the same for heteroaryl and for the heteroaryl portion of -alkylheteroaryl, and the like).

The term "alkoxy" means an alkyl-O— group (i.e., the bond to the parent moiety is through the ether oxygen) in which the alkyl group is as defined below. Non-limiting examples of suitable alkoxy groups include methoxy, ethoxy, n-propoxy, isopropoxy, n-butoxy and heptoxy.

The term "alkyl" (including the alkyl portions of other moieties, such as alkoxy) means an aliphatic hydrocarbon group (chain) that can be straight or branched wherein said group comprises about 1 to about 20 carbon atoms in the chain. In one example said alkyl group comprises about 1 to about 12 carbon atoms in the chain, in another example about 1 to about 6 carbon atoms in the chain; in another example 1 to about 4 carbon atoms in the chain; and in another example 1 to about 2 carbon atoms in the chain. Branched alkyl means that one or more lower alkyl groups, such as methyl, ethyl or propyl, are attached to a linear alkyl chain. "Lower alkyl" means a group comprising about 1 to about 6 carbon atoms in the chain, and said chain can be straight or branched.

The term -alkylcycloalkyl (or cycloalkylalkyl-) means a cycloalkyl, as defined below, bound to an alkyl, as defined above, wherein the cycloalkyl moiety is bound to the rest of the molecule through the alkyl group.

The term "alkylene" (including the alkylene portions of other moieties) means a chain comprising at least one —($CH_2$)— group. Examples of alkylene chains include, but are not limited to: —($CH_2$)$_{1-6}$—, —($CH_2$)$_{1-4}$—, —($CH_2$)$_{1-2}$— and —($CH_2$)—.

The term "amino" means an —$NH_2$ group.

The term "aryl" (including the aryl portions of other moieties, and sometimes abbreviated "ar") means an aromatic monocyclic or multicyclic ring system comprising about 6 to about 14 carbon atoms, preferably about 6 to about 10 carbon atoms. Non-limiting examples of suitable aryl groups include phenyl and naphthyl.

The term "cycloalkyl" means a non-aromatic mono- or multicyclic ring system comprising about 3 to about 7, or 3 to about 6, carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

The term "halo" means fluoro, chloro, bromo, or iodo groups. Preferred halos are fluoro, chloro or bromo, and more preferred are fluoro and chloro.

The term "halogen" means fluorine, chlorine, bromine, or iodine. Preferred halogens are fluorine, chlorine and bromine.

The term "heteroaryl" means an aromatic monocyclic or multicyclic ring system (e.g., a fused ring system) comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls comprise about 5 to about 6 ring atoms. The prefix aza, oxa or thia before the heteroaryl root name means that at least a nitrogen, oxygen or sulfur atom, respectively, is present as a ring atom. A nitrogen atom of a heteroaryl can be optionally oxidized to the corresponding N-oxide. The heteroaryl multicyclic ring system includes two rings fused together (i.e., there are two atoms common to both rings). Examples of the heteroaryl multicyclic ring system include fused heteroarylaryl rings (i.e., a heteroaryl ring fused to an aryl ring), and fused heteroarylheteroaryl rings (i.e., a heteroaryl ring fused to a heteroaryl ring). Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo [1,2-a]pyridinyl, imidazo[2,1-b]thiazolyl, benzofurazanyl, indolyl, azaindolyl, benzimidazolyl, benzothienyl, benzopyrazolyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine

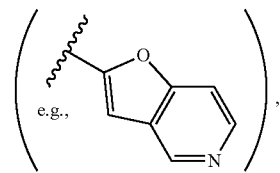

and the like.

The term "heteroarylalkyl-" (or heteroaralkyl-, or -alkyl-heteroaryl) means a heteroaryl-group (as defined above), bound to an alkyl- group (as defined above), wherein the heteroaryl group is bound to the rest of the molecule through the alkyl group; preferred heteroarylalkyls comprise an alkyl group that is a lower alkyl group; non-limiting examples of suitable heteroaralkyl groups include pyridyl-$CH_2$—, pyrimidinyl-$CH_2$—, imidazolyl-$CH_2$; pyrazinyl-$CH_2$—, and thiazolyl-$CH_2$—.

The term "heterocycloalkyl" (or "heterocyclyl") means a non-aromatic saturated monocyclic or multicyclic ring system comprising about 3 to about 10 ring atoms, preferably about 5 to about 10 ring atoms, and in one example 4 to 6 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. The heterocycloalkyl rings of this invention can be "bridged heterocycloalkyl rings. The term "bridged heterocycloalkyl"" (or "bridged heterocyclyl") means a heterocycloalkyl group as defined above having an alkylene chain (generally a 1 or 2 carbon alkylene chain, not counting the atoms in the ring to which the alkylene chain is bound to) bridging two carbon atoms in the ring.

The term -heterocycloalkylaryl (or arylheterocycloalkyl-) means a heterocycloalkyl, as defined above, bound to an aryl, as defined above, wherein the aryl moiety is bound to the rest of the molecule through the heterocycloalkyl group.

Any carbon or heteroatom with unsatisfied valences in the text, schemes, examples, structural formulae, and any tables herein is assumed to have the hydrogen atom or atoms to satisfy the valences. And any one or more of these hydrogen atoms can be deuterium.

Those skilled the art will appreciate that formulas showing a bond that does not have a substituent at the end of the bond represents a methyl group. Thus, for example,

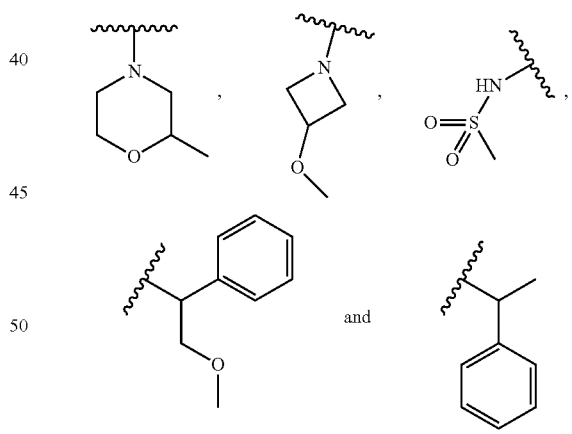

are the same moieties as:

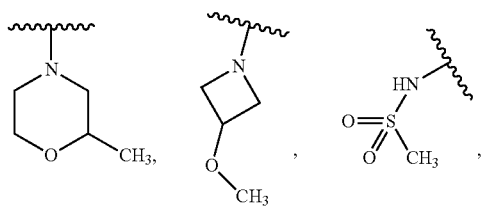

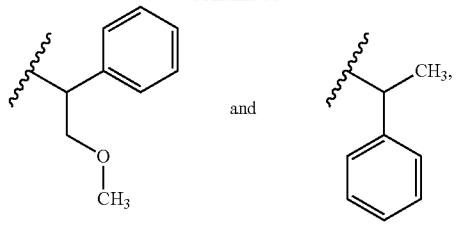 and 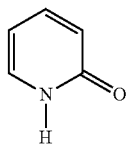, respectively.

One or more compounds of the invention may also exist as, or be optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. Also, for example, all keto-enol and imine-enamine forms of the compounds are included in the invention.

Tautomeric forms such as, for example, the moieties:

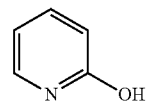

are considered equivalent in certain embodiments of this invention.

Thus, all stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formula (1) may be atropisomers and are considered as part of this invention. Enantiomers can also be separated by use of chiral HPLC column.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula (1) or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

This invention also includes the compounds of this invention in isolated and purified form.

Polymorphic forms of the compounds of formula (1), and of the salts, solvates and prodrugs of the compounds of formula (1), are intended to be included in the present invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

All such acid and base salts are intended to be pharmaceutically acceptable salts within the scope of the invention and all acid and base salts are considered equivalent to the free forms of the corresponding compounds for purposes of the invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

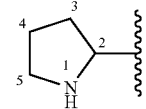

there is no —OH attached directly to carbons marked 2 and 5.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{123}$I, respectively.

Certain isotopically-labelled compounds of formula (1) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (1) can be useful for medical imaging purposes. E.g., those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of formula (1), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

This invention provides compounds that are ERK inhibitors (i.e., ERK2 inhibitors), said compounds being of the formula (1):

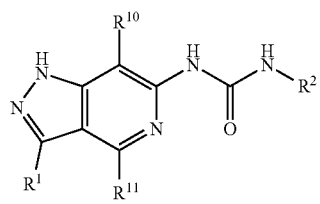

(1)

or a pharmaceutically acceptable salt, ester, solvate or prodrug thereof, wherein:

$R^1$ is —$NR^4R^5$;

$R^2$ is selected from the group consisting of: H, $(C_6$-$C_{10})$ aryl-$(C_1$-$C_3$alkyl)-heterocycloalkyl-, —$(C_1$-$C_6$alkyl), —$(C_1$-$C_6$alkyl)-O—$(C_1$-$C_6$alkyl), —$(C_1$-$C_6$alkyl)-heterocycloalkyl-$(C_6$-$C_{10}$aryl), —$(C_1$-$C_4$alkyl)$(C_6$-$C_{10})$aryl, —$(C_1$-$C_4$alkyl)heteroaryl, —$(C_3$-$C_6$cycloalkyl)-$(C_6$-$C_{10}$aryl), -heterocycloalkyl-$(C_6$-$C_{10}$aryl), —$(C_1$-$C_6$alkyl)-$(C_3$-$C_6$cycloalkyl), —CH$(C_6$-$C_{10}$aryl)$(C_3$-$C_6$cycloalkyl), —CH$(C_6$-$C_{10}$aryl)$((C_1$-$C_6$alkyl)N$(R^{20})_2)$, —CH$(C_6$-$C_{10}$aryl)(heterocycloalkyl), —$(C_3$-$C_6$cycloalkyl-O—$(C_1$-$C_6$alkyl)), —CH$(C_6$-$C_{10}$aryl)C(O)N$(R^{21})_2$ wherein each $R^{21}$ is independently selected, and -fused (heterocycloalkyl)$(C_6$-$C_{10})$ aryl wherein said heterocycloalkyl is a 5 to 8 membered ring (including the two atoms common with said aryl) comprising 1-3 heteroatoms selected from the group consisting of: O, S and N, and wherein the remaining atoms are carbon;

and wherein said aryl, heterocycloalkyl, heteroaryl, and cycloalkyl moieties of said $R^2$ groups are optionally substituted with 1-3 substituents independently selected from the group consisting of: CN, halo (e.g., F, Br, and Cl), —O—$(C_1$-$C_6$alkyl), —OH, —CF$_3$, —$(C_1$-$C_6$alkyl), —O(halo substituted $(C_1$-$C_6$alkyl)), —N$(R^{20})_2$, aryl and heteroaryl;

and wherein said alkyl moieties of said $R^2$ groups are optionally substituted with 1-3 substituents independently selected from the group consisting of: CN, halo (e.g., F, Br, and Cl), —O—$(C_1$-$C_6$alkyl), —OH and —CF$_3$, —O(halo substituted $(C_1$-$C_6$alkyl)) and —S$(C_1$-$C_6$alkyl);

$R^4$ and $R^5$ are each independently selected from the group consisting of: H, —$(C_1$-$C_6$alkyl), —$(C_1$-$C_6$alkyl)-O—$(C_1$-$C_6$alkyl), —C(O)$R^8$, —S(O)$_2R^9$, —$(C_1$-$C_6$alkyl) substituted with 1-3 substituents independently selected from the group consisting of: halo, —OH and —S(O)$_2(C_1$-$C_6$alkyl), —$(C_3$-$C_6$ cycloalkyl), —$(C_3$-$C_6$ cycloalkyl) substituted with 1-3 substituents independently selected from the group consisting of: halo, —$(C_1$-$C_6$alkyl), —NH$_2$, —NH$(C_1$-$C_6$alkyl), —N$(C_1$-$C_6$alkyl)$_2$ wherein each alkyl is independently selected, —$(C_3$-$C_6$ cycloalkenyl), —$(C_3$-$C_6$ oxocycloalkenyl), —$(C_6$-$C_{10}$aryl), —$(C_6$-$C_{10}$aryl) substituted with 1-3 substituents independently selected from the group consisting of: —CN, —O$(C_1$-$C_6$alkyl) and halo, —$(C_1$-$C_6$alkyl)$(C_6$-$C_{10}$aryl), —$(C_1$-$C_6$alkyl)C(O)N$(R^{20})_2$ wherein each $R^{20}$ is independently selected, heteroaryl, heteroaryl substituted with 1-3 substituents independently selected from the group consisting of: —CN, halo and —$(C_1$-$C_6$alkyl), —$(C_1$-$C_6$alkyl)(heteroaryl), —$(C_1$-$C_6$alkyl)(heteroaryl) substituted with 1-3 substitutents independently selected from the group consisting of: —$(C_1$-$C_6$alkyl), —$(C_1$-$C_6$alkyl)$(C_3$-$C_6$cycloalkyl), —$(C_1$-$C_6$alkyl)$(C_3$-$C_6$cycloalkyl) substituted with 1-3 substituents independently selected from the group consisting of: —O—$(C_1$-$C_6$alkyl), -(hydroxyC$_1$-$C_6$alkyl), —$(C_2$-$C_6$alkenyl), —$(C_1$-$C_6$alkyl)heterocycloalkyl, —C(O) (substituted $C_1$-$C_6$alkyl)NHC(O)O$(C_1$-$C_6$alkyl) wherein said substituted alkyl is substituted with a heterocycloalkyl, —C(O)$(C_1$-$C_6$alkyl)NHC(O)O$(C_1$-$C_6$alkyl), heterocycloalkyl, heterocycloalkyl substituted with 1-3 substituents independently selected from the group consisting of: —$(C_1$-$C_6$alkyl) and halo, —$(C_1$-$C_6$alkyl)heterocycloalkenyl, —$(C_1$-$C_6$alkyl)heterocycloalkenyl substituted with 1-3 substituents independently selected from the group consisting of: —$(C_1$-$C_6$alkyl); or $R^4$ and $R^5$ taken together with the nitrogen to which they are bonded to form a 4-6 membered heterocycloalkyl ring, said ring optionally comprising 1 or 2 additional heteroatoms independently selected from the group consisting of: O, S and N, and said heterocycloalkyl ring optionally comprising a 1-2 carbon bridge, and said ring is optionally substituted with 1-3 substituents independently selected from the group consisting of: —O$(C_1$-$C_6$alkyl) and —$(C_1$-$C_6$ alkyl), —OH, —SCH$_3$, halo, —CF$_3$, CN, —$(C_1$-$C_6$alkyl)-O—$(C_1$-$C_6$alkyl), —$(C_1$-$C_6$alkyl)-OH and —C(O)OH; or $R^4$ and $R^5$ taken together with the nitrogen to which they are bonded to form a Spiro ring comprising two independently selected 4-6 membered heterocycloalkyl rings, wherein one of said rings comprises the nitrogen of the —$NR^4R^5$ group, and wherein the other ring of the spiro ring comprises one heteroatom selected from the group consisting of: O, N and S, and wherein each heterocycloalkyl ring optionally comprises 1 or 2 additional heteroatoms independently selected from the group consisting of: O, S and N, and wherein said spiro ring is optionally substituted with 1-3 substituents independently selected from the group consisting of: —OH, —$(C_1$-$C_6$alkyl)-O—$(C_1$-$C_6$alkyl), —$(C_1$-$C_6$alkyl)-OH, —O$(C_1$-$C_6$alkyl) and —$(C_1$-$C_6$ alkyl); or $R^4$ and $R^5$ taken together with the nitrogen to which they are bonded to form a fused bicyclic heterocycloalkyl ring, said ring optionally comprising 1 to 3 additional heteroatoms independently selected from the group consisting of: O, S and N, and said ring optionally comprising a —O— bridge between two ring carbons (i.e., an epoxy bridge), and said ring is optionally substituted with 1-3 substituents independently selected from the group consisting of: halogen, —O$(C_1$-$C_6$alkyl) and —$(C_1$-$C_6$ alkyl); or $R^4$ and $R^5$ taken together with the nitrogen to which they are bonded to form a fused bicyclic ring wherein one ring is a heterocycloalkyl ring, and one ring is a heteroaryl ring, said heterocycloalkyl ring optionally comprising 1 to 3 additional heteroatoms independently selected from the group consisting of: O, S and N, and said bicyclic ring is optionally substituted with 1-3 substituents independently selected from the group consisting of: halogen, —O($C_1$-$C_6$alkyl) and —($C_1$-$C_6$ alkyl); or $R^4$ and $R^{11}$ taken together form a 5-8 membered heterocycloalkyl ring, said ring optionally comprising 1 or 2 additional heteroatoms independently selected from the group consisting of: O, S, N, and —(C=O)—, and said ring is optionally substituted with 1-3 substituents independently selected from $R^{14}$ group.

$R^8$ and $R^9$ are each independently selected from the group consisting of: —$OR^{12}$, —$NHR^{12}$, —$NR^{12}R^{13}$, —($C_1$-$C_6$alkyl), —($C_1$-$C_6$alkyl)-O—($C_1$-$C_6$alkyl), —($C_3$-$C_6$)cycloalkyl, —($C_1$-$C_6$alkyl)-($C_3$-$C_6$)cycloalkyl, heterocycloalkyl, aryl, heteroaryl, —($C_1$-$C_6$alkyl)($C_6$-$C_{10}$aryl), and —($C_1$-$C_6$alkyl)($C_3$-$C_{10}$cycloalkyl), fused bicyclic heterocycloalkyl ring, and wherein said heterocycloalkyl is a 4-6 membered ring comprising 1-3 heteroatoms selected from the group consisting of: O, S and N and the remaining ring atoms are carbon, and wherein said aryl is a $C_6$ to $C_{10}$ aromatic ring, and wherein said heteroaryl is a 5 to 10 membered ring comprising 1-3 heteroatoms selected from the group consisting of: O, S and N and the remaining ring atoms are carbon, and wherein said $R^8$ heterocycloalkyl is optionally substituted with 1-3 substituents independently selected from the group consisting of: halo, —OH, and —($C_1$-$C_6$alkyl), and wherein said $R^8$ —($C_1$-$C_6$alkyl) is optionally substituted with 1-3 substituents independently selected from the group consisting of: halo, —NH($C_1$-$C_6$alkyl) and —N($C_1$-$C_6$alkyl)$_2$ wherein each alkyl is independently selected, and wherein said $R^8$ heteroaryl is optionally substituted with 1-3 substituents independently selected from the group consisting of: —($C_1$-$C_6$alkyl), and wherein said $R^8$ aryl is optionally substituted with 1-3 substituents independently selected from the group consisting of: halo; and $R^{10}$ is independently selected from the group consisting of: H, halo, CN, OH, $NH_2$, —$CF_3$, —O—($C_1$-$C_6$alkyl), —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, and —($C_1$-$C_6$alkyl)-heterocycloalkyl.

$R^{11}$ is independently selected from the group consisting of: H, halo, CN, OH, $NH_2$, aryl, heteroaryl, heterocycloalkyl, —$NHR^{12}$, —$NR^{12}R^{13}$, —NHC(O)$R^8$, —$CF_3$, —O—($C_1$-$C_6$alkyl), —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, —($C_1$-$C_6$alkyl)-heterocycloalkyl each $R^{12}$ is independently selected from the group consisting of: ($C_1$-$C_6$alkyl), ($C_3$-$C_6$cycloalkyl), (($C_3$-$C_6$cycloalkyl)($C_1$-$C_6$alkyl)-), ($C_3$-$C_6$cycloalkenyl), heterocycloalkyl, (heterocycloalkyl($C_1$-$C_6$alkyl))-, ($C_6$-$C_{10}$)aryl, (aryl($C_1$-$C_6$alkyl))-, heteroaryl, (heteroaryl($C_1$-$C_6$alkyl))-, wherein each of said alkyl, cycloalkyl, cycloalkylalkyl, cycloalkenyl, heterocycloalkyl, heterocycloalkylalkyl, aryl, arylalkyl, heteroaryl, and heteroarylalkyl $R^{12}$ groups is optionally substituted with 1 to 3 independently selected $R^{14}$ groups.

each $R^{13}$ is independently selected from the group consisting of: ($C_1$-$C_6$alkyl), ($C_3$-$C_6$cycloalkyl), (($C_3$-$C_6$cycloalkyl)($C_1$-$C_6$alkyl)-), ($C_3$-$C_6$cycloalkenyl), heterocycloalkyl, (heterocycloalkyl($C_1$-$C_6$alkyl))-, ($C_6$-$C_{10}$)aryl, (aryl($C_1$-$C_6$alkyl))-, heteroaryl, (heteroaryl($C_1$-$C_6$alkyl))-, wherein each of said alkyl, cycloalkyl, cycloalkylalkyl, cycloalkenyl, heterocycloalkyl, heterocycloalkylalkyl, aryl, arylalkyl, heteroaryl, heteroarylalkyl $R^{13}$ groups is optionally substituted with 1 to 3 independently selected $R^{14}$ groups, or $R^{12}$ and $R^{13}$ taken together with the nitrogen to which they are bonded to form a 4-8 membered heterocycloalkyl ring, said ring optionally comprising 1 or 2 additional heteroatoms independently selected from the group consisting of: O, S and N, and said ring is optionally substituted with 1-3 substituents independently selected from $R^{14}$ group.

each $R^{14}$ group is independently selected from the group consisting of halo, —$CF_3$, —CN, OH, —$OR^{15}$, ($C_1$-$C_6$alkyl), ($C_3$-$C_6$cycloalkyl), ($C_3$-$C_6$cycloalkenyl), heterocycloalkyl, ($C_6$-$C_{10}$)aryl, heteroaryl and —C(O)($C_1$-$C_6$alkyl);

each $R^{15}$ is independently selected from the group consisting of: ($C_1$-$C_6$alkyl), ($C_3$-$C_6$cycloalkyl), (($C_3$-$C_6$cycloalkyl)($C_1$-$C_6$alkyl)-), ($C_3$-$C_6$cycloalkenyl), heterocycloalkyl, (heterocycloalkyl($C_1$-$C_6$alkyl))-, ($C_6$-$C_{10}$)aryl, (aryl($C_1$-$C_6$alkyl))-, heteroaryl, (heteroaryl($C_1$-$C_6$alkyl))- and —C(O)($C_1$-$C_6$alkyl);

$R^{20}$ is independently selected from the group consisting of H and ($C_1$-$C_6$alkyl); and $R^{21}$ is —($C_1$-$C_6$alkyl).

In one example, this invention provides compounds of formula (1) or a pharmaceutically acceptable salt, ester, solvate or prodrug thereof, wherein:

$R^1$ is —$NR^4R^5$;

$R^2$ is selected from the group consisting of: H, ($C_6$-$C_{10}$) aryl-($C_1$-$C_3$alkyl)-heterocycloalkyl-, —($C_1$-$C_6$alkyl ), —($C_1$-$C_6$alkyl)-O—($C_1$-$C_6$alkyl), —($C_1$-$C_6$alkyl)-heterocycloalkyl-($C_6$-$C_{10}$aryl), —($C_1$-$C_4$alkyl)($C_6$-$C_{10}$)aryl, —($C_1$-$C_3$alkyl)heteroaryl, —($C_3$-$C_6$cycloalkyl)-($C_6$-$C_{10}$aryl), -heterocycloalkyl-($C_6$-$C_{10}$aryl); and wherein said aryl, heterocycloalkyl, heteroaryl, and cycloalkyl moieties of said $R^2$ groups are optionally substituted with 1-3 substituents independently selected from the group consisting of: halo (e.g., F, Br, and Cl), —O—($C_1$-$C_6$alkyl), —OH, —$CF_3$, and —($C_1$-$C_6$alkyl); and wherein said alkyl moieties of said $R^2$ groups are optionally substituted with 1-3 substituents independently selected from the group consisting of: halo (e.g., F, Br, and Cl), —O—($C_1$-$C_6$alkyl), —OH and —$CF_3$;

$R^4$ and $R^5$ are each independently selected from the group consisting of: H, —($C_1$-$C_6$alkyl), —($C_1$-$C_6$alkyl)-O—($C_1$-$C_6$alkyl), —C(O)$R^8$, —S(O)$_2R^9$; or $R^4$ and $R^5$ taken together with the nitrogen to which they are bonded to form a 4-6 membered heterocycloalkyl ring, said ring optionally comprising 1 or 2 additional heteroatoms independently selected from the group consisting of: O, S and N, and said ring is optionally substituted with 1-3 substituents independently selected from the group consisting of: —O($C_1$-$C_6$alkyl) and —($C_1$-$C_6$ alkyl);

$R^8$ and $R^9$ are each independently selected from the group consisting of: —($C_1$-$C_6$alkyl), —($C_1$-$C_6$alkyl)-O—($C_1$-$C_6$alkyl), —($C_3$-$C_6$)cycloalkyl, —($C_1$-$C_6$alkyl)-($C_3$-$C_6$)cycloalkyl, heterocycloalkyl, aryl, and heteroaryl, and wherein said heterocycloalkyl is a 4-6 membered ring comprising 1-3 heteroatoms selected from the group consisting of: O, S and N and the remaining ring atoms are carbon, and wherein said aryl is a $C_6$ to $C_{10}$ aromatic ring, and wherein said heteroaryl is a 5 to 10 membered ring comprising 1-3 heteroatoms selected from the group consisting of: O, S and N and the remaining ring atoms are carbon; and $R^{10}$ and $R^{11}$ are each independently selected from the group consisting of: H, halo, —($C_1$ to $C_6$alkyl), —($C_3$-$C_6$ cycloalkyl), hydroxy substituted —($C_1$-$C_6$alkyl), ($C_1$-$C_6$alkyl)-O—($C_1$-$C_6$alkyl), —($C_1$-$C_6$alkyl)-N($C_1$-$C_6$alkyl)$_2$ wherein each alkyl is independently selected, and —($C_1$-$C_6$alkyl)-heterocycloalkyl.

The following groups are as defined below, unless defined otherwise.

For the $R^2$, $R^{10}$ and $R^{11}$ groups comprising a heterocycloalkyl, each heterocycloalkyl is independently selected and each heterocycloalkyl is a 4 to 8 membered ring, and in one example a 4 to 6 membered ring, comprising 1 to 3 heteroatoms independently selected from the group consisting of: O, N and S, and the remaining ring atoms are carbon. In one example, the heterocycloalkyl is a 4 to 6 membered ring comprising 1-2 heteroatoms independently selected from the group consisting of: O, N and S, and the remaining ring atoms are carbon. In another example, the heterocycloalkyl is a 4 to 6 membered ring comprising 1-2 heteroatoms independently selected from the group consisting of: O and N, and the remaining ring atoms are carbon. In another example, the heterocycloalkyl is a 4 to 6 membered ring comprising 1 heteroatom selected from the group consisting of: O, N and S, and the remaining ring atoms are carbon. In another example, the heterocycloalkyl is a 4 to 6 membered ring comprising 1 heteroatom selected from the group consisting of: O and N, and the remaining ring atoms are carbon. In another example the heterocycloalkyl is a 4 to 6 membered ring comprising 1-2 N atoms, and the remaining ring atoms are carbon. In another example the heterocycloalkyl is a 4 to 6 membered ring comprising 1 heteroatom and said heteroatom is O. In another example the $R^2$ heterocycloalkyl is a 4 membered ring, in another example a 5 membered ring, and in another example a 6 membered ring. Examples of the heterocycloalkyl include, but are not limited to: oxetanyl, tetrahydrofuranyl, tetrahydropyranyl, azetidinyl, pyrrolidinyl, piperidinyl, piperazinyl, morpholinyl, thietanyl, tetrahydrothiophenyl (tetrahydrothienyl), and tetrahydrothiopyranyl. In one example the heterocycloalkyl is

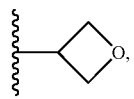 [SMILES: *C1COC1] 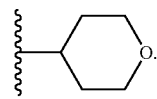

In another example, the hetereocycloalkyl is selected from the group consisting of: piperidinyl, pyrrolidinyl, azetidinyl, piperazinyl, and morpholinyl. In another example the heterocycloalkyl is piperidinyl. Examples the $R^2$ heterocycloalkyl include, but are not limited to, piperidinyl, pyrrolidinyl, azetidinyl, piperazinyl, and morpholinyl. In another example the heterocycloalkyl is piperidinyl. Examples of the $R^2$ heterocycloalkyl include, but are not limited to: oxetanyl, tetrahydrofuranyl, tetrahydropyranyl, azetidinyl, pyrrolidinyl, piperidinyl, piperazinyl, morpholinyl, thietanyl, tetrahydrothiophenyl (tetrahydrothienyl), and tetrahydrothiopyranyl. In one example the $R^2$ heterocycloalkyl is

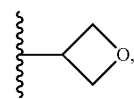

and another example is

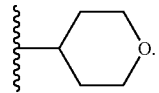

Examples the $R^{10}$ heterocycloalkyl include, but are not limited to, piperidinyl, pyrrolidinyl, azetidinyl, piperazinyl, and morpholinyl. In another example the heterocycloalkyl is piperidinyl. Examples the $R^{11}$ heterocycloalkyl include, but are not limited to, piperidinyl, pyrrolidinyl, azetidinyl, piperazinyl, and morpholinyl. In another example the heterocycloalkyl is piperidinyl.

For the $R^2$ groups comprising a heteroaryl, said heteroaryl is a 5 to 6 membered ring comprising 1 to 3 heteroatoms independently selected from the group consisting of: O, N and S, and the remaining ring atoms are carbon. In one example the heteroaryl is a 6 membered ring comprising 1 or 2 heteroatoms independently selected from the group consisting of: O, N and S. In another example the heteroaryl is a 6 membered ring comprising 1 or 2 N atoms. In another example the heteroaryl is a 6 membered ring comprising 1 N.

For the $R^2$ groups comprising a $C_6$-$C_{10}$ aryl, said $C_6$-$C_{10}$ aryl is a single ring or two fused rings, and the total number of carbons is 6 to 10. In one example of the $C_6$-$C_{10}$ aryl is phenyl. Another example of the $C_6$-$C_{10}$ aryl is naphthyl.

For the $R^2$ optional substituent —O—($C_1$-$C_6$alkyl), one example of the alkyl moiety is —($C_1$-$C_4$alkyl), and another is —($C_1$-$C_2$alkyl), and another is methyl.

For the $R^2$ optional substituent —($C_1$-$C_6$alkyl), one example of the alkyl moiety is —($C_1$-$C_4$alkyl), and another is —($C_1$-$C_2$alkyl), and another is methyl.

The $R^2$ heterocycloalkyl optional substituent, in one example, is a 4 to 6 membered ring (and in one example a 5-6 membered ring) comprising 1-3 heteroatoms selected from the group consisting of: O, N and S. In another example said heterocycloalkyl is a 5 to 6 membered ring comprising 1-3 heteroatoms selected from the group consisting of: O, N and S. In another example said heterocycloalkyl is a 5 to 6 membered ring comprising one heteroatom. In another example said heterocycloalkyl is a 5-6 membered ring comprising one oxygen atom. In another example said heterocycloalkyl ring is tetrahydropyran.

Examples of the $R^4$ and/or $R^5$ —($C_1$-$C_6$alkyl) group include: —($C_1$-$C_4$alkyl), —($C_1$-$C_3$alkyl), and —($C_1$-$C_2$alkyl). In one example the —($C_1$-$C_6$alkyl) group is methyl, in another example ethyl, in another example propyl, and in another example isopropyl, and in another example t-butyl.

In one Example of the $R^4$ and/or $R^5$ is —($C_1$-$C_6$alkyl) substituted with 1-3 substituents independently selected from the group consisting of: halo (e.g., Cl, Br and F, and in one example Cl, and in another F), —OH and —S(O)$_2$($C_1$-$C_6$alkyl) (such as, for example, S(O)$_2$($C_1$-$C_2$alkyl)). In another example $R^4$ and/or $R^5$ is —CH(CH$_3$)CH$_2$C(CH$_3$)$_2$OH, and in another example —CH(CH$_3$)CH$_2$S(O)$_2$CH$_3$, and in another example —CH(CH$_3$)CH$_2$Cl, and in another example —CH(CH$_3$)CHF$_2$. In another example $R^5$ is any one of the substituted —($C_1$-$C_6$alkyl) groups described in this paragraph. In another example $R^4$ is H and $R^5$ is any one of the substituted —($C_1$-$C_6$alkyl) groups described in this paragraph.

Examples of the $R^4$ and/or $R^5$ —($C_1$-$C_6$alkyl)-O—($C_1$-$C_6$alkyl) group include —($C_1$-$C_4$alkyl)-O—($C_1$-$C_4$alkyl), —($C_1$-$C_3$alkyl)-O—($C_1$-$C_3$alkyl), —($C_1$-$C_2$alkyl)-O—($C_1$-$C_2$alkyl), and —($C_1$-$C_2$alkyl)-O—CH$_3$. In one example the —($C_1$-$C_2$alkyl)-O—($C_1$-$C_2$alkyl) group is —($CH_2$)$_2$—O—$CH_3$, and in another example —C($CH_3$)$_2$$CH_2$O$CH_3$.

Examples of the $R^4$ and/or $R^5$ —C(O)$R^8$ group include groups wherein the $R^8$ —($C_1$-$C_6$alkyl) group is selected from the group consisting of: —($C_1$-$C_4$alkyl), —($C_1$-$C_3$alkyl), and —($C_1$-$C_2$alkyl). In one example $R^8$ is methyl. In another example $R^4$ and/or $R^5$ is a —C(O)($C_1$-$C_4$alkyl), and in another example —C(O)CH($CH_3$)$_2$, and in another —C(O)$CH_2$CH($CH_3$)$_2$, and in another —C(O)C($CH_3$)$_3$. In other examples $R^4$ is H, and $R^5$ is —C(O)$R^8$ wherein $R^8$ is as defined in this paragraph. Thus, in one example $R^4$ is H and $R^5$ is —C(O)$CH_3$.

In one example $R^4$ is —($C_1$-$C_6$alkyl) and $R^5$ is a —C(O)$R^8$ wherein $R^8$ is a —($C_1$-$C_6$alkyl) moiety (i.e., $R^5$ is a —C(O)($C_1$-$C_6$alkyl) group). In another example $R^4$ is —($C_1$-$C_4$alkyl), and $R^5$ is any one of the —C(O)$R^8$ groups described in this paragraph. In another example $R^4$ is —($C_1$-$C_2$alkyl), and $R^5$ is any one of the —C(O)$R^8$ groups described in this paragraph. In one example $R^5$ is —C(O)($C_1$-$C_4$alkyl), and in another example —C(O)CH($CH_3$)$_2$, and in another example —C(O)$CH_2$CH($CH_3$)$_2$, and in another example —C(O)($CH_3$). In another example $R^4$ is methyl and $R^5$ is —C(O)$CH_3$, and in another example $R^4$ is ethyl and $R^5$ is —C(O)$CH_3$.

In one example $R^4$ and/or $R^5$ is a —C(O)$R^8$ wherein $R^8$ is a substituted —($C_1$-$C_6$alkyl) (i.e., $R^4$ and/or $R^5$ is a substituted —C(O)($C_1$-$C_6$alkyl, and in another example a substituted —C(O)($C_1$-$C_4$alkyl)). In one example the $R^4$ and/or $R^5$ substituted —C(O)($C_1$-$C_6$alkyl) is substituted with 1-3 substituents independently selected from the group consisting of: halo (e.g., F, Br, and Cl and in one example F), —NH($C_1$-$C_6$alkyl), and —N($C_1$-$C_6$alkyl)$_2$ wherein each alkyl is independently selected. Examples of the $C_1$-$C_6$alkyl moiety in the —NH($C_1$-$C_6$alkyl), and —N($C_1$-$C_6$alkyl)$_2$ substitutents include $C_1$-$C_4$alkyl and $C_1$-$C_2$alkyl, and in one example methyl. In one example said substituted —C(O)($C_1$-$C_6$alkyl) is —C(O)$CH_2$$CF_3$, and in another —C(O)$CH_2$N($CH_3$)$_2$. In another example $R^5$ is any one of the substituted —C(O)($C_1$-$C_6$alkyl) groups described in this paragraph. In another example $R^4$ is H and $R^5$ is any one of the substituted —C(O)($C_1$-$C_6$alkyl) groups described in this paragraph.

In one example the $R^4$ and/or $R^5$ is —S(O)$_2$$R^9$ wherein $R^9$ is a —($C_1$-$C_6$alkyl). In one example $R^9$ is selected from the group consisting of: —($C_1$-$C_4$alkyl), —($C_1$-$C_3$alkyl), and —($C_1$-$C_2$alkyl). In another example, $R^9$ is methyl, and in another example $R^9$ is ethyl. In other examples $R^4$ is H, and $R^5$ is —S(O)$_2$$R^9$ wherein $R^9$ is as defined in any one of the examples in this paragraph.

In one example the $R^4$ and/or $R^5$ is —S(O)$_2$$R^9$ wherein $R^9$ is a —($C_1$-$C_6$alkyl)-O—($C_1$-$C_6$alkyl). In one example $R^9$ is selected from the group consisting of: —($C_1$-$C_4$alkyl)-O—($C_1$-$C_4$alkyl), —($C_1$-$C_4$alkyl)-O—($C_1$-$C_2$alkyl), and —($C_1$-$C_2$alkyl)-O—($C_1$-$C_2$alkyl). In another example $R^9$ is —$CH_2$$CH_2$O$CH_3$. In other examples $R^4$ is H, and $R^5$ is —S(O)$_2$$R^9$ wherein $R^9$ is as defined in any one of the examples in this paragraph.

In one example the $R^4$ and/or $R^5$ is —S(O)$_2$$R^9$ wherein $R^9$ is a —($C_3$-$C_6$)cycloalkyl. In one example $R^9$ is a —($C_3$-$O_5$)cycloalkyl. In another example $R^9$ is cyclopropyl. In another example $R^9$ is cyclobutyl. In other examples $R^4$ is H, and $R^5$ is —S(O)$_2$$R^9$ wherein $R^9$ is as defined in any one of the examples in this paragraph.

In one example the $R^4$ and/or $R^5$ is —S(O)$_2$$R^9$ wherein $R^9$ is a —($C_1$-$C_6$alkyl)-($C_3$-$C_6$)-cycloalkyl. In one example $R^9$ is selected from the group consisting of: —($C_1$-$C_4$alkyl)-($C_3$-$C_6$)cycloalkyl, —($C_1$-$C_4$alkyl)-($C_3$-$C_4$)cycloalkyl and —($C_1$-$C_2$alkyl)-($C_3$-$C_4$)cycloalkyl. In another example $R^9$ is —$CH_2$-cyclopropyl. In other examples $R^4$ is H, and $R^5$ is —S(O)$_2$$R^9$ wherein $R^9$ is as defined in any one of the examples in this paragraph.

In one example the $R^4$ and/or $R^5$ is —S(O)$_2$$R^9$ wherein $R^9$ is a heterocycloalkyl ring. In one example $R^9$ is a 4-6 membered hetereocycloalkyl comprising 1 to 3 heteroatoms selected from the group consisting of O, N and S wherein the remaining ring atoms are carbon. In another example $R^9$ is a 4-6 membered hetereocycloalkyl ring comprising 1 to 3 heteroatoms selected from the group consisting of O and N wherein the remaining ring atoms are carbon. In another example $R^9$ is a 4-6 membered hetereocycloalkyl ring comprising 1 to 2 heteroatoms selected from the group consisting of O, N and S wherein the remaining ring atoms are carbon. In another example $R^9$ is a 4-6 membered hetereocycloalkyl ring comprising 1 to 2 heteroatoms selected from the group consisting of O and N wherein the remaining ring atoms are carbon. In another example $R^9$ is a 4-5 membered heterocycloalkyl ring comprising 1 or 2 nitrogen atoms wherein the remaining atoms are carbon. In another example $R^9$ is a 4-5 membered ring comprising 1 nitrogen atom wherein the remaining atoms are carbon. In another example $R^9$ is azetidinyl. In another example $R^9$ is pyrrolidinyl. In another example $R^9$ is a 6 membered heterocycloalkyl ring comprising 1 to 3 hetero atoms independently selected from the group consisting of: O, N and S wherein the remaining ring atoms are carbon. In another example $R^9$ is a 6 membered heterocycloalkyl ring comprising 1 to 2 hetero atoms independently selected from the group consisting of O and N wherein the remaining atoms are carbon. In another example $R^9$ is a 6 membered heterocycloalkyl ring comprising 1 or 2 nitrogen atoms wherein the remaining atoms are carbon. In another example $R^9$ is piperidinyl. In another example $R^9$ is piperazinyl. In another example $R^9$ is morpholinyl. In other examples $R^4$ is H, and $R^5$ is —S(O)$_2$$R^9$ wherein $R^9$ is as defined in any one of the examples in this paragraph.

In one example the $R^4$ and/or $R^5$ is —S(O)$_2$$R^9$ wherein $R^9$ is an aryl. In one example $R^9$ is phenyl. In another example $R^9$ is naphthyl. In other examples $R^4$ is H, and $R^5$ is —S(O)$_2$$R^9$ wherein $R^9$ is as defined in any one of the examples in this paragraph.

In one example the $R^4$ and/or $R^5$ is —S(O)$_2$$R^9$ wherein $R^9$ is heteroaryl. In another example $R^9$ is a 5 or 6 membered heteroaryl ring. In another example $R^9$ is a 5 or 6 membered heteroaryl ring comprising 1-3 nitrogen atoms wherein the remaining atoms are carbon. In another example $R^9$ is a 5 or 6 membered heteroaryl ring comprising 1-2 nitrogen atoms wherein the remaining atoms are carbon. In another example $R^9$ is a 5 or 6 membered heteroaryl ring comprising one nitrogen atom wherein the remaining atoms are carbon. In another example $R^9$ is pyridyl, and in another pyrimidinyl, and in another pyrazinyl, and in another triazolyl, and in another pyrazolyl, and in another imidazolyl, in another pyrrolyl, in another thiazolyl, in another thienyl, and in another oxazolyl. In other examples $R^4$ is H, and $R^5$ is —S(O)$_2$$R^9$ wherein $R^9$ is as defined in any one of the examples in this paragraph.

In one example the $R^4$ and/or $R^5$ is —($C_3$-$C_6$ cycloalkyl). In another example $R^4$ and/or $R^5$ is —($C_4$-$C_6$ cycloalkyl). In another example, $R^4$ and/or $R^5$ is cyclopropyl, and in another example cyclobutyl, and in another example cyclopentyl, and in another example cyclohexyl. In another example, $R^5$ is any one of the —($C_3$-$C_6$ cycloalkyl) groups described in this paragraph. In another example, $R^4$ is H and $R^5$ is any one of the —($C_3$-$C_6$ cycloalkyl) groups described in this paragraph.

In one example the $R^4$ and/or $R^5$ is —($C_3$-$C_6$ cycloalkyl) substituted with 1-3 substituents independently selected from the group consisting of: halo (e.g., F,Cl and Br, and in one example F), —($C_1$-$C_6$alkyl) (e.g., —($C_1$-$C_4$alkyl), and in another example —($C_1$-$C_2$alkyl), and in another example methyl), —$NH_2$, —NH($C_1$-$C_6$alkyl), and —N($C_1$-$C_6$alkyl)$_2$ wherein each alkyl is independently selected. In one example, said —($C_3$-$C_6$ cycloalkyl) moiety is —($C_4$-$C_6$ cycloalkyl). In another example, said —($C_3$-$C_6$ cycloalkyl) is cyclobutyl, and in another example cyclohexyl. In another example the —NH($C_1$-$C_6$alkyl) substituent is —NH($C_1$-$C_3$alkyl). In another example said —N($C_1$-$C_6$alkyl)$_2$ substituent is —N($C_1$-$C_3$alkyl)$_2$ wherein each alkyl is independently selected. In another example said —($C_3$-$C_6$ cycloalkyl) moiety is substituted with —N($C_1$-$C_6$alkyl)$_2$ wherein each alkyl is independently selected, and in another example substituted with —N($CH_3$)$_2$. In another example the substituted —($C_3$-$C_6$ cycloalkyl) group is dimethylaminocyclobutyl, and in another example dimetylaminocyclohexyl, and in another example difluorocyclohexyl, and in another example methylcyclobutyl, and in another example aminocyclobutyl. In another example, $R^5$ is any one of the substituted —($C_3$-$C_6$ cycloalkyl) groups defined in this paragraph. In another example $R^4$ is H and $R^5$ is any one of the substituted —($C_3$-$C_6$ cycloalkyl) groups defined in this paragraph.

In one example the $R^4$ and/or $R^5$ is —($C_3$-$C_6$ cycloalkenyl). In another example $R^4$ and/or $R^5$ is —($C_3$-$C_5$ cycloalkenyl). In another example, $R^4$ and/or $R^5$ is cyclopentenyl. In another example, $R^5$ is cyclopentenyl. In another example, $R^4$ is H and $R^5$ is cyclopentenyl.

In one example the $R^4$ and/or $R^5$ is —($C_3$-$C_6$ oxocycloalkenyl) (i.e., a $C_3$-$C_6$ cycloalkenyl substituted with a =O). In another example $R^4$ and/or $R^5$ is —($C_3$-$C_5$oxocycloalkenyl). In another example, $R^4$ and/or $R^5$ is oxocyclopentenyl-. In another example, $R^5$ is oxocyclopentenyl-. In another example, $R^4$ is H and $R^5$ is oxocyclopentenyl-.

In one example the $R^4$ and/or $R^5$ is —($C_6$-$C_{10}$ aryl). In another example $R^4$ and/or $R^5$ is phenyl. In another example, $R^4$ is H and $R^5$ is phenyl.

In one example the $R^4$ and/or $R^5$ is —($C_6$-$C_{10}$aryl) (e.g., phenyl) substituted with 1-3 substituents independently selected from the group consisting of: —CN, —O($C_1$-$C_6$alkyl) and halo (e.g., Br, Cl and F). Examples of the —O($C_1$-$C_6$alkyl) substituent include, for example, —O($C_1$-$C_3$alkyl), and in another example —$OCH_3$. In one example phenyl is substituted with —CN. In one example the halo substituent is F. In one example, the $R^4$ and/or $R^5$ group is phenyl substituted with 1-3 substituents, as the substituents are as defined in this paragraph. In another example the $R^4$ and/or $R^5$ is methoxyphenyl. In one example, $R^5$ is any one of the substituted —($C_6$-$C_{10}$aryl) (e.g., phenyl) groups defined in this paragraph. In another example, $R^4$ is H and $R^5$ is any one of the substituted —($C_6$-$C_{10}$aryl) (e.g., phenyl) groups defined in this paragraph.

In another example $R^4$ and or $R^5$ is —($C_1$-$C_6$alkyl)($C_6$-$C_{10}$aryl), and in another example —($C_1$-$C_2$alkyl)($C_6$-$C_{10}$aryl), and in another example —($C_1$-$C_2$alkyl)(phenyl), and in another example —$CH_2$phenyl. In another example $R^5$ is any one of the —($C_1$-$C_6$alkyl)($C_6$-$C_{10}$aryl) groups described in this paragraph, and in another example $R^5$ is —$CH_2$phenyl. In another example $R^4$ is H, and $R^5$ is any one of the —($C_1$-$C_6$alkyl)($C_6$-$C_{10}$aryl) groups described in this paragraph. In another example $R^4$ is H and $R^5$ is —$CH_2$phenyl.

In one example $R^4$ and/or $R^5$ is —($C_1$-$C_6$alkyl)C(O)N($R^{20}$)$_2$ wherein each $R^{20}$ is independently selected, and in another example —($C_1$-$C_3$alkyl)C(O)N($R^{20}$)$_2$ wherein each $R^{20}$ is independently selected, and in another example —($C_1$-$C_3$alkyl)C(O)N($R^{20}$)$_2$ wherein each $R^{20}$ is independently selected from the group consisting of: —($C_1$-$C_3$alkyl), and in another example each $R^{20}$ is methyl. In another example said —($C_1$-$C_6$alkyl)C(O)N($R^{20}$)$_2$ is —$CH_2$C(O)N($CH_3$)$_2$, and in another example —($CH_2$)$_2$C(O)N($CH_3$)$_2$. In another example $R^5$ is any one of the —($C_1$-$C_6$alkyl)C(O)N($R^{20}$)$_2$ groups described in this paragraph. In another example $R^4$ is H and $R^5$ is any one of the —($C_1$-$C_6$alkyl)C(O)N($R^{20}$)$_2$ groups described in this paragraph.

In one example the $R^4$ and/or $R^5$ is heteroaryl. In another example $R^4$ and/or $R^5$ is a 5 to 6 membered ring comprising 1-2 heteroatoms independently selected from the group consisting of: N, O and S. In another example $R^4$ and/or $R^5$ is a 5 to 6 membered ring comprising 1-2 nitrogen atoms. In another example $R^4$ and/or $R^5$ is pyridyl. In another example $R^5$ is any one of the heteroaryl groups, as described in this paragraph. In another example, $R^4$ is H and $R^5$ is any one of the heteroaryl groups as defined in this paragraph. In another example $R^4$ is H, and $R^5$ is pyridyl.

In one example the $R^4$ and/or $R^5$ is heteroaryl substituted with 1-3 substituents independently selected from the group consisting of: —CN, halo (e.g., F, Cl and Br, and in one example F) and —($C_1$-$C_6$alkyl). In another example the —($C_1$-$C_6$alkyl) substituent is —($C_1$-$C_3$alkyl), and in another example methyl. In another example the $R^4$ and/or $R^5$ heteroaryl moiety is a 5 to 6 membered ring comprising 1-2 heteroatoms independently selected from the group consisting of: N, O and S. In another example the $R^4$ and/or $R^5$ heteroaryl moiety is a 5 to 6 membered ring comprising 1-2 nitrogen atoms. In another example the $R^4$ and/or $R^5$ heteroaryl moiety is pyridyl. In another example the substituted heteroaryl is methylpyridyl, and in another example methylpyrazolyl, and in another example cyanopyridyl, and in another example fluoropyridyl. In another example $R^5$ is any one of the substituted heteroaryl groups described in this paragraph. In another example, $R^4$ is H and $R^5$ is any one of the substituted heteroaryl groups described in this paragraph.

In one example $R^4$ and/or $R^5$ is —C(O)($C_1$-$C_6$alkyl)NHC(O)O($C_1$-$C_6$alkyl), and in another example —C(O)($C_1$-$C_4$alkyl)NHC(O)O($C_1$-$C_4$alkyl), and in another example —C(O)CH(CH($CH_3$)$_2$)NHC(O)O$CH_3$. In another example, $R^5$ is any one of the —C(O)($C_1$-$C_6$alkyl)NHC(O)O($C_1$-$C_6$alkyl) groups described in this paragraph. In another example, $R^4$ is H and $R^5$ is any one of the —C(O)($C_1$-$C_6$alkyl)NHC(O)O($C_1$-$C_6$alkyl) groups described in this paragraph.

In one example $R^4$ and/or $R^5$ is —C(O)(substituted $C_1$-$C_6$alkyl)NHC(O)O($C_1$-$C_6$alkyl), wherein said substituted alkyl is substituted with a heterocycloalkyl, and in another example, —C(O)(substituted $C_1$-$C_4$alkyl)NHC(O)O($C_1$-$C_4$alkyl), wherein said substituted alkyl is substituted with a heterocycloalkyl. In another example said heterocycloalkyl substituent on said substituted alkyl is a 5 to 6 membered ring comprising 1-2 heteroatoms selected from the group consisting of: O, S and N. In another example said heterocycloalkyl substituent on said substituted alkyl is a 6 membered ring comprising 1-2 heteroatoms selected from the group consisting of: O, S, and N. In another example, said heterocycloalkyl substituent is teterahydropyran. In another example, $R^5$ is any one of the —C(O)(substituted $C_1$-$C_6$alkyl)NHC(O)O($C_1$-$C_6$alkyl) groups described in this paragraph. In another example, $R^4$ is H and $R^5$ is any one of the —C(O)(substituted $C_1$-$C_6$alkyl)NHC(O)O($C_1$-$C_6$alkyl) groups described in this paragraph.

In one example $R^4$ and/or $R^5$ is heterocycloalkyl. In one example, said heterocycloalkyl is a 4 to 6 membered ring comprising 1-2 heteroatoms selected from the group consisting of: O, N and SO (i.e., S=O). In another example said heterocycloalkyl is a 4 membered ring. In another example, said heterocycloalkyl is a 5 membered ring, and in another example a six membered ring. In another example said heterocycloalkyl ring is a 4 membered ring comprising one oxygen atom. In another example, said heterocycloalkyl ring is a 5 membered ring comprising one oxygen atom. In another example said heterocycloalkyl is a 5 membered ring, and in another example a 6 membered ring, comprising one nitrogen. In another example said heterocycloalkyl is tetrahydrofuranyl, and in another example piperidinyl, and in another example azetidinyl, and in another example tetrahydropyran, and in another example pyrrolidinyl, and in another example oxetanyl, and in another example tetrahydrothiophenyl, and in another example oxidotetrahydrothiophenyl. In another example $R^5$ is any one of the heterocycloalkyls described in this paragraph. In another example $R^4$ is H, and $R^5$ is any one of the heterocycloalkyls described in this paragaraph.

In one example $R^4$ and/or $R^5$ is a heterocycloalkyl substituted with 1-3 substituents independently selected from the group consisting of —($C_1$-$C_6$ alkyl) and halo (e.g., F, Br and Cl, and in one example F). In one example, the substituted heterocycloalkyl is a 5 to 6 membered ring comprising 1-2 heteroatoms selected from the group consisting of: O, N, and S. In another example, the substituted heterocycloalkyl is a 5 membered ring, and in another example a six membered ring. In another example the substituted heterocycloalkyl comprises one oxygen atom. In another example, the substituted heterocycloalkyl is a 5 membered ring comprising one oxygen atom. In another example, the substituted heterocycloalkyl is a 5-6 membered ring (and in one example a 5 membered ring) comprising one oxygen and 1-2 —($C_1$-$C_6$ alkyl) substituents (and in one example said substituents are methyl). In another example, the substituted heterocycloalkyl is a 5-6 membered ring (and in one example a 5 membered ring) comprising one oxygen and 1-2 and a halo atom substituent (e.g., F). In another example said substituted heterocycloalkyl is dimethyltetrahydrofuranyl, and in another example fluorotetrahydrofuran. In another example $R^5$ is any one of the substituted heterocycloalkyls described in this paragraph. In another example $R^4$ is H, and $R^5$ is any one of the substituted heterocycloalkyls described in this paragaraph.

In one example $R^4$ and/or $R^5$ is —($C_1$-$C_6$alkyl)heteroaryl, and in one example —($C_1$-$C_2$alkyl)heteroaryl. In one example the heteroaryl moiety is a 5-6 membered ring (e.g. 6) comprising 1-3 heteroatoms selected from the group consisting of: O, N and S. In one example the heteroaryl moiety is a 5 to 6 membered ring comprising 1-2 nitrogen atoms, and in one example the heteroaryl moiety is pyridyl. In another example the $R^4$ and/or $R^5$ is a —($C_1$-$C_2$alkyl)pyridyl, and in another example —$CH_2$pyridyl. In another example $R^5$ is any one of the alkylheteroaryls described in this paragraph. In another example $R^4$ is H and $R^5$ is any one of the alkylheteroaryls described in this paragraph.

In one example $R^4$ and/or $R^5$ is substituted —($C_1$-$C_6$alkyl)heterocycloalkenyl, and in another example substituted —($C_1$-$C_2$alkyl)heterocycloalkenyl, substituted with 1-3 substituents independently selected from the group consisting of: —($C_1$-$C_6$alkyl)(such as, for example, —($C_1$-$C_3$alkyl), and in one example methyl), and wherein said heterocycloalkenyl comprises 1-2 double bonds (and in one example one double bond). In one example the heterocycloalkenyl moiety is a substituted 5-6 membered ring (and in one example 5) comprising 1-3 heteroatoms (and in one example 1-2) selected from the group consisting of: O, N and S. In another example the $R^4$ and/or $R^5$ is a substituted —($C_1$-$C_2$alkyl)heterocycloalkenyl, and in another example —$CH_2$(methyldihydroisoxazolyl). In another example $R^5$ is any one of the substituted —($C_1$-$C_6$alkyl)heterocycloalkenyls described in this paragraph. In another example $R^4$ is H and $R^5$ is any one of the substituted —($C_1$-$C_6$alkyl)heterocycloalkenyls described in this paragraph.

In one example $R^4$ and/or $R^5$ is —C(O)$R^8$ wherein $R^8$ is heterocycloalkyl (i.e., $R^4$ and/or $R^5$ is —C(O)heterocyloalkyl). In another example said heterocycloalkyl moiety is a 4 to 6 membered (and in one example 4, and in another example 5 and in another example 6) ring comprising 1-2 heteroatoms selected from the group consisting of: O, N and S. In another example said heterocycloalkyl is a 4 to 6 membered ring comprising 1-2 heteroatoms independently selected from O and N. In another example said heterocycloalkyl moiety is a 4 to 6 membered ring comprising 1-2 nitrogen atoms. In another example said heterocycloalkyl moiety is a 4 to 5 membered ring comprising one nitrogen. In another example said heterocycloalkyl moiety is azetidinyl, and in another example pyrrolidinyl, and in another example morpholinyl, and in another example tetrahydropyran. In another example said $R^5$ is any one of the —C(O)heterocyloalkyl groups described in this paragraph. In another example $R^4$ is H and $R^5$ is any one of the —C(O)heterocyloalkyl groups described in this paragraph.

In one example $R^4$ and/or $R^5$ is —C(O)$R^8$ wherein $R^8$ is a substituted -heterocycloalkyl (i.e., $R^4$ and/or $R^5$ is a substituted —C(O)heterocycloalkyl group). In one example said substituted heterocycloalkyl moiety is substituted with 1-3 substituents independently selected from the group consistin of: halo (e.g., F, Cl and Br, and in another example F, and in another example two F atoms), —OH, —($C_1$-$C_6$alkyl) (such as, for example, methyl). In another example said substituted heterocycloalkyl moiety is a 4 to 6 membered (and in one example 4, and in another example 5 and in another example 6) ring comprising 1-2 heteroatoms selected from the group consisting of: O, N and S. In another example said substituted heterocycloalkyl moiety is a 4 to 6 membered ring comprising one nitrogen and one oxygen atom. In another example said substituted heterocycloalkyl moiety is a 4 to 6 membered ring comprising 1-2 nitrogen atoms. In another example said substituted heterocycloalkyl moiety is a 4 membered ring, and in another example a 5 membered ring, and in another example a 6 membered ring. In another example said substituted heterocycloalkyl moiety is a 4 to 6 membered ring comprising 1 nitrogen. In another example said substituted heterocycloalkyl moiety is difluoroazetidinyl, and in another example difluoropyrrolidinyl, and in another example difluoropiperidinyl, and in another example hydroxymethylazetidinyl. In another example said $R^5$ is any one of the substituted —C(O) heterocycloalkyl groups described in this paragraph. In another example $R^4$ is H and $R^5$ is any one of the substituted —C(O)heterocycloalkyl groups described in this paragraph.

In one example $R^4$ and/or $R^5$ is a —C(O)$R^8$ wherein $R^8$ is a heteroaryl (i.e., $R^4$ and/or $R^5$ is —C(O)heteroaryl). In one example said heteroaryl moiety is a 5 membered ring comprising 1-3 heteroatoms, and in another example said heteroaryl moiety is a 5 membered ring comprising 3 heteroatoms. In another example said heteroaryl ring is thiadiazolyl, and in another example furanyl, and in another pyridyl. In another example, $R^5$ is any one of the —C(O)heteroaryls described in this paragraph. In another example $R^4$ is H and $R^5$ is any one of the —C(O)heteroaryls described in this paragraph.

In one example $R^4$ and/or $R^5$ is a —C(O)$R^8$ wherein $R^8$ is a substituted heteroaryl (i.e., $R^4$ and/or $R^5$ is a substituted —C(O)heteroaryl) wherein said substituted heteroaryl is substituted with 1-3 substituents independently selected from the group consisting of —($C_1$-$C_6$alkyl) (e.g., —($C_1$-$C_4$alkyl) and in another example methyl). In one example said substituted heteroaryl moiety is a 5 membered ring comprising 1-3 heteroatoms, and in another example said substituted heteroaryl moiety is a 5 membered ring comprising 3 heteroatoms. In another example, said 5 membered ring is substituted with a —($C_1$-$C_4$alkyl) (e.g., methyl). In another example said substituted heteroaryl ring is thiadiazolyl, and in another example said substituted heteroaryl is methylthiadiazolyl. In another example, $R^5$ is any one of the —C(O)heteroaryls described in this paragraph. In another example $R^4$ is H and $R^5$ is any one of the —C(O)heteroaryls described in this paragraph.

In one example $R^4$ and/or $R^5$ is a —C(O)$R^8$ wherein $R^8$ is a —($C_3$-$C_6$)cycloalkyl (i.e., $R^4$ and or $R^5$ is —C(O)($C_3$-$C_6$cycloalkyl). In another example $R^8$ is cyclopropyl, and in another cyclobutyl, and in another cyclopentyl, and in another cyclohexyl. In another example $R^5$ is any one of the —C(O)($C_3$-$C_6$cycloalkyl)s described in this paragraph. In another example $R^4$ is H and $R^5$ is any one of the —C(O)($C_3$-$C_6$cycloalkyl)s described in this paragraph.

In one example $R^4$ and/or $R^5$ is a —C(O)$R^8$ wherein $R^8$ is a —($C_1$-$C_6$alkyl)($C_6$-$C_{10}$aryl) (i.e., $R^4$ and/or $R^5$ is a —C(O)($C_1$-$C_6$alkyl)($C_6$-$C_{10}$aryl) group). In another example said $R^8$ is —($C_1$-$C_2$alkyl)($C_6$-$C_{10}$aryl), and in another example —($C_1$-$C_2$alkyl)(phenyl), and in another example —CH$_2$phenyl. In another example, $R^5$ is any one of the —C(O)($C_1$-$C_6$alkyl)($C_6$-$C_{10}$aryl) groups described in this paragraph. In another example $R^4$ is H and $R^5$ is any one of the —C(O)($C_1$-$C_6$alkyl)($C_6$-$C_{10}$aryl) groups described in this paragraph.

In one example $R^4$ and/or $R^5$ is a —C(O)$R^8$ wherein $R^8$ is a substituted —($C_1$-$C_6$alkyl)($C_6$-$C_{10}$aryl) (i.e., $R^4$ and/or $R^5$ is a substituted —C(O)($C_1$-$C_6$alkyl)($C_6$-$C_{10}$aryl) group) wherein said substituted —C(O)($C_1$-$C_6$alkyl)($C_6$-$C_{10}$aryl) group is substituted with 1-3 substituents independently selected from the group consisting of halo (e.g., Br, Cl and F, and in one example F). In another example said $R^8$ is a substituted —($C_1$-$C_2$alkyl)($C_6$-$C_{10}$aryl), and in another example substituted —($C_1$-$C_2$alkyl)(phenyl). In other examples the $C_6$-$C_{10}$aryl moiety is substituted and the $C_1$-$C_6$alkyl moiety is unsubstituted. In another example said $R^8$ is a substituted —CH$_2$phenyl, and in another example —CH$_2$(fluorophenyl). In another example, $R^5$ is any one of the —C(O)($C_1$-$C_6$alkyl)($C_6$-$C_{10}$aryl) groups described in this paragraph. In another example $R^4$ is H and $R^5$ is any one of the —C(O)($C_1$-$C_6$alkyl)($C_6$-$C_{10}$aryl) groups described in this paragraph.

In one example $R^4$ and/or $R^5$ is a —C(O)$R^8$ wherein $R^8$ is a —($C_1$-$C_6$alkyl)($C_3$-$C_6$cycloalkyl) (i.e., $R^4$ and/or $R^5$ is a —C(O)($C_1$-$C_6$alkyl)($C_3$-$C_6$cycloalkyl) group). In another example said $R^8$ is —($C_1$-$C_2$alkyl)($C_3$-$C_6$cycloalkyl), and in another example —($C_1$-$C_2$alkyl)(cyclohexyl), and in another example —CH$_2$cyclohexyl, and in another —CH$_2$cyclopentyl. In another example, $R^5$ is any one of the —C(O)($C_1$-$C_6$alkyl)($C_3$-$C_6$cycloalkyl) groups described in this paragraph. In another example $R^4$ is H and $R^5$ is any one of the —C(O)($C_1$-$C_6$alkyl)($C_3$-$C_6$cycloalkyl) groups described in this paragraph.

In one example $R^4$ and/or $R^5$ is a —C(O)$R^8$ wherein $R^8$ is —O$R^{12}$ wherein $R^{12}$ is a —($C_1$-$C_6$alkyl), i.e., said —C(O)$R^8$ group is —C(O)O$R^{12}$. In one example $R^{12}$ is —($C_1$-$C_4$alkyl). In another example $R^{12}$ is —C(CH$_3$)$_3$, and in another —CH$_2$CH(CH$_3$)$_2$, and in another —CH$_3$, and in another example —CH(CH$_3$)$_2$, and in another example —CH$_2$C(CH$_3$)$_3$. In another example $R^5$ is any one of the —C(O)O$R^{12}$ groups described in this paragraph. In another example $R^4$ is H and $R^5$ is any one of the —C(O)O$R^{12}$ groups described in this paragraph. In one example $R^4$ is H and $R^5$ is —C(O)CH$_3$.

In one example $R^4$ and/or $R^5$ is a —C(O)$R^8$ wherein $R^8$ is —O$R^{12}$ wherein $R^{12}$ is a —($C_1$-$C_6$alkyl) that is substituted with $R^{14}$. In one example said $R^{14}$ is —O$R^{15}$. In another example said $R^{15}$ is a —($C_1$-$C_6$alkyl). In other examples the —($C_1$-$C_6$alkyl) moiety of said $R^{12}$ and said $R^{15}$ are —($C_1$-$C_4$alkyl), and each alkyl is independently selected. In one example said $R^8$ moiety is —CH$_2$CH$_2$OCH$_3$. In other examples $R^5$ is any one of the —C(O)$R^8$ groups described in this paragraph. In other examples $R^4$ is H and $R^5$ is any one of the —C(O)$R^8$ groups described in this paragraph.

In one example $R^4$ and/or $R^5$ is a —C(O)$R^8$ wherein $R^8$ is —O$R^{12}$ wherein $R^{12}$ is a ($C_6$-$C_{10}$aryl), such as, for example phenyl. In other examples $R^5$ is any one of the —C(O)$R^8$ groups described in this paragraph. In other examples $R^4$ is H and $R^5$ is any one of the —C(O)$R^8$ groups described in this paragraph.

In one example $R^4$ and/or $R^5$ is a —C(O)$R^8$ wherein $R^8$ is —O$R^{12}$ wherein $R^{12}$ is a —($C_1$-$C_6$alkyl)($C_6$-$C_{10}$aryl). In one example said $R^{12}$ is —($C_1$-$C_2$alkyl)($C_6$-$C_{10}$aryl), and in another example —($C_1$-$C_2$alkyl)(phenyl), and in another example —CH$_2$phenyl. In other examples $R^5$ is any one of the —C(O)$R^8$ groups described in this paragraph. In other examples $R^4$ is H and $R^5$ is any one of the —C(O)$R^8$ groups described in this paragraph.

In one example $R^4$ and/or $R^5$ is a —C(O)$R^8$ wherein $R^8$ is —NH$R^{12}$ wherein $R^{12}$ is a —($C_1$-$C_6$alkyl), i.e., said —C(O)$R^8$ group is —C(O)NH$R^{12}$. In one example $R^{12}$ is —($C_1$-$C_4$alkyl).

In another example $R^{12}$ is —CH(CH$_3$)$_2$, and in another example —CH$_2$CH$_3$. In another example $R^5$ is any one of the —C(O)NH$R^{12}$ groups described in this paragraph. In another example $R^4$ is H and $R^5$ is any one of the —C(O)NH$^{12}$ groups described in this paragraph.

In one example $R^4$ and/or $R^5$ is a —C(O)$R^8$ wherein $R^8$ is —NH$R^{12}$ wherein $R^{12}$ is a ($C_1$-$C_6$alkyl)($C_6$-$C_{10}$aryl) optionally substituted with 1-3 independently selected $R^{14}$ groups. In one example said $R^{12}$ ($C_1$-$C_6$alkyl)($C_6$-$C_{10}$aryl) moiety is substituted with 1-3 substituents independently selected from the group consisting of $R^{14}$. In another example said $R^{12}$ ($C_1$-$C_6$alkyl)($C_6$-$C_{10}$aryl) moiety is substituted with 1-3 substituents independently selected from the group consisting of: —CF$_3$, halo (e.g., F, Cl and Br, and in one example F, and in another Cl), —O($C_1$-$C_6$alkyl), and —OH. In another example said $R^{12}$ is a ($C_1$-$C_2$alkyl)(phenyl) optionally substituted with 1-3 independently selected $R^{14}$ groups. In another example said $R^{12}$ is a ($C_1$-$C_2$alkyl)(phenyl) substituted with 1-3 independently selected $R^{14}$ groups. In another example said $R^{12}$ is a ($C_1$-$C_2$alkyl)(phenyl) substituted with 1-3 substituents independently selected from the group consisting of: —CF$_3$ halo (e.g., F, Cl and Br, and in one example F, and in another Cl), —O($C_1$-$C_6$alkyl), and —OH. In one example said $R^8$ group is —NHCH(CH$_3$)(hydroxychlorophenyl), and in another —NHCH(CH$_3$)(triflurormethylchlorophenyl), and in another example —NHCH(CH$_3$)(chloromethoxyphenyl). In another example $R^5$ is any one of the —C(O)$R^8$ groups described in this paragraph. In another example $R^4$ is H and $R^5$ is any one of the —C(O)$R^8$ groups described in this paragraph.

In one example $R^4$ and/or $R^5$ is a —C(O)$R^8$ wherein $R^8$ is —NH$R^{12}$ wherein $R^{12}$ is a ($C_1$-$C_6$alkyl)(heteroaryl) optionally substituted with 1-3 independently selected $R^{14}$ groups. In one example said $R^{12}$ ($C_1$-$C_6$alkyl)(heteroaryl) moiety is substituted with 1-3 substituents independently selected from the group consisting of $R^{14}$. In another example said $R^{12}$ ($C_1$-$C_6$alkyl)(heteroaryl) moiety is substituted with 1-3 substituents independently selected from the group consisting of: halo (e.g., F, Cl and Br, and in another Cl). In another example said $R^{12}$ is a ($C_1$-$C_2$alkyl)(pyridyl) optionally substituted with 1-3 independently selected $R^{14}$ groups. In another example said $R^{12}$ is a ($C_1$-$C_2$alkyl)(pyridyl) substituted with 1-3 independently selected $R^{14}$ groups. In another example said $R^{12}$ is a ($C_1$-$C_2$alkyl)(pyridyl) substituted with 1-3 substituents independently selected from the group consisting of: halo (e.g., F, Cl and Br, and in another Cl). In one example said $R^8$ group is —NHCH($CH_3$)(chloropyridyl). In another example $R^5$ is any one of the —C(O)$R^8$ groups described in this paragraph. In another example $R^4$ is H and $R^5$ is any one of the —C(O)$R^8$ groups described in this paragraph.

In one example $R^4$ and/or $R^5$ is a —C(O)$R^8$ wherein $R^8$ is —($C_1$-$C_6$alkyl)-O—($C_1$-$C_6$alkyl). In another example $R^8$ is —($C_1$-$C_2$alkyl)-O—($C_1$-$C_2$alkyl). In another example $R^8$ is —$CH_2OCH_3$. In another example $R^5$ is any one of the —C(O)$R^8$ groups described in this paragraph. In another example $R^4$ is H and $R^5$ is any one of the —C(O)$R^8$ groups described in this paragraph.

In one example $R^4$ and/or $R^5$ is a —C(O)$R^8$ wherein $R^8$ is a fused bicyclic heterocycloalkyl ring. The $R^8$ fused bicyclic heterocycloalkyl ring comprises two fused heterocycloalkyl rings, wherein each heterocycloalkyl ring is 5-6 members (the ring size includes the atoms common to both rings) and each heterocycloalkyl ring comprises 1-3 heteroatoms independently selected from the group consisting of: O, N and S. The ring sizes of the rings of the bicyclic ring are, in one example, 5-6, and in another example 5-5, and in another example 6-5, and in another example, 6-6, wherein the ring size numbers include the atoms common to both rings. In one example, each heterocycloalkyl ring is a 5 membered ring (including the atoms common to both rings). In one example, one ring comprises one nitrogen atom and the other ring comprises one oxygen atom. In one example said fused bicyclic heterocycloalkyl bicyclic ring is tetrahydrofuropyrrolidinyl (i.e., a tetrahydrofuran fused to pyrrolidine).

In one example $R^4$ and/or $R^5$ is a —($C_1$-$C_6$alkyl)($C_3$-$C_6$cycloalkyl). In another example $R^4$ and/or $R^5$ is a —($C_1$-$C_2$alkyl)($C_3$-$C_6$cycloalkyl), and in another example a —($C_1$-$C_2$alkyl)($C_3$-$C_4$cycloalkyl), and in another example a —$CH_2$($C_3$-$C_4$cycloalkyl), and in another example —$CH_2$cyclobutyl. In another example $R^5$ is any one of the —($C_1$-$C_6$alkyl)($C_3$-$C_6$cycloalkyl) groups described in this paragraph. In another example $R^4$ is H and $R^5$ is any one of the —($C_1$-$C_6$alkyl)($C_3$-$C_6$cycloalkyl) groups in this paragraph. In another example $R^4$ is H and $R^5$ is —$CH_2$cyclobutyl. In another example, $R^4$ and $R^5$ are each the same or different —($C_1$-$C_6$alkyl)($C_3$-$C_6$cycloalkyl). In another example, $R^4$ and $R^5$ are each the same or different —($C_1$-$C_6$alkyl)($C_3$-$C_4$cycloalkyl). In another example $R^4$ and $R^5$ are each —$CH_2$cyclobutyl.

In one example $R^4$ and/or $R^5$ is a substituted —($C_1$-$C_6$alkyl)($C_3$-$C_6$cycloalkyl) substituted with 1-3 substituents independently selected from the group consisting of: —O—($C_1$-$C_6$alkyl) (such as, for example, —O—$C_4$-$C_6$alkyl, and in another example —$OCH_3$), (-hydroxy$C_1$-$C_6$alkyl) (such as for example, (hydroxy$C_1$-$C_3$alkyl, such as, for example, —C($CH_3$)$_2$OH), and —($C_2$-$C_6$alkenyl) (such as, for example, —($C_2$-$C_6$alkenyl) (such as, for example, —($C_2$-$C_4$alkenyl), such as, for example, —CH($CH_3$)C=$CH_2$). In another example $R^4$ and/or $R^5$ is a substituted —($C_1$-$C_2$alkyl)($C_3$-$C_6$cycloalkyl), and in another example a substituted —($C_1$-$C_2$alkyl)($C_3$-$C_4$cycloalkyl), and in another example a substituted —$CH_2$($C_3$-$C_4$cycloalkyl), and in another example substituted —$CH_2$cyclobutyl, and in another example —$CH_2$-cyclobutyl-$OCH_3$, and in another example —$CH_2$cyclobutyl-C($CH_3$)$_2$OH, and in another example —$CH_2$cyclobutyl-CH($CH_3$)C=$CH_2$, and in another example —$CH_2$cyclobutyl-C($CH_3$)$_2$OH. In another example $R^5$ is any one of the substituted —($C_1$-$C_6$alkyl)($C_3$-$C_6$cycloalkyl) groups described in this paragraph. In another example $R^4$ is H and $R^5$ is any one of the substituted —($C_1$-$C_6$alkyl)($C_3$-$C_6$cycloalkyl) groups in this paragraph.

In one example $R^4$ and/or $R^5$ is —($C_1$-$C_6$alkyl)heterocycloalkyl, and in another example —($C_1$-$C_2$alkyl)heterocycloalkyl, and in another example a —$CH_2$heterocycloalkyl. In one example said heterocycloalkyl moiety is a 4 to 6 membered ring, and in another example a 5-6 membered ring, and in another example a 6 membered ring, comprising 1-3 heteroatoms independently selected from the group consisting of 0, N and S. In another example said heterocycloalkyl moiety comprises one heteroatom, and in another example said heteroatom is N, and in another example 0. In another example said —($C_1$-$C_6$alkyl)heterocycloalkyl is —$CH_2$piperidinyl, and in another example —$CH_2$tetrahydropyran, and in another example —CH($CH_3$)-tetrahydropyran, and in another example —CH($CH_3$)$CH_2$morpholinyl, and in another example —CH($CH_3$)$CH_2$piperidinyl, and in another example —$CH_2$tetrahydrofuran, and in another example —($CH_2$)$_2$morpholinyl. In another example $R^5$ is any one of the —($C_1$-$C_6$alkyl)heterocycloalkyl groups described in this paragraph. In another example $R^4$ is H and $R^5$ is any one of the —($C_1$-$C_6$alkyl)heterocycloalkyl groups described in this paragraph.

In one example $R^4$ and $R^5$, taken together with the nitrogen to which they are bonded to, form a 4 to 6 membered heterocycloalkyl ring. In one example said heterocycloalkyl ring is a 4 membered ring, and in another example a 5 membered ring (e.g., pyrrolidinyl), and in another example a 6 membered ring. In another example at least one (e.g., 1-10) H atoms are deuterium (D) atoms (e.g., 1-10 H atoms in a 6 membered ring are deuterium). In another example the heterocycloalkyl ring is substituted. In another example the heterocycloalkyl ring (e.g., a 4 membered ring, and in another example a 5 membered ring) is substituted with a hydroxy group, and in another example a —C(O)OH group, and in another example a —($C_1$-$C_6$alkyl)-O—($C_1$-$C_6$alkyl) (e.g., a —($C_1$-$C_2$alkyl)-O—($C_1$-$C_2$alkyl)) group, and in another example a —($C_1$-$C_6$alkyl)-OH (e.g., —($C_1$-$C_2$alkyl)-OH)) group, and in another example 1-2 halo atoms (e.g., F and in one example difluoro), and in another example a —$CH_2OCH_3$ group, and in another example a —$CH_2OH$ group. In another example the heterocycloalkyl ring is substituted with —($C_1$-$C_6$alkyl) (e.g., a —($C_1$-$C_2$alkyl), such as, for example, methyl). In another example said heterocycloalkyl is substituted with a —OH and a —($C_1$-$C_6$alkyl) (e.g., a —($C_1$-$C_2$alkyl), such as, for example, methyl). In another example said heterocycloalkyl ring (e.g., a 6 membered heterocycloalkyl ring) has a one carbon bridge, and in another example said heterocycloalkyl ring is morpholinyl with a one carbon bridge. In another example said heterocycloalkyl ring (e.g., a 6 membered heterocycloalkyl ring) has a two carbon bridge (e.g., morpholinyl with a two carbon bridge). In another example, said heteocycloalkyl is a methoxypiperidinyl, and in another example cyanopiperidinyl, and in another example hydroxymethylpiperidinyl, and in another example methylsulfanylpiperidinyl, and in another example a dimethylmorpholinyl.

In another example said heterocycloalkyl ring is hydroxyazetidinyl, and in another example methoxymethylazetidinyl, and in another example hydroxymethylazetidinyl, and in another example methylazetidinyl, and in another example hydroxymethylazetidinyl, and in another example prolinyl, and in another example difluoropiperidinyl, and in another example difluoroazetidinyl, and in another example morpholinyl wherein the 8 hydrogen atoms are deuterium atoms.

In one example $R^4$ and $R^5$ taken together with the nitrogen to which they are bonded to form a spiro ring comprising two independently selected 4-6 membered heterocycloalkyl rings (i.e., there is one atom in common with both rings of the spiro ring), wherein one of said rings comprises the nitrogen of the —$NR^4R^5$ group, and wherein the other ring of the spiro ring comprises one heteroatom selected from the group consisting of: O, N and S (and in one example 0), and each heterocycloalkyl ring of the spiro ring optionally comprises 1 or 2 additional heteroatoms independently selected from the group consisting of: O, S and N, and wherein said spiro ring is optionally substituted with 1-3 substituents independently selected from the group consisting of: —OH, —($C_1$-$C_6$alkyl)-O—($C_1$-$C_6$alkyl), —($C_1$-$C_6$alkyl)-OH, —O($C_1$-$C_6$alkyl) and —($C_1$-$C_6$ alkyl). In one example the heterocycloalkyl ring comprising the nitrogen of the —$NR^4R^5$ is a 6 membered ring (including the atom in common with each heterocycloalkyl ring of the spiro ring) and the other heterocycloalkyl ring is a 4-6 membered ring (e.g., a 4 membered ring, including the atom in common with each heterocycloalkyl ring of the spiro ring) comprising an oxygen atom. In one example the ring comprising the nitrogen of the —$NR^4R^5$ group is pyridyl, and the other ring of the spiro ring is oxetanyl.

In one example $R^4$ and $R^5$, taken together with the nitrogen to which they are bonded to, form a fused bicyclic ring wherein one ring is a heterocycloalkyl ring, and one ring is a heteroaryl ring, said heterocycloalkyl ring optionally comprising 1 to 3 additional heteroatoms independently selected from the group consisting of: O, S and N, and said bicyclic ring is optionally substituted with 1-3 substituents independently selected from the group consisting of: halogen, —O($C_1$-$C_6$alkyl) and —($C_1$-$C_6$ alkyl). The one or two of the optional heteroatoms in said heterocycloalkyl ring of said bicyclic ring can be common to the heterocycloalkyl ring and the heteroaryl ring. The heterocycloalkyl ring can be a 5 or 6 membered ring (including the atoms common to both rings), and the heteroaryl ring can be a 5 or 6 membered ring (including the atoms common to both rings). For example, the heterocycloalkyl-heteroaryl ring size can be 5-6, 5-5, 6-5, or 6-6 (wherein the first number represents the heterocycloalkyl ring size and the second number represents the heteroaryl ring size, and the numbers include the atoms common to both rings). The heteroaryl ring comprises 1-3 heteroatoms selected from the group consisting of: O, N and S. In one example, the heteroatoms are selected from the group consisting of: N and S. In one example the bicyclic ring is tetrahydrothiazolopyridine.

In one example $R^4$ and $R^5$, taken together with the nitrogen to which they are bonded to, form a fused bicyclic heterocycloalkyl ring, i.e., each ring of the fused bicyclic ring is a heterocycloalkyl ring. The ring sizes of the rings of the bicyclic ring are, in one example, 5-6, and in another example 5-5, and in another example 6-5, and in another example, 6-6, wherein the ring size numbers include the atoms common to both rings. The heterocycloalkyl bicyclic ring optionally comprises 1 to 3 additional heteroatoms independently selected from the group consisting of: O, S and N, and said ring optionally comprises a —O— bridge between two ring carbons (i.e., an epoxy bridge), and said heterocycloalkyl bicyclic ring is optionally substituted with 1-3 substituents independently selected from the group consisting of: halogen, —O($C_1$-$C_6$alkyl) and —($C_1$-$C_6$ alkyl)(e.g., methyl). One or both of the optional heteroatoms in said heterocycloalkyl bicyclic ring can be common to both rings of the heterocycloalkyl bicyclic ring. In one example the bicyclic ring is methyloctahydroepoxyisoindolyl, and in another example tetrahydrothiazolopyridinyl.

In another example, $R^4$ and $R^{11}$ taken together form a 5-8 membered heterocycloalkyl ring, said ring optionally comprising 1 or 2 additional heteroatoms independently selected from the group consisting of: O, S, N, and —(C═O)—, and said ring is optionally substituted with 1-3 substituents independently selected from $R^{14}$ group. In one example said heterocycloalkyl ring is an unsubstituted piperidinyl ring (see, for example A21 below). In another example said heterocycloalkyl ring is substituted with a —($C_1$-$C_6$alkyl, (e.g., methyl, ethyl or isopropyl) group, and in one example said alkyl group is bonded to a ring carbon, and in another example said alkyl group is bonded to a ring nitrogen. In another example said heterocycloalkyl ring is methyl substituted piperidinyl ring (see A22 and A23, for example), and in another example N-ethyl substituted piperidinyl (see A24, for example), and in another example N-isopropyl substituted piperidinyl (see A25, for example), and in another example N—C(O)CH$_3$ substituted piperidinyl (see A26, for example). In another example said heterocycloalkyl ring is oxepan-one (see A29, for example).

In one example of this invention, $R^4$ and $R^5$ are independently selected from the group consisting of: H, methyl, ethyl, propyl, isopropyl, —(CH$_2$)$_2$—O—CH$_3$, —C(O)CH$_3$, —S(O)$_2$CH$_2$CH$_3$, —S(O)$_2$-azetindinyl, —S(O)$_2$—CH$_2$-cyclopropyl, —S(O)$_2$—(CH$_2$)$_2$—O—CH$_3$, —S(O)$_2$-cyclobutyl, —S(O)$_2$-cyclopropyl, and —S(O)$_2$—CH$_3$. In another example, $R^4$ and $R^5$ are independently selected from the group consisting of: H, methyl, ethyl, isopropyl, —(CH$_2$)$_2$—O—CH$_3$, —C(O)CH$_3$, —S(O)$_2$CH$_2$CH$_3$, —S(O)$_2$-azetindinyl, —S(O)$_2$—CH$_2$-cyclopropyl, —S(O)$_2$—(CH$_2$)$_2$—O—CH$_3$, —S(O)$_2$-cyclobutyl, —S(O)$_2$-cyclopropyl, and —S(O)$_2$—CH$_3$. In another example, $R^4$ and $R^5$ are independently selected from the group consisting of: H, methyl, ethyl, isopropyl, and —(CH$_2$)$_2$—O—CH$_3$. In other examples $R^4$ is H and $R^5$ is any one of the groups defined in this paragaraph.

In one example, $R^4$ is H.

In one example $R^4$ is H and $R^5$ is H.

In one example, $R^4$ is H, and $R^5$ is —($C_1$-$C_6$alkyl). Examples of the $R^5$ —($C_1$-$C_6$alkyl) group include: —($C_1$-$C_4$alkyl), —($C_1$-$C_3$alkyl), and —($C_1$-$C_2$alkyl). In another example $R^5$ is —CH$_3$.

In one example, $R^4$ is H, and $R^5$ is —($C_1$-$C_6$alkyl)-O—($C_1$-$C_6$alkyl). Examples of this $R^5$ group include —($C_1$-$C_4$alkyl)-O—($C_1$-$C_4$alkyl), —($C_1$-$C_3$alkyl)-O—($C_1$-$C_3$alkyl), —($C_1$-$C_2$alkyl)-O—($C_1$-$C_2$alkyl), and —($C_1$-$C_2$alkyl)-O—CH$_3$.

In one example $R^4$ is H, and $R^5$ is selected from the group consisting of: H, methyl, ethyl, propyl, isopropyl, and —(CH$_2$)$_2$—O—CH$_3$. In another example, $R^4$ is H, and $R^5$ is selected from the group consisting of: H, methyl, ethyl, isopropyl, and —(CH$_2$)$_2$—O—CH$_3$.

In another example, $R^4$ is H and $R^5$ is methyl. In another example $R^4$ is H and $R^5$ is ethyl. In another example $R^4$ is H and $R^5$ is isopropyl. In another example $R^4$ is H and $R^5$ is —(CH$_2$)$_2$-O—CH$_3$.

In another example, $R^4$ and $R^5$ are independently selected from the group consisting of: —($C_1$-$C_6$alkyl) (e.g., —($C_1$-$C_4$alkyl), —($C_1$-$C_3$alkyl), —($C_1$-$C_2$alkyl) and —CH$_3$). In another example $R^4$ and $R^5$ are independently selected from the group consisting of —($C_1$-$C_4$alkyl). In another example $R^4$ and $R^5$ are the same —($C_1$-$C_6$alkyl), and in another example the same —($C_1$-$C_4$alkyl). In one example W and $R^5$ are independently selected from the group consisting of:

methyl, ethyl, and isopropyl. In one example R⁴ and R⁵ are each methyl. In another example R⁴ and R⁵ are independently selected from the group consisting of methyl and ethyl. In another example R⁴ and R⁵ are each ethyl. In another example R⁴ is methyl, and R⁵ is ethyl.

In another example of this invention, R⁴ is a —(C₁-C₆alkyl)-O—(C₁-C₆alkyl) group (e.g. —(C₁-C₄alkyl)-O—(C₁-C₄alkyl), —(C₁-C₃alkyl)-O—(C₁-C₃alkyl), —(C₁-C₂alkyl)-O—(C₁-C₂alkyl), and —(C₁-C₂alkyl)-O—CH₃) and R⁵ is a —(C₁-C₆alkyl) (e.g., —(C₁-C₄alkyl), —(C₁-C₃alkyl), —(C₁-C₂alkyl) and —CH₃). In one example R⁴ is —(CH₂)₂—O—CH₃, and R⁵ is selected from the group consisting of: methyl, ethyl, and isopropyl. In one example R⁴ is —(CH₂)₂—O—CH₃, and R⁵ is methyl.

In another example, R⁴ and R⁵ are taken together with the nitrogen to which they are bound to form a 4-6 membered heterocycloalkyl ring, wherein said ring optionally comprises 1 or 2 additional heteroatoms independently selected from the group consisting of: O, S and N, and wherein the remaining ring atoms are carbon, and said ring is optionally substituted with 1-3 substituents independently selected from the group consisting of: —O(C₁-C₆alkyl) (such as, for example, —O(C₁-C₄alkyl), —O(C₁-C₃alkyl), and —O(C₁-C₂alkyl)), and —(C₁-C₆ alkyl) (such as, for example, —(C₁-C₄alkyl), —(C₁-C₃alkyl), —(C₁-C₂alkyl) and —CH₃).

In one example the R¹⁴ —C(O)(C₁-C₆alkyl) optional substituent is —C(O)(C₁-C₄alkyl), and in another example —C(O)CH₃.

In one example, R¹ is a four membered heterocycloalkyl ring. In another example R¹ is a five membered heterocycloalkyl ring. In another example, R¹ is a six membered heterocycloalkyl ring. In one example R¹ is azetidinyl, in another example R¹ is pyrrolidinyl, in another example R¹ is piperazinyl, in another example R¹ is piperidinyl, and in another example R¹ is morpholinyl.

In another example, R¹ is a substituted four membered heterocycloalkyl ring. In another example R¹ is a substituted five membered heterocycloalkyl ring. In another example, R¹ is a substituted six membered heterocycloalkyl ring. In one example R¹ is a substituted azetidinyl ring, in another example a substituted pyrrolidinyl ring, in another example a substituted piperazinyl ring, in another example a substituted piperidinyl ring, and in another example a substituted morpholinyl ring. In another example the substituted rings are substituted with a —C₁-C₂alkyl or a —O(C₁-C₂alkyl) group. In another example the substituted rings are substituted with one methyl. In another example the substituted rings are substituted with a —OCH₃. In one example R¹ is a methyl substituted piperazinyl ring, in another example a methyl substituted morpholinyl ring, and in another example a methyl substituted azetidinyl ring.

In another example R¹ is selected from the group consisting of:

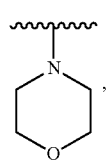
A1

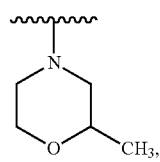
A2

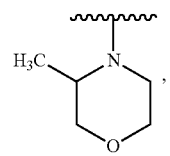
A3

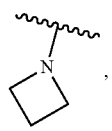
A4

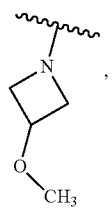
A5

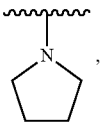
A6

A7

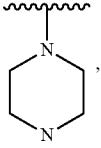
A8

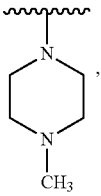
A9

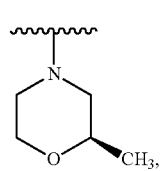
A10

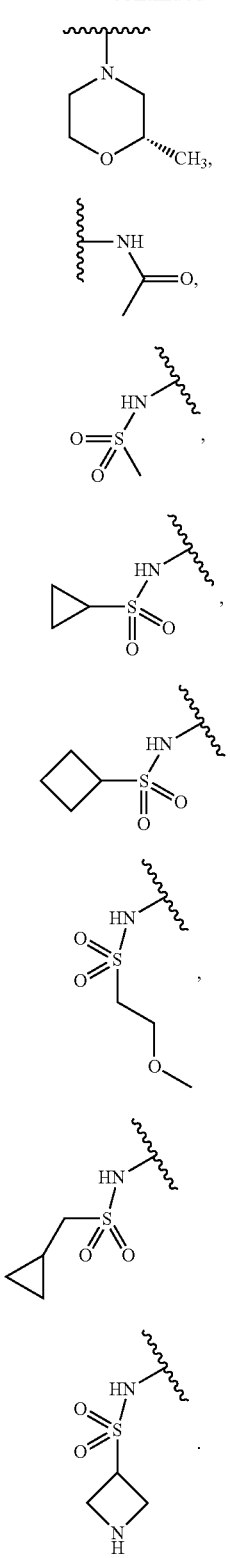

In another example R[1] is selected from the group consisting of: —NH₂, —NHCH₃, —NHCH₂CH₃, —NHCH(CH₃)₂, —NHC(O)CH₃, —NHC(O)NHCH₂CH₃, —NHC(O)cyclopropyl, —NHC(O)OCH₃, —NHC(O)OCH₂CHF, —NHC(O)CH(CH(CH₃)₂)NHC(O)OCH₃, —NH-teterahydrofuran, —NHC(D₂)CD₃ (wherein D represents deuterium), —NHC(O)CD₃, —NHCH₂cyclobutyl, —NH(CH₂cyclobutyl)₂, —NHCH₂cyclopropyl, —NH(CH₂cyclopropyl)₂, —NHC(O)CH(CH₃)₂, —NHCH₂phenyl, —NHCH(CH₃)CH₂C(CH₃)₂OH, —NHCH(CH₃)CH₂S(O)₂CH₃, —NHCH(CH₃)CH₂Cl, —NHC(O)CHCF₃, —NHC(O)cyclobutyl, —NHC(O)CH₂phenyl, —NHC(O)CH₂cyclohexyl, —NHC(O)cyclohexyl, —NHC(O)cyclopentyl, —NHC(O)CH₂N(CH₃)₂, —NHC(O)CH₂CH(CH₃)₂, —NHC(O)CH₂cyclopentyl, —NHC(O)C(CH₃)₃, —NHC(O)OC(CH₃)₃, —NHC(O)NHCH(CH₃)₂, —NHC(O)OCH₂CH(CH₃)₂, —NHC(O)OCH₃, —NHC(O)O(CH₂)₂OCH₃, —NHC(O)Ophenyl, —NHC(O)OCH(CH₃)₂, —NHC(O)OCH₂C(CH₃)₃, —NHC(O)OCH₂phenyl, —NHC(O)OCH₂CH₃, —NHC(O)cyclopropyl, —NHC(O)CH₂OCH₃, —NHtetrahydropyran, —NHcyclopropyl, —NHCH₂CF₃, —NHcyclobutyl, —NHCH₂C(O)N(CH₃)₂, —NH(CH₂)₂C(O)N(CH₃)₂, —N(CH₃)C(O)CH₃, —N(CH₂CH₃)C(O)CH₃, —NHC(CH₃)₃, —NHCH(CH₃)CHF₂, —NHC(CH₃)₂CH₂OCH₃, —NH(CH₂)₂OCH₃, —NHphenyl, —NHcyanopyridyl, —NHfluoropyridyl, —NHcyanophenyl, —NHcyclopentyl, —NHcyclohexyl,

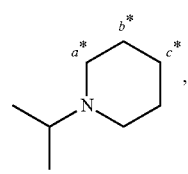 A25
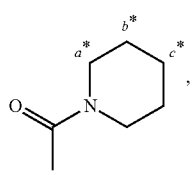 A26
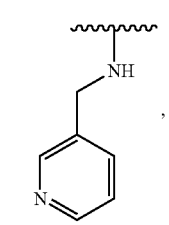 A27
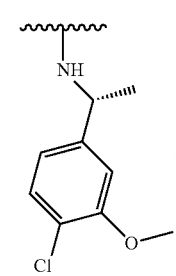 A28
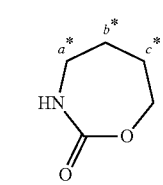 A29
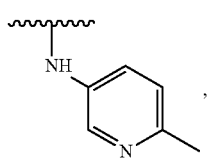 A30
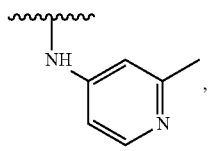 A31
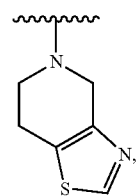 A32
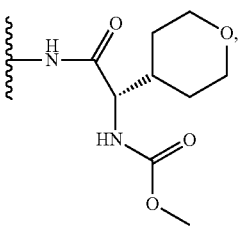 A33
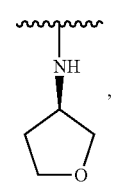 A34
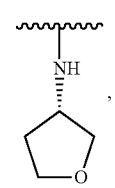 A35
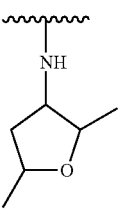 A36
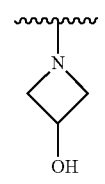 A37
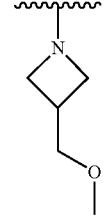 A38
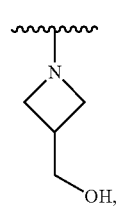 A39
A40

-continued
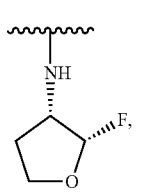 A41
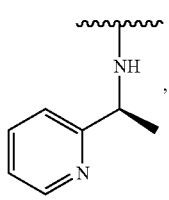 A42
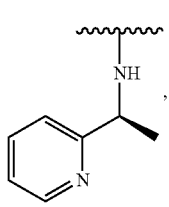 A43
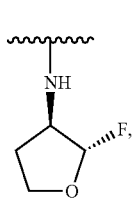 A44
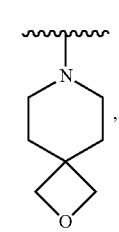 A45
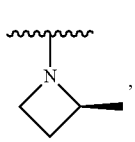 A46
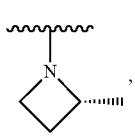 A47
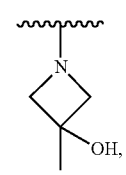 A48
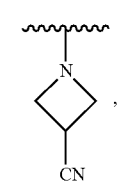 A49
-continued
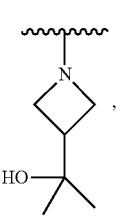 A50
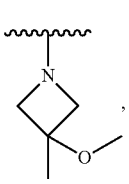 A51
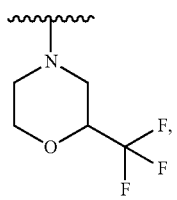 A52
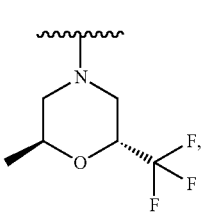 A53
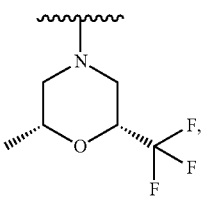 A54
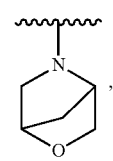 A55
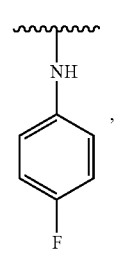 A56
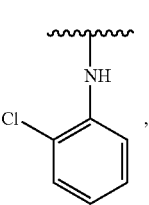 A57

-continued
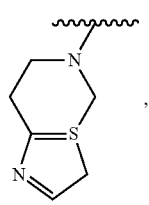 A58
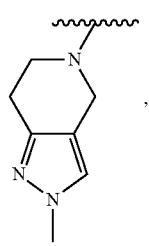 A59
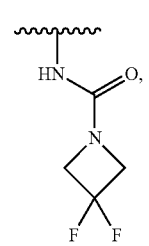 A60
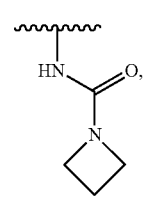 A61
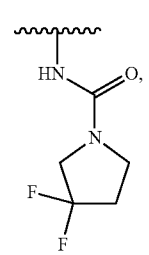 A62
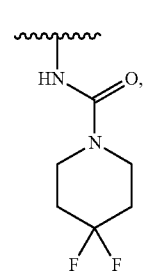 A63
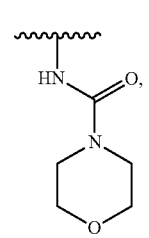 A64
-continued
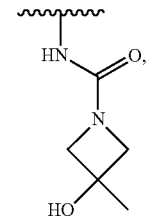 A65
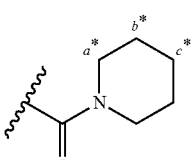 A66
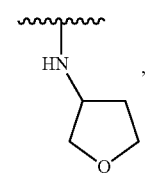 A67
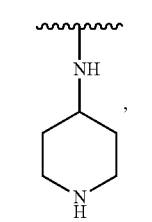 A68
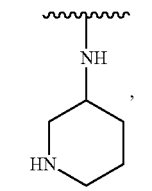 A69
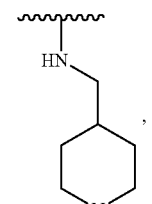 A70
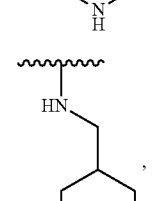 A71
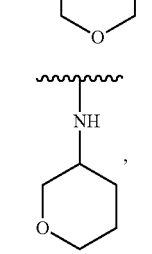 A72

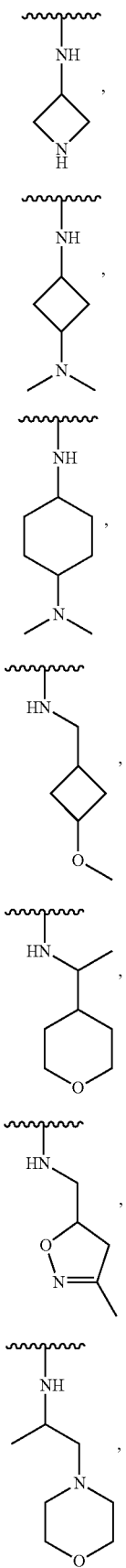
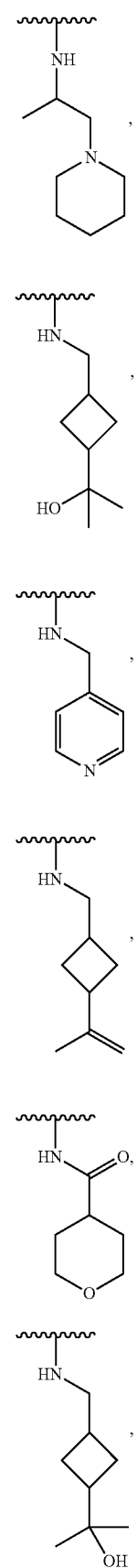

-continued
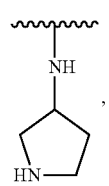 A86
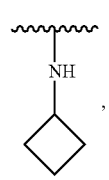 A87
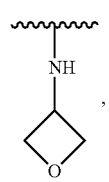 A88
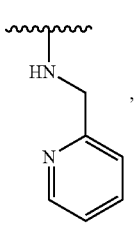 A89
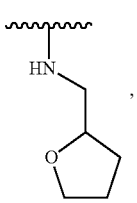 A90
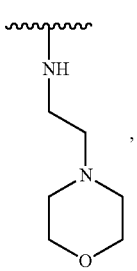 A91
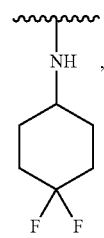 A92
-continued
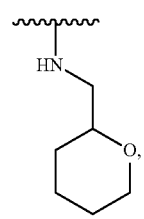 A93
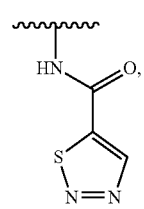 A94
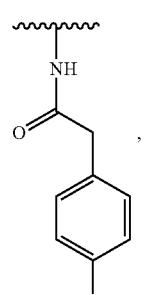 A95
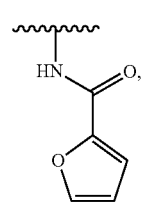 A96
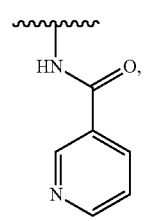 A97
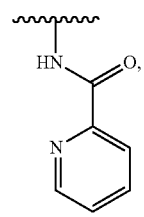 A98
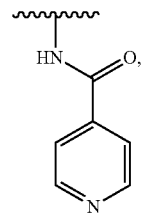 A99

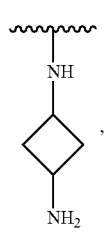 A100
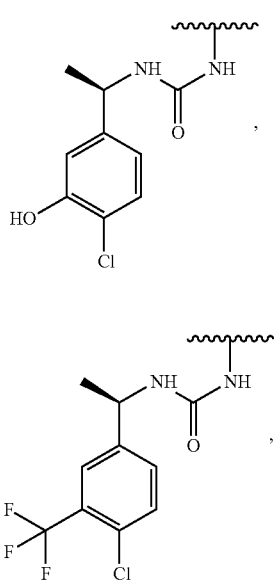 A101
A02
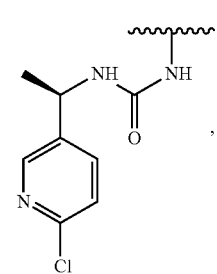 A103
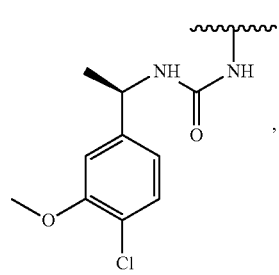 A104
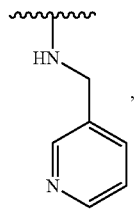 A105
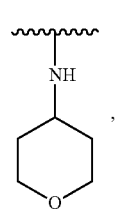 A106
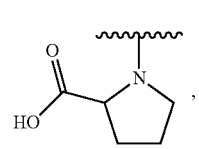 A107
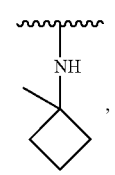 A108
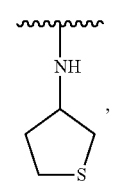 A109
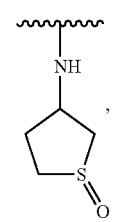 A110
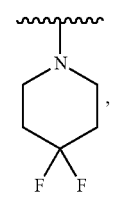 A111
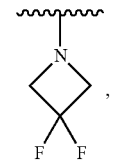 A112
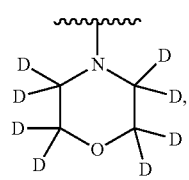 A113

A114 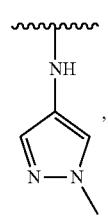
A115 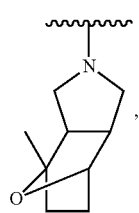
A116 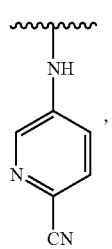
A117 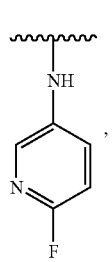
A118 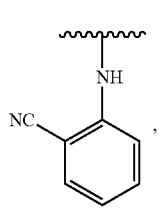
A119 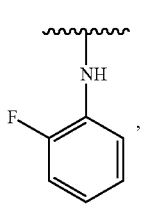
A120 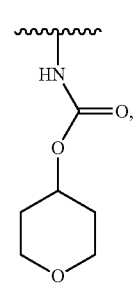
A121 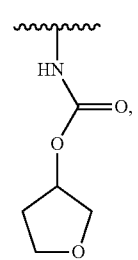
A122 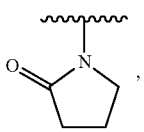
A123 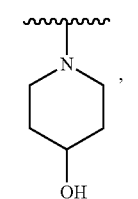
A124 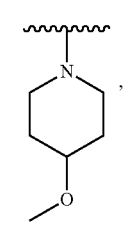
A125 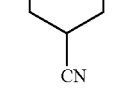
A126 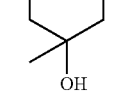
A127 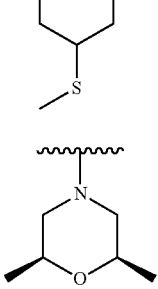
A128

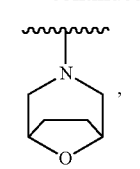
A129

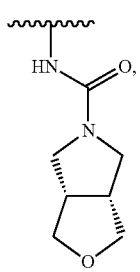
A130

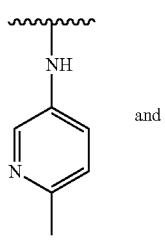
A131 and

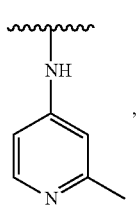
A132

, wherein A21-A25 and A29 represent heterocycloalkyl rings formed when $R^4$ is taken together with $R^{11}$, and wherein in said heterocycloalkyl rings a* represents the carbon atom in common with said heterocycloalkyl rings and the pyrazolyl ring in formula (1), b* represents the carbon atom in common with said heterocycloalkyl rings and with the pyrazolyl and pyridyl rings in formula (1), and c* represents the carbon atom in common with said heterocycloalkyl rings and with the pyridyl ring in formula (1). In other examples $R^1$ is any one of the groups in this paragraph as if each was individually listed as a separate example. Thus, in one example $R^1$ is —NH$_2$, and in another —NHCH$_3$, and in another-NHCH$_2$CH$_3$, and in another —NHCH(CH$_3$)$_2$, and in another —NHC(O)CH$_3$, and in another-NHC(O)NH$_2$CH$_3$, and the like through to A132.

In another example $R^1$ is A1. In another example $R^1$ is A2. In another example $R^1$ is A3. In another example $R^1$ is A4. In another example $R^1$ is A5. In another example $R^1$ is A6. In another example $R^1$ is A7. In another example $R^1$ is A8. In another example $R^1$ is A9. In another example $R^1$ is A10. In another example $R^1$ is A11. In another example $R^1$ is A12. In another example $R^1$ is A13. In another example $R^1$ is A14. In another example $R^1$ is A15. In another example $R^1$ is A16. In another example $R^1$ is A17. In another example $R^1$ is A18.

In one example $R^2$ is —(C$_1$-C$_4$alkyl)heteroaryl.

In one example, $R^2$ is selected from the group consisting of: H, —(C$_1$-C$_3$alkyl)(C$_6$-C$_{10}$aryl), —CH(C$_6$-C$_{10}$aryl)(C$_1$-C$_3$alkyl-O—(C$_1$-C$_3$alkyl), —(C$_1$-C$_3$alkyl)heteroaryl, -heterocycloalkyl(C$_6$-C$_{10}$aryl), and —(C$_1$-C$_6$alkyl)-O—(C$_1$-C$_6$alkyl) and wherein said aryl (e.g. phenyl and naphthyl, and usually phenyl), heteroaryl and heterocycloalkyl groups are optionally substituted with 1-3 substitutents independently selected from the group consisting of: —(C$_1$-C$_6$alkyl) (e.g., —(C$_1$-C$_4$alkyl), —(C$_1$-C$_3$alkyl), and —(C$_1$-C$_2$alkyl), and in one example methyl), halo (e.g., F, Br, and Cl, and in one example F); and wherein said heteroaryl group is a 5 to 6 membered aromatic ring comprising 1 to 3 heteroatoms independently selected from the group consisting of: N, O and S, and the remaining ring members are carbon; and wherein said heterocycloalkyl group is a 4-6 membered ring comprising 1-2 heteroatoms independently selected from the group consisting of: N, O and S, and wherein the remaining ring members are carbon.

For $R^2$ examples of the —(C$_1$-C$_4$alkyl)(C$_6$-C$_{10}$aryl) group include —(C$_1$-C$_2$alkyl) (C$_6$-C$_{10}$aryl), —(C$_1$-C$_3$alkyl)phenyl, —CH(CH$_3$)phenyl, —CH$_2$CH$_2$phenyl, and —CH$_2$phenyl. Examples of the —CH(C$_6$-C$_{10}$aryl)((C$_1$-C$_3$alkyl)-O—(C$_1$-C$_3$alkyl)) group include: —CH(phenyl)((C$_1$-C$_2$alkyl)-O—(C$_1$-C$_2$alkyl)), and —CH(phenyl)CH$_2$OCH$_3$. Examples of the —(C$_1$-C$_3$alkyl)-heteroaryl group include —(C$_1$-C$_2$alkyl) heteroaryl, —(C$_1$-C$_3$alkyl)pyridyl, —(C$_1$-C$_2$alkyl)pyridyl, and —CH(CH$_3$)pyridyl. Examples of the -heterocycloalkyl (C$_6$-C$_{10}$aryl) group include -heterocycloalkylphenyl, and -pyrrolidinylphenyl. Examples of the —(C$_1$-C$_6$alkyl)-O—(C$_1$-C$_6$alkyl) include —(C$_1$-C$_3$alkyl)-O—(C$_1$-C$_2$)alkyl, —(CH$_2$)$_2$—O—CH$_3$, and —CH(CH$_3$)CH$_2$OCH$_3$.

For $R^2$ examples of the substituted groups include groups wherein the phenyl moiety is substituted with halo (e.g., F), and the heterocycloalkyl (e.g., pyrrolidinyl) moiety is substituted with a —C$_1$-C$_2$alkyl (e.g., methyl).

In one example $R^2$ is selected from the group consisting of: H,

B1

B2

B3

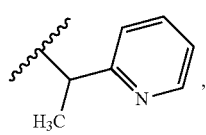 B4
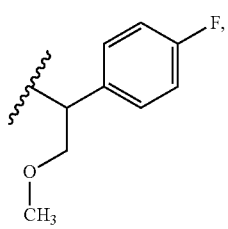 B5
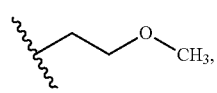 B6
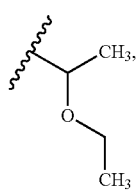 B7
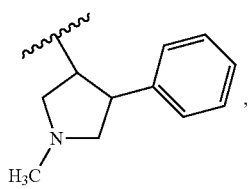 B8
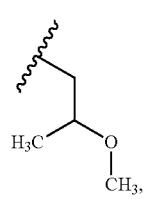 B9
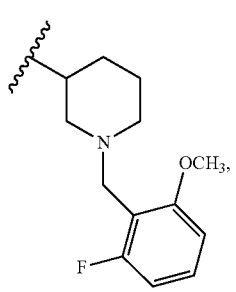 B10
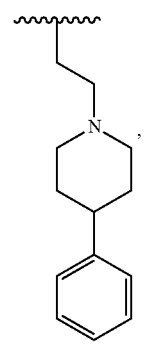 B11
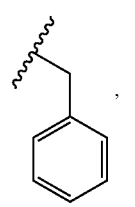 B12
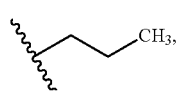 B13
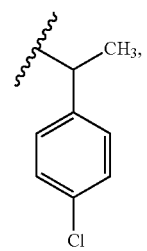 B14
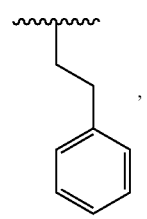 B15
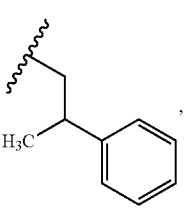 B16
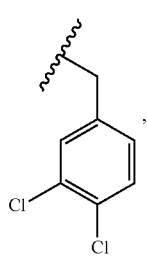 B17

-continued
B18 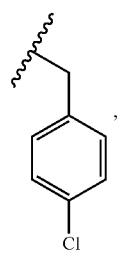
B19 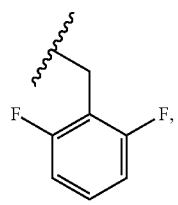
B20 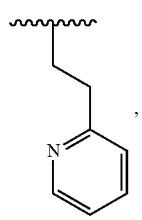
B21 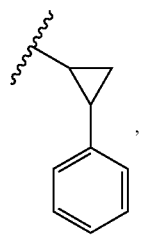
B22 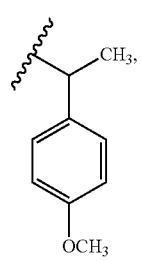
B23 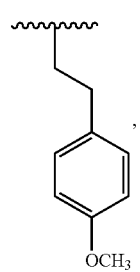
-continued
B24 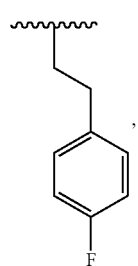
B25 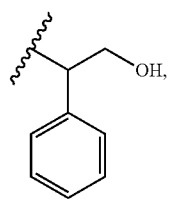
B26 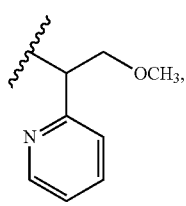
B27 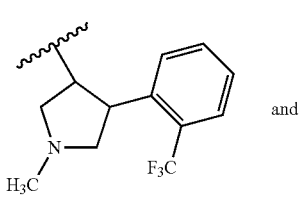
and
B28 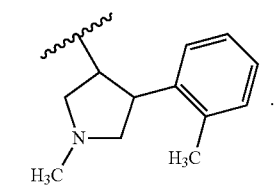
.
In another example $R^2$ is selected from the group consisting of: H,
B29 ,
B30

B31 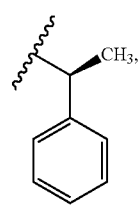
B32 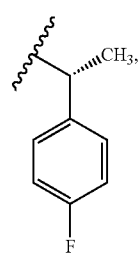
B33 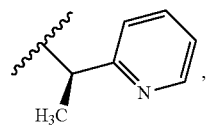
B34 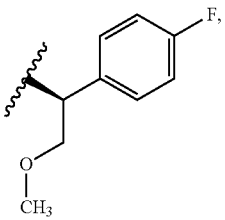
B35 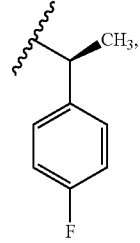
B36 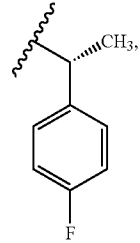
B37 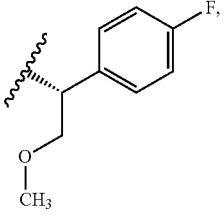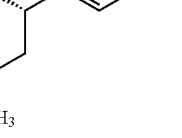
B38 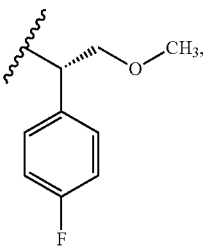
B39 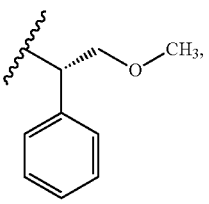
B40 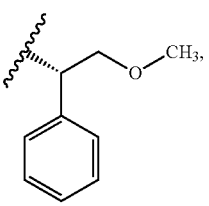
B41 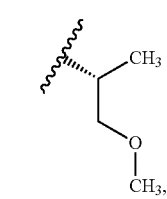
B42 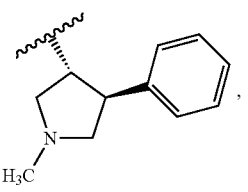
B43 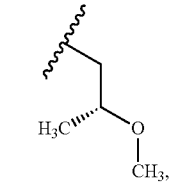
B44 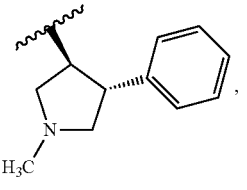

B45 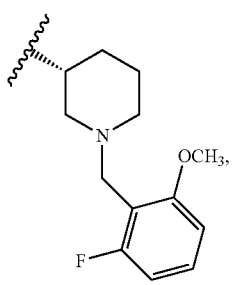
B46 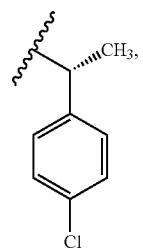
B47 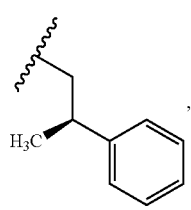
B48 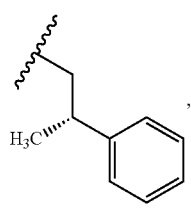
B49 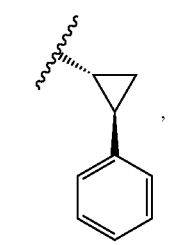
B50 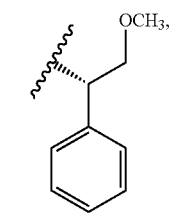
B51 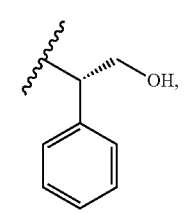
B52 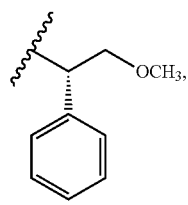
B53 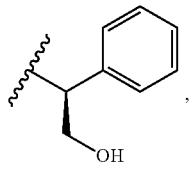
B54 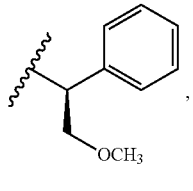
B55 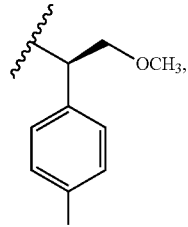
B56 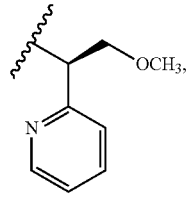
B57 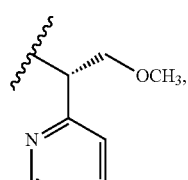
B58 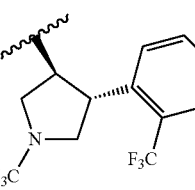
B59 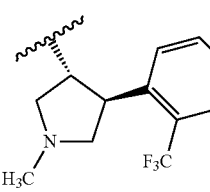

-continued

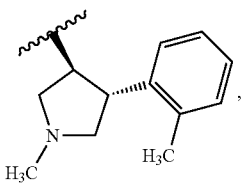
B60

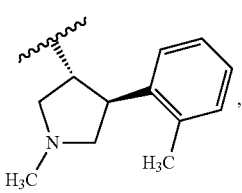
B61

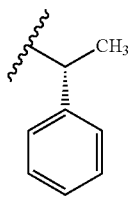
B62 and

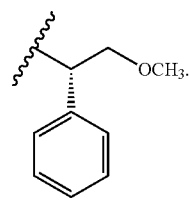
B63

In one example $R^2$ is selected from the group consisting of: H, B1, B2, B3, B4, B5, B6, B7, B8, B9, B29, B30, B31, B32, B33, B34, B35, B36, B37, B38, B39, B40, B41, B42, B43 and B44.

In one example $R^2$ is $(C_6\text{-}C_{10}\text{aryl})\text{-}(C_1\text{-}C_3\text{alkyl})$-heterocycloalkyl-. One example of this $R^2$ group is $(C_6\text{-}C_{10}\text{aryl})\text{-}(C_1\text{-}C_2\text{alkyl})$-heterocycloalkyl-, and another is phenyl-$(C_1\text{-}C_2\text{alkyl})$-heterocycloalkyl-, and another is phenyl-$CH_2$-heterocycloalkyl-. In another example $R^2$ is a substituted $(C_6\text{-}C_{10}\text{aryl})\text{-}(C_1\text{-}C_3\text{alkyl})$-heterocycloalkyl- and in another example substituted $(C_6\text{-}C_{10}\text{aryl})\text{-}(C_1\text{-}C_2\text{alkyl})$-heterocycloalkyl-, and in another example substituted phenyl-$(C_1\text{-}C_2\text{alkyl})$-heterocycloalkyl-, and in another example substituted phenyl-$CH_2$-heterocycloalkyl-. In another example the phenyl moiety is substituted with 1-3 substituents, and in another example 1-2 substituents, independently selected from the group consisting of: halo (e.g., F, Br, and Cl), and —O—$(C_1\text{-}C_6\text{alkyl})$ (and in one example —O—$(C_1\text{-}C_2)$ alkyl). In another example the phenyl moiety is substituted with 1-2 substituents independently selected from the group consisting of: F and —O—$(C_1\text{-}C_6\text{alkyl})$ (and in one example —O—$(C_1\text{-}C_2)$alkyl, and in another —$OCH_3$). In one example the heterocycloalkyl moiety is piperidinyl. One example of the $R^2$ substituted $(C_6\text{-}C_{10}\text{aryl})\text{-}(C_1\text{-}C_3\text{alkyl})$-heterocycloalkyl- group is (F, $OCH_3$-phenyl)-$CH_2$-piperidinyl-. In another example $R^2$ is:

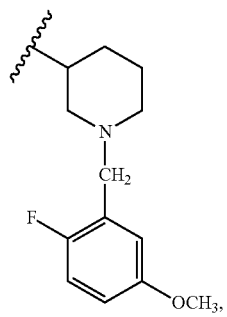
B64 and in another example

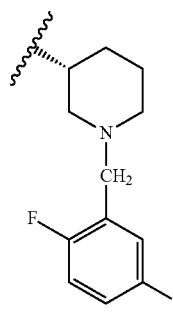
B65

The aryl and heterocycloalkyl moieties of the $R^2$ —$(C_1\text{-}C_6\text{alkyl})$-heterocycloalkyl-$(C_6\text{-}C_{10})$aryl are defined the same as for the $(C_6\text{-}C_{10}\text{aryl})\text{-}(C_1\text{-}C_3\text{alkyl})$-heterocycloalkyl- described above. One example of the —$(C_1\text{-}C_6\text{alkyl})$ moiety of the —$(C_1\text{-}C_6\text{alkyl})$-heterocycloalkyl-$(C_6\text{-}C_{10}\text{aryl})$ is —$(C_1\text{-}C_4\text{alkyl})$, and another is —$(C_1\text{-}C_2\text{alkyl})$. One example of the $R^2$ —$(C_1\text{-}C_6\text{alkyl})$-heterocycloalkyl-$(C_6\text{-}C_{10}\text{aryl})$ group is —$CH_2CH_2$-heterocycloalkyl-phenyl, and another example is —$CH_2CH_2$-piperidyl-phenyl. The $R^2$ —$(C_1\text{-}C_6\text{alkyl})$-heterocycloalkyl-$(C_6\text{-}C_{10}\text{aryl})$ group can be optionally substituted with 1-3 substituents independently selected from the group consisting of: halo (e.g., F, Br, and Cl), and —O—$(C_1\text{-}C_6\text{alkyl})$ (and in one example —O—$(C_1\text{-}C_2)$ alkyl). The $R^2$ $(C_6\text{-}C_{10}\text{aryl})$-heterocycloalkyl- group can be optionally substituted with 1-3 substituents independently selected from the group consisting of: halo (e.g., F, Br and Cl) and O—$(C_1\text{-}C_6\text{alkyl})$ (and in one example —O—$(C_1\text{-}C_2)$ alkyl). One example of the $R^2$ —$(C_1\text{-}C_6\text{alkyl})$-heterocycloalkyl-$(C_6\text{-}C_{10})$aryl is:

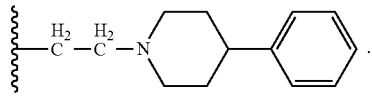
B66

One example of the —$(C_1\text{-}C_6\text{alkyl})$ $R^2$ group is —$(C_1\text{-}C_4\text{alkyl})$, and another is —$(C_1\text{-}C_3\text{alkyl})$, and another is —$(C_1\text{-}C_2\text{alkyl})$. One example of $R^2$ is methyl, another example is ethyl and another example is propyl.

In one example $R^2$ is —$(C_1\text{-}C_4\text{alkyl})(C_6\text{-}C_{10}\text{aryl})$. One example of this group is —$(C_1\text{-}C_2\text{alkyl})(C_6\text{-}C_{10}\text{aryl})$, another example is —$(C_1\text{-}C_2\text{alkyl})$phenyl. In one example the $R^2$ —$(C_1\text{-}C_3\text{alkyl})(C_6\text{-}C_{10}\text{aryl})$ group is —$CH(CH_3)$phenyl, in another example —CH-phenyl, and in another example —CH$_2$CH$_2$phenyl, and in another example —CH$_2$CH(CH$_3$)phenyl. In another example R$^2$ is:

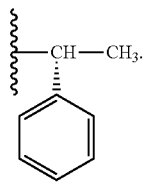
B67

In another example the R$^2$ —(C$_1$-C$_4$alkyl)(C$_6$-C$_{10}$aryl) group is substituted with 1-3 substituents independently selected from the group consisting of: halo (e.g., F, Br, and Cl), —O—(C$_1$-C$_6$alkyl) (and in one example —O—(C$_1$-C$_2$)alkyl), and —OH. In one example the R$^2$ group is —CH(CH$_3$)-methoxyphenyl, and in another example —(CH$_2$)$_2$-methoxyphenyl. Examples of —O—(C$_1$-C$_6$alkyl) substituted R$^2$ groups include, but are not limited to:

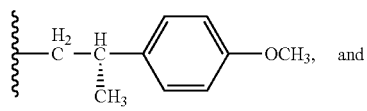
B68

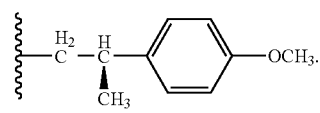
B69

For the R$^2$ —O(halo substituted (C$_1$-C$_6$alkyl)) optional substituent, examples of said halo include Cl, F and Br, and in one example said halo is F. Examples of the (C$_1$-C$_6$alkyl) moiety for said —O(halo substituted (C$_1$-C$_6$alkyl)) substituent include (C$_1$-C$_4$alkyl), and (C$_1$-C$_2$alkyl). In one example the —O(halo substituted (C$_1$-C$_6$alkyl)) substituent is —OCHF$_2$. In one example the —(C$_1$-C$_4$alkyl) moiety of the R$^2$ —(C$_1$-C$_4$alkyl)(C$_6$-C$_{10}$aryl) group is substituted with —O(halo substituted (C$_1$-C$_6$alkyl)), and in one example —OCHF$_2$.

For the R$^2$ —S(C$_1$-C$_6$alkyl) optional substituent, examples of the alkyl moiety include —(C$_1$-C$_4$alkyl), and —(C$_1$-C$_2$alkyl). In one example, said —S(C$_1$-C$_6$alkyl) optional substituent is —SCH$_3$.

In one example, the R$^2$ aryl optional substituent is phenyl.

In one example the R$^2$ heteroaryl optional substituent is a 5-6 membered ring comprising 1 to 3 heteroatoms (e.g., 1-2) independently selected from the group consisting of: O, N and S. In another example the R$^2$ heteroaryl optional substituent is a 5 membered ring comprising 1-2 heteroatoms independently selected from the group consisting of: O, N and S, and in another example independently selected from the group consisting of O and N. In another example the R$^2$ heteroaryl optional substituent is oxazolyl.

In one example the R$^2$ —(C$_1$-C$_4$alkyl)(C$_6$-C$_{10}$aryl) group is substituted with 1-3 substituents independently selected from the group consisting of: —OH, halo (e.g., F, Br, and Cl), —O—(C$_1$-C$_6$alkyl) (and in one example —O—(C$_1$-C$_2$)alkyl), —O(halo substituted(C$_1$-C$_6$alkyl)), and —S(C$_1$-C$_6$alkyl), wherein for example, the —O(halo substituted(C$_1$-C$_6$alkyl)), and —S(C$_1$-C$_6$alkyl) substituents are as above defined. In one example the R$^2$ group is —CH(CH$_3$)chloromethoxyphenyl, and in another example —CH(phenyl)CH$_2$OCHF$_2$, and in another example —CH(phenyl)CH$_2$SCH$_3$, and in another example —CH(phenyl)CH$_2$OH, and in another example —CH(fluorophenyl)C(CH$_3$)$_2$OCH$_3$, and in another example —CH(phenyl)C(CH$_3$)$_2$OCH$_3$.

In one example the R$^2$ —(C$_1$-C$_4$alkyl)-(C$_6$-C$_{10}$aryl) group is substituted on the (C$_1$-C$_4$alkyl) moiety with a —O—(C$_1$-C$_6$alkyl). An example of this R$^2$ group is —CH(C$_6$-C$_{10}$aryl)(C$_1$-C$_3$alkyl)-O—(C$_1$-C$_6$alkyl). Another example is —CH(C$_6$-C$_{10}$aryl)(C$_1$-C$_3$alkyl)-O—(C$_1$-C$_3$alkyl). Another example is —CH(C$_6$-C$_{10}$aryl)(C$_1$-C$_3$alkyl)-O—(C$_1$-C$_2$alkyl). Another example is —CH(phenyl)(C$_1$-C$_3$alkyl)-O—(C$_1$-C$_6$alkyl), another example is —CH(phenyl)(C$_1$-C$_3$alkyl)-O—(C$_1$-C$_4$alkyl), and another example is —CH(phenyl)(C$_1$-C$_3$alkyl)-O—(C$_1$-C$_2$alkyl). In one example R$^2$ is —CH(CH$_2$OCH$_3$)-phenyl, and in another example —CH(CH$_2$OH)-phenyl. In another example the (R$^2$ —CH(C$_6$-C$_{10}$aryl)(C$_1$-C$_3$alkyl)-O—(C$_1$-C$_6$alkyl) group is substituted with 1-3 substituents independently selected from the group consisting of: halo (e.g., F, Br, and Cl), —O—(C$_1$-C$_6$alkyl) (and in one example —O—(C$_1$-C$_2$)alkyl), and —OH. In another example the R$^2$ group is substituted —CH(phenyl)(C$_1$-C$_3$alkyl)-O—(C$_1$-C$_4$alkyl), and in another example substituted —CH(phenyl)(C$_1$-C$_3$alkyl)-O—(C$_1$-C$_2$alkyl), wherein in each example the R$^2$ group is substituted with 1-3 substituents independently selected from the group consisting of: halo (e.g., F, Br, and Cl), —O—(C$_1$-C$_6$alkyl) (and in one example —O—(C$_1$-C$_2$)alkyl), and —OH. In one example the R$^2$ group is —CH(fluorophenyl)CH$_2$OCH$_3$. Examples of the R$^2$ groups include, but are not limited to:

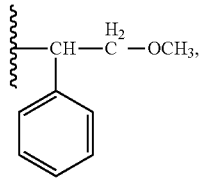
B70

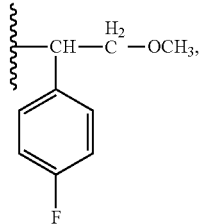
B71

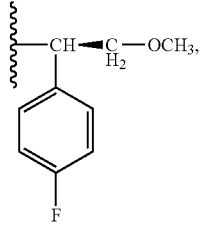
B72

-continued

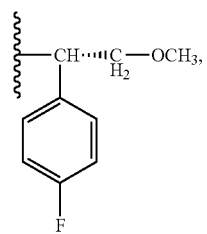
B73

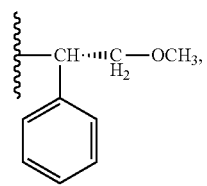
B74

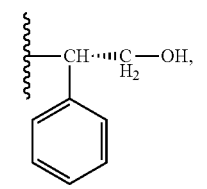
B75

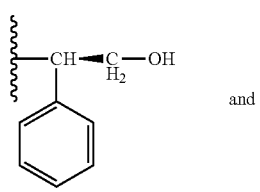
B76 and

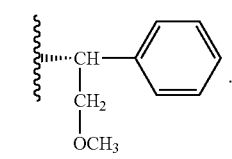
B77

In one example, the $R^2$ —($C_1$-$C_4$alkyl)($C_6$-$C_{10}$aryl) (and in another —($C_1$-$C_2$alkyl)($C_6$-$C_{10}$)aryl), and in another —($C_1$-$C_2$alkyl)phenyl, and in another —CH($CH_3$)phenyl, and in another —CH-phenyl, and in another —$CH_2CH_2$phenyl, and in another —$CH_2CH(CH_3$)phenyl) is substituted with 1-3 independently selected halo atoms, and in another example, 1-2 independently selected halo atoms, and in another example one halo atom. In one example the $R^2$ —($C_1$-$C_3$alkyl)($C_6$-$C_{10}$aryl) group is —CH($CH_3$)fluorophenyl, and in another example —CH($CH_3$)-chlorophenyl, and in another example —$CH_2$-chlorophenyl, and in another example —$CH_2$-dichlorophenyl, and in another example —$CH_2$-difluorophenyl, and in another example —$CH_2$fluorophenyl. Examples of the halo substituted $R^2$ —($C_1$-$C_4$alkyl)($C_6$-$C_{10}$aryl) groups include, but are not limited to:

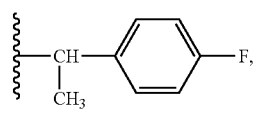
B78

-continued

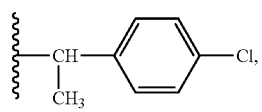
B79

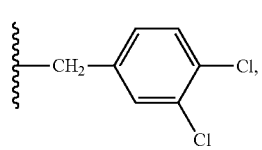
B80

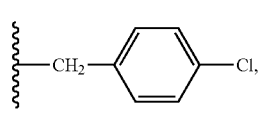
B81

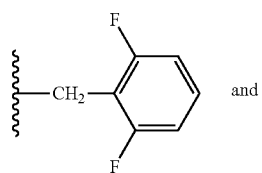
B82 and

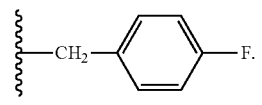
B83

In one example $R^2$ is —($C_1$-$C_3$alkyl)heteroaryl. One example of the —($C_1$-$C_3$alkyl)heteroaryl $R^2$ group is —($C_1$-$C_2$alkyl)heteroaryl, and another is —($C_1$-$C_3$alkyl)pyridyl, and another is —($C_1$-$C_2$alkyl)pyridyl. In one example $R^2$ is —$CH_2CH_2$-pyridyl, and in another example $R^2$ is

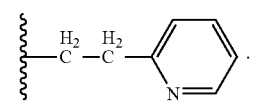
B84

In one example the $R^2$ —($C_1$-$C_3$alkyl)heteroaryl group is substituted on the ($C_1$-$C_4$alkyl) moiety with a —O—($C_1$-$C_6$alkyl). Thus, in one example $R^2$ is —CH(heteroaryl)-($C_1$-$C_6$alkyl)-O—($C_1$-$C_6$alkyl). Examples of this $R^2$ group include, but are not limited to: —CH(heteroaryl)-($C_1$-$C_4$alkyl)-O—($C_1$-$C_4$alkyl), —CH(heteroaryl)-($C_1$-$C_2$ alkyl)-O—($C_1$-$C_2$ alkyl), and —CH(pyridyl)-($C_1$-$C_2$alkyl)-O—($C_1$-$C_2$alkyl). In one example the $R^2$ group is —CH(pyridyl)-$CH_2$—$OCH_3$. In another example the $R^2$ group is

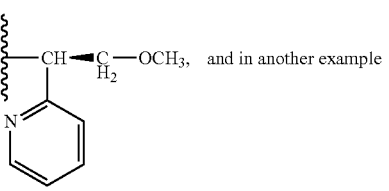
B85 and in another example

-continued

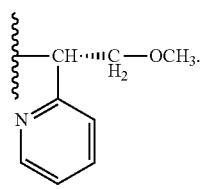

B86

In one example the $R^2$ —($C_1$-$C_3$alkyl)heteroaryl is —$CH_2$thiadiazolyl, and in another example —$CH_2$pyridyl, and in another example —$CH(CH_2CH_3)$pyridyl.

In one example the $R^2$ —($C_1$-$C_3$alkyl)heteroaryl group is substituted, and in one example said substituted $R^2$ —($C_1$-$C_3$alkyl)heteroaryl group is —($C_1$-$C_3$alkyl)(substituted heteroaryl). In another example the substituent on said substituted heteroaryl moiety is —O($C_1$-$C_6$alkyl), and in another example —O($C_1$-$C_4$alkyl), and in another example —$OCH_2CH_3$. In another example said substituent is —$N(R^{20})_2$, and in another example —$NHR^{20}$ and in another example —$N(CH_3)_2$. In another example said substituent is halo, and in another example Cl, and in another example F. In another example said substituent is —($C_1$-$C_6$alkyl), and in another example —($C_1$-$C_3$alkyl), and in another example methyl. In one example said substituted heteroaryl moiety is substituted pyridyl. In one example said $R^2$ group is —$CH_2$ethoxypyridyl, and in another example —$CH_2$dimethylaminopyridyl, and in another example —$CH_2$chloropyridyl, and in another example —$CH_2$fluoropyridyl, and in another example —$CH(CH_3)$methylpyridyl, and in another example —$CH(CH_3)$fluoropyridyl.

In one example $R^2$ is —($C_3$-$C_6$cycloalkyl)-($C_6$-$C_{10}$aryl). One example of this $R^2$ group is —($C_3$-$C_6$cycloalkyl)-phenyl, another is ($C_3$-$C_4$cycloalkyl)-phenyl, and another is -cyclopropyl-phenyl. Another example is -cyclopentylphenyl.

In one example $R^2$ is -heterocycloalkyl-($C_6$-$C_{10}$aryl). One example of this $R^2$ group is -heterocycloalkyl-phenyl, and another is a -pyrrolidinyl-phenyl. In another example $R^2$ is -heteroacycloalkyl-($C_6$-$C_{10}$aryl) substituted with 1-3 substitutents independently selected from the group consisting of: —$CF_3$, and —($C_1$-$C_6$alkyl) (and in one example —($C_1$-$C_4$alkyl), and in another example —($C_1$-$C_2$alkyl), and in another example methyl). In one example $R^2$ is:

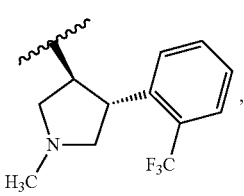

B87 and in another example

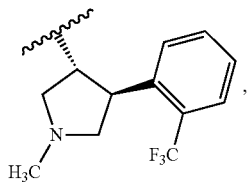

B88 and in another example

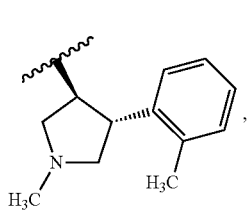

B89 and in another example

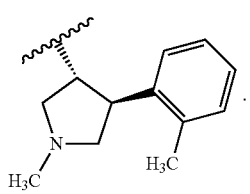

B90

In one example $R^2$ is a -fused (heterocycloalkyl)($C_6$-$C_{10}$) aryl group. In another example said $R^2$ group is a -fused (heterocycloalkyl)($C_6$-$C_{10}$)aryl wherein said heterocycloalkyl moiety is a seven membered ring (including the two atoms in common with said aryl. In another example said $R^2$ group is a -fused(heterocycloalkyl)($C_6$-$C_{10}$aryl) wherein said heterocycloalkyl moiety is a 6 membered ring (including the two atoms in common with said aryl). In another example said $R^2$ group is a -fused (heterocycloalkyl)(phenyl) group. In another example said $R^2$ group is a -fused (heterocycloalkyl) (phenyl) group wherein said heterocycloalkyl moiety is a seven membered ring (including the two atoms in common with said phenyl ring. In another example said $R^2$ group is a -fused (heterocycloalkyl)(phenyl) group wherein said heterocycloalkyl moiety is a six membered ring (including the two atoms in common with said phenyl ring. In another example said $R^2$ is a tetrahydrobenzoxepine, and in another example tetrahydroquinolinyl, and in another example dihydrochromenyl, and in another example tetrahydroquinolinyl, and in another example dihydrochromenyl, and in another example dihydrobenzofuranyl. In another example said -fused (heterocycloalkyl)($C_6$-$C_{10}$)aryl group is substituted, and in one example substituted with —OH. In one example said -fused (heterocycloalkyl)($C_6$-$C_{10}$)aryl group is hydroxytetrahydrobenzoxepine.

In one example $R^2$ is —($C_1$-$C_6$alkyl)-($C_3$-$C_6$cycloalkyl), and in another example —($C_1$-$C_2$alkyl)-($C_3$-$C_6$cycloalkyl), and in another example —($C_1$-$C_2$alkyl)-(cyclohexyl), and in another example —$CH(CH_3)$cyclohexyl.

In one example R² is —CH(C₆-C₁₀aryl)(C₃-C₆cycloalkyl), and in another example —CH(phenyl)(C₃-C₆cycloalkyl), and in another example —CH(phenyl)(C₅-C₆cycloalkyl), and in another example —CH(phenyl)(cyclopentyl).

In another example said R² —CH(C₆-C₁₀aryl)(C₃-C₆cycloalkyl) is substituted. In one example said substituted —CH(C₆-C₁₀aryl)(C₃-C₆cycloalkyl) is —CH(phenyl)(hydroxy substituted C₃-C₆cycloalkyl), and in another example said substituted R² group is —CH(phenyl)(hydroxycyclopentyl).

In one example R² is —CH(C₆-C₁₀aryl)(C₃-C₆cycloalkyl) substituted with 1-3 substituents independently selected from the group consisting of: —OH and halo (e.g., F. Br and Cl, and in one example F). In one example said substituted —CH(C₆-C₁₀aryl)(C₃-C₆cycloalkyl) is a substituted —CH(phenyl)(C₃-C₅cycloalkyl), and in another example a substituted —CH(phenyl)(cyclobutyl), and in another example a —CH(phenyl)(cyclopentyl). In one example said substituted —CH(C₆-C₁₀aryl)(C₃-C₆cycloalkyl) is —CH(phenyl)(hydroxy substituted C₃-C₆cycloalkyl), and in another example said substituted R² group is —CH(phenyl)(hydroxycyclopentyl), and in another example —CH(phenyl)(hydroxycyclobutyl).

In another example said substituted —CH(C₆-C₁₀aryl)(C₃-C₆cycloalkyl) is substituted with —OH and halo (e.g., F), and in one example said substituted —CH(C₆-C₁₀aryl)(C₃-C₆cycloalkyl) is —CH(hydroxycyclobutyl)(fluorophenyl).

In one example R² is —CH(C₆-C₁₀aryl)(heterocycloalkyl), and in another example —CH(phenyl)(heterocycloalkyl), and in another example —CH(phenyl)(heterocycloalkyl) wherein said heterocycloalkyl is a 5-6 membered ring comprising 1-3 heteroatoms selected from the group consisting of: O, S, and N. In one example said heterocycloalkyl ring is a 5 membered ring. In another example said heterocycloalkyl ring is a 5 membered ring comprising one oxygen atom. In another example said R² group is —CH(phenyl)tetrahydrofuranyl.

In one example R² is —CH(C₆-C₁₀aryl)((C₁-C₆alkyl)N(R²⁰)₂, wherein each R²⁰ is independently selected from the group consisting of H and (C₁-C₆alkyl). In another example said R² group is —CH(phenyl)((C₁-C₆alkyl)N(R²⁰)₂), and in another example —CH(phenyl)((C₁-C₂alkyl)N(R²⁰)₂), and in another example —CH(phenyl)CHN(R²⁰)₂, wherein each R²⁰ is independently selected. In one example each R²⁰ is alkyl, and in another example each R²⁰ is the same alkyl, and in another example each R²⁰ is methyl.

In one example R² is a —(C₃-C₆cycloalkyl-O—(C₁-C₆alkyl)). In another example R² is a —(C₅-C₆cycloalkyl-O—(C₁-C₂alkyl)), and in another example methoxycyclopentyl.

In one example R² is a —CH(C₆-C₁₀aryl)C(O)N(R²¹)₂ wherein each R²¹ is independently selected. Each R²¹ is an independently selected —(C₁-C₆alkyl), and in one example each R²¹ is an independently selected —(C₁-C₂alkyl), and in another example each R²¹ is independently selected from the group consisting of: methyl and ethyl, and in another example both R²¹ groups are the same. In one example R² is —CH(phenyl)(C(O)N(R²¹)₂ wherein R²¹ is as defined in this paragraph. In another example R² is a —CH(C₆-C₁₀aryl)C(O)N(R²¹)₂ substituted with a halo (e.g., F), wherein the C₆-C₁₀aryl moiety, and R²¹ is as defined in this paragraph. In one example R² is —CH(fluorophenyl)C(O)N(CH₃)₂, and in another example —CH(fluorophenyl)C(O)N(CH₂CH₃)₂.

Examples R² include, for example:

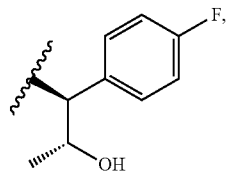
B100

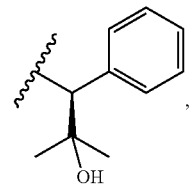
B101

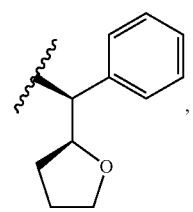
B102

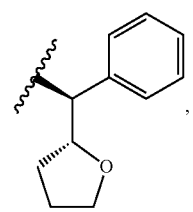
B103

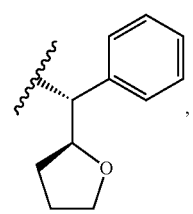
B104

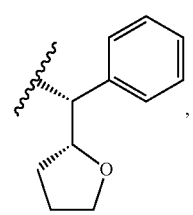
B105

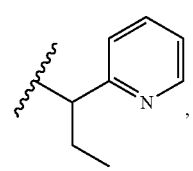
B106

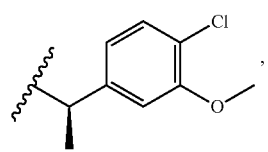
B107

B108 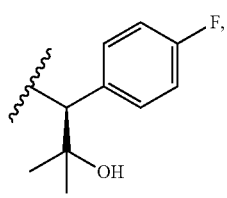
B109 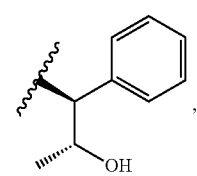
B110 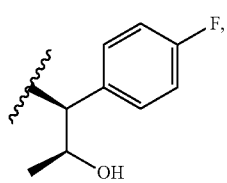
B111 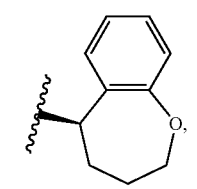
B112 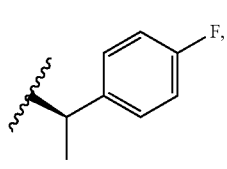
B113 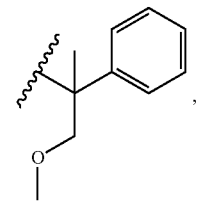
B114 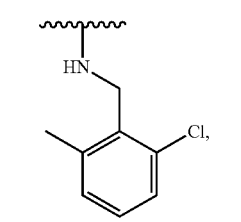
B115 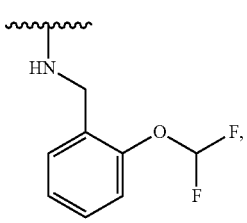
B116 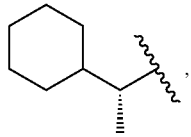
B117 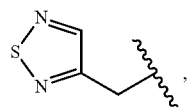
B118 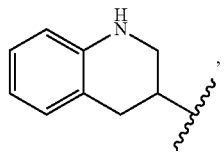
B119 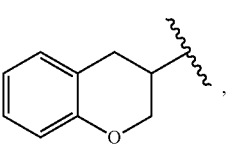
B120 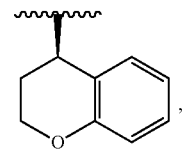
B121 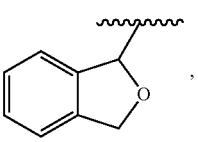
B122 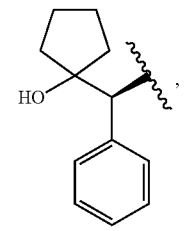
B123 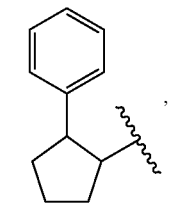
B124 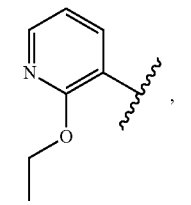

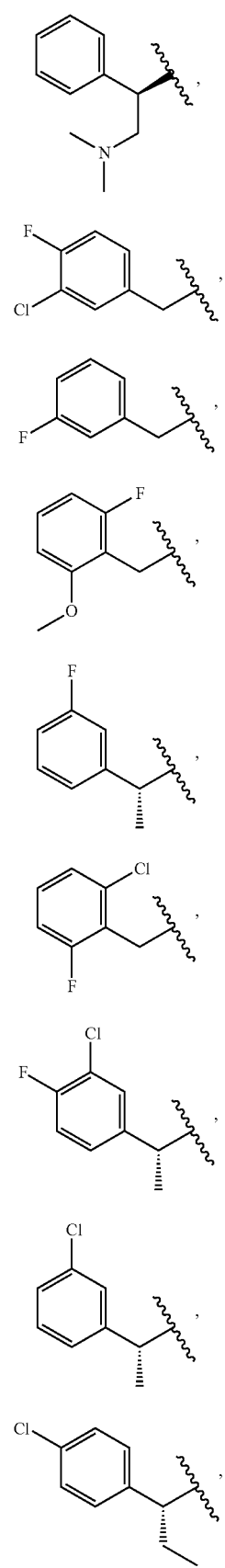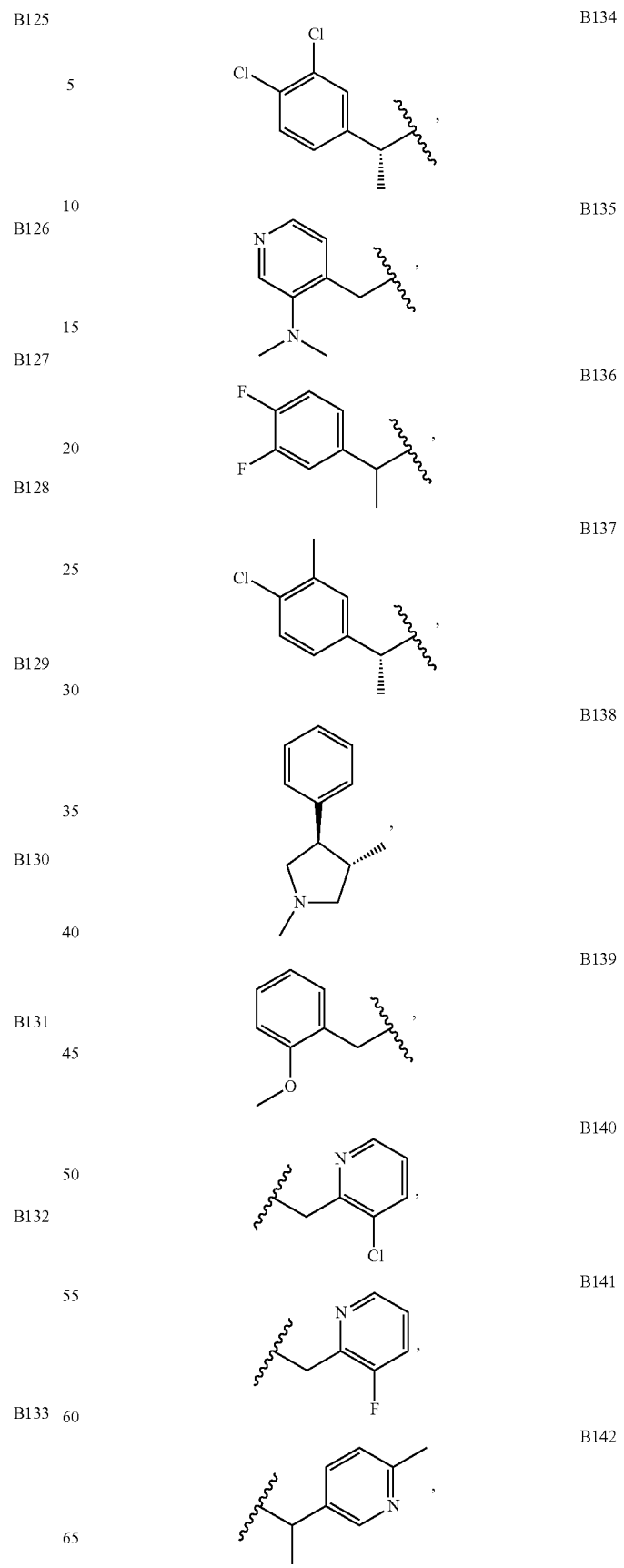

| | |
|---|---|
| 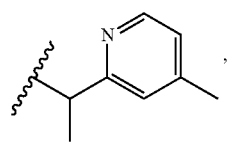 | B143 |
| 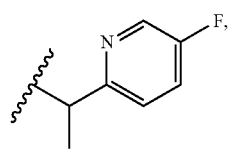 | B144 |
| 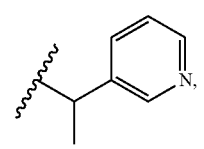 | B145 |
| 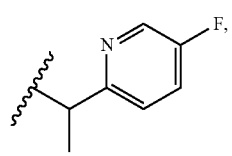 | B146 |
| 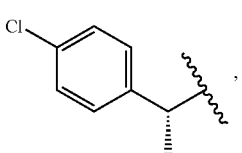 | B147 |
| 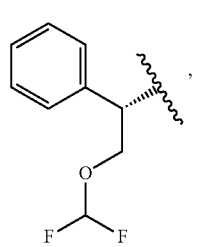 | B148 |
| 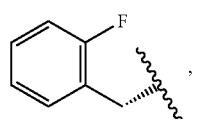 | B149 |
| 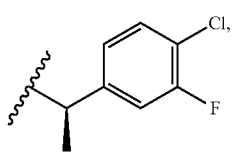 | B150 |
| 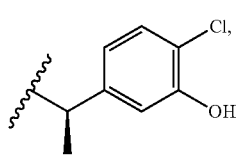 | B151 |
| 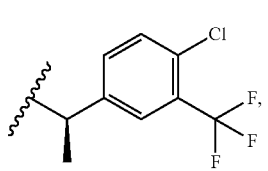 | B152 |
| | |
|---|---|
| 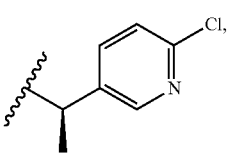 | B153 |
| 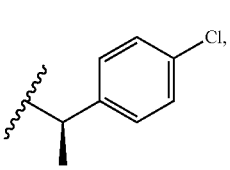 | B154 |
| 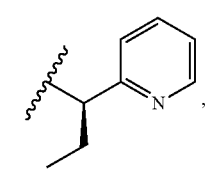 | B155 |
| 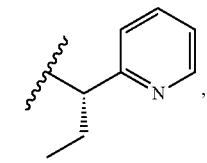 | B156 |
| 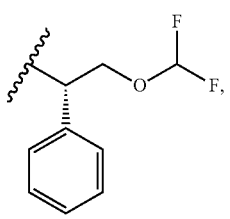 | B157 |
| 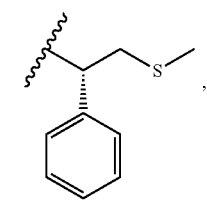 | B158 |
| 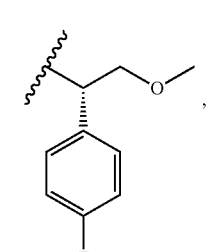 | B159 |
| 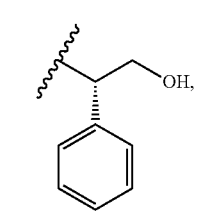 | B160 |

| | |
|---|---|
| B161 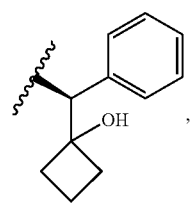 | B168 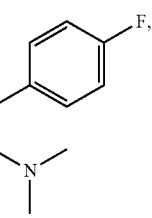 |
| B162 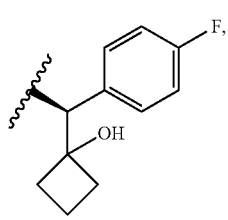 | B169 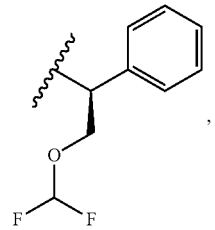 |
| B163 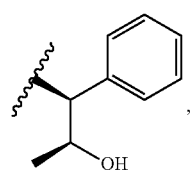 | B170 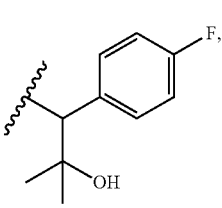 |
| B164 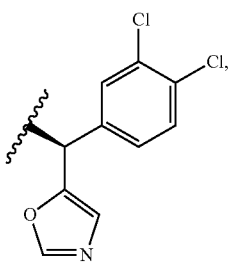 | B171 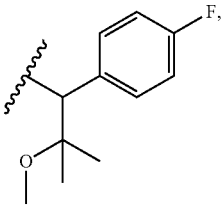 |
| B165 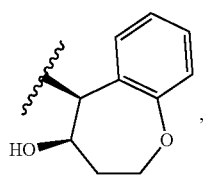 | B172 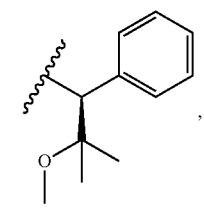 |
| B166 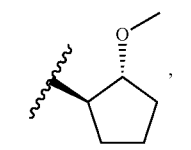 | B173 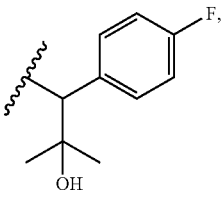 |
| B167 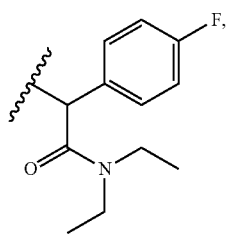 | B174 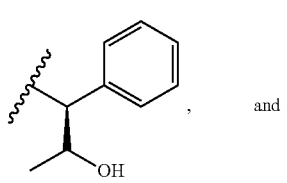, and |

B175

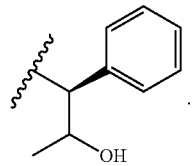

Examples of substituted R² groups include groups comprising a phenyl substituted with 1 to 3 substitutents independently selected from the group consisting of: halo (e.g., F and Cl), —CF₃, and —(C₁-C₃alkyl) (and in one example methyl). Examples of substituted R² groups include groups comprising a heterocycloalkyl (e.g., pyrrolidinyl) substituted with a —(C₁-C₂alkyl) (and in one example methyl).

Examples of substituted R² groups include groups comprising a phenyl substituted with 1-3 substituents selected from the group consisting of: Cl, F and —OCH₃. For example wherein R² is a —CH₂phenyl, or a —CH(CH₃)phenyl, or a —CH(CH₂CH₃)phenyl, wherein the phenyl moiety is substituted with 1-3 substituents selected from the group consisting of: Cl, F and —OCH₃.

In one example R² is —(C₁-C₆alkyl)-O—(C₁-C₆alkyl). One example of this R² group is —(C₁-C₃alkyl)-O—(C₁-C₃alkyl). In one example R² is —(CH₂)₂—O—CH₃, and in another —CH(CH₃)CH₂—O—CH₃.

In one example R² is selected from the group consisting of: (F, OCH₃-phenyl)-CH₂-piperidinyl-, —CH₂CH₂-piperidylphenyl, methyl, ethyl, propyl, —CH(CH₃)phenyl, —CH—phenyl, —CH₂CH₂phenyl, —CH₂CH(CH₃)phenyl, —CH(CH₃)-methoxyphenyl, —(CH₂)₂-methoxyphenyl, —CH(CH₂OCH₃)-phenyl, —CH(CH₂OH)-phenyl, —CH(fluorophenyl)CH₂OCH₃, —CH(CH₃)phenyl, —CH(CH₃)fluorophenyl, —CH(CH₃)-chlorophenyl, —CH₂-chlorophenyl, —CH₂-dichlorophenyl, —CH₂-difluorophenyl, —CH₂fluorophenyl, —CH₂CH₂-pyridyl, —CH(pyridyl)-CH₂—OCH₃, -cyclopropyl-phenyl, -pyrrolidinyl-phenyl, B64-B89, and B90.

In one example R² is B1. In another example R² is B2. In another example R² is B3. In another example R² is B4. In another example R² is B5. In another example R² is B6. In another example R² is B7. In another example R² is B8. In another example R² is B9. In another example R² is B10. In another example R² is B11. In another example R² is B12. In another example R² is B13. In another example R² is B14. In another example R² is B15. In another example R² is B16. In another example R² is B17. In another example R² is B18. In another example R² is B19. In another example R² is B20. In another example R² is B21. In another example R² is B22. In another example R² is B23. In another example R² is B24. In another example R² is B25. In another example R² is B26. In another example R² is B27. In another example R² is B28. In another example R² is B29. In another example R² is B30. In another example R² is B31. In another example R² is B32. In another example R² is B33. In another example R² is B34. In another example R² is B35. In another example R² is B36. In another example R² is B37. In another example R² is B38. In another example R² is B39. In another example R² is B40. In another example R² is B41. In another example R² is B42. In another example R² is B43. In another example R² is B44. In another example R² is B45. In another example R² is B46. In another example R² is B47. In another example R² is B48. In another example R² is B49. In another example R² is B50. In another example R² is B51. In another example R² is B52. In another example R² is B53. In another example R² is B54. In another example R² is B55. In another example R² is B56. In another example R² is B57. In another example R² is B58. In another example R² is B59. In another example R² is B60. In another example R² is B61. In another example R² is B62. In another example R² is B63. In another example R² is B64. In another example R² is B65. In another example R² is B66. In another example R² is B67. In another example R² is B68. In another example R² is B69. In another example R² is B70. In another example R² is B71. In another example R² is B72. In another example R² is B73. In another example R² is B74. In another example R² is B75. In another example R² is B76. In another example R² is B77. In another example R² is B78. In another example R² is B79. In another example R² is B80. In another example R² is B81. In another example R² is B82. In another example R² is B83. In another example R² is B84. In another example R² is B85. In another example R² is B86. In another example R² is B87. In another example R² is B88. In another example R² is B89. In another example R² is B90. In other examples R² is any one of B100-175 as if each was individually listed as a separate example.

In another example, R² is H.

In another example R² is selected from the group consisting of: —(C₁-C₃alkyl)(C₆-C₁₀aryl), —CH(C₆-C₁₀aryl)((C₁-C₃alkyl)-O—(C₁-C₃alkyl)), —(C₁-C₃alkyl)heteroaryl, -heterocycloalkyl(C₆-C₁₀aryl), and —(C₁-C₆alkyl)-O—(C₁-C₆alkyl), as these groups are described above (in any of the definitions of R²). For example, R² is selected from the group consisting of: (1) —(C₁-C₃alkyl)(C₆-C₁₀aryl) (such as, for example, —(C₁-C₂alkyl)(C₆-C₁₀aryl), —(C₁-C₃alkyl)phenyl, —CH(CH₃)phenyl, —CH₂CH₂phenyl, and —CH₂phenyl), (2) —CH(C₆-C₁₀aryl)((C₁-C₃alkyl)-O—(C₁-C₃alkyl)) (such as, for example, —CH(phenyl)-((C₁-C₂alkyl)-O—(C₁-C₂alkyl)), and —CH(phenyl)CH₂OCH₃), (3) —(C₁-C₃alkyl)heteroaryl (such as, for example, —(C₁-C₂alkyl)heteroaryl, —(C₁-C₃alkyl)pyridyl, —(C₁-C₂alkyl)pyridyl, and —CH(CH₃)pyridyl), (4) -heterocycloalkyl(C₆-C₁₀aryl) (such as, for example, -heterocycloalkyl-phenyl, and -pyrrolidinylphenyl), (5) —(C₁-C₆alkyl)-O—(C₁-C₆alkyl) (such as, for example, —(C₁-C₃alkyl)-O—(C₁-C₂alkyl), —(CH₂)₂—O—CH₃, and —CH(CH₃)CH₂OCH₃), (6) any one of the groups in (1), (2), (3), and (4) wherein the aryl, heteroaryl or heterocycloalkyl moiety is substituted with 1-3 substituents independently selected from the group consisting of halo (e.g., F, Br, and Cl, and in one example F) and —(C₁-C₆alkyl) (e.g., —(C₁-C₄alkyl), —(C₁-C₃alkyl), and —(C₁-C₂alkyl), and in one example methyl), (7) any one of the groups in (1), (2), (3), and (4) wherein the aryl, heteroaryl or heterocycloalkyl moiety is substituted with 1 substituent selected from the group consisting of halo (e.g., F, Br, and Cl, and in one example F) and —(C₁-C₆alkyl) (e.g., —(C₁-C₄alkyl), —(C₁-C₃alkyl), and —(C₁-C₂alkyl), and in one example methyl), (8) any one of the groups in (1), (2), (3), and (4) wherein the aryl, heteroaryl or heterocycloalkyl moiety is substituted with 1 substituent selected from the group consisting of F and methyl, and (9) any one of the groups in (1), (2), (3), and (4) wherein the aryl (e.g., phenyl) is substituted with 1-3 independently selected halos (e.g., F, Br, and Cl, and in one example F) and the heteroaryl (e.g., pyridyl) or heterocycloalkyl (e.g., pyrrolidine) moiety is substituted with 1-3 substituents independently selected from —(C₁-C₆alkyl) (e.g., —(C₁-C₄alkyl), —(C₁-C₃alkyl), and —(C₁-C₂alkyl), and in one example methyl), (10) any one of the groups in (1), (2), (3), and (4) wherein the aryl (e.g., phenyl) is substituted with 1 halo (e.g., F, Br, or Cl, and in one example F) and the heteroaryl (e.g., pyridyl) or heterocycloalkyl (e.g., pyrrolidine) moiety is substituted with 1 —(C₁-C₆alkyl) (e.g., —(C₁-C₄alkyl), —(C₁-C₃alkyl), and —(C₁-C₂alkyl), and in one example methyl), and (11) any one of the groups in (1), (2), (3), and (5) wherein the alkyl is substituted with 1-3 substituents independently selected from the group consisting of: halo (e.g., F, Br, and Cl), —O—($C_1$-$C_6$alkyl), —OH and —$CF_3$.

In one example $R^{10}$ is selected from the group consisting of: H, halo, CN, —$CF_3$, OH, $NH_2$, —O—($C_1$-$C_6$alkyl), —($C_1$-$C_6$alkyl), and —($C_5$-$C_6$cycloalkyl).

In one example $R^{10}$ is selected from the group consisting of: CN, —OH, and $NH_2$.

In one example the $R^{10}$ or $R^{11}$ —O—($C_1$-$C_6$alkyl) is —O—($C_1$-$C_2$alkyl).

In one example $R^{10}$ is selected from the group consisting of: H, F, Cl, Br, —$CF_3$, methyl, ethyl, isopropyl, cyclopropyl, —$OCH_3$, —CH(OH)$CH_3$, —$CH_2OH$, —$CH_2OCH_3$, —$CH_2$—N($CH_3$)$_2$, and —$CH_2$-morpholinyl. In another example $R^{10}$ is selected from the group consisting of: H, methyl, F and OH. In another example $R^{10}$ is selected from the group consisting of: H and methyl.

In one example $R^{11}$ is selected from the group consisting of: CN, OH, $NH_2$, aryl and heterocycloalkyl, —$NHR^{12}$, —$NR^{12}R^{13}$, and —NHC(O)$R^8$.

In one example $R^{11}$ is selected from the group consisting of: H, F, Cl, Br, —$CF_3$ methyl, ethyl, isopropyl, cyclopropyl, —$OCH_3$, —CH(OH)$CH_3$, —$CH_2OH$, —$CH_2OCH_3$, —$CH_2$—N($CH_3$)$_2$, and —$CH_2$-morpholinyl. In another example $R^{11}$ is selected from the group consisting of: H and —$CH_2OH$.

In one example $R^{10}$ is selected from the group consisting of: H, Cl, F and —$CF_3$.

In one example $R^{11}$ is selected from the group consisting of: H, Cl, —$CH_3$, —$OCH_3$, —$CH_2OH$, and —$CH_2OCH_3$.

In one example $R^{10}$ is selected from the group consisting of: H, Cl, F and —$CF_3$, and $R^{11}$ is selected from the group consisting of: H, Cl, —$CH_3$, —$OCH_3$, —$CH_2OH$, and —$CH_2OCH_3$.

In one example $R^{10}$ is selected from the group consisting of: H, F, Cl, Br, methyl, ethyl, isopropyl, cyclopropyl, —CH(OH)$CH_3$, —$CH_2OCH_3$, —$CH_2$—N($CH_3$)$_2$, and —$CH_2$-morpholinyl. In another example $R^{10}$ is selected from the group consisting of: H, F and methyl.

In one example $R^{11}$ is selected from the group consisting of: H, F, Cl, Br, methyl, ethyl, isopropyl, cyclopropyl, —CH(OH)$CH_3$, —$CH_2OCH_3$, —$CH_2$—N($CH_3$)$_2$, and —$CH_2$-morpholinyl.

In another example $R^{11}$ is selected from the group consisting of: H and methyl.

In one example $R^{10}$ is H. In another example $R^{10}$ is halo. In another example $R^{10}$ is halo selected from the group consisting of: F, Cl and Br. In another example $R^{10}$ is F. In another example $R^{10}$ is Br, and in another example Cl. In another example $R^{10}$ is —($C_1$-$C_6$alkyl), and in another example —($C_1$-$C_6$alkyl), and in another example —($C_1$-$C_4$alkyl), and in another example —($C_1$-$C_3$alkyl), and in another example —($C_1$-$C_2$alkyl). In another example $R^{10}$ is methyl. In another example $R^{10}$ is ethyl. In another example $R^{10}$ is isopropyl. In another example $R^{10}$ is —($C_3$-$C_6$ cycloalkyl). In another example $R^{10}$ is cyclopropyl. In another example $R^{10}$ is hydroxy substituted —($C_1$-$C_6$alkyl), and in another example hydroxy substituted —($C_1$-$C_3$alkyl), and in another example hydroxy substituted —($C_1$-$C_3$alkyl). In another example $R^{10}$ is —CH(OH)$CH_3$. In another example $R^{10}$ is —($C_1$-$C_6$alkyl)-O—($C_1$-$C_6$alkyl), and in another example —($C_1$-$C_4$alkyl)-O—($C_1$-$C_4$alkyl), and in another example —($C_1$-$C_2$alkyl)-O—($C_1$-$C_2$alkyl). In another example $R^{10}$ is —$CH_2OCH_3$. In another example $R^{10}$ is —($C_1$-$C_6$alkyl)-N($C_1$-$C_6$alkyl)$_2$ wherein each alkyl is independently selected, and in another example —($C_1$-$C_4$alkyl)-N($C_1$-$C_4$alkyl)$_2$ wherein each alkyl is independently selected, and in another example —($C_1$-$C_2$alkyl)-N($C_1$-$C_2$alkyl)$_2$ wherein each alkyl is independently selected. In another example $R^{10}$ is —$CH_2$—N($CH_3$)$_2$. In another example $R^{10}$ is —($C_1$-$C_6$alkyl)-heterocycloalkyl, and in another example —($C_1$-$C_4$alkyl)-heterocycloalkyl, and in another example —($C_1$-$C_2$alkyl)-heterocycloalkyl, and in another example —($C_1$-$C_2$alkyl)-(6 membered heterocycloalkyl). In another example $R^{10}$ is —$CH_2$-morpholinyl.

In one example $R^{11}$ is H. In another example $R^{11}$ is halo. In another example $R^{11}$ is halo selected from the group consisting of: F, Cl and Br. In another example $R^{11}$ is F. In another example $R^{11}$ is Br, and in another example Cl. In another example $R^{11}$ is —($C_1$-$C_6$alkyl), and in another example —($C_1$-$C_6$alkyl), and in another example —($C_1$-$C_4$alkyl), and in another example —($C_1$-$C_3$alkyl), and in another example —($C_1$-$C_2$alkyl). In another example $R^{11}$ is methyl. In another example $R^{11}$ is ethyl. In another example $R^{11}$ is isopropyl. In another example $R^{11}$ is —($C_3$-$C_6$ cycloalkyl). In another example $R^{11}$ is cyclopropyl. In another example $R^{11}$ is hydroxyl substituted —($C_1$-$C_6$alkyl), and in another example hydroxy substituted —($C_1$-$C_3$alkyl), and in another example hydroxy substituted —($C_1$-$C_3$alkyl). In another example $R^{11}$ is —CH(OH)$CH_3$. In another example $R^{11}$ is —($C_1$-$C_6$alkyl)-O—($C_1$-$C_6$alkyl), and in another example —($C_1$-$C_4$alkyl)-O—($C_1$-$C_4$alkyl), and in another example —($C_1$-$C_2$alkyl)-O—($C_1$-$C_2$alkyl). In another example $R^{11}$ is —$CH_2OCH_3$. In another example $R^{11}$ is —($C_1$-$C_6$alkyl)-N($C_1$-$C_6$alkyl)$_2$ wherein each alkyl is independently selected, and in another example —($C_1$-$C_4$alkyl)-N($C_1$-$C_4$alkyl)$_2$ wherein each alkyl is independently selected, and in another example —($C_1$-$C_2$alkyl)-N($C_1$-$C_2$alkyl)$_2$ wherein each alkyl is independently selected. In another example $R^{11}$ is —$CH_2$—N($CH_3$)$_2$. In another example $R^{11}$ is —($C_1$-$C_6$alkyl)-heterocycloalkyl, and in another example —($C_1$-$C_4$alkyl)-heterocycloalkyl, and in another example —($C_1$-$C_2$alkyl)-heterocycloalkyl, and in another example —($C_1$-$C_2$alkyl)-(6 membered heterocycloalkyl). In another example $R^{11}$ is —$CH_2$-morpholinyl. In other examples $R^{10}$ is selected from the group consisting of: H, Br, Cl, F and —($C_1$-$C_3$alkyl) (and in one example methyl, and in another example ethyl), and $R^{11}$ is as defined in any one of the examples described in this paragraph. In other examples $R^{10}$ is selected from the group consisting of: H, F and methyl, and $R^{11}$ is as defined in any one of the examples described in this paragraph.

In another example $R^{10}$ is H and $R^{11}$ is H. $R^{10}$ is halo and $R^{11}$ is H. In another example $R^{10}$ is F and $R^{11}$ is H. In another example $R^{10}$ is Br and $R^{11}$ is H. In another example $R^{10}$ is Cl and $R^{11}$ is H. In another example $R^{10}$ is —($C_1$-$C_6$alkyl) and $R^{11}$ is H. In another example $R^{10}$ is —($C_1$-$C_4$alkyl) and $R^{11}$ is H. In another example $R^{10}$ is —($C_1$-$C_3$alkyl) and $R^{11}$ is H. In another example $R^{10}$ is —($C_1$-$C_2$alkyl) and $R^{11}$ is H. In another example $R^{10}$ is methyl and $R^{11}$ is H. In another example $R^{10}$ is ethyl and $R^{11}$ is H. In other examples $R^{10}$ and $R^{11}$ are as defined in any one of the examples in this paragraph, and $R^1$ and $R^2$ are as defined in any one of the examples given above.

In another example $R^{10}$ is H and $R^{11}$ is —($C_1$-$C_3$alkyl) (and in one example methyl, and in another example ethyl, and in another example isopropyl). In another example $R^{10}$ is H and $R^{11}$ is —($C_3$-$C_6$ cycloalkyl) (and in another example cyclopropyl). In another example $R^{10}$ is H and $R^{11}$ is —($C_1$-$C_2$alkyl)-O—($C_1$-$C_2$alkyl) (and in another example —$CH_2OCH_3$). In another example $R^{10}$ is H and $R^{11}$ is —($C_1$-$C_2$alkyl)-N($C_1$-$C_2$alkyl)$_2$ wherein each alkyl is independently selected (and in another example —$CH_2$—N($CH_3$)$_2$). In another example $R^{10}$ is H and $R^{11}$ is —($C_1$-$C_2$alkyl)-heterocycloalkyl (and in another example —CH$_2$-morpholinyl). In another example R$^{10}$ is H and R$^{11}$ is hydroxy substituted —(C$_1$-C$_3$alkyl) (and in another example —CH(OH)CH$_3$). In other examples R$^{10}$ and R$^{11}$ are as defined in any one of the examples in this paragraph, and R$^1$ and R$^2$ are as defined in any one of the examples given above.

In other examples R$^{10}$ is selected from the group consisting of: H, halo (for example, F, or Br, or Cl), and —(C$_1$-C$_6$alkyl) (for example, a —(C$_1$-C$_4$alkyl), or —(C$_1$-C$_3$alkyl) or —(C$_1$-C$_2$alkyl, and in one example methyl and in another ethyl), and R$^{11}$ is selected from the group consisting of: halo (for example, F or Br or Cl), and —(C$_1$-C$_6$alkyl) (for example, a —(C$_1$-C$_4$alkyl), or —(C$_1$-C$_3$alkyl) or —(C$_1$-C$_2$alkyl), and in one example methyl and in another ethyl). In other examples R$^{10}$ is selected from the group consisting of: H, F, Br, Cl, methyl and ethyl, and R$^{11}$ is selected from the group consisting of: F, Br, Cl, methyl and ethyl. In other examples R$^{10}$ is selected from the group consisting of: H, F, methyl and ethyl, and R$^{11}$ is selected from the group consisting of: F, methyl and ethyl. In other examples R$^{10}$ is selected from the group consisting of: H, F, and methyl, and R$^{11}$ is selected from the group consisting of: F, and methyl. In other examples R$^{10}$ is H and R$^{11}$ is selected from the group consisting of: F, methyl and ethyl. In other examples R$^{10}$ is H and R$^{11}$ is selected from the group consisting of: F, and methyl. In other examples R$^{10}$ and R$^{11}$ are as defined in any one of the examples in this paragraph, and R$^1$ and R$^2$ are as defined in any one of the examples given above.

In other examples of this invention, R$^1$, R$^{10}$ and R$^{11}$ are as defined for formula (1), and R$^4$ and R$^5$ are each independently selected from the group consisting of: —(C$_1$-C$_6$alkyl) and —(C$_1$-C$_4$alkyl), and R$^2$ is selected from the group consisting of: B1 to B9, and B29 to B44. In other examples of this invention R$^1$, R$^{10}$ and R$^{11}$ are as defined for formula (1), and R$^4$ and R$^5$ are each independently selected from the group consisting of: —(C$_1$-C$_6$alkyl) and —(C$_1$-C$_4$alkyl), and R$^2$ is, in one example, B1, and in another example B2, and in another example B3, and in another example B9, and in another example B29, and in another example B30, and in another example B31, and in another example B32, and in another example B33, and in another example B34, and in another example B35, and in another example B36, and in another example B37, and in another example B38, and in another example B39, and in another example B40, and in another example B41, and in another example B42, and in another example B43, and in another example B44. In other examples of this invention, R$^1$, R$^{10}$ and R$^{11}$ are as defined for formula (1), and R$^4$ and R$^5$ are each independently selected from the group consisting of: methyl and ethyl, and R$^2$ is selected from the group consisting of: B1 to B9, and B29 to B44. In other examples of this invention R$^1$, R$^{10}$ and R$^{11}$ are as defined for formula (1), and R$^4$ and R$^5$ are each independently selected from the group consisting of: methyl and ethyl, and R$^2$ is, in one example, B1, and in another example B2, and in another example B3, and in another example B9, and in another example B29, and in another example B30, and in another example B31, and in another example B32, and in another example B33, and in another example B34, and in another example B35, and in another example B36, and in another example B37, and in another example B38, and in another example B39, and in another example B40, and in another example B41, and in another example B42, and in another example B43, and in another example B44. Other examples include any one of the examples in this paragraph wherein R$^4$ and R$^5$ are the same. Other examples include any one of examples in this paragraph wherein R$^{10}$ is selected from the group consisting of H, F, and methyl, and R$^{11}$ is selected from the group consisting of: H, F and methyl. Other examples include any one of the examples in this paragraph wherein R$^{10}$ is H, and R$^{11}$ is selected from the group consisting of: H, F and methyl. Other examples include any one of the examples in this paragraph wherein R$^{10}$ is F, and R$^{11}$ is selected from the group consisting of: H, F and methyl. Other examples include any one of the examples in this paragraph wherein R$^{10}$ is F, and R$^{11}$ is selected from the group consisting of: H, F and methyl. Other examples include any one of the examples in this paragraph wherein R$^{10}$ is methyl, and R$^{11}$ is selected from the group consisting of: H, F and methyl. Other examples include any one of the examples in this paragraph wherein R$^{10}$ is H, and R$^{11}$ is H. Other examples include any one of the examples in this paragraph wherein R$^{10}$ is F, and R$^{11}$ is H. Other examples include any one of the examples in this paragraph wherein R$^{10}$ is methyl, and R$^{11}$ is H.

In another example R$^4$ and R$^5$ are independently selected from the group consisting of: H, methyl, ethyl, propyl, isopropyl, and —(CH$_2$)$_2$—O—CH$_3$; R$^2$ is selected from the group consisting of: (1) —(C$_1$-C$_3$alkyl)aryl (such as, for example, —(C$_1$-C$_2$alkyl)aryl, —(C$_1$-C$_3$alkyl)phenyl, —CH(CH$_3$)phenyl, —CH$_2$CH$_2$phenyl, and —CH$_2$phenyl), (2) —CH(aryl)((C$_1$-C$_3$alkyl)-O—(C$_1$-C$_3$alkyl)) (such as, for example, —CH(phenyl)((C$_1$-C$_2$alkyl)-O—(C$_1$-C$_2$alkyl)), and —CH(phenyl)CH$_2$OCH$_3$), (3) —(C$_1$-C$_3$alkyl)heteroaryl (such as, for example, —(C$_1$-C$_2$alkyl)heteroaryl, —(C$_1$-C$_3$alkyl)pyridyl, —(C$_1$-C$_2$alkyl)pyridyl, and —CH(CH$_3$)pyridyl), (4) -heterocycloalkylaryl (such as, for example, -heterocycloalkylphenyl, and -pyrrolidinyl-phenyl), (5) —(C$_1$-C$_6$alkyl)-O—(C$_1$-C$_6$alkyl) (such as, for example, —(C$_1$-C$_3$alkyl)-O—(C$_1$-C$_2$alkyl), —(CH$_2$)$_2$—O—CH$_3$, and —CH(CH$_3$)CH$_2$OCH$_3$), (6) any one of the groups in (1), (2), (3), and (4) wherein the aryl, heteroaryl or heterocycloalkyl moiety is substituted with 1-3 substituents independently selected from the group consisting of halo (e.g., F, Br, and Cl, and in one example F) and —(C$_1$-C$_6$alkyl) (e.g., —(C$_1$-C$_4$alkyl), —(C$_1$-C$_3$alkyl), and —(C$_1$-C$_2$alkyl), and in one example methyl), (7) any one of the groups in (1), (2), (3), and (4) wherein the aryl, heteroaryl or heterocycloalkyl moiety is substituted with 1 substituent selected from the group consisting of halo (e.g., F, Br, and Cl, and in one example F) and —(C$_1$-C$_6$alkyl) (e.g., —(C$_1$-C$_4$alkyl), —(C$_1$-C$_3$alkyl), and —(C$_1$-C$_2$alkyl), and in one example methyl), (8) any one of the groups in (1), (2), (3), and (4) wherein the aryl, heteroaryl or heterocycloalkyl moiety is substituted with 1 substituent selected from the group consisting of F and methyl, and (9) any one of the groups in (1), (2), (3), and (4) wherein the aryl (e.g., phenyl) is substituted with 1-3 independently selected halos (e.g., F, Br, and Cl, and in one example F) and the heteroaryl (e.g., pyridyl) or heterocycloalkyl (e.g., pyrrolidine) moiety is substituted with 1-3 substituents independently selected from —(C$_1$-C$_6$alkyl) (e.g., —(C$_1$-C$_4$alkyl), —(C$_1$-C$_3$alkyl), and —(C$_1$-C$_2$alkyl), and in one example methyl), and (10) any one of the groups in (1), (2), (3), and (4) wherein the aryl (e.g., phenyl) is substituted with 1 halo (e.g., F, Br, or Cl, and in one example F) and the heteroaryl (e.g., pyridyl) or heterocycloalkyl (e.g., pyrrolidine) moiety is substituted with 1 —(C$_1$-C$_6$alkyl) (e.g., —(C$_1$-C$_4$alkyl), —(C$_1$-C$_3$alkyl), and —(C$_1$-C$_2$alkyl), and in one example methyl). Other examples include any one of the examples described in this paragraph wherein R$^{10}$ is selected from the group consisting of H, F, and methyl, and R$^{11}$ is selected from the group consisting of: H, F and methyl. Other examples include any one of the examples described in this paragraph wherein R$^{10}$ is selected from the group consisting of H, and R$^{11}$ is selected from the group consisting of: H, F and methyl. Other examples include any one of the examples described in this paragraph wherein $R^{10}$ is F, and $R^{11}$ is selected from the group consisting of: H, F and methyl. Other examples include any one of the examples described in this paragraph wherein $R^{10}$ is methyl, and $R^{11}$ is selected from the group consisting of: H, F and methyl. Other examples include any one of the examples described in this paragraph wherein $R^{10}$ is H, and $R^{11}$ is H. Other examples include any one of the examples described in this paragraph wherein $R^{10}$ is F, and $R^{11}$ is H. Other examples include any one of the examples described in this paragraph wherein $R^{10}$ is methyl, and $R^{11}$ is H.

In another example $R^4$ and $R^5$ are independently selected from the group consisting of: H, methyl, ethyl, propyl, isopropyl, and —$(CH_2)_2$—O—$CH_3$; $R^2$ is selected from the group consisting of: B1, B2, B3, B4, B5, B6, B7, B8, and B9, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example $R^4$ and $R^5$ are independently selected from the group consisting of: H, methyl, ethyl, propyl, isopropyl, and —$(CH_2)_2$—O—$CH_3$; $R^2$ is selected from the group consisting of: B29, B30, B31, B32, B33, B34, B35, B36, B37, B38, B39, B40, B41, B42, B43, and B44, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example, $R^4$ is H, $R^5$ is selected from the group consisting of: methyl, ethyl, propyl, isopropyl, and —$(CH_2)_2$—O—$CH_3$, $R^2$ is selected from the group consisting of: B1, B2, B3, B4, B5, B6, B7, B8, and B9, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example, $R^4$ is H, $R^5$ is selected from the group consisting of: methyl, ethyl, propyl, isopropyl, and —$(CH_2)_2$—O—$CH_3$, $R^2$ is selected from the group consisting of: B29, B30, B31, B32, B33, B34, B35, B36, B37, B38, B39, B40, B41, B42, B43, and B44, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example, $R^4$ is H, $R^5$ is selected from the group consisting of: methyl, ethyl, propyl, and isopropyl, $R^2$ is selected from the group consisting of: B1, B2, B3, B4, B5, B6, B7, B8, and B9, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example, $R^4$ is H, $R^5$ is selected from the group consisting of: methyl, ethyl, propyl, and isopropyl, $R^2$ is selected from the group consisting of: B29, B30, B31, B32, B33, B34, B35, B36, B37, B38, B39, B40, B41, B42, B43, and B44, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In other examples of this invention, $R^1$, $R^{10}$ and $R^{11}$ are as defined for formula (1), and $R^4$ is H, and $R^5$ is selected from the group consisting of: methyl, ethyl, propyl, and isopropyl, and $R^2$ is selected from the group consisting of: B1 to B9, and B29 to B44. In other examples of this invention, $R^1$, $R^{10}$ and $R^{11}$ are as defined for formula (1), and $R^4$ is H, and $R^5$ is selected from the group consisting of: methyl, ethyl, propyl, and isopropyl, and $R^2$ is, in one example, B1, and in another example B2, and in another example B3, and in another example B9, and in another example B29, and in another example B30, and in another example B31, and in another example B32, and in another example B33, and in another example B34, and in another example B35, and in another example B36, and in another example B37, and in another example B38, and in another example B39, and in another example B40, and in another example B41, and in another example B42, and in another example B43, and in another example B44. For ease of identification, the examples in this paragraph are the examples of Group 1.

In other examples of this invention, $R^1$, $R^{10}$ and $R^{11}$ are as defined for formula (1), and $R^4$ is H, and $R^5$ is selected from the group consisting of: methyl and ethyl, and $R^2$ is selected from the group consisting of: B1 to B9, and B29 to B44. In other examples of this invention, $R^1$, $R^{10}$ and $R^{11}$ are as defined for formula (1), and $R^4$ is H, and $R^5$ is selected from the group consisting of: methyl and ethyl, and $R^2$ is, in one example, B1, and in another example B2, and in another example B3, and in another example B9, and in another example B29, and in another example B30, and in another example B31, and in another example B32, and in another example B33, and in another example B34, and in another example B35, and in another example B36, and in another example B37, and in another example B38, and in another example B39, and in another example B40, and in another example B41, and in another example B42, and in another example B43, and in another example B44. For ease of identification, the examples in this paragraph are the examples of Group 2.

In another example $R^4$ and $R^5$ are independently selected from the group consisting of: H, methyl, and ethyl, $R^2$ is selected from the group consisting of: B1, B2, B3, B4, B5, B6, B7, B8, and B9, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example $R^4$ and $R^5$ are independently selected from the group consisting of: H, methyl, and ethyl, $R^2$ is selected from the group consisting of: B29, B30, B31, B32, B33, B34, B35, B36, B37, B38, B39, B40, B41, B42, B43, and B44, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example, $R^4$ is H, $R^5$ is selected from the group consisting of: methyl and ethyl, $R^2$ is selected from the group consisting of: B1, B2, B3, B4, B5, B6, B7, B8, and B9, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example, $R^4$ is H, $R^5$ is selected from the group consisting of: methyl and ethyl, $R^2$ is selected from the group consisting of: B29, B30, B31, B32, B33, B34, B35, B36, B37, B38, B39, B40, B41, B42, B43, and B44, $R^{10}$ is selected from the group consisting of: H, F, and methyl, and $R^{11}$ is selected from the group consisting of: H, F and methyl. In another example, $R^2$, $R^4$, and $R^5$ are as defined in this paragraph and $R^{10}$ is H and $R^{11}$ is H. In another example, $R^2$, $R^4$, and $R^5$ are as defined in this paragraph and $R^{10}$ is F and $R^{11}$ is H. In another example, $R^2$, $R^4$, and $R^5$ are as defined in this paragraph and $R^{10}$ is methyl and $R^{11}$ is H.

In another example, $R^1$ is selected from the group consisting of: —NH$_2$, A1, A2, A3, A4, A5, A6, A7, A8, A9, A10, A11, A12, A13, A14, A15, A16, A17 and A18, and $R^2$ is selected from the group consisting of: B1, B2, B3, B4, B5, B6, B7, B8, and B9. In another example, $R^1$ is selected from the group consisting of: —NH$_2$, A1, A2, A3, A4, A5, A6, A7, A8, A9, A10, A11, A12, A13, A14, A15, A16, A17 and A18, and $R^2$ is selected from the group consisting of: B29, B30, B31, B32, B33, B34, B35, B36, B37, B38, B39, B40, B41, B42, B43, and B44.

In another example, $R^1$ is selected from the group consisting of: A1, A2, A3, A4, A5, A6, A7, A8, A9, A10, A11, A12, A13, A14, A15, A16, A17 and A18, and $R^2$ is selected from the group consisting of: B1, B2, B3, B4, B5, B6, B7, B8, and B9.

In another example, $R^1$ is selected from the group consisting of: A1, A2, A3, A4, A5, A6, A7, A8, A9, A10, A11, A12, A13, A14, A15, A16, A17 and A18, and $R^2$ is selected from the group consisting of: B29, B30, B31, B32, B33, B34, B35, B36, B37, B38, B39, B40, B41, B42, B43, and B44.

In other examples of this invention, $R^{10}$ and $R^{11}$ are as defined for formula (1), $R^1$ is selected from the group consisting of: A1, A2, A3, A4, A5, A6, A7, A8, A9, A10, A11, A12, A13, A14, A15, A16, A17 and A18, and $R^2$ is, in one example, B1, and in another example B2, and in another example B3, and in another example B9, and in another example B29, and in another example B30, and in another example B31, and in another example B32, and in another example B33, and in another example B34, and in another example B35, and in another example B36, and in another example B37, and in another example B38, and in another example B39, and in another example B40, and in another example B41, and in another example B42, and in another example B43, and in another example B44. In other examples of this invention, $R^{10}$ and $R^{11}$ are as defined for formula (1), $R^1$ is selected from the group consisting of: A1, A2, A3, A4, A5, A6, A8, A9, A10, A11, A12, A13, A14, A15, A16, A17 and A18, and $R^2$ is, in one example, B1, and in another example B2, and in another example B3, and in another example B9, and in another example B29, and in another example B30, and in another example B31, and in another example B32, and in another example B33, and in another example B34, and in another example B35, and in another example B36, and in another example B37, and in another example B38, and in another example B39, and in another example B40, and in another example B41, and in another example B42, and in another example B43, and in another example B44. For ease of identification, the examples in this paragraph are the examples of Group 3.

Other examples include any example in anyone of Groups 1, 2 and 3 above, wherein $R^{10}$ is selected from the group consisting of: H, F, and methyl, and $R^{11}$ is selected from the group consisting of: H, F and methyl. Other examples include any example in anyone of Groups 1, 2 and 3 above, wherein $R^{10}$ is H and $R^{11}$ is H, and in another example $R^{10}$ is F and $R^{11}$ is H, and in another example $R^{10}$ is methyl and $R^{11}$ is H.

Representative compounds of the invention include, but are not limited to, the final compounds of Examples 1 to 60. Representative compounds of this invention also include, but are not limited to, the final compounds of Examples 61-458. Thus, one example of this invention is the compound of Ex. 1, another is the compound of Ex. 2, another is the compound of Ex. 3, another is the compound of Ex. 4, another is the compound of Ex. 5, another is the compound of Ex. 6, another is the compound of Ex. 7, another is the compound of Ex. 8, another is the compound of Ex. 9, another is the compound of Ex. 10, another is the compound of Ex. 11, another is the compound of Ex. 12, another is the compound of Ex. 13, another is the compound of Ex. 14, another is the compound of Ex. 15, another is the compound of Ex. 16, another is the compound of Ex. 17, another is the compound of Ex. 18, another is the compound of Ex. 19, another is the compound of Ex. 20, another is the compound of Ex. 21, another is the compound of Ex. 22, another is the compound of Ex. 23, another is the compound of Ex. 24, another is the compound of Ex. 25, another is the compound of Ex. 26, another is the compound of Ex. 27, another is the compound of Ex. 28, another is the compound of Ex. 29, another is the compound of Ex. 30, another is the compound of Ex. 31, another is the compound of Ex. 32, another is the compound of Ex. 33, another is the compound of Ex. 34, another is the compound of Ex. 35, another is the compound of Ex. 36, another is the compound of Ex. 37, another is the compound of Ex. 38, another is the compound of Ex. 39, another is the compound of Ex. 40, another is the compound of Ex. 41, another is the compound of Ex. 42, another is the compound of Ex. 43, another is the compound of Ex. 44, another is the compound of Ex. 45, another is the compound of Ex. 46, another is the compound of Ex. 47, another is the compound of Ex. 48, another is the compound of Ex. 49, another is the compound of Ex. 50, another is the compound of Ex. 51, another is the compound of Ex. 52, another is the compound of Ex. 53, another is the compound of Ex. 54, another is the compound of Ex. 55, another is the compound of Ex. 56, another is the compound of Ex. 57, another is the compound of Ex. 58, another is the compound of Ex. 59, another is the compound of Ex. 60. Other examples include any one of the final compounds of Examples 61-458 as if each was listed individually as a separate example.

Other examples of this invention include pharmaceutically acceptable salts of the compounds of formula (1).

Other examples include the pharmaceutically acceptable salts of any one of the final compounds of Examples 1 to 60, and in other examples the pharmaceutically acceptable salts of any one of the final compounds of Examples 61-458.

Other examples of this invention include pharmaceutically acceptable esters of the compounds of formula (1). Other examples of this invention include pharmaceutically acceptable esters of any one of the final compounds of Examples 1 to 60, and in other examples the pharmaceutically acceptable esters of any one of the final compounds of Examples 61-458.

Other examples of this invention include solvates of the compounds of formula (1). Other examples of this invention include the solvates of any one of the final compounds of Examples 1 to 60, and in other examples the solvates of any one of the final compounds of Examples 61-458.

Other examples of this invention include pharmaceutical compositions comprising at least one compound of formula (1), and a pharmaceutically acceptable carrier.

Other examples of this invention include pharmaceutical compositions comprising at least one compound selected from the group consisting of the final compounds of Examples 1 to 60, and a pharmaceutically acceptable carrier, and in other examples at least one compound selected from the group consisting of the final compounds of Examples 61-458, and a pharmaceutically acceptable carrier.

Other examples of this invention include pharmaceutical compositions comprising one compound of formula (1), and a pharmaceutically acceptable carrier.

Other examples of this invention include pharmaceutical compositions comprising one compound selected from the group consisting of the final compounds of Examples 1 to 60, and a pharmaceutically acceptable carrier, and in other examples one compound selected from the group consisting of the final compounds of Examples 61-458, and a pharmaceutically acceptable carrier.

Other examples of this invention include pharmaceutical compositions comprising at least one pharmaceutically acceptable salt of at least one compound of formula (1), and a pharmaceutically acceptable carrier.

Other examples of this invention include pharmaceutical compositions comprising at least one pharmaceutically acceptable salt of one compound selected from the group consisting of the final compounds of Examples 1 to 60, and a pharmaceutically acceptable carrier, and in other examples at least one pharmaceutically acceptable salt of one compound selected from the group consisting of the final compounds of Examples 61-458, and a pharmaceutically acceptable carrier.

Other examples of this invention include pharmaceutical compositions comprising one pharmaceutically acceptable salt of one compound of formula (1), and a pharmaceutically acceptable carrier.

Other examples of this invention include pharmaceutical compositions comprising one pharmaceutically acceptable salt of one compound selected from the group consisting of the final compounds of Examples 1 to 60, and a pharmaceutically acceptable carrier, and in other examples one pharmaceutically acceptable salt of one compound selected from the group consisting of the final compounds of Examples 61-458, and a pharmaceutically acceptable carrier.

Other examples of this invention include the compounds of formula (1) in pure and isolate form.

Other examples of this invention include any one of the final compounds of Examples 1 to 60 in pure and isolated form, and in other examples at least one pharmaceutically acceptable salt of one compound selected from the group consisting of the final compounds of Examples 61-458, and a pharmaceutically acceptable carrier.

Another example of this invention is a pharmaceutical composition comprising an effective amount of a compound of formula (1) (e.g., a final compound of Examples 1 to 60), a chemotherapeutic agent, and a pharmaceutically acceptable carrier.

The compounds of the invention are useful in preparing a medicament that is useful in treating cancer.

The compounds of this invention inhibit the activity of ERK2. Thus, this invention further provides a method of inhibiting ERK in mammals, especially humans, by the administration of an effective amount of one or more (e.g., one) compounds of this invention. The administration of the compounds of this invention to patients, to inhibit ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention. In the treatment of breast cancer, the compounds of formula (1) can be be administered in a treatment protocol which also includes the administration of an effective amount of at least one (e.g., 1-3, or 1-2, or 1) antihormonal agent (i.e., the methods of treating breast cancer can include hormonal therapies).

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

The methods of treating cancer described herein include methods comprising administering a therapeutically effective amount of a compound of the instant invention in combination with radiation therapy and/or in combination with a second compound selected from the group consisting of: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of this invention is a method of treating cancer in a patient in need of such treatment, said method comprising administering an effective amount of a compound of formula (1). Another example of this invention is a method of treating cancer in a patient in need of such treatment, said method comprising administering to said patient an effective amount of a compound of formula (1), and an effective amount of at least one (e.g., 1-3, 1-2, or 1) chemotherapeutic agent.

The compounds, compositions and methods provided herein are useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one example of this invention the cancer treated is colo-rectal cancer (such as, for example, colon adenocarcinoma and colon adenoma). Thus, another example of this invention is a method of treating colo-rectal cancer in a patient in need of such treatment, said method comprising administering an effective amount of a compound of formula (1) (e.g., a final compound of Examples 1 to 60, and in another example the final compounds of Examples 61-458), or a pharmaceutically acceptable salt thereof, to said patient. Another example is a method of treating colo-rectal cancer in a patient in need of such treatment, said method comprising administering to said patient an effective amount of a compound selected from the group consisting of: the final compounds of Examples 2, 5, 27-35, 39-40, 42, 43, 46-49, 68-70, 109-110, 113-115, 123-127, 129, 130, 220-222, 229, 272-273, 287-289, 366-367, 385-386 and 389-390, and in another example the final compounds of Examples 2, 5, 27-35, 39-40, 42, 43, and 47-49, or a pharmaceutically acceptable salt thereof. Another example of this invention is a method of treating colo-rectal cancer in a patient in need of such treatment, said method comprising administering to said patient an effective amount of a compound of formula (1) (e.g., a final compound of Examples 1 to 60, and in another example the final compounds of Examples 61-458), or a pharmaceutically acceptable salt thereof, and an effective amount of at least one (e.g., 1-3, or 1-2, or 1) chemotherapeutic agent.

In one example of this invention the cancer treated is melanoma. Thus, another example of this invention is directed to a method of treating melanoma in a patient in need of such treatment, said method comprising administering an effective amount of a compound of formula (1) (e.g. a final compound of Examples 1 to 60, and in another example the final compounds of Examples 61-458), or a pharmaceutically acceptable salt thereof, to said patient. Another example is a method of treating melanoma in a patient in need of such treatment, said method comprising administering to said patient an effective amount of a compound selected from the group consisting of: the final compounds of Examples 2, 5, 27-35, 39-40, 42, 43, 46-49, 68-70, 109-110, 113-115, 123-127, 129, 130, 220-222, 229, 272-273, 287-289, 366-367, 385-386 and 389-390, and in another example the final compounds of Examples 2, 5, 27-35, 39-40, 42, 43, and 47-49, or a pharmaceutically acceptable carrier thereof. Another example of this invention is a method of treating melanoma in a patient in need of such treatment, said method comprising administering to said patient an effective amount of a compound of formula (1) (e.g., a final compound of Examples 1 to 60, and in another example the final compounds of Examples 61-458), or a pharmaceutically acceptable salt thereof, and an effective amount of at least one (e.g., 1-3, or 1-2, or 1) chemotherapeutic agent.

The compounds of the invention are also useful in preparing a medicament that is useful in treating cancer.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. Compounds of this invention can be administered in a total daily dose of 10 mg to 3000 mg. For example, compounds of the instant invention can be administered in a total daily dose of up to 3000 mg. Compounds of the instant invention can be administered once daily (QD), or divided into multiple daily doses such as twice daily (BID), and three times daily (TID). Compounds of the instant invention can be administered at a total daily dosage of up to 3000 mg, e.g., 200 mg, 300 mg, 400 mg, 600 mg, 800 mg, 1000 mg, 2000 mg or 3000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days. The compounds of this invention may be administered discontinuously rather than continuously during the treatment cycle. Thus, the compounds of this invention may be administered daily for one or more weeks during the cycle and discontinued for one or more weeks during the cycle, with this pattern of administration repeating during the treatment cycle (e.g., administration for a week and then discontinued for a week). This discontinuous treatment may also be based upon numbers of days rather than a full week. The number of days (or weeks) that the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal to or greater than the number of days or weeks that the compounds of this invention are not dosed.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter refered to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis [diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR; see U.S. Pat. Nos. 4,231,938, 4,294,926 and 4,319,039), simvastatin (ZOCOR; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734188, 60/652737, 60/670469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

Combinations with compounds other than anti-cancer compounds are also encompassed in the instant methods. For example, combinations of the instantly claimed compounds with PPAR-γ (i.e., PPAR-gamma) agonists and PPAR-6 (i.e., PPAR-delta) agonists are useful in the treatment of certain malingnancies. PPAR-γ and PPAR-6 are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In one example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCHinhibitors, agents that interfere with receptor tyrosine kinases (RTKs), an agent that interferes with a cell cycle checkpoint, and any of the therapeutic agents listed above.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians'Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), the Physicians' Desk Reference, 60$^{th}$ Edition, 2006 (published by Thompson PDR, Montvale, N.J. 07645-1742), and the Physicians' Desk Reference, 64$^{th}$ Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula (1) hereinabove.

General Schemes

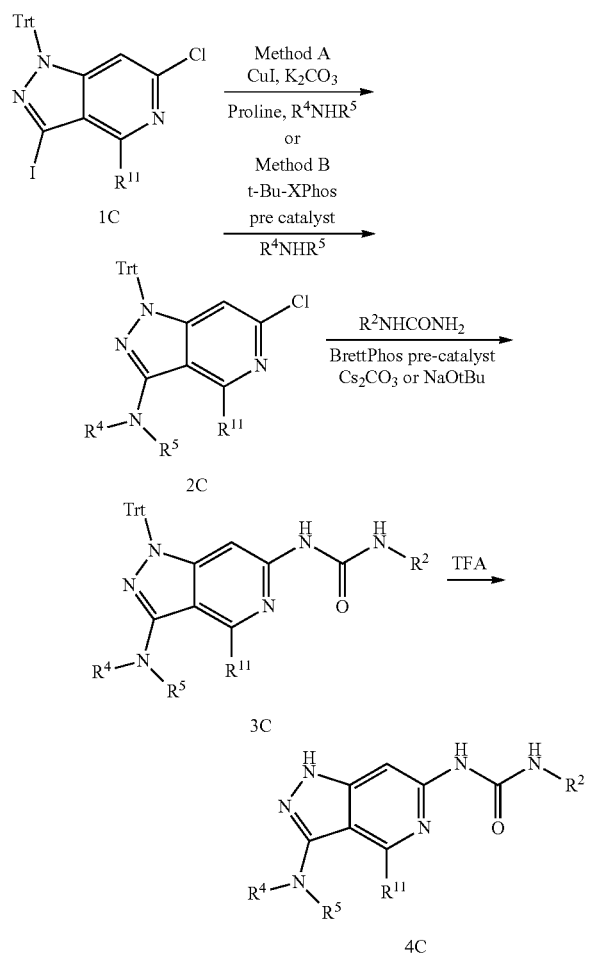

Step 1: Amine derivatives have been prepared by treating various 6-chloro-3-iodo-1-trityl-1H-pyrazolo[4,3-c]pyridine intermediates 1C with the appropriate amine in the presence of CuI, proline, and a suitable base (i.e. $K_2CO_3$) in DMSO at 70° C. to afford 2C.

Step 2: Aryl urea derivatives have been prepared by heating 2C to 100° C. (from 1 to 16 h) with the appropriate primary urea (commercial or synthesized by heating the appropriate amine in the presence of HCl and potassium cyanate), $Cs_2CO_3$, and BrettPhos pre-catalyst in 1,4-dioxane. The residue was treated with TFA and triethylsilane (with or without DCM) to yield the desired product 4C.

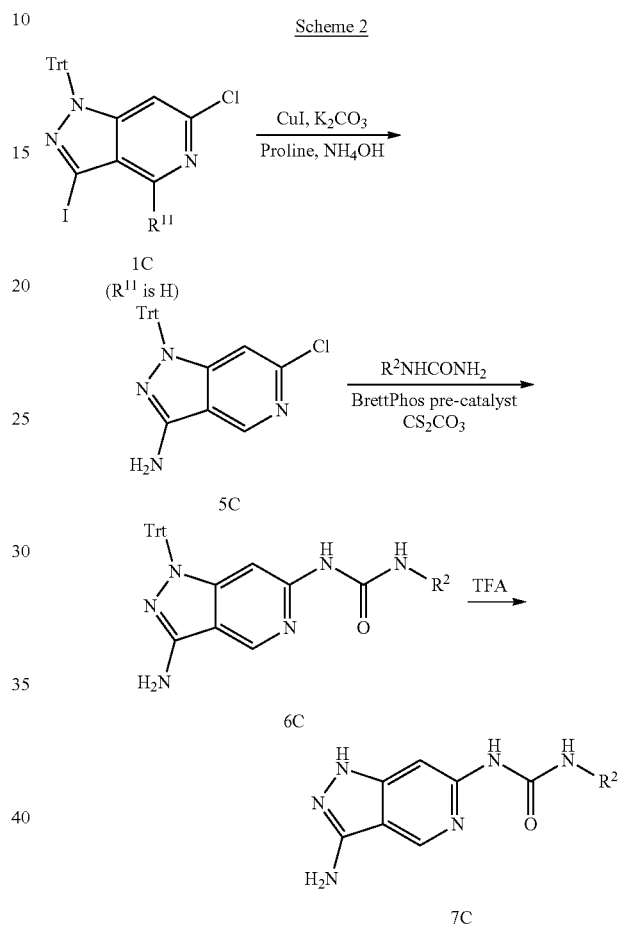

Aryl urea derivatives have been prepared by heating 5C to 100° C. (from 1 to 16 h) 6-chloro-1-trityl-1H-pyrazolo[4,3-c]pyridin-3-amine with the appropriate primary urea (commercial or synthesized by heating the appropriate amine in the presence of HCl and potassium cyanate), $Cs_2CO_3$, and BrettPhos pre-catalyst in 1,4-dioxane. The residue was treated with TFA and triethylsilane (with or without DCM) to yield the desired product 7C.

Scheme 3

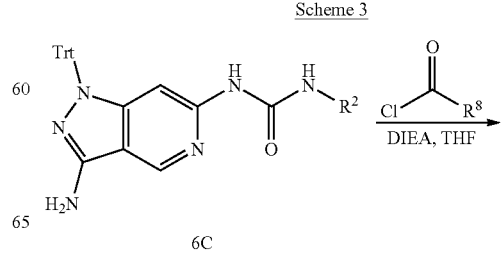

-continued

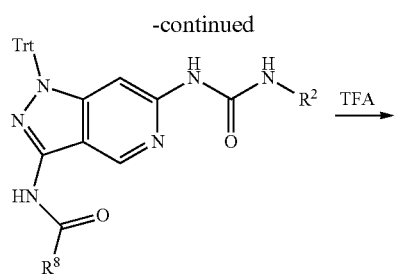

8C

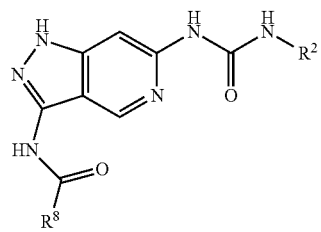

9C

Amide derivatives have been prepared by treating 6C (Scheme 2) with the appropriate acid chloride in the presence of DIEA in THF at ambient temperature. The residue was treated with TFA and triethylsilane to yield the desired product 9C.

Scheme 4

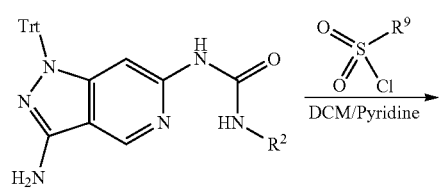

6C

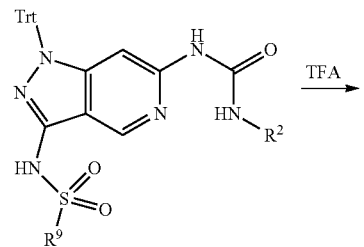

10C

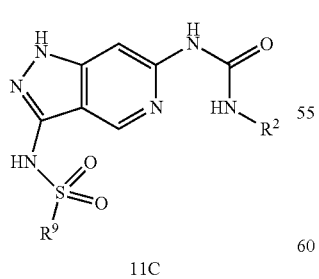

11C

Sulfonamide derivatives have been prepared by treating 6C (Scheme 2) with the appropriate sulfonyl chloride in DCM/pyridine at ambient temperature. The residue was treated with TFA and triethylsilane to yield the desired product 11C.

Scheme 5

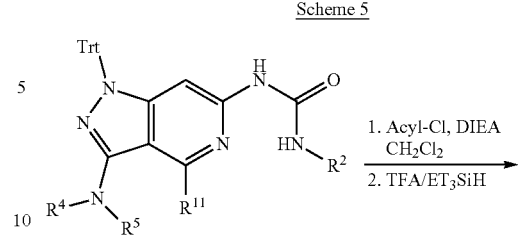

3C
($R^4$, $R^{11}$ = H)

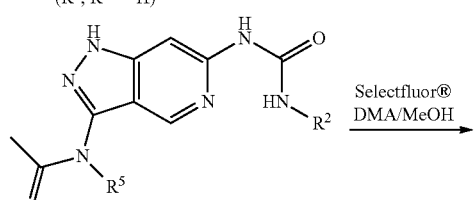

12C

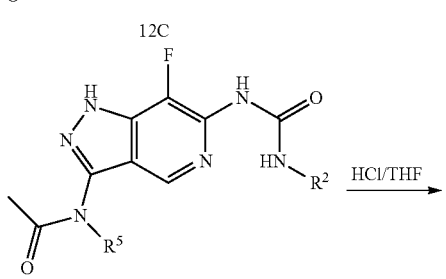

13C

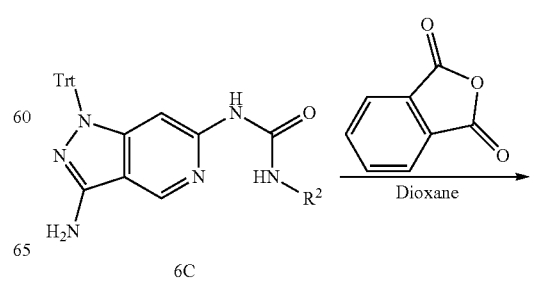

14C

Step 1: Acyl derivatives have been prepared by treating 3C (Scheme 1) with acetyl chloride in the presence of DIEA in DCM at 0° C. The residue was treated with TFA and triethylsilane to yield the desired product 12C.

Step 2: Fluorinated compounds have been prepared by heating 12C to 60° C. (from 2 to 8 h) with Selectfluor® in DMA/MeOH to afford 13C. The residue was treated with HCl in THF at 60° C. to yield the desired product 14C.

Scheme 6

6C

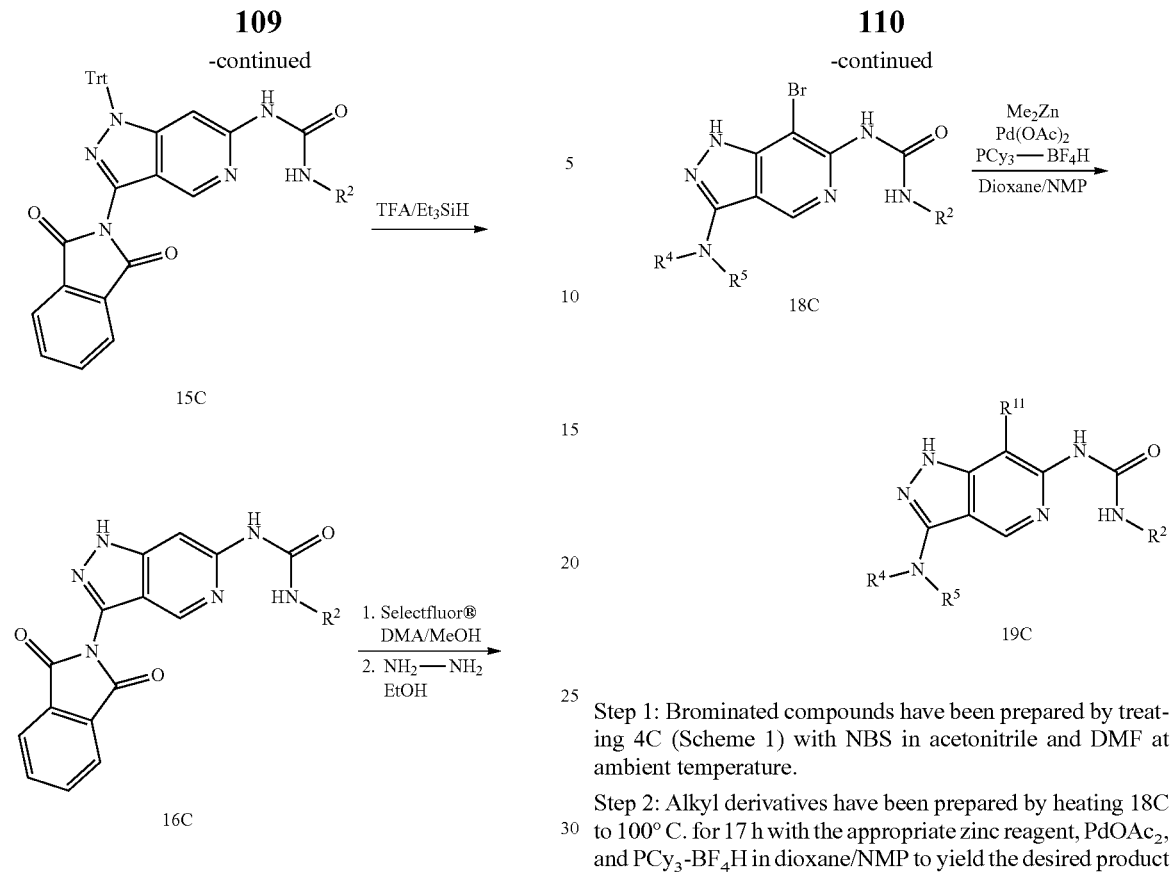

Step 1: Protected amine aryl urea derivatives have been prepared by treating 6C (Scheme 2) with isobenzofuran-1,3-dione in dioxane at 110° C. followed by TFA and triethylsilane to yield the desired product 16C.

Step 2: Fluorinated compounds have been prepared by heating 16C to 60° C. (from 2 to 8 h) with Selectfluor® in DMA/MeOH. The residue was treated with hydrazine hydrate in ethanol at 85° C. to yield the desired product 17C.

Step 1: Brominated compounds have been prepared by treating 4C (Scheme 1) with NBS in acetonitrile and DMF at ambient temperature.

Step 2: Alkyl derivatives have been prepared by heating 18C to 100° C. for 17 h with the appropriate zinc reagent, PdOAc$_2$, and PCy$_3$-BF$_4$H in dioxane/NMP to yield the desired product 19C.

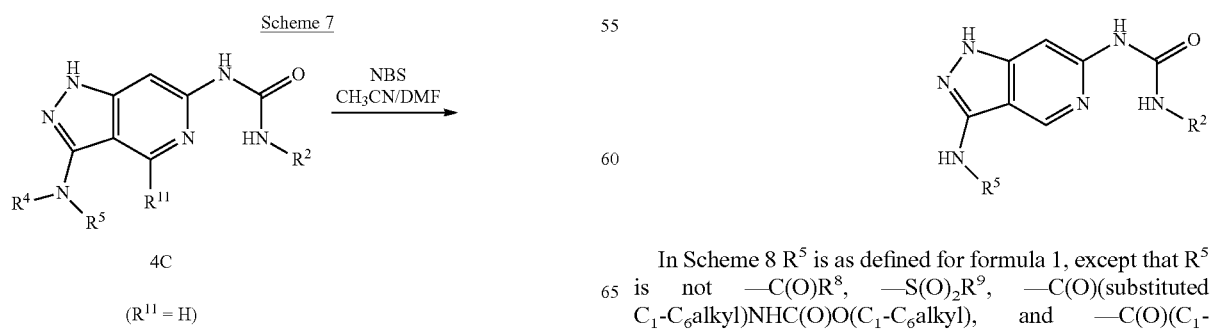

In Scheme 8 $R^5$ is as defined for formula 1, except that $R^5$ is not —C(O)$R^8$, —S(O)$_2R^9$, —C(O)(substituted $C_1$-$C_6$alkyl)NHC(O)O($C_1$-$C_6$alkyl), and —C(O)($C_1$-$C_6$alkyl)NHC(O)O($C_1$-$C_6$alkyl).

Scheme 9
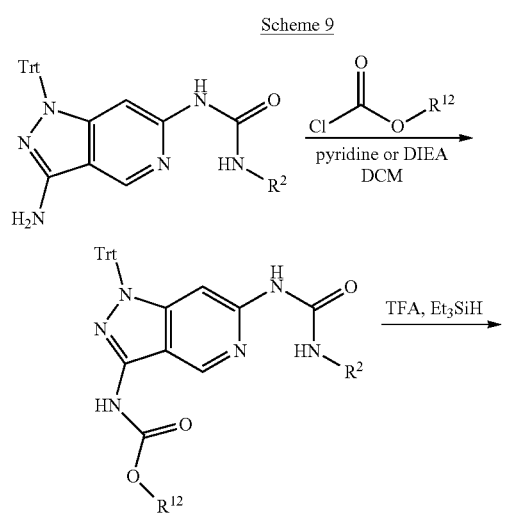
Scheme 10
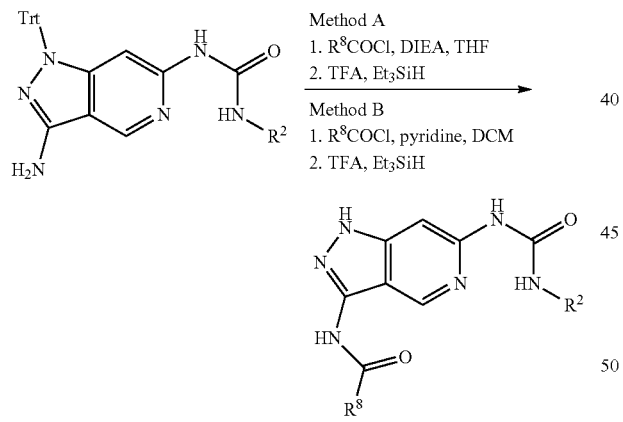
In Scheme 10 R$^8$ is as defined for formula 1, except that R$^8$ is not —OR$^{12}$, —NHR$^{12}$ and —NR$^{12}$R$^{13}$.
Scheme 11
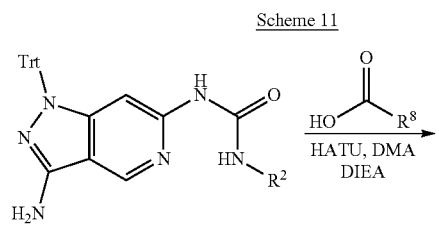
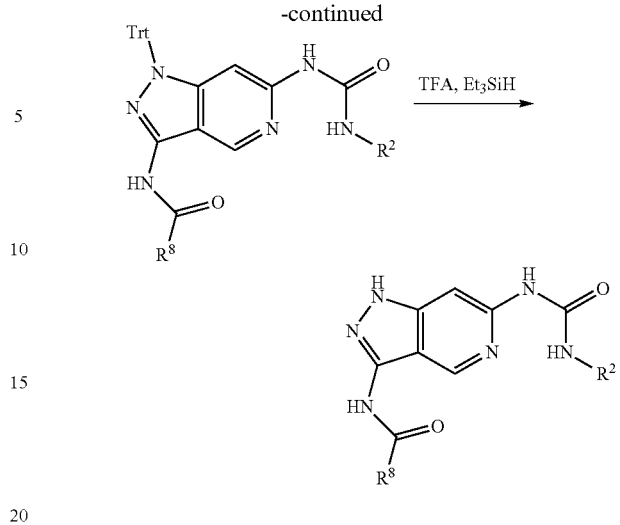
In Scheme 11 R$^8$ is as defined for formula 1, except that R$^8$ is not —OR$^{12}$, —NHR$^{12}$ and —NR$^{12}$R$^{13}$.
Scheme 12
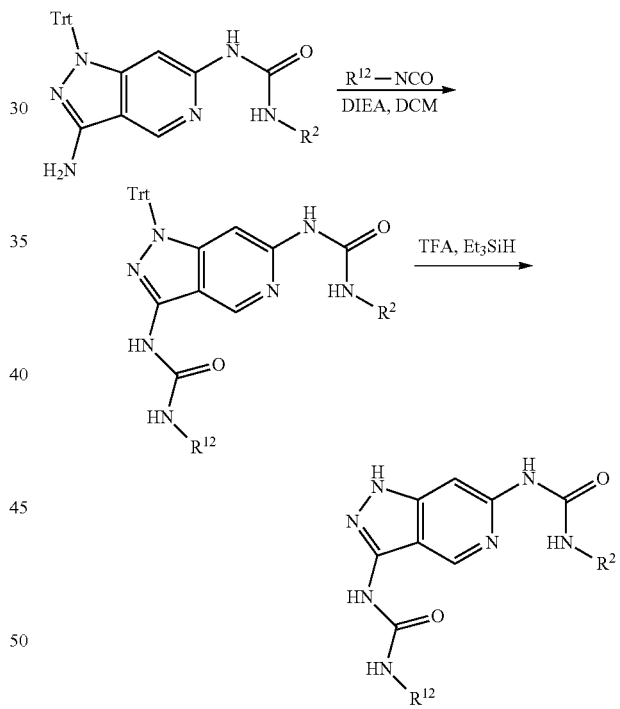
Scheme 13
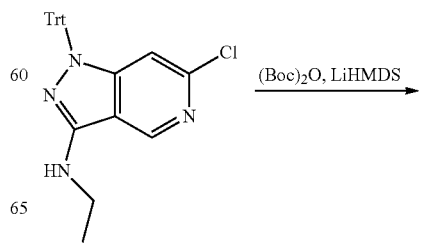

113
-continued
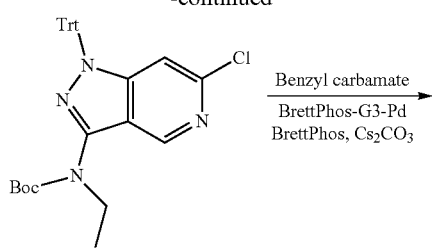
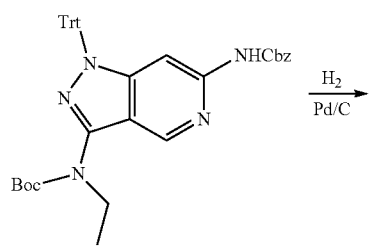
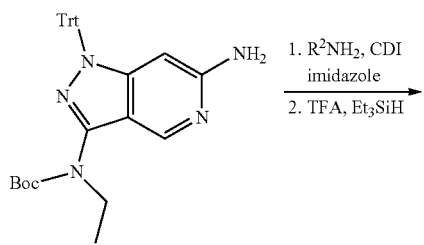
Scheme 14
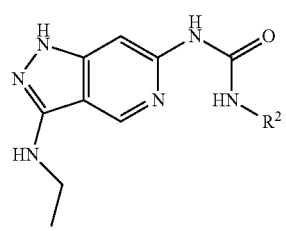
114
-continued
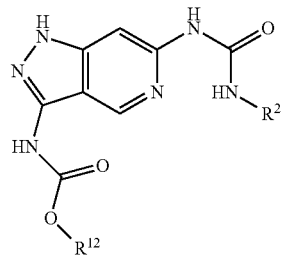
Scheme 15
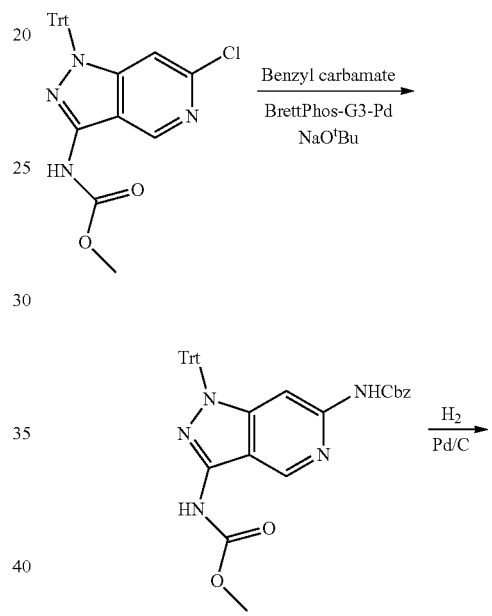
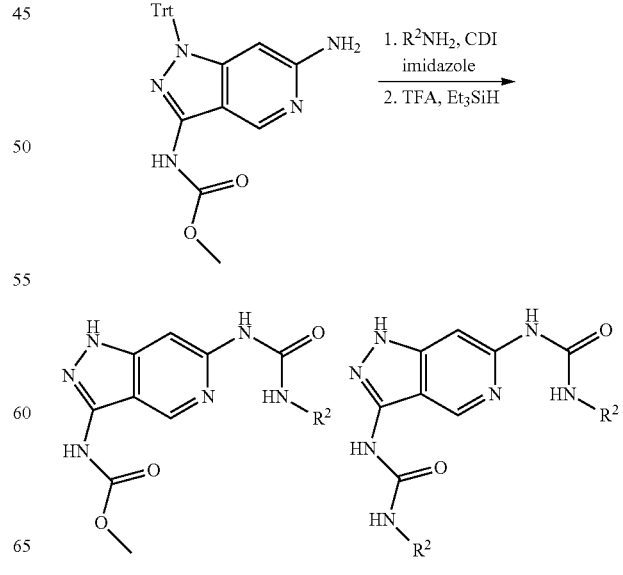

Intermediates

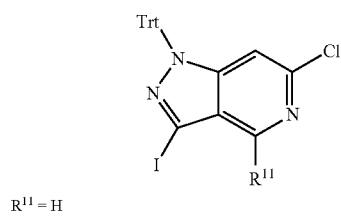

Intermediate 1C $R^{11}$ = H

6-Chloro-3-iodo-1-trityl-1H-pyrazolo[4,3-c]pyridine

6-Chloro-3-iodo-1-trityl-1H-pyrazolo[4,3-c]pyridine was synthesized according to the following scheme and procedures.

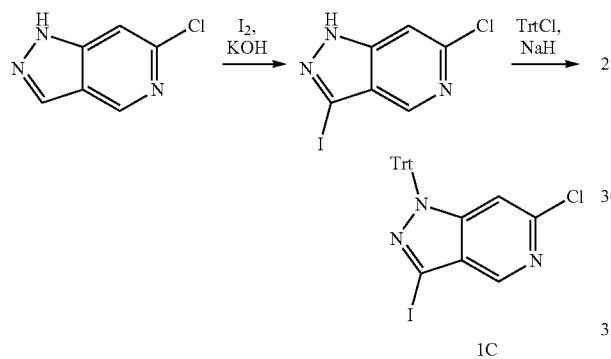

Step 1: 6-Chloro-3-iodo-1H-pyrazolo[4,3-c]pyridine

A flask was charged with 6-chloro-1H-pyrazolo[4,3-c]pyridine (3.0 g, 19.54 mmol), iodine (13.11 g, 51.7 mmol), KOH (3.29 g, 58.6 mmol) and DMF (60 mL). The mixture was heated at 40° C. for 16 h and then additional iodine (7.8 g, 30.7 mmol) and KOH (1.6 g, 28.4 mmol) were added. The mixture was heated at 70° C. for 3 h then quenched with 1N $Na_2S_2O_3$ and extracted with EtOAc. The organic phase was washed with water, brine, and dried over $Na_2SO_4$. After evaporation of volatiles DCM was added. A solid precipitated and filtered to yield 6-chloro-3-iodo-1H-pyrazolo[4,3-c]pyridine, which was carried onto the next step without further purification. MS ESI calc'd. for $C_6H_4ClIN_3$ [M+1]$^+$ 280. found 280.

Step 2: 6-Chloro-3-iodo-1-trityl-1H-pyrazolo[4,3-c]pyridine

A solution of 6-chloro-3-iodo-1H-pyrazolo[4,3-c]pyridine (1.874 g, 6.71 mmol) in THF (20 mL) was treated with NaH (60% in mineral oil; 0.402 g, 10.06 mmol) at 0° C. and the mixture was stirred for 50 min. Trityl chloride (2.244 g, 8.05 mmol) was added at 0° C. and the mixture was stirred for 16 h at room temperature, quenched with saturated $NH_4Cl$, and extracted with EtOAc. The organic phase was washed with water, brine, dried over $Na_2SO_4$, and concentrated in vacuo. The residue was purified via flash chromatography (0-10% EtOAc-hexanes) to yield 6-chloro-3-iodo-1-trityl-1H-pyrazolo[4,3-c]pyridine. MS ESI calc'd. for $C_{25}H_{18}ClIN_3$[M+1]$^+$ 522. found 522.

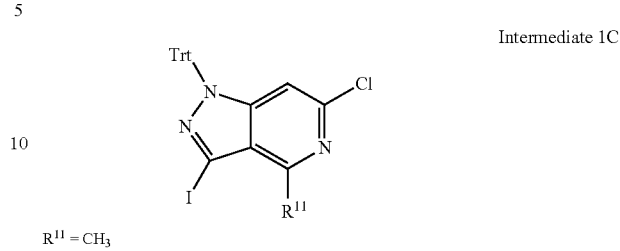

Intermediate 1C $R^{11}$ = $CH_3$

6-Chloro-3-iodo-4-methyl-1-trityl-1H-pyrazolo[4,3-c]pyridine

6-Chloro-3-iodo-4-methyl-1-trityl-1H-pyrazolo[4,3-c]pyridine was synthesized according to the following scheme and procedures.

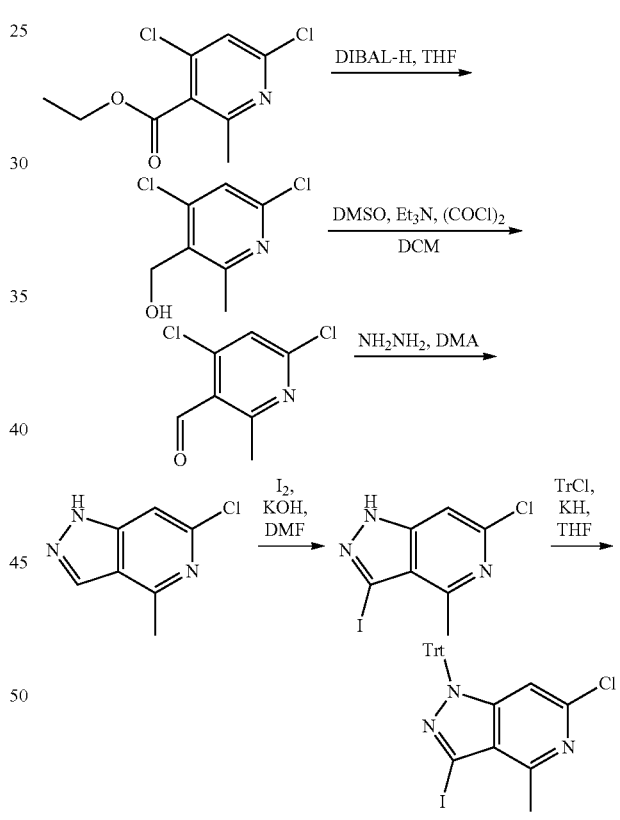

Step 1: (4,6-Dichloro-2-methylpyridin-3-yl)methanol

THF (52.3 mL) was cooled to 0° C. in a dry round bottomed flask under an atmosphere of $N_2$. Ethyl 4,6-dichloro-2-methylnicotinate (4.60 mL, 26.1 mmol) was then added followed by diisobutylaluminum hydride (57.5 mL, 57.5 mmol). The reaction was stirred at 0° C. for 3 h. The reaction was then poured into cold saturated sodium potassium tartrate solution. The mixture was stirred for several hours to allow the precipitate to dissolve, then the aqueous phase was extracted with EtOAc. The organic layer was dried over magnesium sulfate, filtered, and concentrated in vacuo. The residue was purified by flash chromatography (0-50% EtOAc/hexanes) to give (4,6-dichloro-2-methylpyridin-3-yl)methanol. MS ESI calc'd. for $C_7H_7Cl_2NO$ [M+1]$^+$ 192. found 192.

Step 2: 4,6-Dichloro-2-methylnicotinaldehyde

A dry flask was charged with DCM (59.9 mL) and oxalyl chloride (3.15 mL, 35.9 mmol) and cooled to −78° C. Dimethyl sulfoxide (3.40 mL, 47.9 mmol) was added and the reaction was stirred for 30 min. A solution of (4,6-dichloro-2-methylpyridin-3-yl)methanol (4.60 g, 23.95 mmol) in DCM (2 mL) was then added. The reaction was stirred for 30 min then triethylamine (6.74 mL, 71.9 mmol) was added and the reaction mixture was stirred at −78° C. for 30 min. The reaction was warmed to 0° C. and stirred for 1 h. The reaction was then quenched with sodium bicarbonate, diluted with water, and the aqueous layer extracted with EtOAc. The organic phase was washed with sat. sodium bicarbonate, dried over $MgSO_4$, filtered, and concentrated in vacuo to afford 4,6-dichloro-2-methylnicotinaldehyde, which was carried onto the next step without further purification. $^1$H NMR (500 MHz, DMSO-$d_6$) δ 10.60 (s, 1H), 7.37 (s, 1H), 2.80 (s, 3H).

Step 3: 6-Chloro-4-methyl-1H-pyrazolo[4,3-c]pyridine

A solution of 4,6-dichloro-2-methylnicotinaldehyde (5.25 g, 23.48 mmol) in DMA (50 mL) was treated with hydrazine (7.37 mL, 235 mmol) at 0° C. The reaction was stirred for 15 min and then warmed to 80° C. for 2 h. The reaction was cooled and diluted with EtOAc and washed with water. The organic phase was dried over $MgSO_4$, filtered, and concentrated in vacuo. The residue was purified by flash chromatography (0-100% EtOAc/hexanes) to give 6-chloro-4-methyl-1H-pyrazolo[4,3-c]pyridine. MS ESI calc'd. for $C_7H_6ClN_3$ [M+1]$^+$ 168. found 168.

Step 4: 6-Chloro-3-iodo-4-methyl-1H-pyrazolo[4,3-c]pyridine

A 100 mL round bottom flask was charged with 6-chloro-4-methyl-1H-pyrazolo[4,3-c]pyridine (1.20 g, 7.16 mmol) and DMF (28.5 mL). The reaction flask was warmed to 70° C. and KOH (1.2 g, 21.48 mmol) was added. Iodine (5.45 g, 21.48 mmol) was added gradually over 1 h. The reaction mixture was stirred for 3 h then additional KOH (3.2 g, 57.0 mmol) and iodine (15.6 g, 61.5 mmol) were added. The reaction was heated at 70° C. for 2 h. The reaction was poured into saturated sodium thiosulfate (500 mL) and diluted with EtOAc (200 mL). The aqueous phase was extracted with EtOAc (200 mL, ×2). The combined organic phase was washed with water (200 mL) and brine (200 mL), dried over $MgSO_4$, filtered, and concentrated in vacuo to give 6-chloro-3-iodo-4-methyl-1H-pyrazolo[4,3-c]pyridine. MS ESI calc'd. for $C_7H_5ClIN_3$ [M+1]$^+$ 294. found 294.

Step 5: 6-Chloro-3-iodo-4-methyl-1-trityl-1H-pyrazolo[4,3-c]pyridine

A flask containing 6-chloro-3-iodo-4-methyl-1H-pyrazolo[4,3-c]pyridine (2.06 g, 7.02 mmol) in THF (60 mL) was cooled to 0° C. and potassium hydride (1.126 g, 14.04 mmol) was added. The reaction was stirred for 30 min followed by addition of trityl chloride (2.94 g, 10.53 mmol). The reaction mixture was warmed to room temperature and stirred for 4 h. The reaction was poured into sat. sodium bicarbonate and extracted with EtOAc. The organic phase was dried over $MgSO_4$, filtered, and concentrated in vacuo. The residue was purified by flash chromatography (0-10% DCM/EtOAc) to give 6-chloro-3-iodo-4-methyl-1-trityl-1H-pyrazolo[4,3-c]pyridine. MS ESI calc'd. for $C_{26}H_{19}ClIN_3$ [M+1]$^+$ 536. found 536.

Intermediate 20C

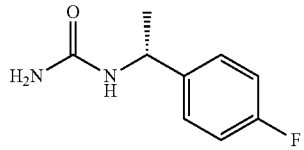

(R)-1-(1-(4-Fluorophenyl)ethyl)urea (R)-1-(1-(4-Fluorophenyl)ethyl)urea was prepared according to the following scheme and procedure.

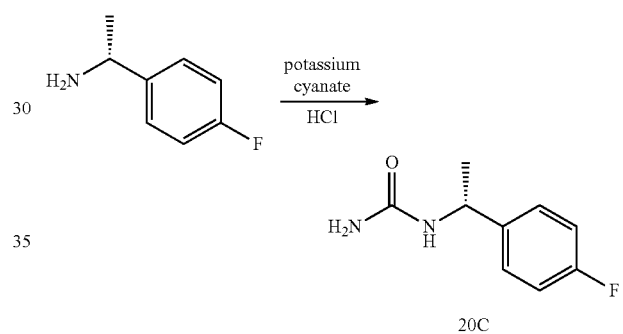

20C (R)-1-(4-Fluorophenyl)ethanamine (5.15 g, 37.0 mmol) was taken up in HCl (2N, 40 mL) and potassium cyanate (15.01 g, 185 mmol) was added. The mixture was stirred at 80° C. for 3 h. Upon cooling to room temperature, a precipitate formed which was collected by filtration and washed with water. The solid was partitioned between water and EtOAc, and the aqueous phase extracted once more with EtOAc. The combined organic extracts were dried over $Na_2SO_4$, filtered, and concentrated in vacuo to give (R)-1-(1-(4-fluorophenyl)ethyl)urea. MS ESI calc'd. for $C_9H_{11}FN_2O$ [M+1]$^+$ 183. found 183.

Intermediate 21C

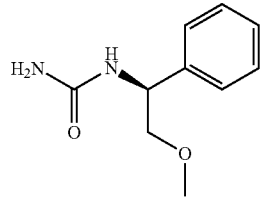

(S)-1-(2-Methoxy-1-phenylethyl)urea (S)-1-(2-Methoxy-1-phenylethyl)urea was prepared according to the following scheme and procedure.

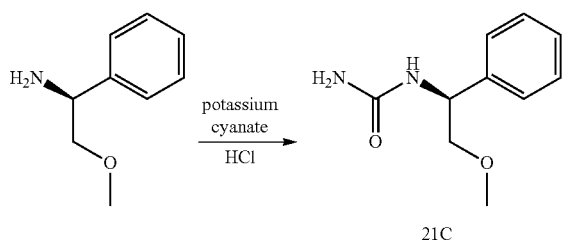

21C (S)-2-Methoxy-1-phenylethanamine (5.6 g, 37.0 mmol) and potassium cyanate (8.12 g, 100 mmol) were taken up in HCl (1 N, 40 mL, 40.0 mmol) and water (40 mL). The reaction mixture was heated to 100° C. for 3 h. Room temperature was attained, water was added, and the products extracted into EtOAc (×3) followed by 10% MeOH-DCM (×2). The combined organic extracts were washed with brine, dried over $Na_2SO_4$, filtered, and concentrated in vacuo. The residue was triturated in $Et_2O$ to give (S)-1-(2-methoxy-1-phenylethyl)urea. MS ESI calc'd. for $C_{10}H_{14}N_2O_2$ [M+1]$^+$ 195. found 195.

Intermediates 22C and 23C

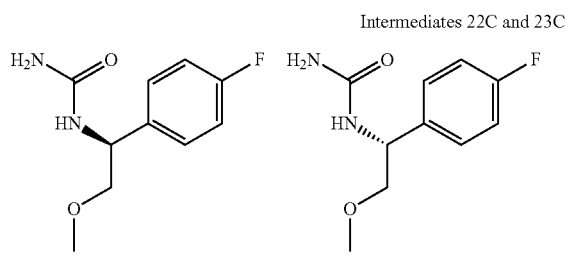

(S)-1-(1-(4-Fluorophenyl)-2-methoxyethyl)urea (Intermediate 22C) and (R)-1-(1-(4-fluorophenyl)-2-methoxyethyl)urea (Intermediate 23C)

(S)-1-(1-(4-Fluorophenyl)-2-methoxyethyl)urea and (R)-1-(1-(4-fluorophenyl)-2-methoxyethyl)urea were prepared according to the following scheme and procedures.

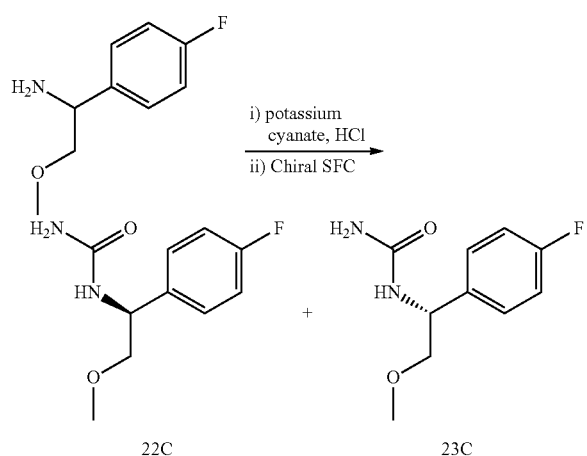

Step 1: 1-(1-(4-Fluorophenyl)-2-methoxyethyl)urea

To a microwave vial equipped with a stir bar was added 1-(4-fluorophenyl)-2-methoxyethanamine (1.2 g, 7.09 mmol) and water (10 mL). To this mixture was added HCl (1N, 7.23 mL, 7.23 mmol) and potassium cyanate (2.88 g, 35.5 mmol). The mixture was heated in a microwave reactor to 80° C. for 1 h. Saturated sodium bicarbonate was added and the products extracted into EtOAc (×4). The organic layers were combined, washed with brine (×2), and dried over $MgSO_4$. The material was concentrated in vacuo while loading onto silica gel. Purification by flash chromatography (0-10% EtOAc-Hexanes) gave 1-(1-(4-fluorophenyl)-2-methoxyethyl)urea. MS ESI calc'd. for $C_{10}H_{13}FN_2O_2$ [M+1]$^+$ 213. found 213.

Step 2: (S)-1-(1-(4-Fluorophenyl)-2-methoxyethyl) urea and (R)-1-(1-(4-fluorophenyl)-2-methoxyethyl) urea The enantiomers of 1-(1-(4-fluorophenyl)-2-methoxyethyl)urea (1.411 g, 6.65 mmol) were separated by SFC (Berger Multigram II SFC, column: Chiral Technology IC-H 2.1×25 cm, 5 uM, mobile phase: 20% to 80% MeOH in $CO_{2(l)}$, flow rate: 70 mL/min, 4 min run time). The fractions were collected and the solvent evaporated in vacuo to afford (S)-1-(1-(4-fluorophenyl)-2-methoxyethyl)urea and (R)-1-(1-(4-fluorophenyl)-2-methoxyethyl)urea. MS ESI calc'd. for $C_{10}H_{13}FN_2O_2$ [M+1]$^+$ 213. found 213 (Intermediate 22C) and MS ESI calc'd. for $C_{10}H_{13}FN_2O_2$ [M+1]$^+$ 213. found 213 (Intermediate 23C).

Intermediate 24C

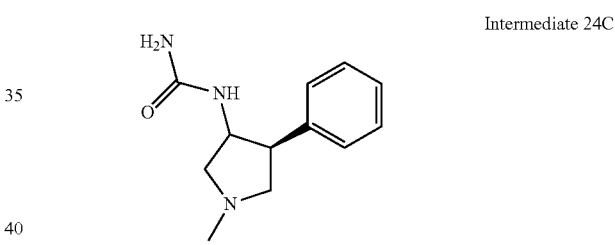

1-((3R and S, 4S and R)-1-Methyl-4-phenylpyrrolidin-3-yl)urea 1-((3R and S, 4S and R)-1-Methyl-4-phenylpyrrolidin-3-yl)urea was prepared according to the following scheme and procedures.

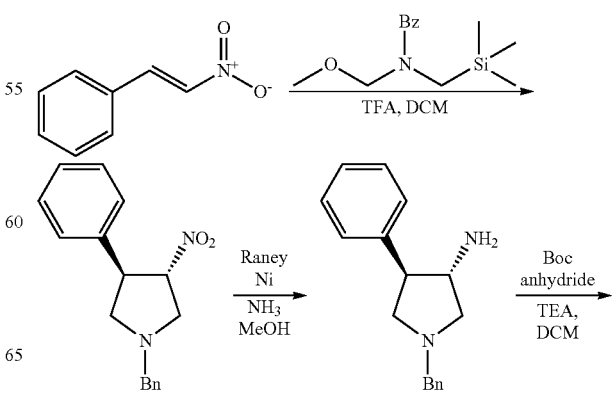

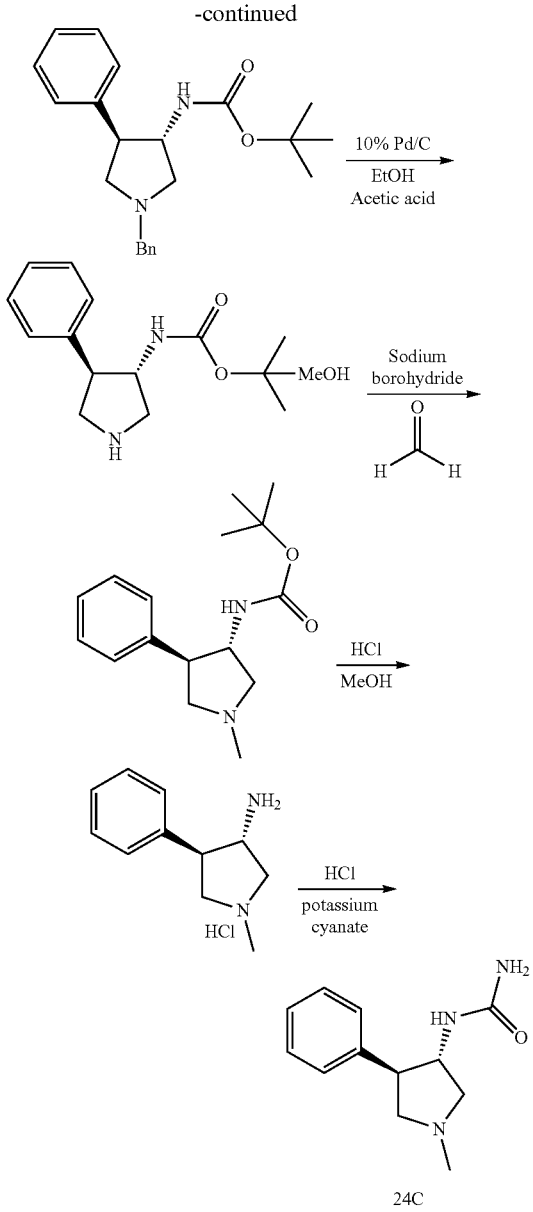

24C

Step 1: (3S and R, 4R and S)-1-Benzyl-3-nitro-4-phenylpyrrolidine

To a solution of (E)-(2-nitrovinyl)benzene (110 g, 0.738 mol) and TFA (8.42 g, 0.073 mol) in DCM (500 mL) was added N-benzyl-1-methoxy-N-((trimethylsilyl)methyl)-methanamine (351.4 g, 1.476 mol) in DCM (500 mL) drop-wise at 0° C. for a period of 30 min. Then the reaction mixture was stirred at room temperature for 48 h. After completion of the reaction, the mixture was concentrated in vacuo, dissolved in water, and extracted into EtOAc (×2, 1.0 L). The organic layer was separated, dried over anhydrous sodium sulfate, and concentrated in vacuo. The residue was purified via flash chromatography (20-80% petroleum ether/EtOAc) to afford (3S and R, 4R and S)-1-benzyl-3-nitro-4-phenylpyrrolidine. MS ESI calc'd. For $C_{17}H_{18}N_2O_2$ [M+1]$^+$ 283. found 283.

Step 2: (3S and R, 4R and S)-1-Benzyl-4-phenylpyrrolidin-3-amine

To a stirred solution of (3S and R, 4R and S)-1-benzyl-3-nitro-4-phenylpyrrolidine (100 g, 0.354 mol) in methanolic ammonia (1 L) was added Raney Ni (20 g) at room temperature in a 2.0 L hydrogenation flask. The reaction was hydrogenated at 100 psi for 12 h at room temperature. After completion of the reaction, the mixture was filtered through Celite and the filtrate was concentrated in vacuo to afford (3S and R, 4R and S)-1-benzyl-4-phenylpyrrolidin-3-amine, which was carried onto the next step without further purification. MS ESI calc'd. For $C_{17}H_{20}N_2$ [M+1]$^+$ 253. found 253.

Step 3: tert-Butyl ((3S and R, 4R and S)-1-benzyl-4-phenylpyrrolidin-3-yl)carbamate To a stirred solution of (3S and R, 4R and S)-1-benzyl-4-phenylpyrrolidin-3-amine (120.5 g, 0.476 mol) in DCM (1.2 L) was added triethylamine (48.1 g, 0.476 mol) and the reaction mixture was cooled to 0° C. Boc anhydride (103.84 g, 0.476 mol) was added drop-wise over a period of 30 min at 0° C. The resulting reaction mixture was stirred at room temperature for 12 h. After completion of the reaction, the mixture was diluted with water (3.0 L), the separated organic layer was dried over anhydrous sodium sulfate, and concentrated in vacuo to afford tert-butyl((3S and R, 4R and S)-1-benzyl-4-phenylpyrrolidin-3-yl)carbamate, which was carried onto the next step without further purification. MS ESI calc'd. For $C_{22}H_{28}N_2O_2$ [M+1]$^+$ 353. found 353.

Step 4: tert-Butyl((3S and R, 4R and S)-4-phenylpyrrolidin-3-yl)carbamate

To a stirred solution of ((3S and R, 4R and S)-1-benzyl-4-phenylpyrrolidin-3-yl)carbamate (115 g, 0.325 mol) and acetic acid (5 mL, 0.097 mol) in ethanol (1.5 L) was added 10% Pd-C (20 g) in a hydrogenation flask. The reaction was hydrogenated at 150 psi at 50° C. for 12 h. After completion of the reaction, the mixture was filtered through Celite and the filtrate was concentrated in vacuo. The crude compound was triturated with a minimum amount of EtOAc and dried under vacuum to afford tert-butyl((3S and R, 4R and S)-4-phenylpyrrolidin-3-yl)carbamate. MS ESI calc'd. For $C_{15}H_{22}N_2O_2$ [M+1]$^+$ 263. found 263.

Step 5: tert-Butyl((3R and S, 4S and R)-1-methyl-4-phenylpyrrolidin-3-yl)carbamate tert-Butyl((3R and S, 4S and R)-4-phenylpyrrolidin-3-yl)carbamate (1 g, 3.81 mmol) and formaldehyde (0.795 mL, 10.67 mmol) were dissolved in MeOH (15.25 mL) and treated with sodium borohydride (0.433 g, 11.44 mmol) at 0° C. The reaction was warmed to room temperature and stirred overnight. The crude reaction mixture was diluted with EtOAc and washed with water and brine. The aqueous layer was extracted with EtOAc and the combined organic layers were dried over sodium sulfate, filtered, and concentrated in vacuo to afford tert-butyl((3R and S, 4S and R)-1-methyl-4-phenylpyrrolidin-3-yl)carbamate, which was carried onto the next step without further purification. MS ESI calc'd. For $C_{16}H_{24}N_2O_2$ [M+1]$^+$ 277. found 277.

Step 6: (3R and S, 4S and R)-1-Methyl-4-phenylpyrrolidin-3-amine hydrochloride tert-Butyl((3R and S, 4S and R)-1-methyl-4-phenylpyrrolidin-3-yl)carbamate (860 mg, 3.11 mmol) was dissolved in methanolic HCl, (3N, 20 mL) and heated to 50° C. for 2 h. The reaction mixture was concentrated in vacuo to afford (3R and S,4S and R)-1-methyl-4-phenylpyrrolidin-3-amine hydrochloride as a white solid, which was carried onto the next step without further purification. MS ESI calc'd. For $C_{11}H_{16}N_2$ [M+1]$^+$ 177. found 177.

Step 7: 1-((3R and S, 4S and R)-1-Methyl-4-phenylpyrrolidin-3-yl)urea 1-((3R and S, 4S and R)-1-Methyl-4-phenylpyrrolidin-3-yl)urea was prepared using the same procedure described for (R)-1-(1-(4-fluorophenyl)ethyl)urea (Intermediate 20C). MS ESI calc'd. For $C_{12}H_{17}N_3O$ [M+1]$^+$ 220. found 220.

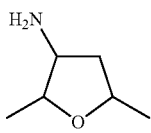

Intermediate 78A 2,5-Dimethyltetrahydrofuran-3-amine hydrochloride

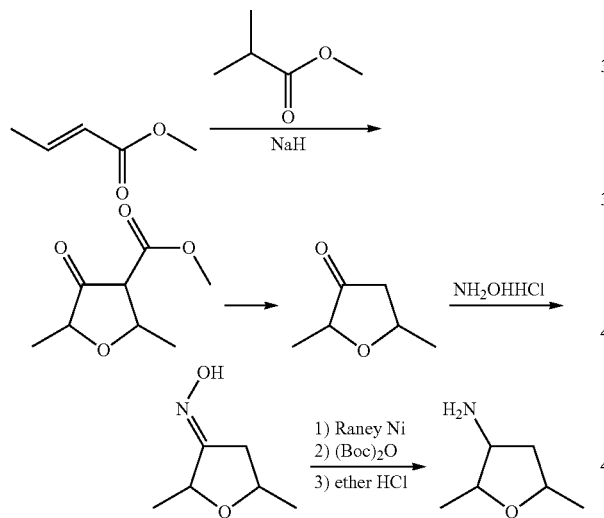

Step 1: Methyl 2,5-dimethyl-4-oxotetrahydrofuran-3-carboxylate

Methyl lactate (20.8 g, 0.2 mol) was added to a suspension of NaH (4.8 g, 0.2 mol) in ether (200 mL). After the cessation of hydrogen evolution the solvent was evaporated in vacuum and replaced by dry DMSO (100 mL). Methyl crotonate (22 g, 0.22 mol) was then added at 0° C. and allowed to warm up to 20° C. The mixture was poured into diluted $H_2SO_4$ and extracted with ether (×3, 150 mL). The organic phase was extracted with brine (×3) and dried over magnesium sulfate to give methyl 2,5-dimethyl-4-oxotetrahydrofuran-3-carboxylate.

Step 2: 2,5-Dimethyldihydrofuran-3(2H)-one

Methyl 2,5-dimethyl-4-oxotetrahydrofuran-3-carboxylate was refluxed in $H_2SO_4$ (10%, 100 mL) for 2 hours. After extraction with ether and washing with aqueous sodium bicarbonate solution, the organic layer was dried over magnesium sulfate. Distillation affords 2,5-dimethyldihydrofuran-3(2H)-one. $^1$H NMR (ppm, 300 MHz, CDCl$_3$): δ 4.4-4.6 (m, 1H), 4.0-4.2 (m, 2H), 3.7-3.8 (m, 1H), 2.5-2.7 (m, 2H), 2.2-2.3 (m, 2H), 1.2-1.5 (4d, 12H).

Step 3: 2,5-Dimethyldihydrofuran-3(2H)-one oxime

To a solution of 2,5-dimethyldihydrofuran-3(2H)-one (20 g, 0.175 mol) and NaOAc (43 g, 0.526 mol) in EtOH (300 mL), NH$_2$OH.HCl (15.8 g, 0.228 mol) was added portion in the mixture at 0° C. After addition, the reaction was stirred at rt for 3 h. Filtered, the filtrate was concentrated and the residue was dissolved in DCM, filtered, the filtrate was concentrated to give 2,5-dimethyldihydrofuran-3(2H)-one oxime. $^1$H NMR (ppm, 300 MHz, CDCl$_3$) δ 3.7-4.9 (m, 2H), 2.0-3.0 (m, 2H), 1.2-1.4 (m, 6H).

Step 4: 2,5-Dimethyltetrahydrofuran-3-amine hydrochloride

To a mixture of 2,5-dimethyldihydrofuran-3(2H)-one oxime (23 g, 0.175 mol) and Raney Ni (4 g) in THF/NH$_3$.H$_2$O (1:1, 200 mL) was stirred at 60° C. under 4 MPa for overnight. The mixture was cooled and filtered, the filtrate was concentrated to give 2,5-dimethyltetrahydrofuran-3-amine To a mixture of 2,5-dimethyltetrahydrofuran-3-amine and Et$_3$N (53.2 g, 0.526 mol) in DCM (300 mL), (Boc)$_2$O (42 g, 0.193 mol) was dissolved in DCM (100 mL) and dropwise added in the mixture at 0° C. After addition, the reaction mixture was stirred at rt. for 4 hours before water was added in the reaction. The aqueous phase was extracted with DCM, the organic layer was washed with H$_2$O, dried over Na$_2$SO$_4$, concentrated. The residue was purified by column to give tert-butyl (2,5-dimethyltetrahydrofuran-3-yl)carbamate hydrochloride. To a solution of tert-butyl(2,5-dimethyltetrahydrofuran-3-yl)carbamate hydrochloride in ether, ether.HCl was added dropwise at 0° C. After addition, the mixture was filtered to give 2,5-dimethyltetrahydrofuran-3-amine hydrochloride. $^1$H NMR (ppm, 300 MHz, D$_2$O) δ 3.5-4.4 (m, 3H), 1.5-2.7 (m, 2H), 1.2-1.3 (m, 6H).

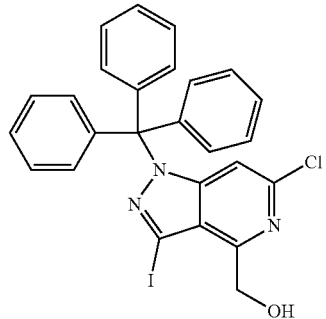

Intermediate 101A (6-Chloro-3-iodo-1-trityl-1H-pyrazolo[4,3-c]pyridin-4-yl)methanol

Step 1: 6-Chloro-3-iodo-1-trityl-1H-pyrazolo[4,3-c]pyridine-4-carbaldehyde

6-Chloro-3-iodo-4-methyl-1-trityl-1H-pyrazolo[4,3-c]pyridine (20 g, 37.3 mmol) was dissolved in dioxane (400 mL)

and selenium dioxide (12.43 g, 112 mmol) was added. The reaction mixture was stirred at 100° C. for 6 hrs. Selenium dioxide (4.14 g, 37.3 mmol) was added and the reaction mixture continued stirring at 100° C. overnight. The reaction was filtered over celite, rinsed with DCM, and concentrated in vacuo. The residue was dissolved in DCM (1.0 L) and filtered over celite. The material was concentrated in vacuo while loading on silica gel. Purification by flash chromatography (0-5% DCM/EtOAc) gave 6-chloro-3-iodo-1-trityl-1H-pyrazolo[4,3-c]pyridine-4-carbaldehyde (10.88 g, 19.79 mmol, 53.0%). $^1$H NMR (ppm, 500 MHz, DMSO-$d_6$) δ 10.54 (s, 1H), 7.39-7.35 (m, 10H), 7.17-7.11 (m, 5H), 6.29 (s, 1H).

Step 2: (6-Chloro-3-iodo-1-trityl-1H-pyrazolo[4,3-c]pyridin-4-yl)methanol

6-Chloro-3-iodo-1-trityl-1H-pyrazolo[4,3-c]pyridine-4-carbaldehyde (10.26 g, 18.66 mmol) was dissolved in DCM (250 mL) and methanol (125 mL). The reaction mixture was then cooled to 0° C. and sodium borohydride (0.706 g, 18.66 mmol) was added. The reaction mixture was stirred at room temperature for 15 min. The reaction was quenched with water and extracted with DCM. The combined organic layer was washed with brine, dried over sodium sulfate, filtered, and concentrated in vacuo while loading on silica gel. Purification by flash chromatography (2-10% DCM/EtOAc) gave (6-chloro-3-iodo-1-trityl-1H-pyrazolo[4,3-c]pyridin-4-yl)methanol (7.09 g, 12.85 mmol, 69%). MS ESI calc'd. for $C_{26}H_{19}ClN_3O$ [M+H]$^+$ 552. found 552.

Intermediate 128A

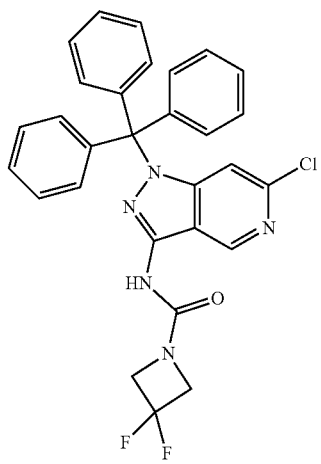

N-(6-chloro-1-trityl-1H-pyrazolo[4,3-c]pyridin-3-yl)-3,3-difluoroazetidine-1-carboxamide

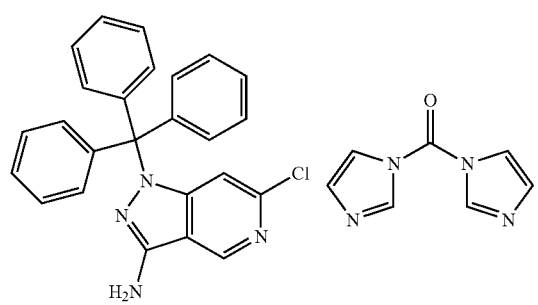

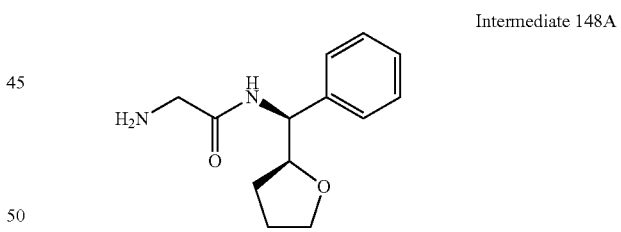

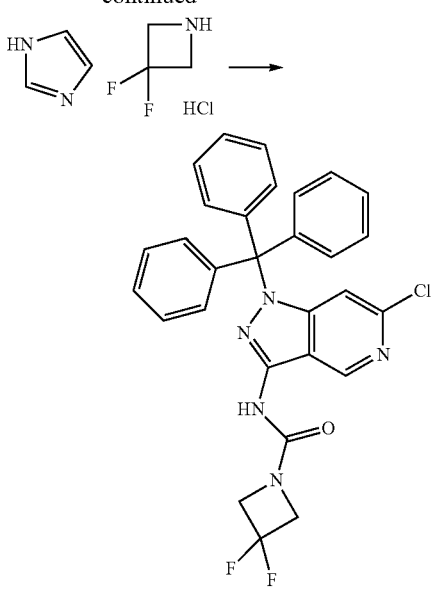

Di(1H-imidazol-1-yl)methanone (197 mg, 1.217 mmol) was added to a stirred mixture of 1H-imidazole (166 mg, 2.434 mmol) and 6-chloro-1-trityl-1H-pyrazolo[4,3-c]pyridin-3-amine (250 mg, 0.608 mmol) in CH$_2$Cl$_2$ (4 ml) and the mixture was stirred at room temperature for overnight. The second day, 3,3-difluoroazetidine hydrochloride (190 mg) was added and the mixture was heated at 50° C. for 3 hours, LCMS and TLC showed clean reaction. The mixture was directly loaded to a silica gel column eluting with EtOAc/Hexane=0% to 100% gradient to give N-(6-chloro-1-trityl-1H-pyrazolo[4,3-c]pyridin-3-yl)-3,3-difluoroazetidine-1-carboxamide (320 mg, 0.604 mmol, 99% yield).

Intermediate 148A

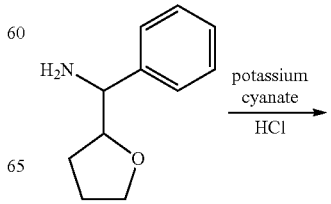

1-((S)-phenyl((S)-tetrahydrofuran-2-yl)methyl)urea

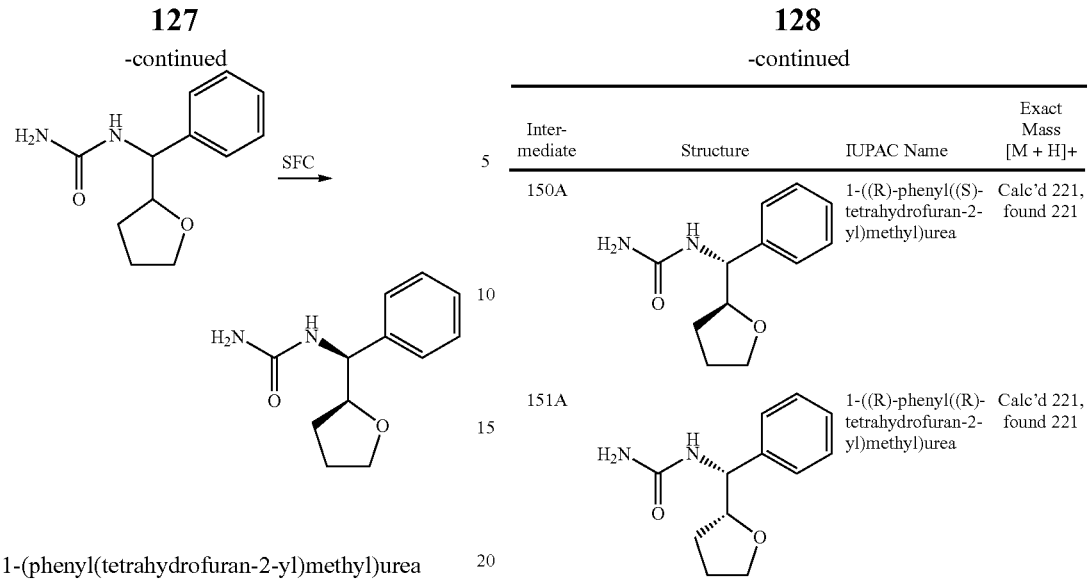

Step 1: 1-(phenyl(tetrahydrofuran-2-yl)methyl)urea

Phenyl(tetrahydrofuran-2-yl)methanamine HCl (640 mg, 2.99 mmol) was taken up in water (3 ml). Potassium cyanate (1215 mg, 14.97 mmol) and HCl (3 ml, 36.5 mmol) were then added. The reaction mixture was allowed to stir under microwave irradition at 80° C. for 1 hr. Saturated NaHCO$_3$ and EtOAc were added. The products were extracted into EtOAc (3×). The combined organic layers were washed with brine, dried over MgSO$_4$, and concentrated in vacuo to give 1-(phenyl(tetrahydrofuran-2-yl)methyl)urea. $^1$H NMR (ppm, 500 MHz, DMSO-d$_6$) δ 7.23 (m, 4H), 7.18 (m, 1H), 6.43 (d, J=9.5, 1H), 5.57 (br s, 2H), 4.68-4.47 (dd, J=3.5, J=5.5, 1H), 3.97 (m, 1H), 3.76 (q, J=8.0 1H), 3.56 (q, J=7.0, 1H), 1.79-1.75 (m, 3H), 1.73 (m, 1H).

Step 2: 1-((S)-phenyl((S)-tetrahydrofuran-2-yl)methyl)urea

The enantiomers of 1-(phenyl(tetrahydrofuran-2-yl)methyl)urea (150 mg, 0.681 mmol) were separated by SFC (Berger Multigram II, Column: Chiral Technology OZ-H 2.1×25 cm, 5uM, UV wavelength: 220 nM, mobile phase: 40%/60% Methanol+0.25% dimethyl ethylamine/CO$_{2(l)}$, flow rate: 70 mL/Min, 7 min run time). Elution was observed at 2.46 min. The fractions were collected and the solvent evaporated in vacuo to afford 1-((S)-phenyl((S)-tetrahydrofuran-2-yl)methyl)urea and Intermediates 149A-151A. $^1$H NMR (ppm, 500 MHz, DMSO-d$_6$) δ 7.23 (m, 4H), 7.18 (m, 1H), 6.43 (d, J=9.5, 1H), 5.57 (br s, 2H), 4.68-4.47 (dd, J=3.5, J=5.5, 1H), 3.97 (m, 1H), 3.76 (q, J=8.0 1H), 3.56 (q, J=7.0, 1H), 1.79-1.75 (m, 3H), 1.73 (m, 1H).

| Intermediate | Structure | IUPAC Name | Exact Mass [M + H]+ |
| --- | --- | --- | --- |
| 149A | 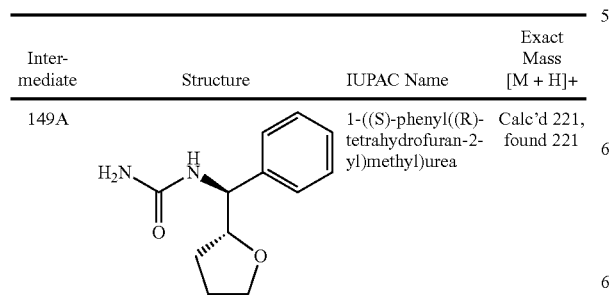 | 1-((S)-phenyl((R)-tetrahydrofuran-2-yl)methyl)urea | Calc'd 221, found 221 |
| 150A | 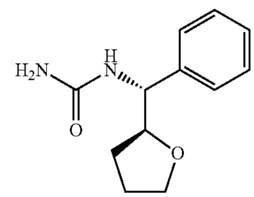 [SMILES: NC(=O)N[C@H](c1ccccc1)[C@@H]1CCCO1] | 1-((R)-phenyl((S)-tetrahydrofuran-2-yl)methyl)urea | Calc'd 221, found 221 |
| 151A | 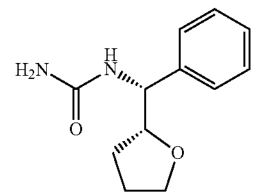 [SMILES: NC(=O)N[C@H](c1ccccc1)[C@H]1CCCO1] | 1-((R)-phenyl((R)-tetrahydrofuran-2-yl)methyl)urea | Calc'd 221, found 221 |

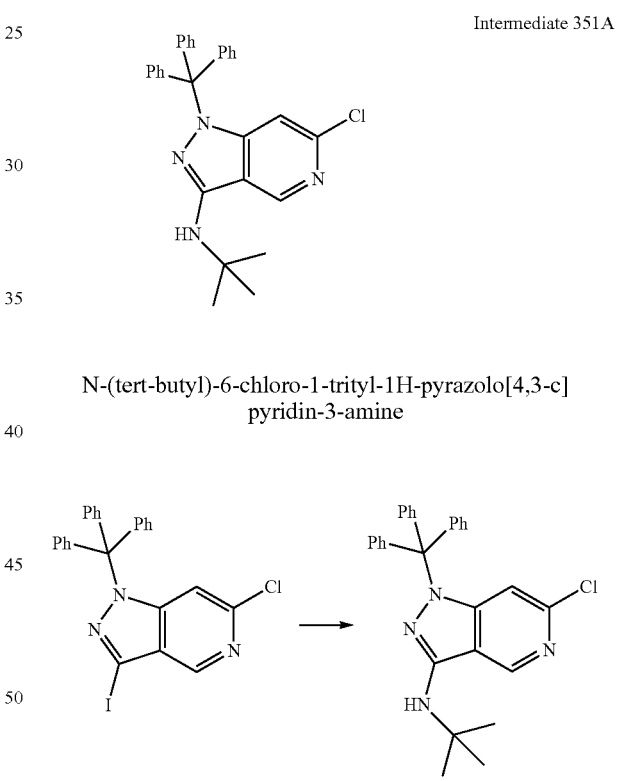

Intermediate 351A

N-(tert-butyl)-6-chloro-1-trityl-1H-pyrazolo[4,3-c]pyridin-3-amine

Step 1: N-(tert-butyl)-6-chloro-1-trityl-1H-pyrazolo[4,3-c]pyridin-3-amine

A mixture of 6-chloro-3-iodo-1-trityl-1H-pyrazolo[4,3-c]pyridine (1000 mg, 1.917 mmol), tert-butylamine (565 µl, 5.75 mmol), brettphos palladacycle (77 mg, 0.096 mmol), 2-dicyclohexylphosphino-2',6'-di-i-propoxy-1,1'-biphenyl (44.7 mg, 0.096 mmol) and sodium tert-butoxide (553 mg, 5.75 mmol) were degassed. Toluene (9583 µl) was added to and reaction system was degassed and heated at 110° C. for 8 h. Solvent was evaporated in vacuo and partioned between water and EtOAc. Aqueous layer was extracted with EtOAc (2×) and combined organics were washed with water and saturated aqeous Brine, dried over Na2SO4 and concentrated in vacuo on silica. Material was purified by normal phase column chromotography eluting with EtOAc/Hex (0-15%) affording N-(tert-butyl)-6-chloro-1-trityl-1H-pyrazolo[4,3-c]pyridin-3-amine (219 mg, 0.469 mmol, 24.47% yield) as a white solid. 1H NMR (ppm, 500 MHz, DMSO-d6) δ 8.81 (s, 1H), 7.52-7.13 (m, 15H), 6.30 (s, 1H), 5.76 (s, 1H), 1.24 (s, 9H). MS ESI calc'd. For $C_{29}H_{27}ClN_4[M+H]^+$ 467. found 467.

Intermediate 419A

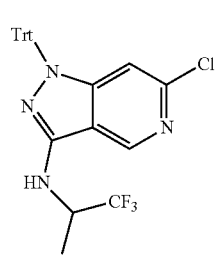

6-chloro-N-(1,1,1-trifluoropropan-2-yl)-1-trityl-1H-pyrazolo[4,3-c]pyridin-3-amine To a solution of 6-chloro-3-iodo-1-trityl-1H-pyrazolo[4,3-c]pyridine (0.5 g, 0.96 mmol) in anhydrous THF (5 mL) was added 1,1,1-trifluoropropan-2-amine (0.13 g, 1.2 mmol), t-Bu-X-Phos precatalyst (0.1 g, 0.14 mmol) and sodium-t-Butoxide (0.27 g, 2.8 mmol). The contents were heated to 80° C. in a sealed reaction vessel under inert atmosphere. After 4 h, the reaction mixture was brought back to ambient temperature, the reaction was quenched with H$_2$O (10 mL) and the organic contents were extracted with EtOAc (2×50 mL), dried over Na$_2$SO$_4$ and concentrated. The residue thus obtained was purified by flash column chromatography, to afford the title compound (0.32 g, 67% yield). MS ESI calc'd. for $C_{28}H_{22}ClF_3N_4$ [M+H]$^+$ 507. Found 507.

Intermediate 431A

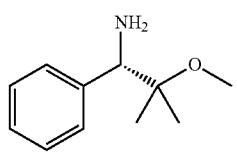

(S)-2-methoxy-2-methyl-1-phenylpropan-1-amine

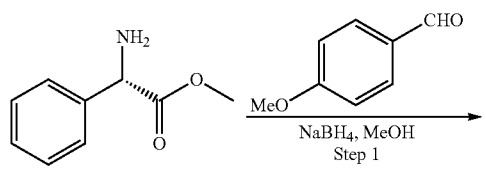

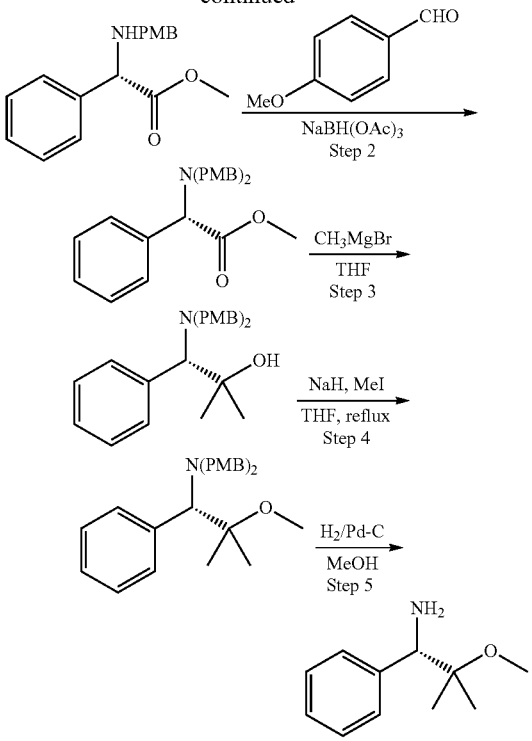

Step 1: Synthesis of (S)-methyl 2-((4-methoxybenzyl)amino)-2-phenylacetate

To a solution of (S)-methyl 2-amino-2-phenylacetate (1.0 g, 6.06 mmol) in anhydrous MeOH (20 mL) was added 4-methoxy benzaldehyde (0.82 g, 6.06 mmol) and few drops of HOAc. After 30 min, the reaction mixture was cooled to 0° C., NaBH$_4$ (0.69 g, 12.12 mmol) was added and the contents were stirred at ambient temperature. After 2 h, the reaction was quenched with ice cold H$_2$O (10 mL), MeOH was removed under reduced pressure and the organic contents were extracted with EtOAc (3×25 mL). The combined organic extracts were washed with brine (1×20 mL), dried over Na$_2$SO$_4$, concentrated and the residue thus obtained was taken directly for step 2. MS ES+APCI calc'd. for $C_{17}H_{19}NO_3$ [M+H]$^+$ 286. Found 286.

Step 2: Synthesis of (S)-methyl 2-(bis(4-methoxybenzyl)amino)-2-phenylacetate

To a solution of (S)-methyl 2-((4-methoxybenzyl)amino)-2-phenylacetate (1.6 g, 5.61 mmol) in anhydrous dichloroethane (20 mL) was added 4-methoxy benzaldehyde (0.76 g, 5.61 mmol) and few drops of HOAc. After 30 min, the reaction mixture was cooled to 0° C., sodium triacetoxy borohydride (2.38 g, 11.22 mmol) was added and the contents were allowed to stir at ambient temperature. After 2 h, the reaction was quenched with ice cold H$_2$O (10 mL), and the organic contents were extracted with CH$_2$Cl$_2$ (2×25 mL). The combined organic extracts were washed with brine (1×20 mL), dried over Na$_2$SO$_4$, concentrated and the residue thus obtained was purified by flash column chromatography to afford the title compoundas pale yellow liquid (1.5 g, 66%). MS ES+APCI calc'd. for $C_{25}H_{27}NO_4$ [M+H]$^+$ 406. Found 406.

Step 3: Synthesis of (S)-1-(bis(4-methoxybenzyl) amino)-2-methyl-1-phenylpropan-2-ol At 0° C., to a solution of (S)-methyl 2-(bis(4-methoxybenzyl)amino)-2-phenylacetate (1.5 g, 3.7 mmol) in anhydrous THF (15 mL), was added MeMgBr (3M solution in Et$_2$O, 12.3 mL, 37.0 mmol) and resultant mixture was allowed to warm and stirred at ambient temperature. After 10 h, the reaction was carefully quenched with saturated aqueous NH$_4$Cl solution (25 mL), and the organic contents were extracted with CH$_2$Cl$_2$ (3×50 mL). The volatiles were removed under reduced pressure and the residue thus obtained was further purified by flash column chromatography to afford the title compound. MS ES+APCI calc'd. for C$_{26}$H$_{31}$NO$_3$ [M+H]$^+$ 406. Found 406.

Step 4: Synthesis of (S)-2-methoxy-N,N-bis(4-methoxybenzyl)-2-methyl-1-phenylpropan-1-amine At 0° C., to a suspension of NaH (0.13 g, 2.96 mmol) in anhydrous THF (5 mL), was added a solution of (S)-1-(bis (4-methoxybenzyl)amino)-2-methyl-1-phenylpropan-2-ol (1.0 g, 2.47 mmol) in anhydrous THF (10 mL). After 15 min, MeI (0.55 g, 3.71 mmol) was added and the contents were heated to reflux. After 8 h, the reaction was brought back to ambient temperature, quenched carefully with ice cold H$_2$O (10 mL), and the organic contents were extracted with EtOAc (3×25 mL). The combined organic extracts were washed with brine (1×20 mL), dried over Na$_2$SO$_4$, concentrated to afford the title compound. H$^1$NMR (ppm, 400 MHz, CD$_3$OD) δ 7.45-7.44 (m, 2H), 7.37-7.34 (m, 2H), 7.33-7.28 (m, 5H), 6.88-6.86 (m, 4H), 4.20 (s, 1H), 3.78 (s, 6H), 3.25 (s, 4H), 2.81 (s, 3H), 1.4 (s, 3H), 0.81 (s, 3H). MS ES+APCI calc'd. for C$_{27}$H$_{33}$NO$_3$ [M+H]$^+$ 420. Found 420.

Step 5: Synthesis of (S)-2-methoxy-2-methyl-1-phenylpropan-1-amine

A solution of (S)-2-methoxy-N,N-bis(4-methoxybenzyl)-2-methyl-1-phenylpropan-1-amine (0.7 g, 1.67 mmol) in anhydrous MeOH was added Pd on C (0.1 g) and the contents were stirred at ambient temperature in H$_2$ atmosphere. After 14 h, the reaction mixture was filtered through a pad of celite and the volatiles were removed under reduced pressure. The residue thus obtained was further purified by preparative HPLC to afford the title compound. H$^1$NMR (ppm, 400 MHz, CDCl$_3$) δ 7.45-7.44 (m, 2H), 7.35-7.33 (m, 3H), 4.1 (s, 1H), 3.32 (s, 3H), 1.2 (s, 3H), 1.12 (s, 3H).

EXAMPLES

Examples 1-42 were prepared according to scheme 1.

Example 1

1-[(1R)-1-(4-Fluorophenyl)ethyl]-3-[3-(methylamino)-1H-pyrazolo[4,3-c]pyridin-6-yl]urea

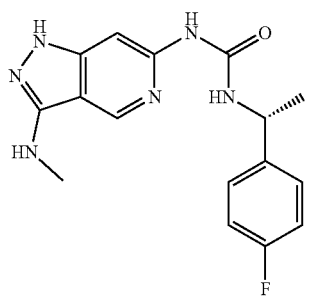

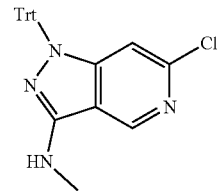

Step 1: 6-Chloro-N-methyl-1-trityl-1H-pyrazolo[4,3-c]pyridin-3-amine

6-Chloro-3-iodo-1-trityl-1H-pyrazolo[4,3-c]pyridine (Intermediate 1C; 6.08 g, 11.65 mmol), proline (0.42 g, 3.65 mmol), copper(I) iodide (0.24 g, 1.260 mmol), potassium carbonate (9.83 g, 71.1 mmol), and methylamine hydrochloride (3.26 g, 48.3 mmol) were stirred in DMSO (45 mL) at 70° C. for 24 h. Room temperature was attained, ammonium hydroxide was added, and the products extracted into DCM (×2). The combined organic extracts were washed with brine, dried over MgSO$_4$, filtered, and concentrated in vacuo. Purification of the residue by flash chromatography (6-50% EtOAc-hexanes) gave 6-chloro-N-methyl-1-trityl-1H-pyrazolo[4,3-c]pyridin-3-amine MS ESI calc'd. For C$_{26}$H$_{21}$ClN$_4$ [M+1]$^+$ 425. found 425.

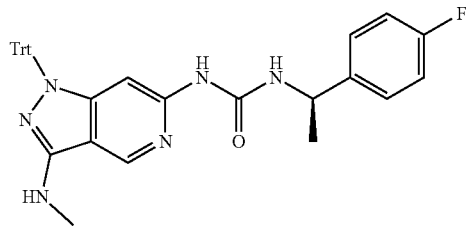

Step 2: (R)-1-(1-(4-Fluorophenyl)ethyl)-3-(3-(methylamino)-1-trityl-1H-pyrazolo[4,3-c]pyridin-6-yl) urea 6-Chloro-N-methyl-1-trityl-1H-pyrazolo[4,3-c]pyridin-3-amine (332 mg, 0.781 mmol), (R)-1-(1-(4-fluorophenyl) ethyl)urea (Intermediate 20C; 193 mg, 1.059 mmol), BrettPhos pre-catalyst (48.0 mg, 0.060 mmol), and cesium carbonate (759 mg, 2.330 mmol) were taken up in 1,4-dioxane (6 mL) in a 20 mL microwave vial. The vial was evacuated and back-filled with N$_2$ (×3) and the reaction was stirred at 100° C. for 3 h. Room temperature was attained, the reaction mixture was filtered through Celite, eluting with MeOH, and the filtrate was concentrated in vacuo. Purification of the residue by flash chromatography (0-100% EtOAc-DCM) gave (R)-1-(1-(4-fluorophenyl)ethyl)-3-(3-(methylamino)-1-trityl-1H-pyrazolo[4,3-c]pyridin-6-yl)urea. MS ESI calc'd. For C$_{35}$H$_{31}$FN$_6$O [M+1]$^+$ 571. found 571.

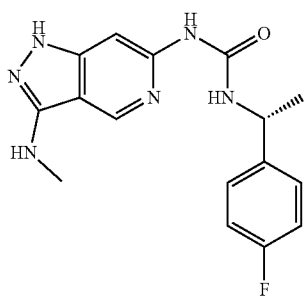

Step 3: 1-[(1R)-1-(4-Fluorophenyl)ethyl]-3-[3-(methylamino)-1H-pyrazolo[4,3-c]pyridin-6-yl]urea (R)-1-(1-(4-Fluorophenyl)ethyl)-3-(3-(methylamino)-1-trityl-1H-pyrazolo[4,3-c]pyridin-6-yl)urea (404 mg, 0.708 mmol) and triethylsilane (0.170 mL, 1.062 mmol) were stirred in TFA (5 mL) at room temperature for 30 min. The solvent was removed in vacuo, saturated NaHCO$_3$ was added, and the products extracted into EtOAc (×2). The combined organic extracts were washed with brine, dried over Na$_2$SO$_4$, filtered through Celite, and concentrated in vacuo. Purification of the residue by flash chromatography (0-15% MeOH-EtOAc) gave 1-[(1R)-1-(4-fluorophenyl)ethyl]-3-[3-(methylamino)-1H-pyrazolo[4,3-c]pyridin-6-yl]urea. MS ESI calc'd. For C$_{16}$H$_{17}$FN$_6$O [M+1]$^+$ 329. found 329. $^1$H NMR (500 MHz, DMSO-d$_6$) δ 11.48 (s, 1H), 8.86 (s, 1H), 8.54 (s, 1H), 8.05 (br s, 1H), 7.36 (dd, J=8.5, 5.5 Hz, 2H), 7.24 (s, 1H), 7.14 (t, J=9.0 Hz, 2H), 6.25 (q, J=5.0 Hz, 1H), 4.88-4.83 (m, 1H), 2.81 (d, J=5.0 Hz, 3H), 1.38 (d, J=6.5 Hz, 3H).

Example 2

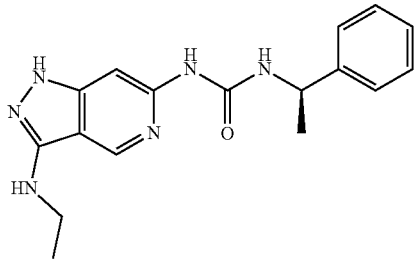

(R)-1-(3-(Ethylamino)-1H-pyrazolo[4,3-c]pyridin-6-yl)-3-(1-phenylethyl)urea

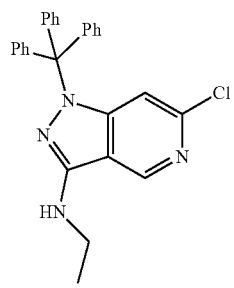

Step 1: 6-Chloro-N-ethyl-1-trityl-1H-pyrazolo[4,3-c]pyridin-3-amine

6-Chloro-3-iodo-1-trityl-1H-pyrazolo[4,3-c]pyridine (Intermediate 1C; 5.53 g, 10.60 mmol), proline (0.42 g, 3.65 mmol), copper (I) iodide (0.21 g, 1.103 mmol), potassium carbonate (7.40 g, 53.5 mmol), and ethylamine hydrochloride (2.78 g, 34.1 mmol) were stirred in DMSO (30 mL) at 70° C. for 24 h. Room temperature was attained, ammonium hydroxide was added and the products extracted into DCM (×2). The combined organic extracts were washed with brine, dried over MgSO$_4$, filtered, and concentrated in vacuo. Purification of the residue by flash chromatography (6-50% EtOAc-hexanes) gave 6-chloro-N-ethyl-1-trityl-1H-pyrazolo[4,3-c]pyridin-3-amine. MS ESI calc'd. For C$_{27}$H$_{23}$ClN$_4$ [M+1]$^+$ 439. found 439.

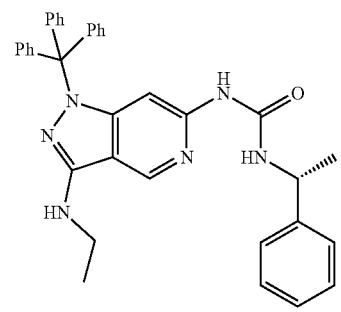

Step 2: (R)-1-(3-(Ethylamino)-1-trityl-1H-pyrazolo[4,3-c]pyridin-6-yl)-3-(1-phenylethyl)urea 6-Chloro-N-ethyl-1-trityl-1H-pyrazolo[4,3-c]pyridin-3-amine (3 g, 6.83 mmol), (R)-1-(1-phenylethyl)urea (1.68 g, 10.25 mmol), and BrettPhos pre-catalyst (546 mg, 0.68 mmol) were taken up in THF (13 mL). The resulting mixture was degassed for 5 min followed by addition of sodium tert-butoxide (6834 µL, 13.67 mmol) at room temperature. After the mixture was degassed again for 5 min, the reaction was heated to 50° C. under N$_2$ for 6 h, Room temperature was attained, sat NH$_4$Cl was added, and the mixture was extracted with EtOAc. The organic layer was washed with water, dried, filtered, and concentrated in vacuo. Purification of the residue by flash chromatography (0-100% EtOAc/Hexanes) gave (R)-1-(3-(ethylamino)-1-trityl-1H-pyrazolo[4,3-c]pyridin-6-yl)-3-(1-phenylethyl)urea. MS ESI calc'd. For C$_{36}$H$_{34}$N$_6$O [M+1]$^+$ 567. found 567.

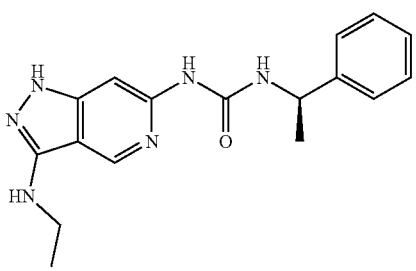

Step 3: (R)-1-(3-(Ethylamino)-1H-pyrazolo[4,3-c]pyridin-6-yl)-3-(1-phenylethyl)urea (R)-1-(3-(Ethylamino)-1-trityl-1H-pyrazolo[4,3-c]pyridin-6-yl)-3-(1-phenylethyl)urea (187 mg, 0.330 mmol) and triethylsilane (0.080 mL, 0.501 mmol) were stirred in TFA (2 mL) at room temperature for 30 min. The solvent was removed in vacuo, saturated NaHCO$_3$ was added, and the products extracted into EtOAc (×2). The combined organic extracts were washed with brine, dried over Na$_2$SO$_4$, filtered through Celite, and concentrated in vacuo. Purification of the residue by flash chromatography (0-10% MeOH-EtOAc) gave (R)-1-(3-(ethylamino)-1H-pyrazolo[4,3-c]pyridin-6-yl)-3-(1-phenylethyl)urea. MS ESI calc'd. For C$_{17}$H$_{20}$N$_6$O [M+1]$^+$ 325. found 325. $^1$H NMR (500 MHz, DMSO-d$_6$) δ 11.45 (s, 1H), 8.86 (s, 1H), 8.57 (s, 1H), 8.09 (br s, 1H), 7.34-7.31 (m, 4H), 7.25-7.20 (m, 2H), 6.21 (t, J=5.5 Hz, 1H), 4.89-4.83 (m, 1H), 3.25-3.19 (m, 2H), 1.39 (d, J=7.0 Hz, 3H), 1.18 (t, J=7.0 Hz, 3H). Examples 3-38 (Table 1) were prepared according to Scheme 1 following a similar procedure to that described for Example 1 using the appropriate pyrazolopyridine (Intermediate 1C), the appropriate aryl chlorides, and commercial or synthesized ureas (prepared using the same procedure as intermediates 20C-24C), which can be achieved by those of ordinary skill in the art of organic synthesis. The compounds of examples 6, 8, 9, 11, 12, 16, 17, 18, 21, 25, 27, 28, 30, and 38 were obtained as the trifluoroacetic acid salt.

TABLE 1

| Ex | Structure | IUPAC Name | Exact Mass [M + H]+ |
|---|---|---|---|
| 3 | 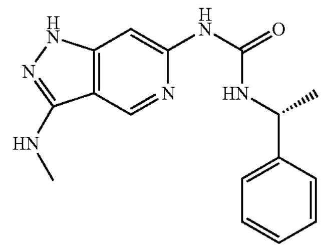 [SMILES: CNc1n[nH]c2cc(NC(=O)N[C@H](C)c3ccccc3)ncc12] | 1-[3-(methylamino)-1H-pyrazolo[4,3-c]pyridin-6-yl]-3-[(1R)-1-phenylethyl]urea | Calc'd 311, Found 311 |
| 4 | 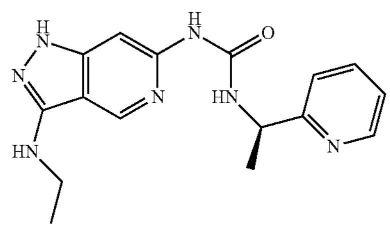 [SMILES: CCNc1n[nH]c2cc(NC(=O)N[C@H](C)c3ccccn3)ncc12] | 1-[3-(ethylamino)-1H-pyrazolo[4,3-c]pyridin-6-yl]-3-[(1R)-1-pyridin-2-ylethyl]urea | Calc'd 326, Found 326 |
| 5 | 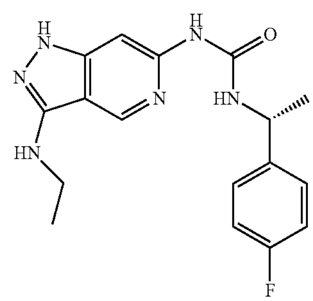 [SMILES: CCNc1n[nH]c2cc(NC(=O)N[C@H](C)c3ccc(F)cc3)ncc12] | 1-[3-(ethylamino)-1H-pyrazolo[4,3-c]pyridin-6-yl]-3-[(1R)-1-(4-fluorophenyl)ethyl]urea | Calc'd 343, Found 343 |
| 6 | 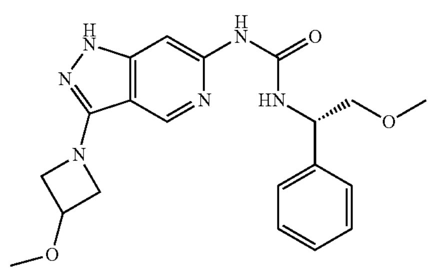 | 1-[3-(3-methoxyazetidin-1-yl)-1H-pyrazolo[4,3-c]pyridin-6-yl]-3-[(1S)-2-methoxy-1-phenylethyl]urea | Calc'd 397, Found 397 |

TABLE 1-continued

| Ex | Structure | IUPAC Name | Exact Mass [M + H]+ |
|---|---|---|---|
| 7 | 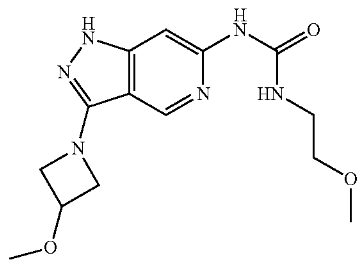 [SMILES: COCCNC(=O)Nc1cc2[nH]nc(N3CC(OC)C3)c2cn1] | 1-[3-(3-methoxyazetidin-1-yl)-1H-pyrazolo[4,3-c]pyridin-6-yl]-3-(2-methoxyethyl)urea | Calc'd 321, Found 321 |
| 8 | 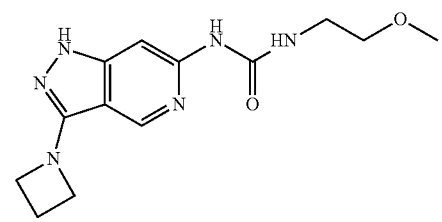 [SMILES: COCCNC(=O)Nc1cc2[nH]nc(N3CCC3)c2cn1] | 1-(3-azetidin-1-yl-1H-pyrazolo[4,3-c]pyridin-6-yl)-3-(2-methoxyethyl)urea | Calc'd 291, Found 291 |
| 9 | 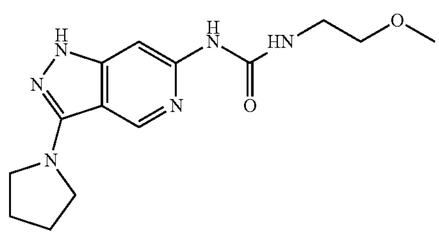 [SMILES: COCCNC(=O)Nc1cc2[nH]nc(N3CCCC3)c2cn1] | 1-(2-methoxyethyl)-3-(3-pyrrolidin-1-yl-1H-pyrazolo[4,3-c]pyridin-6-yl)urea | Calc'd 305, Found 305 |
| 10 | 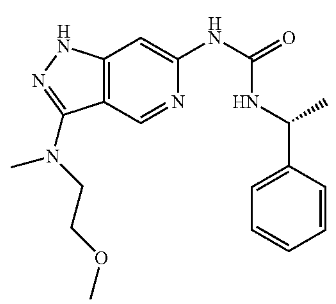 [SMILES: COCCN(C)c1n[nH]c2cc(NC(=O)N[C@H](C)c3ccccc3)ncc12] | 1-{3-[(2-methoxyethyl)(methyl)amino]-1H-pyrazolo[4,3-c]pyridin-6-yl}-3-[(1R)-1-phenylethyl]urea | Calc'd 369, Found 369 |
| 11 | 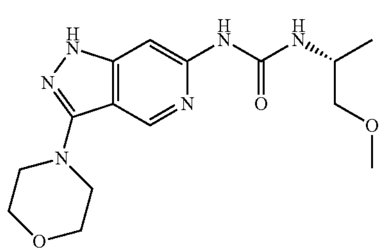 [SMILES: COC[C@@H](C)NC(=O)Nc1cc2[nH]nc(N3CCOCC3)c2cn1] | 1-[(1R)-2-methoxy-1-methylethyl]-3-(3-morpholin-4-yl-1H-pyrazolo[4,3-c]pyridin-6-yl)urea | Calc'd 335, Found 335 |
| 12 | 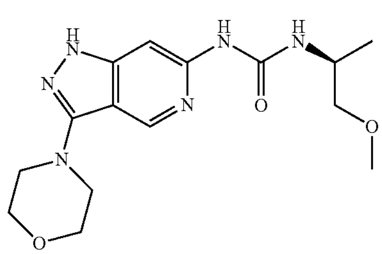 [SMILES: COC[C@H](C)NC(=O)Nc1cc2[nH]nc(N3CCOCC3)c2cn1] | 1-[(1S)-2-methoxy-1-methylethyl]-3-(3-morpholin-4-yl-1H-pyrazolo[4,3-c]pyridin-6-yl)urea | Calc'd 335, Found 335 |

TABLE 1-continued

| Ex | Structure | IUPAC Name | Exact Mass [M + H]+ |
|---|---|---|---|
| 13 | 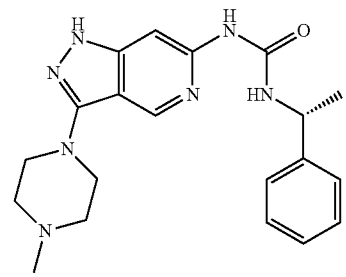 [SMILES: C[C@@H](NC(=O)Nc1cc2[nH]nc(N3CCN(C)CC3)c2cn1)c1ccccc1] | 1-[3-(4-methylpiperazin-1-yl)-1H-pyrazolo[4,3-c]pyridin-6-yl]-3-[(1R)-1-phenylethyl]urea | Calc'd 380, Found 380 |
| 14 | 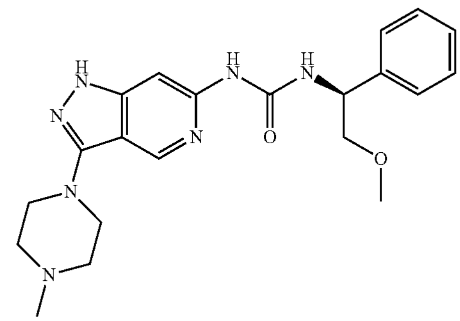 [SMILES: COC[C@@H](NC(=O)Nc1cc2[nH]nc(N3CCN(C)CC3)c2cn1)c1ccccc1] | 1-[(1S)-2-methoxy-1-phenylethyl]-3-[3-(4-methylpiperazin-1-yl)-1H-pyrazolo[4,3-c]pyridin-6-yl]urea | Calc'd 410, Found 410 |
| 15 | 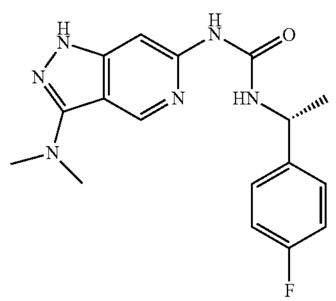 [SMILES: C[C@@H](NC(=O)Nc1cc2[nH]nc(N(C)C)c2cn1)c1ccc(F)cc1] | 1-[3-(dimethylamino)-1H-pyrazolo[4,3-c]pyridin-6-yl]-3-[(1R)-1-(4-fluorophenyl)ethyl]urea | Calc'd 343, Found 343 |
| 16 | 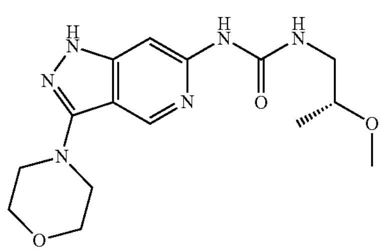 [SMILES: CO[C@H](C)CNC(=O)Nc1cc2[nH]nc(N3CCOCC3)c2cn1] | 1-[(2R)-2-methoxypropyl]-3-(3-morpholin-4-yl-1H-pyrazolo[4,3-c]pyridin-6-yl)urea | Calc'd 335, Found 335 |
| 17 | 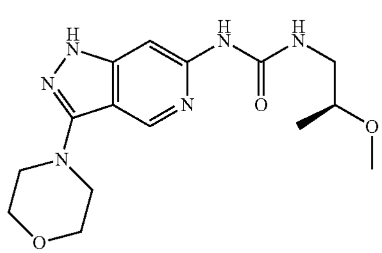 [SMILES: CO[C@@H](C)CNC(=O)Nc1cc2[nH]nc(N3CCOCC3)c2cn1] | 1-[(2S)-2-methoxypropyl]-3-(3-morpholin-4-yl-1H-pyrazolo[4,3-c]pyridin-6-yl)urea | Calc'd 335, Found 335 |

TABLE 1-continued

| Ex | Structure | IUPAC Name | Exact Mass [M + H]+ |
|---|---|---|---|
| 18 | 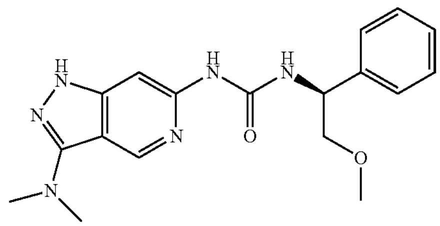 [SMILES: COC[C@@H](NC(=O)Nc1cc2[nH]nc(N(C)C)c2cn1)c1ccccc1] | 1-[3-(dimethylamino)-1H-pyrazolo[4,3-c]pyridin-6-yl]-3-[(1S)-2-methoxy-1-phenylethyl]urea | Calc'd 355, Found 355 |
| 19 | 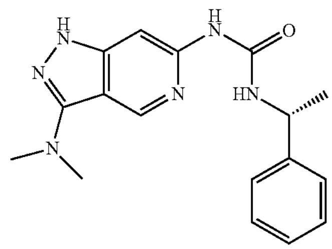 [SMILES: C[C@@H](NC(=O)Nc1cc2[nH]nc(N(C)C)c2cn1)c1ccccc1] | 1-[3-(dimethylamino)-1H-pyrazolo[4,3-c]pyridin-6-yl]-3-[(1R)-1-phenylethyl]urea | Calc'd 325, Found 325 |
| 20 | 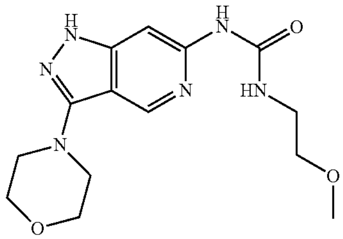 [SMILES: COCCNC(=O)Nc1cc2[nH]nc(N3CCOCC3)c2cn1] | 1-(2-methoxyethyl)-3-(3-morpholin-4-yl-1H-pyrazolo[4,3-c]pyridin-6-yl)urea | Calc'd 321, Found 321 |
| 21 | 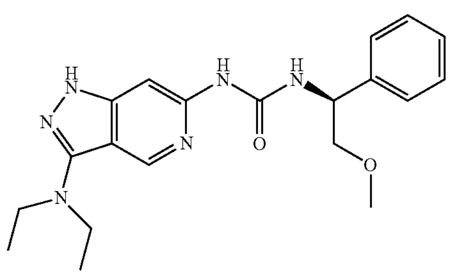 [SMILES: CCN(CC)c1n[nH]c2cc(NC(=O)N[C@H](COC)c3ccccc3)ncc12] | 1-[3-(diethylamino)-1H-pyrazolo[4,3-c]pyridin-6-yl]-3-[(1S)-2-methoxy-1-phenylethyl]urea | Calc'd 383, Found 383 |
| 22 | 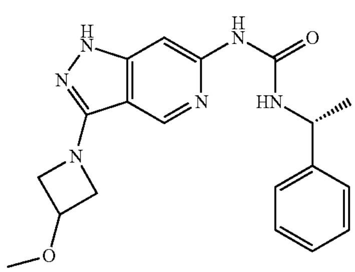 [SMILES: COC1CN(c2n[nH]c3cc(NC(=O)N[C@H](C)c4ccccc4)ncc23)C1] | 1-[3-(3-methoxyazetidin-1-yl)-1H-pyrazolo[4,3-c]pyridin-6-yl]-3-[(1R)-1-phenylethyl]urea | Calc'd 367, Found 367 |
| 23 | 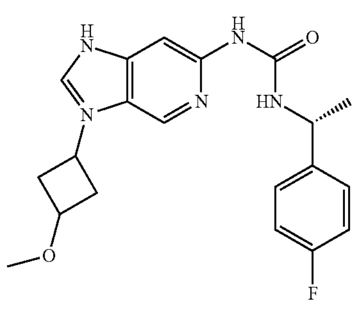 | 1-[(1R)-1-(4-fluorophenyl)ethyl]-3-[3-(3-methoxyazetidin-1-yl)-1H-pyrazolo[4,3-c]pyridin-6-yl]urea | Calc'd 385, Found 385 |

TABLE 1-continued

| Ex | Structure | IUPAC Name | Exact Mass [M + H]+ |
|---|---|---|---|
| 24 | 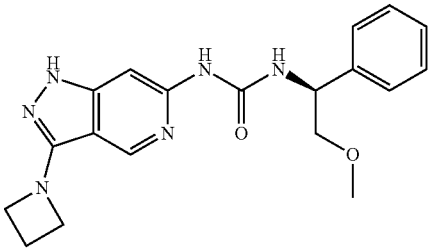 [SMILES: COC[C@@H](NC(=O)Nc1cc2[nH]nc(N3CCC3)c2cn1)c1ccccc1] | 1-(3-azetidin-1-yl-1H-pyrazolo[4,3-c]pyridin-6-yl)-3-[(1S)-2-methoxy-1-phenylethyl]urea | Calc'd 367, Found 367 |
| 25 | 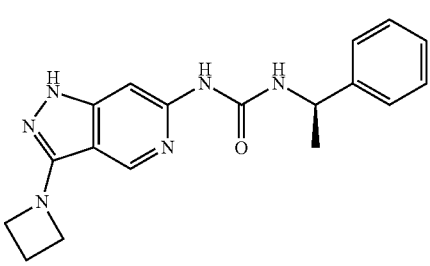 [SMILES: C[C@@H](NC(=O)Nc1cc2[nH]nc(N3CCC3)c2cn1)c1ccccc1] | 1-(3-azetidin-1-yl-1H-pyrazolo[4,3-c]pyridin-6-yl)-3-[(1R)-1-phenylethyl]urea | Calc'd 337, Found 337 |
| 26 | 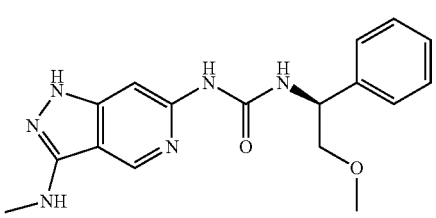 [SMILES: CNc1n[nH]c2cc(NC(=O)N[C@H](COC)c3ccccc3)ncc12] | 1-[(1S)-2-methoxy-1-phenylethyl]-3-[3-(methylamino)-1H-pyrazolo[4,3-c]pyridin-6-yl]urea | Calc'd 341, Found 341 |
| 27 | 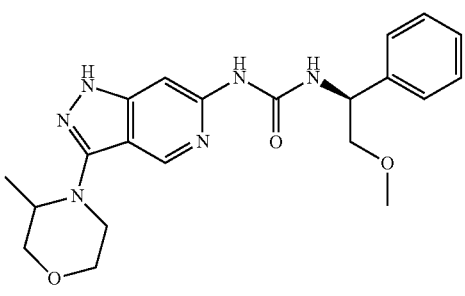 [SMILES: COC[C@@H](NC(=O)Nc1cc2[nH]nc(N3CCOCC3C)c2cn1)c1ccccc1] | 1-[(1S)-2-methoxy-1-phenylethyl]-3-[3-(3-methylmorpholin-4-yl)-1H-pyrazolo[4,3-c]pyridin-6-yl]urea | Calc'd 411, Found 411 |
| 28 | 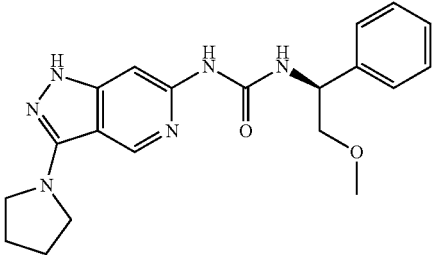 [SMILES: COC[C@@H](NC(=O)Nc1cc2[nH]nc(N3CCCC3)c2cn1)c1ccccc1] | 1-[(1S)-2-methoxy-1-phenylethyl]-3-(3-pyrrolidin-1-yl-1H-pyrazolo[4,3-c]pyridin-6-yl)urea | Calc'd 381, Found 381 |
| 29 | 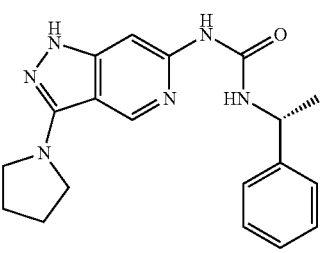 [SMILES: C[C@@H](NC(=O)Nc1cc2[nH]nc(N3CCCC3)c2cn1)c1ccccc1] | 1-[(1R)-1-phenylethyl]-3-(3-pyrrolidin-1-yl-1H-pyrazolo[4,3-c]pyridin-6-yl)urea | Calc'd 351, Found 351 |

TABLE 1-continued

| Ex | Structure | IUPAC Name | Exact Mass [M + H]+ |
|---|---|---|---|
| 30 | 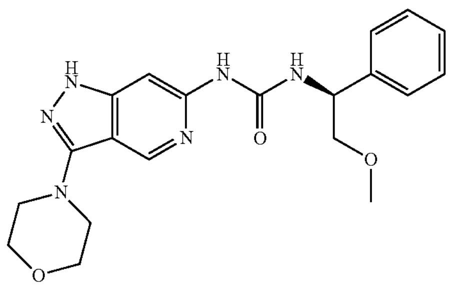 [SMILES: COC[C@@H](NC(=O)Nc1cc2[nH]nc(N3CCOCC3)c2cn1)c1ccccc1] | 1-[(1S)-2-methoxy-1-phenylethyl]-3-(3-morpholin-4-yl-1H-pyrazolo[4,3-c]pyridin-6-yl)urea | Calc'd 397, Found 397 |
| 31 | 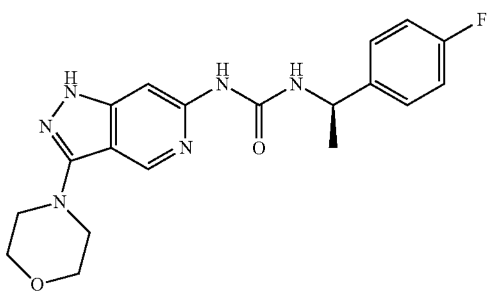 [SMILES: C[C@@H](NC(=O)Nc1cc2[nH]nc(N3CCOCC3)c2cn1)c1ccc(F)cc1] | 1-[(1R)-1-(4-fluorophenyl)ethyl]-3-(3-morpholin-4-yl-1H-pyrazolo[4,3-c]pyridin-6-yl)urea | Calc'd 385, Found 385 |
| 32 | 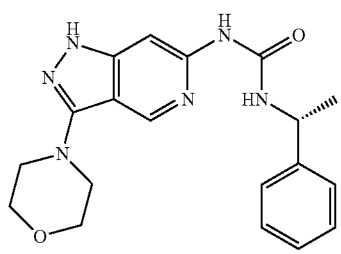 [SMILES: C[C@@H](NC(=O)Nc1cc2[nH]nc(N3CCOCC3)c2cn1)c1ccccc1] | 1-(3-morpholin-4-yl-1H-pyrazolo[4,3-c]pyridin-6-yl)-3-[(1R)-1-phenylethyl]urea | Calc'd 367, Found 367 |
| 33 | 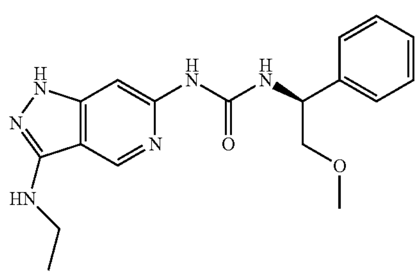 [SMILES: CCNc1n[nH]c2cc(NC(=O)N[C@H](COC)c3ccccc3)ncc12] | 1-[3-(ethylamino)-1H-pyrazolo[4,3-c]pyridin-6-yl]-3-[(1S)-2-methoxy-1-phenylethyl]urea | Calc'd 355, Found 355 |
| 34 | 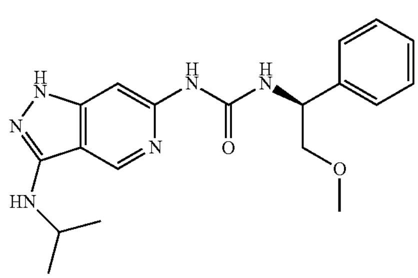 [SMILES: COC[C@@H](NC(=O)Nc1cc2[nH]nc(NC(C)C)c2cn1)c1ccccc1] | 1-[(1S)-2-methoxy-1-phenylethyl]-3-{3-[(1-methylethyl)amino]-1H-pyrazolo[4,3-c]pyridin-6-yl}urea | Calc'd 369, Found 369 |

TABLE 1-continued

| Ex | Structure | IUPAC Name | Exact Mass [M + H]+ |
|---|---|---|---|
| 35 | 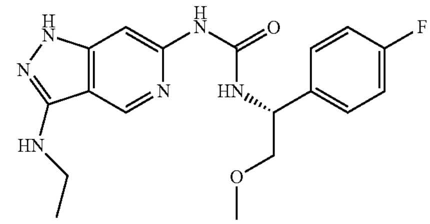 [SMILES: CCNc1n[nH]c2cc(NC(=O)N[C@@H](COC)c3ccc(F)cc3)ncc12] | 1-[3-(ethylamino)-1H-pyrazolo[4,3-c]pyridin-6-yl]-3-[(1R)-1-(4-fluorophenyl)-2-methoxyethyl]urea | Calc'd 373, Found 373 |
| 36 | 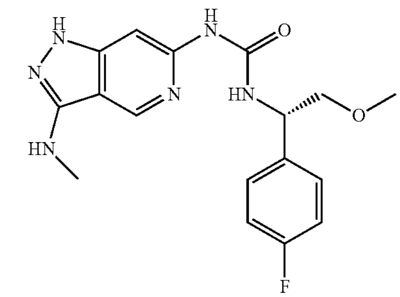 [SMILES: CNc1n[nH]c2cc(NC(=O)N[C@H](COC)c3ccc(F)cc3)ncc12] | 1-[(1S)-1-(4-fluorophenyl)-2-methoxyethyl]-3-[3-(methylamino)-1H-pyrazolo[4,3-c]pyridin-6-yl]urea | Calc'd 359, Found 359 |
| 37 | 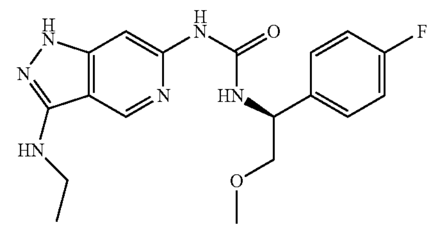 [SMILES: CCNc1n[nH]c2cc(NC(=O)N[C@H](COC)c3ccc(F)cc3)ncc12] | 1-[3-(ethylamino)-1H-pyrazolo[4,3-c]pyridin-6-yl]-3-[(1S)-1-(4-fluorophenyl)-2-methoxyethyl]urea | Calc'd 373, Found 373. |
| 38 | 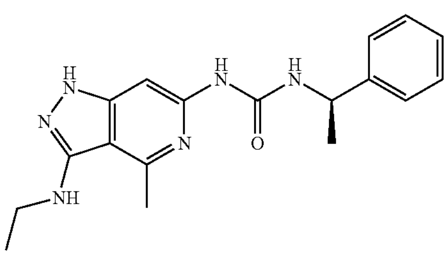 [SMILES: CCNc1n[nH]c2cc(NC(=O)N[C@H](C)c3ccccc3)nc(C)c12] | 1-[3-(ethylamino)-4-methyl-1H-pyrazolo[4,3-c]pyridin-6-yl]-3-[(1R)-1-phenylethyl]urea | Calc'd 339, Found 339 |

Examples 39 and 40

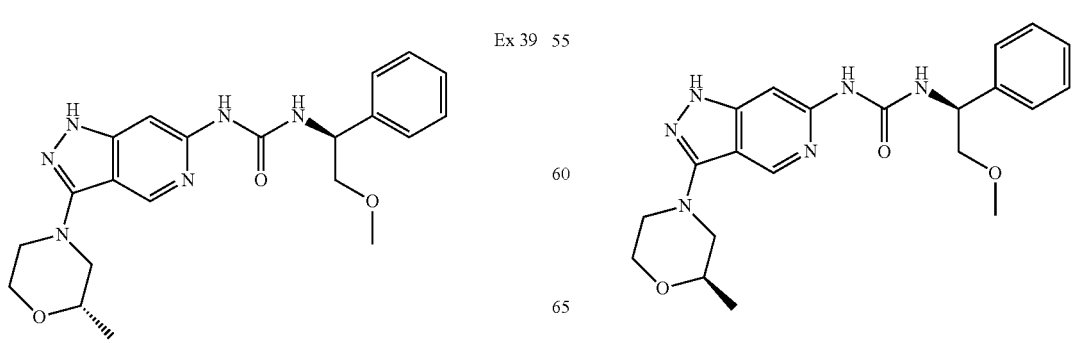

1-[(1S)-2-Methoxy-1-phenylethyl]-3-{3-[(2R)-2-methylmorpholin-4-yl]-1H-pyrazolo[4,3-c]pyridin-6-yl}urea (Example 39) and 1-[(1S)-2-methoxy-1-phenylethyl]-3-{3-[(2S)-2-methylmorpholin-4-yl]-1H-pyrazolo[4,3-c]pyridin-6-yl}urea (Example 40)

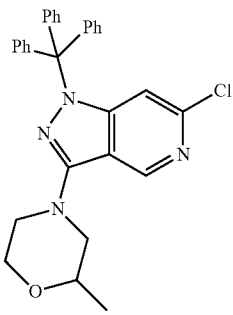 [SMILES: CC1CN(c2nn(C(c3ccccc3)(c3ccccc3)c3ccccc3)c3cc(Cl)ncc23)CCO1]

Step 1: 4-(6-Chloro-1-trityl-1H-pyrazolo[4,3-c]pyridin-3-yl)-2-methylmorpholine 4-(6-Chloro-1-trityl-1H-pyrazolo[4,3-c]pyridin-3-yl)-2-methylmorpholine was prepared using the same procedure described for 6-chloro-N-methyl-1-trityl-1H-pyrazolo[4,3-c]pyridin-3-amine (Example 1, Step 1). MS ESI calc'd. For $C_{30}H_{27}ClN_4O$ [M+1]$^+$ 495. found 495.

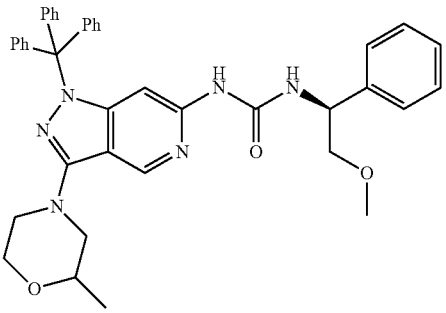 [SMILES: COC[C@@H](NC(=O)Nc1cc2c(cn1)c(N1CCOC(C)C1)nn2C(c1ccccc1)(c1ccccc1)c1ccccc1)c1ccccc1]

Step 2: 1-((S)-2-Methoxy-1-phenylethyl)-3-(3-(2-methylmorpholino)-1-trityl-1H-pyrazolo[4,3-c]pyridin-6-yl)urea 1-((S)-2-Methoxy-1-phenylethyl)-3-(3-(2-methylmorpholino)-1-trityl-1H-pyrazolo[4,3-c]pyridin-6-yl)urea was prepared using the same procedure described for (R)-1-(1-(4-fluorophenyl)ethyl)-3-(3-(methylamino)-1-trityl-1H-pyrazolo[4,3-c]pyridin-6-yl)urea (Example 1, Step 2). MS ESI calc'd. For $C_{40}J_{40}N_6O_3$ [M+1]$^+$ 653. found 653.

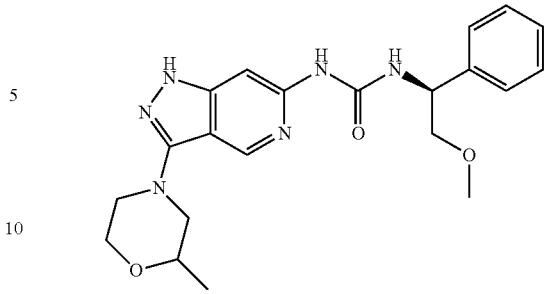

Step 3: 1-((S)-2-Methoxy-1-phenylethyl)-3-(3-(2-methylmorpholino)-1H-pyrazolo[4,3-c]pyridin-6-yl)urea 1-(S)-2-Methoxy-1-phenylethyl)-3-(3-(2-methylmorpholino)-1H-pyrazolo[4,3-c]pyridin-6-yl)urea was prepared using the same procedure described for 1-[(1R)-1-(4-fluorophenyl)ethyl]-3-[3-(methylamino)-1H-pyrazolo[4,3-c]pyridin-6-yl]urea (Example 1, Step 3). MS ESI calc'd. For $C_{21}H_{26}N_6O_3$ [M+1]$^+$ 411. found 411.

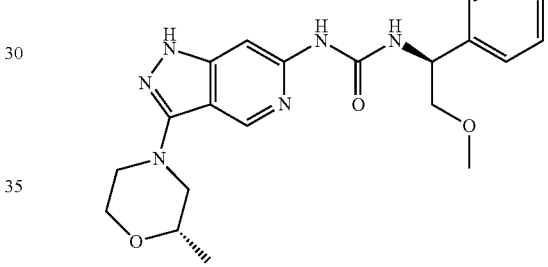

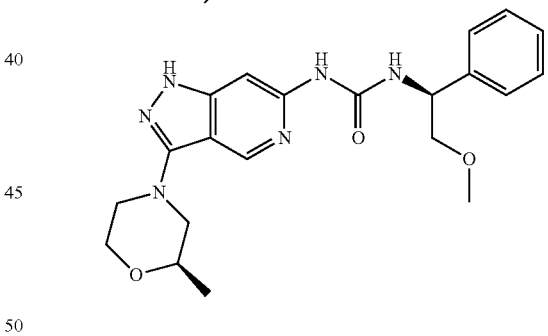

Step 4: 1-[(1S)-2-Methoxy-1-phenylethyl]-3-{3-[(2R)-2-methylmorpholin-4-yl]-1H-pyrazolo[4,3-c]pyridin-6-yl}urea and 1-[(1S)-2-methoxy-1-phenylethyl]-3-{3-[(2S)-2-methylmorpholin-4-yl]-1H-pyrazolo[4,3-c]pyridin-6-yl}urea The enantiomers of 1-((S)-2-Methoxy-1-phenylethyl)-3-(3-(2-methylmorpholino)-1H-pyrazolo[4,3-c]pyridin-6-yl)urea (38 mg, 0.072 mmol) were separated by SFC (Berger Multigram II SFC, column: Chiral Technology IC-H 2.1×25 cm, 5 uM, mobile phase: 39% to 61% MeOH+0.25% dimethyl ethylamine in $CO_{2(1)}$, flow rate: 70 mL/min, 6 min run time). The fractions were collected and the solvent evaporated in vacuo to afford 1-[(1S)-2-methoxy-1-phenylethyl]-3-{3-[(2R)-2-methylmorpholin-4-yl]-1H-pyrazolo[4,3-c]pyridin-6-yl}urea (9.91 mg, 0.024 mmol, 67%) and 1-[(1S)-

2-methoxy-1-phenylethyl]-3-{3-[(2S)-2-methylmorpholin-4-yl]-1H-pyrazolo[4,3-c]pyridin-6-yl}urea. MS ESI calc'd. For $C_{21}H_{26}N_6O_3$ [M+1]$^+$ 411. found 411. $^1$H NMR (500 MHz, DMSO-d$_6$) δ 12.01 (s, 1H), 9.09 (s, 1H), 8.82 (s, 1H), 8.09 (br s, 1H), 7.39 (s, 1H), 7.35-7.31 (m, 4H), 7.26-7.21 (m, 1H), 5.00-4.93 (m, 1H), 3.91-3.83 (m, 1H), 3.78 (d, J=12.0 Hz, 1H), 3.74-3.65 (m, 3H), 3.55 (d, J=5.4 Hz, 2H), 3.25 (s, 3H), 2.91-2.82 (m, 1H), 2.59-2.51 (m, 1H), 1.15 (d, J=6.2 Hz, 3H) (Example 39). MS ESI calc'd. For $C_{21}H_{26}N_6O_3$ [M+1]$^+$ 411. found 411. $^1$H NMR (500 MHz, DMSO-d$_6$) δ 12.02 (s, 1H), 9.35-9.16 (br s, 1H), 9.11 (s, 1H), 8.83 (s, 1H), 8.18-8.09 (br s, 1H), 7.38 (s, 1H), 7.35-7.29 (m, 4H), 7.27-7.20 (m, 8.7, 1H), 5.02-4.90 (m, 1H), 3.93-3.83 (m, 1H), 3.78 (d, J=11.8 Hz, 1H), 3.74-3.64 (m, 3H), 3.55 (d, J=5.4 Hz, 2H), 3.25 (s, 3H), 3.10-3.01 (m, 1H), 2.93-2.82 (m, 1H), 2.60-2.51 (m, 1H), 1.14 (d, J=6.0 Hz, 3H) (Example 40).

Examples 41 and 42

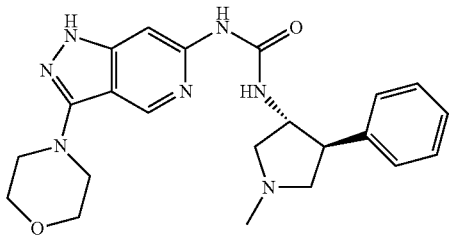

Ex 41

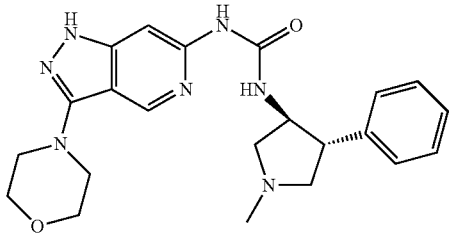

Ex 42

1-[(3R,4S)-1-Methyl-4-phenylpyrrolidin-3-yl]-3-(3-morpholin-4-yl-1H-pyrazolo[4,3-c]pyridin-6-yl)urea (Example 41) and 1-[(3S,4R)-1-methyl-4-phenylpyrrolidin-3-yl]-3-(3-morpholin-4-yl-1H-pyrazolo[4,3-c]pyridin-6-yl)urea (Example 42)

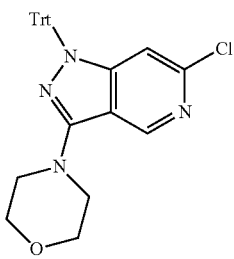

Step 1: 4-(6-Chloro-1-trityl-1H-pyrazolo[4,3-c]pyridin-3-yl)morpholine 4-(6-Chloro-1-trityl-1H-pyrazolo[4,3-c]pyridin-3-yl)morpholine was prepared using the same procedure described for 6-chloro-N-methyl-1-trityl-1H-pyrazolo[4,3-c]pyridin-3-amine (Example 1, Step 1). MS ESI calc'd. For $C_{29}H_{25}ClN_4O$ [M+1]$^+$ 481. found 481.

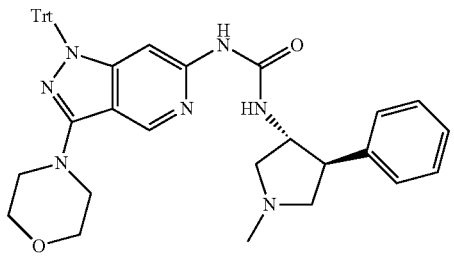

Step 2: 1-((3R and S, 4S and R)-1-Methyl-4-phenylpyrrolidin-3-yl)-3-(3-morpholino-1-trityl-1H-pyrazolo[4,3-c]pyridin-6-yl)urea 4-(6-Chloro-1-trityl-1H-pyrazolo[4,3-c]pyridin-3-yl)morpholine (200 mg, 0.416 mmol), 1-((3R and S, 4S and R)-1-methyl-4-phenylpyrrolidin-3-yl)urea (Intermediate 24C; 137 mg, 0.624 mmol), BrettPhos pre-catalyst (33.2 mg, 0.042 mmol) and potassium tert-butoxide (93 mg, 0.832 mmol) were taken up in DMA (2 mL) in a 5 mL microwave vial. The vial was degassed with argon and the reaction stirred at 100° C. overnight. Room temperature was attained, the reaction mixture was filtered through Celite, eluting with EtOAc. The filtrate was concentrated in vacuo with silica gel. The residue was purified by flash chromatography (0-10% DCM/MeOH) to give 1-((3R and S, 4S and R)-1-methyl-4-phenylpyrrolidin-3-yl)-3-(3-morpholino-1-trityl-1H-pyrazolo[4,3-c]pyridin-6-yl)urea. MS ESI calc'd. For $C_{41}H_{41}N_7O_2$ [M+1]$^+$ 664. found 664.

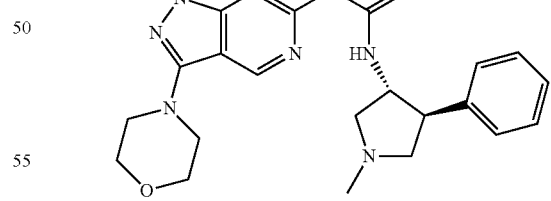

Step 3: 1-[(3R and S, 4S and R)-1-Methyl-4-phenylpyrrolidin-3-yl]-3-(3-morpholin-4-yl-1H-pyrazolo[4,3-c]pyridin-6-yl)urea 1-((3R and S, 4S and R)-1-Methyl-4-phenylpyrrolidin-3-yl)-3-(3-morpholino-1-trityl-1H-pyrazolo[4,3-c]pyridin-6-yl)urea (98.5 mg, 0.148 mmol) was dissolved in TFA (1 mL) and triethylsilane (0.036 mL, 0.223 mmol) was added. The reaction mixture was stirred at room temperature for 30 min. The reaction mixture was diluted with DMF (1 mL), filtered, and purified by mass-triggered reverse-phase HPLC. Fractions containing pure compound were concentrated in vacuo to afford 1-[(3R and S, 4S and R)-1-methyl-4-phenylpyrrolidin-3-yl]-3-(3-morpholin-4-yl-1H-pyrazolo[4,3-c]pyridin-6-yl)urea. MS ESI calc'd. For $C_{22}H_{27}N_7O_2$ $[M+1]^+$ 422. found 422.

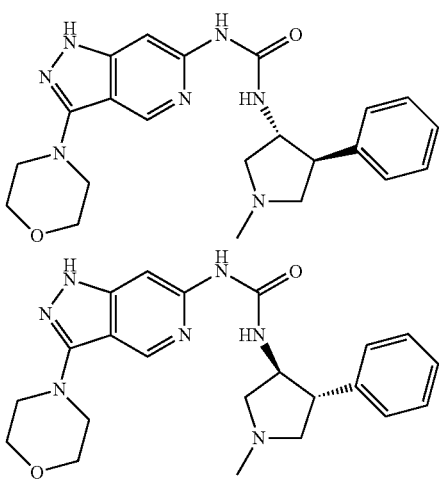

Step 4: 1-[(3R,4S)-1-Methyl-4-phenylpyrrolidin-3-yl]-3-(3-morpholin-4-yl-1H-pyrazolo[4,3-c]pyridin-6-yl)urea and 1-[(3S,4R)-1-methyl-4-phenylpyrrolidin-3-yl]-3-(3-morpholin-4-yl-1H-pyrazolo[4,3-c]pyridin-6-yl)urea The enatiomers of 1-[(3R and S, 4S and R)-1-Methyl-4-phenylpyrrolidin-3-yl]-3-(3-morpholin-4-yl-1H-pyrazolo[4,3-c]pyridin-6-yl)urea (63.5 mg, 0.098 mmol) were separated by SFC (Berger Multigram II SFC, column: Chiral Technology IC 2.1×25 cm, 5 uM, mobile phase: 40% to 60% MeOH+ 0.25% dimethyl ethylamine in $CO_{2(1)}$, flow rate: 70 mL/min, 12 min run time). The fractions were collected and the solvent evaporated in vacuo, dissolved in ACN/water, and lyophilized to afford 1-[(3R,4S)-1-methyl-4-phenylpyrrolidin-3-yl]-3-(3-morpholin-4-yl-1H-pyrazolo[4,3-c]pyridin-6-yl)urea (15.6 mg, 0.037 mmol, 50%) and 1-[(3S,4R)-1-methyl-4-phenylpyrrolidin-3-yl]-3-(3-morpholin-4-yl-1H-pyrazolo[4,3-c]pyridin-6-yl)urea (Example 42 was obtained as the trifluoroacetic acid salt of the compound). MS ESI calc'd. For $C_{22}H_{27}N_7O_2$ $[M+1]^+$ 422. found 422. $^1$H NMR (500 MHz, DMSO-$d_6$) δ 12.0 (s, 1H), 8.90 (s, 1H), 8.79 (s, 1H), 7.88-7.80 (m, 1H), 7.35 (s, 1H), 7.35-7.23 (m, 4H), 7.23-7.14 (m, 1H), 4.21-4.18 (m, 1H), 3.82-3.69 (m, 4H), 3.36-3.30 (m, 4H), 3.13-3.01 (m, 2H), 2.82 (dd, J=4.5, 9.4 Hz, 1H), 2.54 (dd, J=4.5, 9.4 Hz, 1H), 2.43-2.33 (m, 1H), 2.28 (s, 3H) (Example 41). MS ESI calc'd. For $C_{22}H_{27}N_7O_2$ $[M+1]^+$ 422. found 422. $^1$H NMR (500 MHz, DMSO-$d_6$) δ 12.02 (s, 1H), 8.97 (s, 1H), 8.79 (s, 1H), 7.88-7.80 (m, 1H), 7.32 (s, 1H), 7.35-7.23 (m, 4H), 7.23-7.14 (m, 1H), 4.21-4.18 (m, 1H), 3.81-3.70 (m, 4H), 3.36-3.30 (m, 4H), 3.13-3.01 (m, 2H), 2.82 (dd, J=4.5, 9.4 Hz, 1H), 2.54 (dd, J=4.5, 9.4 Hz, 1H), 2.43-2.33 (m, 1H), 2.28 (s, 3H). (Example 42).

Examples 43-46 were prepared according to scheme 2.

Example 43

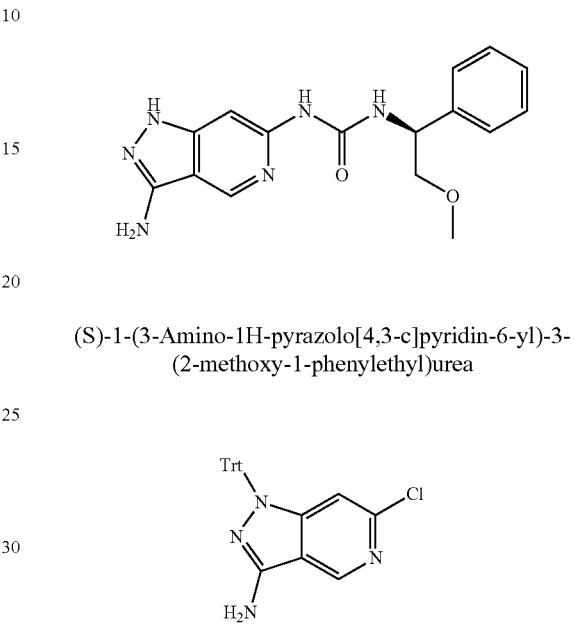

(S)-1-(3-Amino-1H-pyrazolo[4,3-c]pyridin-6-yl)-3-(2-methoxy-1-phenylethyl)urea

Step 1: 6-Chloro-1-trityl-1H-pyrazolo[4,3-c]pyridin-3-amine

A mixture of 6-chloro-3-iodo-1-trityl-1H-pyrazolo[4,3-c]pyridine (Intermediate 1C; 5.0 g, 9.58 mmol), acetylacetone (0.979 mL, 9.58 mmol), cupric acetylacetonate (0.251 g, 0.958 mmol), and cesium carbonate (6.24 g, 19.17 mmol) in DMF (25.2 mL) were charged in a sealed vessel. The system was degassed and ammonium hydroxide (13.33 mL, 96 mmol) was added. The reaction was heated at 60° C. for 16 h. The reaction was then poured into a solution of 10% $NH_4OH$ aq. (150 mL), brine (50 mL), and EtOAc (75 mL). The layers were separated and the aqueous phase was extracted with EtOAc (75 mL). The combined organic layers were washed with brine, dried over $Na_2SO_4$, and evaporated in vacuo. The residue was purified by flash chromatography (0-45% EtOAc/Hexanes) to afford 6-chloro-1-trityl-1H-pyrazolo[4,3-c]pyridin-3-amine. MS ESI calc'd. for $C_{25}H_{19}ClN_4$ $[M+1]^+$ 411. found 411.

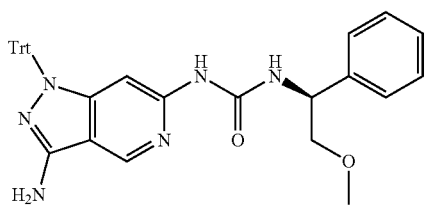

Step 2: (S)-1-(3-Amino-1-trityl-1H-pyrazolo[4,3-c]pyridin-6-yl)-3-(2-methoxy-1-phenylethyl)urea (S)-1-(3-amino-1-trityl-1H-pyrazolo[4,3-c]pyridin-6-yl)-3-(2-methoxy-1-phenylethyl)urea was prepared using the same procedure described for (R)-1-(1-(4-fluorophenyl)ethyl)-3-(3-(methylamino)-1-trityl-1H-pyrazolo[4,3-c]pyridin-6-yl)urea (Example 1, Step 2). MS ESI calc'd. For $C_{35}H_{32}N_6O_2$ [M+1]$^+$ 569. found 569.

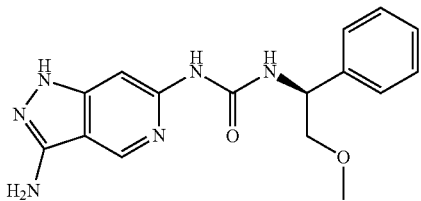 [SMILES: COC[C@@H](NC(=O)Nc1cc2[nH]nc(N)c2cn1)c1ccccc1]

Step 3: (S)-1-(3-Amino-1H-pyrazolo[4,3-c]pyridin-6-yl)-3-(2-methoxy-1-phenylethyl)urea (S)-1-(3-Amino-1H-pyrazolo[4,3-c]pyridin-6-yl)-3-(2-methoxy-1-phenylethyl)urea was prepared using the same procedure described for [(R)-1-(4-fluorophenyl)ethyl]-3-[3-(methylamino)-1H-pyrazolo[4,3-c]pyridin-6-yl]urea (Example 1, Step 3). MS ESI calc'd. For $C_{16}H_{18}N_6O_2$ [M+1]$^+$ 327. found 327. $^1$H NMR (500 MHz, DMSO-$d_6$) δ 11.41 (s, 1H), 8.99 (s, 1H), 8.57 (s, 1H), 8.45-8.19 (br s, 1H), 7.37-7.25 (m, 4H), 7.24-7.13 (m, 1H), 5.62 (s, 2H), 4.98-4.90 (m, 1H), 3.54 (d, J=5.1, 2H), 3.23 (s, 3H).

Example 46

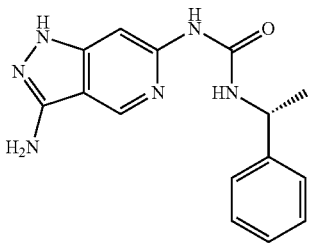 [SMILES: C[C@@H](NC(=O)Nc1cc2[nH]nc(N)c2cn1)c1ccccc1]

1-(3-amino-1H-pyrazolo[4,3-c]pyridin-6-yl)-3-[(1R)-1-phenylethyl]urea (Example 46)

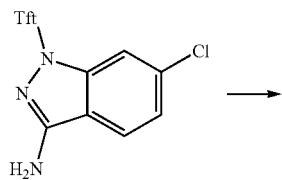

Step 1: (R)-1-(3-amino-1-trityl-1H-pyrazolo[4,3-c]pyridin-6-yl)-3-(1-phenylethyl)urea 6-chloro-1-trityl-1H-pyrazolo[4,3-c]pyridin-3-amine (500 mg, 1.217 mmol), (R)-1-(1-phenylethyl)urea (400 mg, 2.434 mmol), cesium carbonate (1023 mg, 3.14 mmol) and chloro[2-(dicyclohexylphosphino)-3,6-dimethoxy-2'-4'-6'-tri-i-propyl-1,1'-biphenyl][2-(2-aminoethyl)phenyl]palladium(II) (58.3 mg, 0.073 mmol) were charge in a 40 mL vial with dioxane (11 ml). System was degassed and stirred at 100° C. for 3 hours. Reaction mixture was evaporated in vacuo and purified by normal phase column chromotography eluting with hexane/EtOAc (0-50%) affording (R)-1-(3-amino-1-trityl-1H-pyrazolo[4,3-c]pyridin-6-yl)-3-(1-phenylethyl)urea (333 mg, 0.618 mmol, 50.8% yield) as an off white solid. 1H NMR (500 MHz, dmso) δ 8.82 (s, 1H), 8.51 (s, 1H), 8.32 (bs, 1H), 7.38-7.13 (m, 19H), 6.49 (s, 1H), 5.88 (s, 2H), 4.85-4.75 (m, 1H), 1.35 (d, 3H). MS ESI calc'd. For $C_{34}H_{30}N_6O$[M+H]$^+$ 539. found 539.

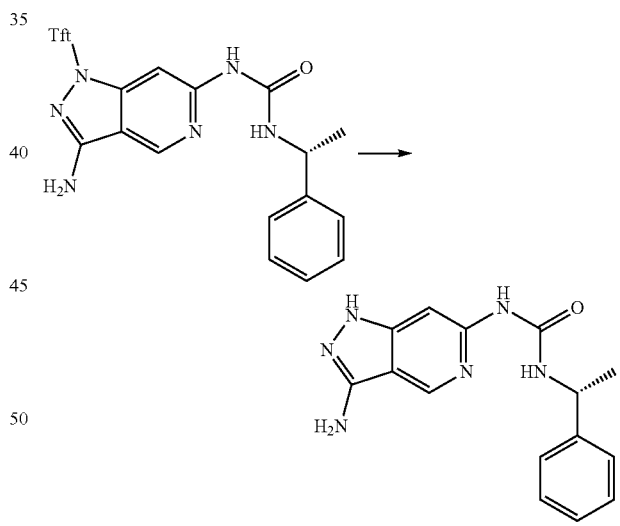

Step 2: (R)-1-(3-amino-1H-pyrazolo[4,3-c]pyridin-6-yl)-3-(1-phenylethyl)urea A solution of (R)-1-(3-amino-1-trityl-1H-pyrazolo[4,3-c]pyridin-6-yl)-3-(1-phenylethyl)urea (310 mg, 0.576 mmol) and triethylsilane (184 μl, 1.151 mmol) in DCM (5232 μl) were treated with trifluoroacetic acid (2660 μl, 34.5 mmol) and stirred for 1 hr at room temperature. Reaction mixture was evaporated in vacuo, partioned between EtOAc/saturated aqeous NaHCO3 and extracted with EtOAc (2×). Combined organics were washed with saturated aqeous NaHCO3, brine, dried over Na2SO4 and evaporated in vacuo affording crude product which was purified by normal phase column chromotography eluting with MeOH/EtOAc (0-10%) affording (R)-1-(3-amino-1H-pyrazolo[4,3-c]pyridin-6-yl)-3-(1-phenylethyl)urea (145 mg, 0.489 mmol, 85% yield) as an off white solid. 1H NMR (500 MHz, dmso) δ 11.42 (s, 1H), 8.87 (s, 1H), 8.57 (s, 1H), 8.07 (s, 1H), 7.39-7.27 (m, 4H), 7.27-7.17 (m, 1H), 5.64 (s, 2H), 4.86 (m, 1H), 1.39 (d, 3H). MS ESI calc'd. For $C_{15}H_{16}N_6O[M+H]^+$ 297. found 297.

Examples 44-46 (Table 2) were prepared according to Scheme 2 following similar procedures described for Example 43 using the appropriate commercial or synthesized ureas (intermediates 20C and 22C).

(R)—N-(6-(3-(1-Phenylethyl)ureido)-1H-pyrazolo[4,3-c]pyridin-3-yl)acetamide

TABLE 2

| Ex | Structure | IUPAC Name | Exact Mass [M + H]+ |
|----|-----------|------------|---------------------|
| 44 | 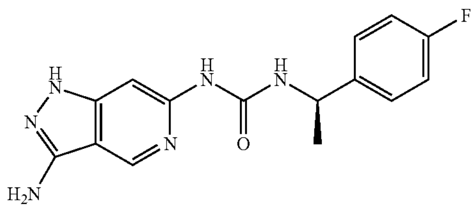 [SMILES: C[C@@H](NC(=O)Nc1cc2[nH]nc(N)c2cn1)c1ccc(F)cc1] | 1-(3-amino-1H-pyrazolo[4,3-c]pyridin-6-yl)-3-[(1R)-1-(4-fluorophenyl)ethyl]urea | Calc'd 315, found 315 |
| 45 | 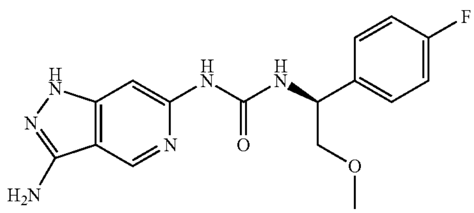 [SMILES: COC[C@@H](NC(=O)Nc1cc2[nH]nc(N)c2cn1)c1ccc(F)cc1] | 1-(3-amino-1H-pyrazolo[4,3-c]pyridin-6-yl)-3-[(1S)-1-(4-fluorophenyl)-2-methoxyethyl]urea | Calc'd 345, found 345 |
| 46 | 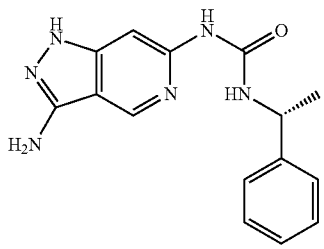 [SMILES: C[C@@H](NC(=O)Nc1cc2[nH]nc(N)c2cn1)c1ccccc1] | 1-(3-amino-1H-pyrazolo[4,3-c]pyridin-6-yl)-3-[(1R)-1-phenylethyl]urea | Calc'd 297, found 297 |

Examples 47-49 were prepared according to scheme 3.

Example 47

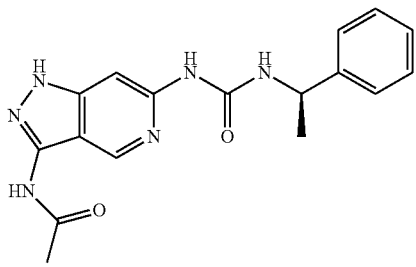 [SMILES: CC(=O)Nc1n[nH]c2cc(NC(=O)N[C@H](C)c3ccccc3)ncc12]

Step 1: (R)-1-(3-Amino-1-trityl-1H-pyrazolo[4,3-c]pyridin-6-yl)-3-(1-phenylethyl)urea 6-Chloro-1-trityl-1H-pyrazolo[4,3-c]pyridin-3-amine (5C; 4.0 g, 9.73 mmol), (R)-1-(1-phenylethyl)urea (2.4 g, 14.60 mmol), cesium carbonate (7.9 g, 24.34 mmol) and BrettPhos pre-catalyst (467 mg, 0.584 mmol) were charged in a 350 mL pressure vessel with 1.4-dioxane (88 mL). The system was degassed and stirred at 100° C. for 8 h. The reaction mixture was filtered through Celite, evaporated in vacuo, dissolved in DCM, and purified by flash chromatography (0-20% EtOAc/DCM) to afford (R)-1-(3-amino-1-trityl-1H-pyrazolo[4,3-c]pyridin-6-yl)-3-(1-phenylethyl)urea. MS ESI calc'd. For $C_{34}H_{30}N_6O_2$ $[M+1]^+$ 539. found 539.

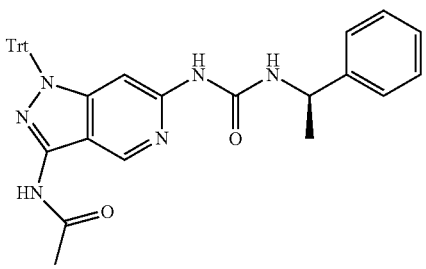

Step 2: (R)—N-(6-(3-(1-Phenylethyl)ureido)-1-trityl-1H-pyrazolo[4,3-c]pyridin-3-yl)acetamide A solution of (R)-1-(3-amino-1-trityl-1H-pyrazolo[4,3-c]pyridin-6-yl)-3-(1-phenylethyl)urea (900 mg, 1.671 mmol) and DIEA (0.584 mL, 3.34 mmol) in THF (16 mL) at 0° C. was treated drop-wise with a solution of acetyl chloride (0.131 mL, 1.838 mmol) in THF (0.5 mL). The reaction was stirred at 0° C. for 10 min, then allowed to warm to room temperature and stirred for 1 h. The solvent was evaporated in vacuo and purified by flash chromatography (0-30% EtOAc/DCM) to afford (R)—N-(6-(3-(1-phenylethyl)ureido)-1-trityl-1H-pyrazolo[4,3-c]pyridin-3-yl)acetamide. MS ESI calc'd. For $C_{36}H_{32}N_6O_2$ [M+1]$^+$ 581. found 581.

Step 3: (R)—N-(6-(3-(1-Phenylethyl)ureido)-1H-pyrazolo[4,3-c]pyridin-3-yl)acetamide A solution of (R)—N-(6-(3-(1-phenylethyl)ureido)-1-trityl-1H-pyrazolo[4,3-c]pyridin-3-yl)acetamide (900 mg, 1.550 mmol) and triethylsilane (0.495 mL, 3.10 mmol) in DCM (14 mL) was treated with TFA (7.16 mL, 93 mmol). The reaction was stirred at room temperature for 1 h. The reaction mixture was evaporated in vacuo and the residue was partitioned between EtOAc and sat. aq. NaHCO$_3$. The aqueous layer was extracted with EtOAc and the combined organics were washed with sat. aq. NaHCO$_3$, brine, dried over Na$_2$SO$_4$, and evaporated in vacuo. The residue was purified by flash chromatography (0-10% MeOH/DCM) to afford (R)—N-(6-(3-(1-phenylethyl)ureido)-1H-pyrazolo[4,3-c]pyridin-3-yl)acetamide. MS ESI calc'd. For $C_{17}H_{18}N_6O_2$ [M+1]$^+$ 339. found 339. $^1$H NMR (500 MHz, DMSO-d$_6$) δ 12.56 (s, 1H), 10.71 (s, 1H), 8.99 (s, 1H), 8.94 (s, 1H), 7.80-7.72 (br s, 1H), 7.50 (s, 1H), 7.36-7.29 (m, 4H), 7.26-7.19 (m, 1H), 4.91-4.81 (m, 1H), 2.09 (s, 3H), 1.39 (d, J=6.9, 3H).

Examples 48 and 49 (Table 3) were prepared according to Scheme 3 following similar procedures described for Example 47 using the appropriate synthesized ureas (intermediates 21C and 22C).

TABLE 3

| Ex | Structure | IUPAC Name | Exact Mass [M + H]+ |
|---|---|---|---|
| 48 | ![structure] | N-[6-({[(1S)-2-methoxy-1-phenylethyl]carbamoyl}-amino)-1H-pyrazolo[4,3-c]pyridin-3-yl]acetamide | Calc'd 369, Found 369 |
| 49 | ![structure] | N-[6-({[(1S)-1-(4-fluorophenyl)-2-methoxyethyl]carbamoyl}-amino)-1H-pyrazolo[4,3-c]pyridin-3-yl]acetamide | Calc'd 387, Found 387 |

Examples 50-56 were prepared according to scheme 4.

Example 50

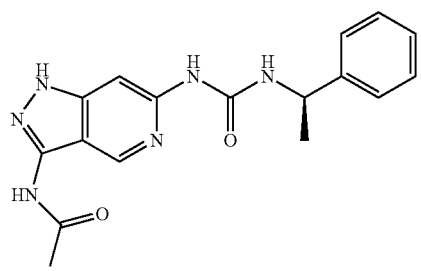 [SMILES: CC(=O)Nc1n[nH]c2cc(NC(=O)N[C@H](C)c3ccccc3)ncc12]

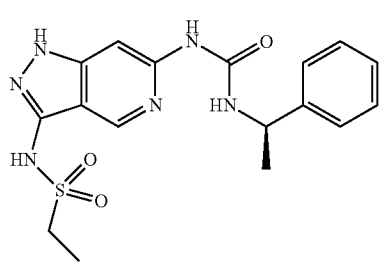 [SMILES: CCS(=O)(=O)Nc1n[nH]c2cc(NC(=O)N[C@H](C)c3ccccc3)ncc12]

(R)—N-(6-(3-(1-Phenylethyl)ureido)-1H-pyrazolo[4,3-c]pyridin-3-yl)ethanesulfonamide To an 8 mL vial charged with ethanesulfonyl chloride (10.53 µL, 0.111 mmol) was added (R)-1-(3-amino-1-trityl-1H-pyrazolo[4,3-c]pyridin-6-yl)-3-(1-phenylethyl)urea (Example 47, Step 1; 20 mg, 0.037 mmol) in DCM (1 mL) and pyridine (0.1 mL). The reaction mixture was stirred at room temperature for 2 h. Excess sulfonyl chloride was quenched by shaking with MP-Trisamine (91 mg, 0.186 mmol) for 3 h. The resin was filtered, the volatiles removed in vacuo, and the resulting residue dissolved in TFA (1 mL) and stirred at room temperature for 1 h. Triethylsilane (5.93 µL, 0.037 mmol) was added and the reaction mixture was stirred for an additional 5 min. The reaction mixture was concentrated in vacuo, the resulting crude residue dissolved in DMSO (1.5 mL), filtered, and purified by mass-triggered reverse phase HPLC to afford (R)—N-(6-(3-(1-phenylethyl)ureido)-1H-pyrazolo[4,3-c]pyridin-3-yl)ethanesulfonamide. MS ESI calc'd. For $C_{17}H_{20}N_6O_3S$ [M+1]$^+$ 389. found 389. $^1$H NMR (500 MHz, DMSO-$d_6$) δ 12.74 (1H, s), 10.63 (1H, s), 9.20 (1H, s), 8.76 (1H, s), 7.70 (1H, s), 7.50 (1H, s), 7.31 (4H, d, J=4.4 Hz), 7.20-7.21 (1H, m), 4.84 (1H, t, J=7.2 Hz), 3.30 (2H, q, J=7.4 Hz), 1.38 (3H, d, J=7.0 Hz), 1.23 (3H, t, J=7.4 Hz).

Examples 51-56 (Table 4) were prepared according to Scheme 4 following similar procedures described for Example 50 using the appropriate sulfonyl chloride. The compounds of Examples 51-56 were obtained as the trifluoroacetic acid salt.

TABLE 4

| Ex | Structure | IUPAC Name | Exact Mass [M + H]+ |
|---|---|---|---|
| 51 | 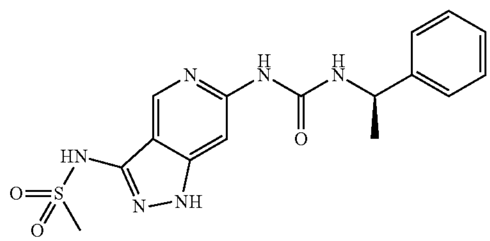 [SMILES: C[C@@H](NC(=O)Nc1cc2[nH]nc(NS(C)(=O)=O)c2cn1)c1ccccc1] | N-[6-({[(1R)-1-phenylethyl]carbamoyl}-amino)-1H-pyrazolo-[4,3-c]pyridin-3-yl]methanesulfonamide | Calc'd 375, Found 375 |
| 52 | 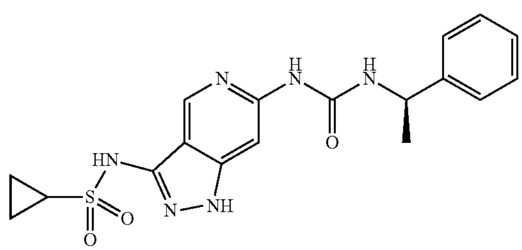 [SMILES: C[C@@H](NC(=O)Nc1cc2[nH]nc(NS(=O)(=O)C3CC3)c2cn1)c1ccccc1] | N-[6-({[(1R)-1-phenylethyl]carbamoyl}-amino)-1H-pyrazolo[4,3-c]pyridin-3-yl]cyclopropanesulfonamide | Calc'd 401, Found 401 |
| 53 | 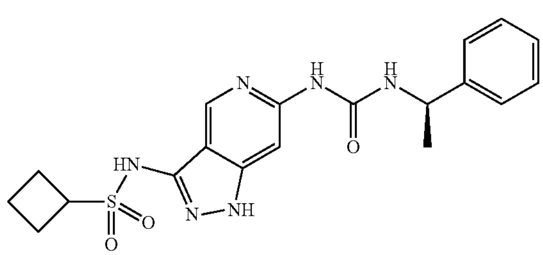 [SMILES: C[C@@H](NC(=O)Nc1cc2[nH]nc(NS(=O)(=O)C3CCC3)c2cn1)c1ccccc1] | N-[6-({[(1R)-1-phenylethyl]carbamoyl}-amino)-1H-pyrazolo[4,3-c]pyridin-3-yl]cyclobutanesulfonamide | Calc'd 415, Found 415 |
| 54 | 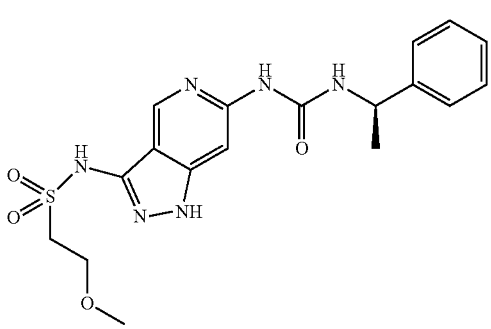 [SMILES: COCCS(=O)(=O)Nc1n[nH]c2cc(NC(=O)N[C@H](C)c3ccccc3)ncc12] | 2-methoxy-N-[6-({[(1R)-1-phenylethyl]-carbamoyl}amino)-1H-pyrazolo[4,3-c]pyridin-3-yl]ethanesulfonamide | Calc'd 419, Found 419 |

TABLE 4-continued

| Ex | Structure | IUPAC Name | Exact Mass [M + H]+ |
|---|---|---|---|
| 55 | 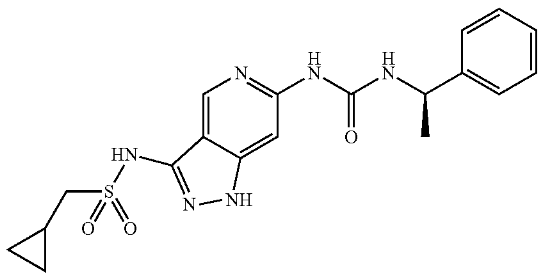 [SMILES: C[C@@H](NC(=O)Nc1cc2[nH]nc(NS(=O)(=O)CC3CC3)c2cn1)c1ccccc1] | 1-cyclopropyl-N-[6-({[(1R)-1-phenylethyl]-carbamoyl}amino)-1H-pyrazolo[4,3-c]pyridin-3-yl]methanesulfonamide | Calc'd 415, Found 415 |
| 56 | 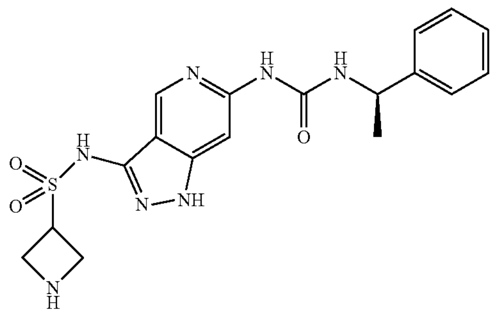 [SMILES: C[C@@H](NC(=O)Nc1cc2[nH]nc(NS(=O)(=O)C3CNC3)c2cn1)c1ccccc1] | N-[6-({[(1R)-1-phenylethyl]carbamoyl-amino)-1H-pyrazolo[4,3-c]pyridin-3-yl]azetidine-3-sulfonamide | Calc'd 416, Found 416 |

Examples 57-58 were prepared according to scheme 5.

Example 57

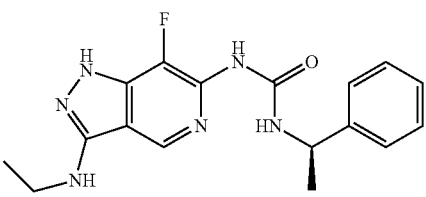 [SMILES: CCNc1n[nH]c2c(F)c(NC(=O)N[C@H](C)c3ccccc3)ncc12]

(R)-1-(3-(Ethylamino)-7-fluoro-1H-pyrazolo[4,3-c]pyridin-6-yl)-3-(1-phenylethyl)urea

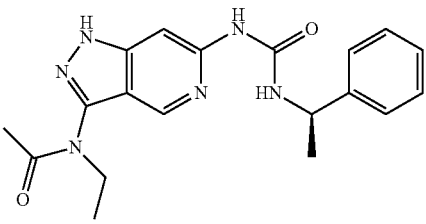 [SMILES: CCN(C(C)=O)c1n[nH]c2cc(NC(=O)N[C@H](C)c3ccccc3)ncc12]

Step 1: (R)—N-Ethyl-N-(6-(3-(1-phenylethyl)ure-ido)-1H-pyrazolo[4,3-c]pyridin-3-yl)acetamide (R)-1-(3-(Ethylamino)-1-trityl-1H-pyrazolo[4,3-c]pyridin-6-yl)-3-(1-phenylethyl)urea (Example 2, Step 2; 680 mg, 1.198 mmol) was dissolved in DCM (20 mL), charged with DIEA (0.42 mL, 2.396 mmol), and cooled to 0° C. Acetyl chloride (0.095 mL, 1.318 mmol) was added drop-wise and the reaction was warmed to room temperature and stirred for 1 h. The reaction was charged with TFA (2.3 mL, 30.0 mmol) and triethylsilane (0.20 mL, 1.198 mmol) and stirred for 1 h at room temperature. The solvents were removed in vacuo and the residue was treated with DCM (3 mL) and triethylamine (1 mL) and stirred for 15 min. The residue was purified by flash chromatography (2-10% MeOH/DCM w/NH$_3$) to afford (R)—N-ethyl-N-(6-(3-(1-phenylethyl)ureido)-1H-pyrazolo[4,3-c]pyridin-3-yl)acetamide. MS ESI calc'd. for $C_{19}H_{22}N_6O_2$ [M+1]$^+$ 366. found 366.

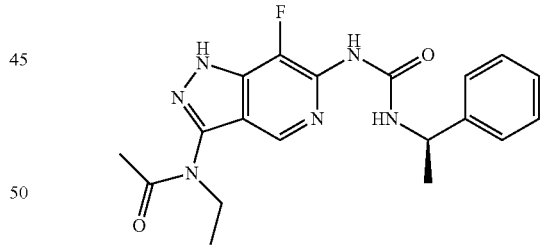

Step 2: (R)—N-Ethyl-N-(7-fluoro-6-(3-(1-phenyl-ethyl)ureido)-1H-pyrazolo[4,3-c]pyridin-3-yl)aceta-mide (R)—N-Ethyl-N-(6-(3-(1-phenylethyl)ureido)-1H-pyra-zolo[4,3-c]pyridin-3-yl)acetamide (154 mg, 0.420 mmol) was dissolved in DMA (1 mL) and methanol (1 mL), charged with powdered Selectfluor® (164 mg, 0.462 mmol), and stirred at room temperature overnight. The reaction was then heated to 55° C. for 8 h. The resulting crude residue was purified by mass-triggered reverse phase HPLC. Fractions containing pure compound were filtered through a PS-HCO$_3$ cartridge and the filtrate was concentrated in vacuo to give (R)-1-(3-(ethylamino)-7-fluoro-1H-pyrazolo[4,3-c]pyridin-6-yl)-3-(1-phenylethyl)urea. MS ESI calc'd. for $C_{19}H_{21}FN_6O_2$ [M+1]$^+$ 385. found 385.

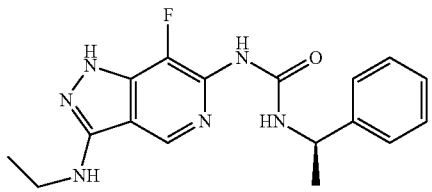 [SMILES: CCNc1n[nH]c2c(F)c(NC(=O)N[C@H](C)c3ccccc3)ncc12]

Step 3: (R)-1-(3-(Ethylamino)-7-fluoro-1H-pyrazolo[4,3-c]pyridin-6-yl)-3-(1-phenylethyl)urea (R)—N-Ethyl-N-(7-fluoro-6-(3-(1-phenylethyl)ureido)-1H-pyrazolo[4,3-c]pyridin-3-yl)acetamide (27 mg, 0.070 mmol) was dissolved in THF (3 mL), charged with HCl (300 µL, 3.65 mmol), and heated to 60° C. for 4 h. The solvents were removed in vacuo and the residue was taken up in DMF and purified by mass-triggered reverse phase HPLC. Fractions containing pure compound were filtered through a PS-HCO$_3$ cartridge and the filtrate was concentrated in vacuo to give (R)-1-(3-(ethylamino)-7-fluoro-1H-pyrazolo[4,3-c]pyridin-6-yl)-3-(1-phenylethyl)urea. MS ESI calc'd. for $C_{17}H_{19}FN_6O$ [M+1]$^+$ 343. found 343. $^1$H NMR (500 MHz, DMSO-d$_6$) δ 12.15 (s, 1H), 8.67 (s, 1H), 8.90 (br s, 1H), 8.49 (s, 1H), 7.39-7.27 (m, 4H), 7.26-7.18 (m, 1H), 4.90 (t, J=7.2 Hz, 1H), 3.25 (m, 2H), 1.42 (d, J=6.9 Hz, 3H), 1.20 (t, J=7.2 Hz, 3H).

Example 58

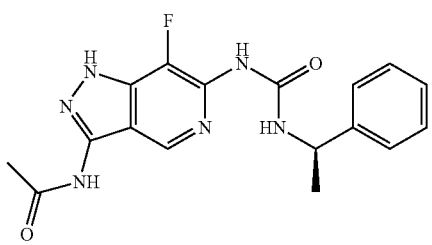 [SMILES: CC(=O)Nc1n[nH]c2c(F)c(NC(=O)N[C@H](C)c3ccccc3)ncc12]

(R)—N-(7-Fluoro-6-(3-(1-phenylethyl)ureido)-1H-pyrazolo[4,3-c]pyridin-3-yl)acetamide (R)—N-(6-(3-(1-Phenylethyl)ureido)-1H-pyrazolo[4,3-c]pyridin-3-yl)acetamide (Example 47; 75 mg, 0.222 mmol) was dissolved in DMA (0.5 mL) and methanol (0.5 mL), charged with powdered Selectfluor® (86 mg, 0.244 mmol), and stirred at room temperature overnight. The reaction was then heated to 65° C. for 2 h. The resulting crude residue was purified by mass-triggered reverse phase HPLC. Fractions containing pure compound were filtered through a PS-HCO$_3$ cartridge and the filtrate was concentrated in vacuo to give (R)—N-(7-fluoro-6-(3-(1-phenylethyl)ureido)-1H-pyrazolo[4,3-c]pyridin-3-yl)acetamide. MS ESI calc'd. for $C_{17}H_{17}FN_6O_2$ [M+1]$^+$ 357. found 357. $^1$H NMR (500 MHz, DMSO-d$_6$) δ 13.83 (s, 1H) 11.15 (s, 1H), 10.79 (s, 1H), 9.86 (s, 1H), 8.28 (d, J=7.3, 1H) 7.34 (m, 4H), 7.34 (m, 1H), 4.88 (m, 1H), 2.20 (S, 3H), 1.43 (d, J=6.9, 3H).

Example 59 was prepared according to Scheme 6.

Example 59

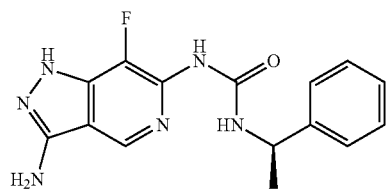 [SMILES: C[C@@H](NC(=O)Nc1ncc2c(N)n[nH]c2c1F)c1ccccc1]

(R)-1-(3-Amino-7-fluoro-1H-pyrazolo[4,3-c]pyridin-6-yl)-3-(1-phenylethyl)urea

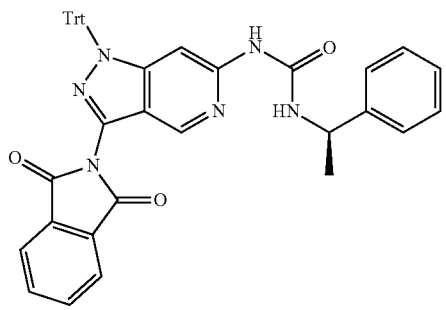

Step 1: (R)-1-(3-(1,3-Dioxoisoindolin-2-yl)-1-trityl-1H-pyrazolo[4,3-c]pyridin-6-yl)-3-(1-phenylethyl)urea (R)-1-(3-Amino-1-trityl-1H-pyrazolo[4,3-c]pyridin-6-yl)-3-(1-phenylethyl)urea (Example 47, Step 1; 503 mg, 0.934 mmol) and isobenzofuran-1,3-dione (159 mg, 1.074 mmol) were added to a 1.5 mL microwave vial, charged with dioxane (4 mL), and heated to 110° C. for 4.5 h. The solvents were concentrated in vacuo and the residue was purified by flash chromatography (2-10% EtOAc/DCM) to give (R)-1-(3-(1,3-dioxoisoindolin-2-yl)-1-trityl-1H-pyrazolo[4,3-c]pyridin-6-yl)-3-(1-phenylethyl)urea. MS ESI calc'd. for $C_{42}H_{32}N_6O_3$ [M+1]$^+$ 669. found 669.

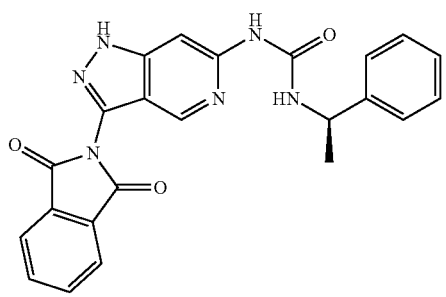 [SMILES: C[C@@H](NC(=O)Nc1cc2[nH]nc(N3C(=O)c4ccccc4C3=O)c2cn1)c1ccccc1]

Step 2: (R)-1-(3-(1,3-Dioxoisoindolin-2-yl)-1H-pyrazolo[4,3-c]pyridin-6-yl)-3-(1-phenylethyl)urea (R)-1-(3-(1,3-Dioxoisoindolin-2-yl)-1-trityl-1H-pyrazolo[4,3-c]pyridin-6-yl)-3-(1-phenylethyl)urea (229 mg, 0.342 mmol) was dissolved in DCM (2 mL), charged with TFA (660 µL, 8.56 mmol) and triethylsilane (54.7 µL, 0.342 mmol), and stirred at room temperature for 30 min. The solvents were concentrated in vacuo and the residue was treated with triethylamine (1 mL). Purification via flash chromatography (10-100% EtOAc/DCM) afforded (R)-1-(3-(1,3-dioxoisoindolin-2-yl)-1H-pyrazolo[4,3-c]pyridin-6-yl)-3-(1-phenylethyl)urea. MS ESI calc'd. for $C_{23}H_{18}N_6O_3$ $[M+1]^+$ 427. found 427.

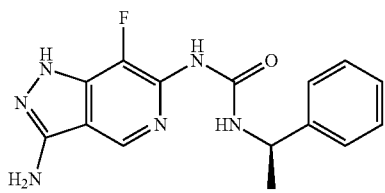 [SMILES: C[C@@H](NC(=O)Nc1ncc2c(N)n[nH]c2c1F)c1ccccc1]

Step 3: (R)-1-(3-Amino-7-fluoro-1H-pyrazolo[4,3-c]pyridin-6-yl)-3-(1-phenylethyl)urea (R)-1-(3-(1,3-Dioxoisoindolin-2-yl)-1H-pyrazolo[4,3-c]pyridin-6-yl)-3-(1-phenylethyl)urea (114 mg, 0.267 mmol) was dissolved in DMA (1 mL) and methanol (1 mL), charged with powdered Selectfluor® (108 mg, 0.305 mmol), and stirred at room temperature for 20 h. The solvents were concentrated in vacuo and the residue was purified by flash chromatography (3-15% MeOH/DCM). The crude mixture obtained was then dissolved in EtOH (3 mL), charged with hydrazine hydrate (0.130 mL, 2.67 mmol), and heated to 85° C. for 30 min. The solvents were concentrated in vacuo and the residue was purified by mass-triggered reverse phase HPLC followed by purification via flash chromatography (2-10% MeOH/DCM) to give (R)-1-(3-amino-7-fluoro-1H-pyrazolo[4,3-c]pyridin-6-yl)-3-(1-phenylethyl)urea. MS ESI calc'd. for $C_{15}H_{15}FN_6O$ $[M+1]^+$ 315. found 315. $^1$H NMR (500 MHz, DMSO-$d_6$) δ 8.55 (s, 1H), 7.42-7.34 (m, 4H), 7.27 (m, 1H) 5.07 (q, J=6.7 Hz, 1H), 1.58 (d, J=7.0 Hz, 4H).

Example 60 was prepared according to scheme 7.

Example 60

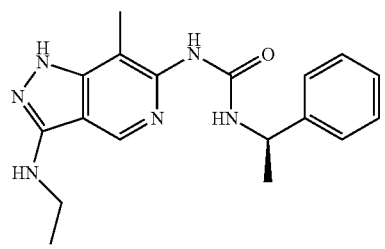 [SMILES: CCNc1n[nH]c2c(C)c(NC(=O)N[C@H](C)c3ccccc3)ncc12]

(R)-1-(3-(Ethylamino)-7-methyl-1H-pyrazolo[4,3-c]pyridin-6-yl)-3-(1-phenylethyl)urea

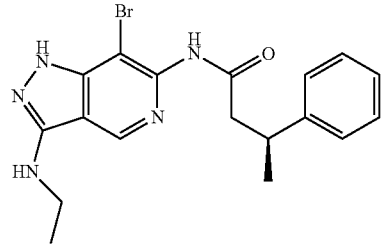 [SMILES: CCNc1n[nH]c2c(Br)c(NC(=O)C[C@H](C)c3ccccc3)ncc12]

Step 1: (R)-1-(7-Bromo-3-(ethylamino)-1H-pyrazolo[4,3-c]pyridin-6-yl)-3-(1-phenylethyl)urea (R)-1-(3-(Ethylamino)-1H-pyrazolo[4,3-c]pyridin-6-yl)-3-(1-phenylethyl)urea (Example 2; 316 mg, 0.974 mmol) was dissolved in acetonitrile (10 mL) and DMF (2 mL) then NBS (225 mg, 1.266 mmol) was added. The reaction was stirred at room temperature overnight. The solvents were concentrated in vacuo and the residue was purified by flash chromatography (2-10% MeOH/DCM) to give (R)-1-(7-bromo-3-(ethylamino)-1H-pyrazolo[4,3-c]pyridin-6-yl)-3-(1-phenylethyl)urea. MS ESI calc'd. for $C_{12}H_{19}BrN_6O$ $[M+1]^+$ 403. found 403.

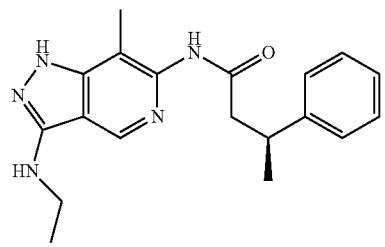

Step 2: (R)-1-(3-(Ethylamino)-7-methyl-1H-pyrazolo[4,3-c]pyridin-6-yl)-3-(1-phenylethyl)urea An oven-dried 5 mL microwave vial was charged with (R)-1-(7-bromo-3-(ethylamino)-1H-pyrazolo[4,3-c]pyridin-6-yl)-3-(1-phenylethyl)urea (100 mg, 0.198 mmol), PdOAc$_2$ (8.5 mg, 0.038 mmol), and PCy$_3$-BF$_4$H (30 mg, 0.08 mmol). The reaction mixture was sealed under N$_2$, then charged with dioxane (1.0 mL) and NMP (0.25 mL), followed by dropwise addition of dimethylzinc (1.653 mL, 1.984 mmol, 1.2 M in toluene). The reaction was heated to 100° C. and stirred for 17 h. The reaction was quenched with TFA until gas evolution ceased and then poured into sat. aq. NaHCO$_3$. The aqueous layer was extracted with EtOAc (×3). The combined organic layers were dried over Na$_2$SO$_4$, filtered, and concentrated in vacuo. The residue was purified by flash chromatography (0-20% MeOH/DCM) followed by purification via mass-triggered reverse-phase HPLC. Fractions containing pure compound were filtered through a PS-HCO$_3$ cartridge and the filtrate was concentrated in vacuo to give (R)-1-(3-(ethylamino)-7-methyl-1H-pyrazolo[4,3-c]pyridin-6-yl)-3-(1-phenylethyl)urea. MS ESI calc'd. for $C_{18}H_{22}N_6O$ [M+1]$^+$ 339. found 339. $^1$H NMR (500 MHz, DMSO-$d_6$) δ 8.55 (s, 1H), 7.42-7.19 (m, 5H), 5.01 (q, J=6.9 Hz, 1H), 3.36 (m, 2H), 2.29 (s, 3H), 1.53 (d, J=7.0 Hz, 3H), 1.30 (t, J=7.2 Hz, 3H).

Example 68

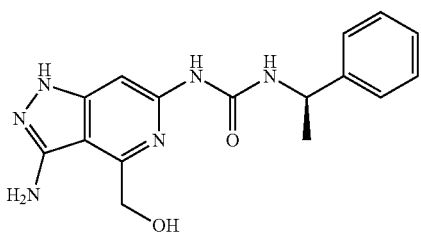 [SMILES: C[C@@H](NC(=O)Nc1cc2[nH]nc(N)c2c(CO)n1)c1ccccc1]

(R)-1-(3-amino-4-(hydroxymethyl)-1H-pyrazolo[4,3-c]pyridin-6-yl)-3-(1-phenylethyl)urea

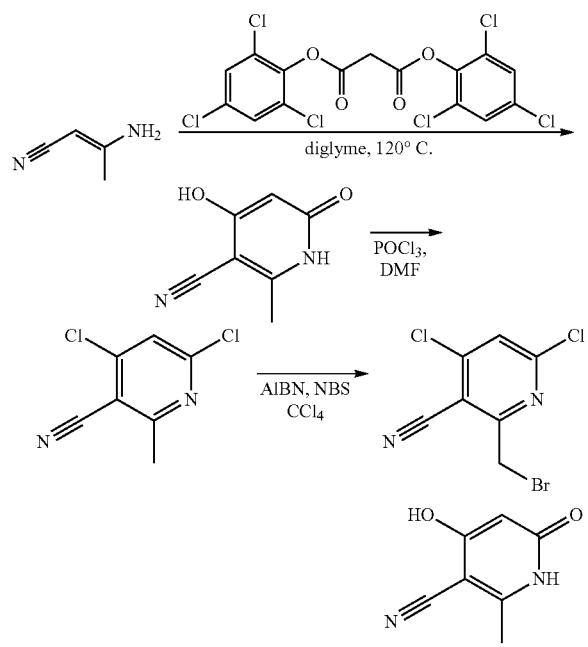

4-hydroxy-2-methyl-6-oxo-1,6-dihydropyridine-3-carbonitrile

A mixture of (E)-3-aminobut-2-enenitrile (9.7 g, 118 mmol) and bis(2,4,6-trichlorophenyl) malonate (58.4 g, 126 mmol) in diglyme (120 ml) was heated to 120° C. for 2.5 hr. The mixture was cooled to RT and poured into Et$_2$O and filtered to collect the precipitate. The precipitate was washed with Et20 to obtain 4-hydroxy-2-methyl-6-oxo-1,6-dihydropyridine-3-carbonitrile. MS ESI calc'd. for $C_7H_7N_2O_2$ [M+H]$^+$ 151. found 151.

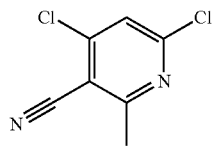

4,6-dichloro-2-methylnicotinonitrile

A mixture of 4-hydroxy-2-methyl-6-oxo-1,6-dihydropyridine-3-carbonitrile (10.36 g, 69.0 mmol) in DMF (21.4 ml, 276 mmol) was charged slowly with POCl$_3$ (25.7 ml, 276 mmol) and heated to 90° C. for 17 hr. The mixture was carefully poured into 200 ml of a 1:1 mixture of 6N KOH and MeCN, rinsing flask with MeCN and carefully basified further with 6N KOH and sat aq NaHCO$_3$, then extracted into Et$_2$O (2×). Organics were washed with brine, dried over MgSO$_4$, filtered and concentrated in vacuo. The residue was purified via flash chromatography (0-30% EtOAc/Hex) to provide 4,6-dichloro-2-methylnicotinonitrile.

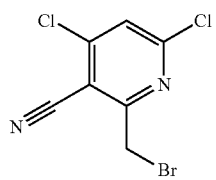 [SMILES: N#Cc1c(Cl)cc(Cl)nc1CBr]

2-(bromomethyl)-4,6-dichloronicotinonitrile

A solution of 4,6-dichloro-2-methylnicotinonitrile (2.15 g, 11.50 mmol) in CCl$_4$ (45 ml) was charged with AIBN (1.93 g, 11.75 mmol) and NBS (4.37 g, 24.55 mmol), sealed and heated to 75° C. for 16 hr. The mixture was poured directly onto SiO$_2$ and purified via flash chromatography (5-15% Et$_2$O/hexane) to provide 2-(bromomethyl)-4,6-dichloronicotinonitrile. MS ESI calc'd. for $C_7H_4BrCl_2N_2$ [M+H]$^+$ 265. found 265.

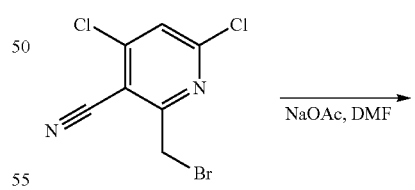

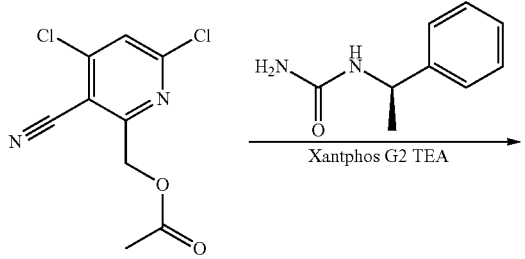

-continued

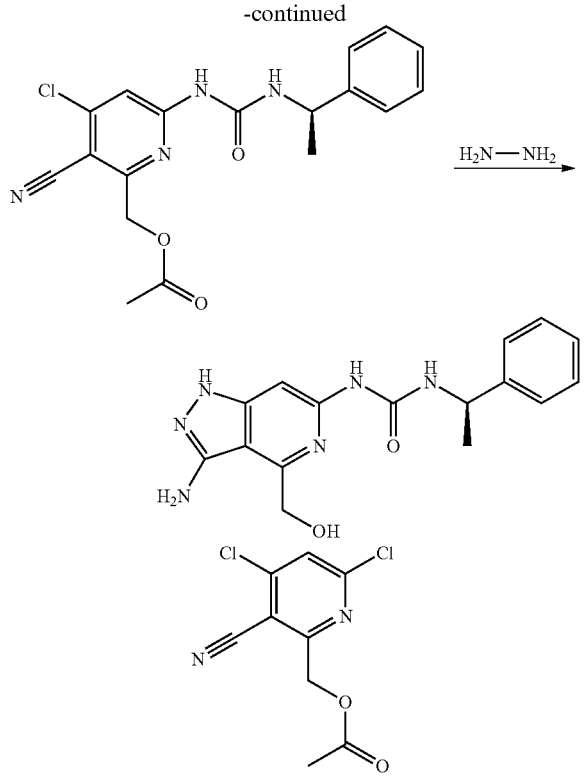

4,6-dichloro-3-cyanopyridin-2-yl)methyl acetate

A solution of 2-(bromomethyl)-4,6-dichloronicotinonitrile (354.8 mg, 1.334 mmol) in DMF (7 ml) was charged with sodium acetate (198 mg, 2.414 mmol) and stirred at RT for 2 hr. The reaction was quenched with water, extracted twice with Et$_2$O. The organics was washed with brine, dried over MgSO$_4$, filtered and concentrated in vacuo to give (4,6-dichloro-3-cyanopyridin-2-yl)methyl acetate. MS ESI calc'd. For C$_9$H$_7$O$_2$N$_2$O$_2$ [M+I-1]$^+$ 245. found 245.

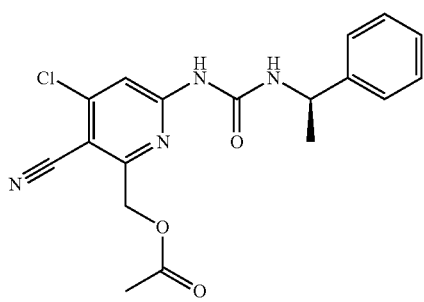 [SMILES: CC(=O)OCc1nc(NC(=O)N[C@H](C)c2ccccc2)cc(Cl)c1C#N]

(R)-(4-chloro-3-cyano-6-(3-(1-phenylethyl)ureido)pyridin-2-yl)methyl acetate

A mixture of (4,6-dichloro-3-cyanopyridin-2-yl)methyl acetate (366.3 mg, 1.495 mmol), (R)-1-(1-phenylethyl)urea (443 mg, 2.70 mmol) and Xantphos G2 precatalyst (130 mg, 0.146 mmol) in THF (2 ml) was sealed, sparged with argon, charged with triethylamine (0.73 ml, 5.24 mmol) and heated to 50° C. for 17 hr. The mixture was filtered through celite, eluted with EtOAc, concentrated in vacuo and purified via flash chromatography (25-100% Et$_2$O/Hex) to provide (R)-(4-chloro-3-cyano-6-(3-(1-phenylethyl)ureido)pyridin-2-yl) methyl acetate. MS ESI calc'd. For C$_{18}$H$_{18}$ClN$_4$O$_3$ [M+H]$^+$ 373. found 373.

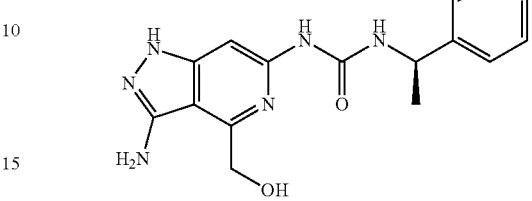

(R)-1-(3-amino-4-(hydroxymethyl)-1H-pyrazolo[4,3-c]pyridin-6-yl)-3-(1-phenylethyl)urea A solution of (R)-(4-chloro-3-cyano-6-(3-(1-phenylethyl)ureido)pyridin-2-yl)methyl acetate (59.1 mg, 0.159 mmol) in ethanol (2 ml) was charged with hydrazine, H$_2$O (46 µl, 0.948 mmol), sealed and heated to 100° C. for 14.5 hr. The mixture was concentrated in vacuo and the residue was purified via flash chromatography (0-20% MeOH/DCM, then 0-20% MeOH/EtOAc) to provide (R)-1-(3-amino-4-(hydroxymethyl)-1H-pyrazolo[4,3-c]pyridin-6-yl)-3-(1-phenylethyl) urea. MS ESI calc'd. For C$_{16}$H$_{19}$N$_6$O$_2$ [M+H]$^+$ 327. found 327. $^1$H NMR (ppm, 500 MHz, DMSO-d6) δ 11.51 (s, 1H), 8.91 (s, 1H), 7.33 (m, 5H), 7.22 (m, 1H), 6.00 (t, J=5.6 Hz, 1H), 5.60 (s, 2H), 4.84 (m, 1H), 4.67 (d, J=5.6, 2H), 1.39 (d, J=7.1 Hz, 3H).

Example 69

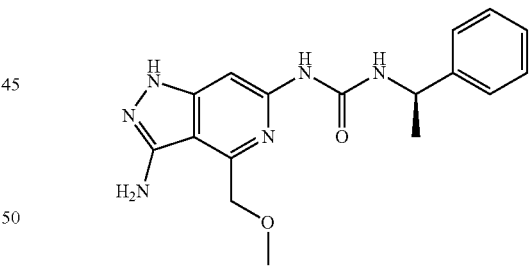

(R)-1-(3-amino-4-(methoxymethyl)-1H-pyrazolo[4,3-c]pyridin-6-yl)-3-(1-phenylethyl)urea

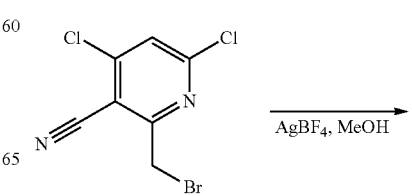

173
-continued

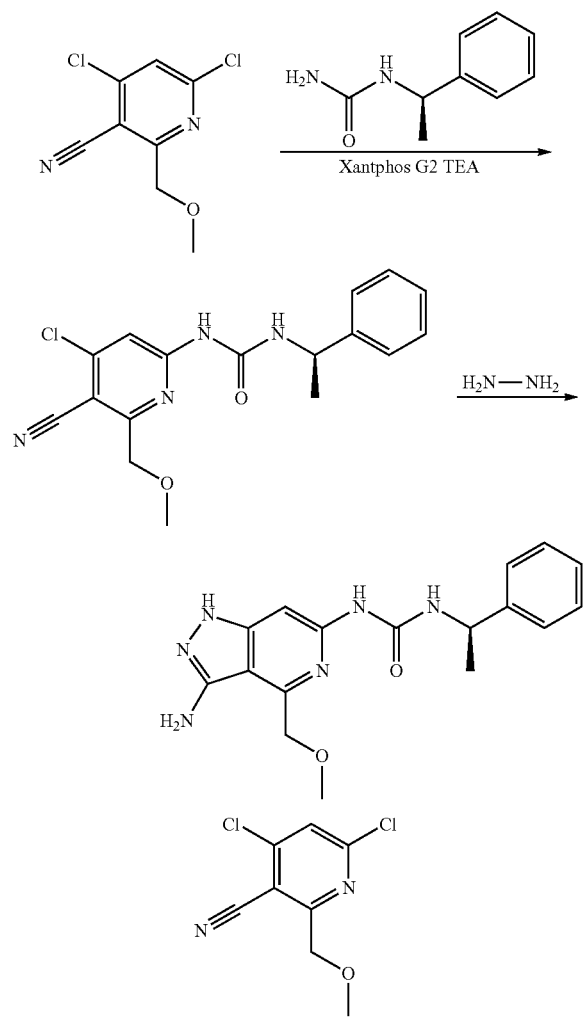

4,6-dichloro-2-(methoxymethyl)nicotinonitrile

A solution of 2-(bromomethyl)-4,6-dichloronicotinonitrile (378.9 mg, 1.425 mmol) in MeOH (5.0 ml) was charged with silver(I) tetrafluoroborate (360 mg, 1.849 mmol) and stirred at 50° C. for 17 hr. LCMS showed conversion to the desired mass. The mixture was concentrated in vacuo and purified via flash chromatography (15-60% Et$_2$O/Hexane) to provide 4,6-dichloro-2-(methoxymethyl)nicotinonitrile. MS ESI calc'd for C$_8$H$_7$Cl$_2$N$_2$O [M+H]$^+$ 217. found 217.

174
(R)-1-(4-chloro-5-cyano-6-(methoxymethyl)pyridin-2-yl)-3-(1-phenylethyl)urea A mixture of 4,6-dichloro-2-(methoxymethyl)nicotinonitrile (75.7 mg, 0.349 mmol), (R)-1-(1-phenylethyl)urea (77 mg, 0.469 mmol) and Xantphos G2 (39 mg, 0.044 mmol) in THF (2 ml) was sealed, sparged with argon, charged with triethylamine (0.17 ml, 1.220 mmol) and heated to 50° C. for 17 hr. The mixture was cooled and filtered through celite, eluted with EtOAc before it was concentrated in vacuo and purified via flash chromatography (25-100% Et$_2$O/hexane) to provide (R)-1-(4-chloro-5-cyano-6-(methoxymethyl)pyridin-2-yl)-3-(1-phenylethyl)urea. MS ESI calc'd for C$_{17}$H$_{18}$ClN$_4$O$_2$ [M+H]$^+$ 345. found 345.

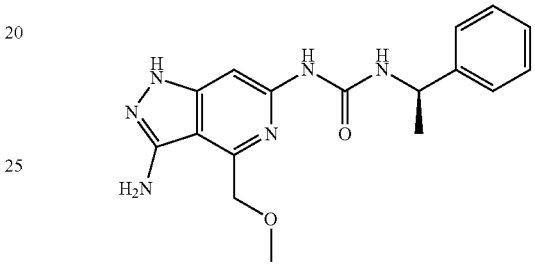

(R)-1-(3-amino-4-(methoxymethyl)-1H-pyrazolo[4,3-c]pyridin-6-yl)-3-(1-phenylethyl)urea A solution of (R)-1-(4-chloro-5-cyano-6-(methoxymethyl)pyridin-2-yl)-3-(1-phenylethyl)urea (151.4 mg, 0.439 mmol) and hydrazine hydrate (75 μl, 1.546 mmol) in EtOH (4 ml) was heated to 100° C. in a sealed vial for 18 hr. The mixture was concentrated in vacuo and purified via flash chromatography (0-20% MeOH/EtOAc) to provide (R)-1-(3-amino-4-(methoxymethyl)-1H-pyrazolo[4,3-c]pyridin-6-yl)-3-(1-phenylethyl)urea. MS ESI calc'd for C$_{17}$H$_{21}$N$_6$O$_2$ [M+H]$^+$ 341. found 341. $^1$H NMR (ppm, 500 MHz, DMSO-d6) δ 11.60 (s, 1H), 8.97 (s, 1H), 7.33 (m, 4H), 7.22 (m, 1H), 7.14 (s, 1H), 5.35 (s, 2H), 4.85 (t, J=7.1, 1H), 4.65 (m, 2H), 3.31 (s, 3H, overlaps with H$_2$O peak), 3.15 (d, J=5.1 Hz, 1H), 1.39 (d, J=7.1 Hz, 1H).

Example 71

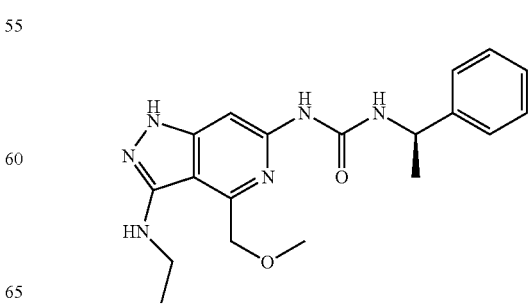

175

(R)-1-(3-(ethylamino)-4-(methoxymethyl)-1H-pyrazolo[4,3-c]pyridin-6-yl)-3-(1-phenylethyl)urea

176

(R)—N-(4-(methoxymethyl)-6-(3-(1-phenylethyl)ureido)-1H-pyrazolo[4,3-c]pyridin-3-yl)acetamide

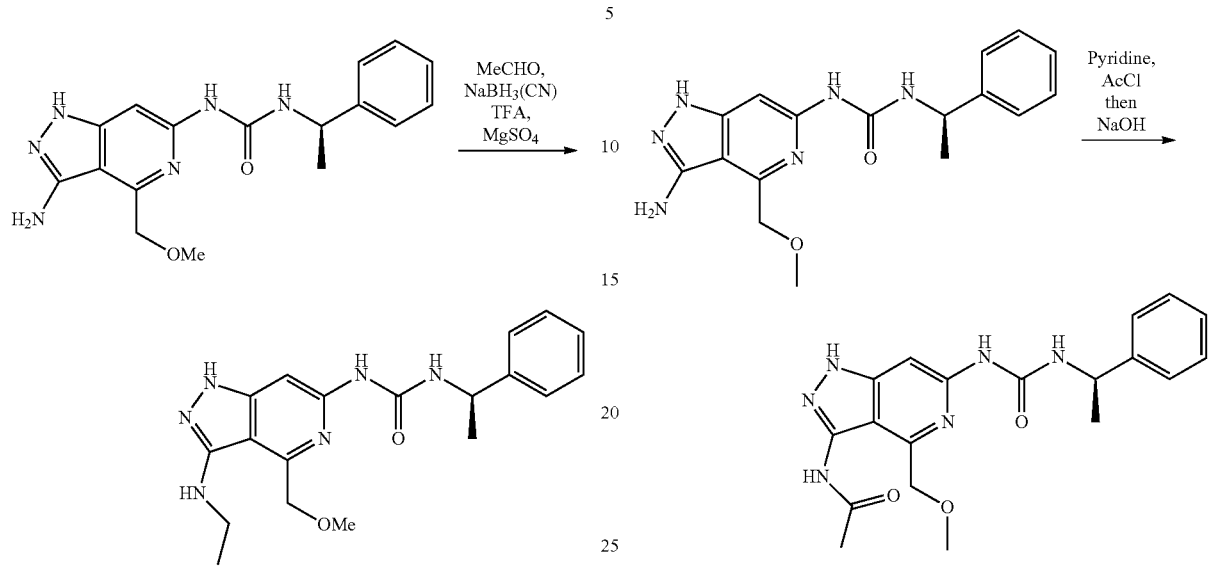

A solution of (R)-1-(3-amino-4-(methoxymethyl)-1H-pyrazolo[4,3-c]pyridin-6-yl)-3-(1-phenylethyl)urea (34.8 mg, 0.102 mmol) in chloroform (0.6 ml) and MeOH (0.3 ml) was charged with MgSO4 (45 mg, 0.374 mmol), TFA (24 µl, 0.312 mmol) and acetaldehyde (0.02 ml, 0.354 mmol). The mixture was stirred at RT for 1 hr, then charged with sodium cyanoborohydride (22 mg, 0.350 mmol) before it was stirred at RT for 1.5 hr. The mixture was filtered to remove insoluble matter, rinsing with MeOH and DCM and concentrated in vacuo. The residue was purified by mass-triggered reverse-phase HPLC to provide (R)-1-(3-(ethylamino)-4-(methoxymethyl)-1H-pyrazolo[4,3-c]pyridin-6-yl)-3-(1-phenylethyl)urea. MS ESI calc'd for $C_{19}H_{25}N_6O_2$ [M+H]$^+$ 369. found 369. $^1$H NMR (ppm, 500 MHz, DMSO-$d_6$) δ 11.64 (s, 1H), 8.96 (s, 1H), 7.33 (m, 4H), 7.23 (m, 1H), 7.15 (s, 1H), 5.56 (t, J=6.5 Hz, 1H), 4.85 (t, J=7.3 Hz), 4.63 (m, 2H), 3.32 (s, 3H, overlaps with H$_2$O peak), 3.22 (m, 2H), 1.39 (d, 6.8 Hz, 3H), 1.20 (t, J=4.9 Hz, 3H).

Example 72

A solution of (R)-1-(3-amino-4-(methoxymethyl)-1H-pyrazolo[4,3-c]pyridin-6-yl)-3-(1-phenylethyl)urea (30 mg, 0.088 mmol) in THF (1 ml) was charged with pyridine (72 µl, 0.890 mmol) and AcCl (62 µl, 0.872 mmol). The mixture was stirred at RT for 17 hr before 1N NaOH (1.2 ml, 1.200 mmol) was added and stirred at RT for 2 hr and then heated to 50° C. for 1 hr. The reaction was quenched with sat aq NH$_4$Cl and extracted into EtOAc. The mixture was washed with sat aq NH$_4$Cl followed by brine, dried over MgSO$_4$, filtered, concentrated in vacuo and purified via flash chromatography (0-20% MeOH/DCM) to give (R)—N-(4-(methoxymethyl)-6-(3-(1-phenylethyl)ureido)-1H-pyrazolo[4,3-c]pyridin-3-yl)acetamide. MS ESI calc'd for $C_{19}H_{23}N_6O_3$ [M+H]$^+$ 383. found 383. $^1$H NMR (ppm, 500 MHz, DMSO-d6) δ 12.81 (s, 1H), 10.01 (s, 1H), 9.13 (s, 1H), 7.33 (m, 5H), 7.22 (m, 1H), 4.89 (t, J=6.8 Hz), 4.59 (s, 2H), 3.28 (s, 3H), 2.06 (s, 3H), 1.39 (d, 5.1 Hz).

Example 73

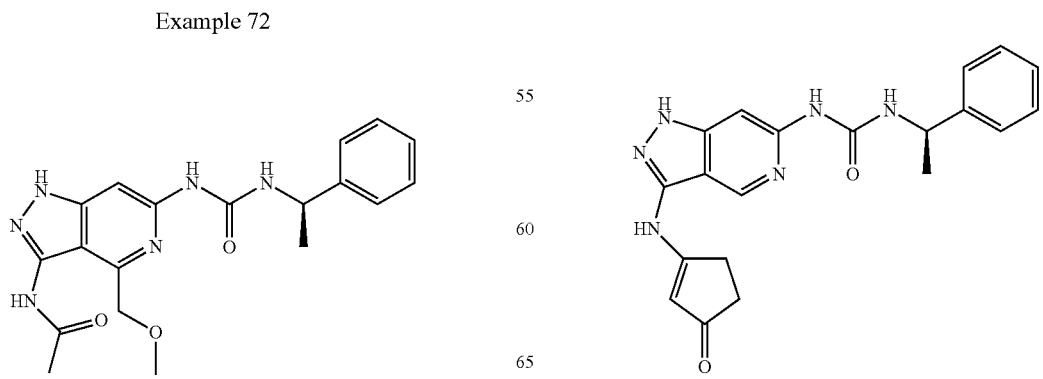

177

(R)-1-(3-((3-oxocyclopent-1-en-1-yl)amino)-1H-pyrazolo[4,3-c]pyridin-6-yl)-3-(1-phenylethyl)urea

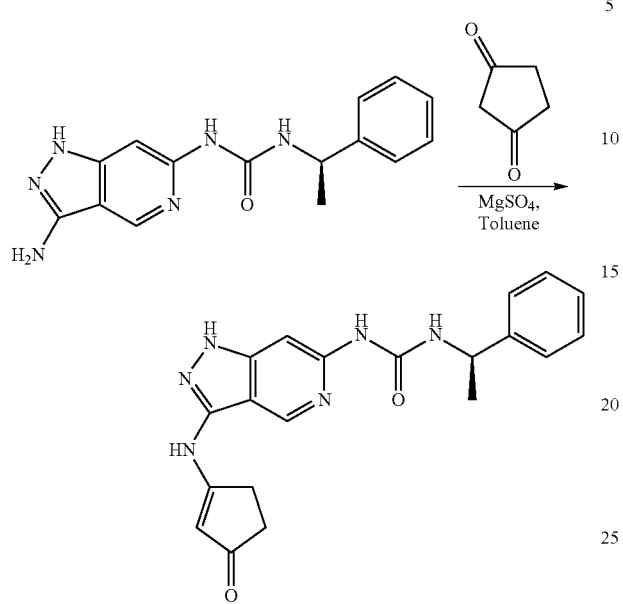

A mixture of (R)-1-(3-amino-1H-pyrazolo[4,3-c]pyridin-6-yl)-3-(1-phenylethyl)urea (52.9 mg, 0.179 mmol), cyclopentane-1,3-dione (34.1 mg, 0.348 mmol) and MgSO$_4$ (167.7 mg, 1.393 mmol) in toluene (2 ml) was heated in a sealed 5 ml microwave vial to 150° C. for 1 hr. LCMS shows formation of product. The mixture was poured directly onto silica gel and purified via flash chromatography (Biotage SNAP 10 g, 0-20% MeOH/DCM) to provide (R)-1-(3-((3-oxocyclopent-1-en-1-yl)amino)-1H-pyrazolo[4,3-c]pyridin-6-yl)-3-(1-phenylethyl)urea (3.11 mg, 8.26 μmol, 4.63% yield) as a yellow solid. MS ESI calc'd. For $C_{20}H_{21}N_6O_2$ [M+H]$^+$ 377. found 377. $^1$H NMR (ppm, 500 MHz, DMSO-d$_6$) δ 12.49 (s, 1H), 10.39 (s, 1H), 8.99 (s, 1H), 8.87 (s, 1H), 7.77 (br s, 1H), 1.53 (s, 1H), 7.34 (m, 5H), 7.23 (s, 1H), 6.11 (br s, 1H), 4.86 (t, J=6.5 Hz, 1H), 3.32 (s, 3H, overlaps with H$_2$O peak), 2.81 (s, 2H), 2.26 (s, 2H), 1.40 (d, J=6.8 Hz, 3H).

Example 106

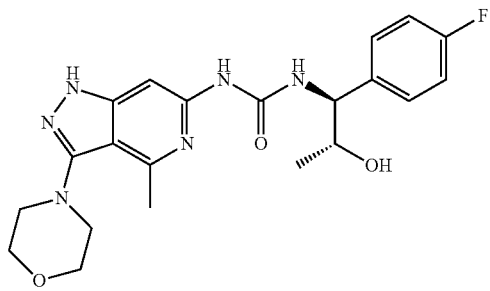 [SMILES: Cc1nc(NC(=O)N[C@@H](c2ccc(F)cc2)[C@@H](C)O)cc2[nH]nc(N3CCOCC3)c12]

178

1-((1S,2R)-1-(4-Fluorophenyl)-2-hydroxypropyl)-3-(4-methyl-3-morpholino-1H-pyrazolo[4,3-c]pyridin-6-yl)urea

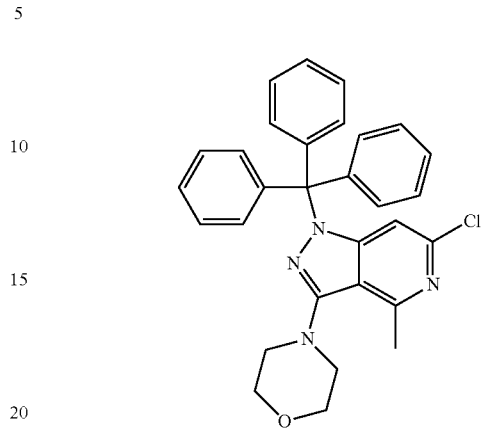

Step 1: 4-(6-Chloro-4-methyl-1-trityl-1H-pyrazolo[4,3-c]pyridin-3-yl)morpholine

6-Chloro-3-iodo-4-methyl-1-trityl-1H-pyrazolo[4,3-c]pyridine (Intermediate 1C; 2 g, 3.73 mmol), morpholine (0.488 mL, 5.60 mmol), sodium tert-butoxide (0.538 g, 5.60 mmol), and chloro(2-dicyclohexylphosphino-2',6'-di-i-propoxy-1,1'-biphenyl)[2-(2-aminoethylphenyl)]palladium(II), methyl-t-butylether adduct (0.152 g, 0.187 mmol) was dissolved in dioxane (10 mL) and degassed under argon for five minutes. The reaction mixture was heated to 60° C. for 30 min under microwave irradation. The reaction mixture was diluted with ethyl acetate and washed with saturated ammonium chloride and brine. The organic layer was dried over sodium sulfate, filtered, and concentrated in vacuo while loading onto silica gel. Purification by flash chromatography (5-30% EtOAc/Hexanes) gave 4-(6-chloro-4-methyl-1-trityl-1H-pyrazolo[4,3-c]pyridin-3-yl)morpholine. MS ESI calc'd. For $C_{30}H_{28}ClN_4O$ [M+H]$^+$ 495. found 495.

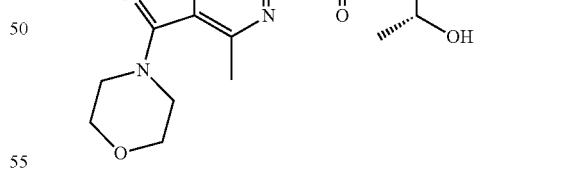

Step 2: 1-((1S,2R)-1-(4-Fluorophenyl)-2-hydroxypropyl)-3-(4-methyl-3-morpholino-1H-pyrazolo[4,3-c]pyridin-6-yl)urea 4-(6-Chloro-4-methyl-1-trityl-1H-pyrazolo[4,3-c]pyridin-3-yl)morpholine (75 mg, 0.152 mmol), 1-((1S,2R)-1-(4-fluorophenyl)-2-hydroxypropyl)urea, (48.2 mg, 0.227 mmol), BrettPhos palladacycle (12.10 mg, 0.015 mmol), cesium carbonate (128 mg, 0.394 mmol) 2-(dicyclohexylphosphino)3,6-dimethoxy-2',4',6'-triisopropyl-1,1'-biphenyl (8.13 mg, 0.015 mmol) were dissolved in dioxane (1 mL) and purged under agron for five minutes. The reaction mixture was heated to 90° C. and stirred for six hrs. The reaction mixture was filtered through celite, rinsed with methanol, and concentrated in vacuo. The crude residue was dissolved in TFA (1 mL) and triethylsilane (0.036 mL, 0.227 mmol) was added. The reaction mixture was stirred at rt for 30 min then diluted with DCM and concentrated in vacuo. The reaction mixture was diluted with DMF (1 mL), filtered, and purified by mass-triggered reverse-phase HPLC. Fractions containing pure compound were filtered through a PS-HCO$_3$ cartridge and the filtrate was concentrated in vacuo to give 1-(1S,2R)-1-(4-fluorophenyl)-2-hydroxypropyl)-3-(4-methyl-3-morpholino-1H-pyrazolo[4,3-c]pyridin-6-yl)urea. MS ESI calc'd. For C$_{21}$H$_{26}$FN$_6$O$_3$ [M+H]$^+$ 429. found 429. $^1$H NMR (ppm, 500 MHz, DMSO-d$_6$) δ 12.17 (s, 1H), 9.11 (s, 1H), 7.31 (dd, J=5.6 Hz, 8.7 Hz, 2H), 7.12 (t, J=8.9 Hz, 2H), 7.06 (s, 1H), 4.91 (s, 1H), 4.69 (dd, J=4.2 Hz, 8.5 Hz, 1H), 3.90 (s, 1H), 3.77-3.73 (m, 5H), 3.08 (d, J=4.2 Hz, 4H), 2.68 (s, 3H), 0.93 (d, J=6.4 Hz, 3H).

Example 108

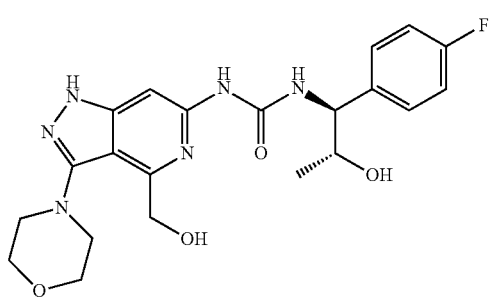 [SMILES: C[C@@H](O)[C@@H](NC(=O)Nc1cc2[nH]nc(N3CCOCC3)c2c(CO)n1)c1ccc(F)cc1]

1-[(1S,2R)-1-(4-Fluorophenyl)-2-hydroxypropyl]-3-[4-(hydroxymethyl)-3-morpholin-4-yl-1H-pyrazolo[4,3-c]pyridin-6-yl]urea

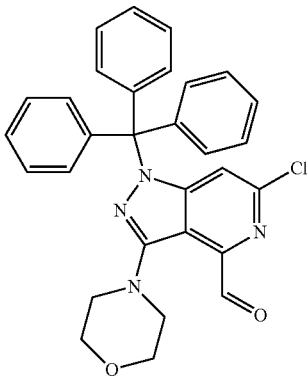 [SMILES: O=Cc1nc(Cl)cc2c1c(N1CCOCC1)nn2C(c1ccccc1)(c1ccccc1)c1ccccc1]

Step 1: 6-Chloro-3-morpholino-1-trityl-1H-pyrazolo[4,3-c]pyridine-4-carbaldehyde 4-(6-Chloro-4-methyl-1-trityl-1H-pyrazolo[4,3-c]pyridin-3-yl)morpholine (Example 106, Step 1; 450.9 mg, 0.911 mmol) was dissolved in dioxane (10 mL) and selenium dioxide (303 mg, 2.73 mmol) was added. The reaction mixture was stirred at reflux over the weekend. The reaction was filtered over celite, rinsed with ethyl acetate, and concentrated in vacuo. The residue was diluted with DCM and filtered over celite. The filtrate was concentrated in vacuo while loading onto silica gel. Purification by flash chromatography (5-40% EtOAc/Hexanes) gave 6-chloro-3-morpholino-1-trityl-1H-pyrazolo[4,3-c]pyridine-4-carbaldehyde. MS ESI calc'd. For C$_{30}$H$_{26}$ClN$_4$O$_2$ [M+H]$^+$ 509. found 509.

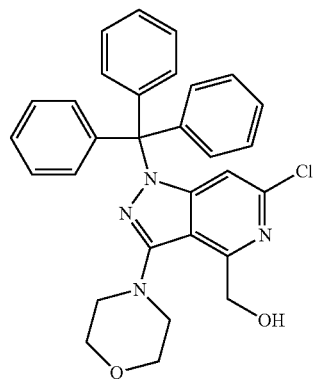 [SMILES: OCc1nc(Cl)cc2c1c(N1CCOCC1)nn2C(c1ccccc1)(c1ccccc1)c1ccccc1]

Step 2: (6-Chloro-3-morpholino-1-trityl-1H-pyrazolo[4,3-c]pyridin-4-yl)methanol

6-Chloro-3-morpholino-1-trityl-1H-pyrazolo [4,3-c]pyridine-4-carbaldehyde (292.2 mg, 0.574 mmol) was dissolved in DCM (3 mL) and methanol (3 mL). Sodium borohydride (21.72 mg, 0.574 mmol) was then added and the reaction mixture was stirred at rt for 15 min. The reaction was quenched with water and extracted with DCM. The organic layer was washed with brine, dried over sodium sulfate, filtered, and concentrated in vacuo while loading onto silica gel. Purification by flash chromatography (5-40% EtOAc/Hexanes) gave (6-chloro-3-morpholino-1-trityl-1H-pyrazolo[4,3-c]pyridin-4-yl)methanol. MS ESI calc'd. For C$_{30}$H$_{28}$ClN$_4$O$_2$ [M+H]$^+$ 511. found 511.

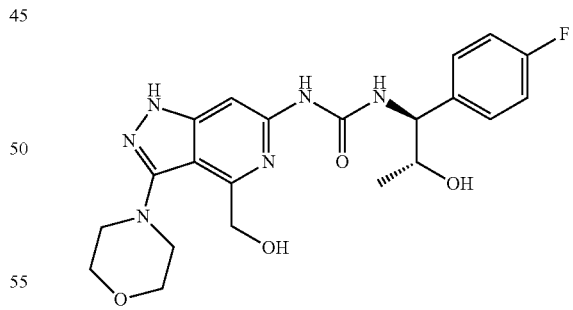

Step 3: 1-[(1S,2R)-1-(4-Fluorophenyl)-2-hydroxypropyl]-3-[4-(hydroxymethyl)-3-morpholin-4-yl-1H-pyrazolo[4,3-c]pyridin-6-yl]urea 1-[(1S,2R)-1-(4-Fluorophenyl)-2-hydroxypropyl]-3-[4-(hydroxymethyl)-3-morpholin-4-yl-1H-pyrazolo[4,3-c]pyridin-6-yl]urea was prepared using the same procedure described for 1-((1S,2R)-1-(4-fluorophenyl)-2-hydroxypropyl)-3-(4-methyl-3-morpholino-1H-pyrazolo[4,3-c]pyridin- 6-yl)urea (Example 106, Step 2). MS ESI calc'd. For $C_{21}H_{25}FN_6O_4$ [M+H]$^+$ 445. found 445. $^1$H NMR (ppm, 500 MHz, DMSO-d$_6$) δ 12.30 (s, 1H), 9.20 (s, 1H), 7.34 (dd, J=5.6 Hz, 8.7 Hz, 2H), 7.18 (s, 1H), 7.11 (t, J=8.9 Hz, 2H), 5.27 (s, 1H), 4.91 (s, 1H), 4.80 (s, 2H), 4.68 (dd, J=4.7 Hz, 8.5 Hz, 1H), 3.89 (s, 1H), 3.79-3.73 (m, 5H), 3.12 (d, J=4.4 Hz, 4H), 0.95 (d, J=6.4 Hz, 3H).

Example 121

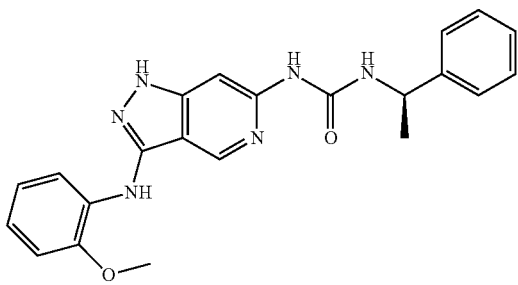 [SMILES: COc1ccccc1Nc1n[nH]c2cc(NC(=O)N[C@H](C)c3ccccc3)ncc12]

1-{3-[(2-methoxyphenyl)amino]-1H-pyrazolo[4,3-c]pyridin-6-yl}-3-[(1R)-1-phenylethyl]urea

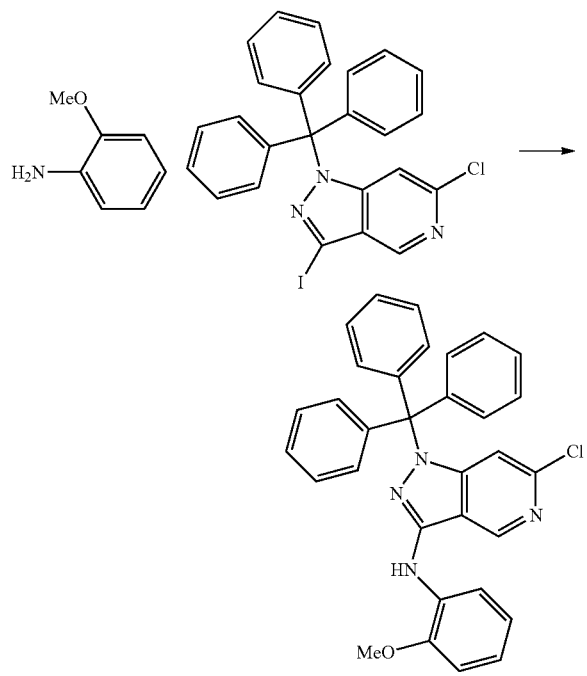

Step 1: 6-chloro-N-(2-methoxyphenyl)-1-trityl-1H-pyrazolo[4,3-c]pyridin-3-amine

A mixture of 2-methoxyaniline (0.18 g), 6-chloro-3-iodo-1-trityl-1H-pyrazolo[4,3-c]pyridine (0.50 g), Cs$_2$CO$_3$ (0.94 g), and (2-dicyclohexylphosphino-2',4',6'-triisopropyl-1,1'-biphenyl)[2-(2-aminoethyl)phenyl]palladium(II) chloride (0.071 g) in toluene (6 mL) was degassed and back filled with nitrogen (3 times) before it was heated at 80° C. for overnight. The reaction was cooled and diluted with ethyl acetate (15 mL) and water (10 mL). The mixture was filtered through celite and the filtrate was separated, the organic layer was wash with with brine (10 mL), dried (MgSO$_4$), filtered and the solvent was evaporated under reduced pressure. The residue was purified by column chromatography on silica gel eluting with EtOAc/isohexane=25% to give 6-chloro-N-(2-methoxyphenyl)-1-trityl-1H-pyrazolo[4,3-c]pyridin-3-amine (380 mg, 77% yield) as a brown solid.

Step 2 and 3: 1-{3-[(2-methoxyphenyl)amino]-1H-pyrazolo[4,3-c]pyridin-6-yl}-3-[(1R)-1-phenylethyl]urea was prepared from 6-chloro-N-(2-methoxyphenyl)-1-trityl-1H-pyrazolo[4,3-c]pyridin-3-amine following a similar procedure in Example 1, steps 2 and 3. MS ESI Calc'd For $C_{22}H_{22}N_6O_2$ [M+H]$^+$ 403. found 403.

Example 135

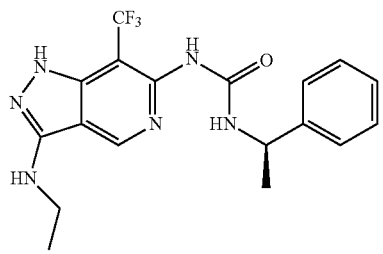 [SMILES: CCNc1n[nH]c2c(C(F)(F)F)c(NC(=O)N[C@H](C)c3ccccc3)ncc12]

(R)-1-(3-(ethylamino)-7-(trifluoromethyl)-1H-pyrazolo[4,3-c]pyridin-6-yl)-3-(1-phenylethyl)urea (R)-1-(3-(ethylamino)-1H-pyrazolo[4,3-c]pyridin-6-yl)-3-(1-phenylethyl)urea (50 mg, 0.154 mmol) and sodium trifluoromethanesulfinate (72.2 mg, 0.462 mmol) were taken in a solvent mixture containing DCE:water:DMSO in a ratio of 2.5:1:0.5, cooled to 0° C. and added tert-butyl hydroperoxide (0.107 mL, 0.771 mmol) and reaction gradually warmed to room temperature. After two more additions of tert-butyl hydroperoxide in equal concentrations in a span of 36 hours, the reaction was partitioned between DCM and aqueous sodium bicarbonate. The organics were washed with brine, dried with sodium sulfate and concentrated. Purification of residue by flash column (0-15% MeOH-DCM) gave (R)-1-(3-(ethylamino)-7-(trifluoromethyl)-1H-pyrazolo[4,3-c]pyridin-6-yl)-3-(1-phenylethyl)urea. MS ESI [M+H]$^+$ calc'd. 393. found 393. $^1$H NMR (ppm, 500 MHz, DMSO-d$_6$) δ 8.60 (s, 1H), 7.40-7.30 (m, 4H), 7.20 (m, 1H), 7.10 (s, 1H), 4.97 (m, 1H), 3.29, (m, 2H), 1.38 (d, J=6.5 Hz, 3H), 1.25 (t, J=7.0 Hz, 3H).

Example 136

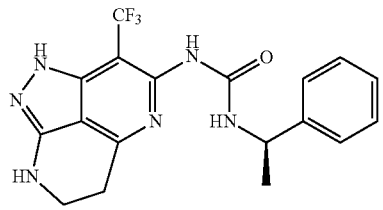 [SMILES: C[C@@H](NC(=O)Nc1nc2c3c(n[nH]c3c1C(F)(F)F)NCC2)c1ccccc1]

183

(R)-1-(1-phenylethyl)-3-(1,3,4,5-tetrahydropyrazolo[3,4,5-de][1,6]naphthyridin-7-yl)urea

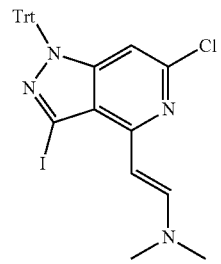

Step 1: (E)-2-(6-chloro-3-iodo-1-trityl-1H-pyrazolo[4,3-c]pyridin-4-yl)-N,N-dimethylethenamine 6-chloro-3-iodo-trityl-1H-pyrazolo[4.3-c]pyridine (Intermediate 1C, 2 g, 3.73 mmol), N, N-dimethylformamide-dimethyl acetal (DMF-DMA) (4.45 g, 37.3 mmol) were stirred at 125° C. for 12 hrs. Reaction was concentrated and excess DMF-DMA azeotroped with toluene. Trituration with cylopentylmethylether gave (E)-2-(6-chloro-3-iodo-1-trityl-1H-pyrazolo[4,3-c]pyridin-4-yl)-N,N-dimethylethenamine. MS ESI calc'd. for $C_{29}H_{24}ClIN_4$ [M+H]$^+$ 591. found 591.

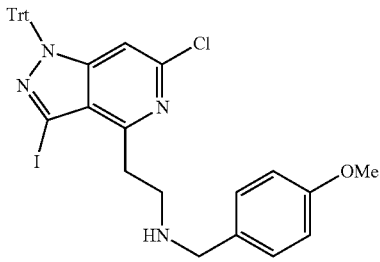

Step 2: 2-(6-chloro-3-iodo-1-trityl-1H-pyrazolo[4,3-c]pyridin-4-yl)-N-(4-methoxybenzyl)ethanamine (E)-2-(6-chloro-3-iodo-1-trityl-1H-pyrazolo[4,3-c]pyridin-4-yl)-N,N-dimethylethenamine (2.2 g, 3.73 mmol) and benzylamine (1.02 g, 7.46 mmol) were stirred in a 3:1:1 solution of DCE:AcOH:EtOH (10 ml) at 85° C. for 3 hrs. Solvent removed by vacuum and residue taken in DCE (15 ml), added sodium triacetoxyborohydride (3.16 g, 14.9 mmol), acetic acid (0.9 g, 14.9 mmol) and stirred at room temperature for 6 hours. Reaction was partitioned between DCM and aqueous sodium bicarbonate and the organics was separated, washed with brine, dried with sodium sulfate and concentrated. Purification of the residue by flash column (0-10% MeOH-EtOAc) gave 2-(6-chloro-3-iodo-1-trityl-1H-pyrazolo[4,3-c]pyridin-4-yl)-N-(4-methoxybenzyl)ethanamine MS ESI calc'd. for $C_{34}H_{28}ClIN_4$ [M+H]$^+$ 685. found 685.

184

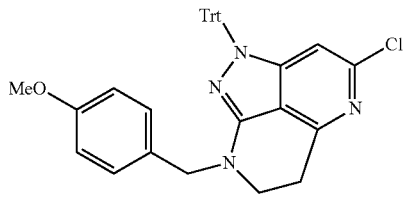

Step 3: 7-chloro-3-(4-methoxybenzyl)-1-trityl-1,3,4,5-tetrahydropyrazolo[3,4,5-de][1,6]naphthyridine 2-(6-chloro-3-iodo-1-trityl-1H-pyrazolo[4,3-c]pyridin-4-yl)-N-(4-methoxybenzyl)ethanamine (268 mg, 0.391 mmol) and RuPhos pre-catalyst (16 mg, 0.02 mmol) were charged in a 1 dram vial, evacuated and backfilled with nitrogen and taken in 1,4-dioxane (2 mL). Added a solution of 2M NaOtBu in THF (0.5 ml, 0.978 mmol) and reaction heated to 55° C. for 1 hour. The reaction mixture was diluted with EtOAc and washed with water, brine, dried with sodium sulfate and concentrated. Purification of the residue by flash column (0-25% EtOAc-hexanes) gave 7-chloro-3-(4-methoxybenzyl)-1-trityl-1,3,4,5-tetrahydropyrazolo[3,4,5-de][1,6]naphthyridine. MS ESI calc'd. for $C_{35}H_{29}ClN_4O$ [M+H]$^+$ 558. found 558.

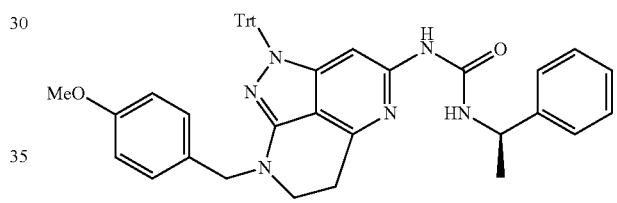

Step 4: (R)-1-(3-(4-methoxybenzyl)-1-trityl-1,3,4,5-tetrahydropyrazolo[3,4,5-de][1,6]naphthyridin-7-yl)-3-(1-phenylethyl)urea 7-chloro-3-(4-methoxybenzyl)-1-trityl-1,3,4,5-tetrahydropyrazolo[3,4,5-de][1,6]naphthyridine (30 mg, 0.054 mmol), (R)-1-(1-phenylethyl)urea (13.26 mg, 0.081 mmol), cesium carbonate (61.4 mg, 0.188 mmol) and BrettPhos pre-catalyst (4.8 mg) were charged in a 1 dram vial, evacuated and backfilled with nitrogen and taken in 1,4-dioxane (0.4 mL) and heated reaction to 100° C. for 1 hour. The reaction mixture was diluted with DCM, washed with water, brine, dried with sodium sulfate and concentrated. Purification of the residue by flash column (0-75% EtOAc-hexanes) gave (R)-1-(3-(4-methoxybenzyl)-1-trityl-1,3,4,5-tetrahydropyrazolo[3,4,5-de][1,6]naphthyridin-7-yl)-3-(1-phenylethyl)urea. MS ESI calc'd. for $C_{44}H_{40}N_6O_2$ [M+H]$^+$ 685. found 685.

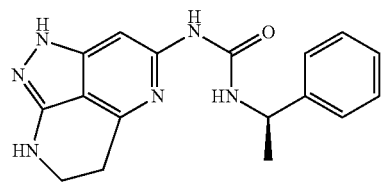 [SMILES: C[C@@H](NC(=O)Nc1cc2[nH]nc3c2c(n1)CCN3)c1ccccc1]

Step 5: (R)-1-(1-phenylethyl)-3-(1,3,4,5-tetrahydro-pyrazolo[3,4,5-de][1,6]naphthyridin-7-yl)urea (R)-1-(3-(4-methoxybenzyl)-1-trityl-1,3,4,5-tetrahydro-pyrazolo[3,4,5-de][1,6]naphthyridin-7-yl)-3-(1-phenylethyl)urea (22 mg, 0.032 mmol) was taken in TFA (0.1 mL) and stirred at room temperature for 30 minutes. To the reaction was added triethylsilane (21 uL, 0.128 mmol) stirred for 15 minutes at room temperature then heated to 80° C. for 30 minutes. The reaction mixture was concentrated, taken in DCM and washed with aqueous sodium bicarbonate, brine, dried with sodium sulfate and concentrated. Purification of the residue by flash column (0-15% MeOH-DCM) gave (R)-1-(1-phenylethyl)-3-(1,3,4,5-tetrahydropyrazolo[3,4,5-de][1,6]naphthyridin-7-yl)urea. MS ESI calc'd. for $C_{17}H_{18}N_6O$ [M+H]$^+$ 323. found 323. $^1$H NMR (ppm, 500 MHz, DMSO-d$_6$) δ 8.98 (s, 1H), 8.45 (br, s, 1H), 7.38 (m, 4H), 7.20 (m, 1H), 7.00 (s, 1H), 6.23 (s, 1H), 4.83 (m, 1H), 3.42 (dd, J=8.0, 5.0 Hz, 2H), 2.80 (dd, J=8.0, 5.0 Hz, 2H), 1.40 (d, J=11 Hz, 3H).

Example 137

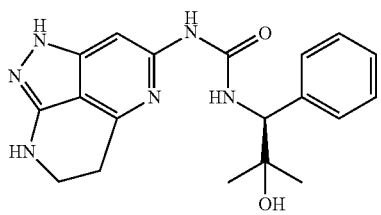 [SMILES: CC(C)(O)[C@@H](NC(=O)Nc1cc2[nH]nc3c2c(n1)CCN3)c1ccccc1]

(S)-1-(2-hydroxy-2-methyl-1-phenylpropyl)-3-(1,3,4-tetrahydropyrazolo[3,4,5-de][1,6]naphthyridin-7-yl)urea

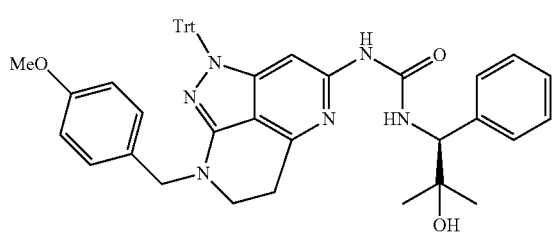

Step 1: (S)-1-(2-hydroxy-2-methyl-1-phenylpropyl)-3-(3-(4-methoxybenzyl)-1-trityl-1,3,4,5-tetrahydro-pyrazolo[3,4,5-de][1,6]naphthyridin-7-yl)urea 7-chloro-3-(4-methoxybenzyl)-1-trityl-1,3,4,5-tetrahydropyrazolo[3,4,5-de][1,6]naphthyridine (40 mg, 0.072 mmol), (S)-1-(2-hydroxy-2-methyl-1-phenylpropyl)urea (22.4 mg, 0.108 mmol), cesium carbonate (82 mg, 0.25 mmol) and BrettPhos pre-catalyst (6.5 mg, 7.18 μM) were charged in a 1 dram vial, evacuated and backfilled with nitrogen and taken in 1,4-dioxane (0.4 mL) and heated reaction to 100° C. for 30 minutes. The reaction mixture was diluted with DCM, washed with water, brine, dried with sodium sulfate and concentrated. Purification of the residue by flash column (0-75% EtOAc-hexanes) gave (S)-1-(2-hydroxy-2-methyl-1-phenylpropyl)-3-(3-(4-methoxybenzyl)-1-trityl-1,3,4,5-tetrahydropyrazolo[3,4,5-de][1,6]naphthyridin-7-yl)urea. MS ESI calc'd. for $C_{46}H_{44}N_6O_3$ [M+H]$^+$ 729. found 729.

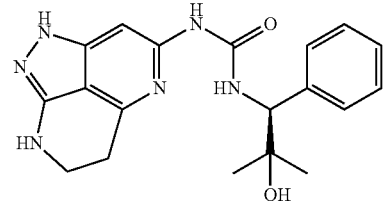 [SMILES: CC(C)(O)[C@@H](NC(=O)Nc1cc2[nH]nc3c2c(n1)CCN3)c1ccccc1]

Step 2: (S)-1-(2-hydroxy-2-methyl-1-phenylpropyl)-3-(1,3,4,5-tetrahydropyrazolo[3,4,5-de][1,6]naphthyridin-7-yl)urea (S)-1-(2-hydroxy-2-methyl-1-phenylpropyl)-3-(3-(4-methoxybenzyl)-1-trityl-1,3,4,5-tetrahydropyrazolo[3,4,5-de][1,6]naphthyridin-7-yl)urea (38 mg, 0.052 mmol) was taken in TFA (0.17 mL) and stirred at room temperature for 30 minutes. To the reaction was added triethylsilane (34 uL, 0.209 mmol) stirred for 15 minutes at room temperature then heated to 80° C. for 30 minutes. The reaction mixture was concentrated, taken in DCM and washed with aqueous sodium bicarbonate, brine, dried with sodium sulfate and concentrated. Purification of the residue by flash column (0-15% MeOH-DCM) gave (S)-1-(2-hydroxy-2-methyl-1-phenylpropyl)-3-(1,3,4,5-tetrahydropyrazolo[3,4,5-de][1,6]naphthyridin-7-yl)urea. MS ESI calc'd. for $C_{19}H_{22}N_6O_2$ [M+H]$^+$ 367. found 367. $^1$H NMR (ppm, 500 MHz, DMSO-d$_6$) δ 9.25 (br, 2H), 7.28 (m, 4H), 7.20 (m, 1H), 6.90 (s, 1H), 4.59 (d, J=14 Hz, 1H), 3.42 (dd, J=8.0, 5.0 Hz, 2H), 2.92 (dd, J=8.0, 5.0 Hz, 2H), 1.95 (s, 3H), 1.0 (s, 3H).

Example 138

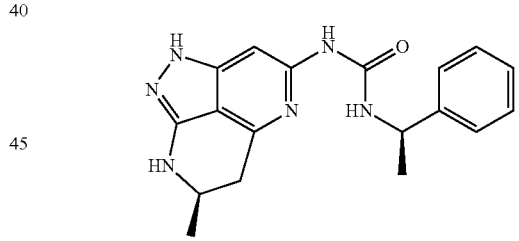

1-((R)-4-methyl-1,3,4,5-tetrahydropyrazolo[3,4,5-de][1,6]naphthyridin-7-yl)-3-((R)-1-phenylethyl)urea

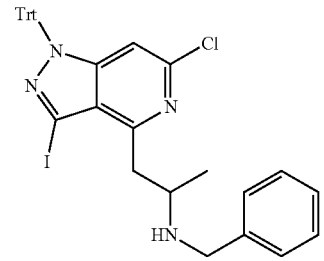

Step 1: N-benzyl-1-(6-chloro-3-iodo-1-trityl-1H-pyrazolo[4,3-c]pyridin-4-yl)propan-2-amine 6-chloro-3-iodo-trityl-1H-pyrazolo[4.3-c]pyridine (Intermediate 1C, 2 g, 3.73 mmol), N, N dimethylacetamide-dimethyl acetal (DMA-DMA) (4.97 g, 37.3 mmol) were stirred at 125° C. for 12 hrs. Reaction was concentrated and excess DMF-DMA azeotroped with Toluene. The resulting intermediate and p-methoxybenzylamine (2.05 g, 14.9 mmol) were stirred in a 3:1:1 solution of DCE:AcOH:EtOH (20 ml) at 85° C. for 3 hrs. Solvent was removed by vacuum and the residue was taken in DCE (15 ml) followed with addition of sodium triacetoxyborohydride (3.16 g, 14.9 mmol) and acetic acid (0.9 g, 14.9 mmol) before the mixture was stirred at room temperature for 6 hours. The reaction mixture was partitioned between DCM and aqueous sodium bicarbonate and the organics was separated, washed with brine, dried with sodium sulfate and concentrated. Purification of the residue by flash column (0-90% -EtOAc-hexanes) gave N-benzyl-1-(6-chloro-3-iodo-1-trityl-1H-pyrazolo[4,3-c]pyridin-4-yl)propan-2-amine MS ESI calc'd. for $C_{35}H_{30}ClIN_4$ [M+H]$^+$ 700. found 700.

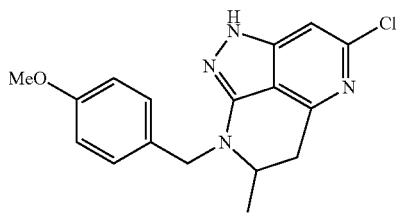 [SMILES: COc1ccc(CN2c3n[nH]c4cc(Cl)nc(c34)CC2C)cc1]

Step 2: 7-chloro-3-(4-methoxybenzyl)-4-methyl-1,3,4,5-tetrahydropyrazolo[3,4,5-de][1,6]naphthyridine N-benzyl-1-(6-chloro-3-iodo-1-trityl-1H-pyrazolo[4,3-c]pyridin-4-yl)propan-2-amine (670 mg, 0.958 mmol) and RuPhos pre-catalyst (70 mg, 0.096 mmol) were charged in a 2 dram vial, evacuated and backfilled with nitrogen and taken in toluene (4.8 mL). A solution of 2M NaOtBu in THF (1.2 ml, 2.4 mmol) was added and the reaction mixture was heated to 55° C. for 12 hours. The reaction mixture was cooled and diluted with EtOAc and washed with water, brine, dried with sodium sulfate and concentrated. Purification of the residue by flash column (0-50% EtOAc-hexanes) gave 7-chloro-3-(4-methoxybenzyl)-4-methyl-1,3,4,5-tetrahydropyrazolo[3,4,5-de][1,6]naphthyridine. MS ESI calc'd. for $C_{35}H_{30}ClIN_4$ [M+H]$^+$ 572. found 572.

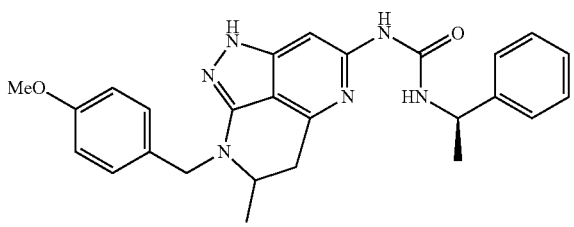 [SMILES: COc1ccc(CN2c3n[nH]c4cc(NC(=O)N[C@H](C)c5ccccc5)nc(c34)CC2C)cc1]

Step 3: 1-(3-(4-methoxybenzyl)-4-methyl-1,3,4,5-tetrahydropyrazolo[3,4,5-de][1,6]naphthyridin-7-yl)-3-((R)-1-phenylethyl)urea 7-chloro-3-(4-methoxybenzyl)-4-methyl-1,3,4,5-tetrahydropyrazolo[3,4,5-de][1,6]naphthyridine (150 mg, 0.263 mmol), (R)-1-(1-phenylethyl)urea (64.7 mg, 0.394 mmol), cesium carbonate (257 mg, 0.788 mmol) and BrettPhos pre-catalyst (23.8 mg, 0.026 mmol) were charged in a 1 dram vial, evacuated and backfilled with nitrogen and taken in 1,4-dioxane (1.4 mL). The mixture was heated at 100° C. for 1 hour before it was diluted with DCM, washed with water, brine, dried with sodium sulfate and concentrated. Purification of the residue by flash column (0-80% EtOAc-hexanes) gave 1-(3-(4-methoxybenzyl)-4-methyl-1,3,4,5-tetrahydropyrazolo[3,4,5-de][1,6]naphthyridin-7-yl)-3-((R)-1-phenylethyl)urea. MS ESI calc'd. for $C_{26}H_{28}N_6O_2$[M+H]$^+$ 699. found 699.

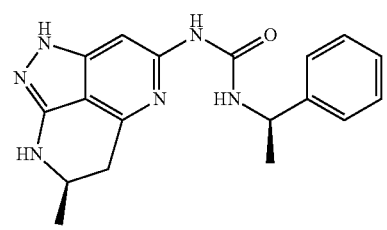 [SMILES: C[C@@H]1Cc2nc(NC(=O)N[C@H](C)c3ccccc3)cc3[nH]nc(c23)N1]

Step 4: 1-((R)-4-methyl-1,3,4,5-tetrahydropyrazolo[3,4,5-de][1,6]naphthyridin-7-yl)-3-((R)-1-phenylethyl)urea 1-(3-(4-methoxybenzyl)-4-methyl-1,3,4,5-tetrahydropyrazolo[3,4,5-de][1,6]naphthyridin-7-yl)-3-((R)-1-phenylethyl)urea (100 mg, 0.143 mmol) was taken in TFA (0.7 mL) and stirred at room temperature for 30 minutes. Triethylsilane (91 uL, 0.572 mmol) was added to the reaction mixture and stirred for 15 minutes at room temperature then heated at 80° C. for 30 minutes. The reaction mixture was concentrated, taken in DCM and washed with aqueous sodium bicarbonate, brine, dried with sodium sulfate and concentrated. Purification of the residue by flash column (0-15% MeOH-DCM) followed by SFC separation with a Chiralpak AS-H column gave 1-((R)-4-methyl-1,3,4,5-tetrahydropyrazolo[3,4,5-de][1,6]naphthyridin-7-yl)-3-((R)-1-phenylethyl)urea as peak 1. MS ESI calc'd. for $C_{18}H_{20}N_6O$ [M+H]$^+$ 337. found 337. $^1$H NMR (ppm, 500 MHz, DMSO-d$_6$) δ 11.29 (s, 1H), 8.90 (s, 1H), 8.40 (br, s, 1H), 7.32 (dd, J=3.4, 7.9, 4H), 7.24-7.14 (m, 1H), 7.00 (s, 1H), 6.30 (s, 1H), 4.83 (m, 1H), 3.65 (m, 1H), 2.88-2.77 (m, 1H), 2.67-2.53 (m, 1H), 1.39 (d, J=6.9, 3H), 1.29 (d, J=6.3, 3H).

Example 139

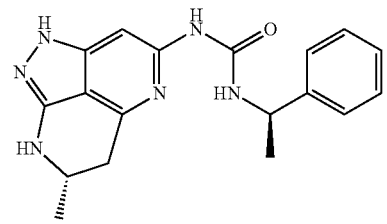 [SMILES: C[C@H]1Cc2nc(NC(=O)N[C@H](C)c3ccccc3)cc3[nH]nc(c23)N1]

1-((S)-4-methyl-1,3,4,5-tetrahydropyrazolo[3,4,5-de][1,6]naphthyridin-7-yl)-3-((R)-1-phenylethyl)urea SFC separation with a Chiralpak AS-H column of Step 4 in Example 138 gave 1-((S)-4-methyl-1,3,4,5-tetrahydropyrazolo[3,4,5-de][1,6]naphthyridin-7-yl)-3-((R)-1-phenylethyl)urea as peak 2. MS ESI calc'd. for $C_{18}H_{20}N_6O$ [M+H]$^+$ 337. found 337. $^1$H NMR (ppm, 500 MHz, DMSO-$d_6$) δ 11.29 (s, 1H), 8.90 (s, 1H), 8.40 (br, s, 1H), 7.32 (dd, J=3.4, 7.9, 4H), 7.24-7.14 (m, 1H), 7.00 (s, 1H), 6.30 (s, 1H), 4.83 (m, 1H), 3.65 (m, 1H), 2.88-2.77 (m, 1H), 2.67-2.53 (m, 1H), 1.39 (d, J=6.9, 3H), 1.29 (d, J=6.3, 3H).

Example 140

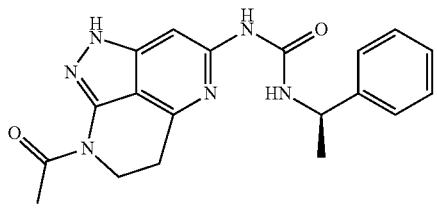 [SMILES: CC(=O)N1CCc2nc(NC(=O)N[C@H](C)c3ccccc3)cc3[nH]nc1c23]

(R)-1-(3-acetyl-1,3,4,5-tetrahydropyrazolo[3,4,5-de][1,6]naphthyridin-7-yl)-3-(1-phenylethyl)urea (R)-1-(1-phenylethyl)-3-(1,3,4,5-tetrahydropyrazolo[3,4,5-de][1,6]naphthyridin-7-yl)urea (Example 136; 13 mg, 0.040 mmol) and triethylamine (50 mg, 0.494 mmol) were taken in DCM (0.15 mL) and added acetyl chloride (20 mg, 0.255 mmol) and stirred for 1 hour. The reaction mixture was diluted with DCM, washed with aqueous sodium bicarbonate, brine, dried with sodium sulfate and concentrated. Purification of the residue by flash column (0-15% MeOH-DCM) gave (R)-1-(3 acetyl-1,3,4,5-tetrahydropyrazolo[3,4,5-de][1,6]naphthyridin-7-yl)-3-(1-phenylethyl)urea. MS ESI calc'd. for $C_{19}H_{20}N_6O_2$ [M+H]$^+$ 365. found 365. $^1$H NMR (ppm, 500 MHz, DMSO-$d_6$) δ 12.35 (s, 1H), 9.13-9.05 (m, 1H), 8.05-7.86 (m, 1H), 7.39-7.28 (m, 6H), 7.27-7.18 (m, 1H), 3.06-2.96 (m, 2H), 1.38 (t, J=9.1, 3H), 1.25-1.18 (m, 2H).

Example 141

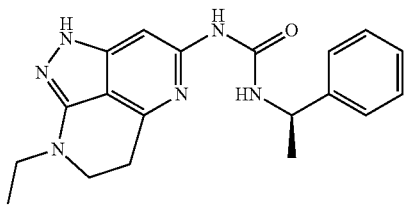 [SMILES: CCN1CCc2nc(NC(=O)N[C@H](C)c3ccccc3)cc3[nH]nc1c23]

(R)-1-(3-ethyl-1,3,4,5-tetrahydropyrazolo[3,4,5-de][1,6]naphthyridin-7-yl)-3-(1-phenylethyl)urea

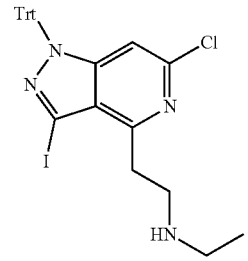

Step 1: 2-(6-chloro-3-iodo-1-trityl-1H-pyrazolo[4,3-c]pyridin-4-yl)-N-ethylethanamine (E)-2-(6-chloro-3-iodo-1-trityl-1H-pyrazolo[4,3-c]pyridin-4-yl)-N,N-dimethylethenamine (1.0 g, 1.692 mmol) and ethanamine HCl (0.552 g, 6.77 mmol) were stirred in a 3:1:1 solution of DCE:AcOH:EtOH (5 ml) at 100° C. for 2 hrs. Solvent was removed by vacuum and the residue was taken in DCE (15 ml) and treated with sodium triacetoxyborohydride (0.9 g, 4.23 mmol), acetic acid (0.4 g, 6.7 mmol) and stirred at room temperature for 6 hours. The eaction mixture was partitioned between DCM and aqueous sodium bicarbonate and the organics was separated, washed with brine, dried with sodium sulfate and concentrated. Purification of the residue by flash column (0-15% MeOH-DCM) gave 2-(6-chloro-3-iodo-1-trityl-1H-pyrazolo[4,3-c]pyridin-4-yl)-N-ethylethanamine. MS ESI calc'd. for $C_{29}H_{26}ClIN_4$ [M+H]$^+$ 593. found 593.

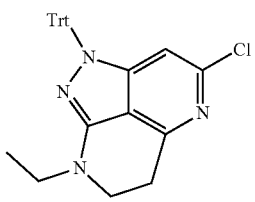

Step 2: 7-chloro-3-ethyl-1-trityl-1,3,4,5-tetrahydropyrazolo[3,4,5-de][1,6]naphthyridine 2-(6-chloro-3-iodo-1-trityl-1H-pyrazolo[4,3-c]pyridin-4-yl)-N-ethylethanamine (160 mg, 0.270 mmol) and RuPhos pre-catalyst (19.6 mg, 0.027 mmol) were charged in a 1 dram vial, evacuated and backfilled with nitrogen and taken in toluene (1.8 mL) before a solution of 2M NaOtBu in THF (0.34 ml, 0.675 mmol) was added. The reaction mixture was heated at 55° C. for 1 hour before it was diluted with EtOAc and washed with water, brine, dried with sodium sulfate and concentrated. Purification of the residue by flash column (0-50% EtOAc-hexanes) gave 7-chloro-3-ethyl-1-trityl-1,3,4,5-tetrahydropyrazolo[3,4,5-de][1,6]naphthyridine. MS ESI calc'd. for $C_{29}H_{25}ClN_4$ [M+H]$^+$ 465. found 465.

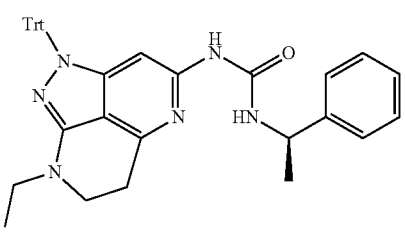

Step 3: (R)-1-(3-ethyl-1-trityl-1,3,4,5-tetrahydropyrazolo[3,4,5-de][1,6]naphthyridin-7-yl)-3-(1-phenylethyl)urea 7-chloro-3-ethyl-1-trityl-1,3,4,5-tetrahydropyrazolo[3,4,5-de][1,6]naphthyridine (35 mg, 0.075 mmol), (R)-1-(1-phenylethyl)urea (18.5 mg, 0.113 mmol), cesium carbonate (73.6 mg, 0.226 mmol) and BrettPhos pre-catalyst (6.8 mg) were charged in a 1 dram vial, evacuated and backfilled with nitrogen and taken in 1,4-dioxane (0.4 mL) and heated reaction at 100° C. for 1 hour. The reaction mixture was diluted with DCM, washed with water, brine, dried with sodium sulfate and concentrated. Purification of the residue by flash column (0-75% EtOAc-hexanes) gave (R)-1-(3-ethyl-1-trityl-1,3,4,5-tetrahydropyrazolo[3,4,5-de][1,6]naphthyridin-7-yl)-3-(1-phenylethyl)urea. MS ESI calc'd. for $C_{38}H_{36}N_6O$ [M+H]$^+$ 593. found 593.

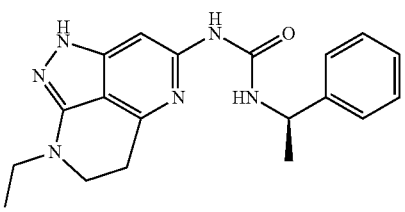 [SMILES: CCN1CCc2nc(NC(=O)N[C@H](C)c3ccccc3)cc3[nH]nc1c23]

Step 4: (R)-1-(3-ethyl-1,3,4,5-tetrahydropyrazolo[3,4,5-de][1,6]naphthyridin-7-yl)-3-(1-phenylethyl)urea (R)-1-(3-ethyl-1-trityl-1,3,4,5-tetrahydropyrazolo[3,4,5-de][1,6]naphthyridin-7-yl)-3-(1-phenylethyl)urea (27 mg, 0.045 mmol) was taken in TFA (0.1 mL) and stirred at room temperature for 30 minutes. To the reaction was added triethylsilane (21 uL, 0.128 mmol) and the mixture was stirred for 15 minutes at room temperature before it was heated at 80° C. for 30 minutes. The reaction mixture was concentrated, taken in DCM and washed with aqueous sodium bicarbonate, brine, dried with sodium sulfate and concentrated. Purification of the residue by flash column (0-15% MeOH-DCM) gave (R)-1-(3-ethyl-1,3,4,5-tetrahydropyrazolo[3,4,5-de][1,6]naphthyridin-7-yl)-3-(1-phenylethyl)urea. MS ESI calc'd. for $C_{19}H_{22}N_6O$ [M+H]$^+$ 351. found 351. $^1$H NMR (ppm, 500 MHz, DMSO-d$_6$) δ 7.32 (dd, J=3.4, 7.9, 4H), 7.24-7.14 (m, 1H), 6.40 (s, 1H), 4.90-4.79 (m, 1H), 4.02-3.89 (m, 2H), 3.40 (m, 2H), 3.01 (m, 2H), 1.40 (d, J=6.9, 3H), 1.24 (t, J=9.4, 3H).

Example 142

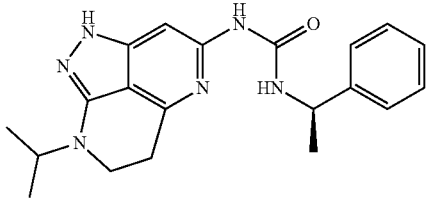 [SMILES: CC(C)N1CCc2nc(NC(=O)N[C@H](C)c3ccccc3)cc3[nH]nc1c23]

(R)-1-(3-isopropyl-1,3,4,5-tetrahydropyrazolo[3,4,5-de][1,6]naphthyridin-7-yl)-3-(1-phenylethyl)urea

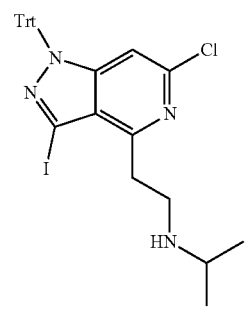

Step 1: N-(2-(6-chloro-3-iodo-1-trityl-1H-pyrazolo[4,3-c]pyridin-4-yl)ethyl)propan-2-amine (E)-2-(6-chloro-3-iodo-1-trityl-1H-pyrazolo[4,3-c]pyridin-4-yl)-N,N-dimethylethenamine (1.0 g, 1.692 mmol) and propan-2-amine HCl (0.647 g, 6.77 mmol) were stirred in a 3:1:1 solution of DCE:AcOH:EtOH (5 ml) at 100° C. for 2 hrs. Solvent was removed by vacuum and the residue was taken in DCE (15 ml) and treated with sodium triacetoxyborohydride (0.9 g, 4.23 mmol), acetic acid (0.4 g, 6.7 mmol) and stirred at room temperature for 6 hours. The reaction mixture was partitioned between DCM and aqueous sodium bicarbonate and the organics separated, washed with brine, dried with sodium sulfate and concentrated. Purification of the residue by flash column (0-15% MeOH-DCM) gave N-(2-(6-chloro-3-iodo-1-trityl-1H-pyrazolo[4,3-c]pyridin-4-yl)ethyl)propan-2-amine MS ESI calc'd. for $C_{30}H_{28}ClIN_4$ [M+H]$^+$ 607. found 607.

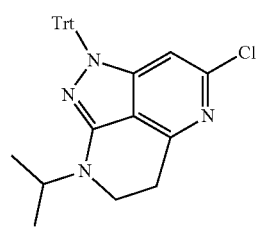

Step 2: 7-chloro-3-isopropyl-1-trityl-1,3,4,5-tetrahydropyrazolo[3,4,5-de][1,6]naphthyridine N-(2-(6-chloro-3-iodo-1-trityl-1H-pyrazolo[4,3-c]pyridin-4-yl)ethyl)propan-2-amine (554 mg, 0.913 mmol) and RuPhos pre-catalyst (66.5 mg, 0.091 mmol) were charged in a 2 dram vial, evacuated and backfilled with nitrogen and taken in toluene (4 mL) before the addition of a solution of 2M NaOtBu in THF (1.15 mL, 2.3 mmol). The reaction mixture was heated at 55° C. for 1 hour before it was diluted with EtOAc and washed with water, brine, dried with sodium sulfate and concentrated. Purification of the residue by flash column (0-50% EtOAc-hexanes) gave 7-chloro-3-isopropyl-1-trityl-1,3,4,5-tetrahydropyrazolo[3,4,5-de][1,6]naphthyridine. MS ESI calc'd. for $C_{30}H_{27}ClN_4$ [M+H]$^+$ 480. found 480.

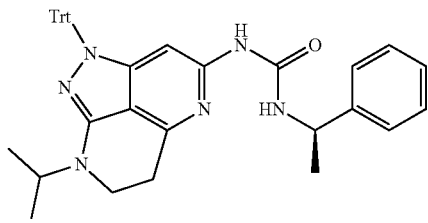

Step 3: (R)-1-(3-isopropyl-1-trityl-1,3,4,5-tetrahydropyrazolo[3,4,5-de][1,6]naphthyridin-7-yl)-3-(1-phenylethyl)urea 7-chloro-3-isopropyl-1-trityl-1,3,4,5-tetrahydropyrazolo[3,4,5-de][1,6]naphthyridine (116 mg, 0.242 mmol), (R)-1-(1-phenylethyl)urea (60 mg, 0.363 mmol), cesium carbonate (237 mg, 0.726 mmol) and BrettPhos pre-catalyst (22 mg, 0.024 mmol) were charged in a 1 dram vial, evacuated and backfilled with nitrogen and taken in 1,4-dioxane (1.2 mL) before the mixture was heated reaction at 100° C. for 1 hour. The reaction mixture was diluted with DCM, washed with water, brine, dried with sodium sulfate and concentrated. Purification of the residue by flash column (0-75% EtOAc-hexanes) gave (R)-1-(3-isopropyl-1-trityl-1,3,4,5-tetrahydropyrazolo[3,4,5-de][1,6]naphthyridin-7-yl)-3-(1-phenylethyl)urea. MS ESI calc'd. for $C_{39}H_{38}N_6O$ [M+H]$^+$ 607. found 607.

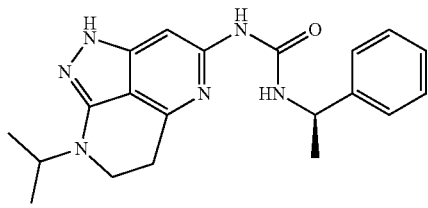 [SMILES: CC(C)N1CCc2nc(NC(=O)N[C@H](C)c3ccccc3)cc3[nH]nc1c23]

Step 4: (R)-1-(3-isopropyl-1,3,4,5-tetrahydropyrazolo[3,4,5-de][1,6]naphthyridin-7-yl)-3-(1-phenylethyl)urea (R)-1-(3-isopropyl-1-trityl-1,3,4,5-tetrahydropyrazolo[3,4,5-de][1,6]naphthyridin-7-yl)-3-(1-phenylethyl)urea (75 mg, 0.123 mmol) was taken in TFA (0.5 mL) and stirred at room temperature for 30 minutes before triethylsilane (155 uL, 0.97 mmol) was added. The reaction mixture was stirred for 15 minutes at room temperature then heated at 80° C. for 30 minutes before it was concentrated, taken in DCM and washed with aqueous sodium bicarbonate, brine, dried with sodium sulfate and concentrated. Purification of the residue by flash column (0-15% MeOH-DCM) gave (R)-1-(3-isopropyl-1,3,4,5-tetrahydropyrazolo[3,4,5-de][1,6]naphthyridin-7-yl)-3-(1-phenylethyl)urea. MS ESI calc'd. for $C_{20}H_{24}N_6O$ [M+H]$^+$ 365. found 365. $^1$H NMR (ppm, 500 MHz, DMSO-$d_6$) δ 7.34-7.23 (m, 4H), 7.18 (m, 1H), 6.40 (s, 1H), 4.90 (m, 1H), 3.40 (m, 2H), 3.22 (m, 2H), 2.90 (m, 1H), 1.38 (d, J=7.0, 3H), 1.07 (d, J=9.4, 6H).

Example 144

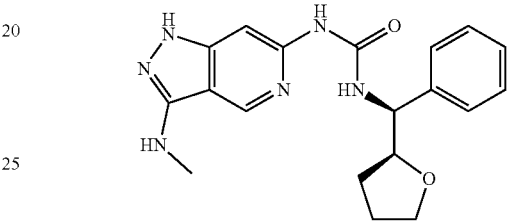

1-(3-(methylamino)-1H-pyrazolo[4,3-c]pyridin-6-yl)-3-((S)-phenyl((S)-tetrahydrofuran-2-yl)methyl)urea

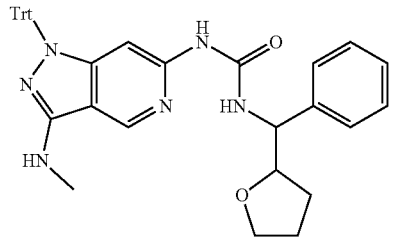

Step 1: 1-(3-(methylamino)-1-trityl-1H-pyrazolo[4,3-c]pyridin-6-yl)-3-(phenyl(tetrahydrofuran-2-yl)methyl)urea 6-chloro-N-methyl-1-trityl-1H-pyrazolo[4,3-c]pyridin-3-amine (400 mg, 0.941 mmol), 1-(phenyl(tetrahydrofuran-2-yl)methyl)urea (228 mg, 1.035 mmol), cesium carbonate (920 mg, 2.82 mmol) and BrettPhos precatalyst (52.6 mg, 0.066 mmol) were taken up in dioxane (9.5 ml) in a 20 mL microwave vial. The vial was evacuated and back-filled with $N_2$ (×3). The reaction mixture was stirred at 100° C. for two hours. Room temperature was attained. The crude reaction mixture was diluted with EtOAc and filtered through celite. The filtrate was concentrated in vacuo, taken up in 5 ml of DCM, and purified on silica gel 5-50% DCM/EtOAc to give 1-(3-(methylamino)-1-trityl-1H-pyrazolo[4,3-c]pyridin-6-yl)-3-(phenyl(tetrahydrofuran-2-yl)methyl)urea. MS ESI calc'd. for $C_{38}H_{37}N_6O_2$ [M+H]$^+$ 609. found 609.

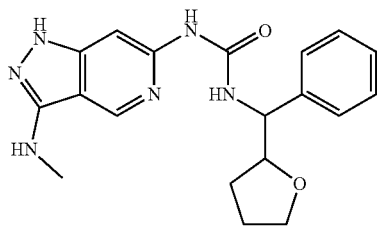 [SMILES: CNc1n[nH]c2cc(NC(=O)NC(c3ccccc3)C3CCCO3)ncc12]

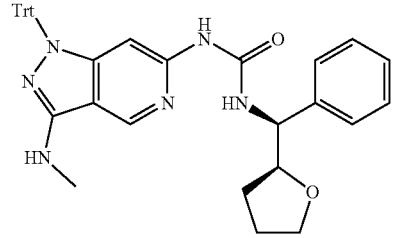

Step 2: 1-(3-(methylamino)-1H-pyrazolo[4,3-c]pyridin-6-yl)-3-(phenyl(tetrahydrofuran-2-yl)methyl)urea 1-(3-(methylamino)-1-trityl-1H-pyrazolo[4,3-c]pyridin-6-yl)-3-(phenyl(tetrahydrofuran-2-yl)methyl)urea (320 mg, 0.526 mmol) was taken up in TFA (3.0 ml). Triethylsilane (0.126 ml, 0.789 mmol) was added and the reaction was allowed to stir at rt for 30 mins. The reaction mixture was concentrated in vacuo. Saturated NaHCO$_3$ was slowly added. The products were then washed with EtOAc (3×). The combined organic layers were then washed with brine, dried over MgSO$_4$, filtered through celite, then concentrated in vacuo. The oil was taken up in 2 ml of DCM and loaded directly onto silica gel. Purification by MPLC 0-15% EtOAc/MeOH gave 1-(3-(methylamino)-1H-pyrazolo[4,3-c]pyridin-6-yl)-3-(phenyl(tetrahydrofuran-2-yl)methyl)urea. MS ESI calc'd. for C$_{19}$H$_{23}$N$_6$O$_2$ [M+H]$^+$ 367. found 367.

Step 3: 1-(3-(methylamino)-1-trityl-1H-pyrazolo[4,3-c]pyridin-6-yl)-3-((S)-phenyl((S)-tetrahydrofuran-2-yl)methyl)urea The enantiomers of 1-(3-(methylamino)-1H-pyrazolo[4,3-c]pyridin-6-yl)-3-(phenyl(tetrahydrofuran-2-yl)methyl)urea (213 mg, 0.518 mmol) were separated by SFC (Berger Multigram II, Column: Phenomenex Lux-4 2.1×25 cm, SuM, UV wavelength: 220 nM, mobile phase: 45%/55% Methanol+ 0.25% dimethyl ethylamine/CO$_{2(l)}$, flow rate: 70 mL/Min, 9 min run time). Elution was observed at 3.46 min. The fractions were collected and the solvent evaporated in vacuo to afford 1-(3-(methylamino)-1-trityl-1H-pyrazolo[4,3-c]pyridin-6-yl)-3-((S)-phenyl((S)-tetrahydrofuran-2-yl)methyl)urea and Examples 145-147. MS ESI calc'd. for C$_{19}$H$_{23}$N$_6$O$_2$ [M+H]$^+$ 367. found 367. $^1$H NMR (ppm, 500 MHz, DMSO-d$_6$) δ 11.46 (s, 1H), 8.99 (s, 1H), 8.61 (br s, 1H), 7.31 (m, 4H), 7.22 (m, 1H), 7.14 (s, 1H), 6.23 (t, J=5.0, 1H), 4.80 (dd, J=5.5, J=3.0, 1H), 4.10 (q, J=5.5, 1H), 3.67-360 (m, 2H), 3.21 (p, J=7.0, 2H), 1.83 (m, 1H), 1.71 (m, 1H), 1.56 (m, 2H), 1.20 (t, J=7.0, 3H).

| No. | Structure | IUPAC Name | Exact Mass [M + H]+ |
|---|---|---|---|
| 145 | 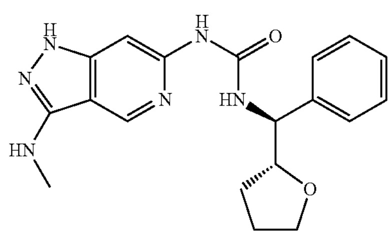 [SMILES: CNc1n[nH]c2cc(NC(=O)N[C@@H](c3ccccc3)[C@H]3CCCO3)ncc12] | 1-(3-(methylamino)-1H-pyrazolo[4,3-c]pyridin-6-yl)-3-((S)-phenyl((R)-tetrahydrofuran-2-yl)methyl)urea | Calc'd 367, found 367 |
| 146 | 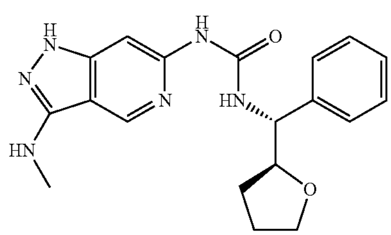 [SMILES: CNc1n[nH]c2cc(NC(=O)N[C@H](c3ccccc3)[C@@H]3CCCO3)ncc12] | 1-(3-(methylamino)-1H-pyrazolo[4,3-c]pyridin-6-yl)-3-((R)-phenyl((S)-tetrahydrofuran-2-yl)methyl)urea | Calc'd 367, found 367 |
| 147 | 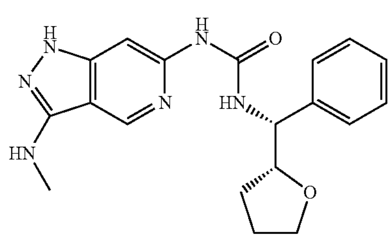 [SMILES: CNc1n[nH]c2cc(NC(=O)N[C@H](c3ccccc3)[C@H]3CCCO3)ncc12] | 1-(3-(methylamino)-1H-pyrazolo[4,3-c]pyridin-6-yl)-3-((R)-phenyl((R)-tetrahydrofuran-2-yl)methyl)urea | Calc'd 367, found 367 |

Example 313

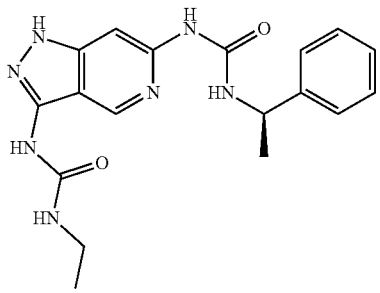 [SMILES: CCNC(=O)Nc1n[nH]c2cc(NC(=O)N[C@H](C)c3ccccc3)ncc12]

(R)-1-(3-(3-ethylureido)-1H-pyrazolo[4,3-c]pyridin-6-yl)-3-(1-phenylethyl)urea

Step 1: (R)-1-(3-(3-ethylureido)-1-trityl-1H-pyrazolo[4,3-c]pyridin-6-yl)-3-(1-phenylethyl)urea To an 8 mL vial charged with (R)-1-(3-amino-1-trityl-1H-pyrazolo[4,3-c]pyridin-6-yl)-3-(1-phenylethyl)urea (25 mg, 0.046 mmol) in DCM (1 ml) was added ethyl isocyanate (5.51 μl, 0.070 mmol) and DIEA (0.024 ml, 0.139 mmol). The vial was capped and the contents stirred at room temperature for 16 h. The course of reaction was followed by LCMS analysis. Only minor product formation was observed. Excess isocyanate (1.5 eq) was added and the reaction mixture heated to 40° C. for a further 16 h. Unreacted isocyanate was quenched by adding MP-Trisamine (229 mg, 0.464 mmol) and tumbling the vial for 3 h. The resin was filtered and the volatiles removed in vacuo to afford crude (R)-1-(3-(3-ethylureido)-1-trityl-1H-pyrazolo[4,3-c]pyridin-6-yl)-3-(1-phenylethyl)urea which was taken forward without purification. MS ESI calc'd. For $C_{37}H_{36}N_7O_2$ [M+H]$^+$ 610. found 610.

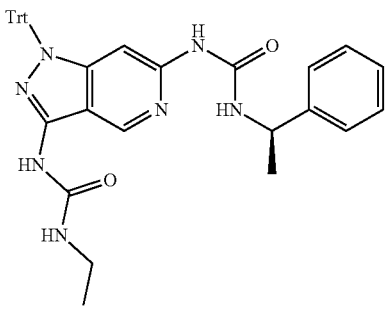

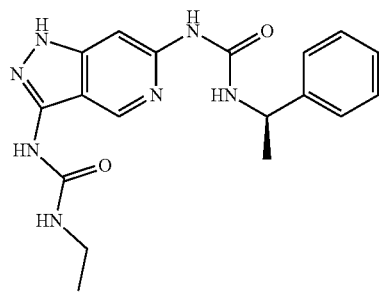 [SMILES: CCNC(=O)Nc1n[nH]c2cc(NC(=O)N[C@H](C)c3ccccc3)ncc12]

Step 2: (R)-1-(3-(3-ethylureido)-1H-pyrazolo[4,3-c]pyridin-6-yl)-3-(1-phenylethyl)urea (R)-1-(3-(3-ethylureido)-1-trityl-1H-pyrazolo[4,3-c]pyridin-6-yl)-3-(1-phenylethyl)urea (0.046 mmol) was taken up in TFA (1 ml) and the reaction mixture stirred at room temperature for 1 h. Triethylsilane (0.008 ml, 0.046 mmol) was added drop wise, and the reaction mixture stirred for an additional 5 minutes. The mixture was concentrated, re-dissolved in DMSO (1.5 mL) and submitted for purification by mass-triggered preparative HPLC to afford (R)-1-(3-(3-ethylureido)-1H-pyrazolo[4,3-c]pyridin-6-yl)-3-(1-phenylethyl)urea.TFA (9.2 mg, 0.019 mmol, 41.2% yield) as a white solid. MS ESI calc'd. For $C_{18}H_{27}N_7O_2$ [M+H]$^+$ 368. found 368. $^1$H NMR (ppm, 600 MHz, DMSO): δ 9.67 (s, 1H); 9.08 (s, 1H); 7.81 (s, 1H); 7.36 (s, 1H); 7.31-7.32 (m, 4H); 7.19-7.22 (m, 1H); 4.81-4.86 (m, 1H); 3.16-3.20 (m, 2H); 1.39 (d, J=7.0 Hz, 3H); 1.07 (t, J=7.2 Hz, 3H).

Example 220

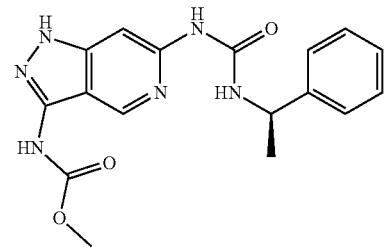 [SMILES: COC(=O)Nc1n[nH]c2cc(NC(=O)N[C@H](C)c3ccccc3)ncc12]

(R)-methyl (6-(3-(1-phenylethyl)ureido)-1-trityl-1H-pyrazolo[4,3-c]pyridin-3-yl)carbamate

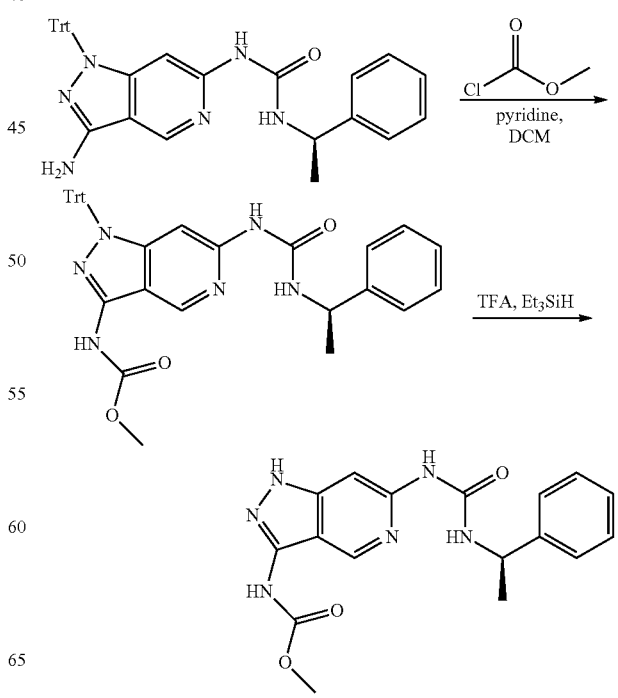

-continued

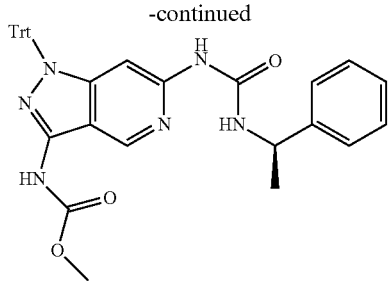

Step 1: (R)-methyl (6-(3-(1-phenylethyl)ureido)-1-trityl-1H-pyrazolo[4,3-c]pyridin-3-yl)carbamate To a 50 mL round bottom flask charged with (R)-1-(3-amino-1-trityl-1H-pyrazolo[4,3-c]pyridin-6-yl)-3-(1-phenylethyl)urea (380 mg, 0.705 mmol) in DCM (10 ml) was added pyridine (1 ml) followed by methyl chloroformate (65 μl, 0.847 mmol). The flask was capped and the contents stirred at room temperature for 16 h. An additional aliquot of methyl chloroformate (65 μL, 0.847 mmol) was added to push the reaction to completion. The volatiles were removed in vacuo, the resulting residue redissolved in DCM and washed with saturated copper sulfate solution (2×10 mL). The organics were separated using a phase separator cartridge and concentrated. The resulting residue was purified by flash column chromatography on silica gel (ISCO; 80 g prepacked) eluting with ethyl acetate/hexanes to give (R)-methyl (6-(3-(1-phenylethyl)ureido)-1-trityl-1H-pyrazolo[4,3-c]pyridin-3-yl)carbamate (371 mg, 0.622 mmol, 88%) as a white solid. MS ESI calc'd. For $C_{36}H_{33}N_6O_3$ [M+H]$^+$ 597. found 597.

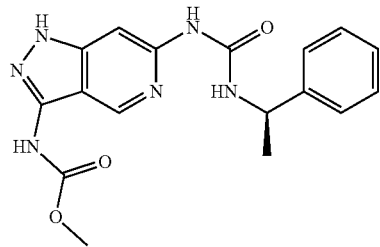 [SMILES: COC(=O)Nc1n[nH]c2cc(NC(=O)N[C@H](C)c3ccccc3)ncc12]

Step 2: (R)-methyl (6-(3-(1-phenylethyl)ureido)-1H-pyrazolo[4,3-c]pyridin-3-yl)carbamate (R)-methyl (6-(3-(1-phenylethyl)ureido)-1-trityl-1H-pyrazolo[4,3-c]pyridin-3-yl)carbamate (0.622 mmol) was taken up in TFA (5 ml) and the reaction mixture stirred at room temperature for 1 h. Triethylsilane (0.113 ml, 0.705 mmol) was added drop wise, and the reaction mixture stirred for an additional 5 minutes. The mixture was concentrated, re-dissolved in DMSO (1.5 mL) and submitted for purification by mass-triggered preparative HPLC to afford (R)-methyl (6-(3-(1-phenylethyl)ureido)-1H-pyrazolo[4,3-c]pyridin-3-yl)carbamate, TFA (190 mg, 0.406 mmol, 57.5% yield) as a white solid. MS ESI calc'd. For $C_{17}H_{19}N_6O_3$ [M+H]$^+$ 355. found 355. $^1$H NMR (600 MHz, DMSO): 12.69 (br s, 1H); 10.39 (br s, 1H); 9.27 (br s, 1H); 8.95 (s, 1H); 7.76 (br s, 1H); 7.43 (s, 1H); 7.31 (d, J=4.5 Hz, 4H); 7.21 (m, 1H); 4.85 (t, J=7.3 Hz, 1H); 3.68 (s, 3H); 1.39 (d, J=6.9 Hz, 3H).

Example 315

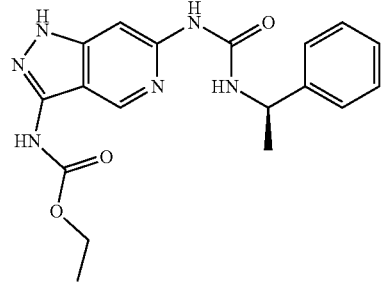

(R)-ethyl(6-(3-(1-phenylethyl)ureido)-1H-pyrazolo[4,3-c]pyridin-3-yl)carbamate

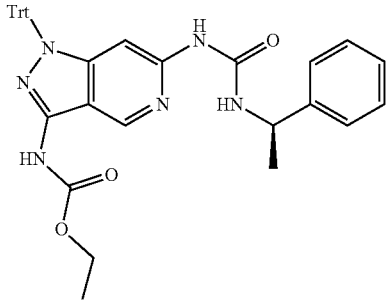

Step 1: (R)-ethyl(6-(3-(1-phenylethyl)ureido)-1-trityl-1H-pyrazolo[4,3-c]pyridin-3-yl)carbamate To an 8 mL vial charged with (R)-1-(3-amino-1-trityl-1H-pyrazolo[4,3-c]pyridin-6-yl)-3-(1-phenylethyl)urea (20 mg, 0.037 mmol) in DCM (1 ml) was added pyridine (0.1 ml) followed by ethyl chloroformate (10.70 μl, 0.111 mmol). The vial was capped and the contents stirred at room temperature for 16 h. Un-reacted chloroformate was quenched by adding MP-Trisamine (91 mg, 0.186 mmol) and tumbling the vial for an additional 3 h. The resin was filtered and the volatiles removed in vacuo to afford crude (R)-ethyl(6-(3-(1-phenylethyl)ureido)-1-trityl-1H-pyrazolo[4,3-c]pyridin-3-yl)carbamate which was taken forward without purification. MS ESI calc'd. For $C_{37}H_{35}N_6O_3$ [M+H]$^+$ 611. found 611.

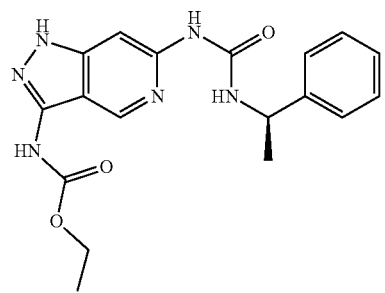 [SMILES: CCOC(=O)Nc1n[nH]c2cc(NC(=O)N[C@H](C)c3ccccc3)ncc12]

Step 2: (R)-ethyl(6-(3-(1-phenylethyl)ureido)-1H-pyrazolo[4,3-c]pyridin-3-yl)carbamate (R)-ethyl(6-(3-(1-phenylethyl)ureido)-1-trityl-1H-pyrazolo[4,3-c]pyridin-3-yl)carbamate (0.037 mmol) was taken up in TFA (1 ml) and the reaction mixture stirred at room temperature for 1 h. Triethylsilane (0.006 ml, 0.037 mmol) was added drop wise, and the reaction mixture stirred for an additional 5 minutes. The mixture was concentrated, re-dissolved in DMSO (1.5 mL) and submitted for purification by mass-triggered preparative HPLC to afford (R)-ethyl(6-(3-(1-phenylethyl)ureido)-1H-pyrazolo[4,3-c]pyridin-3-yl)carbamate (5.7 mg, 0.015 mmol, 41.7% yield) as a white solid. MS ESI calc'd. For $C_{18}H_{21}N_6O_3$ [M+H]$^+$ 369. found 369. $^1$H NMR (ppm, 600 MHz, DMSO): δ 8.95 (s, 1H); 7.78 (s, 1H); 7.42 (s, 1H); 7.30-7.31 (m, 4H); 7.19-7.22 (m, 1H); 4.85 (t, J=7.2 Hz, 1H); 4.14 (q, J=7.1 Hz, 2H); 1.39 (d, J=7.0 Hz, 3H); 1.22 (t, J=7.1 Hz, 3H).

Example 316

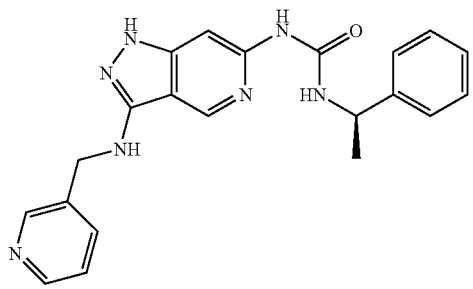 [SMILES: C[C@@H](NC(=O)Nc1cc2[nH]nc(NCc3cccnc3)c2cn1)c1ccccc1]

(R)-1-(1-phenylethyl)-3-(3-((pyridin-3-ylmethyl)amino)-1H-pyrazolo[4,3-c]pyridin-6-yl)urea

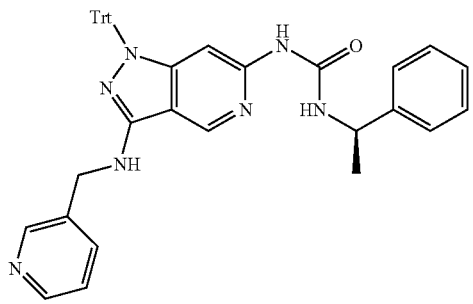

Step 1: (R)-1-(1-phenylethyl)-3-(3-((pyridin-3-ylmethyl)amino)-1-trityl-1H-pyrazolo[4,3-c]pyridin-6-yl)urea To an 8 mL vial charged with nicotinaldehyde (30 mg, 0.278 mmol) was added (R)-1-(3-amino-1-trityl-1H-pyrazolo[4,3-c]pyridin-6-yl)-3-(1-phenylethyl)urea (30 mg, 0.056 mmol) in methanol (1 ml) and acetic acid (0.1 ml). The vial was capped and the contents stirred at room temperature for 2 h. Sodium cyanoborohydride (10.5 mg, 0.167 mmol) was added and the reaction mixture stirred for an additional 16 h. The reaction mixture was diluted with DCM (1 mL), trisamine MP-resin (274 mg, 0.557 mmol) added, and the contents of the vial shaken at room temperature for 3 h. The resin was filtered, and washed through with DCM (1 mL). The volatiles were removed in vacuo to afford crude (R)-1-(1-phenylethyl)-3-(3-((pyridin-3-ylmethyl)amino)-1-trityl-1H-pyrazolo[4,3-c]pyridin-6-yl)urea, which was taken forward without purification. MS ESI calc'd. For $C_{40}H_{36}N_7O$ [M+H]$^+$ 630. found 630.

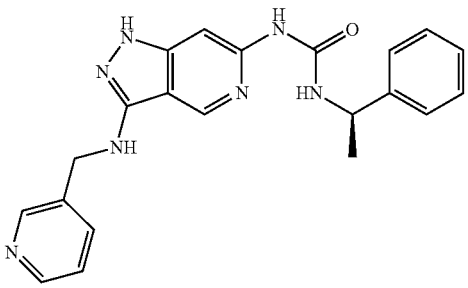 [SMILES: C[C@@H](NC(=O)Nc1cc2[nH]nc(NCc3cccnc3)c2cn1)c1ccccc1]

Step 2: (R)-1-(1-phenylethyl)-3-(3-((pyridin-3-ylmethyl)amino)-1H-pyrazolo[4,3-c]pyridin-6-yl)urea (R)-1-(1-phenylethyl)-3-(3-((pyridin-3-ylmethyl)amino)-1-trityl-1H-pyrazolo[4,3-c]pyridin-6-yl)urea (0.056 mmol) was taken up in TFA (1 ml) and the reaction mixture was stirred at room temperature for 1 h. Triethylsilane (0.009 ml, 0.056 mmol) was added drop wise, and the reaction mixture stirred for an additional 5 minutes. The mixture was concentrated, re-dissolved in DMSO (1.5 mL) and submitted for purification by mass-triggered preparative HPLC to afford (R)-1-(1-phenylethyl)-3-(3-((pyridin-3-ylmethyl)amino)-1H-pyrazolo[4,3-c]pyridin-6-yl)urea. TFA (16.7 mg, 0.033 mmol, 59.5% yield) as a white solid. MS ESI calc'd. For $C_{21}H_{22}N_7O$ [M+H]$^+$ 388. found 388. $^1$H NMR (ppm, 600 MHz, DMSO): δ 8.81 (s, 1H); 8.70 (s, 1H); 8.58 (d, J=5.0 Hz, 1H); 8.09 (s, 1H); 7.96 (s, 1H); 7.62 (s, 1H); 7.31-7.32 (m, 4H); 7.21 (t, J=6.6 Hz, 1H); 7.05 (s, 1H); 4.84 (t, J=7.2 Hz, 1H); 4.52 (s, 2H); 1.40 (d, J=7.0 Hz, 3H).

Example 317

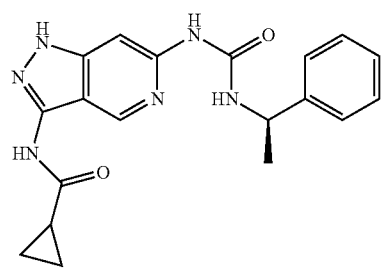 [SMILES: C[C@@H](NC(=O)Nc1cc2[nH]nc(NC(=O)C3CC3)c2cn1)c1ccccc1]

(R)—N-(6-(3-(1-phenylethyl)ureido)-1H-pyrazolo[4,3-c]pyridin-3-yl)cyclopropanecarboxamide

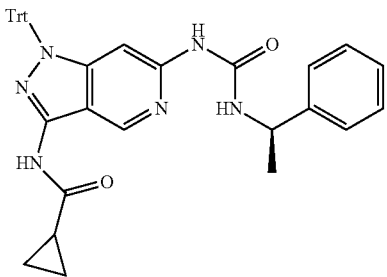

Step 1: (R)—N-(6-(3-(1-phenylethyl)ureido)-1-trityl-1H-pyrazolo[4,3-c]pyridin-3-yl)cyclopropanecarboxamide To an 8 mL vial charged with (R)-1-(3-amino-1-trityl-1H-pyrazolo[4,3-c]pyridin-6-yl)-3-(1-phenylethyl)urea (20 mg, 0.037 mmol), cyclopropanecarboxylic acid (4.79 mg, 0.056 mmol), and HATU (21.18 mg, 0.056 mmol) was added DIEA (0.013 ml, 0.074 mmol) and DMA (1 ml). The vial was capped and the contents heated to 60° C. and stirred for 16 h. The reaction mixture was concentrated to afford crude (R)—N-(6-(3-(1-phenylethyl)ureido)-1-trityl-1H-pyrazolo[4,3-c]pyridin-3-yl)cyclopropanecarboxamide which was taken forward without purification. MS ESI calc'd. For $C_{38}H_{35}N_6O_2$ [M+H]$^+$ 607. found 607.

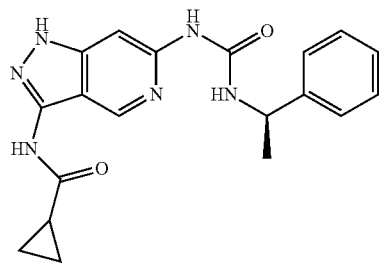 [SMILES: C[C@@H](NC(=O)Nc1cc2[nH]nc(NC(=O)C3CC3)c2cn1)c1ccccc1]

Step 2: (R)—N-(6-(3-(1-phenylethyl)ureido)-1H-pyrazolo[4,3-c]pyridin-3-yl)cyclopropanecarboxamide (R)—N-(6-(3-(1-phenylethyl)ureido)-1-trityl-1H-pyrazolo[4,3-c]pyridin-3-yl)cyclopropanecarboxamide (0.037 mmol) was taken up in TFA (1 ml) and the reaction mixture was stirred at room temperature for 1 h. Triethylsilane (0.006 ml, 0.037 mmol) was added drop wise, and the reaction mixture stirred for an additional 5 minutes. The mixture was concentrated, re-dissolved in DMSO (1.5 mL) and submitted for purification by mass-triggered preparative HPLC to afford (R)—N-(6-(3-(1-phenylethyl)ureido)-1H-pyrazolo[4,3-c]pyridin-3-yl)cyclopropanecarboxamide (4.3 mg, 0.012 mmol, 31.8% yield) as a white solid. MS ESI calc'd. For $C_{19}H_{21}N_6O_2$ [M+H]$^+$ 365. found 365. $^1$H NMR (ppm, 600 MHz, DMSO): δ 11.15 (s, 1H); 9.33 (br s, 1H); 9.05 (s, 1H); 7.79 (br s, 1H); 7.41 (s, 1H); 7.31 (d, J=4.4 Hz, 4H); 7.21 (d, J=5.7 Hz, 1H); 4.84 (t, J=7.2 Hz, 1H); 1.93 (m, 1H); 1.38 (d, J=7.0 Hz, 3H); 0.83 (t, J=6.9 Hz, 4H).

Example 318

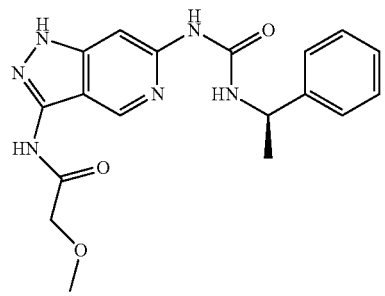 [SMILES: COCC(=O)Nc1n[nH]c2cc(NC(=O)N[C@H](C)c3ccccc3)ncc12]

(R)-2-methoxy-N-(6-(3-(1-phenylethyl)ureido)-1H-pyrazolo[4,3-c]pyridin-3-yl)acetamide

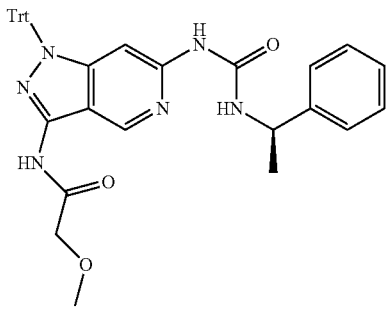

Step 1: (R)-2-methoxy-N-(6-(3-(1-phenylethyl)ureido)-1-trityl-1H-pyrazolo[4,3-c]pyridin-3-yl)acetamide To an 8 mL vial charged with 2-methoxyacetyl chloride (6.6 mg, 0.061 mmol) was added (R)-1-(3-amino-1-trityl-1H-pyrazolo[4,3-c]pyridin-6-yl)-3-(1-phenylethyl)urea (30 mg, 0.056 mmol) in DCM (1 ml) and pyridine (0.045 ml, 0.557 mmol). The vial was capped and the contents stirred at room temperature for 16 h. The reaction mixture was diluted with DCM (1 mL), MP-Trisamine (137 mg, 0.278 mmol) added, and the contents of the vial shaken at room temperature for 3 h. The resin was filtered, and washed through with DCM (1 mL). The volatiles were removed in vacuo to afford crude (R)-2-methoxy-N-(6-(3-(1-phenylethyl)ureido)-1-trityl-1H-pyrazolo[4,3-c]pyridin-3-yl)acetamide, which was taken forward without purification. MS ESI calc'd. For $C_{37}H_{35}N_6O_3$ [M+H]$^+$ 611. found 611.

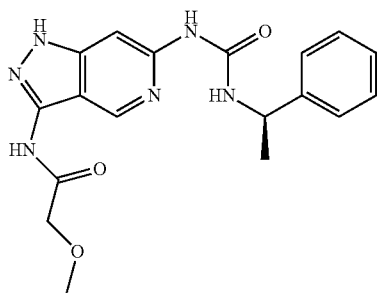

Step 2: (R)-2-methoxy-N-(6-(3-(1-phenylethyl)ureido)-1H-pyrazolo[4,3-c]pyridin-3-yl)acetamide (R)-2-methoxy-N-(6-(3-(1-phenylethyl)ureido)-1-trityl-1H-pyrazolo[4,3-c]pyridin-3-yl)acetamide (0.056 mmol) was taken up in TFA (1 ml) and the reaction mixture was stirred at room temperature for 1 h. Triethylsilane (0.009 ml, 0.056 mmol) was added drop wise, and the reaction mixture stirred for an additional 5 minutes. The mixture was concentrated, re-dissolved in DMSO (1.5 mL) and submitted for purification by mass-triggered prep. HPLC to afford (R)-2-methoxy-N-(6-(3-(1-phenylethyl)ureido)-1H-pyrazolo[4,3-c]pyridin-3-yl)acetamide.TFA (15.9 mg, 0.033 mmol, 58.9% yield) as a white solid. MS ESI calc'd. For $C_{18}H_{21}N_6O_3$ $[M+H]^+$ 369. found 369. $^1H$ NMR (ppm, 600 MHz, DMSO): δ 10.62 (s, 1H); 9.28 (br s, 1H); 9.00 (s, 1H); 7.75 (s, 1H); 7.46 (s, 1H); 7.31-7.32 (m, 4H); 7.19-7.22 (m, 1H); 4.85 (t, J=7.2 Hz, 1H); 4.09 (s, 2H); 3.35 (s, 3H); 1.39 (d, J=6.9 Hz, 3H).

Example 320

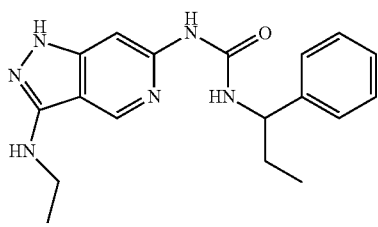 [SMILES: CCNc1n[nH]c2cc(NC(=O)NC(CC)c3ccccc3)ncc12]

1-(3-(ethylamino)-1H-pyrazolo[4,3-c]pyridin-6-yl)-3-(1-(pyridin-2-yl)propyl)urea

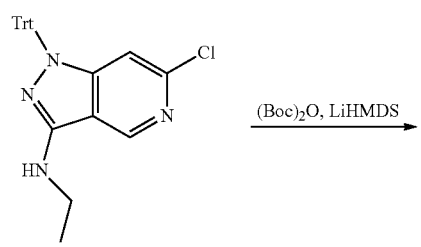

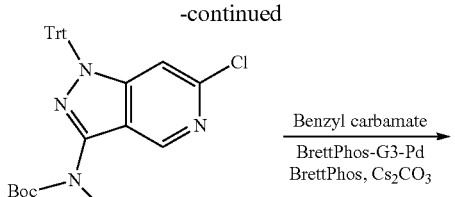

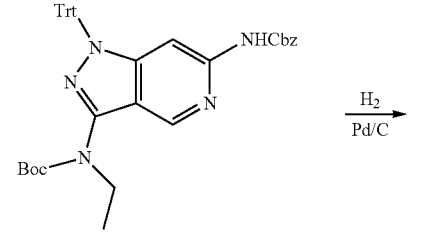

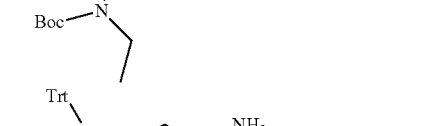

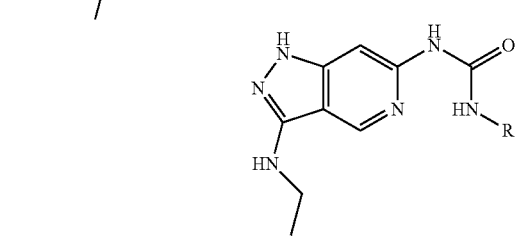

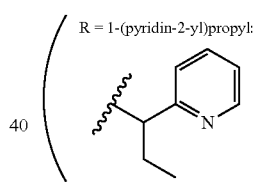

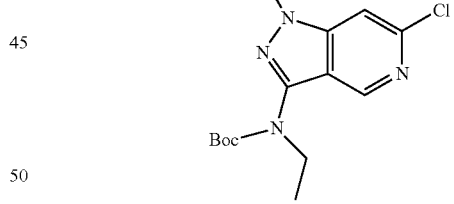

Step 1: tert-butyl(6-chloro-1-trityl-1H-pyrazolo[4,3-c]pyridin-3-yl)(ethyl)carbamate A 200 mL round bottom flask containing 6-chloro-N-ethyl-1-trityl-1H-pyrazolo[4,3-c]pyridin-3-amine (2 g, 4.56 mmol) in THF (30 ml) was cooled to 0° C. under an argon atmosphere and charged with LiHMDS (9.11 ml, 9.11 mmol). The reaction mixture was stirred at 0° C. for 15 minutes. A solution of di-tert-butyl dicarbonate (1.293 g, 5.92 mmol) in THF (10 ml) was added and the reaction mixture warmed to ambient temperature and stirred for 16 h. Water (20 ml) was added and the reaction mixture stirred for an additional 5 minutes. The mixture was extracted with ethyl acetate (3×25 mL). The combined organic fractions were washed with brine (20 mL), dried (MgSO₄), filtered and the solvent was evaporated under reduced pressure. The resulting residue was purified by flash column chromatography on silica gel (ISCO; 40 g prepacked) eluting with ethyl acetate/hexanes to afford tert-butyl(6-chloro-1-trityl-1H-pyrazolo[4,3-c]pyridin-3-yl)(ethyl)carbamate (2.18 g, 4.04 mmol, 89% yield) as a white solid. MS ESI calc'd. For $C_{32}H_{32}ClN_4O_2$ [M+H]⁺ 539. found 539.

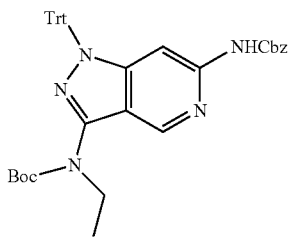

Step 2: tert-butyl(6-(((benzyloxy)carbonyl)amino)-1-trityl-1H-pyrazolo[4,3-c]pyridin-3-yl)(ethyl)carbamate A 20 mL microwave vial was charged with cesium carbonate (907 mg, 2.78 mmol), tert-butyl(6-chloro-1-trityl-1H-pyrazolo[4,3-c]pyridin-3-yl)(ethyl)carbamate (500 mg, 0.928 mmol), benzyl carbamate (421 mg, 2.78 mmol), 2-(dicyclohexylphosphino)3,6-dimethoxy-2',4',6'-triisopropyl-1,1'-biphenyl (34.9 mg, 0.065 mmol) and BrettPhos-G3-Pd (58.9 mg, 0.065 mmol). Dioxane (10 ml) was added, the vial was flushed with argon, capped and the contents heated to 100° C. with stirring for 16 h. The reaction mixture was diluted with DCM/i-PrOH (4:1, 50 mL) and washed with brine (2×50 mL), dried (MgSO₄), filtered and the solvent was evaporated under reduced pressure. The resulting residue was purified by flash column chromatography on silica gel (ISCO; 24 g prepacked) eluting with ethyl acetate/hexanes to afford tert-butyl(6-(((benzyloxy)carbonyl)amino)-1-trityl-1H-pyrazolo[4,3-c]pyridin-3-yl)(ethyl)carbamate (225 mg, 0.344 mmol, 37.1% yield) as a white solid. MS ESI calc'd. For $C_{40}H_{40}N_5O_4$ [M+H]⁺ 654. found 654.

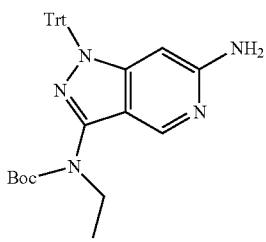

Step 3: tert-butyl(6-amino-1-trityl-1H-pyrazolo[4,3-c]pyridin-3-yl)(ethyl)carbamate To a 50 mL round bottom flask charged with tert-butyl(6-(((benzyloxy)carbonyl)amino)-1-trityl-1H-pyrazolo[4,3-c]pyridin-3-yl)(ethyl)carbamate (225 mg, 0.344 mmol) in ethyl acetate (5 ml) and methanol (5 ml) was added palladium on carbon (73.3 mg, 0.069 mmol). The flask was evacuated and back-filled with hydrogen gas using an attached balloon. This procedure was attempted a further two times. The reaction mixture was stirred under a hydrogen atmosphere at room temperature for 16 h. The palladium was filtered off by passing the reaction mixture through celite and washing through with ethyl acetate. The volatiles were removed in vacuo to afford crude tert-butyl(6-amino-1-trityl-1H-pyrazolo[4,3-c]pyridin-3-yl)(ethyl)carbamate (159 mg, 0.306 mmol, 89% yield) which was taken forward without purification. MS ESI calc'd. For $C_{32}H_{34}N_5O$ [M+H]⁺ 520. found 520.

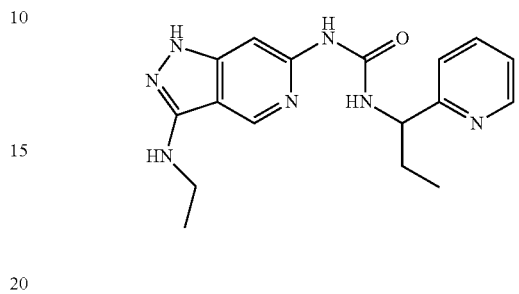

Step 4: 1-(3-(ethylamino)-1H-pyrazolo[4,3-c]pyridin-6-yl)-3-(1-(pyridin-2-yl)propyl)urea To a 8 mL vial charged with imidazole (17.3 mg, 0.26 mmol) and tert-butyl(6-amino-1-trityl-1H-pyrazolo[4,3-c]pyridin-3-yl)(ethyl)carbamate (26.5 mg, 0.051 mmol) in DCM (1 ml) was added 1,1'-carbonyldiimidazole (25 mg, 0.153 mmol). The reaction mixture was stirred at room temperature for 5 h, leading to a clear yellow solution. A solution of 1-(pyridin-2-yl)propan-1-amine, 2HCl (21.33 mg, 0.102 mmol) and DIEA (0.045 ml, 0.255 mmol) in DMF (1 ml) was added. The vial was capped and the contents stirred at room temperature for 16 h. The reaction mixture was concentrated and the resulting residue re-dissolved in TFA (1 ml) and stirred at room temperature for 20 minutes. Triethylsilane (0.008 ml, 0.051 mmol) was added drop wise, and the reaction mixture stirred for an additional 5 minutes. The mixture was concentrated, re-dissolved in DMSO (1.5 mL) and submitted for purification by mass-triggered preparative HPLC to afford 1-(3-(ethylamino)-1H-pyrazolo[4,3-c]pyridin-6-yl)-3-(1-(pyridin-2-yl)propyl)urea (4.1 mg, 0.012 mmol, 23.69% yield) as a white solid. MS ESI calc'd. For $C_{17}H_{21}N_7O$ [M+H]⁺ 340. found 340. ¹H NMR (ppm, 600 MHz, DMSO): δ 8.99 (s, 1H); 8.57 (s, 1H); 8.52 (d, J=4.8 Hz, 1H); 7.73 (td, J=7.7, 1.8 Hz, 1H); 7.31 (d, J=7.8 Hz, 1H); 7.21-7.24 (m, 2H); 4.76 (q, J=7.2 Hz, 1H); 3.19-3.23 (m, 2H); 1.77-1.82 (m, 1H); 1.69-1.74 (m, 1H); 1.17 (t, J=7.2 Hz, 3H); 0.80 (t, J=7.4 Hz, 3H).

Example 321

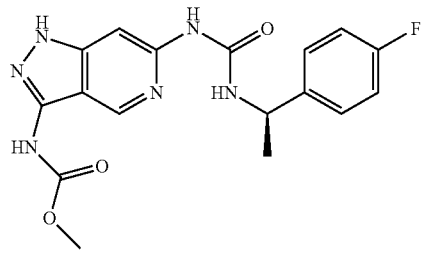 [SMILES: COC(=O)Nc1n[nH]c2cc(NC(=O)N[C@H](C)c3ccc(F)cc3)ncc12]

(R)-methyl (6-(3-(1-(4-fluorophenyl)ethyl)ureido)-1H-pyrazolo[4,3-c]pyridin-3-yl)carbamate

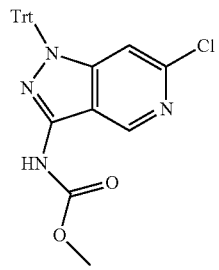

Step 1: methyl (6-chloro-1-trityl-1H-pyrazolo[4,3-c]pyridin-3-yl)carbamate

A 100 mL round bottom flask charged with 6-chloro-1-trityl-1H-pyrazolo[4,3-c]pyridin-3-amine (1500 mg, 3.65 mmol) in DCM (30 ml) and pyridine (3 mL) was cooled to 0° C. using an ice bath. Methyl chloroformate (0.564 ml, 7.30 mmol) was added and the reaction mixture was stirred for 16 h warming to ambient temperature. The mixture was washed with saturated copper sulfate solution (2×50 mL), dried (MgSO$_4$), filtered and the solvent evaporated under reduced pressure. The resulting residue was purified by flash column chromatography on silica gel (ISCO; 40 g prepacked) eluting with ethyl acetate/hexanes to afford methyl (6-chloro-1-trityl-1H-pyrazolo[4,3-c]pyridin-3-yl)carbamate (1492 mg, 3.18 mmol, 87% yield) as a white solid. MS ESI calc'd. For $C_{27}H_{22}ClN_4O_2$ [M+H]$^+$ 469. found 469.

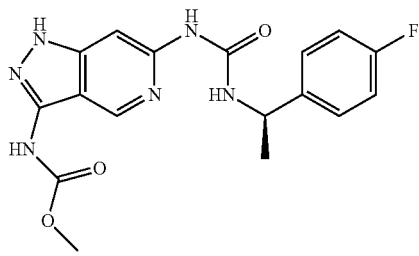 [SMILES: COC(=O)Nc1n[nH]c2cc(NC(=O)N[C@H](C)c3ccc(F)cc3)ncc12]

Step 2: (R)-methyl (6-(3-(1-(4-fluorophenypethypureido)-1H-pyrazolo[4,3-c]pyridin-3-yl)carbamate A 5 mL microwave vial was charged with cesium carbonate (71.7 mg, 0.220 mmol), (6-chloro-1-trityl-1H-pyrazolo[4,3-c]pyridin-3-yl)carbamate (40 mg, 0.085 mmol), (R)-1-(1-(4-fluorophenyl)ethyl)urea (23.3 mg, 0.128 mmol), 2-(dicyclohexylphosphino)3,6-dimethoxy-2',4',6'-triisopropyl-1,1'-biphenyl (3.21 mg, 5.97 µmol) and BrettPhos-G3-Pd (5.41 mg, 5.97 µmol). Dioxane (1 ml) was added, the vial was flushed with argon, capped and the contents heated to 100° C. with stirring for 16 h. The reaction mixture was diluted with DCM (2 ml), MP-TMT (119 mg, 0.119 mmol) added and the contents heated to 65° C. for 4 h with shaking. The reaction mixture was filtered, washing through with DCM (2 mL) and concentrated. The resulting residue was re-dissolved in TFA (1 mL) and stirred at room temperature for 30 minutes. Triethylsilane (0.014 ml, 0.085 mmol) was added drop wise and the reaction mixture was stirred for an additional 5 minutes. The volatiles were removed in vacuo, the resulting residue was re-dissolved in DMSO (1.5 mL) and submitted for purification by mass-triggered HPLC to afford (R)-methyl (6-(3-(1-(4-fluorophenyl)ethyl)ureido)-1H-pyrazolo[4,3-c]pyridin-3-yl)carbamate. TFA (5.4 mg, 0.011 mmol, 13.1% yield) as a white solid. MS ESI calc'd. For $C_{17}H_{18}FN_6O_3$ [M+H]$^+$ 373. found 373. $^1$H NMR (ppm, 600 MHz, DMSO-d$_6$): δ 10.39 (s, 1H); 9.26 (s, 1H); 8.94 (s, 1H); 7.76 (s, 1H); 7.43 (s, 1H); 7.35 (dd, J=8.4, 5.5 Hz, 2H); 7.13 (t, J=8.8 Hz, 2H); 4.84 (t, J=7.2 Hz, 1H); 3.68 (s, 3H); 1.37 (d, J=7.0 Hz, 3H).

Example 322 and 314

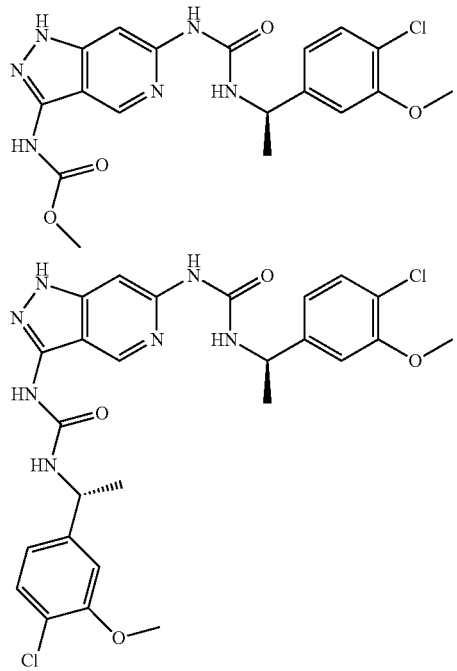

(R)-methyl (6-(3-(1-(4-chloro-3-methoxyphenyl)ethyl)ureido)-1H-pyrazolo[4,3-c]pyridin-3-yl)carbamate (Example 322) and 1,1'-(1H-pyrazolo[4,3-c]pyridine-3,6-diyl)bis(3-((R)-1-(4-chloro-3-methoxyphenyl)ethyl)urea) (Example 314)

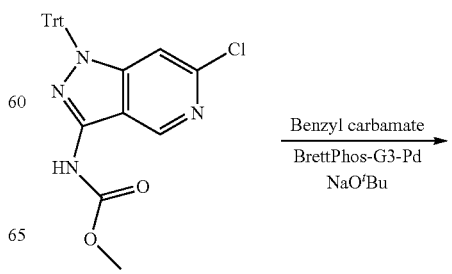

Benzyl carbamate
————————→
BrettPhos-G3-Pd
NaO$^t$Bu

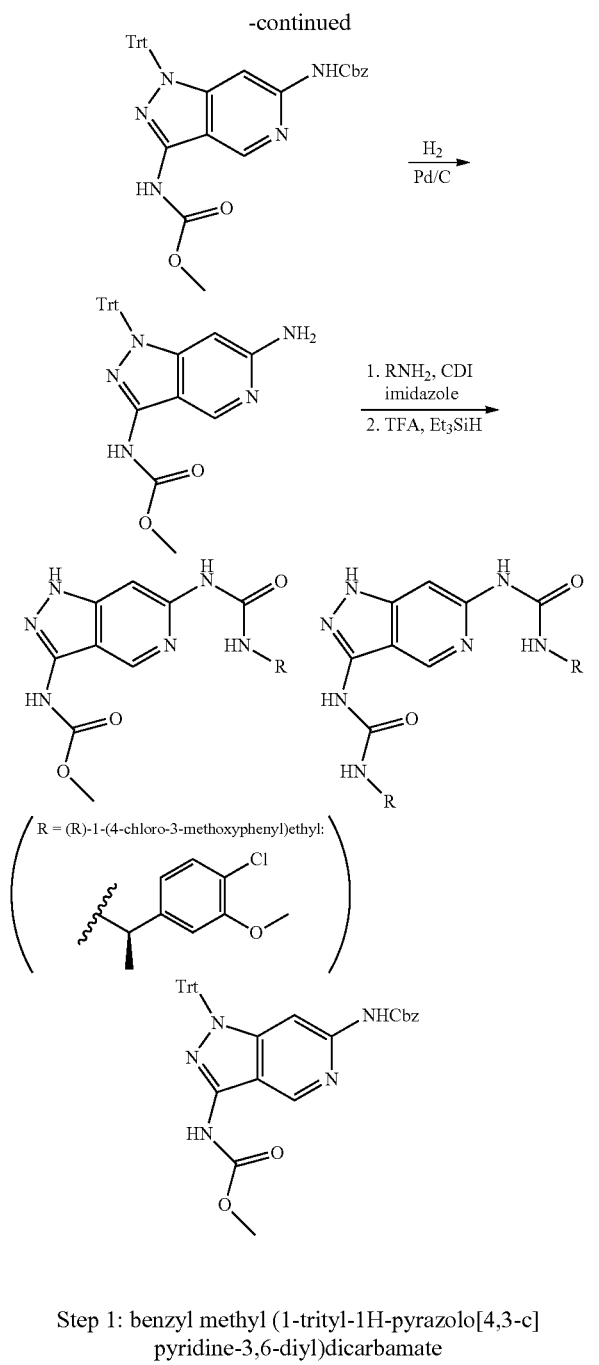

Step 1: benzyl methyl (1-trityl-1H-pyrazolo[4,3-c]pyridine-3,6-diyl)dicarbamate A 20 mL microwave vial was charged with sodium tert-butoxide (103 mg, 1.075 mmol), methyl (6-chloro-1-trityl-1H-pyrazolo[4,3-c]pyridin-3-yl)carbamate (252 mg, 0.537 mmol), benzyl carbamate (122 mg, 0.806 mmol) and BrettPhos-G3-Pd (24.36 mg, 0.027 mmol). THF (6 ml) was added, the vial was flushed with argon, capped and the contents heated to 50° C. with stirring for 10 h. LCMS analysis indicated incomplete conversion to the desired product. Excess benzyl carbamate (61 mg), sodium tert-butoxide (51 mg) and BrettPhos-G3-Pd (12 mg) was added. The vial was flushed with argon, capped and the contents heated to 50° C. for an additional 4 h. The mixture was cooled, diluted with ethyl acetate (10 mL), washed with saturated aqueous sodium hydrogen carbonate (2×20 mL), dried (MgSO$_4$), filtered and the solvent evaporated under reduced pressure. The resulting residue was purified by flash column chromatography on silica gel (ISCO; 24 g prepacked) eluting with ethyl acetate/hexanes to afford benzyl methyl (1-trityl-1H-pyrazolo[4,3-c]pyridine-3,6-diyl)dicarbamate (126 mg, 0.216 mmol, 40.2% yield) as a white solid. MS ESI calc'd. For $C_{35}H_{30}N_5O_4$ [M+H]$^+$ 584. found 584.

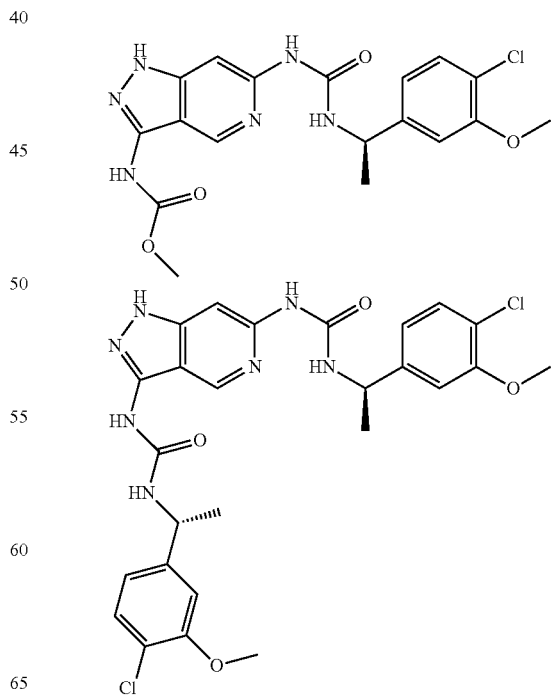

Step 2: methyl (6-amino-1-trityl-1H-pyrazolo[4,3-c]pyridin-3-yl)carbamate

To a 50 mL round bottom flask charged with benzyl methyl (1-trityl-1H-pyrazolo[4,3-c]pyridine-3,6-diyl)dicarbamate (126 mg, 0.216 mmol) in ethyl acetate (4 ml) and methanol (4 ml) was added palladium on carbon (45.9 mg, 0.043 mmol). The flask was evacuated and back-filled with hydrogen gas using an attached balloon. This procedure was attempted a further two times. The reaction mixture was stirred under a hydrogen atmosphere at room temperature for 16 h. The palladium was filtered off by passing the reaction mixture through celite and washing through with ethyl acetate (20 mL). The volatiles were removed in vacuo to afford crude methyl (6-amino-1-trityl-1H-pyrazolo[4,3-c]pyridin-3-yl)carbamate (95 mg, 0.211 mmol, 98% yield) as a white solid. MS ESI calc'd. For $C_{27}H_{24}N_5O_2$ [M+H]$^+$ 450. found 450.

Step 3: (R)-methyl (6-(3-(1-(4-chloro-3-methoxyphenyl)ethyl)ureido)-1H-pyrazolo[4,3-c]pyridin-3-yl)carbamate and 1,1'-(1H-pyrazolo[4,3-c]pyridine-3,6-diyl)bis(3-((R)-1-(4-chloro-3-methoxyphenyl)ethyl)urea)

To a 8 mL vial charged with imidazole (18 mg, 0.26 mmol) and crude methyl (6-amino-1-trityl-1H-pyrazolo[4,3-c]pyridin-3-yl)carbamate (23.8 mg, 0.053 mmol) in DCM (2 ml) was added 1,1'-carbonyldiimidazole (26 mg, 0.159 mmol). The reaction mixture was stirred at room temperature for 5 h, leading to a clear yellow solution. (R)-1-(4-chloro-3-methoxyphenyl)ethanamine HCl (23.41 mg, 0.105 mmol) and DIEA (0.046 ml, 0.264 mmol) was added. The vial was capped and the contents stirred at room temperature for 16 h. The reaction mixture was concentrated and the resulting residue was re-dissolved in TFA (1 ml) and stirred at room temperature for 20 minutes. Triethylsilane (0.013 ml, 0.079 mmol) was added drop wise, and the reaction mixture stirred for an additional 5 minutes. The mixture was concentrated, re-dissolved in DMSO (1.5 mL) and submitted for purification by mass-triggered preparative HPLC to afford (R)-methyl (6-(3-(1-(4-chloro-3-methoxyphenyl)ethyl)ureido)-1H-pyrazolo[4,3-c]pyridin-3-yl)carbamate. TFA (4.4 mg, 8.26 µmol, 15.67% yield) and 1,1'-(1H-pyrazolo[4,3-c]pyridine-3,6-diyl)bis(3-((R)-1-(4-chloro-3-methoxyphenyl)ethyl)urea), TFA (5 mg, 7.28 µmol, 13.82% yield) as white solids. (Example 322) MS ESI calc'd. For $C_{18}H_{20}ClN_6O_4$ [M+H]$^+$ 419. found 419. $^1$H NMR (ppm, 600 MHz, DMSO-d$_6$): δ 10.40 (s, 1H); 8.95 (s, 1H); 7.81 (br s, 1H); 7.43 (s, 1H); 7.35 (d, J=8.1 Hz, 1H); 7.09 (d, J=1.9 Hz, 1H); 6.90 (dd, J=8.2, 1.9 Hz, 1H); 4.84 (t, J=7.2 Hz, 1H); 3.83 (s, 3H); 3.68 (s, 3H); 1.39 (d, J=6.9 Hz, 3H). (Example 314) MS ESI calc'd. For $C_{26}H_{28}Cl_2N_7O_4$ [M+H]$^+$ 572. found 572. $^1$H NMR (600 MHz, DMSO-d$_6$): 9.70 (s, 1H); 9.06 (s, 1H); 7.84 (br s, 2H); 7.34-7.36 (m, 3H); 7.09-7.10 (m, 2H); 6.89-6.91 (m, 2H); 4.89 (t, J=7.2 Hz, 1H); 4.82-4.86 (m, 1H); 3.82 (s, 6H); 1.40 (dd, J=6.9 Hz, 6H).

Example 331

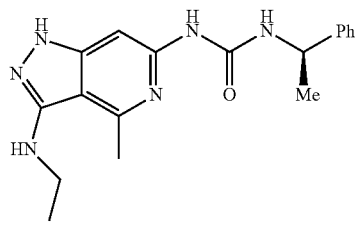 [SMILES: CCNc1n[nH]c2cc(NC(=O)N[C@H](C)c3ccccc3)nc(C)c12]

(R)-1-(3-(ethylamino)-4-methyl-1H-pyrazolo[4,3-c]pyridin-6-yl)-3-(1-phenylethyl)urea A conical vial was charged with (R) -1-(3-amino-4-methyl-1H-pyrazolo[4,3-c]pyridin-6-yl)-3-(1-phenylethyl)urea (32 mg, 0.103 mmol) and magnesium sulfate (37.2 mg, 0.309 mmol). chloroform (666 µl), methanol (333 µl), magnesium sulfate (37.2 mg, 0.309 mmol) and trifluroacetic acid (23.83 µl, 0.309 mmol) were injected and the reaction was stirred at ambient temperature for 1 hour. Sodium cyanoborohydride (19.44 mg, 0.309 mmol) was then added and stirring was continued for one hour. The reaction was diluted with water and the aqueous layer was transferred to a separatory funnel and washed 3×chloroform/IPA. The combined organic washings were dried over magnesium sulfate and then filtered and concentrated. The residue was dissolved in DMSO (2 mL) filtered and delivered to the purification group. Reversed phase mass triggered HPLC was performed. The active fractions were dried down on the Genevac which was free-based with NH$_3$ in MeOH (7N) and concentrated to yield a white solid (14 mg, 40.1%). MS ESI calc'd for $C_{18}H_{22}N_6O$ [M+H]$^+$ 339. found 339. $^1$H NMR (ppm, 500 Mhz, DMSO-d$_6$): δ 11.52 (s, 1H), 8.88 (s, 1H), 8.39 (s, 1H), 7.45-7.09 (m, 5H), 7.00-6.95 (m, 1H), 5.41 (q, J=5.6 Hz, 1H), 4.98-4.69 (m, 1H), 3.26-3.15 (m, 2H), 2.61 (s, 3H), 1.44-1.35 (m, 3H), 1.19 (dd, J=3.6 Hz, 3H).

Example 333

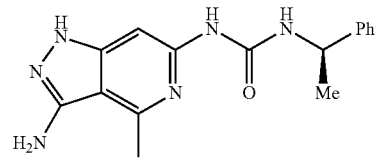 [SMILES: Cc1nc(NC(=O)N[C@H](C)c2ccccc2)cc2[nH]nc(N)c12]

(R)-1-(3-amino-4-methyl-1H-pyrazolo[4,3-c]pyridin-6-yl)-3-(1-phenylethyl)urea

Step 1: (R)-1-(4-chloro-5-cyano-6-methylpyridin-2-yl)-3-(1-phenylethyl)urea

A flask was charged with 4,6-dichloro-2-methylnicotinonitrile (1500 mg), (R)-1-(1-phenylethyl)urea (1449 mg), xantphos (371 mg), palladium(II)acetate (90 mg) and cesium carbonate (5.23 g). Tetrahydrofuran (53 mL) was injected and the reaction was heated to 50° C. for 3 hours. LC/MS showed that the reaction cleanly proceeded to completion. The reaction mixture was filtered through celite and the filtrate was concentrated and purified by silica gel chromatography (0-30% DCM/EtOAc). (R) -1-(4-chloro-5-cyano-6-methylpyridin-2-yl)-3-(1-phenylethyl)urea (2.19 g, 87%) was isolated as an off-white solid. MS ESI calc'd for $C_{16}H_{15}ClN_4O$ [M+H]+ 315. found 315.

Step 2: (R)-1-(3-amino-4-methyl-1H-pyrazolo[4,3-c]pyridin-6-yl)-3-(1-phenylethyl)urea A flask was charged with (S) -1-(4-chloro-5-cyano-6-methylpyridin-2-yl)-3-(1-phenylethyl)urea (920 mg) and ethanol (6989 µl) and hydrazine (183 µl) was added. The reaction was heated to 95° C. for 17 hours. LC/MS showed the reaction was mostly but not entirely complete (~15% remaining starting material by LC/MS integration). The reaction was heated for 5 additional hours. After cooling, HCl (1N, 14.6 mL) was added and the reaction was stirred for 30 minutes. The reaction was poured into a 500 mL separatory funnel containing 150 mL of concentrated sodium bicarbonate solution. The resulting emulsion was washed 3× with chloroform/IPA (4:1, 100 mL portions). The combined organic washings were dried over magnesium sulfate, filtered and concentrated. Silica gel chromatography (0-10% EtOAc/MeOH+0.1% ammonia) was performed and the active fractions were concentrated to dryness yielding the title compound as a white solid (400 mg, 41.1%). MS ESI calc'd for $C_{16}H_{18}N_6O$ [M+H]$^+$ 311. found 311. $^1$H NMR (ppm500 Mhz, DMSO-d$_6$): δ 9.30 (s, 1H), 8.74 (d, J=0.9 Hz, 1H), 8.29 (s, 1H), 8.07

(s, 1H), 7.37-7.32 (m, 5H), 7.28-7.21 (m, 1H), 6.60 (s, 2H), 4.88 (p, J=7.0 Hz), 2.47 (s, 3H), 1.42 (d, J=6.9 Hz, 3H).

Example 337

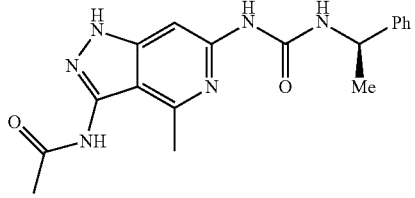 [SMILES: CC(=O)Nc1n[nH]c2cc(NC(=O)N[C@H](C)c3ccccc3)nc(C)c12]

(R)—N-(4-methyl-6-(3-(1-phenylethyl)ureido)-1H-pyrazolo[4,3-c]pyridin-3-yl)acetamide A conical reaction vial was charged with (R)-1-(3-amino-4-methyl-1H-pyrazolo[4,3-c]pyridin-6-yl)-3-(1-phenylethyl)urea (101 mg, 0.325 mmol) and tetrahydrofuran (3000 μl) was injected. To the resulting solution was added pyridine (132 μl, 1.627 mmol) and acetic anhydride (95 μl, 1.009 mmol). The reaction was stirred for 1 hour and no conversion was observed. Acetyl chloride (116 μl, 1.627 mmol) was injected and the reaction became heterogenous. Dichloromethane (3 mL) was added to give a homogeneous reaction solution. The reaction was stirred at ambient temperature for 30 minutes. Solvent was removed on the rotovap. Dioxane (3 ml) was added followed by 1N sodium hydroxide (0.256 ml, 0.256 mmol) and the reaction was heated to 50° C. for 30 minutes. Reversed phase HPLC was performed directly on the crude reaction mixture (5-40% ACN/Water, 30 mm Focus Gradient). The active fractions were frozen and concentrated on the lyophilizer, the residue was dissolved in methanol filtered through immobilized bicarbonate and the filtrate was concentrated to give the title compound. MS ESI calc'd for $C_{18}H_{20}N_6O_2$. [M+H]$^+$ 353. found 353. $^1$H NMR (ppm, 500 Mhz, DMSO-d$_6$): δ 12.72 (s, 1H), 10.01 (s, 1H), 9.26-8.75 (m, 1H), 8.00 (s, 1H), 7.69-7.13 (m, 6H), 5.09-4.69 (m, 1H), 3.31 (s, 3H), 2.06 (s, 3H), 1.39 (d, J=6.9 Hz, 1H).

Example 368

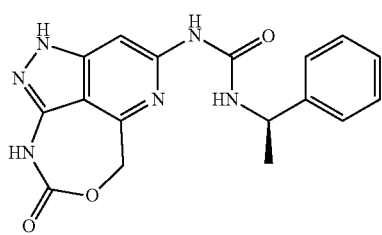 [SMILES: C[C@@H](NC(=O)Nc1cc2[nH]nc3c2c(n1)COC(=O)N3)c1ccccc1]

(R)-1-(8-oxo-2,6,8,9-tetrahydro-7-oxa-1,2,5,9-tetraazabenzo[cd]azulen-4-yl)-3-(1-phenylethyl)urea

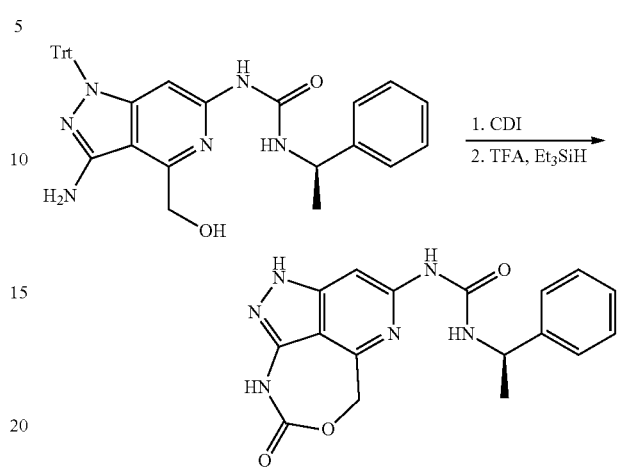

A 20 ml scintillation vial was charged with (R)-1-(3-amino-4-(hydroxymethyl)-1-trityl-1H-pyrazolo[4,3-c]pyridin-6-yl)-3-(1-phenylethyl)urea (15 mg, 0.026 mmol) and CDI (6.42 mg, 0.040 mmol). Acetonitrile (3 ml) was added, the vial was capped and the contents was heated to 60° C. for 16 h. The reaction mixture was concentrated and the resulting residue subjected to TFA (1 ml) hydrolysis for 30 minutes at room temperature. Triethylsilane (8.43 μl, 0.053 mmol) was added drop wise and the reaction mixture stirred for an additional 5 minutes. The volatiles were removed in vacuo and the resulting residue submitted for purification by mass-triggered HPLC to afford (R)-1-(8-oxo-2,6,8,9-tetrahydro-7-oxa-1,2,5,9-tetraazabenzo[cd]azulen-4-yl)-3-(1-phenylethyl)urea, TFA (3.1 mg, 6.65 μmol, 25.2% yield) as a white solid. MS ESI calc'd. For $C_{17}H_{17}N_6O_3$ [M+H]$^+$ 353. found 353. $^1$H NMR (ppm, 500 MHz, DMSO-d$_6$): δ 12.47 (s, 1H); 10.99 (s, 1H); 9.05 (s, 1H); 7.49 (s, 1H); 7.33 (d, J=4.7 Hz, 4H); 7.23 (s, 1H); 5.34 (s, 2H); 4.84 (t, J=7.3 Hz, 1H); 1.38-1.41 (m, 3H).

Example 406

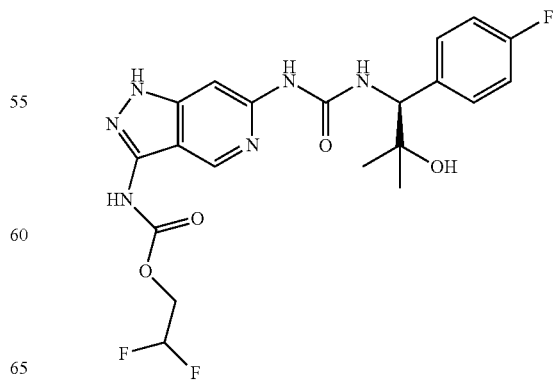

217

2,2-difluoroethyl[6-({[(1S)-1-(4-fluorophenyl)-2-hydroxy-2-methylpropyl]carbamoyl}amino)-1H-pyrazolo[4,3-c]pyridin-3-yl]carbamate

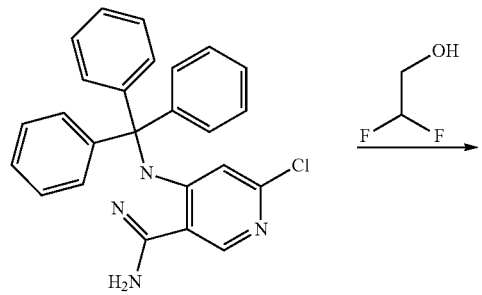
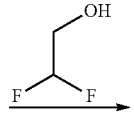

Step 1: 2,2-difluoroethyl (6-chloro-1-trityl-1H-pyrazolo[4,3-c]pyridin-3-yl)carbamate

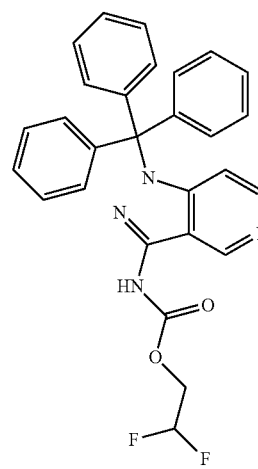

CDI (395 mg, 2.434 mmol) was added to a stirred, room temperature mixture of 6-chloro-1-trityl-1H-pyrazolo[4,3-c]pyridin-3-amine (500 mg, 1.217 mmol) 6-chloro-1-trityl-1H-pyrazolo[4,3-c]pyridin-3-amine and imidazole (331 mg, 4.87 mmol) in tetrahydrofuran (12 mL), and the mixture was stirred at room temperature for overnight. 2,2-Difluoroethanol (0.231 mL, 3.65 mmol) was added to the mixture, and the resultant mixture was kept stirring at room temperature for 2 h before the reaction mixture was heated up to 60° C. for overnight. The mixture was cooled and concentrated, and the residue was loaded directly purified with silica gel column chromatography eluting with EtOAc/isohexane=25%, to give 2,2-difluoroethyl(6-chloro-1-trityl-1H-pyrazolo[4,3-c]pyridin-3-yl)carbamate (570 mg, 1.098 mmol, 90% yield) as a white solid. MS ESI calc'd. for $C_{28}H_{22}ClF_2N_4O_2$ [M+H]$^+$ 519. found 519.

218

Step 2 and 3: Follow the same procedure in Scheme 2, steps 2 and 3 as exemplified in Example 1, 2,2-difluoroethyl[6-({[(1S)-1-(4-fluorophenyl)-2-hydroxy-2-methylpropyl]carbamoyl}amino)-1H-pyrazolo[4,3-c]pyridin-3-yl]carbamate (Example 406) can be prepared from 2,2-difluoroethyl(6-chloro-1-trityl-1H-pyrazolo[4,3-c]pyridin-3-yl)carbamate

Example 420

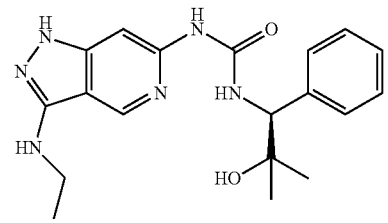 [SMILES: CCNc1n[nH]c2cc(NC(=O)N[C@@H](c3ccccc3)C(C)(C)O)ncc12]

1-(3-Ethylamino-1H-pyrazolo[4,3-c]pyridin-6-yl)-3-(2-hydroxy-2-methyl-1-phenyl-propyl)-urea

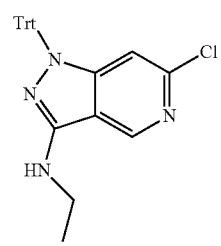

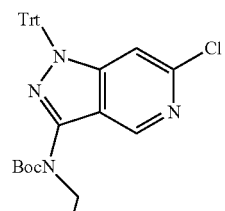
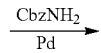

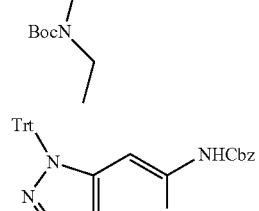

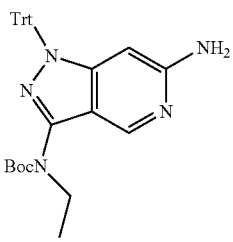
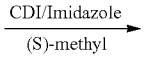
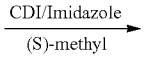

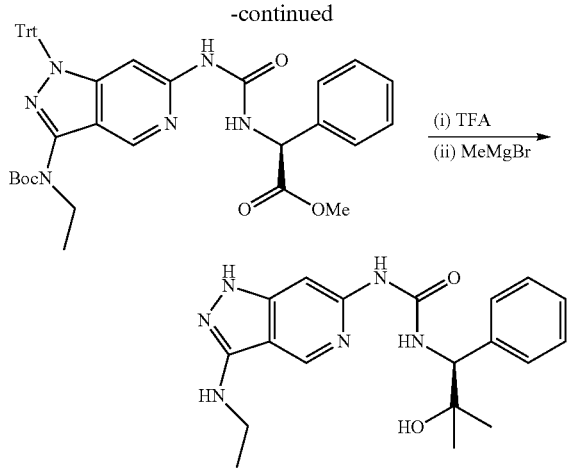

Step 1: Synthesis of tert-butyl(6-chloro-1-trityl-1H-pyrazolo[4,3-c]pyridin-3-yl)(ethyl)carbamate At 0° C., to a solution of 6-chloro-N-ethyl-1-trityl-1H-pyrazolo[4,3-c]pyridin-3-amine (1.0 g, 2.2 mmol) in anhydrous THF (20 mL) was added LiHMDS (1.0 M solution in toluene, 4.5 mL, 4.5 mmol) and the contents were stirred at the same temperature. After 15 min, Boc$_2$O (0.58 g, 2.7 mmol) was added at the same temperature and the contents were allowed to warm to ambient temperature. After 2 h (TLC analysis indicated consumption of starting material), H$_2$O (10 mL) was added and stirred for 5 min. The organic contents were extracted with EtOAc (3×25 mL) and the EtOAc layer washed with brine (1×20 mL), dried over anhydrous Na$_2$SO$_4$ and the solvents were removed under reduced pressure. The residue thus obtained was purified by a filter column to afford the title compound (0.8 g, 70% yield). MS ESI calc'd. for $C_{32}H_{31}ClN_4O_2$ [M+H]$^+$ 539. Found 539.

Step 2: Synthesis of tert-butyl(6-(((benzyloxy)carbonyl)amino)-1-trityl-1H-pyrazolo[4,3-c]pyridin-3-yl)(ethyl)carbamate Under inert atmosphere, to a solution of tert-butyl(6-chloro-1-trityl-1H-pyrazolo[4,3-c]pyridin-3-yl)(ethyl)carbamate 2 (0.52 g, 0.92 mmol) in anhydrous 1,4-dioxane (8.0 mL) was added benzyl carbamate (0.42 g, 2.76 mmol), brettphos pre catalyst (0.04 g, 0.046 mmol), Cs$_2$CO$_3$ (0.9 g, 2.76 mmol) and the contents were heated in a sealed tube at 100° C. After 5 h, the reaction mixture was brought back to ambient temperature and the volatiles were removed under reduced pressure. The residue thus obtained was purified by a flash column chromatography to afford the title compound (0.5 g, 83% yield). MS ESI calc'd. for $C_{40}H_{39}N_5O_4$ [M+H]$^+$ 654. Found 654.

Step 3: Synthesis of tert-butyl(6-amino-1-trityl-1H-pyrazolo[4,3-c]pyridin-3-yl)(ethyl)carbamate To a solution of tert-butyl(6-(((benzyloxy)carbonyl)amino)-1-trityl-1H-pyrazolo[4,3-c]pyridin-3-yl)(ethyl)carbamate (0.2 g, 0.31 mmol) in MeOH (50 mL) was added Pd on carbon (10%, 0.2 g) and the contents were stirred under an atmosphere of H$_2$ (3.0 Kg/cm$^2$). After 5 h, the suspension was filtered through a pad of celite, and the solvent was evaporated under reduced pressure to afford the title compound (0.12 g, 75% yield) and was taken directly for the next step. MS ESI calc'd. for $C_{32}H_{33}N_5O_2$ [M+H]$^+$ 520. Found 520.

Step 4: Synthesis of (S)-methyl 2-(3-(3-((tert-butoxycarbonyl)(ethyl)amino)-1-trityl-1H-pyrazolo[4,3-c]pyridin-6-yl)ureido)-2-phenylacetate To a solution of tert-butyl(6-amino-1-trityl-1H-pyrazolo[4,3-c]pyridin-3-yl)(ethyl)carbamate (0.2 g, 0.385 mmol) in anhydrous 1,4-dioxane (3 mL) was added CDI (0.31 g, 1.92 mmol) followed by the addition of imidazole (0.132 g, 1.92 mmol) and the contents were stirred at ambient temperature. After 16 h (the completion of the reaction was confirmed by quenching small aliquot of the reaction mixture with MeOH and mass obtained corresponds to the methyl carbamate) DIPEA (0.247 g, 1.92 mmol) and (S)-methyl 2-amino-2-phenylacetate (0.194 g, 0.962 mmol) were added and stirred. After 14 h, the reaction mixture was quenched with H$_2$O and the organic contents were extracted with EtOAc (3×20 mL), dried over anhydrous Na$_2$SO$_4$ and concentrated. The residue thus obtained was purified by preparative HPLC to afford the title compound. MS ESI calc'd. for $C_{42}H_{42}N_6O_5$ [M+H]$^+$ 711. Found 711.

Steps 5 and 6: Synthesis of 1-(3-Ethylamino-1H-pyrazolo[4,3-c]pyridin-6-yl)-3-(2-hydroxy-2-methyl-1-phenyl-propyl)-urea To the solution of (S)-methyl 2-(3-(3-((tert-butoxycarbonyl)(ethyl)amino)-1-trityl-1H-pyrazolo[4,3-c]pyridin-6-yl)ureido)-2-phenylacetate (0.078 g, 0.109 mmol) in anhydrous CH$_2$Cl$_2$ (1 mL) was added TFA (imp followed by Et$_3$SiH (2 drops). The resultant mixture was stirred at ambient temperature. After 2 h of stirring, solvent was removed under reduced pressure, the residue (TFA salt) thus obtained was triturated in diethyl ether to afford the compound which was taken as such for next step. At 0° C., to the solution of [3-(3-Ethylamino-1H-pyrazolo[4,3-c]pyridin-6-yl)-ureido]-phenyl-acetic acid methyl ester TFA salt (0.06 g, 0.163 mmol) in anhydrous THF was added methyl magnesium bromide (1 M solution in toluene, 1.63 mL, 1.63 mmol) and resultant mixture was allowed to warm and stirred at ambient temperature. After 10 h, the reaction was quenched with saturated aqueous NH$_4$Cl solution (5 mL), and the organic contents were extracted with CH$_2$Cl$_2$ (3×10 mL). The volatiles were removed under reduced pressure and the residue thus obtained was further purified by prep HPLC to afford the title compound. $^1$H NMR (ppm, 400 MHz, CD$_3$OD): δ 8.69 (s, 1H), 7.44-7.39 (m, 2H), 7.33-7.29 (m, 2H), 7.26-7.23 (m, 1H), 6.99 (s, 1H), 4.78 (s, 1H), 3.36 (q, J=7.2 Hz, 2H), 1.31 (t, J=7.1 Hz, 3H), 1.30 (s, 3H), 1.16 (s, 3H). MS ESI calc'd. for $C_{19}H_{24}N_6O_2$ [M+H]$^+$ 369. Found 369.

Example 425

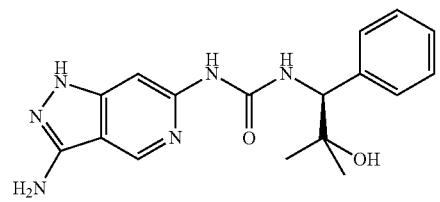 [SMILES: CC(C)(O)[C@@H](NC(=O)Nc1cc2[nH]nc(N)c2cn1)c1ccccc1]

1-(3-amino-1H-pyrazolo[4,3-c]pyridin-6-yl)-3-[(1S)-2-hydroxy-2-methyl-1-phenylpropyl]urea

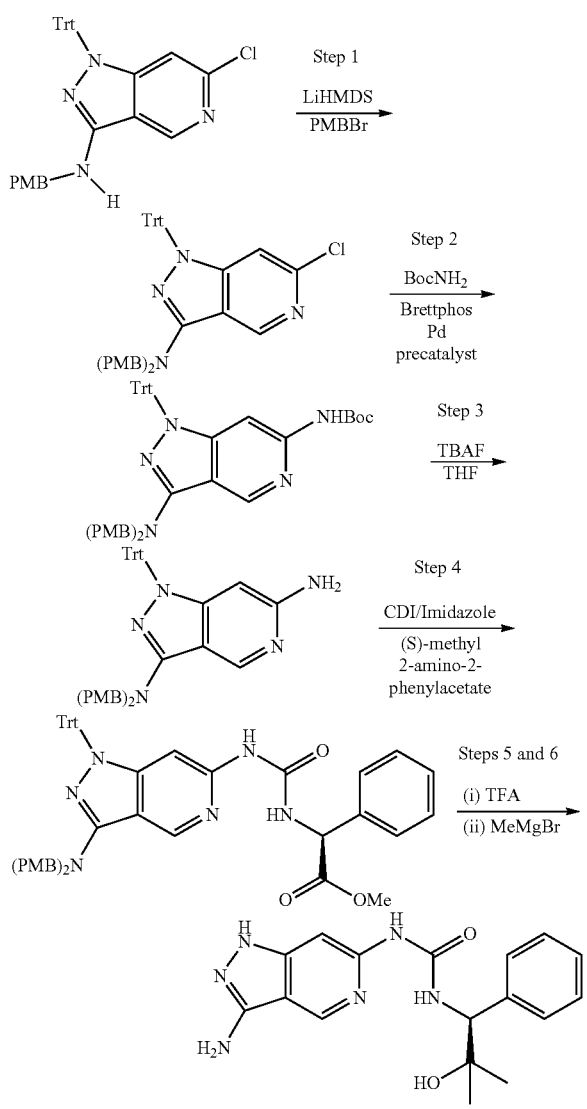

Step 1: Synthesis of 6-chloro-N,N-bis(4-methoxybenzyl)-1-trityl-1H-pyrazolo[4,3-c]pyridin-3-amine At 0° C., to a solution of 6-chloro-N-(4-methoxybenzyl)-1-trityl-1H-pyrazolo[4,3-c]pyridin-3-amine (2.0 g, 3.78 mmol) in anhydrous THF (30 mL) was added LiHMDS (1.0 M solution in Toluene, 7.56 mL, 7.56 mmol) and the contents were stirred at the same temperature. After 15 min, PMBBr (0.92 g, 4.53 mmol) was added at the same temperature and the contents were allowed to warm to ambient temperature. After 3 h, $H_2O$ (10 mL) was added and stirred for 5 min. The organic contents were extracted with EtOAc (3×40 mL) and the EtOAc layer washed with brine (1×20 mL), dried over anhydrous $Na_2SO_4$ and the solvents were removed under reduced pressure. The residue thus obtained was purified by a filter column to afford the title compound (1.0 g, 41% yield). MS ES calc'd. for $C_{41}H_{35}ClN_4O_2$ $[M+H]^+$ 651. Found 651.

Step 2: Synthesis of tert-butyl(3-(bis(4-methoxybenzyl)amino)-1-trityl-1H-pyrazolo[4,3-c]pyridin-6-yl)carbamate Under inert atmosphere, to a solution of 6-chloro-N,N-bis(4-methoxybenzyl)-1-trityl-1H-pyrazolo[4,3-c]pyridin-3-amine (0.5 g, 0.77 mmol) in anhydrous 1,4-dioxane (10.0 mL) was added tert-Butyl carbamate (0.26 g, 2.3 mmol), brettphos pre catalyst (0.03 g, 0.004 mmol), $Cs_2CO_3$ (0.75 g, 2.3 mmol) and the contents were heated in a sealed tube at 100° C. After 6 h, the reaction mixture was brought back to ambient temperature and the volatiles were removed under reduced pressure. The residue thus obtained was purified by a flash column chromatography to afford the title compound (0.4 g, 71% yield). MS ES calc'd. for $C_{46}H_{45}N_5O_4$ $[M+H]^+$ 732. Found 732.

Step 3: Synthesis of 3-N,N-bis(4-methoxybenzyl)-1-trityl-1H-pyrazolo[4,3-c]pyridine-3,6-diamine To a solution of (3-(bis(4-methoxybenzyl)amino)-1-trityl-1H-pyrazolo[4,3-c]pyridin-6-yl)carbamate (0.4 g, 0.55 mmol) in THF (8 mL) was added TBAF (1.0 M solution in THF, 10 mL) and the contents were heated to reflux. After 12 h, the reaction was cooled back to ambient temperature, quenched with 1N HCl (5 mL) and stirred at ambient temperature for 1 h. The reaction mixture was further diluted with EtOAc (25 mL) and the organic layer was separated. The organic layer was washed with brine (1×20 mL), dried over anhydrous $Na_2SO_4$ and the solvents were removed under reduced pressure. The residue thus obtained was purified by a filter column to afford the title compound. MS ES calc'd. for $C_{41}Fl_{37}N_5O_2$ $[M+H]^+$ 632. Found 632.

Step 4: Synthesis of Methyl (S)-2-(3-(3-(bis(4-methoxybenzyl)amino)-1-trityl-1H-pyrazolo[4,3-c]pyridin-6-yl)ureido)-2-phenylacetate To a solution of 3-N,N-bis(4-methoxybenzyl)-1-trityl-1H-pyrazolo[4,3-c]pyridine-3,6-diamine (0.1 g, 0.16 mmol) in anhydrous 1,4-dioxane (3 mL) was added CDI (0.13 g, 0.79 mmol) followed by the addition of imidazole (0.05 g, 0.78 mmol) and the contents were stirred at ambient temperature. After 16 h, DIPEA (0.12 mL, 0.64 mmol) and (S)-methyl-2-amino-2-phenylacetate (0.064 g, 0.32 mmol) were added and stirred. After 2 h, the reaction mixture was quenched with $H_2O$ and the organic contents were extracted with EtOAc (2×20 mL), dried over anhydrous $Na_2SO_4$ and concentrated. The residue thus obtained was purified by preparative HPLC to afford the title compound MS ES calc'd. for $C_{51}H_{46}N_6O_5$ $[M+H]^+$ 823. Found 823.

Steps 5 and 6: Synthesis of (S)-1-(3-amino-1H-pyrazolo[4,3-c]pyridin-6-yl)-3-(2-hydroxy-2-methyl-1-phenylpropyl)urea To the solution of (S)-2-(3-(3-(bis(4-methoxybenzyl)amino)-1-trityl-1H-pyrazolo[4,3-c]pyridin-6-yl)ureido)-2-phenylacetate (0.05 g, 0.06 mmol) was added TFA (2 mL) followed by $Et_3SiH$ (2 drops). The resultant mixture was stirred at 80° C. After 3 h of stirring, solvent was removed under reduced pressure, the residue (TFA salt) thus obtained was triturated in diethyl ether to afford the compound which was taken as such for next step. At 0° C., to the solution methyl (S)-2-(3-(3-amino-1H-pyrazolo[4,3-c]pyridin-6-yl)ureido)-2-phenylacetate (0.05 g, 0.146 mmol) in anhydrous THF was added methyl magnesium bromide (3 M solution in Et₂O, 0.5 mL, 1.5 mmol) and resultant mixture was allowed to warm and stirred at ambient temperature. After 10 h, the reaction was quenched with saturated aqueous NH₄Cl solution (5 mL), and the organic contents were extracted with CH₂Cl₂ (3×10 mL). The volatiles were removed under reduced pressure and the residue thus obtained was further purified by prep HPLC to afford the title compound. ¹H NMR (ppm, 400 MHz, CD₃OD): δ 8.73 (s, 1H), 7.42-7.40 (m, 2H), 7.35-7.30 (m, 3H), 7.28 (s, 1H), 4.80 (s, 1H) 1.31 (s, 3H), 1.17 (s, 3H). MS ES calc'd. for $C_{17}H_{20}N_6O_2$ $[M+H]^+$ 341. Found 341.

Example 444

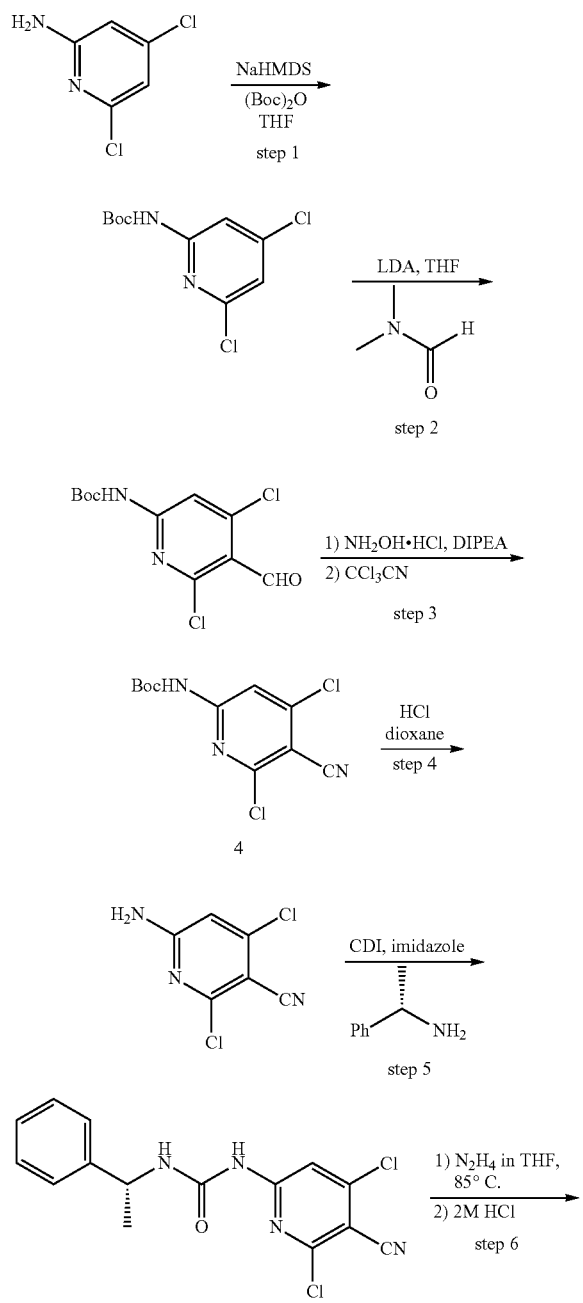

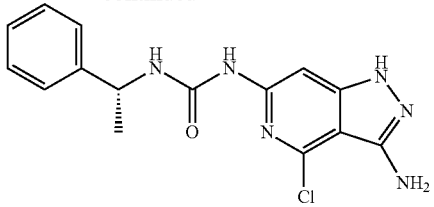

Step 1: tert-butyl(4,6-dichloropyridin-2-yl)carbamate

To a stirred solution of 4,6-dichloropyridin-2-amine (5.0 g, 30.6 mmol) in THF (100.0 mL) was added NaHMDS (67.5 mL, 1M solution in THF, 67.0 mmol) at −78° C. followed by Boc anhydride (8.08 g, 36.7 mmol) and allowed to warm to room temperature over 12 h. After confirming the completion of starting material by TLC, the reaction mixture was quenched with saturated ammonium chloride solution extracted with ethyl acetate. The organic layer was washed with brine, dried over anhydrous Na₂SO₄, filtered, concentrated under reduced pressure to get crude product which was purified by column chromatography (hexanes:ethyl acetate=9:1) to afford desired product. ¹H NMR (ppm, 400 MHz, DMSO-d₆): δ 10.48 (s, 1H), 7.85 (s, 1H), 7.36 (s, 1H), 1.46 (s, 9H), MS ES calc'd. for $C_{10}H_{12}C_{12}N_2O_2$ $[M+H]^+$ 263. Found: 263.

Step 2: tert-butyl(4,6-dichloro-5-formylpyridin-2-yl) carbamate

To a stirred solution of diisopropylethylamine (7.4 mL, 53.2 mmol) in THF was added n-BuLi (18.8 mL, 47.1 mmol, 2.5 M solution in hexanes) at −78° C., and allowed to stir at 0° C. of 30 minutes. The reaction mixture was again cooled to −78° C. and a solution compound tert-butyl(4,6-dichloropyridin-2-yl)carbamate (4.0 g, 15.2 mmol) in THF (20.0 mL) was added dropwise and stirred for 1 h at the same temperature. After 1 h, DMF (8.08 g, 36.7 mmol) was added at the same temperature and stirred for 30 minutes. After confirming the completion of starting material by TLC, the reaction mixture was quenched with saturated ammonium chloride solution extracted with ethyl acetate. The organic layer was washed with brine, dried over anhydrous Na₂SO₄, filtered, concentrated under reduced pressure to get crude product which was purified by column chromatography (hexanes: ethyl acetate=4:1) to afford product. ¹H NMR (ppm, 400 MHz, DMSO-d₆): δ 10.95 (s, 1H), 10.22 (s, 1H), 7.95 (s, 1H), 1.47 (s, 9H).

Step 3: tert-butyl(4,6-dichloro-5-cyanopyridin-2-yl) carbamate

To a stirred solution of compound tert-butyl(4,6-dichloro-5-formylpyridin-2-yl)carbamate (3.0 g, 10.3 mmol) in THF (30.0 mL) was added diisopropylethylamine (2.76 mL, 15.4 mmol) followed by hydroxylamine hydrochloride (0.78 g, 11.3 mmol) at 0° C. and was stirred at room temperature for 3 h. After confirming the completion of starting material by TLC, the reaction mixture was diluted with water and extracted with ethyl acetate. The organic layer was washed with brine, dried over anhydrous Na₂SO₄, filtered, concentrated under reduced pressure to get crude product. To the crude product was added trichloroacetonitrile (30.0 mL) and was heated at 85° C. for 2 h. After confirming the completion of starting material by TLC, the reaction mixture was cooled to room temperature and concentrated under reduced pressure. The residue was purified by column chromatography (hexanes:ethyl acetate=9:1) to afford product. $^1$H NMR (ppm, 400 MHz, DMSO-d$_6$): δ 11.08 (s, 1H), 8.02 (s, 1H), 1.46 (s, 9H), MS ES calc'd. for C$_{11}$K$_{11}$C$_{12}$N$_3$O$_2$ [M+H]$^+$ 288. Found 288.

Step 4: 6-amino-2,4-dichloronicotinonitrile

To a solution of tert-butyl(4,6-dichloro-5-cyanopyridin-2-yl)carbamate (2.1 g, 7.2 mmol) in dichloromethane (30.0 mL) was added TFA (3.0 mL) at 0° C. and stirred at the room temperature for 3 h. After confirming the completion of starting material by TLC, the reaction mixture was concentrated and the crude product was purified by column chromatography (dichloromethane:methanol=9:1) to afford titled compound. $^1$H NMR (ppm, 400 MHz, DMSO-d$_6$): δ 7.81 (bs, 2H), 6.59 (s, 1H), MS ES calc'd. for C$_6$H$_3$C$_{12}$N$_3$ [M+H]$^+$ 188. Found 188.

Step 5: (R)-1-(4,6-dichloro-5-cyanopyridin-2-yl)-3-(1-phenylethyl)urea

To a stirred solution of compound 6-amino-2,4-dichloronicotinonitrile (0.26 g, 1.37 mmol) in chloroform (7.0 mL) was added diisopropylethylamine (0.49 mL, 2.75 mmol) followed by imidazole (0.47 g, 6.87 mmol) and CDI (1.15 g, 6.87 mmol) at 0° C. and allowed to stir at room temperature for 12 h. After the clear solution is formed (R)-(+)-phenyl ethyl amine (1.08 g, 8.9 mmol) was added at room temperature and stirred for 2 h. After confirming the completion of starting material by TLC, the reaction mixture was concentrated under reduced pressure and dissolved in ethyl acetate and then washed with water. The organic layer was washed with brine, dried over anhydrous Na$_2$SO$_4$, filtered, concentrated under reduced pressure to get crude product which was purified by column chromatography (hexanes:ethyl acetate=7:3) to afford desired product. $^1$H NMR (ppm, 400 MHz, DMSO-d$_6$): δ 10.07 (s, 1H), 8.03 (s, 1H), 7.37-7.32 (m, 5H), 7.28-7.24 (m, 1H), 4.84 (t, J=8.00 Hz, 1H), 1.41 (d, J=8.00 Hz, 3H). MS ES calc'd. for C$_{15}$H$_{12}$C$_{12}$N$_4$O [M+H]$^+$ 335. Found 335.

Step 6: (R)-1-(3-amino-4-chloro-1H-pyrazolo[4,3-c]pyridin-6-yl)-3-(1-phenylethyl)urea To a stirred solution of compound (R)-1-(4,6-dichloro-5-cyanopyridin-2-yl)-3-(1-phenylethyl)urea (0.10 g, 0.29 mmol) in ethanol (8.0 mL) was added hydrazine hydrate (0.59 mL, 0.59 mmol, 1M solution in THF) and stirred at 80° C. for 2 h. After the precipitation of white solid, the reaction mixture was cooled to room temperature and a 2M solution of HCl in water (0.29 mL, 0.59 mmol) was added stirred at same temperature for 2 h. After confirming the completion of reaction by TLC, the reaction mixture was concentrated under reduced pressure to give crude product which was purified by preparative HPLC to afford (R)-1-(3-amino-4-chloro-1H-pyrazolo[4,3-c]pyridin-6-yl)-3-(1-phenylethyl)urea. $^1$H NMR (ppm, 400 MHz, DMSO-d$_6$): δ 11.88 (s, 1H), 9.05 (s, 1H), 7.44 (s, 1H), 7.36-7.32 (m, 4H), 7.23 (d, J=8.00 Hz, 2H), 5.42 (s, 2H), 4.84-4.82 (m, 1H), 1.38 (d, J=8.00 Hz, 3H), MS ES calc'd. for C$_{15}$H$_{15}$ClN$_6$O [M+H]$^+$ 331. Found 331.

Example 452

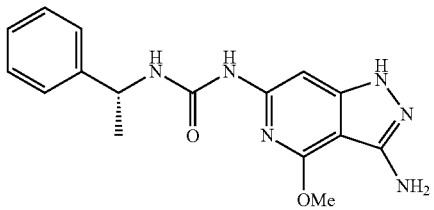 [SMILES: COc1nc(NC(=O)N[C@H](C)c2ccccc2)cc2[nH]nc(N)c12]

1-(3-amino-4-methoxy-1H-pyrazolo[4,3-c]pyridin-6-yl)-3-[(1R)-1-phenylethyl]urea (R)-1-(3-amino-4-methoxy-1H-pyrazolo[4,3-c]pyridin-6-yl)-3-(1-phenylethyl)urea To a stirred solution of (R)-1-(3-amino-4-chloro-1H-pyrazolo[4,3-c]pyridin-6-yl)-3-(1-phenylethyl)urea (0.12 g, 0.36 mmol) in methanol (3.0 mL) was added sodium methoxide (0.78 mL, 3.62 mmol, 25% solution in MeOH) and stirred at 120° C. for 1 h in a microwave reactor. After confirming the completion of reaction by TLC, the reaction mixture was acidified with 1.5N HCl and concentrated under reduced pressure and crude product which was purified by preparative HPLC to afford (R)-1-(3-amino-4-methoxy-1H-pyrazolo[4,3-c]pyridin-6-yl)-3-(1-phenylethyl)urea. $^1$H NMR (ppm, 400 MHz, DMSO-d$_6$): δ 11.48 (s, 1H), 8.76 (s, 1H), 7.94 (s, 1H), 7.35-7.33 (m, 4H), 7.26-7.21 (m, 1H), 6.86 (d, J=8.00 Hz, 1H), 5.12 (s, 2H), 4.88-4.85 (m, 1H), 3.87 (s, 3H), 1.41 (d, J=8.00 Hz, 3H), MS ES calc'd. for C$_{16}$H$_{18}$N$_6$O$_2$ [M+H]$^+$ 327. Found 327.

Example 454

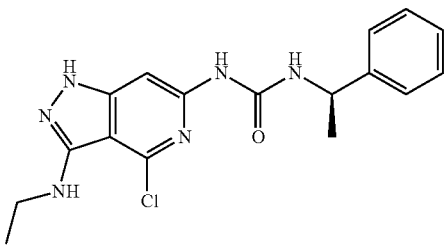

1-[4-chloro-3-(ethylamino)-1H-pyrazolo[4,3-c]pyridin-6-yl]-3-[(1R)-1-phenylethyl]urea

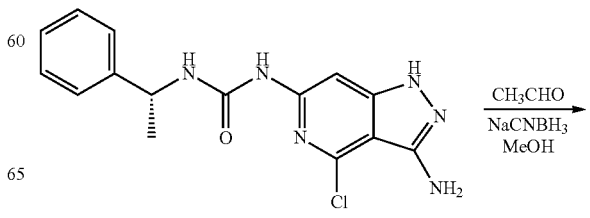

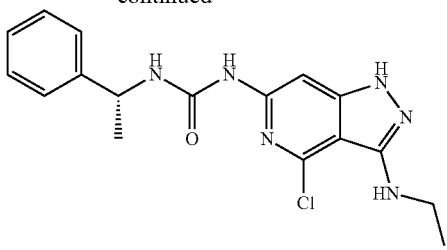

To a stirred solution of (R)-1-(3-amino-4-chloro-1H-pyrazolo[4,3-c]pyridin-6-yl)-3-(1-phenylethyl)urea (0.06 g, 0.18 mmol) in methanol (2.0 mL) was added aqueous acetaldehyde (0.025 mL, 35 wt. % in water, 0.20 mmol) followed by sodium cyanoborohydride (0.03 g, 0.54 mmol) and stirred at room temperature for 12 h. After confirming the completion of reaction by TLC, the reaction mixture was acidified with 1.5 N HCl and concentrated under reduced pressure. The crude product was dissolved in ethyl acetate, washed with 10% NaOH followed by water and brine solution. The organic layer was concentrated under reduced pressure and crude product was purified by preparative HPLC to afford (R)-1-(4-chloro-3-(ethylamino)-1H-pyrazolo[4,3-c]pyridin-6-yl)-3-(1-phenylethyl)urea (0.021 g, 32.0%). $^1$H NMR (ppm, 400 MHz, DMSO-$d_6$): δ 11.92 (s, 1H), 9.05 (s, 1H), 7.44 (s, 1H), 7.37-7.32 (m, 4H), 7.26-7.22 (m, 2H), 5.44 (t, J=5.6 Hz, 1H), 4.84 (m, 1H), 3.28-3.23 (m, 2H), 1.39 (d, J=8.00 Hz, 3H), 1.20 (t, J=6.8 Hz, 3H). MS ES calc'd. for $C_{17}H_{19}ClN_6O_2$ [M+H]$^+$ 359. Found: 359.

The Table below provides data for compounds of this invention.

| No. | Structure | IUPAC Name | Exact Mass [M + H]$^+$ | Route Used |
|---|---|---|---|---|
| 61 | 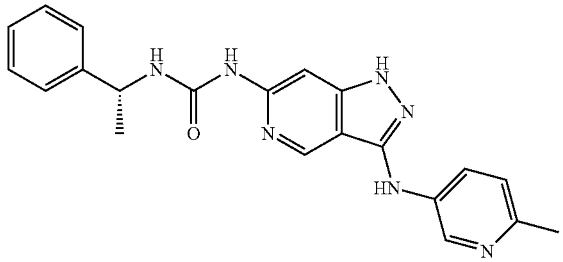 [SMILES: Cc1ccc(Nc2n[nH]c3cc(NC(=O)N[C@H](C)c4ccccc4)ncc23)cn1] | 1-{3-[(6-methylpyridin-3-yl)amino]-1H-pyrazolo[4,3-c]pyridin-6-yl}-3-[(1R)-1-phenylethyl]urea | Calc'd 388, found 388 | Following a similar procedure in Example 121 |
| 62 | 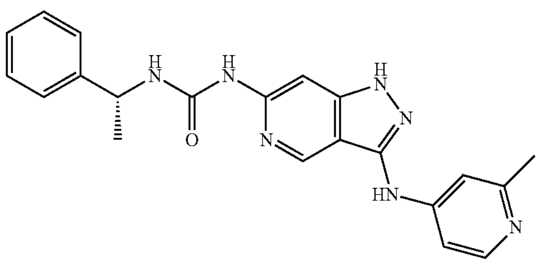 [SMILES: Cc1cc(Nc2n[nH]c3cc(NC(=O)N[C@H](C)c4ccccc4)ncc23)ccn1] | 1-{3-[(2-methylpyridin-4-yl)amino]-1H-pyrazolo[4,3-c]pyridin-6-yl}-3-[(1R)-1-phenylethyl]urea | Calc'd 388, found 388 | Following a similar procedure in Example 121 |
| 63 | 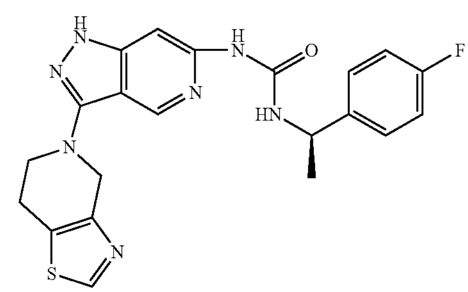 [SMILES: C[C@@H](NC(=O)Nc1cc2[nH]nc(N3CCc4scnc4C3)c2cn1)c1ccc(F)cc1] | 1-[3-(6,7-dihydro[1,3]thiazolo[4,5-c]pyridin-5(4H)-yl)-1H-pyrazolo[4,3-c]pyridin-6-yl]-3-[(1R)-1-(4-fluorophenyl)ethyl]urea | Calc'd 438, found 438 | Scheme 1 |
| 64 | 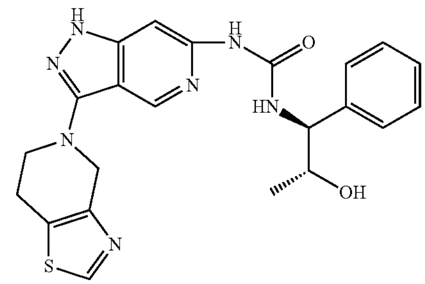 [SMILES: C[C@@H](O)[C@@H](NC(=O)Nc1cc2[nH]nc(N3CCc4scnc4C3)c2cn1)c1ccccc1] | 1-[3-(6,7-dihydro[1,3]thiazolo[4,5-c]pyridin-5(4H)-yl)-1H-pyrazolo[4,3-c]pyridin-6-yl]-3-[(1S,2R)-2-hydroxy-1-phenylpropyl]urea | Calc'd 450, found 450 | Scheme 1 |

| No. | Structure | IUPAC Name | Exact Mass [M + H]+ | Route Used |
|---|---|---|---|---|
| 65 | 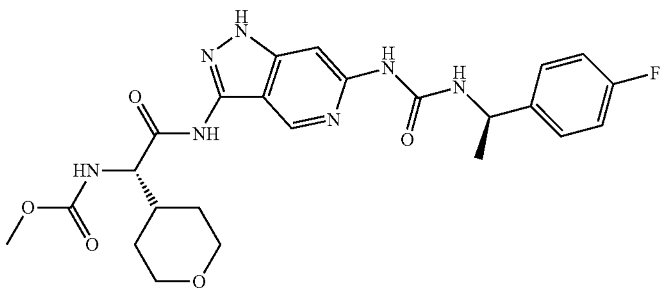 [SMILES: COC(=O)N[C@H](C(=O)Nc1n[nH]c2cc(NC(=O)N[C@H](C)c3ccc(F)cc3)ncc12)C1CCOCC1] | methyl [(1S)-2-{[6-({[(1R)-1-(4-fluoro-phenyl)ethyl]carbamoyl}-amino)-1H-pyrazolo[4,3-c]-pyridin-3-yl]amino}-2-oxo-1-(tetrahydro-2H-pyran-4-yl)-ethyl]carbamate | Calc'd 514, found 514 | Scheme 14, Example 321 using corresponding carboxylic acid (with coupling condition in Scheme 11, step 1) instead of chloroformate |
| 66 | 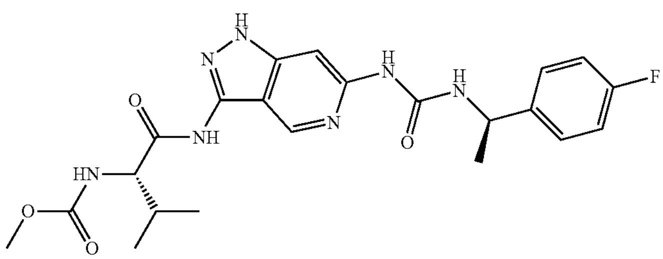 [SMILES: COC(=O)N[C@H](C(=O)Nc1n[nH]c2cc(NC(=O)N[C@H](C)c3ccc(F)cc3)ncc12)C(C)C] | methyl [(1S)-1-{[6-({[(1R)-1-(4-fluoro-phenyl)ethyl]-carbamoyl}-amino)-1H-pyrazolo[4,3-c]-pyridin-3-yl]-carbamoyl}-2-methylpropyl]-carbamate | Calc'd 472, found 472 | Scheme 14, Example 321 using corresponding carboxylic acid (with coupling condition in Scheme 11, step 1) instead of chloroformate |
| 67 | 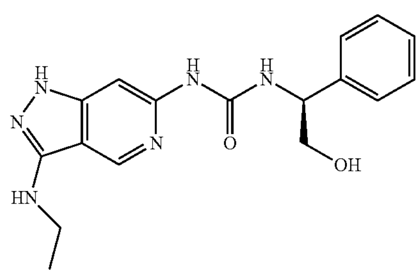 [SMILES: CCNc1n[nH]c2cc(NC(=O)N[C@H](CO)c3ccccc3)ncc12] | 1-[3-(ethylamino)-1H-pyrazolo[4,3-c]pyridin-6-yl]-3-[(1S)-2-hydroxy-1-phenylethyl]urea | Calc'd 341, found 341 | Scheme 1 |
| 68 | 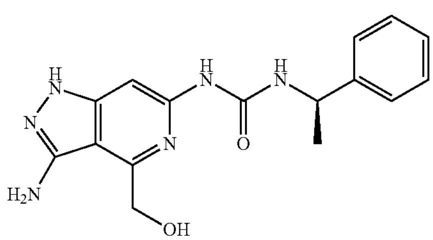 [SMILES: C[C@@H](NC(=O)Nc1cc2[nH]nc(N)c2c(CO)n1)c1ccccc1] | 1-[3-amino-4-(hydroxymethyl)-1H-pyrazolo[4,3-c]-pyridin-6-yl]-3-[(1R)-1-phenylethyl]urea | Calc'd 327, found 327 | Example 68 |
| 69 | 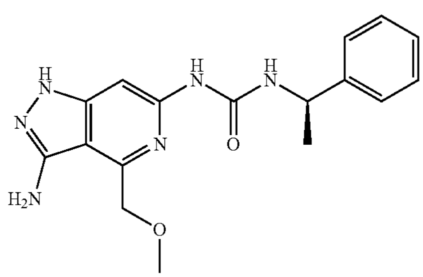 [SMILES: COCc1nc(NC(=O)N[C@H](C)c2ccccc2)cc2[nH]nc(N)c12] | 1-[3-amino-4-(methoxymethyl)-1H-pyrazolo[4,3-c]-pyridin-6-yl]-3-[(1R)-1-phenylethyl]urea | Calc'd 341, found 341 | Example 69 |

-continued

| No. | Structure | IUPAC Name | Exact Mass [M + H]⁺ | Route Used |
|---|---|---|---|---|
| 70 | 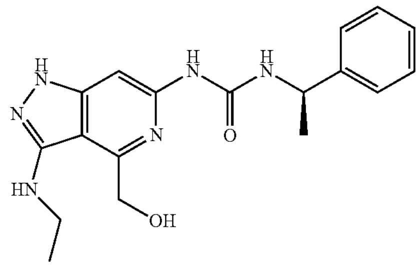 [SMILES: CCNc1n[nH]c2cc(NC(=O)N[C@H](C)c3ccccc3)nc(CO)c12] | 1-[3-(ethylamino)-4-(hydroxymethyl)-1H-pyrazolo[4,3-c]-pyridin-6-yl]-3-[(1R)-1-phenylethyl]urea | Calc'd 355, found 355 | Followed similar procedure in Example 71 |
| 71 | 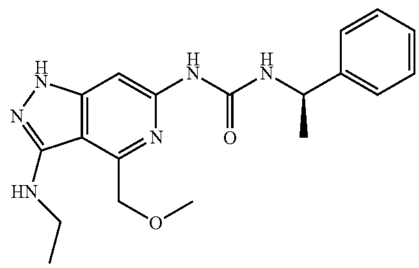 [SMILES: CCNc1n[nH]c2cc(NC(=O)N[C@H](C)c3ccccc3)nc(COC)c12] | 1-[3-(ethylamino)-4-(methoxymethyl)-1H-pyrazolo[4,3-c]-pyridin-6-yl]-3-[(1R)-1-phenylethyl]urea | Calc'd 369, found, 369 | Example 71 |
| 72 | 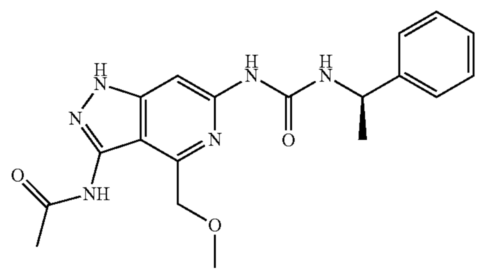 [SMILES: COCc1nc(NC(=O)N[C@H](C)c2ccccc2)cc2[nH]nc(NC(C)=O)c12] | N-[4-(methoxymethyl)-6-({[(1R)-1-phenylethyl]-carbamoyl}amino)-1H-pyrazolo[4,3-c]-pyridin-3-yl]-acetamide | Calc'd 383, found 383 | Example 72 |
| 73 | 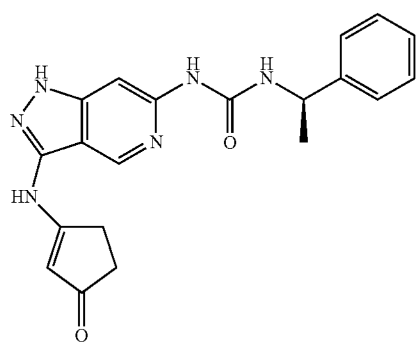 [SMILES: C[C@@H](NC(=O)Nc1cc2[nH]nc(NC3=CC(=O)CC3)c2cn1)c1ccccc1] | 1-{3-[(3-oxocyclopent-1-en-1-yl)amino]-1H-pyrazolo[4,3-c]-pyridin-6-yl}-3-[(1R)-1-phenylethyl]-urea | Calc'd 377, found 377 | Example 73 |
| 74 | 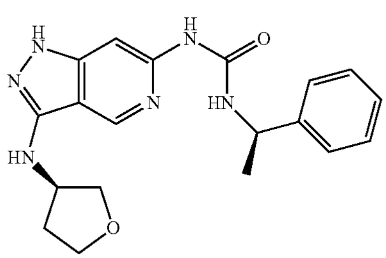 [SMILES: C[C@@H](NC(=O)Nc1cc2[nH]nc(N[C@@H]3CCOC3)c2cn1)c1ccccc1] | 1-[(1R)-1-phenylethyl]-3-{3-[(3R)-tetrahydro-furan-3-ylamino]-1H-pyrazolo[4,3-c]-pyridin-6-yl}urea | Calc'd 367, found 367 | Scheme 1 Example 1 |

| No. | Structure | IUPAC Name | Exact Mass [M + H]+ | Route Used |
|---|---|---|---|---|
| 75 | 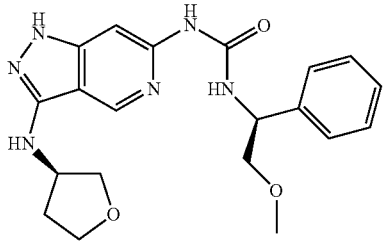 [SMILES: COC[C@@H](NC(=O)Nc1cc2[nH]nc(N[C@@H]3CCOC3)c2cn1)c1ccccc1] | 1-[(1S)-2-methoxy-1-phenylethyl]-3-{3-[(3R)-tetrahydro-furan-3-ylamino]-1H-pyrazolo[4,3-c]-pyridin-6-yl}urea | Calc'd 397, found 397 | Scheme 1 Example 1 |
| 76 | 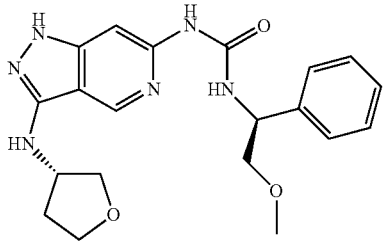 [SMILES: COC[C@@H](NC(=O)Nc1cc2[nH]nc(N[C@H]3CCOC3)c2cn1)c1ccccc1] | 1-[(1S)-2-methoxy-1-phenylethyl]-3-{3-[(3S)-tetrahydro-furan-3-ylamino]-1H-pyrazolo[4,3-c]-pyridin-6-yl}urea | Calc'd 397, found 397 | Scheme 1 Example 1 |
| 77 | 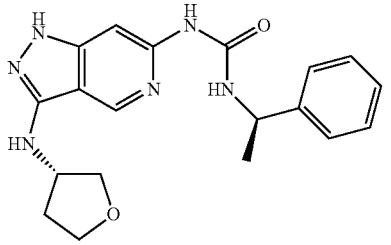 [SMILES: C[C@@H](NC(=O)Nc1cc2[nH]nc(N[C@H]3CCOC3)c2cn1)c1ccccc1] | 1-[(1R)-1-phenylethyl]-3-{3-[(3S)-tetrahydro-furan-3-ylamino]-1H-pyrazolo[4,3-c]-pyridin-6-yl}urea | Calc'd 367, found 367 | Scheme 1 Example 1 |
| 78 | 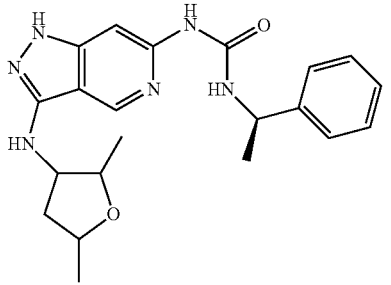 [SMILES: CC1CC(Nc2n[nH]c3cc(NC(=O)N[C@H](C)c4ccccc4)ncc23)C(C)O1] | 1-(3-((2,5-dimethyltetrahydro-furan-3-yl)amino)-1H-pyrazolo[4,3-c]-pyridin-6-yl)-3-((R)-1-phenylethyl)urea | Calc'd 395, found 395 | Scheme 1 Example 1 with Intermediate 78A |
| 79 | 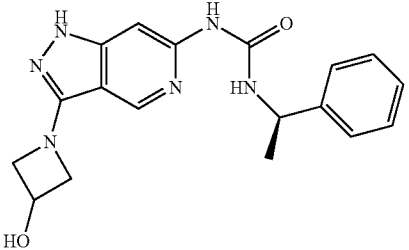 [SMILES: C[C@@H](NC(=O)Nc1cc2[nH]nc(N3CC(O)C3)c2cn1)c1ccccc1] | 1-[3-(3-hydroxy-azetidin-1-yl)-1H-pyrazolo[4,3-c]-pyridin-6-yl]-3-[(1R)-1-phenylethyl]urea | Calc'd 353, found 353 | Scheme 1 Example 1 |

| No. | Structure | IUPAC Name | Exact Mass [M + H]+ | Route Used |
|---|---|---|---|---|
| 80 | 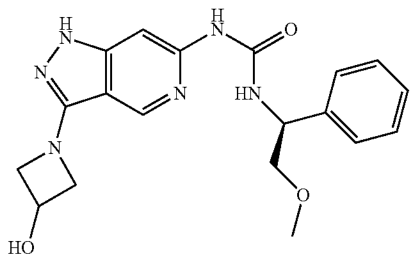 [SMILES: COC[C@@H](NC(=O)Nc1cc2[nH]nc(N3CC(O)C3)c2cn1)c1ccccc1] | 1-[3-(3-hydroxy-azetidin-1-yl)-1H-pyrazolo[4,3-c]-pyridin-6-yl]-3-[(1S)-2-methoxy-1-phenylethyl]urea | Calc'd 383, found 383 | Scheme 1 Example 1 |
| 81 | 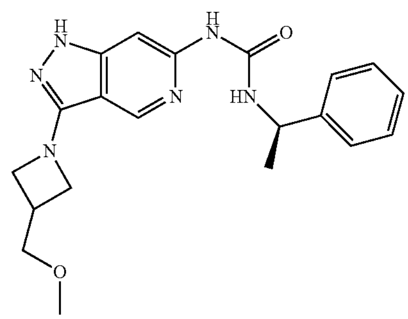 [SMILES: COCC1CN(c2n[nH]c3cc(NC(=O)N[C@H](C)c4ccccc4)ncc23)C1] | 1-{3-[3-(methoxy-methyl)azetidin-1-yl]-1H-pyrazolo[4,3-c]-pyridin-6-yl}-3-[(1R)-1-phenylethyl]-urea | Calc'd 381, found 381 | Scheme 1 Example 1 |
| 82 | 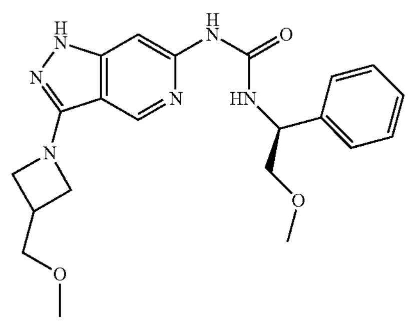 [SMILES: COCC1CN(c2n[nH]c3cc(NC(=O)N[C@H](COC)c4ccccc4)ncc23)C1] | 1-{3-[3-(methoxy-methyl)azetidin-1-yl]-1H-pyrazolo[4,3-c]-pyridin-6-yl}-3-[(1S)-2-methoxy-1-phenylethyl]urea | Calc'd 411, found 411 | Scheme 1 Example 1 |
| 83 | 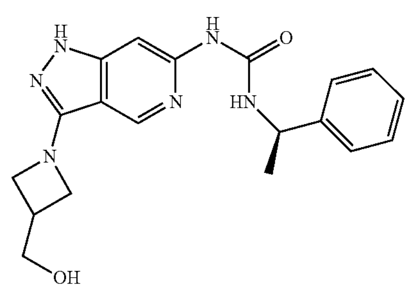 [SMILES: C[C@@H](NC(=O)Nc1cc2[nH]nc(N3CC(CO)C3)c2cn1)c1ccccc1] | 1-{3-[3-(hydroxyl-methyl)azetidin-1-yl]-1H-pyrazolo[4,3-c]-pyridin-6-yl}-3-[(1R)-1-phenylethyl]-urea | Calc'd 367, found 367 | Scheme 1 Example 1 |
| 84 | 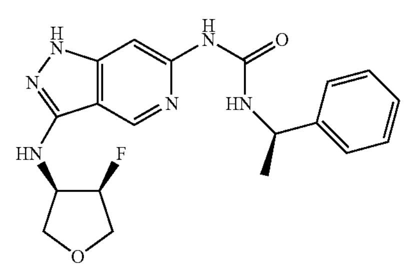 [SMILES: C[C@@H](NC(=O)Nc1cc2[nH]nc(N[C@@H]3COC[C@@H]3F)c2cn1)c1ccccc1] | 1-(3-{[(3R,4R)-4-fluorotetrahydrofuran-3-yl]amino}-1H-pyrazolo[4,3-c]-pyridin-6-yl)-3-[(1R)-1-phenylethyl]urea | Calc'd 385, found 385 | Scheme 1 Example 39/40 |

| No. | Structure | IUPAC Name | Exact Mass [M + H]+ | Route Used |
|---|---|---|---|---|
| 85 | 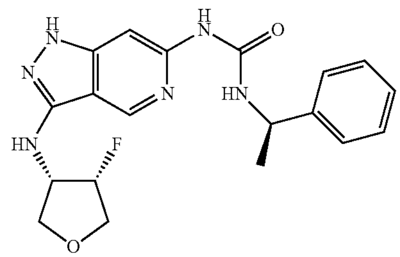 [SMILES: C[C@@H](NC(=O)Nc1cc2[nH]nc(N[C@H]3COC[C@H]3F)c2cn1)c1ccccc1] | 1-(3-{[(3S,4S)-4-fluorotetrahydrofuran-3-yl]amino}-1H-pyrazolo[4,3-c]-pyridin-6-yl)-3-[(1R)-1-phenylethyl]urea | Calc'd 385, found 385 | Scheme 1 Example 39/40 |
| 86 | 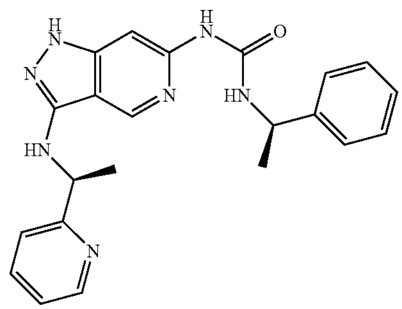 [SMILES: C[C@H](Nc1n[nH]c2cc(NC(=O)N[C@H](C)c3ccccc3)ncc12)c1ccccn1] | 1-[(1R)-1-phenylethyl]-3-(3-{[(1S)-1-pyridin-2-ylethyl]amino}-1H-pyrazolo[4,3-c]-pyridin-6-yl)urea | Calc'd 402, found 402 | Scheme 1 Example 39/40 |
| 87 | 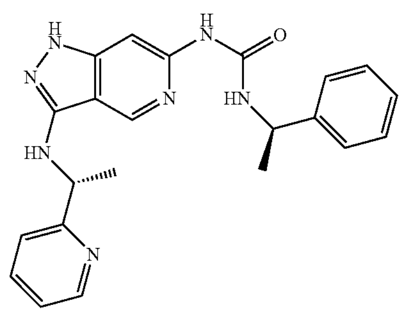 [SMILES: C[C@@H](NC(=O)Nc1cc2[nH]nc(N[C@H](C)c3ccccn3)c2cn1)c1ccccc1] | 1-[(1R)-1-phenylethyl]-3-(3-{[(1R)-1-pyridin-2-ylethyl]amino}-1H-pyrazolo[4,3-c]-pyridin-6-yl)urea | Calc'd 402, found 402 | Scheme 1 Example 39/40 |
| 88 | 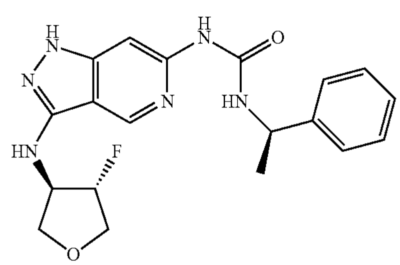 [SMILES: C[C@@H](NC(=O)Nc1cc2[nH]nc(N[C@@H]3COC[C@H]3F)c2cn1)c1ccccc1] | 1-(3-{[(3R,4S)-4-fluorotetrahydrofuran-3-yl]amino}-1H-pyrazolo[4,3-c]-pyridin-6-yl)-3-[(1R)-1-phenylethyl]urea | Calc'd 385, found 385 | Scheme 1 Example 1 |
| 89 | 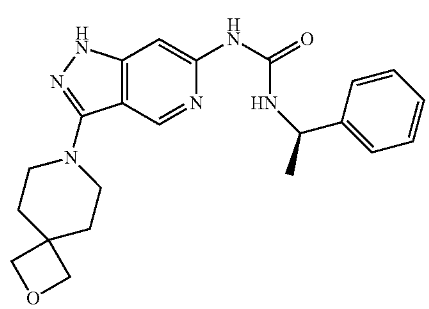 [SMILES: C[C@@H](NC(=O)Nc1cc2[nH]nc(N3CCC4(CC3)COC4)c2cn1)c1ccccc1] | 1-[3-(2-oxa-7-azaspiro[3.5]non-7-yl)-1H-pyrazolo[4,3-c]pyridin-6-yl]-3-[(1R)-1-phenylethyl]-urea | Calc'd 407, found 407 | Scheme 1 Example 1 |

-continued

| No. | Structure | IUPAC Name | Exact Mass [M + H]+ | Route Used |
|---|---|---|---|---|
| 90 | 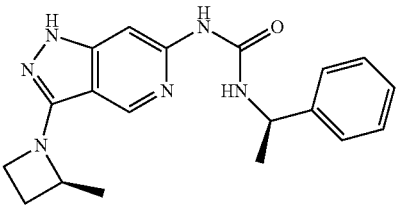 [SMILES: C[C@@H](NC(=O)Nc1cc2[nH]nc(N3CC[C@@H]3C)c2cn1)c1ccccc1] | 1-{3-[(2S)-2-methylazetidin-1-yl]-1H-pyrazolo[4,3-c]pyridin-6-yl}-3-[(1R)-1-phenylethyl]-urea | Calc'd 351, found 351 | Scheme 1 Example 39/40 |
| 91 | 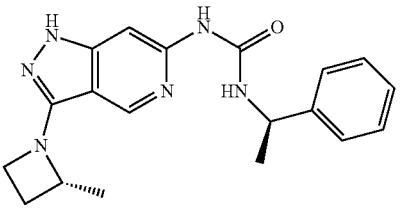 [SMILES: C[C@@H]1CCN1c1n[nH]c2cc(NC(=O)N[C@H](C)c3ccccc3)ncc12] | 1-{3-[(2R)-2-methylazetidin-1-yl]-1H-pyrazolo[4,3-c]pyridin-6-yl}-3-[(1R)-1-phenylethyl]-urea | Calc'd 351, found 351 | Scheme 1 Example 39/40 |
| 92 | 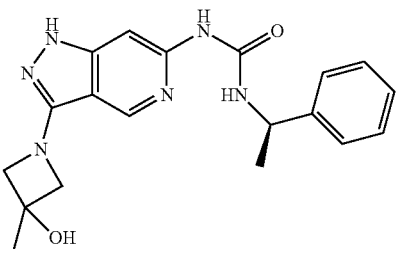 [SMILES: C[C@@H](NC(=O)Nc1cc2[nH]nc(N3CC(C)(O)C3)c2cn1)c1ccccc1] | 1-[3-(3-hydroxy-3-methylazetidin-1-yl)-1H-pyrazolo[4,3-c]pyridin-6-yl]-3-[(1R)-1-phenylethyl]urea | Calc'd 367, found 367 | Scheme 1 Example 1 |
| 93 | 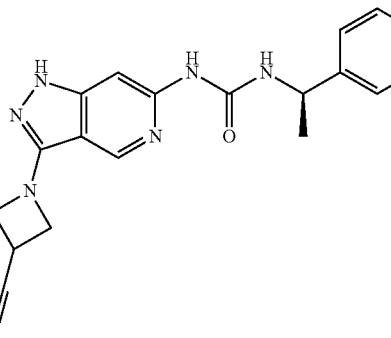 | 1-[3-(3-cyanoazetidin-1-yl)-1H-pyrazolo[4,3-c]pyridin-6-yl]-3-[(1R)-1-phenylethyl]urea | Calc'd 362, found 362 | Scheme 1 Example 1 |
| 94 | 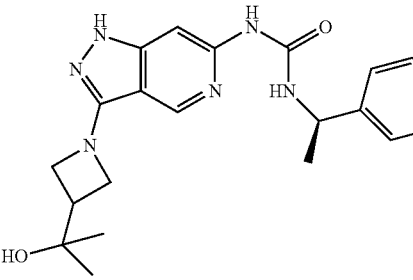 | 1-{3-[3-(1-hydroxy-1-methylethyl)-azetidin-1-yl]-1H-pyrazolo[4,3-c]pyridin-6-yl}-3-[(1R)-1-phenylethyl]-urea | Calc'd 395, found 395 | Scheme 1 Example 1 |

| No. | Structure | IUPAC Name | Exact Mass [M + H]+ | Route Used |
|---|---|---|---|---|
| 95 | 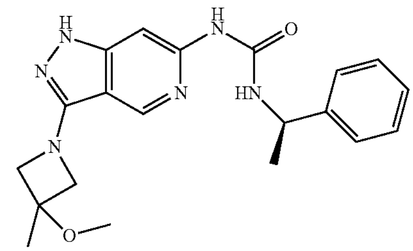 [SMILES: COC1(C)CN(c2n[nH]c3cc(NC(=O)N[C@H](C)c4ccccc4)ncc23)C1] | 1-[3-(3-methoxy-3-methylazetidin-1-yl)-1H-pyrazolo[4,3-c]-pyridin-6-yl]-3-[(1R)-1-phenylethyl]urea | Calc'd 381, found 381 | Scheme 1 Example 1 |
| 96 | 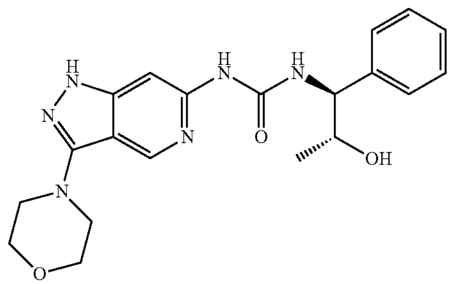 [SMILES: C[C@@H](O)[C@@H](NC(=O)Nc1cc2[nH]nc(N3CCOCC3)c2cn1)c1ccccc1] | 1-[(1S,2R)-2-hydroxy-1-phenylpropyl]-3-(3-morpholin-4-yl-1H-pyrazolo[4,3-c]-pyridin-6-yl)urea | Calc'd 397, found 397 | Scheme 1 Example 1 |
| 97 | 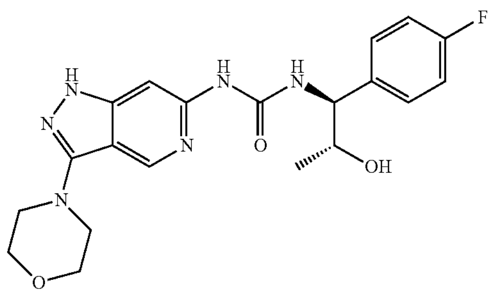 [SMILES: C[C@@H](O)[C@@H](NC(=O)Nc1cc2[nH]nc(N3CCOCC3)c2cn1)c1ccc(F)cc1] | 1-[(1S,2R)-1-(4-fluorophenyl)-2-hydroxypropyl]-3-(3-morpholin-4-yl-1H-pyrazolo[4,3-c]-pyridin-6-yl)urea | Calc'd 415, found 415 | Scheme 1 Example 39/40 |
| 98 | 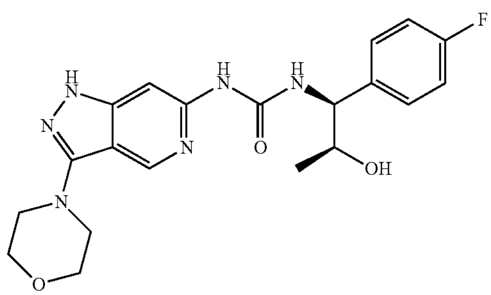 [SMILES: C[C@H](O)[C@@H](NC(=O)Nc1cc2[nH]nc(N3CCOCC3)c2cn1)c1ccc(F)cc1] | 1-[(1S,2S)-1-(4-fluorophenyl)-2-hydroxypropyl]-3-(3-morpholin-4-yl-1H-pyrazolo[4,3-c]-pyridin-6-yl)urea | Calc'd 415, found 415 | Scheme 1 Example 39/40 |
| 99 | 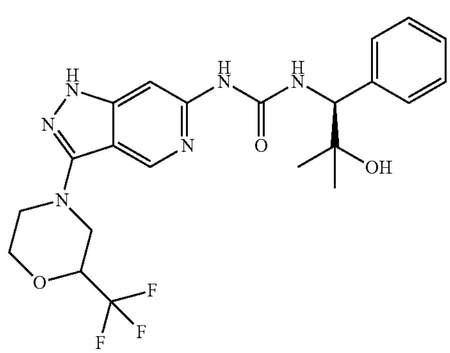 [SMILES: CC(C)(O)[C@@H](NC(=O)Nc1cc2[nH]nc(N3CCOC(C(F)(F)F)C3)c2cn1)c1ccccc1] | 1-[(1S)-2-hydroxy-2-methyl-1-phenylpropyl]-3-{3-[2-(trifluoromethyl)-morpholin-4-yl]-1H-pyrazolo[4,3-c]-pyridin-6-yl}urea | Calc'd 479, found 479 | Scheme 1 Example 1 |

| No. | Structure | IUPAC Name | Exact Mass [M + H]+ | Route Used |
|---|---|---|---|---|
| 100 | 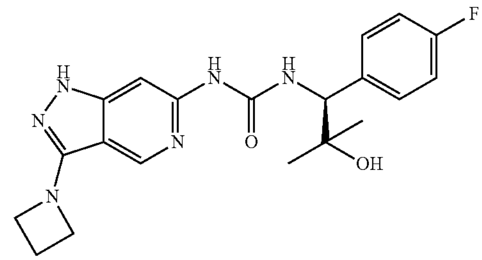 [SMILES: CC(C)(O)[C@@H](NC(=O)Nc1cc2[nH]nc(N3CCC3)c2cn1)c1ccc(F)cc1] | 1-(3-azetidin-1-yl-1H-pyrazolo[4,3-c]-pyridin-6-yl)-3-[(1S)-1-(4-fluorophenyl)-2-hydroxy-2-methylpropyl]urea | Calc'd 399, found 399 | Scheme 1 Example 1 |
| 101 | 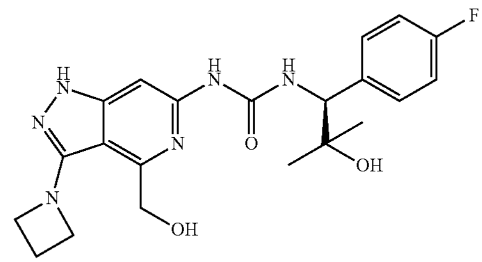 [SMILES: CC(C)(O)[C@@H](NC(=O)Nc1cc2[nH]nc(N3CCC3)c2c(CO)n1)c1ccc(F)cc1] | 1-[3-azetidin-1-yl-4-(hydroxymethyl)-1H-pyrazolo[4,3-c]-pyridin-6-yl]-3-[(1S)-1-(4-fluorophenyl)-2-hydroxy-2-methylpropyl]urea | Calc'd 429, found 429 | Scheme 1 Example 1 with Intermediate 101A |
| 102 | 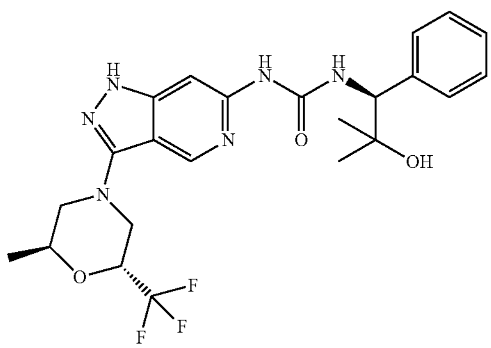 [SMILES: C[C@H]1CN(c2n[nH]c3cc(NC(=O)N[C@@H](c4ccccc4)C(C)(C)O)ncc23)C[C@H](C(F)(F)F)O1] | 1-[(1S)-2-hydroxy-2-methyl-1-phenylpropyl]-3-{3-[(2S,6R)-2-methyl-6-(trifluoromethyl)-morpholin-4-yl]-1H-pyrazolo[4,3-c]-pyridin-6-yl}urea | Calc'd 493, found 493 | Scheme 1 Example 1 |
| 103 | 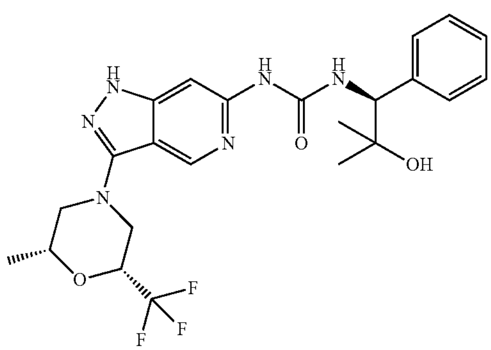 [SMILES: C[C@@H]1CN(c2n[nH]c3cc(NC(=O)N[C@@H](c4ccccc4)C(C)(C)O)ncc23)C[C@H](C(F)(F)F)O1] | 1-[(1S)-2-hydroxy-2-methyl-1-phenylpropyl]-3-{3-[(2R,6R)-2-methyl-6-(trifluoromethyl)-morpholin-4-yl]-1H-pyrazolo[4,3-c]-pyridin-6-yl}urea | Calc'd 493, found 493 | Scheme 1 Example 1 |
| 104 | 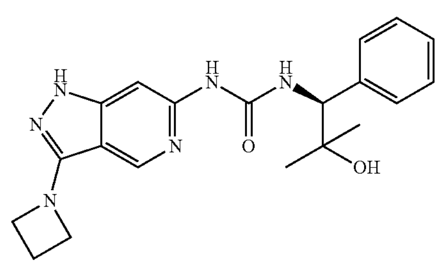 [SMILES: CC(C)(O)[C@@H](NC(=O)Nc1cc2[nH]nc(N3CCC3)c2cn1)c1ccccc1] | 1-(3-azetidin-1-yl-1H-pyrazolo[4,3-c]pyridin-6-yl)-3-[(1S)-2-hydroxy-2-methyl-1-phenylpropyl]urea | Calc'd 381, found 381 | Scheme 1 Example 1 |

| No. | Structure | IUPAC Name | Exact Mass [M + H]+ | Route Used |
|---|---|---|---|---|
| 105 | 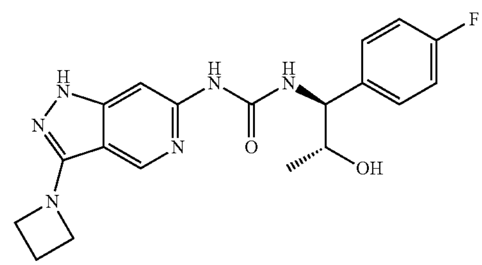 [SMILES: C[C@@H](O)[C@@H](NC(=O)Nc1cc2[nH]nc(N3CCC3)c2cn1)c1ccc(F)cc1] | 1-(3-azetidin-1-yl-1H-pyrazolo[4,3-c]pyridin-6-yl)-3-[(1S,2R)-1-(4-fluorophenyl)-2-hydroxypropyl]urea | Calc'd 385, found 385 | Scheme 1 Example 1 |
| 106 | 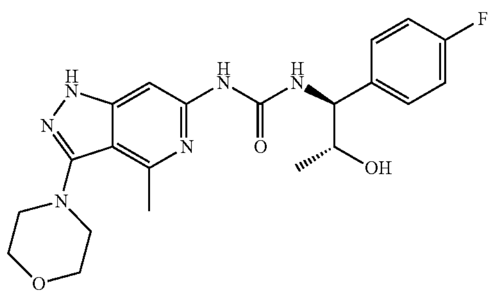 [SMILES: Cc1nc(NC(=O)N[C@@H](c2ccc(F)cc2)[C@@H](C)O)cc2[nH]nc(N3CCOCC3)c12] | 1-[(1S,2R)-1-(4-fluorophenyl)-2-hydroxypropyl]-3-(4-methyl-3-morpholin-4-yl-1H-pyrazolo[4,3-c]-pyridin-6-yl)urea | Calc'd 429, found 429 | Example 106 |
| 107 | 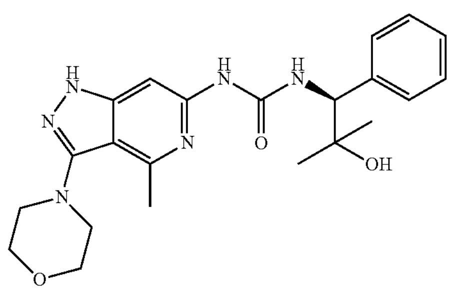 [SMILES: Cc1nc(NC(=O)N[C@@H](c2ccccc2)C(C)(C)O)cc2[nH]nc(N3CCOCC3)c12] | 1-[(1S)-2-hydroxy-2-methyl-1-phenylpropyl]-3-(4-methyl-3-morpholin-4-yl-1H-pyrazolo[4,3-c]-pyridin-6-yl)urea | Calc'd 425, found 425 | Followed similar procedure in Example 106 |
| 108 | 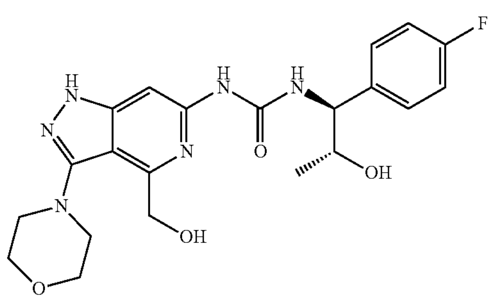 [SMILES: C[C@@H](O)[C@@H](NC(=O)Nc1cc2[nH]nc(N3CCOCC3)c2c(CO)n1)c1ccc(F)cc1] | 1-[(1S,2R)-1-(4-fluorophenyl)-2-hydroxypropyl]-3-[4-(hydroxylmethyl)-3-morpholin-4-yl-1H-pyrazolo[4,3-c]-pyridin-6-yl]urea | Calc'd 445, found 445 | Example 108 |
| 109 | 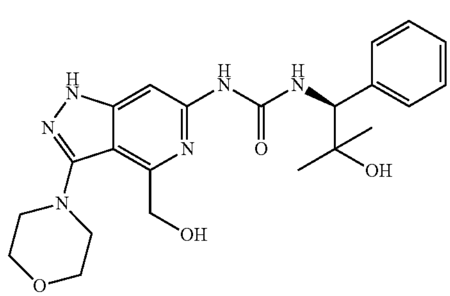 [SMILES: CC(C)(O)[C@@H](NC(=O)Nc1cc2[nH]nc(N3CCOCC3)c2c(CO)n1)c1ccccc1] | 1-[4-(hydroxymethyl)-3-morpholin-4-yl-1H-pyrazolo[4,3-c]-pyridin-6-yl]-3-[(1S)-2-hydroxy-2-methyl-1-phenylpropyl]urea | Calc'd 441, found 441 | Followed similar procedure in Example 108 |

-continued

| No. | Structure | IUPAC Name | Exact Mass [M + H]⁺ | Route Used |
|---|---|---|---|---|
| 110 | 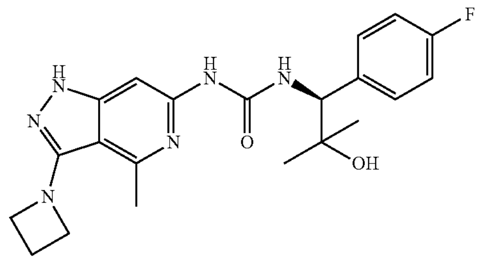 [SMILES: Cc1nc(NC(=O)N[C@@H](c2ccc(F)cc2)C(C)(C)O)cc2[nH]nc(N3CCC3)c12] | 1-(3-azetidin-1-yl-4-methyl-1H-pyrazolo[4,3-c]-pyridin-6-yl)-3-[(1S)-1-(4-fluorophenyl)-2-hydroxy-2-methylpropyl]urea | Calc'd 413, found 413 | Followed similar procedure in Example 106 |
| 111 | 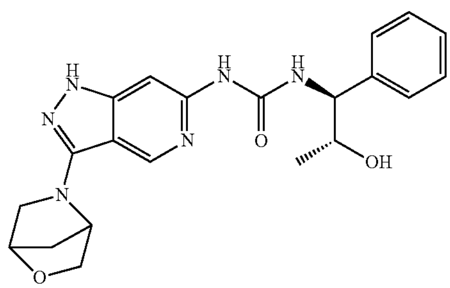 [SMILES: C[C@@H](O)[C@@H](NC(=O)Nc1cc2[nH]nc(N3CC4CC3CO4)c2cn1)c1ccccc1] | 1-[(1S,2R)-2-hydroxy-1-phenylpropyl]-3-[3-(2-oxa-5-azabicyclo[2.2.1]-hept-5-yl)-1H-pyrazolo[4,3-c]-pyridin-6-yl]urea | Calc'd 409, found 409 | Followed similar procedure in Example 106 |
| 112 | 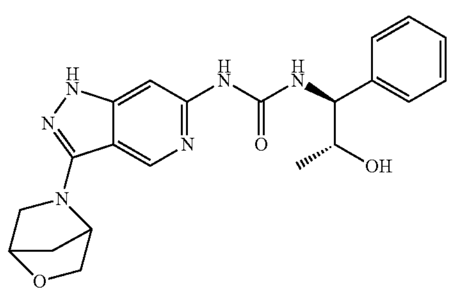 [SMILES: C[C@@H](O)[C@@H](NC(=O)Nc1cc2[nH]nc(N3CC4CC3CO4)c2cn1)c1ccccc1] | 1-[(1S,2R)-2-hydroxy-1-phenylpropyl]-3-[3-(2-oxa-5-azabicyclo[2.2.1]-hept-5-yl)-1H-pyrazolo[4,3-c]-pyridin-6-yl]urea | Calc'd 409, found 409 | Followed similar procedure in Example 106 |
| 113 | 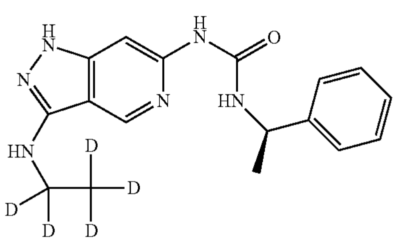 [SMILES: [2H]C([2H])([2H])C([2H])([2H])Nc1n[nH]c2cc(NC(=O)N[C@H](C)c3ccccc3)ncc12] | (R)-1-(3-((ethyl-D5)amino)-1H-pyrazolo[4,3-c]-pyridin-6-yl)-3-(1-phenylethyl)urea | Calc'd 330, found 330 | Scheme 1 |
| 114 | 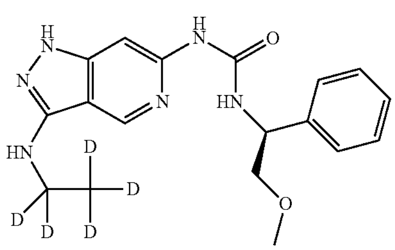 [SMILES: [2H]C([2H])([2H])C([2H])([2H])Nc1n[nH]c2cc(NC(=O)N[C@H](COC)c3ccccc3)ncc12] | (S)-1-(3-((ethyl-D5)amino-1H-pyrazolo[4,3-c]pyridin-6-yl)-3-(2-methoxy-1-phenylethyl)urea | Calc'd 360, found 360 | Scheme 1 |

-continued

| No. | Structure | IUPAC Name | Exact Mass [M + H]+ | Route Used |
|---|---|---|---|---|
| 115 | 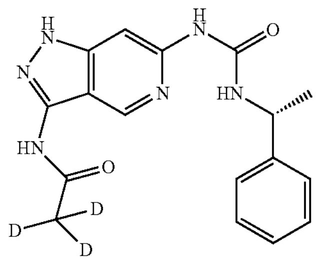 [SMILES: [2H]C([2H])([2H])C(=O)Nc1n[nH]c2cc(NC(=O)N[C@H](C)c3ccccc3)ncc12] | (R)-N-(6-(3-(1-phenylethyl)ureido)-1H-pyrazolo[4,3-c]pyridin-3-yl)(acetamide-D3) | Calc'd 342, found 342 | Scheme 14, Example 321 using acetyl chloride instead of chloroformate |
| 116 | 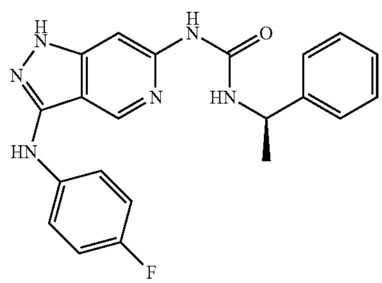 [SMILES: C[C@@H](NC(=O)Nc1cc2[nH]nc(Nc3ccc(F)cc3)c2cn1)c1ccccc1] | 1-{3-[(4-fluorophenyl)-amino]-1H-pyrazolo[4,3-c]pyridin-6-yl}-3-[(1R)-1-phenylethyl]urea | Calc'd 391, found 391 | Following a similar procedure in Example 121. |
| 117 | 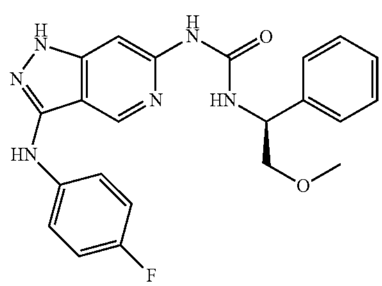 [SMILES: COC[C@@H](NC(=O)Nc1cc2[nH]nc(Nc3ccc(F)cc3)c2cn1)c1ccccc1] | 1-{3-[(4-fluorophenyl)-amino]-1H-pyrazolo[4,3-c]pyridin-6-yl}-3-[(1S)-2-methoxy-1-phenylethyl]urea | Calc'd 421, found 421 | Following a similar procedure in Example 121 |
| 118 | 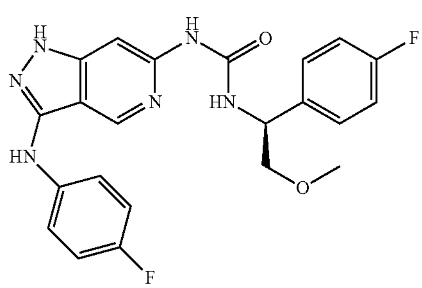 [SMILES: COC[C@@H](NC(=O)Nc1cc2[nH]nc(Nc3ccc(F)cc3)c2cn1)c1ccc(F)cc1] | 1-{3-[(4-fluorophenyl)-amino]-1H-pyrazolo[4,3-c]pyridin-6-yl}-3-[(1S)-1-(4-fluorophenyl)-2-methoxyethyl]urea | Calc'd 439, found 439 | Following a similar procedure in Example 121 |
| 119 | 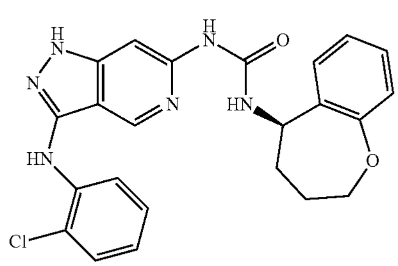 [SMILES: O=C(Nc1cc2[nH]nc(Nc3ccccc3Cl)c2cn1)N[C@@H]1CCCOc2ccccc21] | 1-{3-[(2-chlorophenyl)-amino]-1H-pyrazolo[4,3-c]pyridin-6-yl}-3-[(5R)-2,3,4,5-tetrahydro-1-benzoxepin-5-yl]urea | Calc'd 449, found 449 | Following a similar procedure in Example 121 |

| No. | Structure | IUPAC Name | Exact Mass [M + H]+ | Route Used |
|---|---|---|---|---|
| 120 | 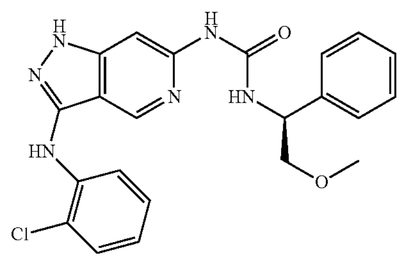 [SMILES: COC[C@@H](NC(=O)Nc1cc2[nH]nc(Nc3ccccc3Cl)c2cn1)c1ccccc1] | 1-{3-[(2-chlorophenyl)-amino]-1H-pyrazolo[4,3-c]pyridin-6-yl}-3-[(1S)-2-methoxy-1-phenylethyl]urea | Calc'd 437, found 437 | Following a similar procedure in Example 121 |
| 121 | 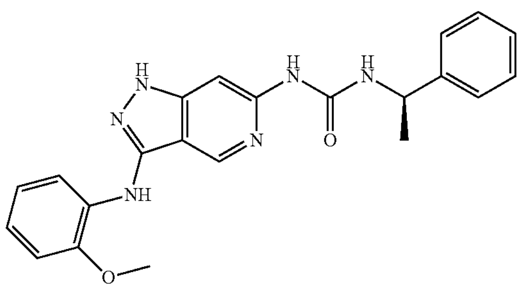 [SMILES: COc1ccccc1Nc1n[nH]c2cc(NC(=O)N[C@H](C)c3ccccc3)ncc12] | 1-{3-[(2-methoxyphenyl)-amino]-1H-pyrazolo[4,3-c]pyridin-6-yl}-3-[(1R)-1-phenylethyl]urea | Calc'd 403, found 403 | Example 121 |
| 122 | 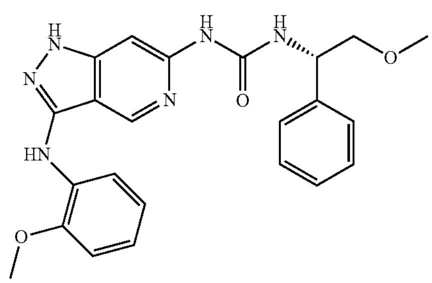 | 1-{3-[(2-methoxyphenyl)-amino]-1H-pyrazolo[4,3-c]pyridin-6-yl}-3-[(1S)-2-methoxy-1-phenylethyl]urea | Calc'd 433, found 433 | Following a similar procedure in Example 121 |
| 123 | 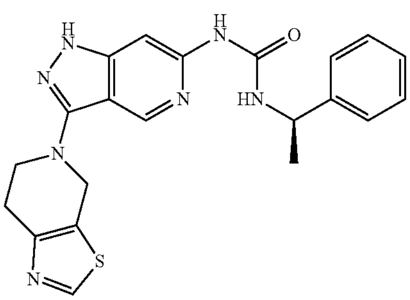 [SMILES: C[C@@H](NC(=O)Nc1cc2[nH]nc(N3CCc4ncsc4C3)c2cn1)c1ccccc1] | 1-[3-(6,7-dihydro[1,3]thiazolo[5,4-c]pyridin-5(4H)-yl)-1H-pyrazolo[4,3-c]pyridin-6-yl]-3-[(1R)-1-phenylethyl]urea | Calc'd 420, found 420 | Scheme 1, Example 1 |
| 124 | 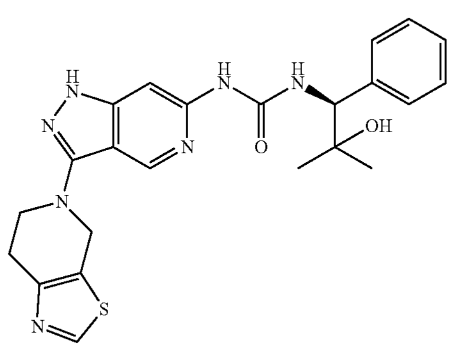 [SMILES: CC(C)(O)[C@@H](NC(=O)Nc1cc2[nH]nc(N3CCc4ncsc4C3)c2cn1)c1ccccc1] | 1-[3-(6,7-dihydro[1,3]thiazolo[5,4-c]pyridin-5(4H)-yl)-1H-pyrazolo[4,3-c]pyridin-6-yl]-3-[(1S)-2-hydroxy-2-methyl-1-phenylpropyl]urea | Calc'd 464, found 464 | Scheme 1, Example 1 |

-continued

| No. | Structure | IUPAC Name | Exact Mass [M + H]+ | Route Used |
|---|---|---|---|---|
| 125 | 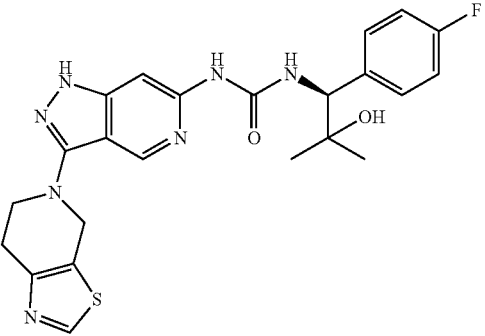 [SMILES: CC(C)(O)[C@@H](NC(=O)Nc1cc2[nH]nc(N3CCc4ncsc4C3)c2cn1)c1ccc(F)cc1] | 1-[3-(6,7-dihydro[1,3]thiazolo-[5,4-c]pyridin-5(4H)-yl)-1H-pyrazolo[4,3-c]pyridin-6-yl]-3-[(1S)-1-(4-fluorophenyl)-2-hydroxy-2-methylpropyl]urea | Calc'd 482, found 482 | Scheme 1, Example 1 |
| 126 | 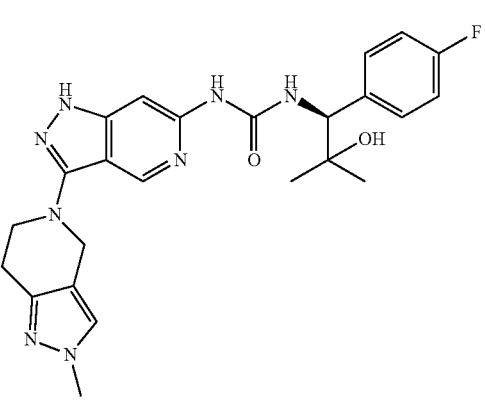 [SMILES: Cn1cc2c(n1)CCN(c1n[nH]c3cc(NC(=O)N[C@@H](c4ccc(F)cc4)C(C)(C)O)ncc13)C2] | 1-[(1S)-1-(4-fluorophenyl)-2-hydroxy-2-methylpropyl]-3-(2'-methyl-2',4',6',7'-tetrahydro-1H-3,5'-bipyrazolo[4,3-c]pyridin-6-yl)urea | Calc'd 479, found 479 | Scheme 1, Example 1 |
| 127 | 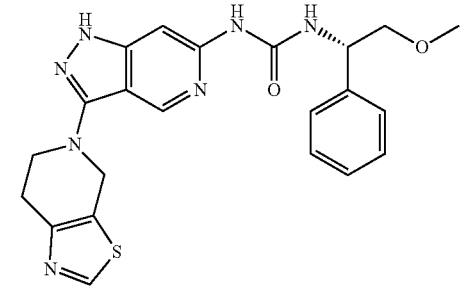 [SMILES: COC[C@@H](NC(=O)Nc1cc2[nH]nc(N3CCc4ncsc4C3)c2cn1)c1ccccc1] | 1-[3-(6,7-dihydro[1,3]-thiazolo[5,4-c]-pyridin-5(4H)-yl)-1H-pyrazolo[4,3-c]pyridin-6-yl]-3-[(1S)-2-methoxy-1-phenylethyl]urea | Calc'd 450, found 450 | Scheme 1, Example 1 |
| 128 | 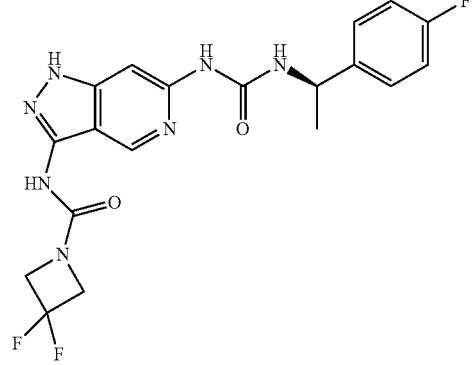 | 3,3-difluoro-N-[6-({[(1R)-1-(4-fluorophenyl)ethyl]carbamoyl}amino)-1H-pyrazolo[4,3-c]pyridin-3-yl]-azetidine-1-carboxamide | Calc'd 434, found 434 | Scheme 1, Example 1 with Intermediate 128A |

| No. | Structure | IUPAC Name | Exact Mass [M + H]+ | Route Used |
|---|---|---|---|---|
| 129 | 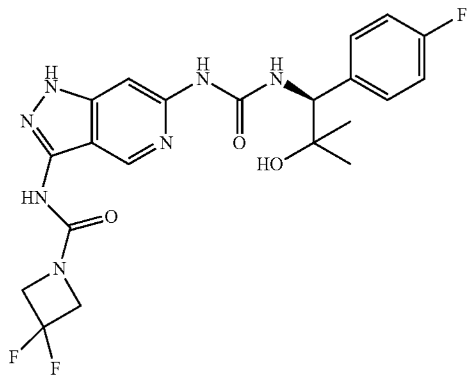 [SMILES: CC(C)(O)[C@@H](NC(=O)Nc1cc2[nH]nc(NC(=O)N3CC(F)(F)C3)c2cn1)c1ccc(F)cc1] | 3,3-difluoro-N-[6-({[(1S)-1-(4-fluorophenyl)-2-hydroxy-2-methylpropyl]-carbamoyl}amino)-1H-pyrazolo[4,3-c]pyridin-3-yl]-azetidine-1-carboxamide | Calc'd 478, found 478 | Following a similar procedure in Example 128 |
| 130 | 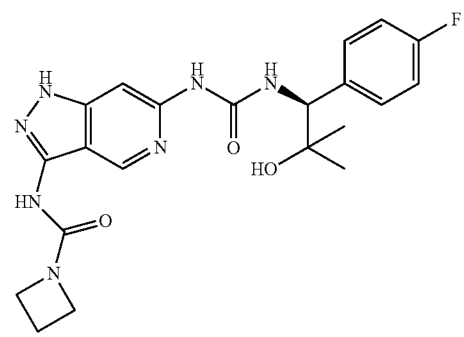 [SMILES: CC(C)(O)[C@@H](NC(=O)Nc1cc2[nH]nc(NC(=O)N3CCC3)c2cn1)c1ccc(F)cc1] | N-[6-({[(1S)-1-(4-fluorophenyl)-2-hydroxy-2-methylpropyl]-carbamoyl}amino)-1H-pyrazolo[4,3-c]pyridin-3-yl]-azetidine-1-carboxamide | Calc'd 442, found 442 | Following a similar procedure in Example 128 |
| 131 | 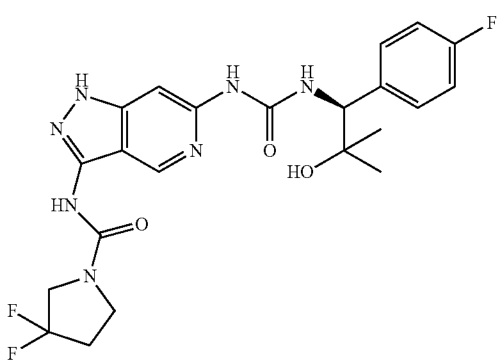 [SMILES: CC(C)(O)[C@@H](NC(=O)Nc1cc2[nH]nc(NC(=O)N3CCC(F)(F)C3)c2cn1)c1ccc(F)cc1] | 3,3-difluoro-N-[6-({[(1S)-1-(4-fluorophenyl)-2-hydroxy-2-methylpropyl]-carbamoyl}amino)-1H-pyrazolo[4,3-c]pyridin-3-yl]-pyrrolidine-1-carboxamide | Calc'd 492, found 492 | Following a similar procedure in Example 128 |
| 132 | 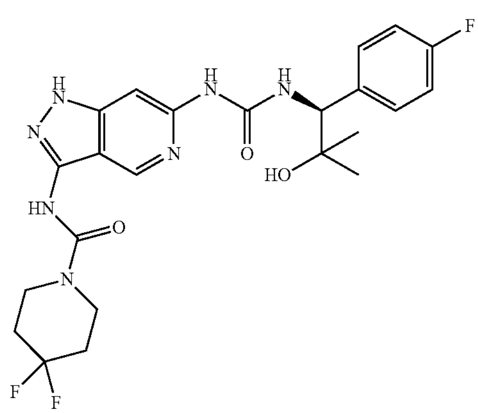 [SMILES: CC(C)(O)[C@@H](NC(=O)Nc1cc2[nH]nc(NC(=O)N3CCC(F)(F)CC3)c2cn1)c1ccc(F)cc1] | 4,4-difluoro-N-[6-({[(1S)-1-(4-fluorophenyl)-2-hydroxy-2-methylpropyl]-carbamoyl}amino)-1H-pyrazolo[4,3-c]pyridin-3-yl]-piperidine-1-carboxamide | Calc'd 506, found 506 | Following a similar procedure in Example 128 |

-continued

| No. | Structure | IUPAC Name | Exact Mass [M + H]+ | Route Used |
|---|---|---|---|---|
| 133 | 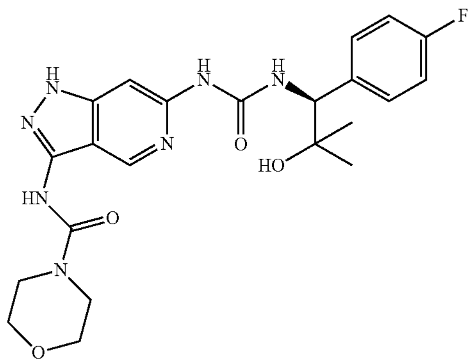 [SMILES: CC(C)(O)[C@@H](NC(=O)Nc1cc2[nH]nc(NC(=O)N3CCOCC3)c2cn1)c1ccc(F)cc1] | N-[6-({[(1S)-1-(4-fluorophenyl)-2-hydroxy-2-methylpropyl]-carbamoyl}amino)-1H-pyrazolo[4,3-c]pyridin-3-yl]-morpholine-4-carboxamide | Calc'd 472, found 472 | Following a similar procedure in Example 128 |
| 134 | 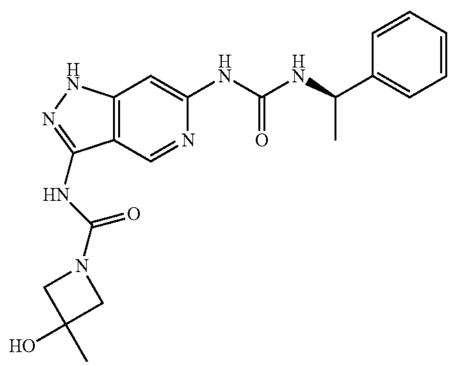 [SMILES: C[C@@H](NC(=O)Nc1cc2[nH]nc(NC(=O)N3CC(C)(O)C3)c2cn1)c1ccccc1] | 3-hydroxy-3-methyl-N-[6-({[(1R)-1-phenylethyl]-carbamoyl}-amino)-1H-pyrazolo[4,3-c]pyridin-3-yl]-azetidine-1-carboxamide | Calc'd 410, found 410 | Following a similar procedure in Example 128 |
| 135 | 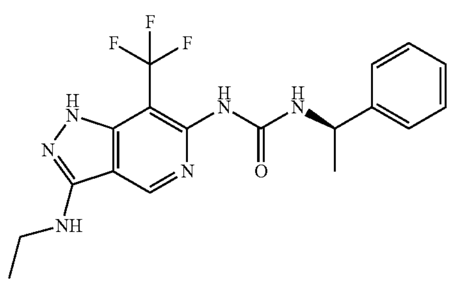 [SMILES: CCNc1n[nH]c2c(C(F)(F)F)c(NC(=O)N[C@H](C)c3ccccc3)ncc12] | 1-[3-(ethylamino)-7-(trifluoromethyl)-1H-pyrazolo[4,3-c]pyridin-6-yl]-3-[(1R)-1-phenylethyl]urea | Calc'd 393, found 393 | Example 135 |
| 136 | 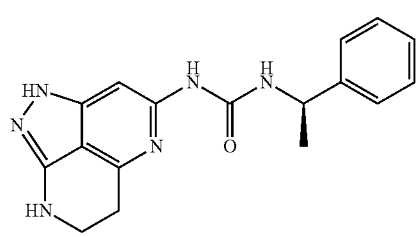 [SMILES: C[C@@H](NC(=O)Nc1cc2[nH]nc3c2c(n1)CCN3)c1ccccc1] | 1-[(1R)-1-phenylethyl]-3-(1,3,4,5-tetrahydro-pyrazolo[3,4,5-de]-[1,6]-naphthyridin-7-yl)-urea | Calc'd 323, found 323 | Example 136 |
| 137 | 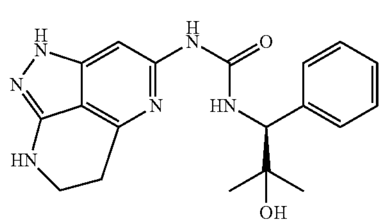 [SMILES: CC(C)(O)[C@@H](NC(=O)Nc1cc2[nH]nc3c2c(n1)CCN3)c1ccccc1] | 1-[(1S)-2-hydroxy-2-methyl-1-phenylpropyl]-3-(1,3,4,5-tetrahydro-pyrazolo[3,4,5-de]-[1,6]-naphthyridin-7-yl)urea | Calc'd 367, found 367 | Example 137 |

| No. | Structure | IUPAC Name | Exact Mass [M + H]+ | Route Used |
|---|---|---|---|---|
| 138 | 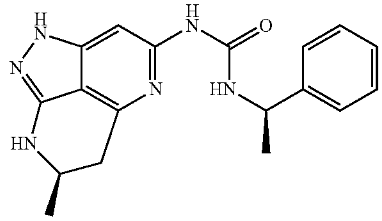 [SMILES: C[C@@H]1Cc2nc(NC(=O)N[C@H](C)c3ccccc3)cc3[nH]nc(c23)N1] | 1-[(4R)-4-methyl-1,3,4,5-tetrahydropyrazolo[3,4,5-de][1,6]naphthyridin-7-yl]-3-[(1R)-1-phenylethyl]urea | Calc'd 337, found 337 | Example 138 |
| 139 | 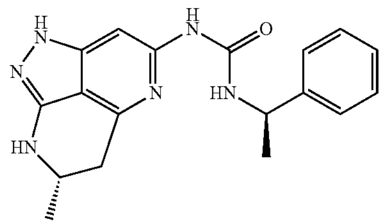 [SMILES: C[C@H]1Cc2nc(NC(=O)N[C@H](C)c3ccccc3)cc3[nH]nc(c23)N1] | 1-[(4S)-4-methyl-1,3,4,5-tetrahydropyrazolo-[3,4,5-de][1,6]-naphthyridin-7-yl]-3-[(1R)-1-phenylethyl]urea | Calc'd 337, found 337 | Example 139 |
| 140 | 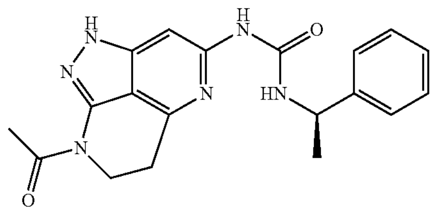 [SMILES: CC(=O)N1CCc2nc(NC(=O)N[C@H](C)c3ccccc3)cc3[nH]nc1c23] | 1-(3-acetyl-1,3,4,5-tetrahydropyrazolo-[3,4,5-de][1,6]-naphthyridin-7-yl)-3-[(1R)-1-phenylethyl]urea | Calc'd 365, found 365 | Example 140 |
| 141 | 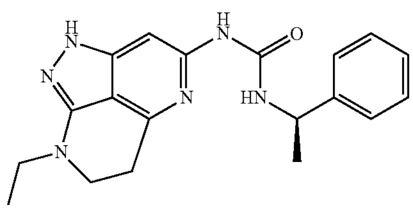 [SMILES: CCN1CCc2nc(NC(=O)N[C@H](C)c3ccccc3)cc3[nH]nc1c23] | 1-(3-ethyl-1,3,4,5-tetrahydropyrazolo-[3,4,5-de][1,6]-naphthyridin-7-yl)-3-[(1R)-1-phenylethyl]urea | Calc'd 351.0, found 351 | Example 141 |
| 142 | 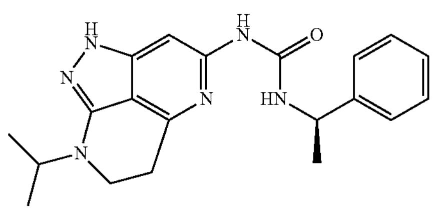 [SMILES: CC(C)N1CCc2nc(NC(=O)N[C@H](C)c3ccccc3)cc3[nH]nc1c23] | 1-[3-(1-methylethyl)-1,3,4,5-tetrahydropyrazolo-[3,4,5-de][1,6]-naphthyridin-7-yl]-3-[(1R)-1-phenylethyl]urea | Calc'd 365, found 365 | Example 142 |
| 143 | 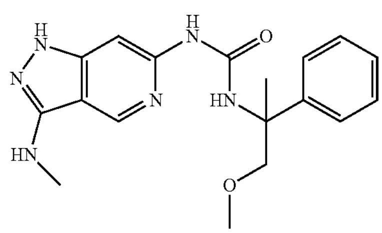 [SMILES: CNc1n[nH]c2cc(NC(=O)NC(C)(COC)c3ccccc3)ncc12] | 1-(2-methoxy-1-methyl-1-phenylethyl)-3-[3-(methylamino)-1H-pyrazolo[4,3-c]-pyridin-6-yl]urea | Calc'd 355, found 355 | Scheme 1 |
| 144 | 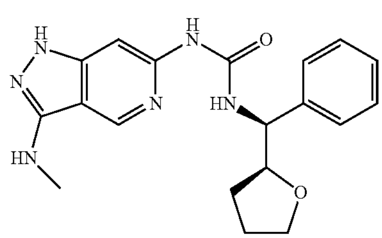 [SMILES: CNc1n[nH]c2cc(NC(=O)N[C@@H](c3ccccc3)[C@@H]3CCCO3)ncc12] | 1-[3-(methylamino)-1H-pyrazolo[4,3-c]-pyridin-6-yl]-3-{(S)-phenyl[(2S)-tetrahydrofuran-2-yl]methyl}urea | Calc'd 367, found 367 | Example 144 |

| No. | Structure | IUPAC Name | Exact Mass [M + H]+ | Route Used |
|---|---|---|---|---|
| 145 | 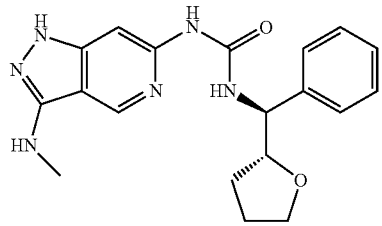 [SMILES: CNc1n[nH]c2cc(NC(=O)N[C@@H](c3ccccc3)[C@H]3CCCO3)ncc12] | 1-[3-(methyl-amino)-1H-pyrazolo[4,3-c]-pyridin-6-yl]-3-{(S)-phenyl[(2R)-tetrahydrofuran-2-yl]methyl}urea | Calc'd 367, found 367 | Example 144 |
| 146 | 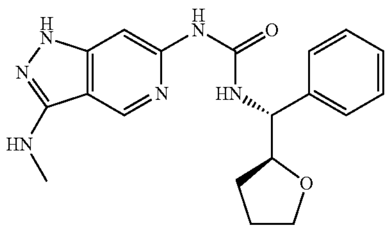 [SMILES: CNc1n[nH]c2cc(NC(=O)N[C@H](c3ccccc3)[C@@H]3CCCO3)ncc12] | 1-[3-(methyl-amino)-1H-pyrazolo[4,3-c]pyridin-6-yl]-3-{(R)-phenyl[(2S)-tetrahydrofuran-2-yl]methyl}urea | Calc'd 367, found 367 | Example 144 |
| 147 | 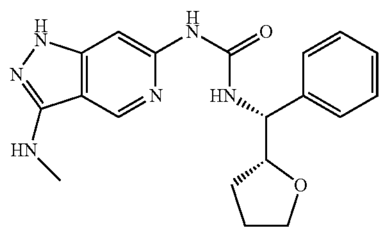 [SMILES: CNc1n[nH]c2cc(NC(=O)N[C@H](c3ccccc3)[C@H]3CCCO3)ncc12] | 1-[3-(methyl-amino)-1H-pyrazolo[4,3-c]-pyridin-6-yl]-3-{(R)-phenyl[(2R)-tetrahydrofuran-2-yl]methyl}urea | Calc'd 367, found 367 | Example 144 |
| 148 | 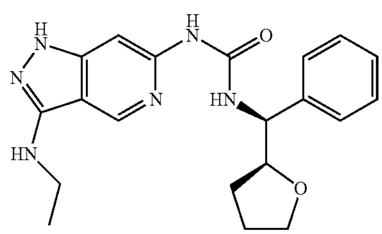 [SMILES: CCNc1n[nH]c2cc(NC(=O)N[C@@H](c3ccccc3)[C@@H]3CCCO3)ncc12] | 1-[3-(ethylamino)-1H-pyrazolo[4,3-c]pyridin-6-yl]-3-{(S)-phenyl[(2S)-tetrahydrofuran-2-yl]methyl}urea | Calc'd 381, found 381 | Scheme 1 With intermediate 148A |
| 149 | 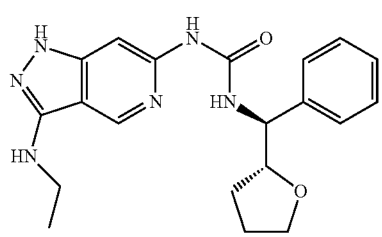 [SMILES: CCNc1n[nH]c2cc(NC(=O)N[C@@H](c3ccccc3)[C@H]3CCCO3)ncc12] | 1-[3-(ethylamino)-1H-pyrazolo[4,3-c]pyridin-6-yl]-3-{(S)-phenyl[(2R)-tetrahydrofuran-2-yl]methyl}urea | Calc'd 381, found 381 | Scheme 1 With intermediate 149A |
| 150 | 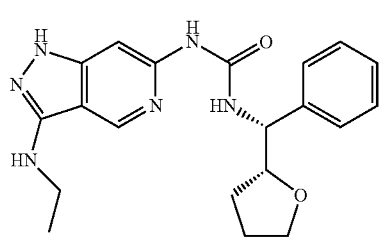 [SMILES: CCNc1n[nH]c2cc(NC(=O)N[C@H](c3ccccc3)[C@H]3CCCO3)ncc12] | 1-[3-(ethylamino)-1H-pyrazolo[4,3-c]pyridin-6-yl]-3-{(R)-phenyl[(2R)-tetrahydrofuran-2-yl]methyl}urea | Calc'd 381, found 381 | Scheme 1 With intermediate 150A |

-continued

| No. | Structure | IUPAC Name | Exact Mass [M + H]+ | Route Used |
|---|---|---|---|---|
| 151 | 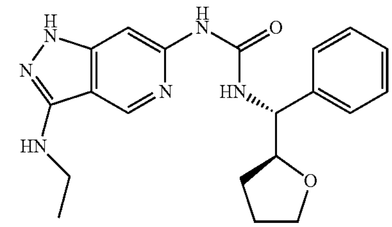 [SMILES: CCNc1n[nH]c2cc(NC(=O)N[C@H](c3ccccc3)[C@@H]3CCCO3)ncc12] | 1-[3-(ethylamino)-1H-pyrazolo[4,3-c]pyridin-6-yl]-3-{(R)-phenyl[(2S)-tetrahydrofuran-2-yl]methyl}urea | Calc'd 381, found 381 | Scheme 1 With intermediate 151A |
| 152 | 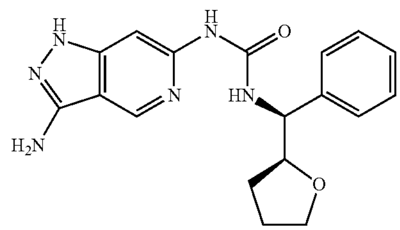 [SMILES: Nc1n[nH]c2cc(NC(=O)N[C@@H](c3ccccc3)[C@@H]3CCCO3)ncc12] | 1-(3-amino-1H-pyrazolo[4,3-c]pyridin-6-yl)-3-{(S)-phenyl[(2S)-tetrahydrofuran-2-yl]methyl}urea | Calc'd 353, found 353 | Scheme 2 With intermediate 148A |
| 153 | 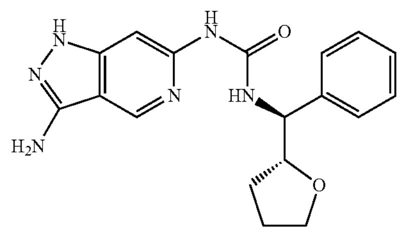 [SMILES: Nc1n[nH]c2cc(NC(=O)N[C@@H](c3ccccc3)[C@H]3CCCO3)ncc12] | 1-(3-amino-1H-pyrazolo[4,3-c]pyridin-6-yl)-3-{(S)-phenyl[(2R)-tetrahydrofuran-2-yl]methyl}urea | Calc'd 353, found 353 | Scheme 2 With intermediate 149A |
| 154 | 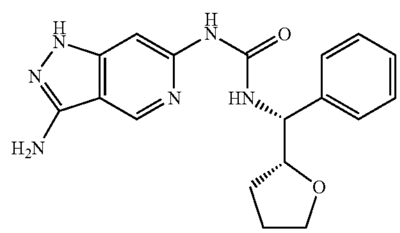 [SMILES: Nc1n[nH]c2cc(NC(=O)N[C@H](c3ccccc3)[C@H]3CCCO3)ncc12] | 1-(3-amino-1H-pyrazolo[4,3-c]pyridin-6-yl)-3-{(R)-phenyl[(2R)-tetrahydrofuran-2-yl]methyl}urea | Calc'd 353, found 353 | Scheme 2 With intermediate 150A |
| 155 | 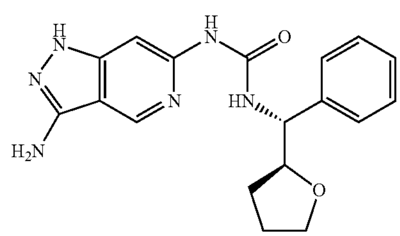 [SMILES: Nc1n[nH]c2cc(NC(=O)N[C@H](c3ccccc3)[C@@H]3CCCO3)ncc12] | 1-(3-amino-1H-pyrazolo[4,3-c]pyridin-6-yl)-3-{(R)-phenyl[(2S)-tetrahydrofuran-2-yl]methyl}urea | Calc'd 353, found 353 | Scheme 2 With intermediate 151A |
| 156 | 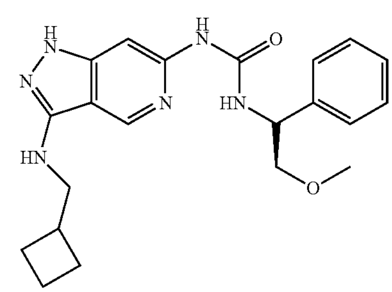 | 1-{3-[(cyclobutylmethyl)amino]-1H-pyrazolo[4,3-c]-pyridin-6-yl}-3-[(1S)-2-methoxy-1-phenylethyl]urea | Calc'd 395, found 395 | Scheme 8 Method C/ Example 316 |

| No. | Structure | IUPAC Name | Exact Mass [M + H]+ | Route Used |
|---|---|---|---|---|
| 157 | 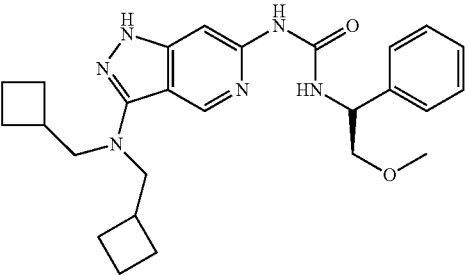 | 1-{3-[bis(cyclobutyl-methyl)amino]-1H-pyrazolo[4,3-c]pyridin-6-yl}-3-[(1S)-2-methoxy-1-phenylethyl]urea | Calc'd 463, found 463 | Scheme 8, Method C/ example 316 |
| 158 | 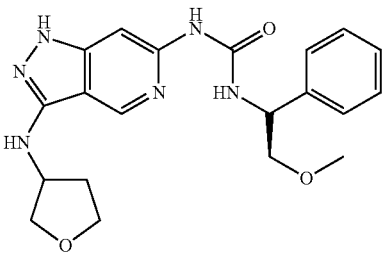 | 1-[(1S)-2-methoxy-1-phenylethyl]-3-[3-(tetrahydro-furan-3-ylamino)-1H-pyrazolo[4,3-c]pyridin-6-yl]urea | Calc'd 397, found 397 | Scheme 8, Method C/ example 316 |
| 159 | 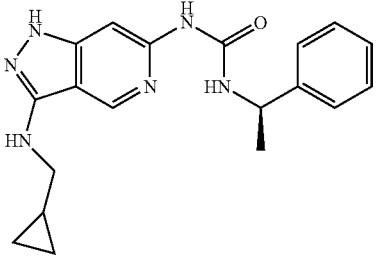 [SMILES: C[C@@H](NC(=O)Nc1cc2[nH]nc(NCC3CC3)c2cn1)c1ccccc1] | 1-{3-[(cyclopropyl-methyl)amino]-1H-pyrazolo[4,3-c]-pyridin-6-yl}-3-[(1R)-1-phenylethyl]urea | Calc'd 351, found 351 | Scheme 8, Method B/ example 316 |
| 160 | 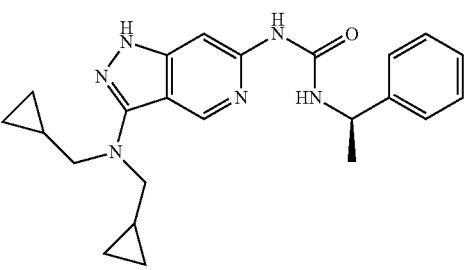 [SMILES: C[C@@H](NC(=O)Nc1cc2[nH]nc(N(CC3CC3)CC3CC3)c2cn1)c1ccccc1] | 1-{3-[bis(cyclopropyl-methyl)amino]-1H-pyrazolo[4,3-c]-pyridin-6-yl}-3-[(1R)-1-phenylethyl]urea | Calc'd 405, found 405 | Scheme 8, Method B/ example 316 |
| 161 | 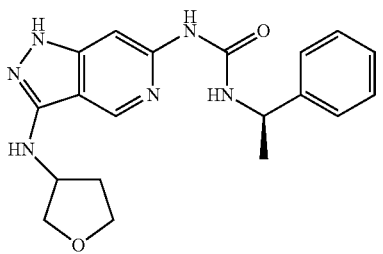 [SMILES: C[C@@H](NC(=O)Nc1cc2[nH]nc(NC3CCOC3)c2cn1)c1ccccc1] | 1-[(1R)-1-phenylethyl]-3-[3-(tetrahydrofuran-3-ylamino)-1H-pyrazolo[4,3-c]pyridin-6-yl]urea | Calc'd 367, found 367 | Scheme 8, Method A/ example 316 |

-continued

| No. | Structure | IUPAC Name | Exact Mass [M + H]+ | Route Used |
|---|---|---|---|---|
| 162 | 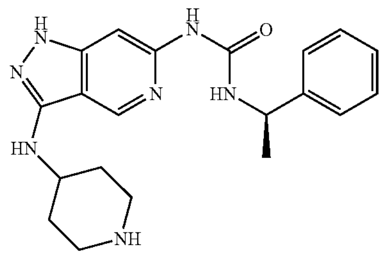 [SMILES: C[C@@H](NC(=O)Nc1cc2[nH]nc(NC3CCNCC3)c2cn1)c1ccccc1] | 1-[(1R)-1-phenylethyl]-3-[3-(piperidin-4-ylamino)-1H-pyrazolo[4,3-c]-pyridin-6-yl]urea | Calc'd 380, found 380 | Scheme 8, Method A/ example 316 |
| 163 | 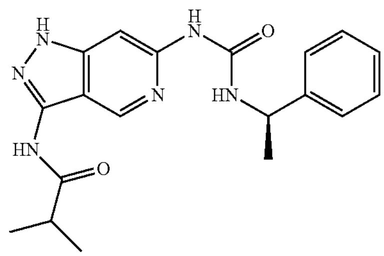 [SMILES: CC(C)C(=O)Nc1n[nH]c2cc(NC(=O)N[C@H](C)c3ccccc3)ncc12] | 2-methyl-N-[6-({[(1R)-1-phenylethyl]-carbamoyl}amino)-1H-pypyrazolo[4,3-c]-pyridin-3-yl]propanamide | Calc'd 367, found 367 | Scheme 10, Method A/ Example 47 |
| 164 | 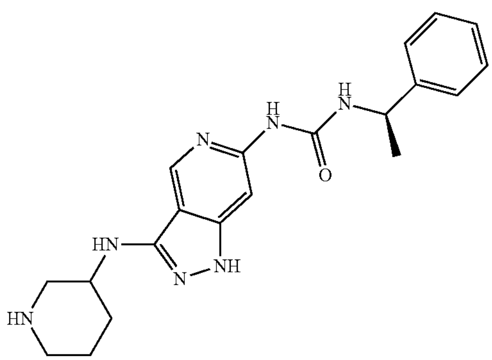 [SMILES: C[C@@H](NC(=O)Nc1cc2[nH]nc(NC3CCCNC3)c2cn1)c1ccccc1] | 1-[(1R)-1-phenylethyl]-3-[3-(piperidin-3-ylamino)-1H-pyrazolo[4,3-c]-pyridin-6-yl]urea | Calc'd 380, found 380 | Scheme 8, Method A/ example 316 |
| 165 | 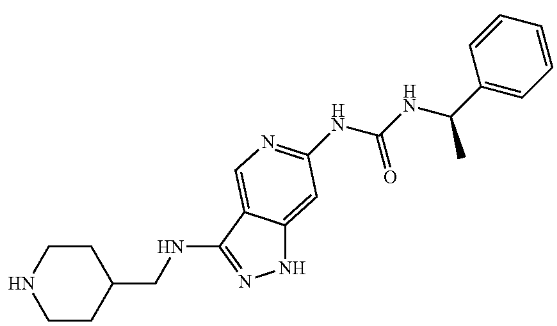 [SMILES: C[C@@H](NC(=O)Nc1cc2[nH]nc(NCC3CCNCC3)c2cn1)c1ccccc1] | 1-[(1R)-1-phenylethyl]-3-{3-[(piperidin-4-ylmethyl)amino]-1H-pyrazolo[4,3-c]pyridin-6-yl}urea | Calc'd 394, found 394 | Scheme 8, Method A/ example 316 |
| 166 | 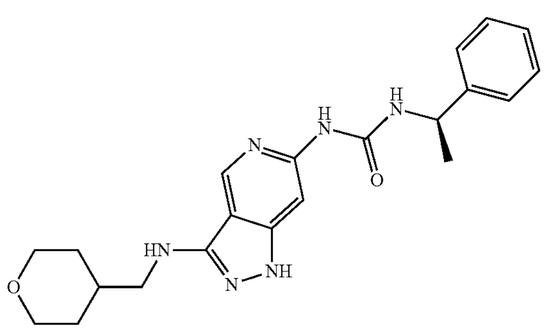 [SMILES: C[C@@H](NC(=O)Nc1cc2[nH]nc(NCC3CCOCC3)c2cn1)c1ccccc1] | 1-[(1R)-1-phenylethyl]-3-{3-[(tetrahydro-2H-pyran-4-yl-methyl)amino]-1H-pyrazolo[4,3-c]pyridin-6-yl}urea | Calc'd 395, found 395 | Scheme 8, Method A/ example 316 |

-continued

| No. | Structure | IUPAC Name | Exact Mass [M + H]+ | Route Used |
|---|---|---|---|---|
| 167 | 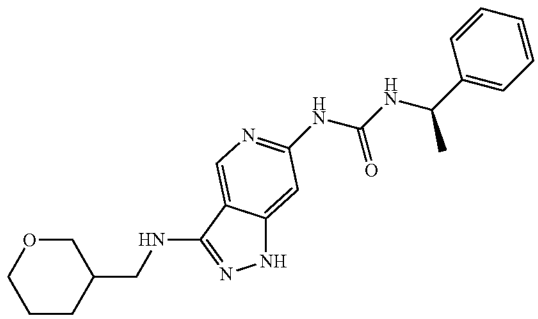 [SMILES: C[C@@H](NC(=O)Nc1cc2[nH]nc(NCC3CCCOC3)c2cn1)c1ccccc1] | 1-[(1R)-1-phenylethyl]-3-{3-[(tetrahydro-2H-pyran-3-yl-methyl)amino]-1H-pyrazolo[4,3-c]pyridin-6-yl}urea | Calc'd 395, found 395 | Scheme 8, Method A/ example 316 |
| 168 | 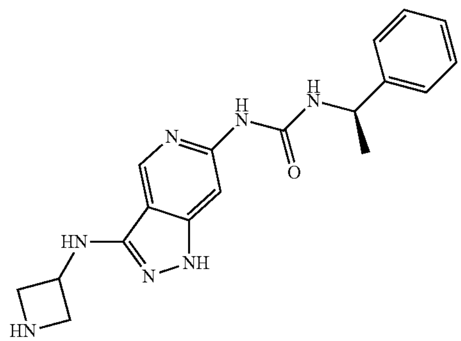 [SMILES: C[C@@H](NC(=O)Nc1cc2[nH]nc(NC3CNC3)c2cn1)c1ccccc1] | 1-[3-(azetidin-3-ylamino)-1H-pyrazolo[4,3-c]-pyridin-6-yl]-3-[(1R)-1-phenylethyl]urea | Calc'd 352, found 352 | Scheme 8, Method A/ example 316 |
| 169 | 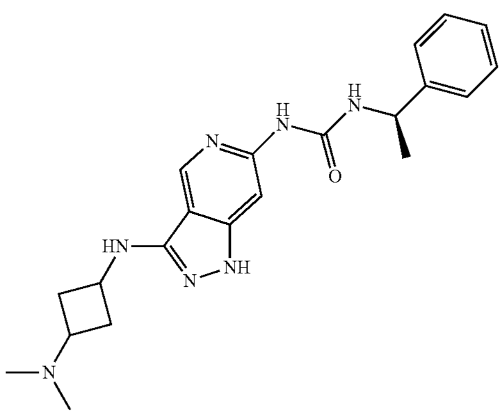 [SMILES: C[C@@H](NC(=O)Nc1cc2[nH]nc(NC3CC(N(C)C)C3)c2cn1)c1ccccc1] | 1-(3-{[3-(dimethylamino)-cyclobutyl]amino}-1H-pyrazolo[4,3-c]pyridin-6-yl)-3-[(1R)-1-phenylethyl]urea | Calc'd 394, found 394 | Scheme 8, Method A/ example 316 |
| 170 | 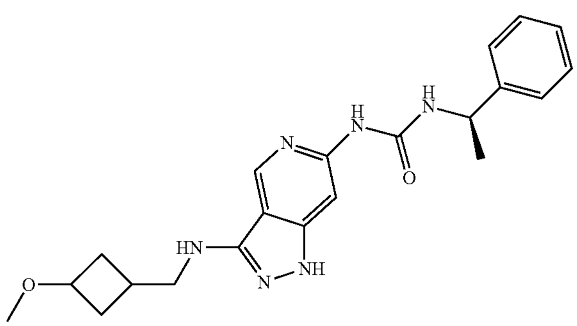 [SMILES: COC1CC(CNc2n[nH]c3cc(NC(=O)N[C@H](C)c4ccccc4)ncc23)C1] | 1-(3-{[(3-methoxy-cyclobutyl)methyl]amino}-1H-pyrazolo[4,3-c]-pyridin-6-yl)-3-[(1R)-1-phenylethyl]urea | Calc'd 395, found 395 | Scheme 8, Method A/ example 316 |

| No. | Structure | IUPAC Name | Exact Mass [M + H]⁺ | Route Used |
|---|---|---|---|---|
| 171 | 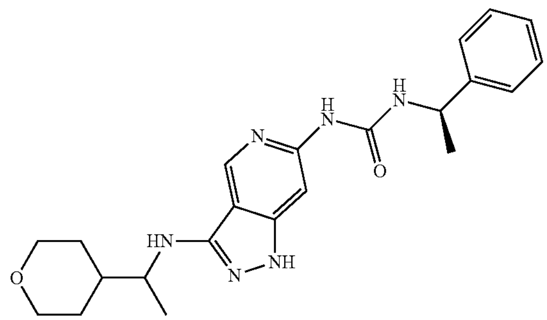 [SMILES: CC(Nc1n[nH]c2cc(NC(=O)N[C@H](C)c3ccccc3)ncc12)C1CCOCC1] | 1-[(1R)-1-phenylethyl]-3-(3-{[1-(tetrahydro-2H-pyran-4-yl)-ethyl]amino}-1H-pyrazolo[4,3-c]-pyridin-6-yl)urea | Calc'd 409, found 409 | Scheme 8, Method A/ example 316 |
| 172 | 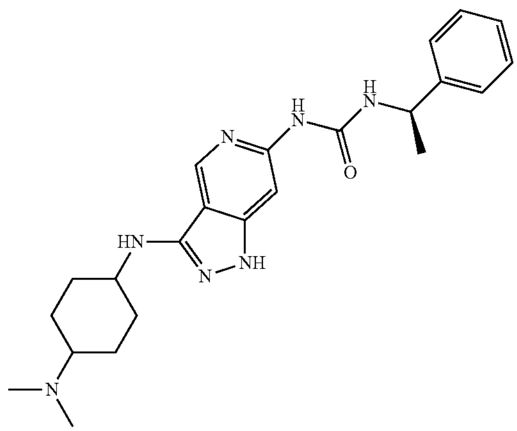 [SMILES: C[C@@H](NC(=O)Nc1cc2[nH]nc(NC3CCC(N(C)C)CC3)c2cn1)c1ccccc1] | 1-(3-{[4-(dimethylamino)-cyclohexyl]amino}-1H-pyrazolo[4,3-c]pyridin-6-yl)-3-[(1R)-1-phenylethyl]urea | Calc'd 422, found 422 | Scheme 8, Method A/ example 316 |
| 173 | 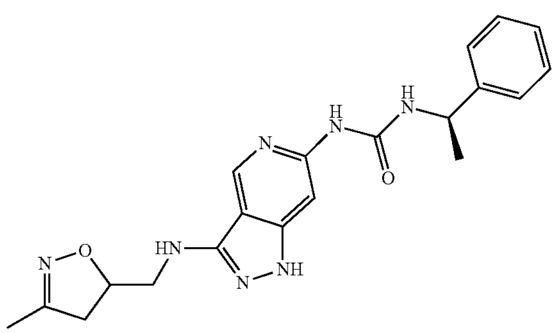 [SMILES: CC1=NOC(CNc2n[nH]c3cc(NC(=O)N[C@H](C)c4ccccc4)ncc23)C1] | 1-(3-{[(3-methyl-4,5-dihydro-isoxazol-5-yl)-methyl]amino}-1H-pyrazolo[4,3-c]-pyridin-6-yl)-3-[(1R)-1-phenylethyl]urea | Calc'd 394, found 394 | Scheme 8, Method A/ example 316 |
| 174 | 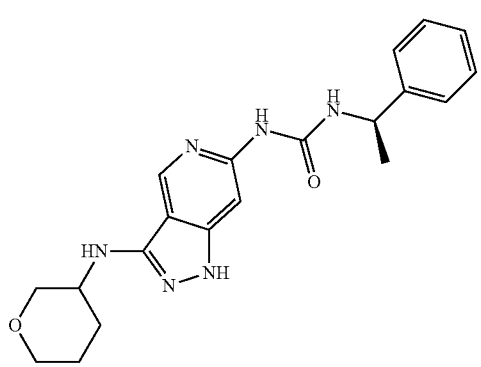 [SMILES: C[C@@H](NC(=O)Nc1cc2[nH]nc(NC3CCCOC3)c2cn1)c1ccccc1] | 1-[(1R)-1-phenylethyl]-3-[3-(tetrahydro-2H-pyran-3-ylamino)-1H-pyrazolo[4,3-c]pyridin-6-yl]urea | Calc'd 381, found 381 | Scheme 8, Method A/ example 316 |

| No. | Structure | IUPAC Name | Exact Mass [M + H]+ | Route Used |
|---|---|---|---|---|
| 175 | 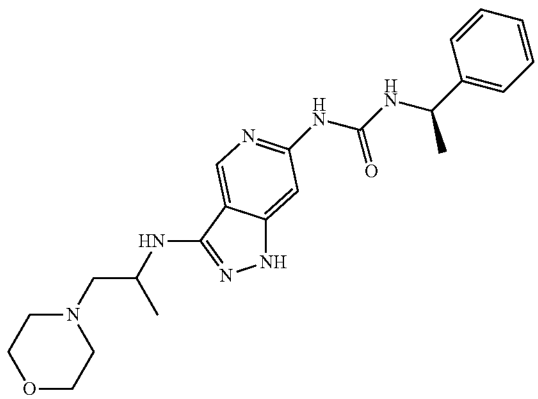 [SMILES: CC(CN1CCOCC1)Nc1n[nH]c2cc(NC(=O)N[C@H](C)c3ccccc3)ncc12] | 1-{3-[(1-methyl-2-morpholin-4-ylethyl)amino]-1H-pyrazolo[4,3-c]pyridin-6-yl}-3-[(1R)-1-phenylethyl]urea | Calc'd 424, found 424 | Scheme 8, Method A/ example 316 |
| 176 | 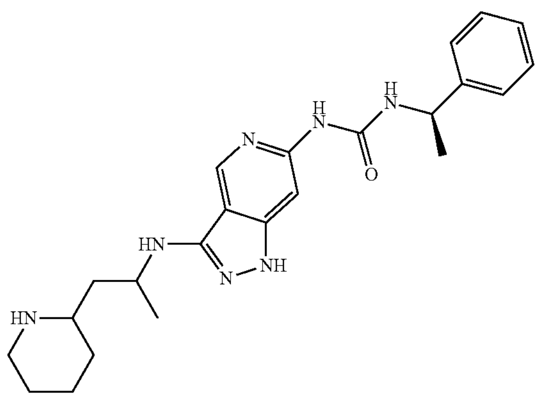 [SMILES: CC(CC1CCCCN1)Nc1n[nH]c2cc(NC(=O)N[C@H](C)c3ccccc3)ncc12] | 1-{3-[(1-methyl-2-piperidin-2-ylethyl)amino]-1H-pyrazolo[4,3-c]pyridin-6-yl}-3-[(1R)-1-phenylethyl]urea | Calc'd 422, found 422 | Scheme 8, Method A/ example 316 |
| 177 | 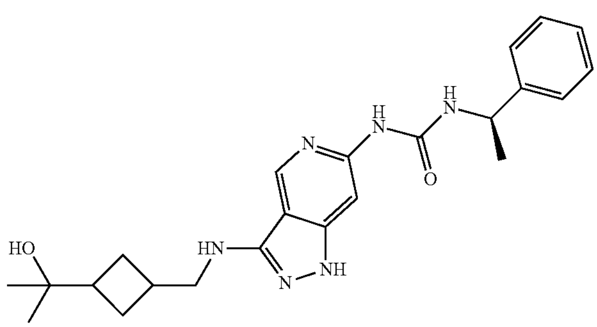 [SMILES: C[C@@H](NC(=O)Nc1cc2[nH]nc(NCC3CC(C(C)(C)O)C3)c2cn1)c1ccccc1] | 1-[3-({[3-(1-hydroxy-1-methyl-ethyl)cyclobutyl]-methyl}amino)-1H-pyrazolo[4,3-c]pyridin-6-yl]-3-[(1R)-1-phenylethyl]urea | Calc'd 423, found 423 | Scheme 8, Method A/ example 316 |
| 178 | 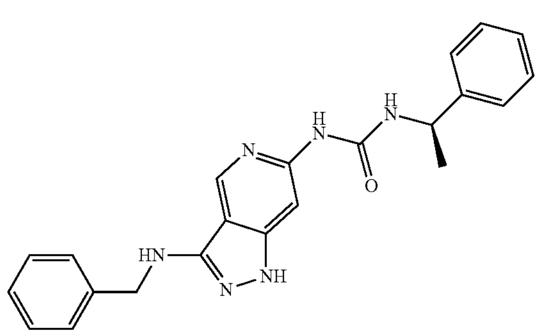 | 1-[3-(benzyl-amino)-1H-pyrazolo[4,3-c]-pyridin-6-yl]-3-1-[(1R)-1-phenylethyl]urea | Calc'd 387, found 387 | Scheme 8, Method A/ example 316 |

-continued

| No. | Structure | IUPAC Name | Exact Mass [M + H]+ | Route Used |
|---|---|---|---|---|
| 179 | 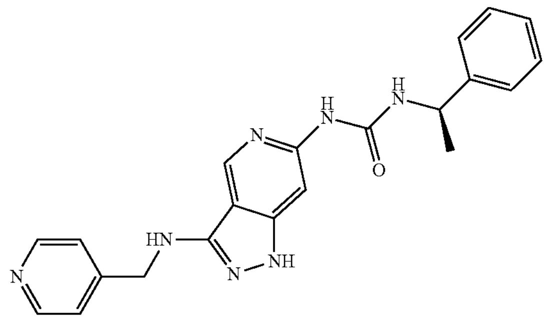 [SMILES: C[C@@H](NC(=O)Nc1cc2[nH]nc(NCc3ccncc3)c2cn1)c1ccccc1] | 1-[(1R)-1-phenylethyl]-3-{3-[(pyridin-4-yl-methyl)amino]-1H-pyrazolo[4,3-c]-pyridin-6-yl}urea | Calc'd 388, found 388 | Scheme 8, Method A/ example 316 |
| 180 | 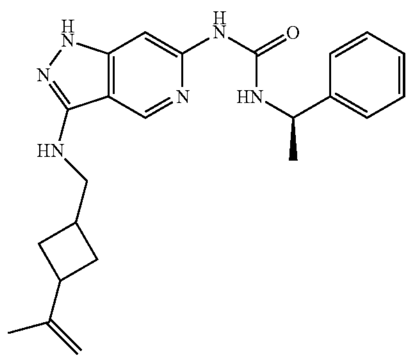 [SMILES: C=C(C)C1CC(CNc2n[nH]c3cc(NC(=O)N[C@H](C)c4ccccc4)ncc23)C1] | 1-[3-({[3-(1-methylethenyl)-cyclobutyl]methyl}amino)-1H-pyrazolo[4,3-c]-pyridin-6-yl]-3-[(1R)-1-phenylethyl]urea | Calc'd 405, found 405 | Scheme 8, Method A/ example 316 |
| 181 | 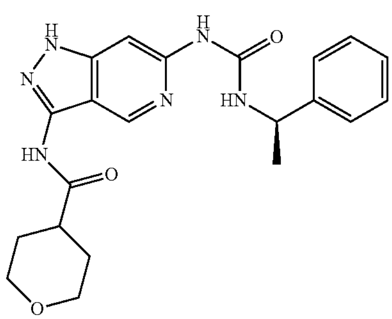 [SMILES: C[C@@H](NC(=O)Nc1cc2[nH]nc(NC(=O)C3CCOCC3)c2cn1)c1ccccc1] | N-[6-({[(1R)-1-phenylethyl]-carbamoyl}amino)-1H-pyrazolo[4,3-c]pyridin-3-yl]-tetrahydro-2H-pyran-4-carboxamide | Calc'd 409, found 409 | Scheme 10, Method B/ Example 318 |
| 182 | 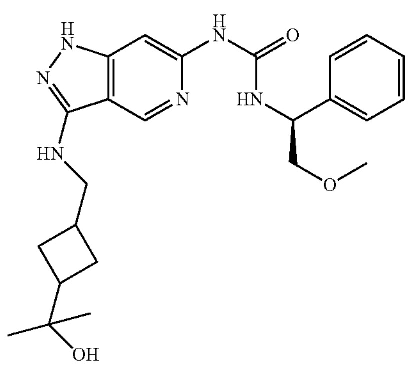 [SMILES: COC[C@@H](NC(=O)Nc1cc2[nH]nc(NCC3CC(C(C)(C)O)C3)c2cn1)c1ccccc1] | 1-[3-({[3-(1-hydroxy-1-methylethyl)-cyclobutyl]methyl}amino)-1H-pyrazolo[4,3-c]pyridin-6-yl]-3-[(1S)-2-methoxy-1-phenylethyl]urea | Calc'd 453, found 453 | Scheme 8, Method D/ example 316 |

-continued

| No. | Structure | IUPAC Name | Exact Mass [M + H]⁺ | Route Used |
|---|---|---|---|---|
| 183 | 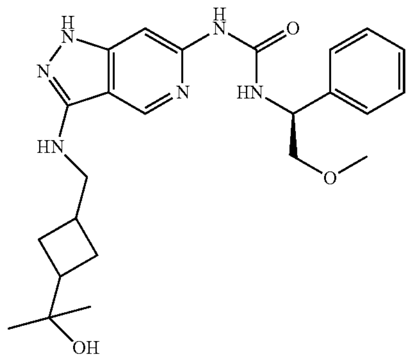 [SMILES: COC[C@@H](NC(=O)Nc1cc2[nH]nc(NCC3CC(C(C)(C)O)C3)c2cn1)c1ccccc1] | 1-[3-({[3-(1-hydroxy-1-methylethyl)-cyclobutyl]methyl}amino)-1H-pyrazolo[4,3-c]pyridin-6-yl]-3-[(1S)-2-methoxy-1-phenylethyl]urea | Calc'd 453, found 453 | Scheme 8, Method D/ example 316 |
| 184 | 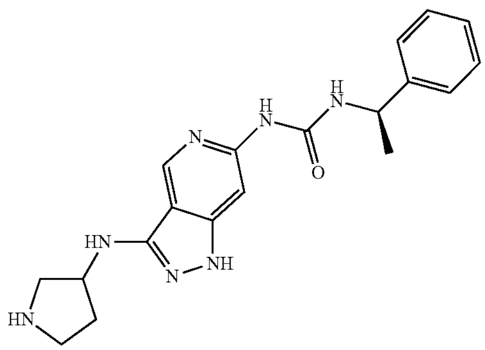 [SMILES: C[C@@H](NC(=O)Nc1cc2[nH]nc(NC3CCNC3)c2cn1)c1ccccc1] | 1-[(1R)-1-phenylethyl]-3-[3-(pyrrolidin-3-ylamino)-1H-pyrazolo[4,3-c]pyridin-6-yl]urea | Calc'd 366, found 366 | Scheme 8, Method A/ example 316 |
| 185 | 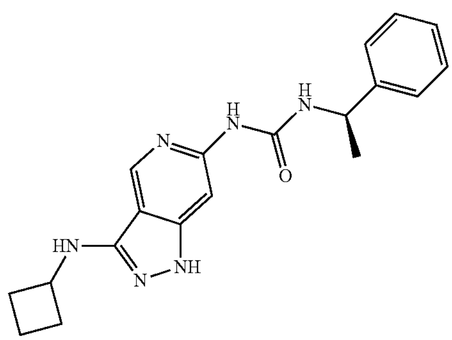 [SMILES: C[C@@H](NC(=O)Nc1cc2[nH]nc(NC3CCC3)c2cn1)c1ccccc1] | 1-[3-(cyclobutylamino)-1H-pyrazolo[4,3-c]pyridin-6-yl]-3-[(1R)-1-phenylethyl]urea | Calc'd 351, found 351 | Scheme 8, Method A/ example 316 |
| 186 | 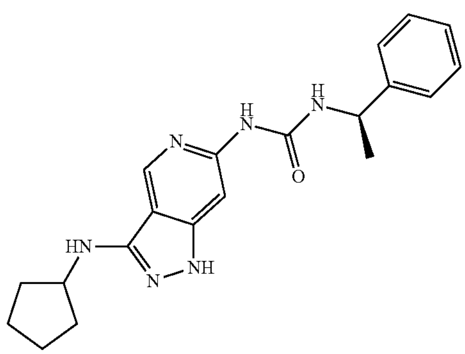 [SMILES: C[C@@H](NC(=O)Nc1cc2[nH]nc(NC3CCCC3)c2cn1)c1ccccc1] | 1-[3-(cyclopentyl-amino)-1H-pyrazolo[4,3-c]-pyridin-6-yl]-3-[(1R)-1-phenylethyl]urea | Calc'd 365, found 365 | Scheme 8, Method A/ example 316 |

| No. | Structure | IUPAC Name | Exact Mass [M + H]+ | Route Used |
|---|---|---|---|---|
| 187 | 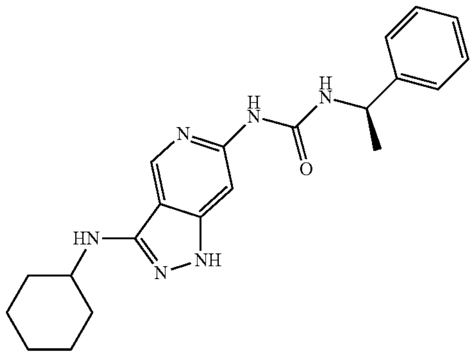 [SMILES: C[C@@H](NC(=O)Nc1cc2[nH]nc(NC3CCCCC3)c2cn1)c1ccccc1] | 1-[3-(cyclohexyl-amino)-1H-pyrazolo[4,3-c]pyridin-6-yl]-3-[(1R)-1-phenylethyl]urea | Calc'd 379, found 379 | Scheme 8, Method A/ example 316 |
| 188 | 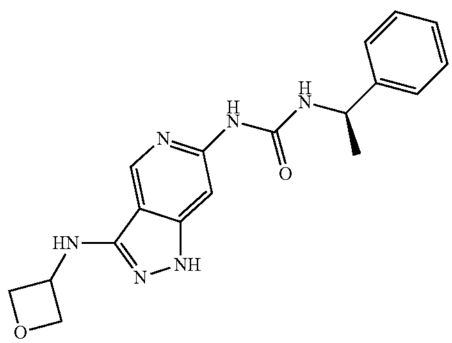 [SMILES: C[C@@H](NC(=O)Nc1cc2[nH]nc(NC3COC3)c2cn1)c1ccccc1] | 1-[3-(oxetan-3-yl-amino)-1H-pyrazolo[4,3-c]pyridin-6-yl]-3-[(1R)-1-phenylethyl]urea | Calc'd 353, found 353 | Scheme 8, Method A/ example 316 |
| 189 | 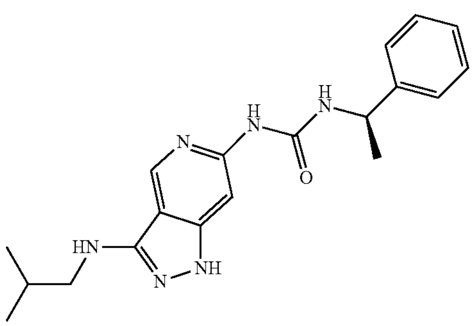 [SMILES: CC(C)CNc1n[nH]c2cc(NC(=O)N[C@H](C)c3ccccc3)ncc12] | 1-{3-[(2-methylpropyl)-amino]-1H-pyrazolo[4,3-c]-pyridin-6-yl}-3-[(1R)-1-phenylethyl]urea | Calc'd 353, found 353 | Scheme 8, Method A/ example 316 |
| 190 | 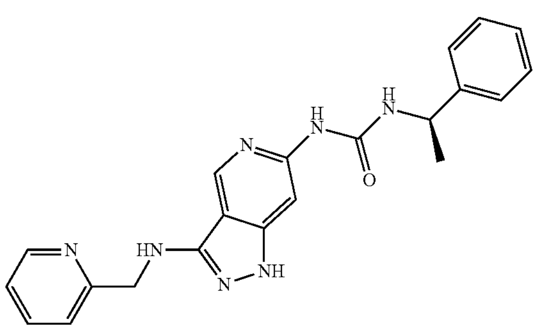 [SMILES: C[C@@H](NC(=O)Nc1cc2[nH]nc(NCc3ccccn3)c2cn1)c1ccccc1] | 1-[(1R)-1-phenylethyl]-3-{3-[(pyridin-2-yl-methyl)amino]-1H-pyrazolo[4,3-c]-pyridin-6-yl}urea | Calc'd 388, found 388 | Scheme 8, Method A/ example 316 |

-continued

| No. | Structure | IUPAC Name | Exact Mass [M + H]+ | Route Used |
|---|---|---|---|---|
| 191 | 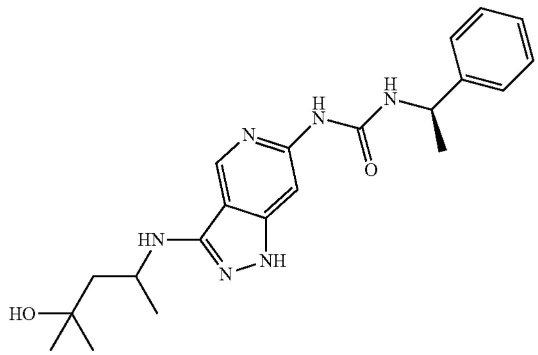 [SMILES: CC(CC(C)(C)O)Nc1n[nH]c2cc(NC(=O)N[C@H](C)c3ccccc3)ncc12] | 1-{3-[(3-hydroxy-1,3-dimethylbutyl)-amino]-1H-pyrazolo[4,3-c]-pyridin-6-yl}-3-[(1R)-1-phenylethyl]urea | Calc'd 397, found 397 | Scheme 8, Method A/ example 316 |
| 192 | 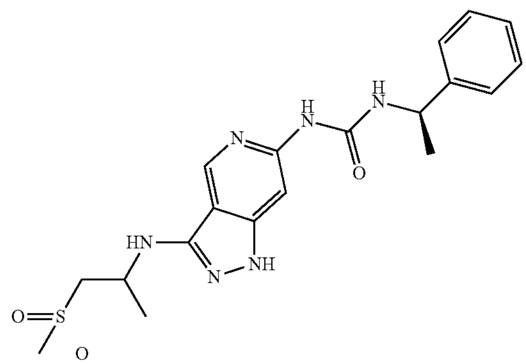 | 1-(3-{[1-methyl-2-(methylsulfonyl)-ethyl]amino}-1H-pyrazolo[4,3-c]-pyridin-6-yl)-3-[(1R)-1-phenylethyl]urea | Calc'd 417, found 417 | Scheme 8, Method A/ example 316 |
| 193 | 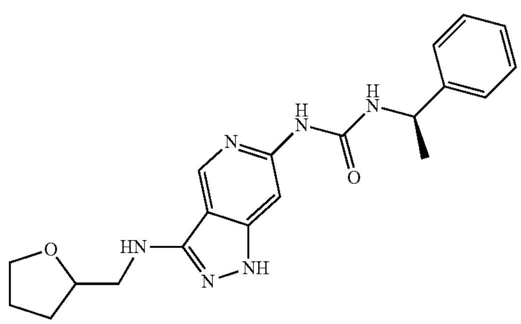 [SMILES: C[C@@H](NC(=O)Nc1cc2[nH]nc(NCC3CCCO3)c2cn1)c1ccccc1] | 1-[(1R)-1-phenylethyl]-3-{3-[(tetrahydrofuran-2-ylmethyl)amino]-1H-pyrazolo[4,3-c]pyridin-6-yl}urea | Calc'd 381, found 381 | Scheme 8, Method A/ example 316 |
| 194 | 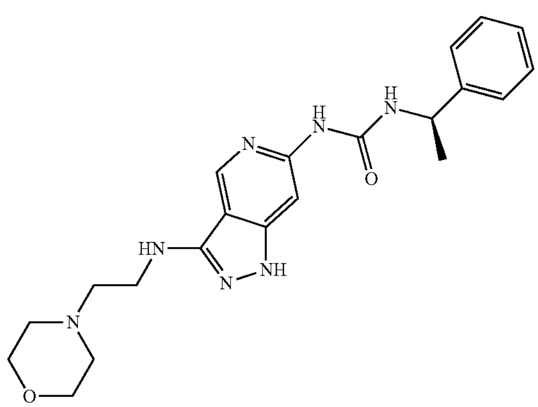 [SMILES: C[C@@H](NC(=O)Nc1cc2[nH]nc(NCCN3CCOCC3)c2cn1)c1ccccc1] | 1-{3-[(2-morpholin-4-ylethyl)amino]-1H-pyrazolo[4,3-c]-pyridin-6-yl}-3-[(1R)-1-phenylethyl]urea | Calc'd 410, found 410 | Scheme 8, Method A/ example 316 |

-continued

| No. | Structure | IUPAC Name | Exact Mass [M + H]+ | Route Used |
|---|---|---|---|---|
| 195 | 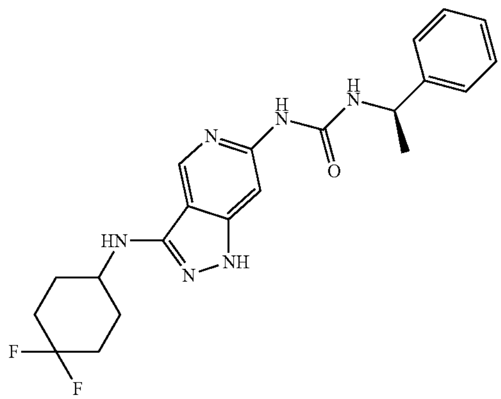 [SMILES: C[C@@H](NC(=O)Nc1cc2[nH]nc(NC3CCC(F)(F)CC3)c2cn1)c1ccccc1] | 1-{3-[(4,4-difluorocyclohexyl)amino]-1H-pyrazolo[4,3-c]-pyridin-6-yl}-3-[(1R)-1-phenylethyl]urea | Calc'd 415, found 415 | Scheme 8, Method A/ example 316 |
| 196 | 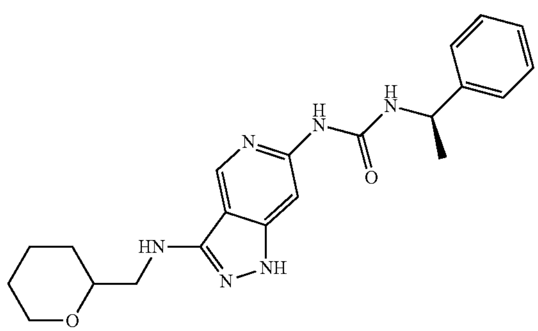 [SMILES: C[C@@H](NC(=O)Nc1cc2[nH]nc(NCC3CCCCO3)c2cn1)c1ccccc1] | 1-[(1R)-1-phenylethyl]-3-{3-[(tetrahydro-2H-pyran-2-yl-methyl)amino]-1H-pyrazolo[4,3-c]-pyridin-6-yl}urea | Calc'd 395, found 395 | Scheme 8, Method A/ example 316 |
| 197 | 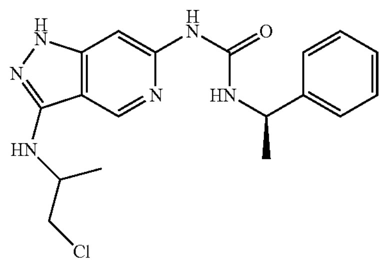 [SMILES: CC(CCl)Nc1n[nH]c2cc(NC(=O)N[C@H](C)c3ccccc3)ncc12] | 1-{3-[(2-chloro-1-methylethyl)amino]-1H-pyrazolo[4,3-c]pyridin-6-yl}-3-[(1R)-1-phenylethyl]urea | Calc'd 373, found 373 | Scheme 8, Method A/ example 316 |
| 198 | 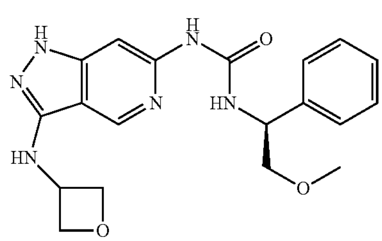 [SMILES: COC[C@@H](NC(=O)Nc1cc2[nH]nc(NC3COC3)c2cn1)c1ccccc1] | 1-[(1S)-2-methoxy-1-phenylethyl]-3-[3-(oxetan-3-yl-amino)-1H-pyrazolo[4,3-c]-pyridin-6-yl]urea | Calc'd 383, found 383 | Scheme 8, Method D/ example 316 |

-continued

| No. | Structure | IUPAC Name | Exact Mass [M + H]+ | Route Used |
|---|---|---|---|---|
| 199 | 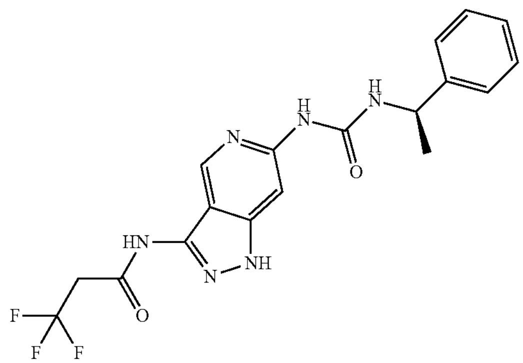 [SMILES: C[C@@H](NC(=O)Nc1cc2[nH]nc(NC(=O)CC(F)(F)F)c2cn1)c1ccccc1] | 3,3,3-trifluoro-N-[6-({[(1R)-1-phenylethyl]-carbamoyl}amino)-1H-pyrazolo[4,3-c]-pyridin-3-yl]-propanamide | Calc'd 407, found 407 | Scheme 10, Method B/ Example 318 |
| 200 | 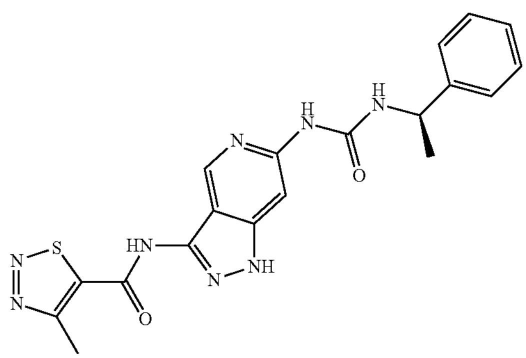 [SMILES: Cc1nnsc1C(=O)Nc1n[nH]c2cc(NC(=O)N[C@H](C)c3ccccc3)ncc12] | 4-methyl-N-[6-({[(1R)-1-phenylethyl]-carbamoyl}amino)-1H-pyrazolo[4,3-c]pyridin-3-yl]-1,2,3-thiadiazole-5-carboxamide | Calc'd 423, found 423 | Scheme 10, Method B/ Example 318 |
| 201 | 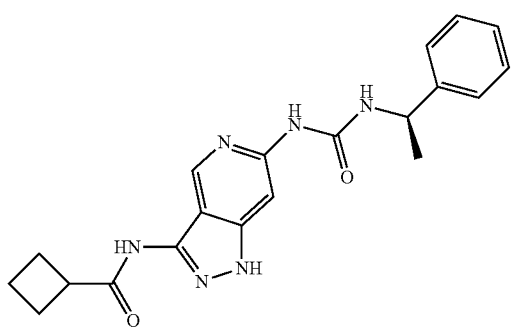 [SMILES: C[C@@H](NC(=O)Nc1cc2[nH]nc(NC(=O)C3CCC3)c2cn1)c1ccccc1] | N-[6-({[(1R)-1-phenylethyl]-carbamoyl}amino)-1H-pyrazolo[4,3-c]pyridin-3-yl]-cyclobutane-carboxamide | Calc'd 379, found 379 | Scheme 10, Method B/ Example 318 |
| 202 | 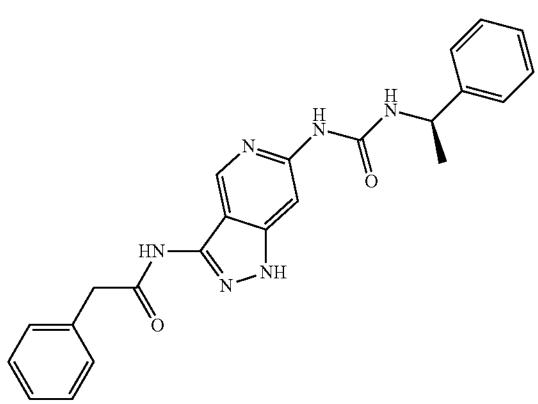 [SMILES: C[C@@H](NC(=O)Nc1cc2[nH]nc(NC(=O)Cc3ccccc3)c2cn1)c1ccccc1] | 2-phenyl-N-[6-({[(1R)-1-phenylethyl]-carbamoyl}amino)-1H-pyrazolo[4,3-c]pyridin-3-yl]-acetamide | Calc'd 415, found 415 | Scheme 10, Method B/ Example 318 |

| No. | Structure | IUPAC Name | Exact Mass [M + H]+ | Route Used |
|---|---|---|---|---|
| 203 | 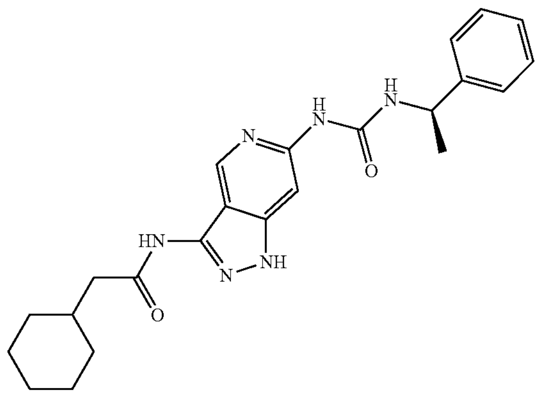 [SMILES: C[C@@H](NC(=O)Nc1cc2[nH]nc(NC(=O)CC3CCCCC3)c2cn1)c1ccccc1] | 2-cyclohexyl-N-[6-({[(1R)-1-phenylethyl]-carbamoyl}amino)-1H-pyrazolo[4,3-c]pyridin-3-yl]-acetamide | Calc'd 421, found 421 | Scheme 10, Method B/ Example 318 |
| 204 | 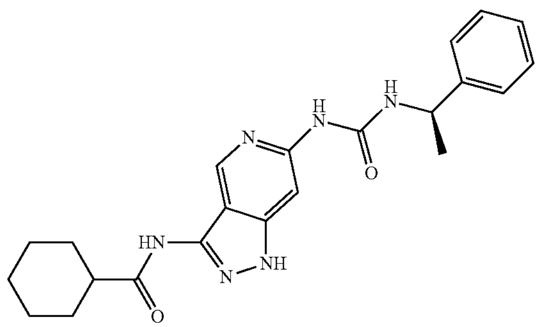 [SMILES: C[C@@H](NC(=O)Nc1cc2[nH]nc(NC(=O)C3CCCCC3)c2cn1)c1ccccc1] | N-[6-({[(1R)-1-phenylethyl]-carbamoyl}amino)-1H-pyrazolo[4,3-c]pyridin-3-yl]-cyclohexane-carboxamide | Calc'd 407, found 407 | Scheme 10, Method B/ Example 318 |
| 205 | 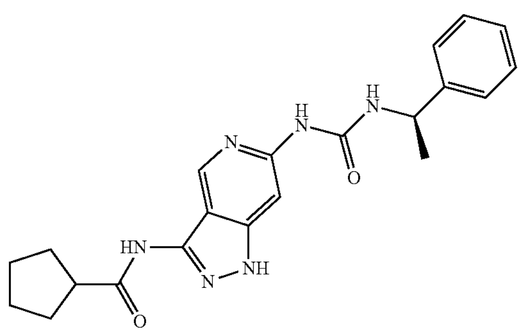 [SMILES: C[C@@H](NC(=O)Nc1cc2[nH]nc(NC(=O)C3CCCC3)c2cn1)c1ccccc1] | N-[6-({[(1R)-1-phenylethyl]-carbamoyl}amino)-1H-pyrazolo[4,3-c]pyridin-3-yl]-cyclopentane-carboxamide | Calc'd 393, found 393 | Scheme 10, Method B/ Example 318 |
| 206 | 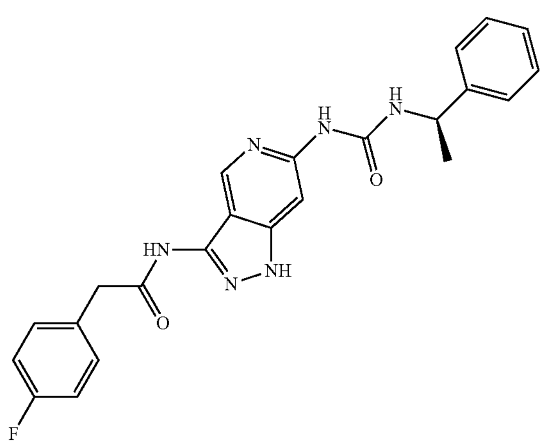 [SMILES: C[C@@H](NC(=O)Nc1cc2[nH]nc(NC(=O)Cc3ccc(F)cc3)c2cn1)c1ccccc1] | 2-(4-fluorophenyl)-N-[6-({[(1R)-1-phenylethyl]-carbamoyl}amino)-1H-pyrazolo[4,3-c]pyridin-3-yl]-acetamide | Calc'd 433, found 433 | Scheme 10, Method B/ Example 318 |

-continued

| No. | Structure | IUPAC Name | Exact Mass [M + H]+ | Route Used |
|---|---|---|---|---|
| 207 | 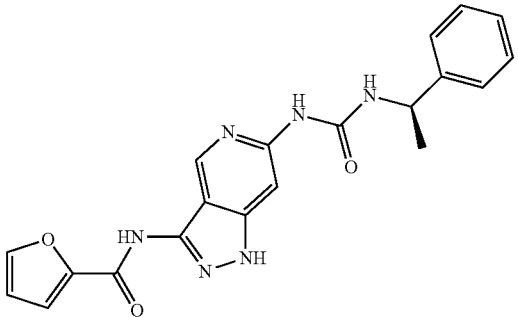 [SMILES: C[C@@H](NC(=O)Nc1cc2[nH]nc(NC(=O)c3ccco3)c2cn1)c1ccccc1] | N-[6-({[(1R)-1-phenylethyl]-carbamoyl}amino)-1H-pyrazolo[4,3-c]pyridin-3-yl]-furan-2-carboxamide | Calc'd 391, found 391 | Scheme 10, Method B/ Example 318 |
| 208 | 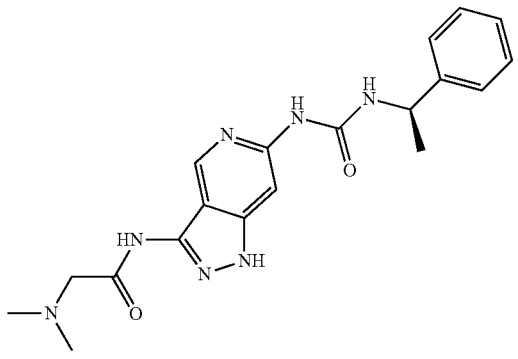 [SMILES: C[C@@H](NC(=O)Nc1cc2[nH]nc(NC(=O)CN(C)C)c2cn1)c1ccccc1] | N~2~,N~2~-dimethyl-N46-({[(1R)-1-phenylethyl]-carbamoyl}amino)-1H-pyrazolo[4,3-c]pyridin-3-yl]-glycinamide | Calc'd 382, found 382 | Scheme 10, Method B/ Example 318 |
| 209 | 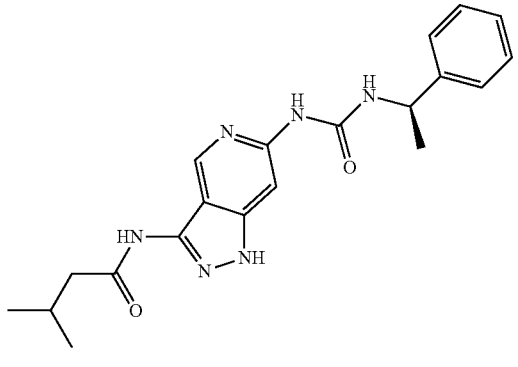 [SMILES: CC(C)CC(=O)Nc1n[nH]c2cc(NC(=O)N[C@H](C)c3ccccc3)ncc12] | 3-methyl-N-[6-({[(1R)-1-phenylethyl]-carbamoyl}amino)-1H-pyrazolo[4,3-c]pyridin-3-yl]-butanamide | Calc'd 381, found 381 | Scheme 10, Method B/ Example 318 |
| 210 | 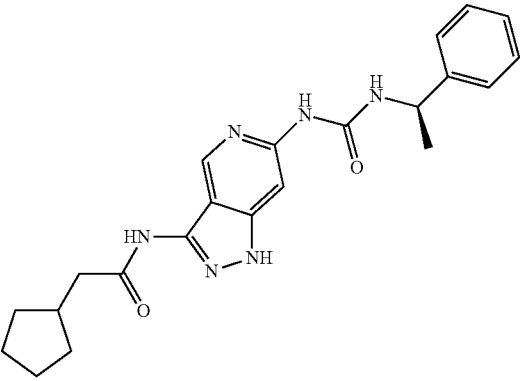 [SMILES: C[C@@H](NC(=O)Nc1cc2[nH]nc(NC(=O)CC3CCCC3)c2cn1)c1ccccc1] | 2-cyclopentyl-N-[6-({[(1R)-1-phenylethyl]-carbamoyl}amino)-1H-pyrazolo[4,3-c]pyridin-3-yl]-acetamide | Calc'd 407, found 407 | Scheme 10, Method B/ Example 318 |

-continued

| No. | Structure | IUPAC Name | Exact Mass [M + H]+ | Route Used |
|---|---|---|---|---|
| 211 | 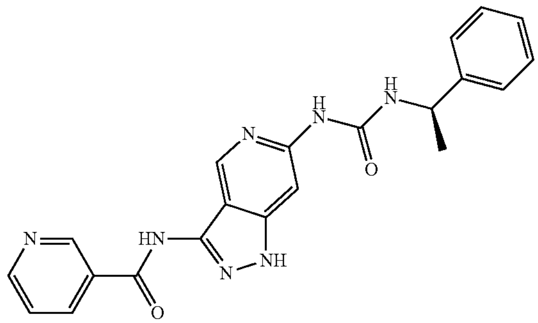 [SMILES: C[C@@H](NC(=O)Nc1cc2[nH]nc(NC(=O)c3cccnc3)c2cn1)c1ccccc1] | N-[6-({[(1R)-1-phenylethyl]-carbamoyl}amino)-1H-pyrazolo[4,3-c]pyridin-3-yl]-pyridine-3-carboxamide | Calc'd 402, found 402 | Scheme 10, Method B/ Example 318 |
| 212 | 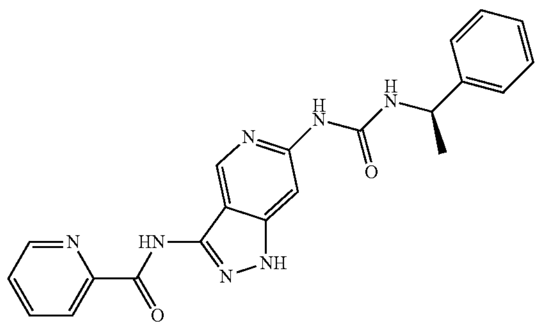 [SMILES: C[C@@H](NC(=O)Nc1cc2[nH]nc(NC(=O)c3ccccn3)c2cn1)c1ccccc1] | N-[6-({[(1R)-1-phenylethyl]-carbamoyl}amino)-1H-pyrazolo[4,3-c]pyridin-3-yl]-pyridine-2-carboxamide | Calc'd 402, found 402 | Scheme 10, Method B/ Example 318 |
| 213 | 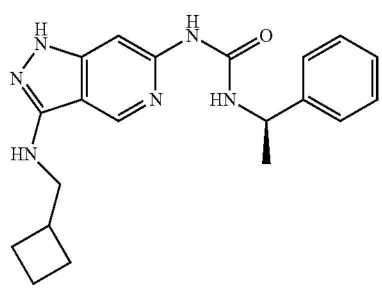 [SMILES: C[C@@H](NC(=O)Nc1cc2[nH]nc(NCC3CCC3)c2cn1)c1ccccc1] | 1-{3-[(cyclobutylmethyl)amino]-1H-pyrazolo[4,3-c]-pyridin-6-yl}-3-[(1R)-1-phenylethyl]urea | Calc'd 365, found 365 | Scheme 8, Method D/ example 316 |
| 214 | 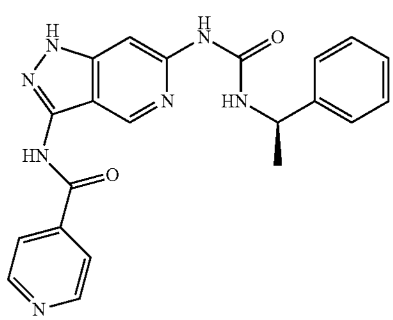 [SMILES: C[C@@H](NC(=O)Nc1cc2[nH]nc(NC(=O)c3ccncc3)c2cn1)c1ccccc1] | N-[6-({[(1R)-1-phenylethyl]-carbamoyl}amino)-1H-pyrazolo[4,3-c]pyridin-3-yl]-pyridine-4-carboxamide | Calc'd 402, found 402 | Scheme 10, Method B/ Example 318 |
| 215 | 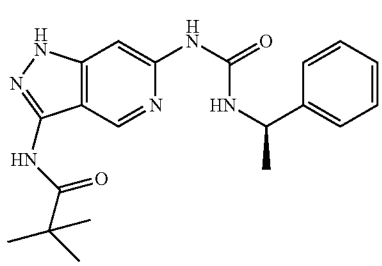 [SMILES: C[C@@H](NC(=O)Nc1cc2[nH]nc(NC(=O)C(C)(C)C)c2cn1)c1ccccc1] | 2,2-dimethyl-N-[6-({[(1R)-1-phenylethyl]-carbamoyl}amino)-1H-pyrazolo[4,3-c]pyridin-3-yl]-propanamide | Calc'd 381, found 381 | Scheme 10, Method B/ Example 318 |

-continued

| No. | Structure | IUPAC Name | Exact Mass [M + H]+ | Route Used |
|---|---|---|---|---|
| 216 | 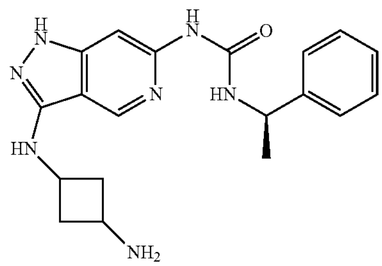 [SMILES: C[C@@H](NC(=O)Nc1cc2[nH]nc(NC3CC(N)C3)c2cn1)c1ccccc1] | 1-{3-[(3-amino-cyclobutyl)amino]-1H-pyrazolo[4,3-c]pyridin-6-yl}-3-[(1R)-1-phenylethyl]urea | Calc'd 366, found 366 | Scheme 8, Method A/ example 316 |
| 217 | 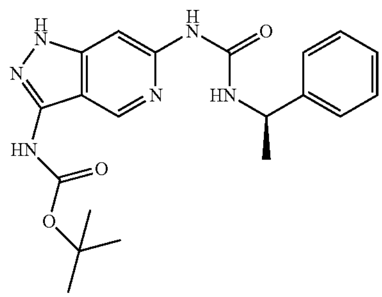 [SMILES: C[C@@H](NC(=O)Nc1cc2[nH]nc(NC(=O)OC(C)(C)C)c2cn1)c1ccccc1] | tert-butyl [6-({[(1R)-1-phenylethyl]-carbamoyl}amino)-1H-pyrazolo[4,3-c]pyridin-3-yl]-carbamate | Calc'd 397, found 397 | Scheme 9, example 315 |
| 218 | 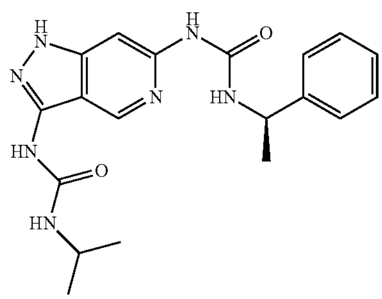 [SMILES: CC(C)NC(=O)Nc1n[nH]c2cc(NC(=O)N[C@H](C)c3ccccc3)ncc12] | 1-(1-methylethyl)-3-[6-({[(1R)-1-phenylethyl]-carbamoyl}amino)-1H-pyrazolo[4,3-c]pyridin-3-yl]urea | Calc'd 382, found 382 | Scheme 12, Example 313 |
| 219 | 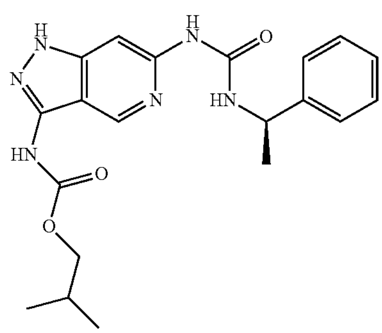 [SMILES: CC(C)COC(=O)Nc1n[nH]c2cc(NC(=O)N[C@H](C)c3ccccc3)ncc12] | 2-methylpropyl [6-({[(1R)-1-phenylethyl]-carbamoyl}amino)-1H-pyrazolo[4,3-c]pyridin-3-yl]-carbamate | Calc'd 397, found 397 | Scheme 9, example 315 |
| 220 | 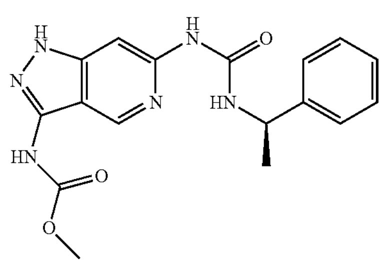 [SMILES: COC(=O)Nc1n[nH]c2cc(NC(=O)N[C@H](C)c3ccccc3)ncc12] | methyl[6-({[(1R)-1-phenylethyl]-carbamoyl}amino)-1H-pyrazolo[4,3-c]pyridin-3-yl]-carbamate | Calc'd 355, found 355 | Scheme 9, example 315 |

| No. | Structure | IUPAC Name | Exact Mass [M + H]+ | Route Used |
|---|---|---|---|---|
| 221 | 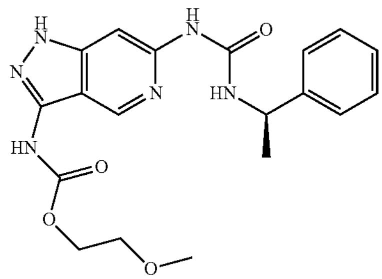 [SMILES: COCCOC(=O)Nc1n[nH]c2cc(NC(=O)N[C@H](C)c3ccccc3)ncc12] | 2-methoxyethyl [6-({[(1R)-1-phenyl-ethyl]carbamoyl}-amino)-1H-pyrazolo[4,3-c]-pyridin-3-yl]-carbamate | Calc'd 399, found 399 | Scheme 9, example 315 |
| 222 | 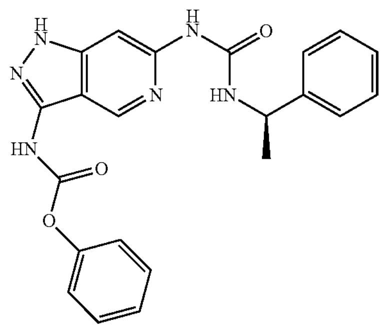 [SMILES: C[C@@H](NC(=O)Nc1cc2[nH]nc(NC(=O)Oc3ccccc3)c2cn1)c1ccccc1] | phenyl[6-({[(1R)-1-phenylethyl]-carbamoyl}amino)-1H-pyrazolo[4,3-c]pyridin-3-yl]-carbamate | Calc'd 417, found 417 | Scheme 9, example 315 |
| 223 | 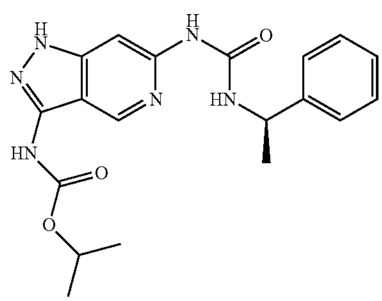 [SMILES: CC(C)OC(=O)Nc1n[nH]c2cc(NC(=O)N[C@H](C)c3ccccc3)ncc12] | 1-methylethyl[6-({[(1R)-1-phenylethyl]-carbamoyl}amino)-1H-pyrazolo[4,3-c]pyridin-3-yl]-carbamate | Calc'd 383, found 383 | Scheme 9, example 315 |
| 224 | 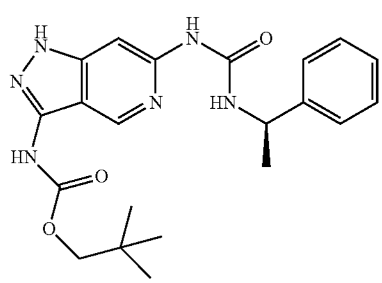 [SMILES: C[C@@H](NC(=O)Nc1cc2[nH]nc(NC(=O)OCC(C)(C)C)c2cn1)c1ccccc1] | 2,2-dimethylpropyl [6-({[(1R)-1-phenylethyl]-carbamoyl}amino)-1H-pyrazolo[4,3-c]pyridin-3-yl]-carbamate | Calc'd 411, found 411 | Scheme 9, example 315 |
| 225 | 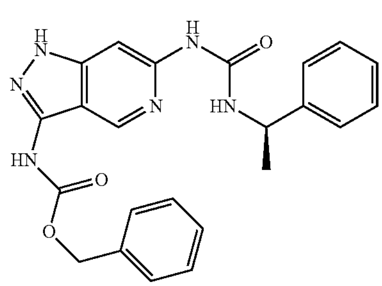 [SMILES: C[C@@H](NC(=O)Nc1cc2[nH]nc(NC(=O)OCc3ccccc3)c2cn1)c1ccccc1] | benzyl [6-({[(1R)-1-phenylethyl]-carbamoyl}amino)-1H-pyrazolo[4,3-c]pyridin-3-yl]-carbamate | Calc'd 431, found 431 | Scheme 9, example 315 |

-continued

| No. | Structure | IUPAC Name | Exact Mass [M + H]+ | Route Used |
|-----|-----------|------------|---------------------|------------|
| 226 | 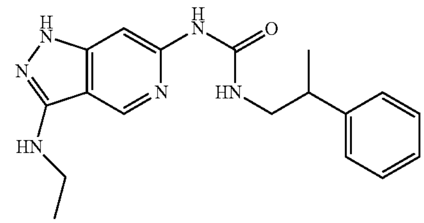 [SMILES: CCNc1n[nH]c2cc(NC(=O)NCC(C)c3ccccc3)ncc12] | 1-[3-(ethylamino)-1H-pyrazolo[4,3-c]pyridin-6-yl]-3-(2-phenylpropyl)-urea | Calc'd 339, found 339 | Scheme 1, Example 1 |
| 227 | 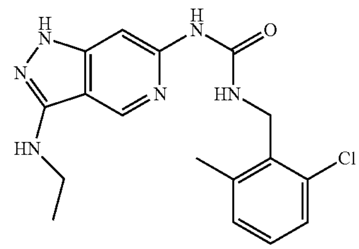 [SMILES: CCNc1n[nH]c2cc(NC(=O)NCc3c(C)cccc3Cl)ncc12] | 1-(2-chloro-6-methylbenzyl)-3-[3-(ethylamino)-1H-pyrazolo[4,3-c]pyridin-6-yl]urea | Calc'd 359, found 359 | Scheme 1, Example 1 |
| 228 | 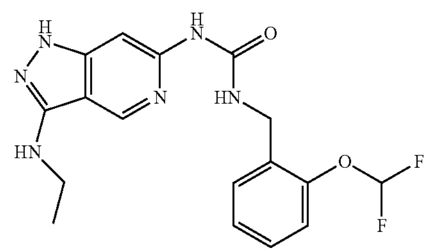 [SMILES: CCNc1n[nH]c2cc(NC(=O)NCc3ccccc3OC(F)F)ncc12] | 1-[2-(difluoromethoxy)benzyl]-3-[3-(ethylamino)-1H-pyrazolo[4,3-c]pyridin-6-yl]urea | Calc'd 377, found 377 | Scheme 1, Example 1 |
| 229 | 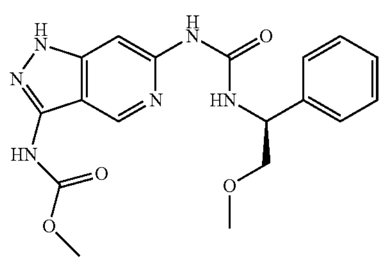 [SMILES: COC[C@@H](NC(=O)Nc1cc2[nH]nc(NC(=O)OC)c2cn1)c1ccccc1] | methyl [6-({[(1S)-2-methoxy-1-phenylethyl]carbamoyl}amino)-1H-pyrazolo[4,3-c]pyridin-3-yl]-carbamate | Calc'd 385, found 385 | Scheme 9, example 315 |
| 230 | 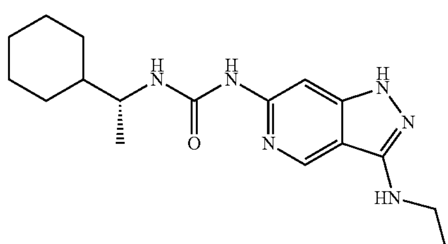 | 1-[(1R)-1-cyclohexylethyl]-3-[3-(ethylamino)-1H-pyrazolo[4,3-c]pyridin-6-yl]urea | Calc'd 331, found 331 | Scheme 1, Example 1 |
| 231 | 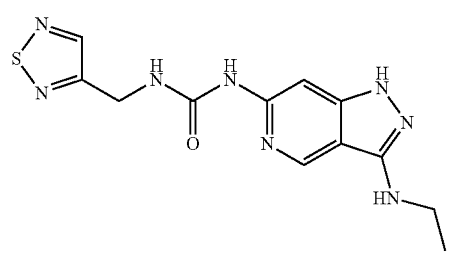 [SMILES: CCNc1n[nH]c2cc(NC(=O)NCc3cnsn3)ncc12] | 1-[3-(ethylamino)-1H-pyrazolo[4,3-c]pyridin-6-yl]-3-(1,2,5-thiadiazol-3-ylmethyl)urea | Calc'd 319, found 319 | Scheme 1, Example 1 |

-continued

| No. | Structure | IUPAC Name | Exact Mass [M + H]+ | Route Used |
|---|---|---|---|---|
| 232 | 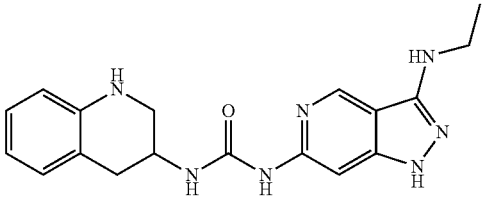 [SMILES: CCNc1n[nH]c2cc(NC(=O)NC3CNc4ccccc4C3)ncc12] | 1-[3-(ethylamino)-1H-pyrazolo[4,3-c]pyridin-6-yl]-3-(1,2,3,4-tetrahydro-quinolin-3-yl)urea | Calc'd 352, found 352 | Scheme 1, Example 1 |
| 233 | 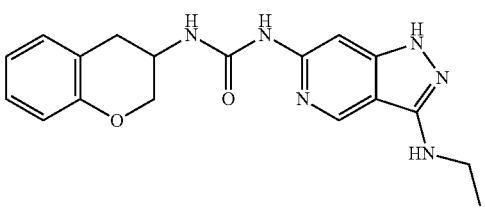 [SMILES: CCNc1n[nH]c2cc(NC(=O)NC3COc4ccccc4C3)ncc12] | 1-(3,4-dihydro-2H-chromen-3-yl)-3-[3-(ethylamino)-1H-pyrazolo[4,3-c]pyridin-6-yl]urea | Calc'd 353, found 353 | Scheme 1, Example 1 |
| 234 | 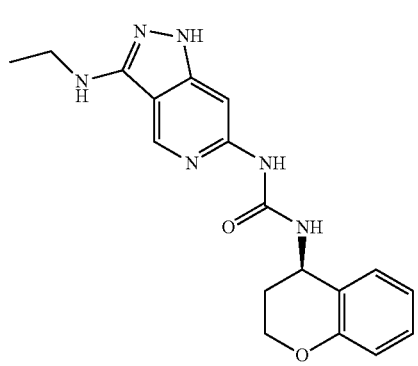 [SMILES: CCNc1n[nH]c2cc(NC(=O)N[C@@H]3CCOc4ccccc43)ncc12] | 1-[(4R)-3,4-dihydro-2H-chromen-4-yl]-3-[3-(ethylamino)-1H-pyrazolo[4,3-c]pyridin-6-yl]urea | Calc'd 353, found 353 | Scheme 1, Example 1 |
| 235 | 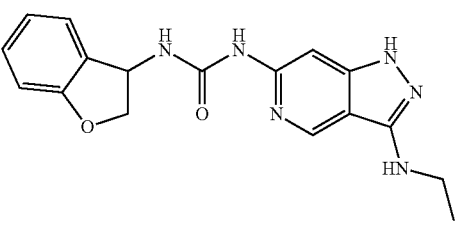 [SMILES: CCNc1n[nH]c2cc(NC(=O)NC3COc4ccccc43)ncc12] | 1-(2,3-dihydro-1-benzofuran-3-yl)-3-[3-(ethylamino)-1H-pyrazolo[4,3-c]pyridin-6-yl]urea | Calc'd 339, found 339 | Scheme 1, Example 1 |
| 236 | 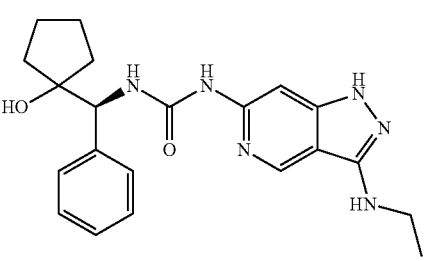 [SMILES: CCNc1n[nH]c2cc(NC(=O)N[C@@H](c3ccccc3)C3(O)CCCC3)ncc12] | 1-[3-(ethylamino)-1H-pyrazolo[4,3-c]pyridin-6-yl]-3-[(S)-(1-hydroxy-cyclopentyl)-(phenyl)methyl]-urea | Calc'd 395, found 395 | Scheme 1, Example 1 |
| 237 | 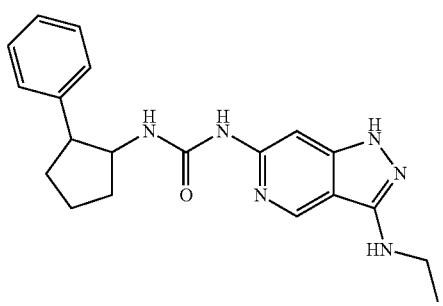 [SMILES: CCNc1n[nH]c2cc(NC(=O)NC3CCCC3c3ccccc3)ncc12] | 1-[3-(ethylamino)-1H-pyrazolo[4,3-c]pyridin-6-yl]-3-(2-phenyl-cyclopentyl)urea | Calc'd 365, found 365 | Scheme 1, Example 1 |

-continued

| No. | Structure | IUPAC Name | Exact Mass [M + H]+ | Route Used |
|---|---|---|---|---|
| 238 | 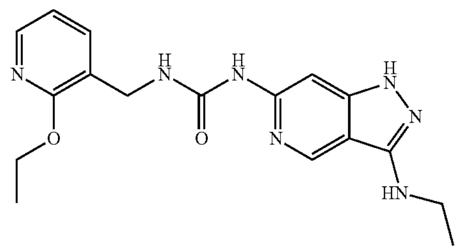 [SMILES: CCNc1n[nH]c2cc(NC(=O)NCc3cccnc3OCC)ncc12] | 1-[(2-ethoxy-pyridin-3-yl)-methyl]-3-[3-(ethylamino)-1H-pyrazolo[4,3-c]pyridin-6-yl]urea | Calc'd 356, found 356 | Scheme 1, Example 1 |
| 239 | 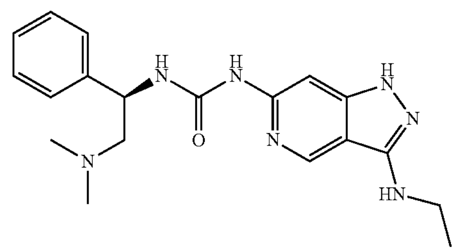 [SMILES: CCNc1n[nH]c2cc(NC(=O)N[C@@H](CN(C)C)c3ccccc3)ncc12] | 1-[(1R)-2-(dimethylamino)-1-phenylethyl]-3-[3-(ethylamino)-1H-pyrazolo[4,3-c]pyridin-6-yl]urea | Calc'd 368, found 368 | Scheme 1, Example 1 |
| 240 | 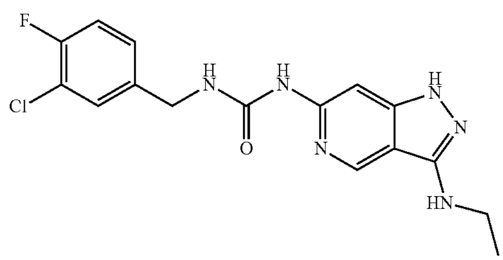 [SMILES: CCNc1n[nH]c2cc(NC(=O)NCc3ccc(F)c(Cl)c3)ncc12] | 1-(3-chloro-4-fluorobenzyl)-3-[3-(ethylamino)-1H-pyrazolo[4,3-c]-pyridin-6-yl]urea | Calc'd 363, found 363 | Scheme 1, Example 1 |
| 241 | 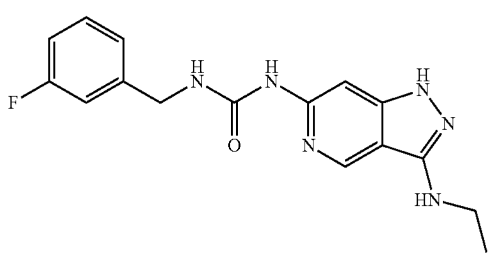 [SMILES: CCNc1n[nH]c2cc(NC(=O)NCc3cccc(F)c3)ncc12] | 1-[3-(ethylamino)-1H-pyrazolo[4,3-c]pyridin-6-yl]-3-(3-fluorobenzyl)-urea | Calc'd 329, found 329 | Scheme 1, Example 1 |
| 242 | 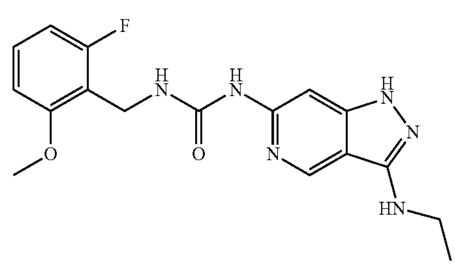 [SMILES: CCNc1n[nH]c2cc(NC(=O)NCc3c(F)cccc3OC)ncc12] | 1-[3-(ethylamino)-1H-pyrazolo[4,3-c]pyridin-6-yl]-3-(2-fluoro-6-methoxybenzyl)-urea | Calc'd 359, found 359 | Scheme 1, Example 1 |

-continued

| No. | Structure | IUPAC Name | Exact Mass [M + H]+ | Route Used |
|---|---|---|---|---|
| 243 | 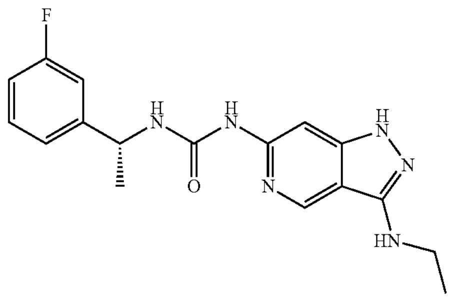 [SMILES: CCNc1n[nH]c2cc(NC(=O)N[C@H](C)c3cccc(F)c3)ncc12] | 1-[3-(ethylamino)-1H-pyrazolo[4,3-c]pyridin-6-yl]-3-[(1R)-1-(3-fluorophenyl)-ethyl]urea | Calc'd 343, found 343 | Scheme 1, Example 1 |
| 244 | 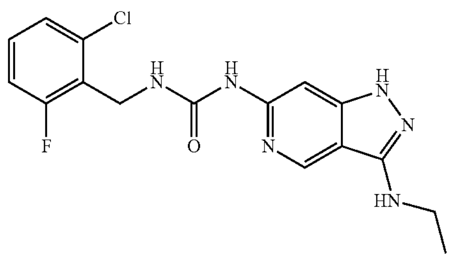 [SMILES: CCNc1n[nH]c2cc(NC(=O)NCc3c(F)cccc3Cl)ncc12] | 1-(2-chloro-6-fluorobenzyl)-3-[3-(ethylamino)-1H-pyrazolo[4,3-c]-pyridin-6-yl]urea | Calc'd 363, found 363 | Scheme 1, Example 1 |
| 245 | 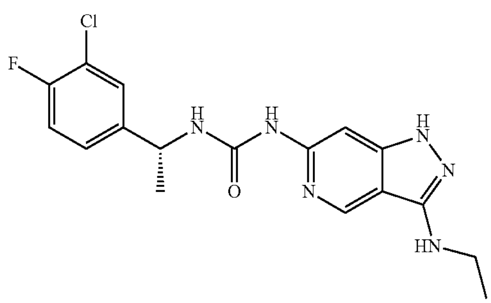 [SMILES: CCNc1n[nH]c2cc(NC(=O)N[C@H](C)c3ccc(F)c(Cl)c3)ncc12] | 1-[(1R)-1-(3-chloro-4-fluorophenyl)ethyl]-3-[3-(ethylamino)-1H-pyrazolo[4,3-c]pyridin-6-yl]urea | Calc'd 377, found 377 | Scheme 1, Example 1 |
| 246 | 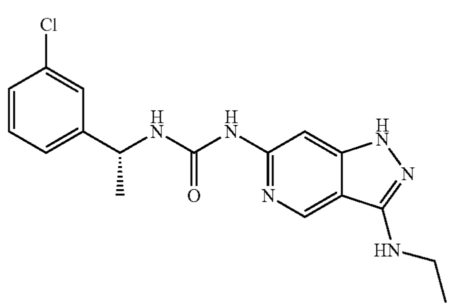 | 1-[(1R)-1-(3-chlorophenyl)ethyl]-3-[3-(ethylamino)-1H-pyrazolo[4,3-c]pyridin-6-yl]urea | Calc'd 359, found 359 | Scheme 1, Example 1 |
| 247 | 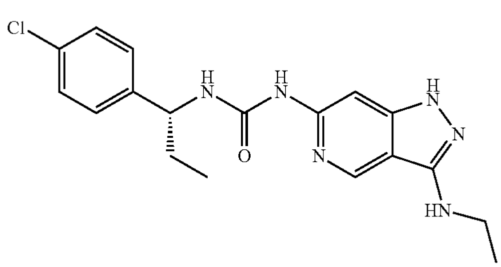 [SMILES: CCNc1n[nH]c2cc(NC(=O)N[C@H](CC)c3ccc(Cl)cc3)ncc12] | 1-[(1R)-1-(4-chlorophenyl)propyl]-3-[3-(ethylamino)-1H-pyrazolo[4,3-c]-pyridin-6-yl]urea | Calc'd 373, found 373 | Scheme 1, Example 1 |

-continued

| No. | Structure | IUPAC Name | Exact Mass [M + H]+ | Route Used |
|---|---|---|---|---|
| 248 | 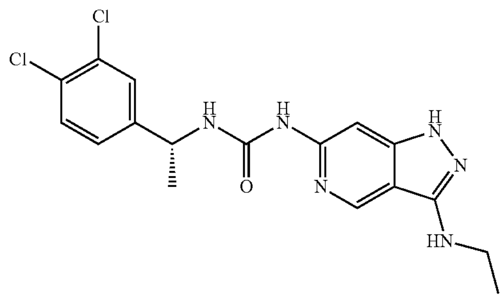 [SMILES: CCNc1n[nH]c2cc(NC(=O)N[C@H](C)c3ccc(Cl)c(Cl)c3)ncc12] | 1-[(1R)-1-(3,4-dichlorophenyl)ethyl]-3-[3-(ethylamino)-1H-pyrazolo[4,3-c]-pyridin-6-yl]urea | Calc'd 393, found 393 | Scheme 1, Example 1 |
| 249 | 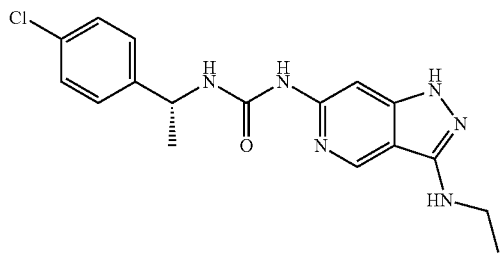 [SMILES: CCNc1n[nH]c2cc(NC(=O)N[C@H](C)c3ccc(Cl)cc3)ncc12] | 1-[(1R)-1-(4-chlorophenyl)ethyl]-3-[3-(ethylamino)-1H-pyrazolo[4,3-c]pyridin-6-yl]urea | Calc'd 359, found 359 | Scheme 1, Example 1 |
| 250 | 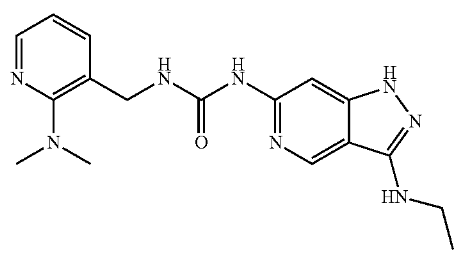 [SMILES: CCNc1n[nH]c2cc(NC(=O)NCc3cccnc3N(C)C)ncc12] | 1-{[2-(dimethylamino)pyridin-3-yl]methyl}-3-[3-(ethylamino)-1H-pyrazolo[4,3-c]-pyridin-6-yl]urea | Calc'd 355, found 355 | Scheme 1, Example 1 |
| 251 | 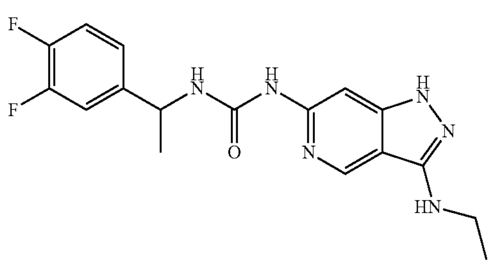 [SMILES: CCNc1n[nH]c2cc(NC(=O)NC(C)c3ccc(F)c(F)c3)ncc12] | 1-[1-(3,4-difluorophenyl)ethyl]-3-[3-(ethylamino)-1H-pyrazolo[4,3-c]-pyridin-6-yl]urea | Calc'd 361, found 361 | Scheme 1, Example 1 |
| 252 | 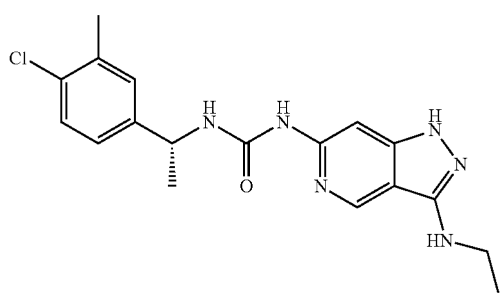 [SMILES: CCNc1n[nH]c2cc(NC(=O)N[C@H](C)c3ccc(Cl)c(C)c3)ncc12] | 1-[(1R)-1-(4-chloro-3-methylphenyl)ethyl]-3-[3-(ethylamino)-1H-pyrazolo[4,3-c]-pyridin-6-yl]urea | Calc'd 373, found 373 | Scheme 1, Example 1 |

-continued

| No. | Structure | IUPAC Name | Exact Mass [M + H]+ | Route Used |
|---|---|---|---|---|
| 253 | 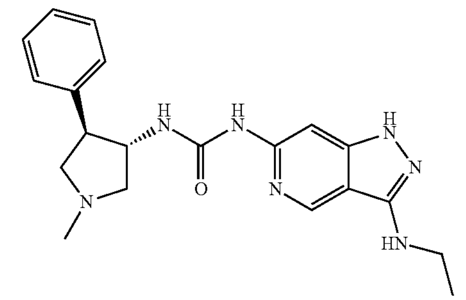 [SMILES: CCNc1n[nH]c2cc(NC(=O)N[C@@H]3CN(C)C[C@H]3c3ccccc3)ncc12] | 1-[3-(ethylamino)-1H-pyrazolo[4,3-c]pyridin-6-yl]-3-[(3S,4R)-1-methyl-4-phenylpyrrolidin-3-yl]urea | Calc'd 380, found 380 | Scheme 1, Example 1 |
| 254 | 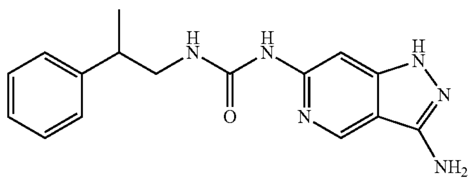 [SMILES: CC(CNC(=O)Nc1cc2[nH]nc(N)c2cn1)c1ccccc1] | 1-(3-amino-1H-pyrazolo[4,3-c]pyridin-6-yl)-3-(2-phenyl-propyl)urea | Calc'd 311, found 311 | Scheme 2, Example 43 |
| 255 | 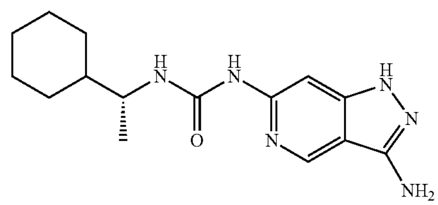 [SMILES: C[C@@H](NC(=O)Nc1cc2[nH]nc(N)c2cn1)C1CCCCC1] | 1-(3-amino-1H-pyrazolo[4,3-c]pyridin-6-yl)-3-[(1R)-1-cyclohexyl-ethyl]urea | Calc'd 303, found 303 | Scheme 2, Example 43 |
| 256 | 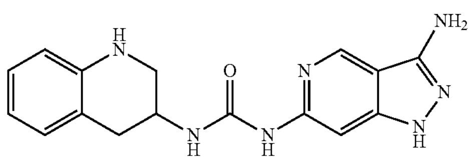 [SMILES: Nc1n[nH]c2cc(NC(=O)NC3CNc4ccccc4C3)ncc12] | 1-(3-amino-1H-pyrazolo[4,3-c]pyridin-6-yl)-3-(1,2,3,4-tetrahydro-quinolin-3-yl)urea | Calc'd 324, found 324 | Scheme 2, Example 43 |
| 257 | 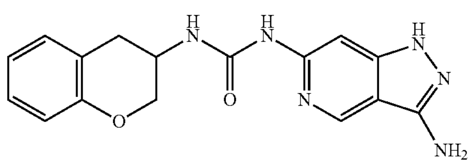 [SMILES: Nc1n[nH]c2cc(NC(=O)NC3COc4ccccc4C3)ncc12] | 1-(3-amino-1H-pyrazolo[4,3-c]pyridin-6-yl)-3-(3,4-dihydro-2H-chromen-3-yl)urea | Calc'd 325, found 325 | Scheme 2, Example 43 |
| 258 | 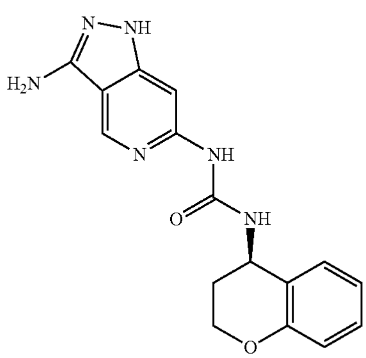 [SMILES: Nc1n[nH]c2cc(NC(=O)N[C@@H]3CCOc4ccccc43)ncc12] | 1-(3-amino-1H-pyrazolo[4,3-c]pyridin-6-yl)-3-[(4R)-3,4-dihydro-2H-chromen-4-yl]-urea | Calc'd 325, found 325 | Scheme 2, Example 43 |
| 259 | 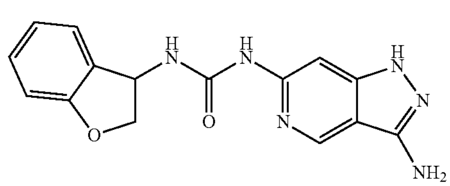 [SMILES: Nc1n[nH]c2cc(NC(=O)NC3COc4ccccc43)ncc12] | 1-(3-amino-1H-pyrazolo[4,3-c]pyridin-6-yl)-3-(2,3-dihydro-1-benzofuran-3-yl)-urea | Calc'd 311, found 311 | Scheme 2, Example 43 |

| No. | Structure | IUPAC Name | Exact Mass [M + H]+ | Route Used |
|---|---|---|---|---|
| 260 | 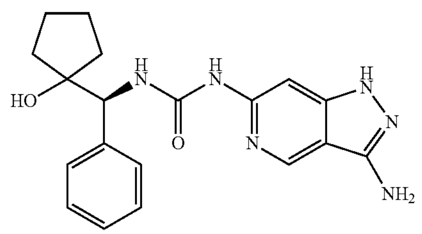 [SMILES: Nc1n[nH]c2cc(NC(=O)N[C@@H](c3ccccc3)C3(O)CCCC3)ncc12] | 1-(3-amino-1H-pyrazolo[4,3-c]-pyridin-6-yl)-3-[(S)-(1-hydroxy-cyclopentyl)-(phenyl)methyl]-urea | Calc'd 367, found 367 | Scheme 2, Example 43 |
| 261 | 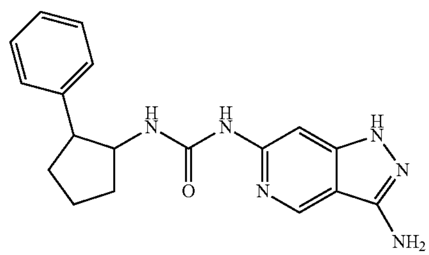 [SMILES: Nc1n[nH]c2cc(NC(=O)NC3CCCC3c3ccccc3)ncc12] | 1-(3-amino-1H-pyrazolo[4,3-c]-pyridin-6-yl)-3-(2-phenylcyclopentyl)urea | Calc'd 337, found 337 | Scheme 2, Example 43 |
| 262 | 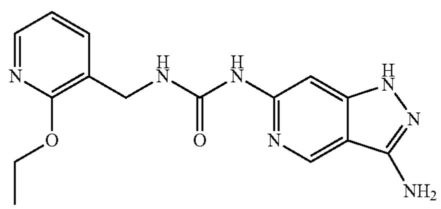 [SMILES: CCOc1ncccc1CNC(=O)Nc1cc2[nH]nc(N)c2cn1] | 1-(3-amino-1H-pyrazolo[4,3-c]pyridin-6-yl)-3-[(2-ethoxypyridin-3-yl)methyl]urea | Calc'd 328, found 328 | Scheme 2, Example 43 |
| 263 | 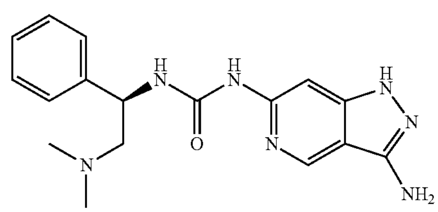 [SMILES: CN(C)C[C@H](NC(=O)Nc1cc2[nH]nc(N)c2cn1)c1ccccc1] | 1-(3-amino-1H-pyrazolo[4,3-c]-pyridin-6-yl)-3-[(1R)-2-(dimethylamino)-1-phenylethyl]urea | Calc'd 340, found 340 | Scheme 2, Example 43 |
| 264 | 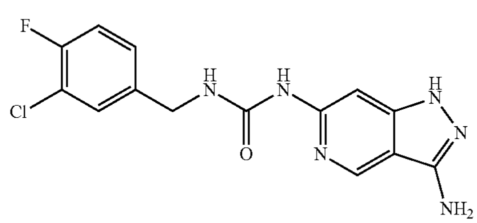 [SMILES: Nc1n[nH]c2cc(NC(=O)NCc3ccc(F)c(Cl)c3)ncc12] | 1-(3-amino-1H-pyrazolo[4,3-c]-pyridin-6-yl)-3-(3-chloro-4-fluorobenzyl)urea | Calc'd 335, found 335 | Scheme 2, Example 43 |
| 265 | 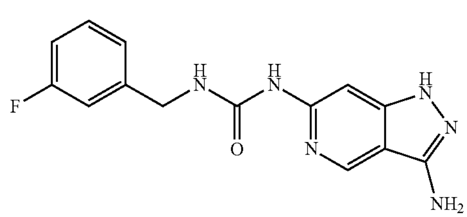 [SMILES: Nc1n[nH]c2cc(NC(=O)NCc3cccc(F)c3)ncc12] | 1-(3-amino-1H-pyrazolo[4,3-c]-pyridin-6-yl)-3-(3-fluorobenzyl)urea | Calc'd 301, found 301 | Scheme 2, Example 43 |

-continued

| No. | Structure | IUPAC Name | Exact Mass [M + H]⁺ | Route Used |
|---|---|---|---|---|
| 266 | 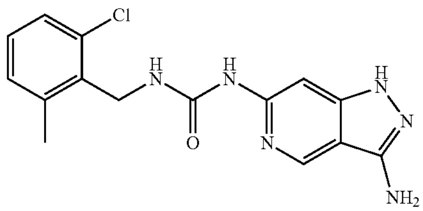 [SMILES: Cc1cccc(Cl)c1CNC(=O)Nc1cc2[nH]nc(N)c2cn1] | 1-(3-amino-1H-pyrazolo[4,3-c]pyridin-6-yl)-3-(2-chloro-6-methylbenzyl)urea | Calc'd 331, found 331 | Scheme 2, Example 43 |
| 267 | 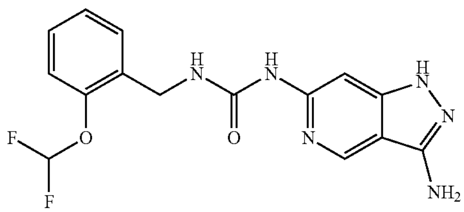 [SMILES: Nc1n[nH]c2cc(NC(=O)NCc3ccccc3OC(F)F)ncc12] | 1-(3-amino-1H-pyrazolo[4,3-c]pyridin-6-yl)-3-[2-(difluoro-methoxy)benzyl]-urea | Calc'd 349, found 349 | Scheme 2, Example 43 |
| 268 | 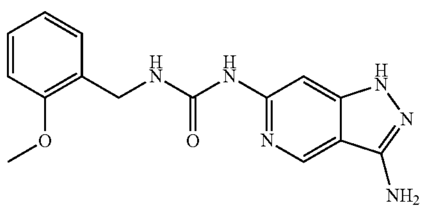 [SMILES: COc1ccccc1CNC(=O)Nc1cc2[nH]nc(N)c2cn1] | 1-(3-amino-1H-pyrazolo[4,3-c]pyridin-6-yl)-3-(2-methoxy-benzyl)urea | Calc'd 313, found 313 | Scheme 2, Example 43 |
| 269 | 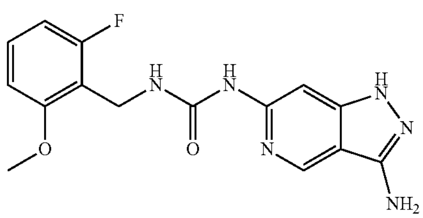 [SMILES: COc1cccc(F)c1CNC(=O)Nc1cc2[nH]nc(N)c2cn1] | 1-(3-amino-1H-pyrazolo[4,3-c]pyridin-6-yl)-3-(2-fluoro-6-methoxy-benzyl)urea | Calc'd 331, found 331 | Scheme 2, Example 43 |
| 270 | 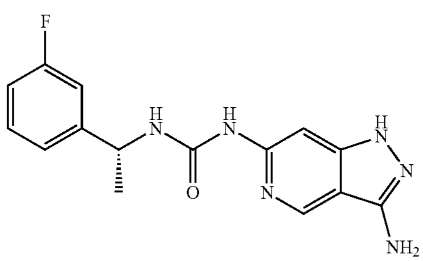 [SMILES: C[C@@H](NC(=O)Nc1cc2[nH]nc(N)c2cn1)c1cccc(F)c1] | 1-(3-amino-1H-pyrazolo[4,3-c]pyridin-6-yl)-3-[(1R)-1-(3-fluorophenyl)ethyl]urea | Calc'd 315, found 315 | Scheme 2, Example 43 |
| 271 | 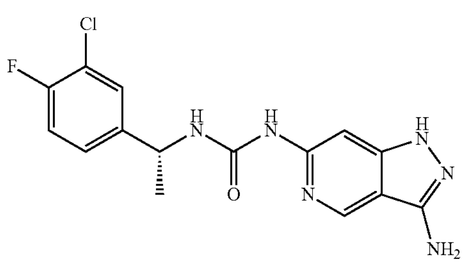 [SMILES: C[C@@H](NC(=O)Nc1cc2[nH]nc(N)c2cn1)c1ccc(F)c(Cl)c1] | 1-(3-amino-1H-pyrazolo[4,3-c]pyridin-6-yl)-3-[(1R)-1-(3-chloro-4-fluorophenyl)-ethyl]urea | Calc'd 349, found 349 | Scheme 2, Example 43 |

-continued

| No. | Structure | IUPAC Name | Exact Mass [M + H]+ | Route Used |
|---|---|---|---|---|
| 272 | 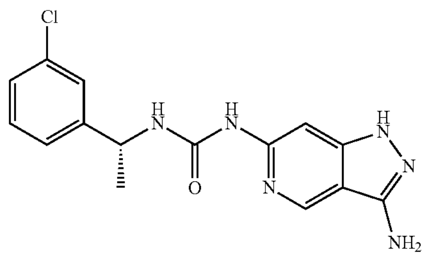 [SMILES: C[C@@H](NC(=O)Nc1cc2[nH]nc(N)c2cn1)c1cccc(Cl)c1] | 1-(3-amino-1H-pyrazolo[4,3-c]pyridin-6-yl)-3-[(1R)-1-(3-chlorophenyl)ethyl]urea | Calc'd 331, found 331 | Scheme 2, Example 43 |
| 273 | 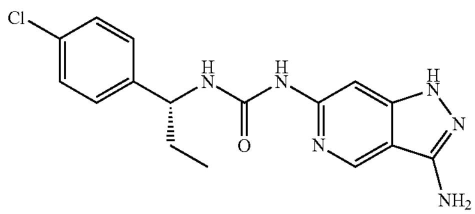 [SMILES: CC[C@@H](NC(=O)Nc1cc2[nH]nc(N)c2cn1)c1ccc(Cl)cc1] | 1-(3-amino-1H-pyrazolo[4,3-c]pyridin-6-yl)-3-[(1R)-1-(4-chlorophenyl)propyl]urea | Calc'd 345, found 345 | Scheme 2, Example 43 |
| 274 | 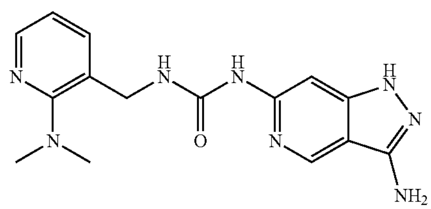 [SMILES: CN(C)c1ncccc1CNC(=O)Nc1cc2[nH]nc(N)c2cn1] | 1-(3-amino-1H-pyrazolo[4,3-c]-pyridin-6-yl)-3-{[2-(dimethylamino)-pyridin-3-yl]-methyl}urea | Calc'd 327, found 327 | Scheme 2, Example 43 |
| 275 | 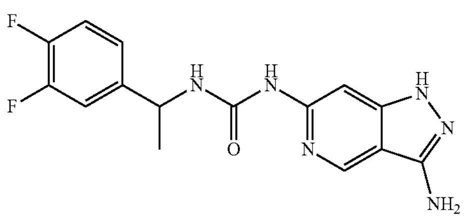 [SMILES: CC(NC(=O)Nc1cc2[nH]nc(N)c2cn1)c1ccc(F)c(F)c1] | 1-(3-amino-1H-pyrazolo[4,3-c]-pyridin-6-yl)-3-[1-(3,4-difluorophenyl)-ethyl]urea | Calc'd 333, found 333 | Scheme 2, Example 43 |
| 276 | 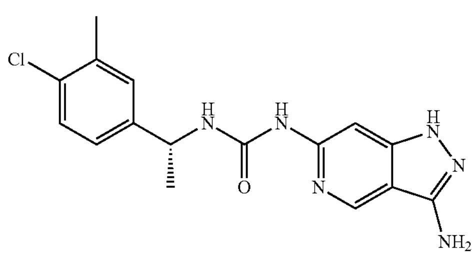 [SMILES: Cc1cc([C@@H](C)NC(=O)Nc2cc3[nH]nc(N)c3cn2)ccc1Cl] | 1-(3-amino-1H-pyrazolo[4,3-c]pyridin-6-yl)-3-[(1R)-1-(4-chloro-3-methylphenyl)-ethyl]urea | Calc'd 345, found 345 | Scheme 2, Example 43 |
| 277 | 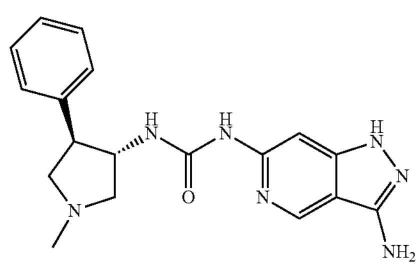 [SMILES: CN1C[C@@H](NC(=O)Nc2cc3[nH]nc(N)c3cn2)[C@H](c2ccccc2)C1] | 1-(3-amino-1H-pyrazolo[4,3-c]pyridin-6-yl)-3-[(3S,4R)-1-methyl-4-phenylpyrrolidin-3-yl]urea | Calc'd 352, found 352 | Scheme 2, Example 43 |

-continued

| No. | Structure | IUPAC Name | Exact Mass [M + H]+ | Route Used |
|---|---|---|---|---|
| 278 | 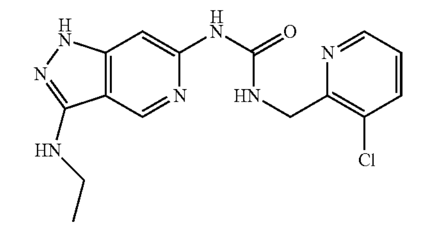 [SMILES: CCNc1n[nH]c2cc(NC(=O)NCc3ncccc3Cl)ncc12] | 1-[(3-chloro-pyridin-2-yl)-methyl]-3-[3-(ethylamino)-1H-pyrazolo[4,3-c]-pyridin-6-yl]urea | Calc'd 346, found 346 | Scheme 13, Example 320 |
| 279 | 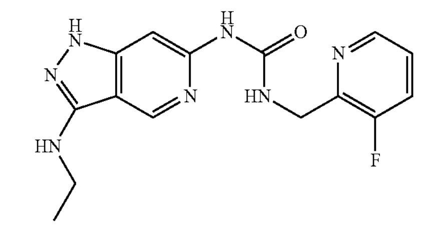 [SMILES: CCNc1n[nH]c2cc(NC(=O)NCc3ncccc3F)ncc12] | 1-[3-(ethylamino)-1H-pyrazolo[4,3-c]pyridin-6-yl]-3-[(3-fluoropyridin-2-yl)methyl]urea | Calc'd 330, found 330 | Scheme 13, Example 320 |
| 280 | 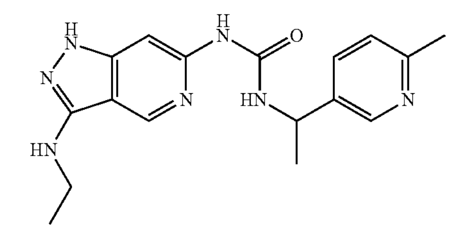 [SMILES: CCNc1n[nH]c2cc(NC(=O)NC(C)c3ccc(C)nc3)ncc12] | 1-[3-(ethylamino)-1H-pyrazolo[4,3-c]pyridin-6-yl]-3-[1-(6-methyl-pyridin-3-yl)-ethyl]urea | Calc'd 340, found 340 | Scheme 13, Example 320 |
| 281 | 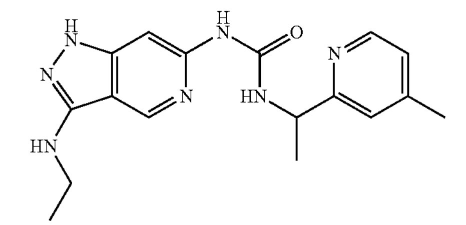 [SMILES: CCNc1n[nH]c2cc(NC(=O)NC(C)c3cc(C)ccn3)ncc12] | 1-[3-(ethylamino)-1H-pyrazolo[4,3-c]pyridin-6-yl]-3-[1-(4-methyl-pyridin-2-yl)-ethyl]urea | Calc'd 340, found 340 | Scheme 13, Example 320 |
| 282 | 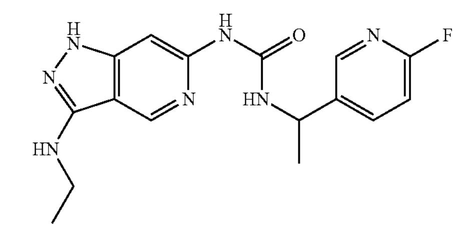 [SMILES: CCNc1n[nH]c2cc(NC(=O)NC(C)c3ccc(F)nc3)ncc12] | 1-[3-(ethylamino)-1H-pyrazolo[4,3-c]pyridin-6-yl]-3-[1-(6-fluoropyridin-3-yl)ethyl]urea | Calc'd 344, found 344 | Scheme 13, Example 320 |
| 283 | 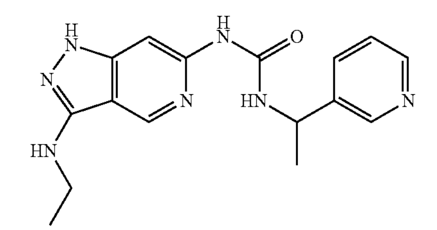 [SMILES: CCNc1n[nH]c2cc(NC(=O)NC(C)c3cccnc3)ncc12] | 1-[3-(ethylamino)-1H-pyrazolo[4,3-c]pyridin-6-yl]-3-(1-pyridin-3-ylethyl)urea | Calc'd 326, found 326 | Scheme 13, Example 320 |

-continued

| No. | Structure | IUPAC Name | Exact Mass [M + H]+ | Route Used |
|---|---|---|---|---|
| 284 | 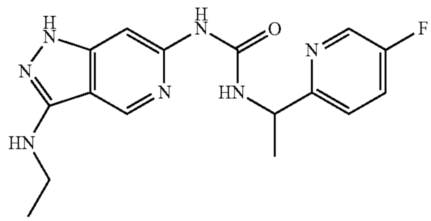 [SMILES: CCNc1n[nH]c2cc(NC(=O)NC(C)c3ccc(F)cn3)ncc12] | 1-[3-(ethylamino)-1H-pyrazolo[4,3-c]pyridin-6-yl]-3-[1-(5-fluoropyridin-2-yl)ethyl]urea | Calc'd 344, found 344 | Scheme 13, Example 320 |
| 285 | 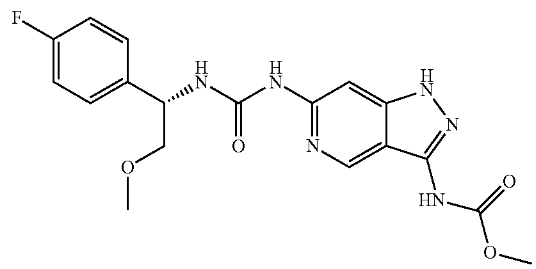 [SMILES: COC[C@@H](NC(=O)Nc1cc2[nH]nc(NC(=O)OC)c2cn1)c1ccc(F)cc1] | methyl [6-({[(1S)-1-(4-fluorophenyl)-2-methoxyethyl]carbamoyl}amino)-1H-pyrazolo[4,3-c]pyridin-3-yl]carbamate | Calc'd 403, found 403 | Scheme 14, Example 321 |
| 286 | 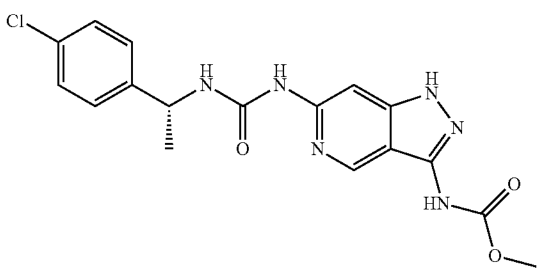 [SMILES: COC(=O)Nc1n[nH]c2cc(NC(=O)N[C@H](C)c3ccc(Cl)cc3)ncc12] | methyl [6-({[(1R)-1-(4-chlorophenyl)ethyl]carbamoyl}amino)-1H-pyrazolo[4,3-c]pyridin-3-yl]carbamate | Calc'd 389, found 389 | Scheme 14, Example 321 |
| 287 | 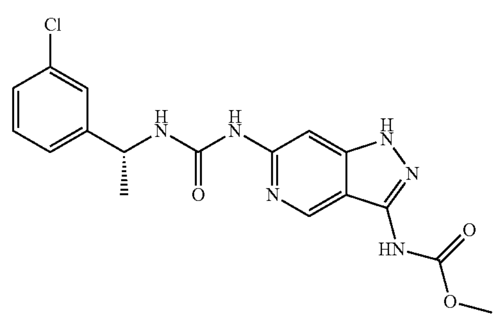 | methyl [6-({[(1R)-1-(3-chlorophenyl)ethyl]carbamoyl}amino)-1H-pyrazolo[4,3-c]pyridin-3-yl]carbamate | Calc'd 389, found 389 | Scheme 14, Example 321 |
| 288 | 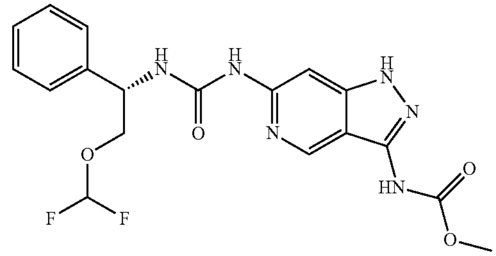 [SMILES: COC(=O)Nc1n[nH]c2cc(NC(=O)N[C@H](COC(F)F)c3ccccc3)ncc12] | methyl [6-({[(1S)-2-(difluoromethoxy)-1-phenylethyl]carbamoyl}amino)-1H-pyrazolo[4,3-c]pyridin-3-yl]carbamate | Calc'd 421, found 421 | Scheme 14, Example 321 |

| No. | Structure | IUPAC Name | Exact Mass [M + H]+ | Route Used |
|---|---|---|---|---|
| 289 | 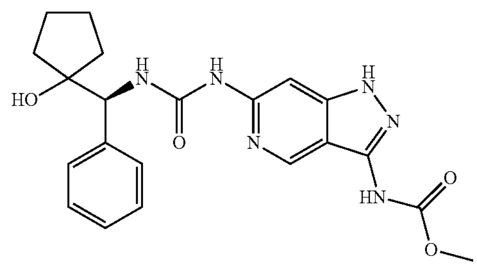 [SMILES: COC(=O)Nc1n[nH]c2cc(NC(=O)N[C@@H](c3ccccc3)C3(O)CCCC3)ncc12] | methyl [6-({[(S)-(1-hydroxycyclopentyl)(phenyl)-methyl]carbamoyl}amino)-1H-pyrazolo[4,3-c]-pyridin-3-yl]-carbamate | Calc'd 425, found 425 | Scheme 14, Example 321 |
| 290 | 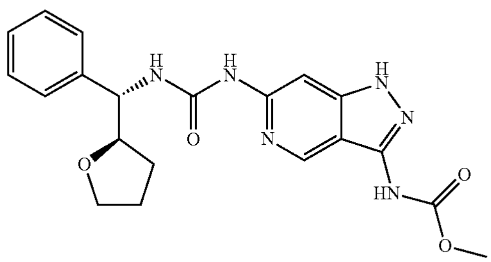 [SMILES: COC(=O)Nc1n[nH]c2cc(NC(=O)N[C@@H](c3ccccc3)[C@H]3CCCO3)ncc12] | methyl {6-[({(S)-phenyl[(2R)-tetrahydrofuran-2-yl]-methyl}carbamoyl)amino]-1H-pyrazolo[4,3-c]-pyridin-3-yl}-carbamate | Calc'd 411, found 411 | Scheme 14, Example 321 |
| 291 | 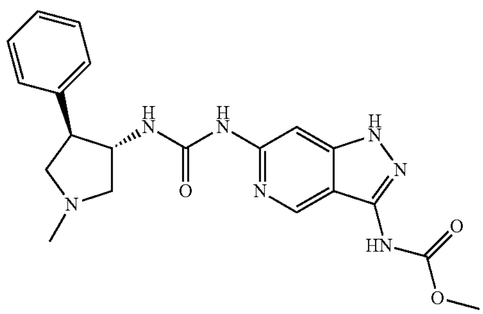 [SMILES: COC(=O)Nc1n[nH]c2cc(NC(=O)N[C@@H]3CN(C)C[C@H]3c3ccccc3)ncc12] | methyl[6-({[(3S,4R)-1-methyl-4-phenyl-pyrrolidin-3-yl]carbamoyl}-amino)-1H-pyrazolo[4,3-c]pyridin-3-yl]-carbamate | Calc'd 410, found 410 | Scheme 14, Example 321 |
| 292 | 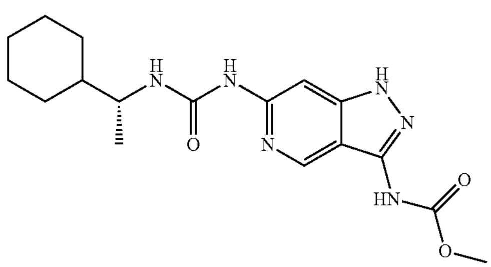 [SMILES: COC(=O)Nc1n[nH]c2cc(NC(=O)N[C@H](C)C3CCCCC3)ncc12] | methyl [6-({[(1R)-1-cyclohexylethyl]-carbamoyl}amino)-1H-pyrazolo[4,3-c]pyridin-3-yl]-carbamate | Calc'd 361, found 361 | Scheme 14, Example 321 |
| 293 | 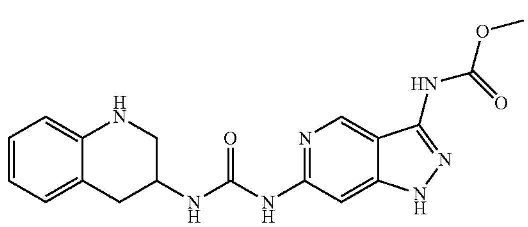 [SMILES: COC(=O)Nc1n[nH]c2cc(NC(=O)NC3CNc4ccccc4C3)ncc12] | methyl {6-[(1,2,3,4-tetrahydroquinolin-3-ylcarbamoyl)-amino]-1H-pyrazolo[4,3-c]-pyridin-3-yl}-carbamate | Calc'd 382, found 382 | Scheme 14, Example 321 |
| 294 | 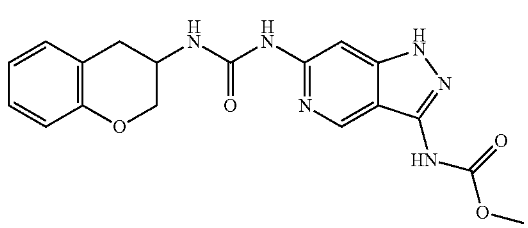 [SMILES: COC(=O)Nc1n[nH]c2cc(NC(=O)NC3COc4ccccc4C3)ncc12] | methyl {6-[(3,4-dihydro-2H-chromen-3-ylcarbamoyl)amino]-1H-pyrazolo[4,3-c]pyridin-3-yl}-carbamate | Calc'd 383, found 383 | Scheme 14, Example 321 |

-continued

| No. | Structure | IUPAC Name | Exact Mass [M + H]+ | Route Used |
|---|---|---|---|---|
| 295 | 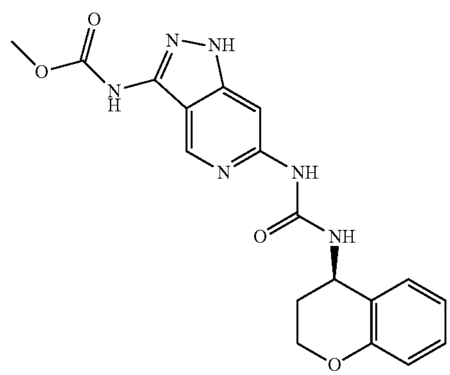 [SMILES: COC(=O)Nc1n[nH]c2cc(NC(=O)N[C@@H]3CCOc4ccccc43)ncc12] | methyl (6-{[(4R)-3,4-dihydro-2H-chromen-4-ylcarbamoyl]-amino}-1H-pyrazolo[4,3-c]-pyridin-3-yl)-carbamate | Calc'd 383, found 383 | Scheme 14, Example 321 |
| 296 | 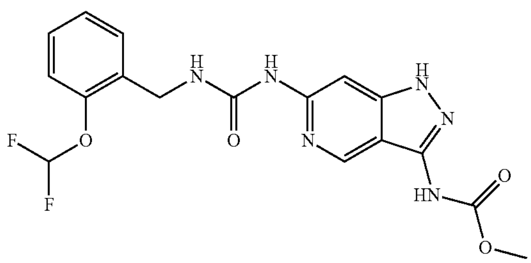 [SMILES: COC(=O)Nc1n[nH]c2cc(NC(=O)NCc3ccccc3OC(F)F)ncc12] | methyl [6-({[2-(difluoromethoxy)-benzyl]carbamoyl}-amino)-1H-pyrazolo[4,3-c]-pyridin-3-yl]-carbamate | Calc'd 407, found 407 | Scheme 14, Example 321 |
| 297 | 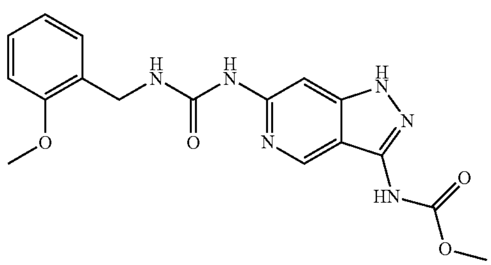 [SMILES: COC(=O)Nc1n[nH]c2cc(NC(=O)NCc3ccccc3OC)ncc12] | methyl (6-{[(2-methoxybenzyl)-carbamoyl]amino}-1H-pyrazolo[4,3-c]pyridin-3-yl)-carbamate | Calc'd 371, found 371 | Scheme 14, Example 321 |
| 298 | 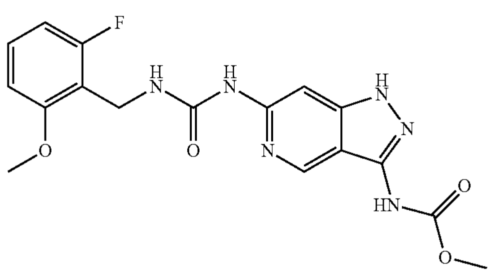 [SMILES: COC(=O)Nc1n[nH]c2cc(NC(=O)NCc3c(F)cccc3OC)ncc12] | methyl (6-{[(2-fluoro-6-methoxy-benzyl)carbamoyl]-amino}-1H-pyrazolo[4,3-c]-pyridin-3-yl)-carbamate | Calc'd 389, found 389 | Scheme 14, Example 321 |
| 299 | 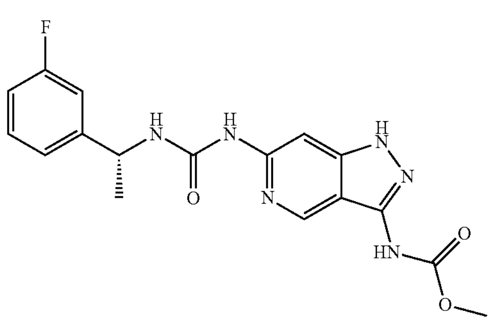 [SMILES: COC(=O)Nc1n[nH]c2cc(NC(=O)N[C@H](C)c3cccc(F)c3)ncc12] | methyl [6-({[(1R)-1-(3-fluorophenyl)-ethyl]carbamoyl}-amino)-1H-pyrazolo[4,3-c]-pyridin-3-yl}-carbamate | Calc'd 373, found 373 | Scheme 14, Example 321 |

| No. | Structure | IUPAC Name | Exact Mass [M + H]+ | Route Used |
|---|---|---|---|---|
| 300 | 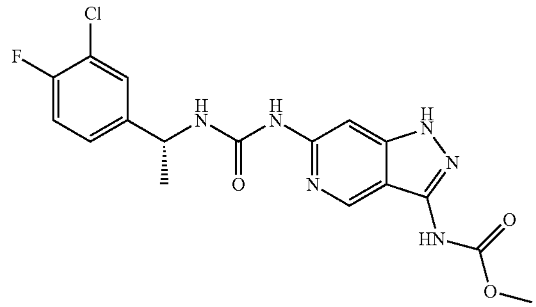 [SMILES: COC(=O)Nc1n[nH]c2cc(NC(=O)N[C@H](C)c3ccc(F)c(Cl)c3)ncc12] | methyl [6-({[(1R)-1-(3-chloro-4-fluorophenyl)ethyl]carbamoyl}amino)-1H-pyrazolo[4,3-c]pyridin-3-yl]-carbamate | Calc'd 407, found 407 | Scheme 14, Example 321 |
| 301 | 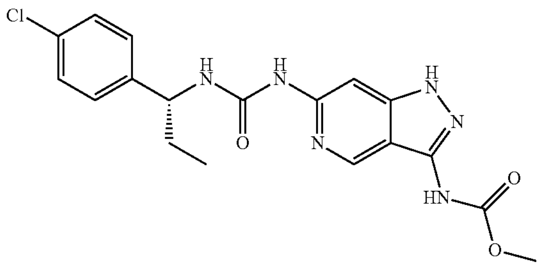 [SMILES: CC[C@@H](NC(=O)Nc1cc2[nH]nc(NC(=O)OC)c2cn1)c1ccc(Cl)cc1] | methyl [6-({[(1R)-1-(4-chlorophenyl)-propyl]carbamoyl}amino)-1H-pyrazolo[4,3-c]-pyridin-3-yl]-carbamate | Calc'd 403, found 403 | Scheme 14, Example 321 |
| 302 | 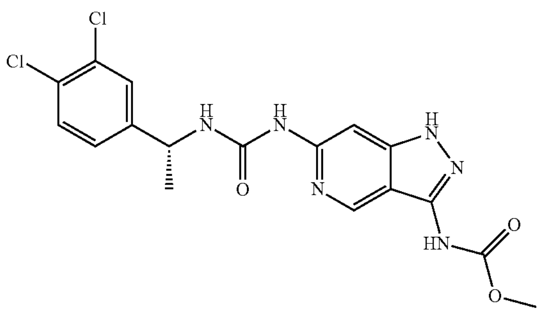 [SMILES: COC(=O)Nc1n[nH]c2cc(NC(=O)N[C@H](C)c3ccc(Cl)c(Cl)c3)ncc12] | methyl [6-({[(1R)-1-(3,4-dichloro-phenyl)ethyl]-carbamoyl}amino)-1H-pyrazolo[4,3-c]pyridin-3-yl]-carbamate | Calc'd 423, found 423 | Scheme 14, Example 321 |
| 303 | 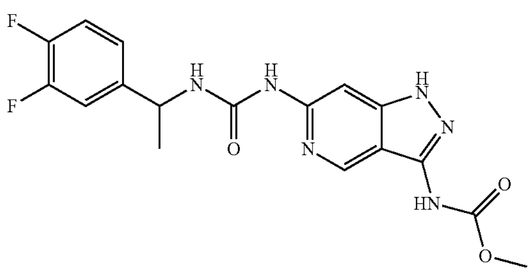 [SMILES: COC(=O)Nc1n[nH]c2cc(NC(=O)NC(C)c3ccc(F)c(F)c3)ncc12] | methyl [6-({[1-(3,4-difluoro-phenyl)ethyl]-carbamoyl}amino)-1H-pyrazolo[4,3-c]pyridin-3-yl]-carbamate | Calc'd 391, found 391 | Scheme 14, Example 321 |
| 304 | 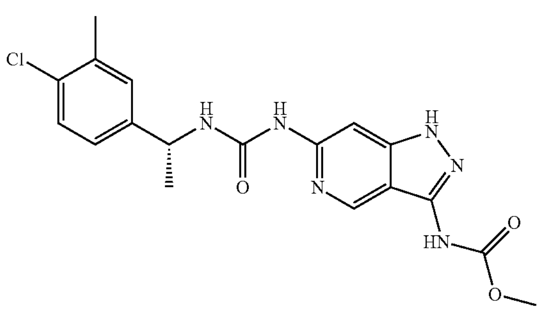 [SMILES: COC(=O)Nc1n[nH]c2cc(NC(=O)N[C@H](C)c3ccc(Cl)c(C)c3)ncc12] | methyl [6-({[(1R)-1-(4-chloro-3-methyl-phenyl)ethyl]-carbamoyl}amino)-1H-pyrazolo[4,3-c]pyridin-3-yl]-carbamate | Calc'd 403, found 403 | Scheme 14, Example 321 |

-continued

| No. | Structure | IUPAC Name | Exact Mass [M + H]+ | Route Used |
|---|---|---|---|---|
| 305 | 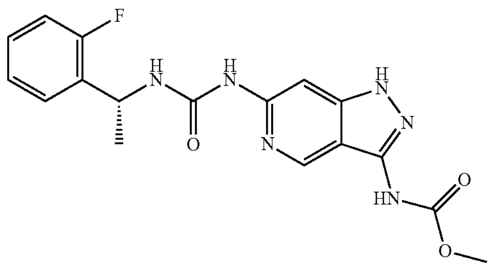 [SMILES: COC(=O)Nc1n[nH]c2cc(NC(=O)N[C@H](C)c3ccccc3F)ncc12] | methyl [6-({[(1R)-1-(2-fluorophenyl)-ethyl]carbamoyl}-amino)-1H-pyrazolo[4,3-c]-pyridin-3-yl]-carbamate | Calc'd 373, found 373 | Scheme 14, Example 321 |
| 306 | 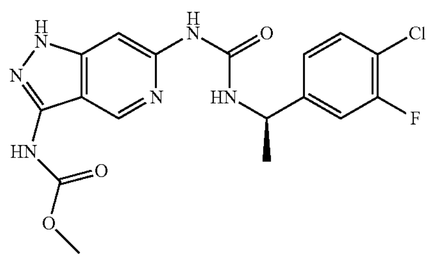 [SMILES: COC(=O)Nc1n[nH]c2cc(NC(=O)N[C@H](C)c3ccc(Cl)c(F)c3)ncc12] | methyl [6-({[(1R)-1-(4-chloro-3-fluorophenyl)ethyl]carbamoyl}amino)-1H-pyrazolo[4,3-c]pyridin-3-yl]-carbamate | Calc'd 407, found 407 | Scheme 15, Example 322 |
| 307 | 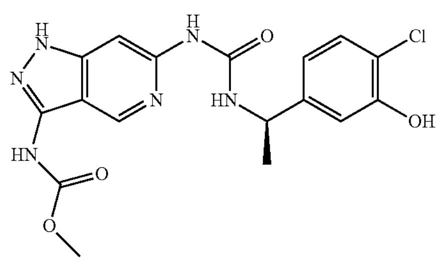 [SMILES: COC(=O)Nc1n[nH]c2cc(NC(=O)N[C@H](C)c3ccc(Cl)c(O)c3)ncc12] | methyl [6-({[(1R)-1-(4-chloro-3-hydroxyphenyl)-ethyl]carbamoyl}-amino)-1H-pyrazolo[4,3-c]-pyridin-3-yl]-carbamate | Calc'd 405, found 405 | Scheme 15, Example 322 |
| 308 | 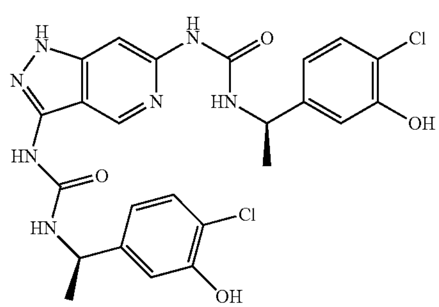 [SMILES: C[C@@H](NC(=O)Nc1cc2[nH]nc(NC(=O)N[C@H](C)c3ccc(Cl)c(O)c3)c2cn1)c1ccc(Cl)c(O)c1] | N',N'''-1H-pyrazolo[4,3-c]-pyridine-3,6-diylbis{1-[(1R)-1-(4-chloro-3-hydroxyphenyl)-ethyl]urea} | Calc'd 544, found 544 | Scheme 15, Example 322 |
| 309 | 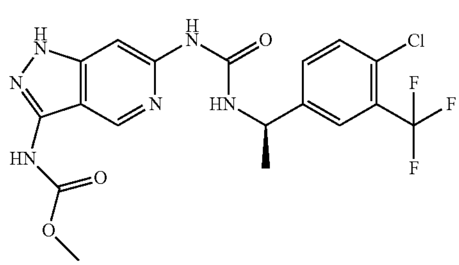 [SMILES: COC(=O)Nc1n[nH]c2cc(NC(=O)N[C@H](C)c3ccc(Cl)c(C(F)(F)F)c3)ncc12] | methyl {6-[({(1R)-1-[4-chloro-3-(trifluoromethyl)-phenyl]ethyl}-carbamoyl)amino]-1H-pyrazolo[4,3-c]pyridin-3-yl}-carbamate | Calc'd 457, found 457 | Scheme 15, Example 322 |

| No. | Structure | IUPAC Name | Exact Mass [M + H]+ | Route Used |
|---|---|---|---|---|
| 310 | 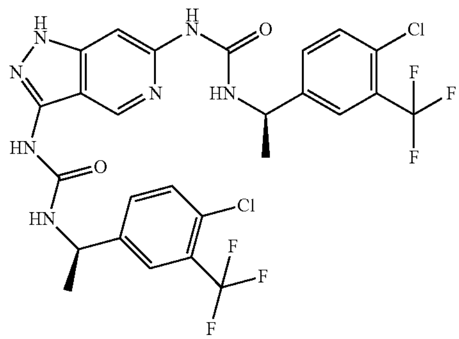 [SMILES: C[C@@H](NC(=O)Nc1cc2[nH]nc(NC(=O)N[C@H](C)c3ccc(Cl)c(C(F)(F)F)c3)c2cn1)c1ccc(Cl)c(C(F)(F)F)c1] | N',N'''-1H-pyrazolo[4,3-c]-pyridine-3,6-diylbis(1-{(1R)-1-[4-chloro-3-(trifluoromethyl)-phenyl]ethyl}urea) | Calc'd 648, found 648 | Scheme 15, Example 314 |
| 311 | 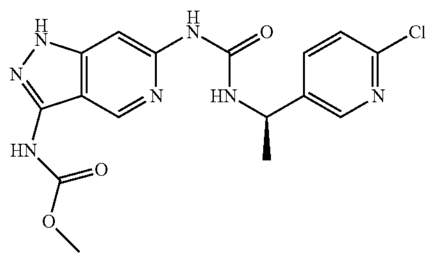 [SMILES: COC(=O)Nc1n[nH]c2cc(NC(=O)N[C@H](C)c3ccc(Cl)nc3)ncc12] | methyl [6-({[(1R)-1-(6-chloropyridin-3-yl)ethyl]-carbamoyl}amino)-1H-pyrazolo[4,3-c]pyridin-3-yl]-carbamate | Calc'd 390, found 390 | Scheme 15, Example 322 |
| 312 | 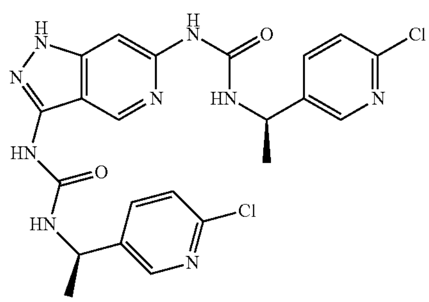 [SMILES: C[C@@H](NC(=O)Nc1cc2[nH]nc(NC(=O)N[C@H](C)c3ccc(Cl)nc3)c2cn1)c1ccc(Cl)nc1] | N',N'''-1H-pyrazolo[4,3-c]pyridine-3,6-diylbis{1-[(1R)-1-(6-chloropyridin-3-yl)ethyl]urea} | Calc'd 514, found 514 | Scheme 15, Example 314 |
| 313 | 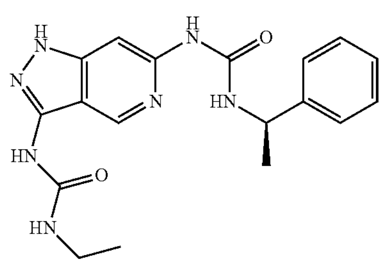 [SMILES: CCNC(=O)Nc1n[nH]c2cc(NC(=O)N[C@H](C)c3ccccc3)ncc12] | (R)-1-(3-(3-ethylureido)-1H-pyrazolo[4,3-c]pyridin-6-yl)-3-(1-phenylethyl)urea | Calc'd 368, found 368 | Example 313 |
| 314 | 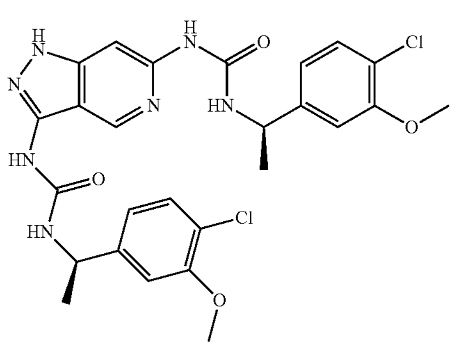 [SMILES: COc1cc([C@@H](C)NC(=O)Nc2cc3[nH]nc(NC(=O)N[C@H](C)c4ccc(Cl)c(OC)c4)c3cn2)ccc1Cl] | 1,1'-(1H-pyrazolo[4,3-c]pyridine-3,6-diyl)bis(3-((R)-1-(4-chloro-3-methoxyphenyl)-ethyl)urea) | Calc'd 572.4, found 572 | Example 314 |

-continued

| No. | Structure | IUPAC Name | Exact Mass [M + H]+ | Route Used |
|---|---|---|---|---|
| 315 | 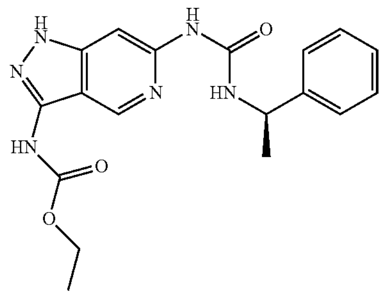 [SMILES: CCOC(=O)Nc1n[nH]c2cc(NC(=O)N[C@H](C)c3ccccc3)ncc12] | (R)-ethyl (6-(3-(1-phenylethyl)ureido)-1H-pyrazolo[4,3-c]pyridin-3-yl)-carbamate | Calc'd 369, found 369 | Example 315 |
| 316 | 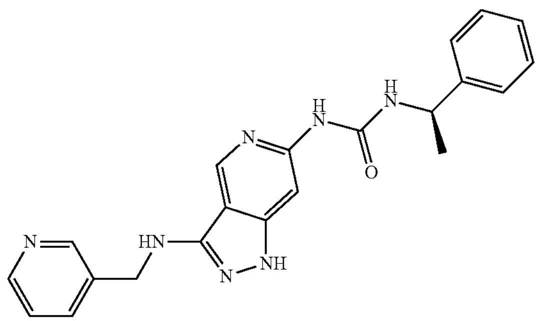 [SMILES: C[C@@H](NC(=O)Nc1cc2[nH]nc(NCc3cccnc3)c2cn1)c1ccccc1] | (R)-1-(1-phenylethyl)-3-(3-((pyridin-3-yl-methyl)amino)-1H-pyrazolo[4,3-c]-pyridin-6-yl)urea | Calc'd 388, found 388 | Example 316 |
| 317 | 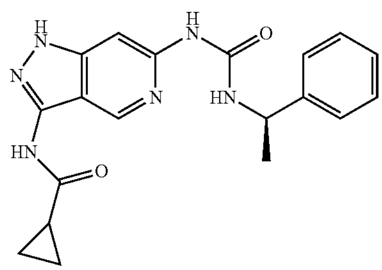 [SMILES: C[C@@H](NC(=O)Nc1cc2[nH]nc(NC(=O)C3CC3)c2cn1)c1ccccc1] | (R)-N-(6-(3-(1-phenylethyl)ureido)-1H-pyrazolo[4,3-c]pyridin-3-yl)-cyclopropane-carboxamide | Calc'd 365, found 365 | Example 317 |
| 318 | 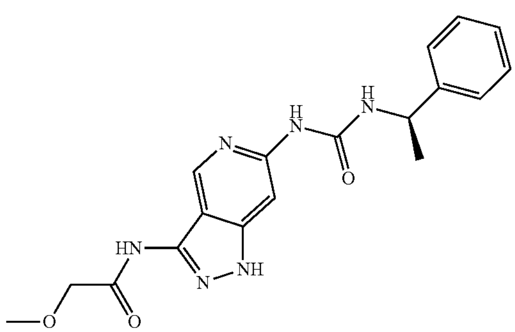 [SMILES: COCC(=O)Nc1n[nH]c2cc(NC(=O)N[C@H](C)c3ccccc3)ncc12] | (R)-2-methoxy-N-(6-(3-(1-phenyl-ethyl)ureido)-1H-pyrazolo[4,3-c]-pyridin-3-yl)-acetamide | Calc'd 369, found 369 | Example 318 |
| 319 | 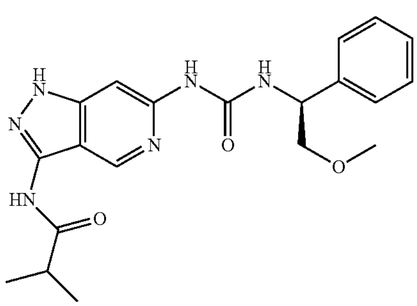 [SMILES: COC[C@@H](NC(=O)Nc1cc2[nH]nc(NC(=O)C(C)C)c2cn1)c1ccccc1] | (S)-N-(6-(3-(2-methoxy-1-phenylethyl)ureido)-1H-pyrazolo[4,3-c]pyridin-3-yl)-isobutyramide | Calc'd 397, found 397 | Scheme 11, Example 317 |

-continued

| No. | Structure | IUPAC Name | Exact Mass [M + H]+ | Route Used |
|---|---|---|---|---|
| 320 | 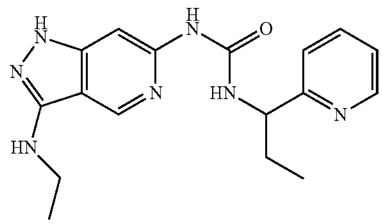 [SMILES: CCNc1n[nH]c2cc(NC(=O)NC(CC)c3ccccn3)ncc12] | 1-(3-(ethylamino)-1H-pyrazolo[4,3-c]pyridin-6-yl)-3-(1-(pyridin-2-yl)propyl)urea | Calc'd 340, found 340 | Example 320 |
| 321 | 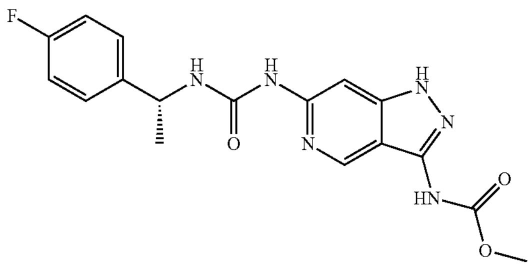 [SMILES: COC(=O)Nc1n[nH]c2cc(NC(=O)N[C@H](C)c3ccc(F)cc3)ncc12] | (R)-methyl (6-(3-(1-(4-fluorophenyl)ethyl)-ureido)-1H-pyrazolo[4,3-c]-pyridin-3-yl)-carbamate | Calc'd 373, found 373 | Example 321 |
| 322 | 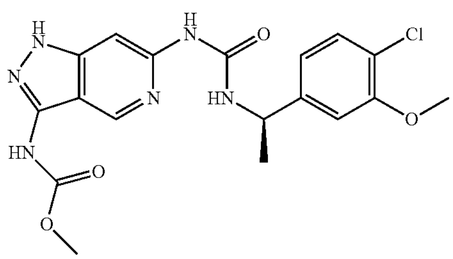 [SMILES: COC(=O)Nc1n[nH]c2cc(NC(=O)N[C@H](C)c3ccc(Cl)c(OC)c3)ncc12] | (R)-methyl (6-(3-(1-(4-chloro-3-methoxyphenyl)-ethyl)ureido)-1H-pyrazolo[4,3-c]-pyridin-3-yl)-carbamate | Calc'd 420, found 420 | Example 322 |
| 323 | 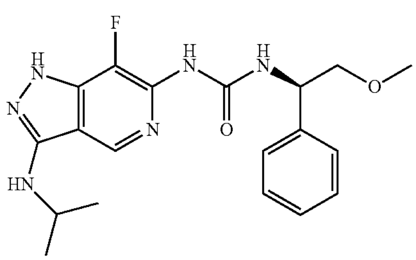 [SMILES: COC[C@H](NC(=O)Nc1ncc2c(NC(C)C)n[nH]c2c1F)c1ccccc1] | 1-{7-fluoro-3-[(1-methylethyl)amino]-1H-pyrazolo[4,3-c]pyridin-6-yl}-3-[(1R)-2-methoxy-1-phenylethyl]urea | Calc'd 387, found 387 | Scheme 5 |
| 324 | 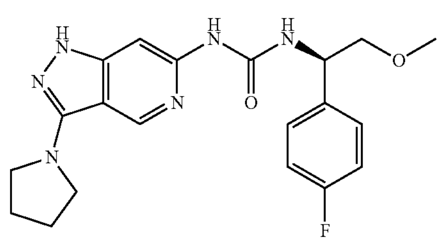 [SMILES: COC[C@H](NC(=O)Nc1cc2[nH]nc(N3CCCC3)c2cn1)c1ccc(F)cc1] | 1-[(1R)-1-(4-fluorophenyl)-2-methoxyethyl]-3-(3-pyrrolidin-1-yl-1H-pyrazolo[4,3-c]pyridin-6-yl)urea | Calc'd 399, found 399 | Scheme 1 |
| 325 | 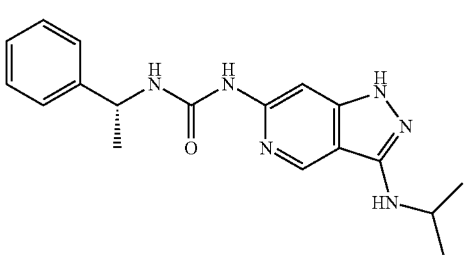 [SMILES: CC(C)Nc1n[nH]c2cc(NC(=O)N[C@H](C)c3ccccc3)ncc12] | 1-{3-[(1-methylethyl)amino]-1H-pyrazolo[4,3-c]-pyridin-6-yl}-3-[(1R)-1-phenylethyl]urea | Calc'd 339, found 339 | Scheme 1 |

-continued

| No. | Structure | IUPAC Name | Exact Mass [M + H]+ | Route Used |
|---|---|---|---|---|
| 326 | 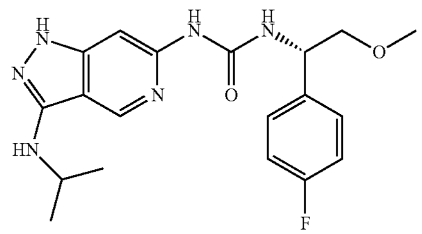 [SMILES: COC[C@@H](NC(=O)Nc1cc2[nH]nc(NC(C)C)c2cn1)c1ccc(F)cc1] | 1-[(1S)-1-(4-fluorophenyl)-2-methoxyethyl]-3-{3-[(1-methylethyl)amino]-1H-pyrazolo[4,3-c]-pyridin-6-yl}urea | Calc'd 387, found 387 | Scheme 1 |
| 327 | 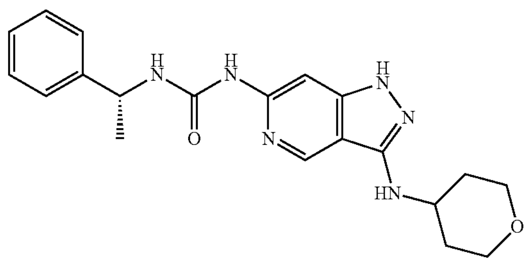 [SMILES: C[C@@H](NC(=O)Nc1cc2[nH]nc(NC3CCOCC3)c2cn1)c1ccccc1] | 1-[(1R)-1-phenylethyl]-3-[3-(tetrahydro-2H-pyran-4-ylamino)-1H-pyrazolo[4,3-c]pyridin-6-yl]urea | Calc'd 381, found 381 | Scheme 1 |
| 328 | 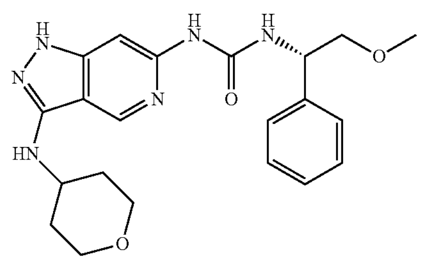 [SMILES: COC[C@@H](NC(=O)Nc1cc2[nH]nc(NC3CCOCC3)c2cn1)c1ccccc1] | 1-[(1S)-2-methoxy-1-phenylethyl]-3-[3-(tetrahydro-2H-pyran-4-ylamino)-1H-pyrazolo[4,3-c]pyridin-6-yl]urea | Calc'd 411, found 411 | Scheme 1 |
| 329 | 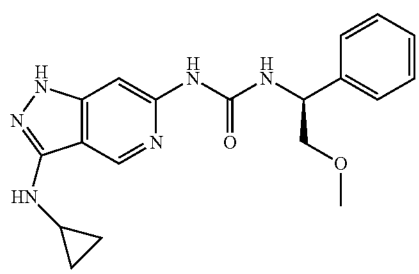 [SMILES: COC[C@@H](NC(=O)Nc1cc2[nH]nc(NC3CC3)c2cn1)c1ccccc1] | 1-[3-(cyclopropyl-amino)-1H-pyrazolo[4,3-c]-pyridin-6-yl]-3-[(1S)-2-methoxy-1-phenylethyl]urea | Calc'd 367, found 367 | Scheme 1 |
| 330 | 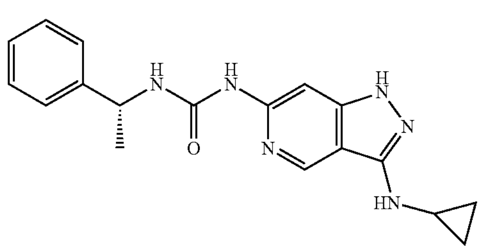 [SMILES: C[C@@H](NC(=O)Nc1cc2[nH]nc(NC3CC3)c2cn1)c1ccccc1] | 1-[3-(cyclopropyl-amino)-1H-pyrazolo[4,3-c]pyridin-6-yl]-3-[(1R)-1-phenylethyl]urea | Calc'd 337, found 337 | Scheme 1 |
| 331 | 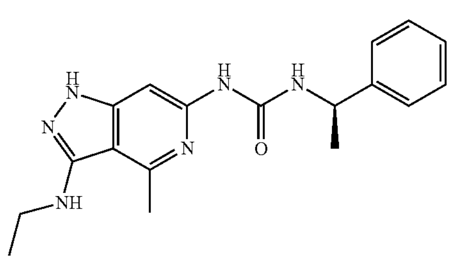 [SMILES: CCNc1n[nH]c2cc(NC(=O)N[C@H](C)c3ccccc3)nc(C)c12] | 1-[3-(ethylamino)-4-methyl-1H-pyrazolo[4,3-c]pyridin-6-yl]-3-[(1R)-1-phenylethyl]urea | Calc'd 339, found 339 | Example 331 |

-continued

| No. | Structure | IUPAC Name | Exact Mass [M + H]+ | Route Used |
|---|---|---|---|---|
| 332 | 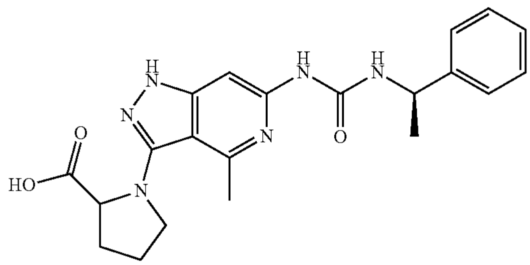 [SMILES: Cc1nc(NC(=O)N[C@H](C)c2ccccc2)cc2[nH]nc(N3CCCC3C(=O)O)c12] | 1-[4-methyl-6-({[(1R)-1-phenyl-ethyl]carbamoyl}-amino)-1H-pyrazolo[4,3-c]-pyridin-3-yl]proline | Calc'd 409, found 409 | Scheme 1 |
| 333 | 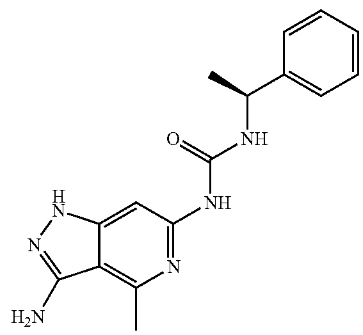 [SMILES: Cc1nc(NC(=O)N[C@@H](C)c2ccccc2)cc2[nH]nc(N)c12] | 1-(3-amino-4-methyl-1H-pyrazolo[4,3-c]-pyridin-6-yl)-3-[(1S)-1-phenylethyl]urea | Calc'd 311, found 311 | Example 333 |
| 334 | 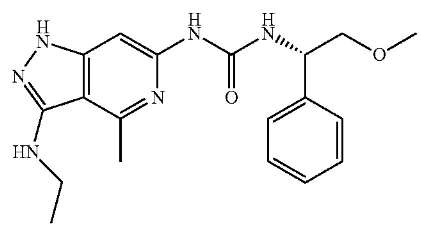 [SMILES: CCNc1n[nH]c2cc(NC(=O)N[C@H](COC)c3ccccc3)nc(C)c12] | 1-[3-(ethylamino)-4-methyl-1H-pyrazolo[4,3-c]-pyridin-6-yl]-3-[(1S)-2-methoxy-1-phenylethyl]urea | Calc'd 369, found 369 | Scheme 1 |
| 335 | 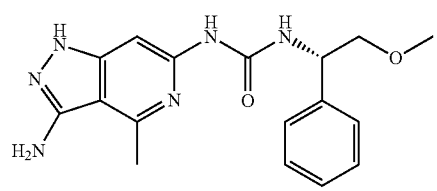 [SMILES: COC[C@@H](NC(=O)Nc1cc2[nH]nc(N)c2c(C)n1)c1ccccc1] | 1-(3-amino-4-methyl-1H-pyrazolo[4,3-c]-pyridin-6-yl)-3-[(1S)-2-methoxy-1-phenylethyl]urea | Calc'd 341, found 341 | Scheme 1 |
| 336 | 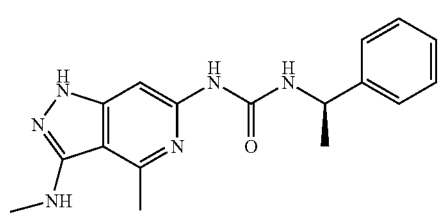 [SMILES: CNc1n[nH]c2cc(NC(=O)N[C@H](C)c3ccccc3)nc(C)c12] | 1-[4-methyl-3-(methylamino)-1H-pyrazolo[4,3-c]pyridin-6-yl]-3-[(1R)-1-phenylethyl]urea | Calc'd 325, found 325 | Similar procedure in Example 331 |
| 337 | 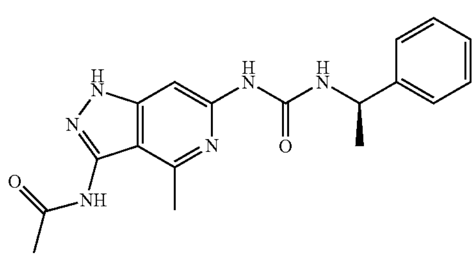 [SMILES: CC(=O)Nc1n[nH]c2cc(NC(=O)N[C@H](C)c3ccccc3)nc(C)c12] | N-[4-methyl-6-({[(1R)-1-phenyl-ethyl]carbamoyl}-amino)-1H-pyrazolo[4,3-c]-pyridin-3-yl]-acetamide | Calc'd 353, found 353 | Example 337 |

-continued

| No. | Structure | IUPAC Name | Exact Mass [M + H]+ | Route Used |
|---|---|---|---|---|
| 338 | 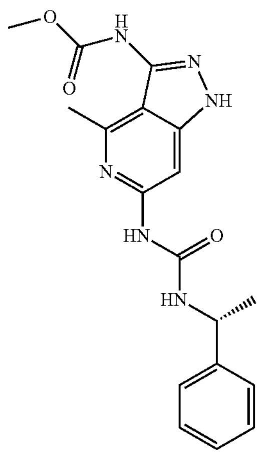 [SMILES: COC(=O)Nc1n[nH]c2cc(NC(=O)N[C@H](C)c3ccccc3)nc(C)c12] | methyl [4-methyl-6-({[(1R)-1-phenyl-ethyl]carbamoyl}-amino)-1H-pyrazolo[4,3-c]-pyridin-3-yl]-carbamate | Calc'd 369, found 369 | Similar procedure in Example 337 |
| 339 | 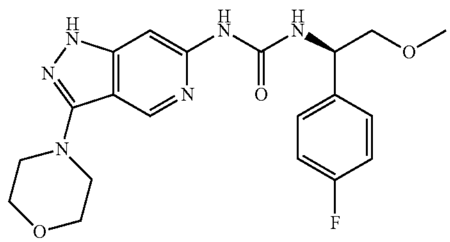 [SMILES: COC[C@H](NC(=O)Nc1cc2[nH]nc(N3CCOCC3)c2cn1)c1ccc(F)cc1] | (R)-1-(1-(4-fluorophenyl)-2-methoxyethyl)-3-(3-morpholino-1H-pyrazolo[4,3-c]-pyridin-6-yl)urea | Calc'd 415, found 415 | Scheme 1, Example 1 |
| 340 | 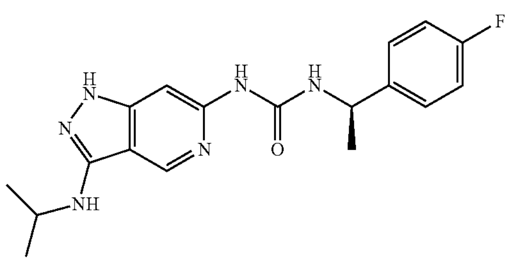 [SMILES: CC(C)Nc1n[nH]c2cc(NC(=O)N[C@H](C)c3ccc(F)cc3)ncc12] | (R)-1-(1-(4-fluorophenyl)ethyl)-3-(3-(isopropyl-amino)-1H-pyrazolo[4,3-c]-pyridin-6-yl)urea | Calc'd 357, found 357 | Scheme 1, Example 1 |
| 341 | 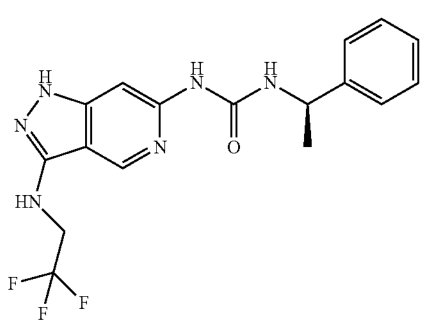 [SMILES: C[C@@H](NC(=O)Nc1cc2[nH]nc(NCC(F)(F)F)c2cn1)c1ccccc1] | 1-[(1R)-1-phenylethyl]-3-{3-[(2,2,2-trifluoro-ethyl)amino]-1H-pyrazolo[4,3-c]-pyridin-6-yl}urea | Calc'd 379, found 379 | Scheme 1, Example 1 |

| No. | Structure | IUPAC Name | Exact Mass [M + H]+ | Route Used |
|---|---|---|---|---|
| 342 | 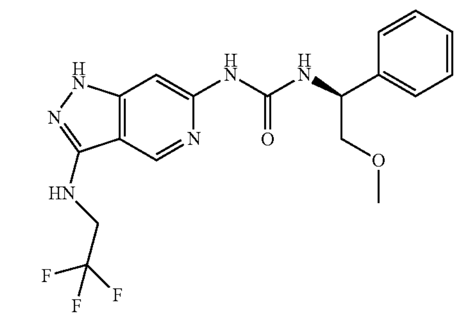 [SMILES: COC[C@@H](NC(=O)Nc1cc2[nH]nc(NCC(F)(F)F)c2cn1)c1ccccc1] | 1-[(1S)-2-methoxy-1-phenylethyl]-3-{3-[(2,2,2-trifluoro-ethyl)amino]-1H-pyrazolo[4,3-c]-pyridin-6-yl}urea | Calc'd 409, found 409 | Scheme 1, Example 1 |
| 343 | 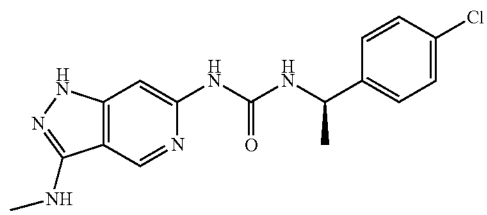 [SMILES: CNc1n[nH]c2cc(NC(=O)N[C@H](C)c3ccc(Cl)cc3)ncc12] | 1-[(1R)-1-(4-chlorophenyl)ethyl]-3-[3-(methyl-amino)-1H-pyrazolo[4,3-c]-pyridin-6-yl]urea | Calc'd 345, found 345 | Scheme 1, Example 1 |
| 344 | 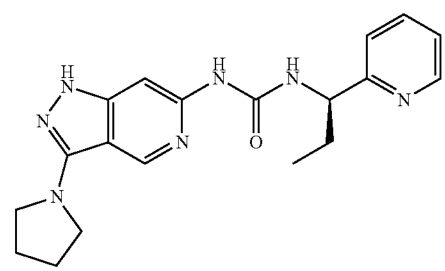 [SMILES: CC[C@@H](NC(=O)Nc1cc2[nH]nc(N3CCCC3)c2cn1)c1ccccn1] | 1-[(1R)-1-pyridin-2-ylpropyl]-3-(3-pyrrolidin-1-yl-1H-pyrazolo[4,3-c]-pyridin-6-yl)urea | Calc'd 366, found 366 | Scheme 1, Example 9 with chrial resolution. |
| 345 | 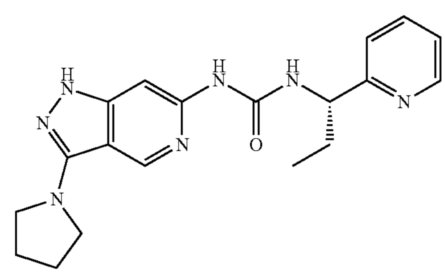 [SMILES: CC[C@H](NC(=O)Nc1cc2[nH]nc(N3CCCC3)c2cn1)c1ccccn1] | 1-[(1S)-1-pyridin-2-ylpropyl]-3-(3-pyrrolidin-1-yl-1H-pyrazolo[4,3-c]-pyridin-6-yl)urea | Calc'd 366, found 366 | Scheme 1, Example 9 with chrial resolution. |
| 346 | 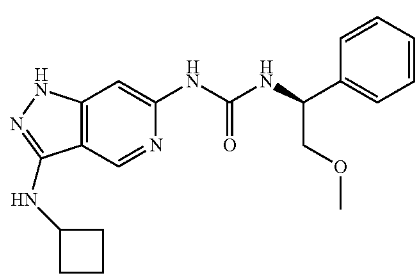 [SMILES: COC[C@@H](NC(=O)Nc1cc2[nH]nc(NC3CCC3)c2cn1)c1ccccc1] | 1-[3-(cyclobutyl-amino)-1H-pyrazolo[4,3-c]-pyridin-6-yl]-3-[(1S)-2-methoxy-1-phenylethyl]urea | Calc'd 381, found 381 | Scheme 1, Example 1 |

-continued

| No. | Structure | IUPAC Name | Exact Mass [M + H]+ | Route Used |
|---|---|---|---|---|
| 347 | 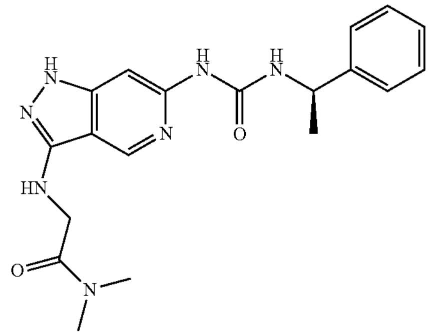 [SMILES: C[C@@H](NC(=O)Nc1cc2[nH]nc(NCC(=O)N(C)C)c2cn1)c1ccccc1] | N,N-dimethyl-N~2~-[6-({[(1R)-1-phenylethyl]-carbamoyl}-amino)-1H-pyrazolo[4,3-c]-pyridin-3-yl]-glycinamide | Calc'd 382, found 382 | Scheme 1, Example 1 |
| 348 | 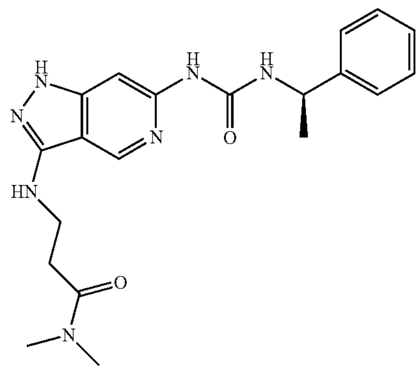 [SMILES: C[C@@H](NC(=O)Nc1cc2[nH]nc(NCCC(=O)N(C)C)c2cn1)c1ccccc1] | N,N-dimethyl-N~3~-[6-({[(1R)-1-phenylethyl]-carbamoyl}amino)-1H-pyrazolo[4,3-c]pyridin-3-yl]-beta-alaninamide | Calc'd 396, found 396 | Scheme 1, Example 1 |
| 349 | 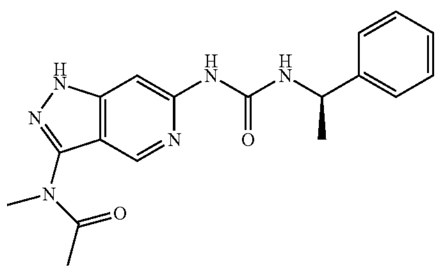 [SMILES: CC(=O)N(C)c1n[nH]c2cc(NC(=O)N[C@H](C)c3ccccc3)ncc12] | N-methyl-N-[6-({[(1R)-1-phenyl-ethyl]carbamoyl}-amino)-1H-pyrazolo[4,3-c]-pyridin-3-yl]-acetamide | Calc'd 353, found 353 | Scheme 5/ Step 1, Example 10 |
| 350 | 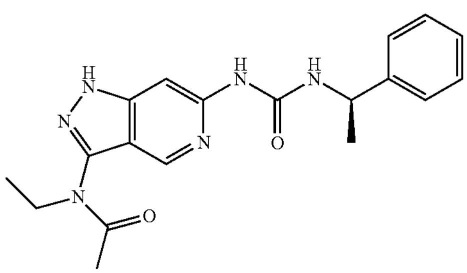 [SMILES: CCN(C(C)=O)c1n[nH]c2cc(NC(=O)N[C@H](C)c3ccccc3)ncc12] | N-ethyl-N-[6-({[(1R)-1-phenyl-ethyl]carbamoyl}-amino)-1H-pyrazolo[4,3-c]-pyridin-3-yl]-acetamide | Calc'd 367, found 367 | Scheme 5/ Step 1, Example 10 |
| 351 | 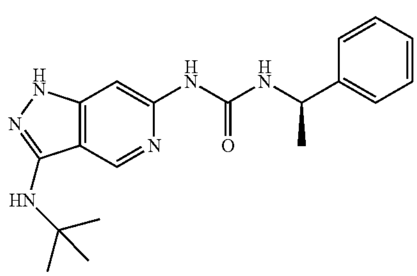 [SMILES: C[C@@H](NC(=O)Nc1cc2[nH]nc(NC(C)(C)C)c2cn1)c1ccccc1] | 1-[3-(tert-butylamino)-1H-pyrazolo[4,3-c]-pyridin-6-yl]-3-[(1R)-1-phenylethyl]urea | Calc'd 353, found 353 | Scheme 1, Example 1 with Intermediate 351A |

-continued

| No. | Structure | IUPAC Name | Exact Mass [M + H]+ | Route Used |
|---|---|---|---|---|
| 352 | 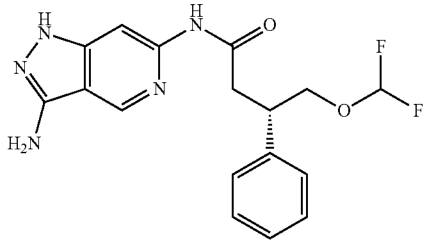 [SMILES: Nc1n[nH]c2cc(NC(=O)C[C@H](COC(F)F)c3ccccc3)ncc12] | 1-(3-amino-1H-pyrazolo[4,3-c]-pyridin-6-yl)-3-[(1S)-2-(difluoromethoxy)-1-phenylethyl]urea | Calc'd 363, found 363 | Scheme 1 Example 1 |
| 353 | 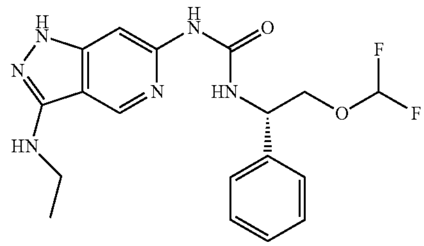 [SMILES: CCNc1n[nH]c2cc(NC(=O)N[C@H](COC(F)F)c3ccccc3)ncc12] | 1-[(1S)-2-(difluoromethoxy)-1-phenylethyl]-3-[3-(ethylamino)-1H-pyrazolo[4,3-c]pyridin-6-yl]urea | Calc'd 391, found 391 | Scheme 1 Example 1 |
| 354 | 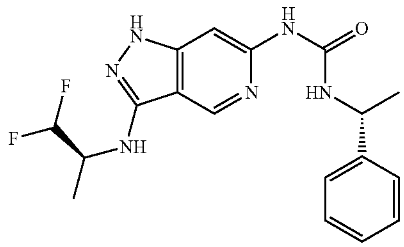 [SMILES: C[C@H](Nc1n[nH]c2cc(NC(=O)N[C@H](C)c3ccccc3)ncc12)C(F)F] | 1-(3-{[(1S)-2,2-difluoro-1-methylethyl]amino}-1H-pyrazolo[4,3-c]-pyridin-6-yl)-3-[(1R)-1-phenylethyl]urea | Calc'd 375, found 375 | Scheme 8, Method A with chrial resolution. |
| 355 | 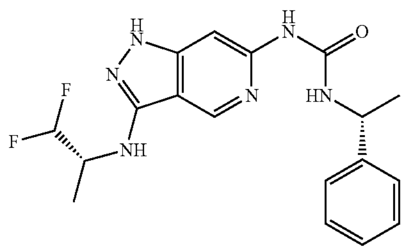 [SMILES: C[C@@H](NC(=O)Nc1cc2[nH]nc(N[C@H](C)C(F)F)c2cn1)c1ccccc1] | 1-(3-{[(1R)-2,2-difluoro-1-methylethyl]amino}-1H-pyrazolo[4,3-c]-pyridin-6-yl)-3-[(1R)-1-phenylethyl]urea | Calc'd 375, found 375 | Scheme 8, Method A with chrial resolution |
| 356 | 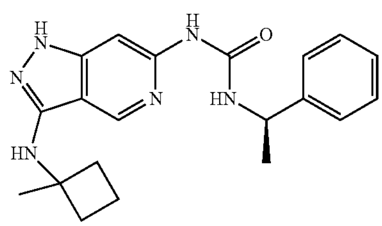 [SMILES: C[C@@H](NC(=O)Nc1cc2[nH]nc(NC3(C)CCC3)c2cn1)c1ccccc1] | 1-{3-[(1-methylcyclobutyl)amino]-1H-pyrazolo[4,3-c]-pyridin-6-yl}-3-[(1R)-1-phenylethyl]urea | Calc'd 365, found 365 | Scheme 1, Example 1 with Intermediate prepared according to procedure of intermediate 351A |
| 357 | 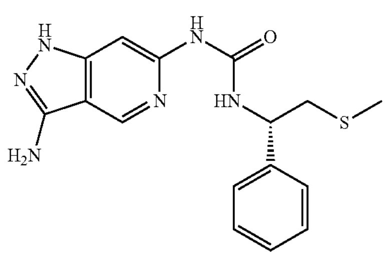 [SMILES: CSC[C@@H](NC(=O)Nc1cc2[nH]nc(N)c2cn1)c1ccccc1] | 1-(3-amino-1H-pyrazolo[4,3-c]-pyridin-6-yl)-3-[(1S)-2-(methylsulfanyl)-1-phenylethyl]urea | Calc'd 343, found 343 | Scheme 1, Example 1 |

| No. | Structure | IUPAC Name | Exact Mass [M + H]+ | Route Used |
|---|---|---|---|---|
| 358 | 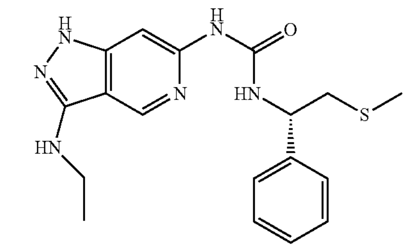 [SMILES: CCNc1n[nH]c2cc(NC(=O)N[C@H](CSC)c3ccccc3)ncc12] | 1-[3-(ethylamino)-1H-pyrazolo[4,3-c]pyridin-6-yl]-3-[(1S)-2-(methylsulfanyl)-1-phenylethyl]urea | Calc'd 371, found 371 | Scheme 1, Example 1 |
| 359 | 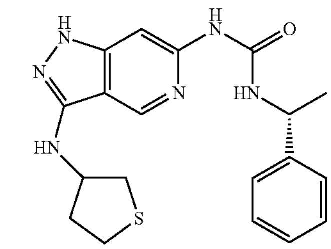 [SMILES: C[C@@H](NC(=O)Nc1cc2[nH]nc(NC3CCSC3)c2cn1)c1ccccc1] | 1-[(1R)-1-phenylethyl]-3-[3-(tetrahydrothiophen-3-ylamino)-1H-pyrazolo[4,3-c]-pyridin-6-yl]urea | Calc'd 383, found 383 | Scheme 8, Method A |
| 360 | 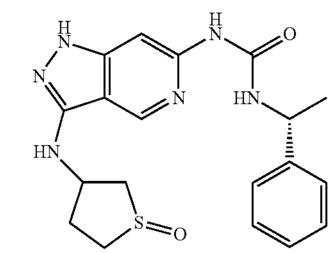 [SMILES: C[C@@H](NC(=O)Nc1cc2[nH]nc(NC3CCS(=O)C3)c2cn1)c1ccccc1] | 1-{3-[(1-oxidotetrahydrothiophen-3-yl)amino]-1H-pyrazolo[4,3-c]pyridin-6-yl}-3-[(1R)-1-phenylethyl]urea | Calc'd 399, found 399 | Scheme 8 Method A (byproduct from Example 359) |
| 361 | 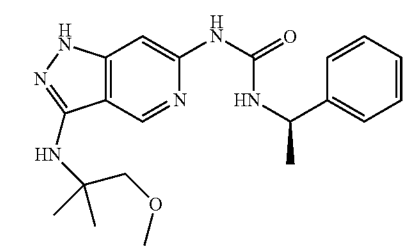 [SMILES: COCC(C)(C)Nc1n[nH]c2cc(NC(=O)N[C@H](C)c3ccccc3)ncc12] | 1-{3-[(2-methoxy-1,1-dimethylethyl)-amino]-1H-pyrazolo[4,3-c]-pyridin-6-yl}-3-[(1R)-1-phenylethyl]urea | Calc'd 383, found 383 | Scheme 1, Example 1 (with Intermediate prepared according to procedure of intermediate 351A) |
| 362 | 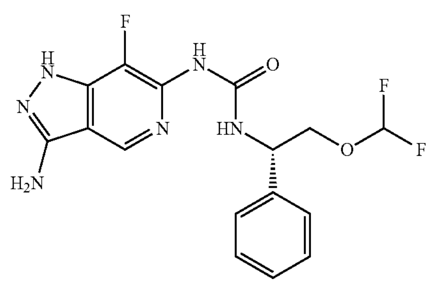 [SMILES: Nc1n[nH]c2c(F)c(NC(=O)N[C@H](COC(F)F)c3ccccc3)ncc12] | 1-(3-amino-7-fluoro-1H-pyrazolo[4,3-c]-pyridin-6-yl)-3-[(1S)-2-(difluoromethoxy)-1-phenylethyl]urea | Calc'd 381, found 381 | Scheme 6, example 5a |
| 363 | 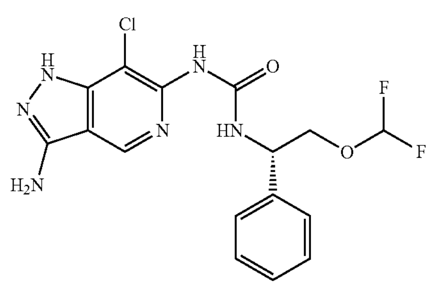 | 1-(3-amino-7-chloro-1H-pyrazolo[4,3-c]pyridin-6-yl)-3-[(1S)-2-(difluoromethoxy)-1-phenylethyl]urea | Calc'd 397, found 397 | Scheme 6, example 5a |

| No. | Structure | IUPAC Name | Exact Mass [M + H]+ | Route Used |
|---|---|---|---|---|
| 364 | 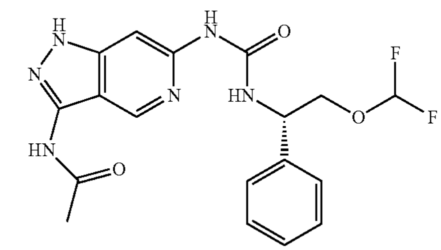 [SMILES: CC(=O)Nc1n[nH]c2cc(NC(=O)N[C@H](COC(F)F)c3ccccc3)ncc12] | N-[6-({[(1S)-2-(difluoromethoxy)-1-phenylethyl]-carbamoyl}amino)-1H-pyrazolo[4,3-c]pyridin-3-yl]-acetamide | Calc'd 405, found 405 | Scheme 3, example 47 |
| 365 | 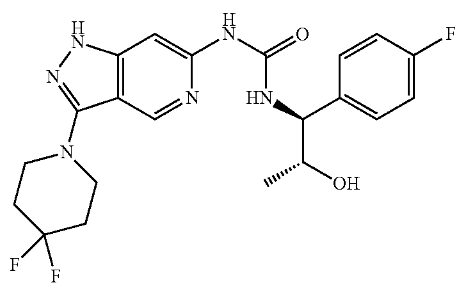 [SMILES: C[C@@H](O)[C@@H](NC(=O)Nc1cc2[nH]nc(N3CCC(F)(F)CC3)c2cn1)c1ccc(F)cc1] | 1-[3-(4,4-difluoropiperidin-1-yl)-1H-pyrazolo[4,3-c]pyridin-6-yl]-3-[(1S,2R)-1-(4-fluorophenyl)-2-hydroxypropyl]urea | Calc'd 449, found 449 | Scheme 1 Example 1 |
| 366 | 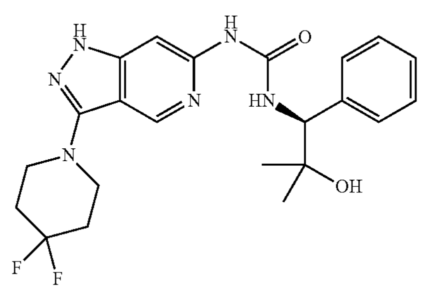 [SMILES: CC(C)(O)[C@@H](NC(=O)Nc1cc2[nH]nc(N3CCC(F)(F)CC3)c2cn1)c1ccccc1] | 1-[3-(4,4-difluoropiperidin-1-yl)-1H-pyrazolo[4,3-c]pyridin-6-yl]-3-[(1S)-2-hydroxy-2-methyl-1-phenylpropyl]urea | Calc'd 445, found 445 | Scheme 1 Example 1 |
| 367 | 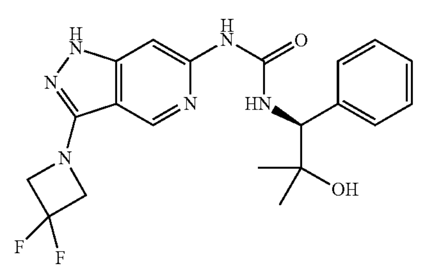 [SMILES: CC(C)(O)[C@@H](NC(=O)Nc1cc2[nH]nc(N3CC(F)(F)C3)c2cn1)c1ccccc1] | 1-[3-(3,3-difluoro-azetidin-1-yl)-1H-pyrazolo[4,3-c]-pyridin-6-yl]-3-[(1S)-2-hydroxy-2-methyl-1-phenylpropyl]urea | Calc'd 417, found 417 | Scheme 1 Example 1 |
| 368 | 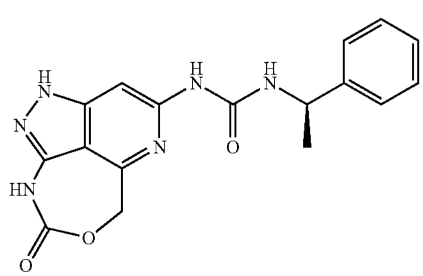 [SMILES: C[C@@H](NC(=O)Nc1cc2[nH]nc3c2c(n1)COC(=O)N3)c1ccccc1] | 1-(8-oxo-2,6,8,9-tetrahydro-7-oxa-1,2,5,9-tetraazabenzo[cd]-azulen-4-yl)-3-[(1R)-1-phenylethyl]urea | Calc'd 353, found 353 | Example 368 |

-continued

| No. | Structure | IUPAC Name | Exact Mass [M + H]+ | Route Used |
|---|---|---|---|---|
| 369 | 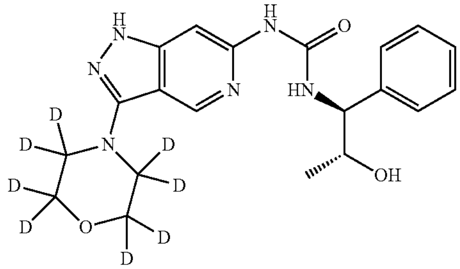 [SMILES: [2H]C1([2H])OC([2H])([2H])C([2H])([2H])N(c2n[nH]c3cc(NC(=O)N[C@@H](c4ccccc4)[C@@H](C)O)ncc23)C1([2H])[2H]] | 1-((1S,2R)-2-hydroxy-1-phenylpropyl)-3-(3-(morpholino-D8)-1H-pyrazolo[4,3-c]pyridin-6-yl)urea | Calc'd 405, found 405 | Scheme 1, Example 1 |
| 370 | 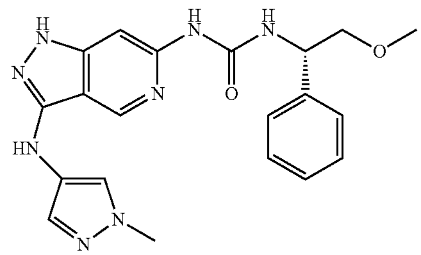 [SMILES: COC[C@@H](NC(=O)Nc1cc2[nH]nc(Nc3cnn(C)c3)c2cn1)c1ccccc1] | 1-[(1S)-2-methoxy-1-phenylethyl]-3-{3-[(1-methyl-1H-pyrazol-4-yl)-amino]-1H-pyrazolo[4,3-c]-pyridin-6-yl}urea | Calc'd 407, found 407 | Scheme 1 |
| 371 | 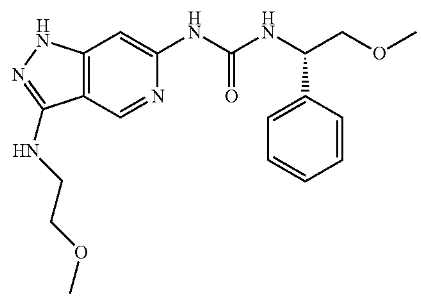 [SMILES: COCCNc1n[nH]c2cc(NC(=O)N[C@H](COC)c3ccccc3)ncc12] | 1-{3-[(2-methoxy-ethyl)amino]-1H-pyrazolo[4,3-c]-pyridin-6-yl}-3-[(1S)-2-methoxy-1-phenylethyl]urea | Calc'd 385, found 385 | Scheme 1 |
| 372 | 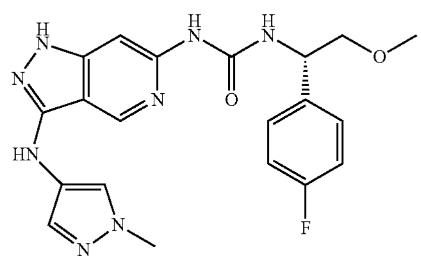 [SMILES: COC[C@@H](NC(=O)Nc1cc2[nH]nc(Nc3cnn(C)c3)c2cn1)c1ccc(F)cc1] | 1-[(1S)-1-(4-fluorophenyl)-2-methoxyethyl]-3-{3-[(1-methyl-1H-pyrazol-4-yl)-amino]-1H-pyrazolo[4,3-c]-pyridin-6-yl}urea | Calc'd 425, found 425 | Scheme 1 |
| 373 | 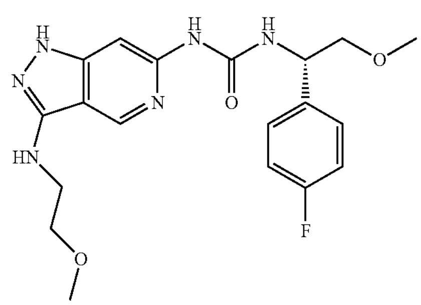 [SMILES: COCCNc1n[nH]c2cc(NC(=O)N[C@H](COC)c3ccc(F)cc3)ncc12] | 1-[(1S)-1-(4-fluorophenyl)-2-methoxyethyl]-3-{3-[(2-methoxy-ethyl)amino]-1H-pyrazolo[4,3-c]-pyridin-6-yl}urea | Calc'd 403, found 403 | Scheme 1 |

| No. | Structure | IUPAC Name | Exact Mass [M + H]+ | Route Used |
|---|---|---|---|---|
| 374 | 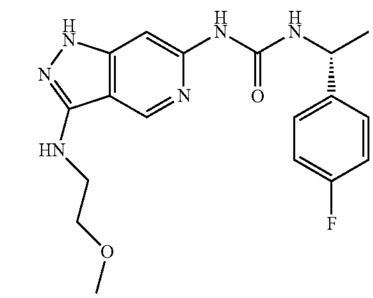 [SMILES: COCCNc1n[nH]c2cc(NC(=O)N[C@H](C)c3ccc(F)cc3)ncc12] | 1-[(1R)-1-(4-fluorophenyl)ethyl]-3-{3-[(2-methoxyethyl)amino]-1H-pyrazolo[4,3-c]pyridin-6-yl}urea | Calc'd 373, found 373 | Scheme 1 |
| 375 | 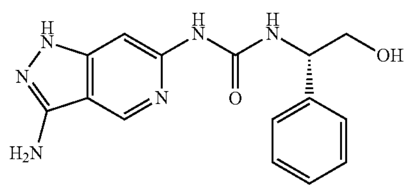 [SMILES: Nc1n[nH]c2cc(NC(=O)N[C@H](CO)c3ccccc3)ncc12] | 1-(3-amino-1H-pyrazolo[4,3-c]pyridin-6-yl)-3-[(1S)-2-hydroxy-1-phenylethyl]urea | Calc'd 313, found 313 | Scheme 2 |
| 376 | 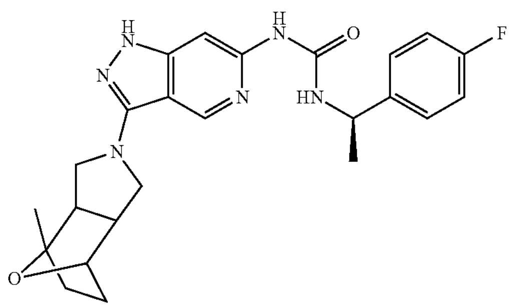 [SMILES: C[C@@H](NC(=O)Nc1cc2[nH]nc(N3CC4C5CCC(C)(O5)C4C3)c2cn1)c1ccc(F)cc1] | 1-[(1R)-1-(4-fluorophenyl)ethyl]-3-[3-(4-methyloctahydro-2H-4,7-epoxyisoindol-2-yl)-1H-pyrazolo[4,3-c]pyridin-6-yl]urea | Calc'd 451, found 451 | Scheme 1, Example 1 |
| 377 | 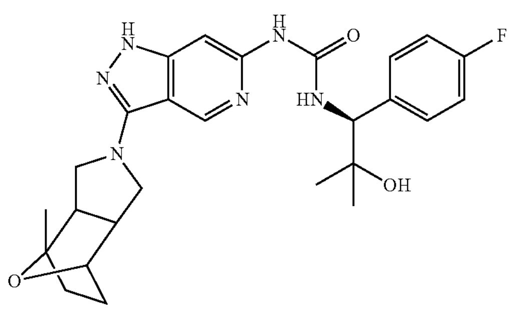 [SMILES: CC12CCC(O1)C1CN(c3n[nH]c4cc(NC(=O)N[C@@H](c5ccc(F)cc5)C(C)(C)O)ncc34)CC12] | 1-[(1S)-1-(4-fluorophenyl)-2-hydroxy-2-methylpropyl]-3-[3-(4-methyloctahydro-2H-4,7-epoxyisoindol-2-yl)-1H-pyrazolo[4,3-c]pyridin-6-yl]urea | Calc'd 495, found 495 | Scheme 1, Example 1 |
| 378 | 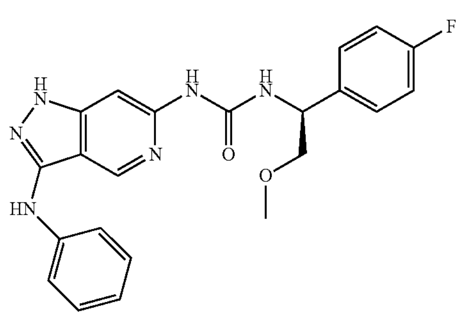 [SMILES: COC[C@@H](NC(=O)Nc1cc2[nH]nc(Nc3ccccc3)c2cn1)c1ccc(F)cc1] | 1-[(1S)-1-(4-fluorophenyl)-2-methoxyethyl]-3-[3-(phenylamino)-1H-pyrazolo[4,3-c]pyridin-6-yl]urea | Calc'd 421, found 421 | similar procedure in Example 121 |

| No. | Structure | IUPAC Name | Exact Mass [M + H]⁺ | Route Used |
|---|---|---|---|---|
| 379 | 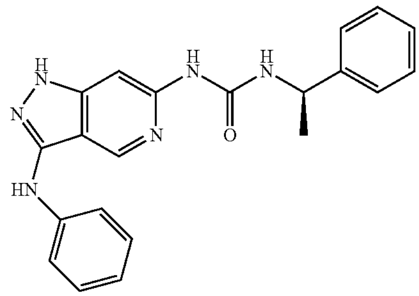 [SMILES: C[C@@H](NC(=O)Nc1cc2[nH]nc(Nc3ccccc3)c2cn1)c1ccccc1] | 1-[3-(phenyl-amino)-1H-pyrazolo[4,3-c]-pyridin-6-yl]-3-[(1R)-1-phenylethyl]urea | Calc'd 373, found 373 | similar procedure in Example 121 |
| 380 | 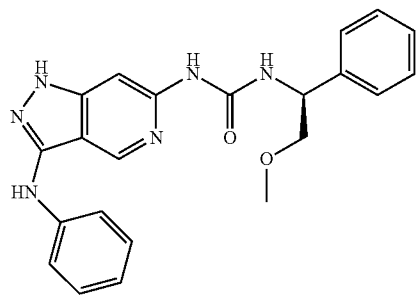 [SMILES: COC[C@@H](NC(=O)Nc1cc2[nH]nc(Nc3ccccc3)c2cn1)c1ccccc1] | 1-[(1S)-2-methoxy-1-phenylethyl]-3-[3-(phenylamino)-1H-pyrazolo[4,3-c]-pyridin-6-yl]urea | Calc'd 403, found 403 | similar procedure in Example 121 |
| 381 | 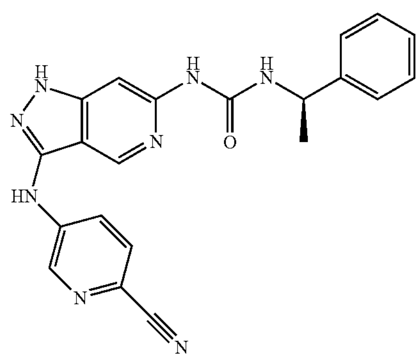 [SMILES: C[C@@H](NC(=O)Nc1cc2[nH]nc(Nc3ccc(C#N)nc3)c2cn1)c1ccccc1] | 1-{3-[(6-cyanopyridin-3-yl)amino]-1H-pyrazolo[4,3-c]-pyridin-6-yl}-3-[(1R)-1-phenylethyl]urea | Calc'd 399, found 399 | similar procedure in Example 121 |
| 382 | 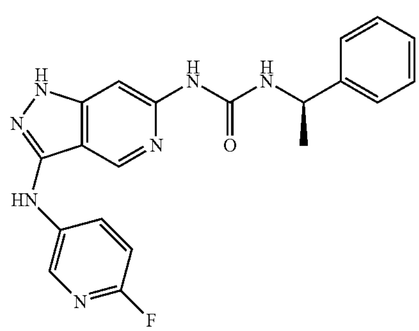 [SMILES: C[C@@H](NC(=O)Nc1cc2[nH]nc(Nc3ccc(F)nc3)c2cn1)c1ccccc1] | 1-{3-[(6-fluoropyridin-3-yl)amino]-1H-pyrazolo[4,3-c]-pyridin-6-yl}-3-[(1R)-1-phenylethyl]urea | Calc'd 392, found 392 | similar procedure in Example 121 |

| No. | Structure | IUPAC Name | Exact Mass [M + H]+ | Route Used |
|---|---|---|---|---|
| 383 | 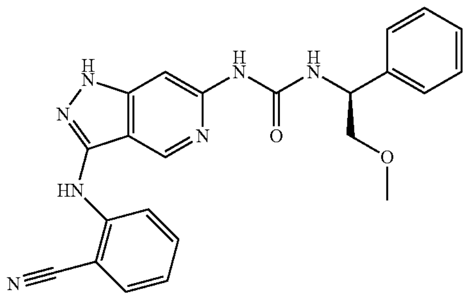 [SMILES: COC[C@@H](NC(=O)Nc1cc2[nH]nc(Nc3ccccc3C#N)c2cn1)c1ccccc1] | 1-{3-[(2-cyanophenyl)amino]-1H-pyrazolo[4,3-c]pyridin-6-yl}-3-[(1S)-2-methoxy-1-phenylethyl]urea | Calc'd 428, found 428 | similar procedure in Example 121 |
| 384 | 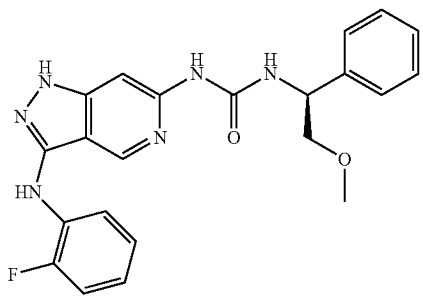 [SMILES: COC[C@@H](NC(=O)Nc1cc2[nH]nc(Nc3ccccc3F)c2cn1)c1ccccc1] | 1-{3-[(2-fluorophenyl)amino]-1H-pyrazolo[4,3-c]-pyridin-6-yl}-3-[(1S)-2-methoxy-1-phenylethyl]urea | Calc'd 421, found 421 | similar procedure in Example 121 |
| 385 | 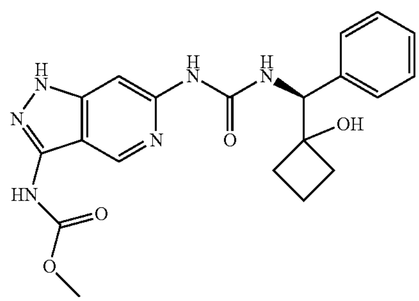 [SMILES: COC(=O)Nc1n[nH]c2cc(NC(=O)N[C@@H](c3ccccc3)C3(O)CCC3)ncc12] | methyl [6-({[(S)-(1-hydroxycyclobutyl)(phenyl)-methyl]carbamoyl}amino)-1H-pyrazolo[4,3-c]-pyridin-3-yl]-carbamate | Calc'd 411, found 411 | Scheme 14, Example 321 |
| 386 | 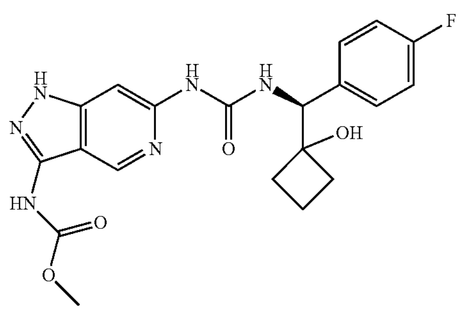 [SMILES: COC(=O)Nc1n[nH]c2cc(NC(=O)N[C@@H](c3ccc(F)cc3)C3(O)CCC3)ncc12] | methyl [6-({[(S)-(4-fluorophenyl)(1-hydroxycyclobutyl)methyl]carbamoyl}amino)-1H-pyrazolo[4,3-c]-pyridin-3-yl]-carbamate | Calc'd 429, found 429 | Scheme 14, Example 321 |
| 387 | 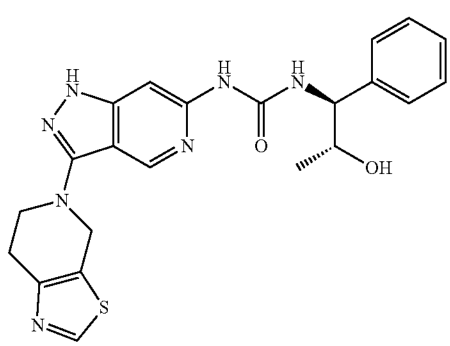 [SMILES: C[C@@H](O)[C@@H](NC(=O)Nc1cc2[nH]nc(N3CCc4ncsc4C3)c2cn1)c1ccccc1] | 1-[3-(6,7-dihydro[1,3]-thiazolo[5,4-c]-pyridin-5(4H)-yl)-1H-pyrazolo[4,3-c]pyridin-6-yl]-3-[(1S,2R)-2-hydroxy-1-phenylpropyl]urea | Calc'd 450, found 450 | Scheme 1, Example 1 |

| No. | Structure | IUPAC Name | Exact Mass [M + H]+ | Route Used |
|---|---|---|---|---|
| 388 | 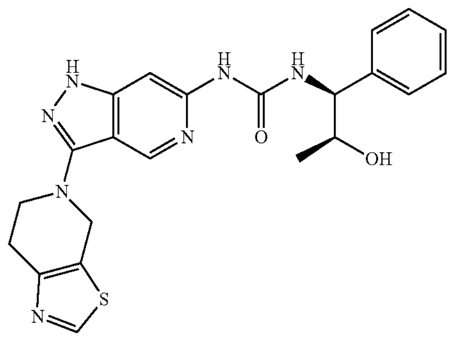 [SMILES: C[C@H](O)[C@@H](NC(=O)Nc1cc2[nH]nc(N3CCc4ncsc4C3)c2cn1)c1ccccc1] | 1-[3-(6,7-dihydro[1,3]-thiazolo[5,4-c]pyridin-5(4H)-yl)-1H-pyrazolo[4,3-c]-pyridin-6-yl]-3-[(1S,2S)-2-hydroxy-1-phenylpropyl]urea | Calc'd 450, found 450 | Scheme 1, Example 1 |
| 389 | 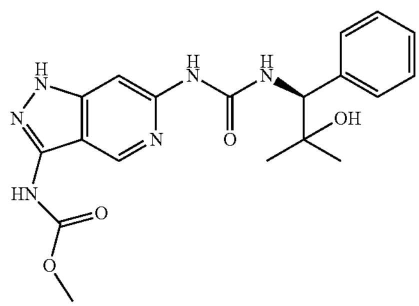 [SMILES: COC(=O)Nc1n[nH]c2cc(NC(=O)N[C@@H](c3ccccc3)C(C)(C)O)ncc12] | methyl [6-({[(1S)-2-hydroxy-2-methyl-1-phenyl-propyl]carbamoyl}amino)-1H-pyrazolo[4,3-c]-pyridin-3-yl]-carbamate | Calc'd 399, found 399 | Scheme 14, Example 321 |
| 390 | 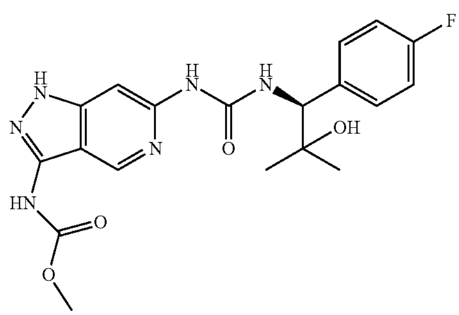 [SMILES: COC(=O)Nc1n[nH]c2cc(NC(=O)N[C@@H](c3ccc(F)cc3)C(C)(C)O)ncc12] | methyl [6-({[(1S)-1-(4-fluorophenyl)-2-hydroxy-2-methylpropyl]-carbamoyl}amino)-1H-pyrazolo[4,3-c]pyridin-3-yl]-carbamate | Calc'd 417, found 417 | Scheme 14, Example 321 |
| 391 | 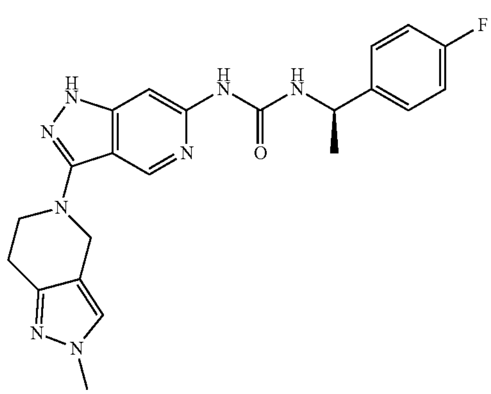 [SMILES: C[C@@H](NC(=O)Nc1cc2[nH]nc(N3CCc4nn(C)cc4C3)c2cn1)c1ccc(F)cc1] | 1-[(1R)-1-(4-fluorophenyl)ethyl]-3-(2'-methyl-2',4',6',7'-tetrahydro-1H-3,5'-bipyrazolo[4,3-c]-pyridin-6-yl)urea | Calc'd 435, found 435 | Scheme 1, Example 1 |

| No. | Structure | IUPAC Name | Exact Mass [M + H]+ | Route Used |
|---|---|---|---|---|
| 392 | 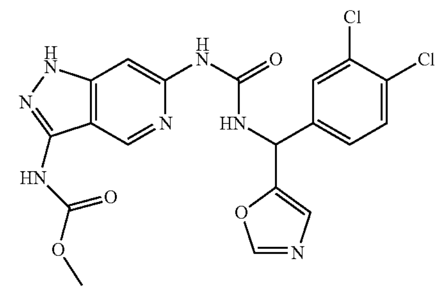 [SMILES: COC(=O)Nc1n[nH]c2cc(NC(=O)NC(c3ccc(Cl)c(Cl)c3)c3cnco3)ncc12] | methyl [6-({[(3,4-dichlorophenyl)(1,3-oxazol-5-yl)-methyl]carbamoyl}amino)-1H-pyrazolo[4,3-c]-pyridin-3-yl]-carbamate | Calc'd 476, found 476 | Scheme 14, Example 321 |
| 393 | 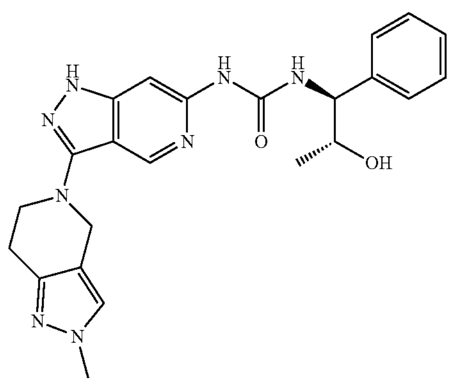 [SMILES: C[C@@H](O)[C@@H](NC(=O)Nc1cc2[nH]nc(N3CCc4nn(C)cc4C3)c2cn1)c1ccccc1] | 1-[(1S,2R)-2-hydroxy-1-phenylpropyl]-3-(2'-methyl-2',4',6',7'-tetrahydro-1H-3,5'-bipyrazolo[4,3-c]-pyridin-6-yl)urea | Calc'd 447, found 447 | Scheme 1, Example 1 |
| 394 | 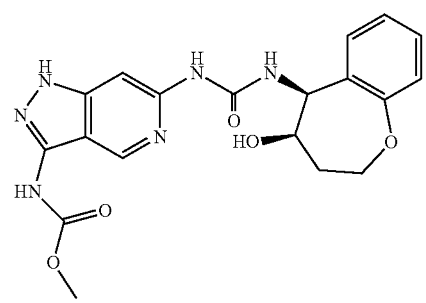 [SMILES: COC(=O)Nc1n[nH]c2cc(NC(=O)N[C@H]3c4ccccc4OCC[C@H]3O)ncc12] | methyl [6-({[(4R,5S)-4-hydroxy-2,3,4,5-tetrahydro-1-benzoxepin-5-yl]-carbamoyl}amino)-1H-pyrazolo[4,3-c]pyridin-3-yl]-carbamate | Calc'd 413, found 413 | Scheme 14, Example 321 |
| 395 | 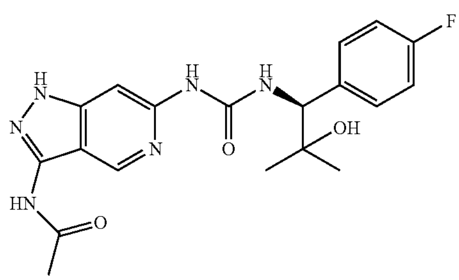 [SMILES: CC(=O)Nc1n[nH]c2cc(NC(=O)N[C@@H](c3ccc(F)cc3)C(C)(C)O)ncc12] | N-[6-({[(1S)-1-(4-fluorophenyl)-2-hydroxy-2-methylpropyl]-carbamoyl}amino)-1H-pyrazolo[4,3-c]-pyridin-3-yl]-acetamide | Calc'd 401, found 401 | Scheme 14, Example 321 using acetyl chloride instead of chloroformate. |

-continued

| No. | Structure | IUPAC Name | Exact Mass [M + H]+ | Route Used |
|---|---|---|---|---|
| 396 | 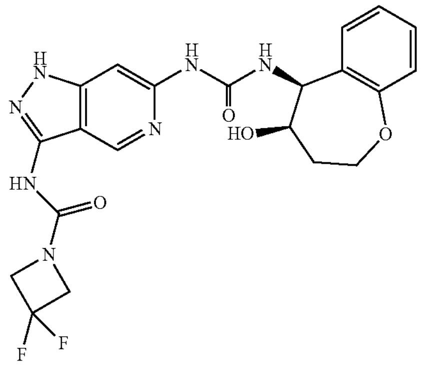 [SMILES: O=C(Nc1cc2[nH]nc(NC(=O)N3CC(F)(F)C3)c2cn1)N[C@H]1c2ccccc2OCC[C@H]1O] | 3,3-difluoro-N-[6-{[(4R,5S)-4-hydroxy-2,3,4,5-tetrahydro-1-benzoxepin-5-yl]-carbamoyl}-amino)-1H-pyrazolo[4,3-c]-pyridin-3-yl]-azetidine-1-carboxamide | Calc'd 474, found 474 | Following a similar procedure in Example 128 |
| 397 | 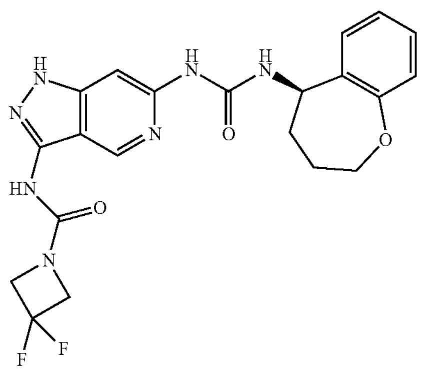 [SMILES: O=C(Nc1cc2[nH]nc(NC(=O)N3CC(F)(F)C3)c2cn1)N[C@@H]1CCCOc2ccccc21] | 3,3-difluoro-N-(6-{[(5R)-2,3,4,5-tetrahydro-1-benzoxepin-5-yl-carbamoyl]amino}-1H-pyrazolo[4,3-c]pyridin-3-yl)-azetidine-1-carboxamide | Calc'd 458, found 458 | Following a similar procedure in Example 128 |
| 398 | 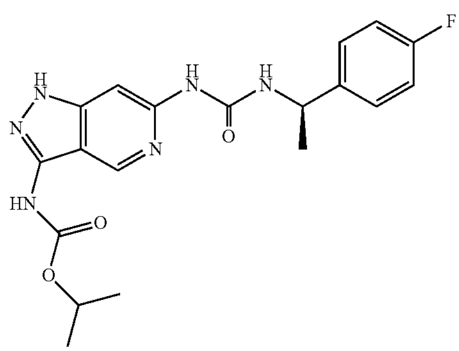 [SMILES: CC(C)OC(=O)Nc1n[nH]c2cc(NC(=O)N[C@H](C)c3ccc(F)cc3)ncc12] | 1-methylethyl [6-({[(1R)-1-(4-fluorophenyl)ethyl]carbamoyl}amino)-1H-pyrazolo[4,3-c]pyridin-3-yl]-carbamate | Calc'd 401, found 401 | Following a similar procedure in Example 406 |
| 399 | 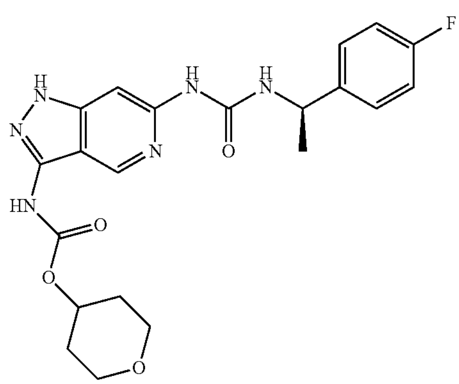 [SMILES: C[C@@H](NC(=O)Nc1cc2[nH]nc(NC(=O)OC3CCOCC3)c2cn1)c1ccc(F)cc1] | tetrahydro-2H-pyran-4-yl [6-({[(1R)-1-(4-fluorophenyl)ethyl]carbamoyl}amino)-1H-pyrazolo[4,3-c]pyridin-3-yl]-carbamate | Calc'd 443, found 443 | Following a similar procedure in Example 406 |

-continued

| No. | Structure | IUPAC Name | Exact Mass [M + H]+ | Route Used |
|---|---|---|---|---|
| 400 | 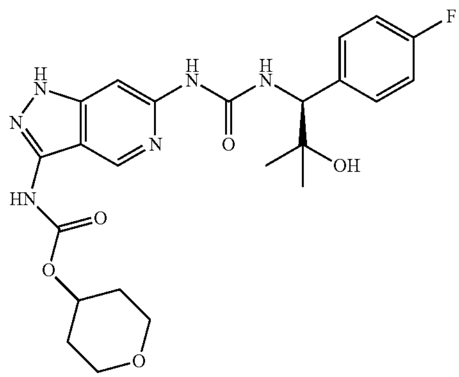 [SMILES: CC(C)(O)[C@@H](NC(=O)Nc1cc2[nH]nc(NC(=O)OC3CCOCC3)c2cn1)c1ccc(F)cc1] | tetrahydro-2H-pyran-4-yl [6-({[(1S)-1-(4-fluorophenyl)-2-hydroxy-2-methylpropyl]carbamoyl}amino)-1H-pyrazolo[4,3-c]pyridin-3-yl]-carbamate | Calc'd 487, found 487 | Following a similar procedure in Example 406 |
| 401 | 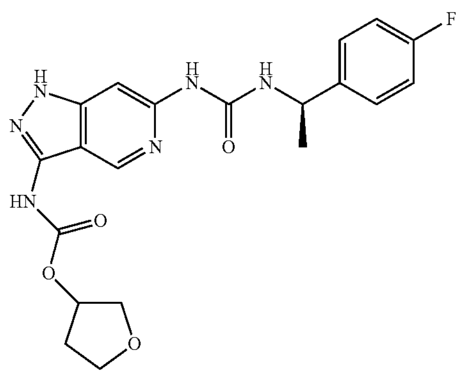 [SMILES: C[C@@H](NC(=O)Nc1cc2[nH]nc(NC(=O)OC3CCOC3)c2cn1)c1ccc(F)cc1] | tetrahydrofuran-3-yl [6-({[(1R)-1-(4-fluorophenyl)ethyl]carbamoyl}amino)-1H-pyrazolo[4,3-c]pyridin-3-yl]-carbamate | Calc'd 429, found 429 | Following a similar procedure in Example 406 |
| 402 | 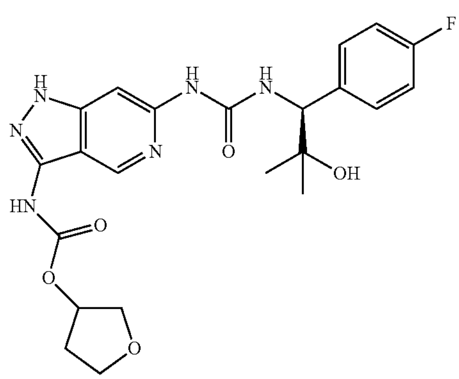 [SMILES: CC(C)(O)[C@@H](NC(=O)Nc1cc2[nH]nc(NC(=O)OC3CCOC3)c2cn1)c1ccc(F)cc1] | tetrahydrofuran-3-yl [6-({[(1S)-1-(4-fluorophenyl)-2-hydroxy-2-methyl-propyl]carbamoyl}amino)-1H-pyrazolo[4,3-c]-pyridin-3-yl]-carbamate | Calc'd 473, found 473 | Following a similar procedure in Example 406 |
| 403 | 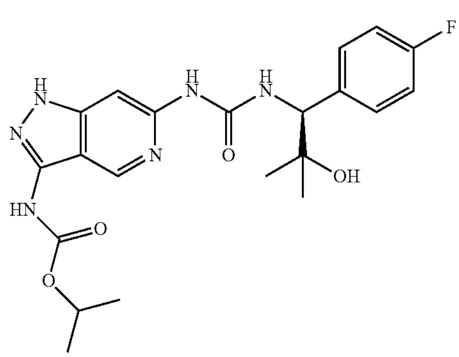 [SMILES: CC(C)OC(=O)Nc1n[nH]c2cc(NC(=O)N[C@@H](c3ccc(F)cc3)C(C)(C)O)ncc12] | 1-methylethyl [6-({[(1S)-1-(4-fluorophenyl)-2-hydroxy-2-methyl-propyl]carbamoyl}amino)-1H-pyrazolo[4,3-c]-pyridin-3-yl]-carbamate | Calc'd 445, found 445 | Following a similar procedure in Example 406 |

| No. | Structure | IUPAC Name | Exact Mass [M + H]+ | Route Used |
|---|---|---|---|---|
| 404 | 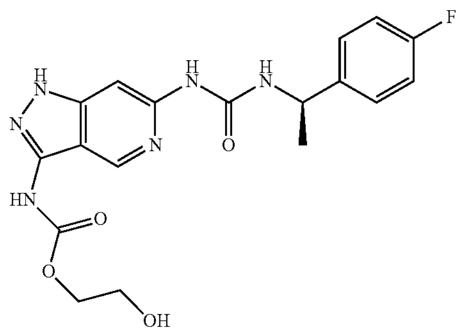 [SMILES: C[C@@H](NC(=O)Nc1cc2[nH]nc(NC(=O)OCCO)c2cn1)c1ccc(F)cc1] | 2-hydroxyethyl [6-({[(1R)-1-(4-fluorophenyl)ethyl]carbamoyl}amino)-1H-pyrazolo[4,3-c]pyridin-3-yl]-carbamate | Calc'd 403, found 403 | Following a similar procedure in Example 406 |
| 405 | 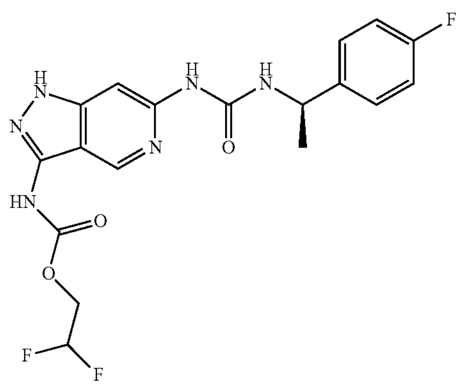 [SMILES: C[C@@H](NC(=O)Nc1cc2[nH]nc(NC(=O)OCC(F)F)c2cn1)c1ccc(F)cc1] | 2,2-difluoroethyl [6-({[(1R)-1-(4-fluorophenyl)ethyl]carbamoyl}amino)-1H-pyrazolo[4,3-c]pyridin-3-yl]-carbamate | Calc'd 423, found 423 | Following a similar procedure in Example 406 |
| 406 | 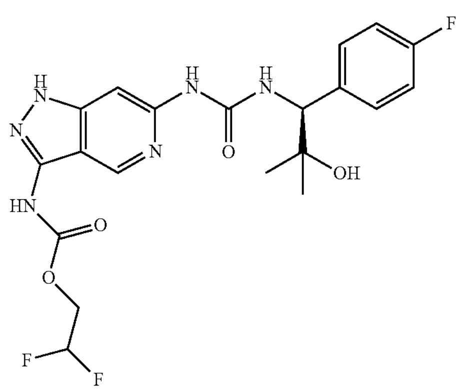 [SMILES: CC(C)(O)[C@@H](NC(=O)Nc1cc2[nH]nc(NC(=O)OCC(F)F)c2cn1)c1ccc(F)cc1] | 2,2-difluoroethyl [6-({[(1S)-1-(4-fluorophenyl)-2-hydroxy-2-methyl-propyl]carbamoyl}amino)-1H-pyrazolo[4,3-c]-pyridin-3-yl]-carbamate | Calc'd 467, found 467 | Following a similar procedure in Example 406 |
| 407 | 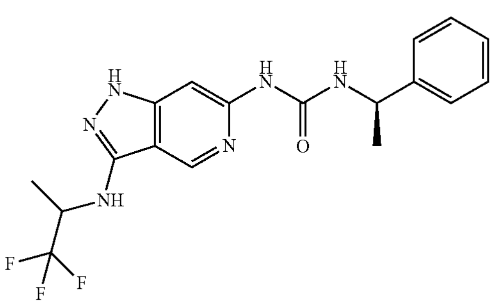 [SMILES: CC(Nc1n[nH]c2cc(NC(=O)N[C@H](C)c3ccccc3)ncc12)C(F)(F)F] | 1-[(1R)-1-phenylethyl]-3-{3-[(2,2,2-trifluoro-1-methylethyl)amino]-1H-pyrazolo[4,3-c]pyridin-6-yl}urea | Calc'd 393, found 393 | Scheme 1 |

| No. | Structure | IUPAC Name | Exact Mass [M + H]+ | Route Used |
|---|---|---|---|---|
| 408 | 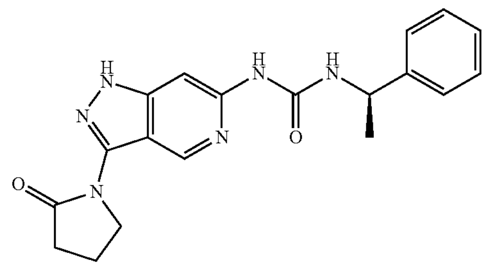 [SMILES: C[C@@H](NC(=O)Nc1cc2[nH]nc(N3CCCC3=O)c2cn1)c1ccccc1] | 1-[3-(2-oxopyrrolidin-1-yl)-1H-pyrazolo[4,3-c]-pyridin-6-yl]-3-[(1R)-1-phenylethyl]urea | Calc'd 365, found 365 | Scheme 1 |
| 409 | 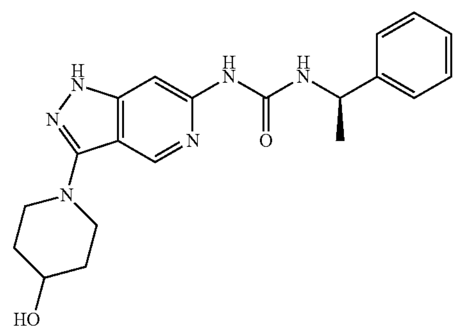 [SMILES: C[C@@H](NC(=O)Nc1cc2[nH]nc(N3CCC(O)CC3)c2cn1)c1ccccc1] | 1-[3-(4-hydroxypiperidin-1-yl)-1H-pyrazolo[4,3-c]-pyridin-6-yl]-3-[(1R)-1-phenylethyl]urea | Calc'd 381, found 381 | Scheme 1 |
| 410 | 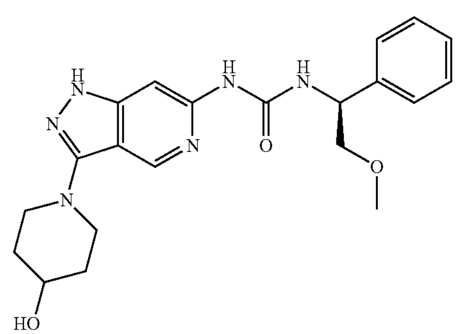 [SMILES: COC[C@@H](NC(=O)Nc1cc2[nH]nc(N3CCC(O)CC3)c2cn1)c1ccccc1] | 1-[3-(4-hydroxypiperidin-1-yl)-1H-pyrazolo[4,3-c]-pyridin-6-yl]-3-[(1S)-2-methoxy-1-phenylethyl]urea | Calc'd 411, found 411 | Scheme 1 |
| 411 | 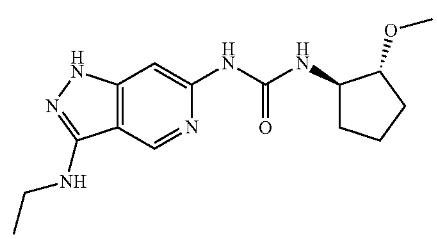 [SMILES: CCNc1n[nH]c2cc(NC(=O)N[C@@H]3CCC[C@H]3OC)ncc12] | 1-[3-(ethylamino)-1H-pyrazolo[4,3-c]pyridin-6-yl]-3-[(1R,2R)-2-methoxy-cyclopentyl]urea | Calc'd 319, found 319 | Scheme 1 |
| 412 | 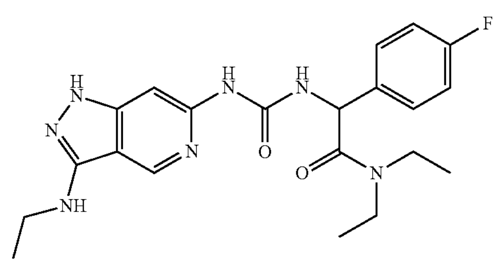 [SMILES: CCNc1n[nH]c2cc(NC(=O)NC(C(=O)N(CC)CC)c3ccc(F)cc3)ncc12] | N,N-diethyl-2-({[3-(ethylamino)-1H-pyrazolo[4,3-c]-pyridin-6-yl]-carbamoyl}amino)-2-(4-fluoro-phenyl)acetamide | Calc'd 428, found 428 | Scheme 1 |

| No. | Structure | IUPAC Name | Exact Mass [M + H]+ | Route Used |
|---|---|---|---|---|
| 413 | 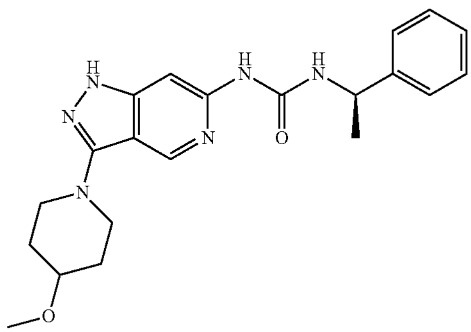 [SMILES: COC1CCN(c2n[nH]c3cc(NC(=O)N[C@H](C)c4ccccc4)ncc23)CC1] | 1-[3-(4-methoxypiperidin-1-yl)-1H-pyrazolo[4,3-c]-pyridin-6-yl]-3-[(1R)-1-phenylethyl]urea | Calc'd 395, found 395 | Scheme 1 |
| 414 | 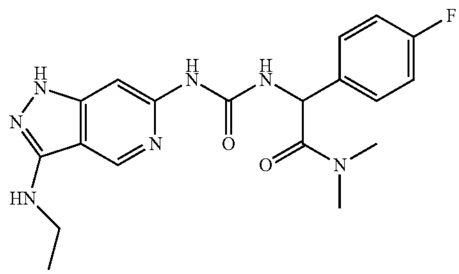 [SMILES: CCNc1n[nH]c2cc(NC(=O)NC(C(=O)N(C)C)c3ccc(F)cc3)ncc12] | 2-({[3-(ethylamino)-1H-pyrazolo[4,3-c]-pyridin-6-yl]-carbamoyl}amino)-2-(4-fluorophenyl)-N,N-dimethyl-acetamide | Calc'd 400, found 400 | Scheme 1 |
| 415 | 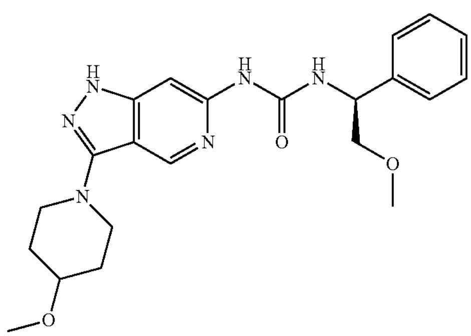 [SMILES: COC[C@@H](NC(=O)Nc1cc2[nH]nc(N3CCC(OC)CC3)c2cn1)c1ccccc1] | 1-[(1S)-2-methoxy-1-phenylethyl]-3-[3-(4-methoxypiperidin-1-yl)-1H-pyrazolo[4,3-c]pyridin-6-yl]urea | Calc'd 425, found 425 | Scheme 1 |
| 416 | 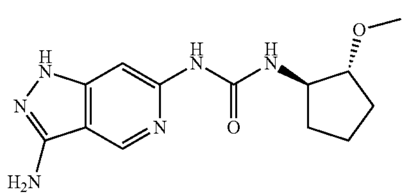 [SMILES: CO[C@@H]1CCC[C@H]1NC(=O)Nc1cc2[nH]nc(N)c2cn1] | 1-(3-amino-1H-pyrazolo[4,3-c]pyridin-6-yl)-3-[(1R,2R)-2-methoxy-cyclopentyl]urea | Calc'd 291, found 291 | Scheme 2 |
| 417 | 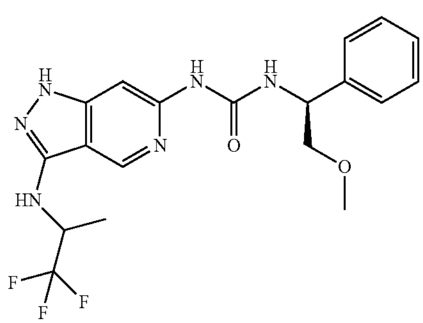 [SMILES: COC[C@@H](NC(=O)Nc1cc2[nH]nc(NC(C)C(F)(F)F)c2cn1)c1ccccc1] | 1-[(1S)-2-methoxy-1-phenylethyl]-3-{3-[(2,2,2-trifluoro-1-methylethyl)-amino]-1H-pyrazolo[4,3-c]-pyridin-6-yl}urea | Calc'd 423, found 423 | Scheme 1 |

-continued

| No. | Structure | IUPAC Name | Exact Mass [M + H]+ | Route Used |
|---|---|---|---|---|
| 418 | 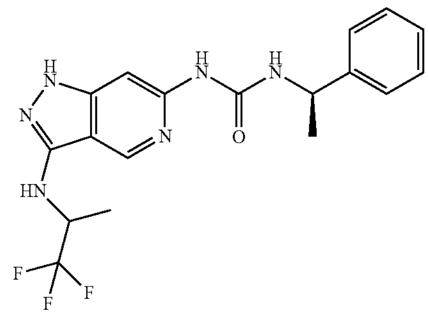 [SMILES: CC(Nc1n[nH]c2cc(NC(=O)N[C@H](C)c3ccccc3)ncc12)C(F)(F)F] | 1-[(1R)-1-phenylethyl]-3-{3-[(2,2,2-trifluoro-1-methylethyl)amino]-1H-pyrazolo[4,3-c]pyridin-6-yl}urea | Calc'd 393, found 393 | Scheme 1 |
| 419 | 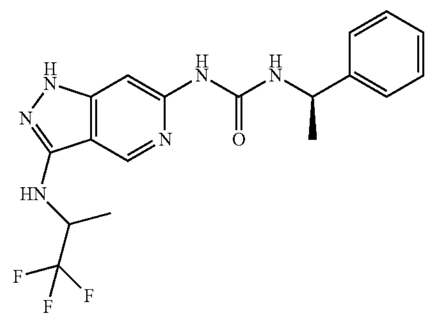 [SMILES: CC(Nc1n[nH]c2cc(NC(=O)N[C@H](C)c3ccccc3)ncc12)C(F)(F)F] | 1-[(1R)-1-phenylethyl]-3-{3-[(2,2,2-trifluoro-1-methylethyl)amino]-1H-pyrazolo[4,3-c]pyridin-6-yl}urea | Calc'd 393, found 393 | Scheme 1 |
| 420 | 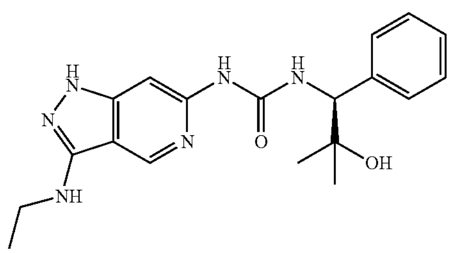 [SMILES: CCNc1n[nH]c2cc(NC(=O)N[C@@H](c3ccccc3)C(C)(C)O)ncc12] | 1-[3-(ethylamino)-1H-pyrazolo[4,3-c]pyridin-6-yl]-3-[(1S)-2-hydroxy-2-methyl-1-phenylpropyl]urea | Calc'd 369, found 369 | Example 420 |
| 421 | 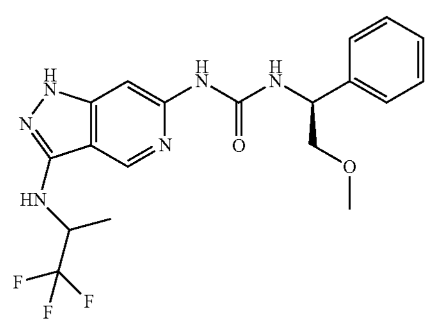 [SMILES: COC[C@@H](NC(=O)Nc1cc2[nH]nc(NC(C)C(F)(F)F)c2cn1)c1ccccc1] | 1-[(1S)-2-methoxy-1-phenylethyl]-3-{3-[(2,2,2-trifluoro-1-methylethyl)-amino]-1H-pyrazolo[4,3-c]-pyridin-6-yl}urea | Calc'd 423, found 423 | Scheme 1 |
| 422 | 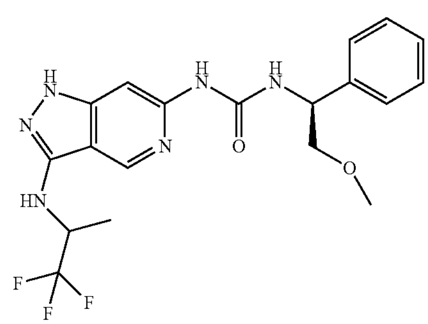 [SMILES: COC[C@@H](NC(=O)Nc1cc2[nH]nc(NC(C)C(F)(F)F)c2cn1)c1ccccc1] | 1-[(1S)-2-methoxy-1-phenylethyl]-3-{3-[(2,2,2-trifluoro-1-methylethyl)-amino]-1H-pyrazolo[4,3-c]-pyridin-6-yl}urea | Calc'd 423, found 423 | Scheme 1 |

-continued

| No. | Structure | IUPAC Name | Exact Mass [M + H]+ | Route Used |
|---|---|---|---|---|
| 423 | 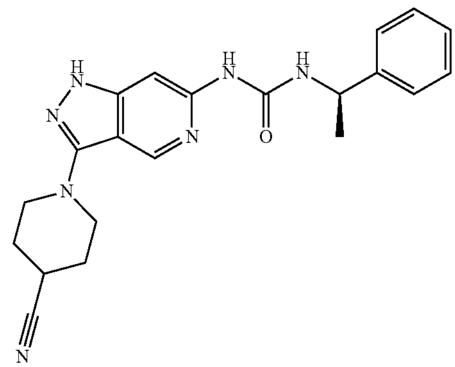 [SMILES: C[C@@H](NC(=O)Nc1cc2[nH]nc(N3CCC(C#N)CC3)c2cn1)c1ccccc1] | 1-[3-(4-cyanopiperidin-1-yl)-1H-pyrazolo[4,3-c]-pyridin-6-yl]-3-[(1R)-1-phenylethyl]urea | Calc'd 390, found 390 | Scheme 1 |
| 424 | 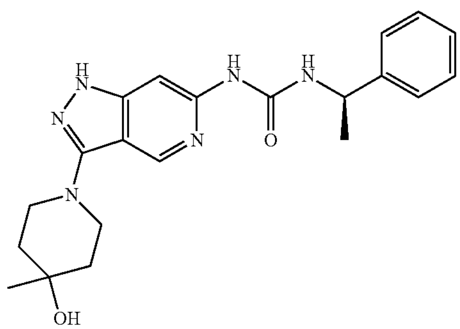 [SMILES: C[C@@H](NC(=O)Nc1cc2[nH]nc(N3CCC(C)(O)CC3)c2cn1)c1ccccc1] | 1-[3-(4-hydroxy-4-methylpiperidin-1-yl)-1H-pyrazolo[4,3-c]-pyridin-6-yl]-3-[(1R)-1-phenylethyl]urea | Calc'd 395, found 395 | Scheme 1 |
| 425 | 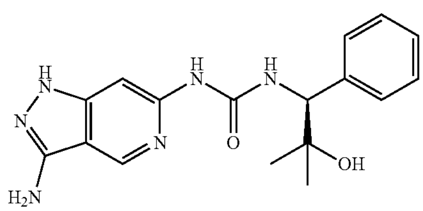 [SMILES: CC(C)(O)[C@@H](NC(=O)Nc1cc2[nH]nc(N)c2cn1)c1ccccc1] | 1-(3-amino-1H-pyrazolo[4,3-c]-pyridin-6-yl)-3-[(1S)-2-hydroxy-2-methyl-1-phenylpropyl]urea | Calc'd 341, found 341 | Example 425 |
| 426 | 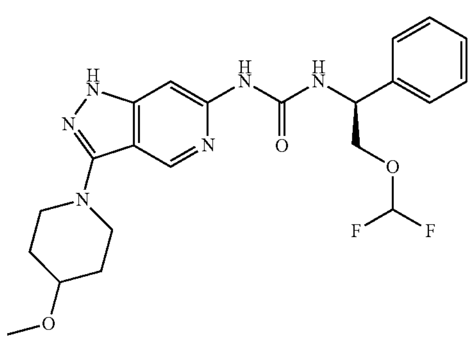 [SMILES: COC1CCN(c2n[nH]c3cc(NC(=O)N[C@H](COC(F)F)c4ccccc4)ncc23)CC1] | 1-[(1S)-2-(difluoromethoxy)-1-phenylethyl]-3-[3-(4-methoxy-piperidin-1-yl)-1H-pyrazolo[4,3-c]-pyridin-6-yl]urea | Calc'd 461, found 461 | Scheme 1 |

| No. | Structure | IUPAC Name | Exact Mass [M + H]+ | Route Used |
|---|---|---|---|---|
| 427 | 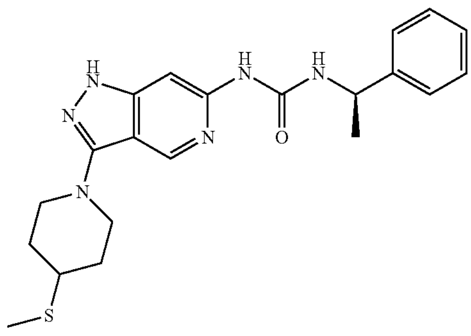 [SMILES: CSC1CCN(c2n[nH]c3cc(NC(=O)N[C@H](C)c4ccccc4)ncc23)CC1] | 1-{3-[4-(methylsulfanyl)-piperidin-1-yl]-1H-pyrazolo[4,3-c]-pyridin-6-yl}-3-[(1R)-1-phenylethyl]urea | Calc'd 411, found 411 | Scheme 1 |
| 428 | 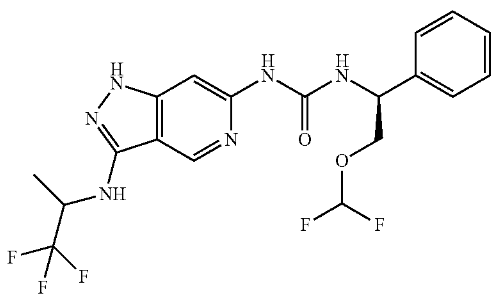 [SMILES: CC(Nc1n[nH]c2cc(NC(=O)N[C@H](COC(F)F)c3ccccc3)ncc12)C(F)(F)F] | 1-[(1S)-2-(difluoromethoxy)-1-phenylethyl]-3-{3-[(2,2,2-trifluoro-1-methylethyl)-amino]-1H-pyrazolo[4,3-c]-pyridin-6-yl}urea | Calc'd 459, found 459 | Scheme 1 |
| 429 | 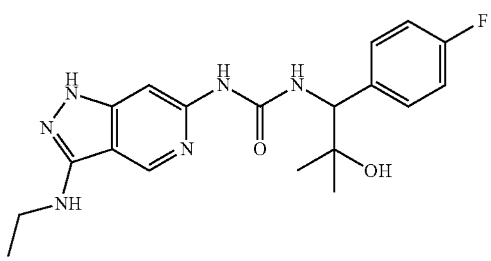 [SMILES: CCNc1n[nH]c2cc(NC(=O)NC(c3ccc(F)cc3)C(C)(C)O)ncc12] | 1-[3-(ethylamino)-1H-pyrazolo[4,3-c]pyridin-6-yl]-3-[1-(4-fluorophenyl)-2-hydroxy-2-methylpropyl]urea | Calc'd 387, found 387 | Scheme 1 |
| 430 | 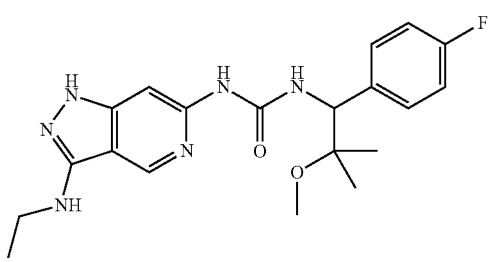 [SMILES: CCNc1n[nH]c2cc(NC(=O)NC(c3ccc(F)cc3)C(C)(C)OC)ncc12] | 1-[3-(ethylamino)-1H-pyrazolo[4,3-c]pyridin-6-yl]-3-[1-(4-fluorophenyl)-2-methoxy-2-methylpropyl]urea | Calc'd 401, found 401 | Scheme 1 |
| 431 | 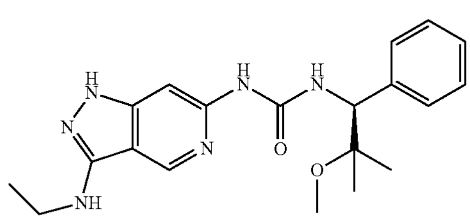 [SMILES: CCNc1n[nH]c2cc(NC(=O)N[C@@H](c3ccccc3)C(C)(C)OC)ncc12] | 1-[3-(ethylamino)-1H-pyrazolo[4,3-c]pyridin-6-yl]-3-[(1S)-2-methoxy-2-methyl-1-phenylpropyl]urea | Calc'd 383, found 383 | Scheme 1 |

-continued

| No. | Structure | IUPAC Name | Exact Mass [M + H]+ | Route Used |
|-----|-----------|------------|---------------------|------------|
| 432 | 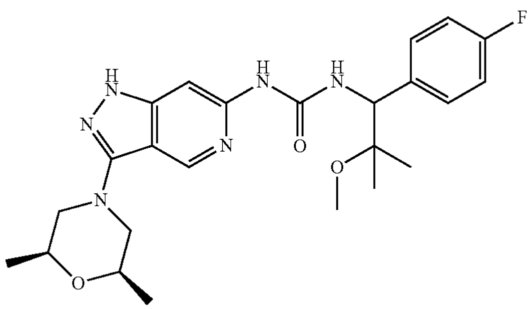 [SMILES: COC(C)(C)C(NC(=O)Nc1cc2[nH]nc(N3C[C@@H](C)O[C@@H](C)C3)c2cn1)c1ccc(F)cc1] | 1-{3-[(2R,6S)-2,6-dimethylmorpholin-4-yl]-1H-pyrazolo[4,3-c]-pyridin-6-yl}-3-[1-(4-fluorophenyl)-2-methoxy-2-methylpropyl]urea | Calc'd 471, found 471 | Scheme 1 |
| 433 | 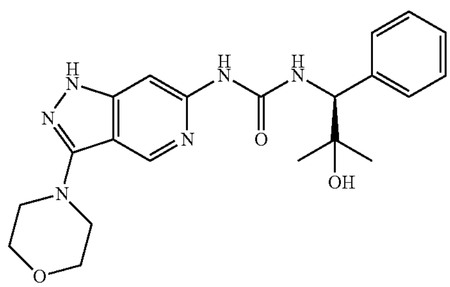 [SMILES: CC(C)(O)[C@@H](NC(=O)Nc1cc2[nH]nc(N3CCOCC3)c2cn1)c1ccccc1] | 1-[(1S)-2-hydroxy-2-methyl-1-phenylpropyl]-3-(3-morpholin-4-yl-1H-pyrazolo[4,3-c]-pyridin-6-yl)urea | Calc'd 411, found 411 | Scheme 1 |
| 434 | 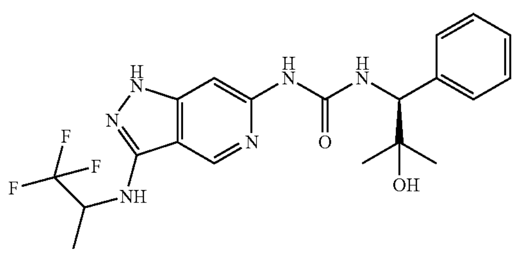 [SMILES: CC(Nc1n[nH]c2cc(NC(=O)N[C@@H](c3ccccc3)C(C)(C)O)ncc12)C(F)(F)F] | 1-[(1S)-2-hydroxy-2-methyl-1-phenylpropyl]-3-{3-[(2,2,2-trifluoro-1-methylethyl)-amino]-1H-pyrazolo[4,3-c]-pyridin-6-yl}urea | Calc'd 437, found 437 | Scheme 1 |
| 435 | 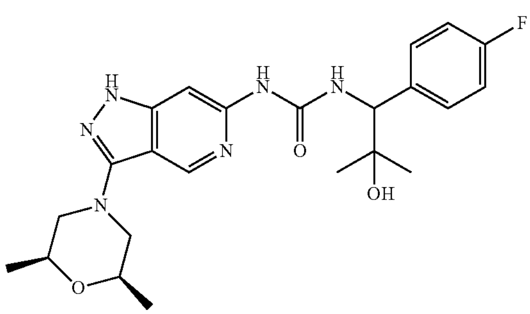 [SMILES: C[C@@H]1CN(c2n[nH]c3cc(NC(=O)NC(c4ccc(F)cc4)C(C)(C)O)ncc23)C[C@H](C)O1] | 1-{3-[(2R,6S)-2,6-dimethylmorpholin-4-yl]-1H-pyrazolo[4,3-c]-pyridin-6-yl}-3-[1-(4-fluorophenyl)-2-hydroxy-2-methylpropyl]urea | Calc'd 457, found 457 | Scheme 1 |
| 436 | 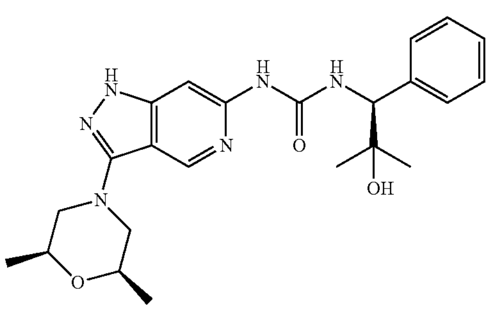 [SMILES: C[C@@H]1CN(c2n[nH]c3cc(NC(=O)N[C@@H](c4ccccc4)C(C)(C)O)ncc23)C[C@H](C)O1] | 1-{3-[(2R,6S)-2,6-dimethylmorpholin-4-yl]-1H-pyrazolo[4,3-c]-pyridin-6-yl}-3-[(1S)-2-hydroxy-2-methyl-1-phenylpropyl]urea | Calc'd 439, found 439 | Scheme 1 |

| No. | Structure | IUPAC Name | Exact Mass [M + H]+ | Route Used |
|---|---|---|---|---|
| 437 | 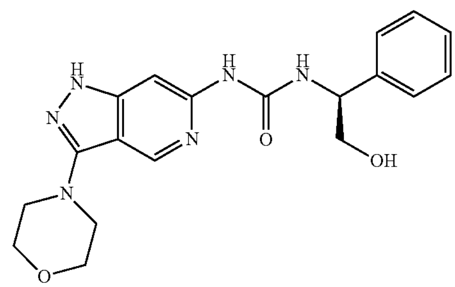 [SMILES: O=C(Nc1cc2[nH]nc(N3CCOCC3)c2cn1)N[C@H](CO)c1ccccc1] | 1-[(1S)-2-hydroxy-1-phenylethyl]-3-(3-morpholin-4-yl-1H-pyrazolo[4,3-c]pyridin-6-yl)urea | Calc'd 383, found 383 | Scheme 1 |
| 438 | 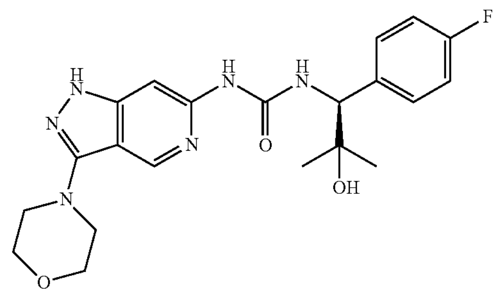 [SMILES: CC(C)(O)[C@@H](NC(=O)Nc1cc2[nH]nc(N3CCOCC3)c2cn1)c1ccc(F)cc1] | 1-[(1S)-1-(4-fluorophenyl)-2-hydroxy-2-methylpropyl]-3-(3-morpholin-4-yl-1H-pyrazolo[4,3-c]-pyridin-6-yl)urea | Calc'd 429, found 429 | Scheme 1 |
| 439 | 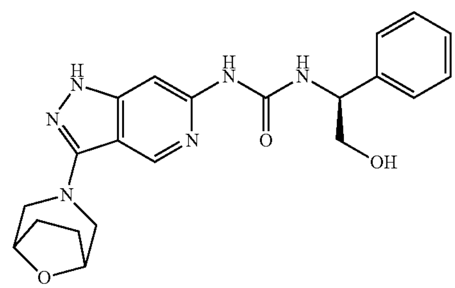 [SMILES: O=C(Nc1cc2[nH]nc(N3CC4CCC(C3)O4)c2cn1)N[C@H](CO)c1ccccc1] | 1-[(1S)-2-hydroxy-1-phenylethyl]-3-[3-(8-oxa-3-azabicyclo[3.2.1]-oct-3-yl)-1H-pyrazolo[4,3-c]-pyridin-6-yl]urea | Calc'd 409, found 409 | Scheme 1 |
| 440 | 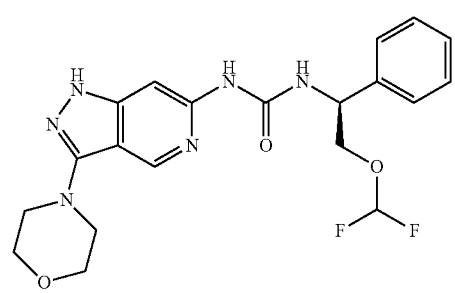 [SMILES: O=C(Nc1cc2[nH]nc(N3CCOCC3)c2cn1)N[C@H](COC(F)F)c1ccccc1] | 1-[(1S)-2-(difluoromethoxy)-1-phenylethyl]-3-(3-morpholin-4-yl-1H-pyrazolo[4,3-c]pyridin-6-yl)urea | Calc'd 433, found 433 | Scheme 1 |
| 441 | 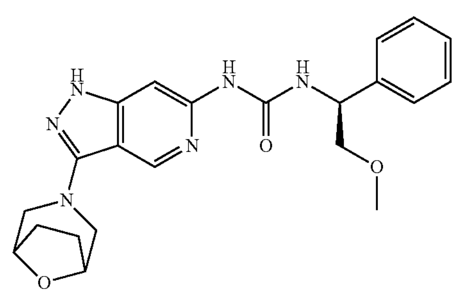 [SMILES: COC[C@@H](NC(=O)Nc1cc2[nH]nc(N3CC4CCC(C3)O4)c2cn1)c1ccccc1] | 1-[(1S)-2-methoxy-1-phenylethyl]-3-[3-(8-oxa-3-azabicyclo[3.2.1]-oct-3-yl)-1H-pyrazolo[4,3-c]-pyridin-6-yl]urea | Calc'd 423, found 423 | Scheme 1 |

-continued

| No. | Structure | IUPAC Name | Exact Mass [M + H]+ | Route Used |
|---|---|---|---|---|
| 442 | 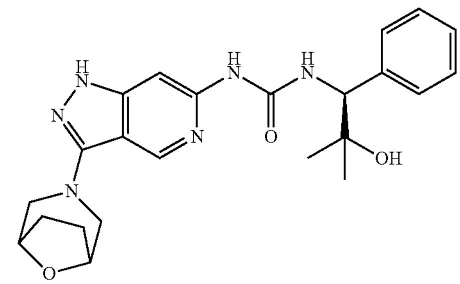 [SMILES: CC(C)(O)[C@@H](NC(=O)Nc1cc2[nH]nc(N3CC4CCC(C3)O4)c2cn1)c1ccccc1] | 1-[(1S)-2-hydroxy-2-methyl-1-phenylpropyl]-3-[3-(8-oxa-3-azabicyclo[3.2.1]-oct-3-yl)-1H-pyrazolo[4,3-c]-pyridin-6-yl]urea | Calc'd 437, found 437 | Scheme 1 |
| 443 | 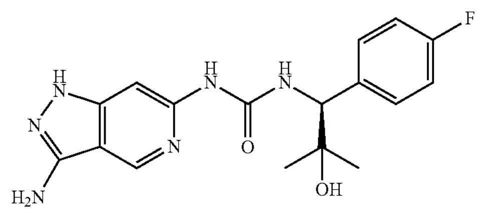 [SMILES: CC(C)(O)[C@@H](NC(=O)Nc1cc2[nH]nc(N)c2cn1)c1ccc(F)cc1] | 1-(3-amino-1H-pyrazolo[4,3-c]-pyridin-6-yl)-3-[(1S)-1-(4-fluorophenyl)-2-hydroxy-2-methylpropyl]urea | Calc'd 359, found 359 | Scheme 2 |
| 444 | 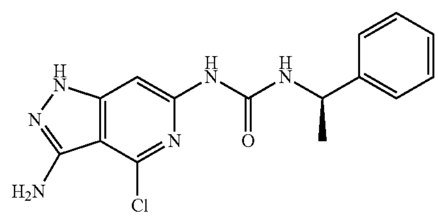 [SMILES: C[C@@H](NC(=O)Nc1cc2[nH]nc(N)c2c(Cl)n1)c1ccccc1] | 1-(3-amino-4-chloro-1H-pyrazolo[4,3-c]-pyridin-6-yl)-3-[(1R)-1-phenylethyl]urea | Calc'd 331, found 331 | Example 444 |
| 445 | 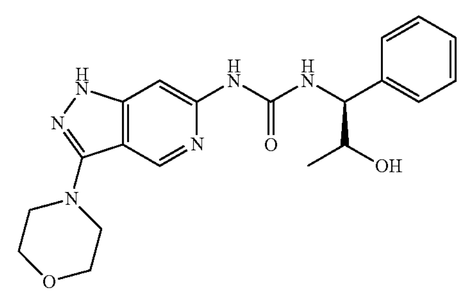 [SMILES: CC(O)[C@@H](NC(=O)Nc1cc2[nH]nc(N3CCOCC3)c2cn1)c1ccccc1] | 1-[(1S,2R)-2-hydroxy-1-phenylpropyl]-3-(3-morpholin-4-yl-1H-pyrazolo[4,3-c]-pyridin-6-yl)urea | Calc'd 397, found 397 | Scheme 1 |
| 446 | 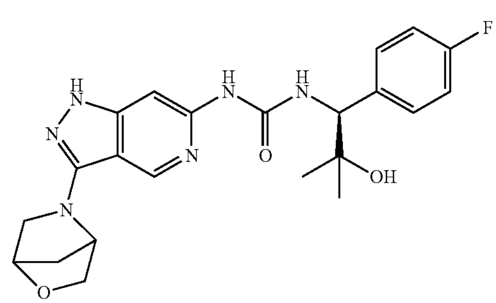 [SMILES: CC(C)(O)[C@@H](NC(=O)Nc1cc2[nH]nc(N3CC4CC3CO4)c2cn1)c1ccc(F)cc1] | 1-[(1S)-1-(4-fluorophenyl)-2-hydroxy-2-methylpropyl]-3-[3-(2-oxa-5-azabicyclo[2.2.1]hept-5-yl)-1H-pyrazolo[4,3-c]pyridin-6-yl]urea | Calc'd 441, found 441 | Scheme 1 |

-continued

| No. | Structure | IUPAC Name | Exact Mass [M + H]+ | Route Used |
|---|---|---|---|---|
| 447 | 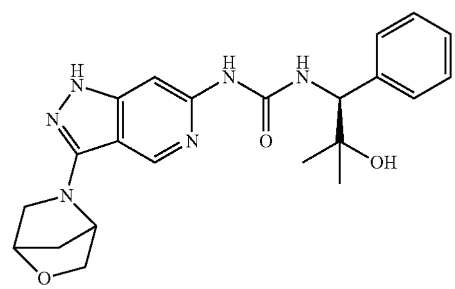 [SMILES: CC(C)(O)[C@@H](NC(=O)Nc1cc2[nH]nc(N3CC4CC3CO4)c2cn1)c1ccccc1] | 1-[(1S)-2-hydroxy-2-methyl-1-phenylpropyl]-3-[3-(2-oxa-5-azabicyclo[2.2.1]-hept-5-yl)-1H-pyrazolo[4,3-c]-pyridin-6-yl]urea | Calc'd 423, found 423 | Scheme 1 |
| 448 | 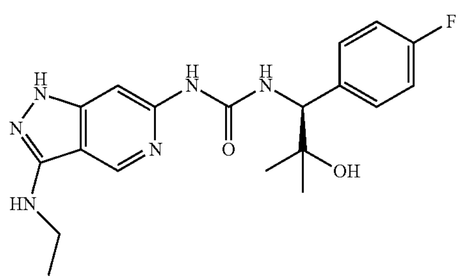 [SMILES: CCNc1n[nH]c2cc(NC(=O)N[C@@H](c3ccc(F)cc3)C(C)(C)O)ncc12] | 1-[3-(ethylamino)-1H-pyrazolo[4,3-c]pyridin-6-yl]-3-[(1S)-1-(4-fluorophenyl)-2-hydroxy-2-methylpropyl]urea | Calc'd 387, found 387 | Scheme 1 |
| 449 | 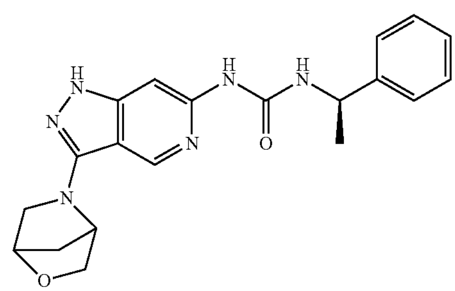 [SMILES: C[C@@H](NC(=O)Nc1cc2[nH]nc(N3CC4CC3CO4)c2cn1)c1ccccc1] | 1-[3-(2-oxa-5-azabicyclo[2.2.1]-hept-5-yl)-1H-pyrazolo[4,3-c]-pyridin-6-yl]-3-[(1R)-1-phenylethyl]urea | Calc'd 379, found 379 | Scheme 1 |
| 450 | 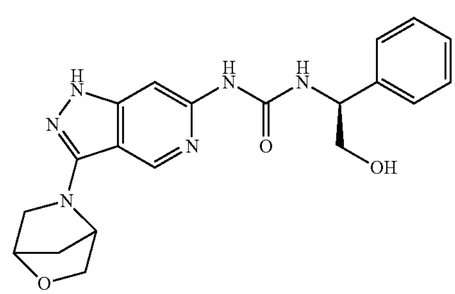 [SMILES: O=C(Nc1cc2[nH]nc(N3CC4CC3CO4)c2cn1)N[C@H](CO)c1ccccc1] | 1-[(1S)-2-hydroxy-1-phenylethyl]-3-[3-(2-oxa-5-azabicyclo[2.2.1]-hept-5-yl)-1H-pyrazolo[4,3-c]-pyridin-6-yl]urea | Calc'd 395, found 395 | Scheme 1 |
| 451 | 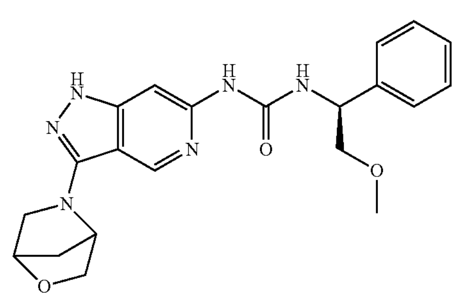 [SMILES: COC[C@@H](NC(=O)Nc1cc2[nH]nc(N3CC4CC3CO4)c2cn1)c1ccccc1] | 1-[(1S)-2-methoxy-1-phenylethyl]-3-[3-(2-oxa-5-azabicyclo[2.2.1]-hept-5-yl)-1H-pyrazolo[4,3-c]-pyridin-6-yl]urea | Calc'd 409, found 409 | Scheme 1 |

-continued

| No. | Structure | IUPAC Name | Exact Mass [M + H]+ | Route Used |
|---|---|---|---|---|
| 452 | 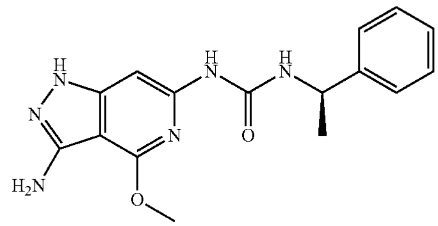 [SMILES: COc1nc(NC(=O)N[C@H](C)c2ccccc2)cc2[nH]nc(N)c12] | 1-(3-amino-4-methoxy-1H-pyrazolo[4,3-c]-pyridin-6-yl)-3-[(1R)-1-phenylethyl]urea | Calc'd 327, found 327 | Example 452 |
| 453 | 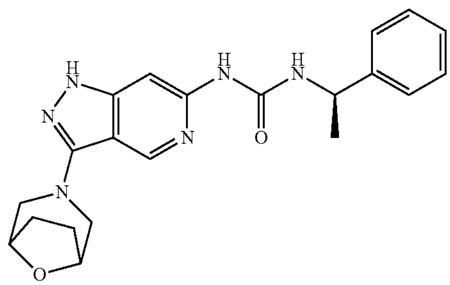 [SMILES: C[C@@H](NC(=O)Nc1cc2[nH]nc(N3CC4CCC(C3)O4)c2cn1)c1ccccc1] | 1-[3-(8-oxa-3-azabicyclo[3.2.1]-oct-3-yl)-1H-pyrazolo[4,3-c]-pyridin-6-yl]-3-[(1R)-1-phenylethyl]urea | Calc'd 393, found 393 | Scheme 1 |
| 454 | 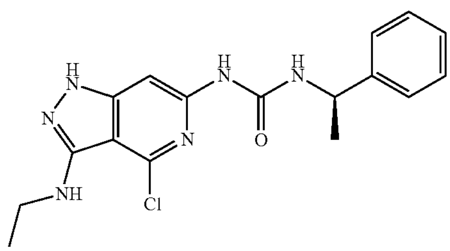 | 1-[4-chloro-3-(ethylamino)-1H-pyrazolo[4,3-c]pyridin-6-yl]-3-[(1R)-1-phenylethyl]urea | Calc'd 359, found 359 | Example 454 |
| 455 | 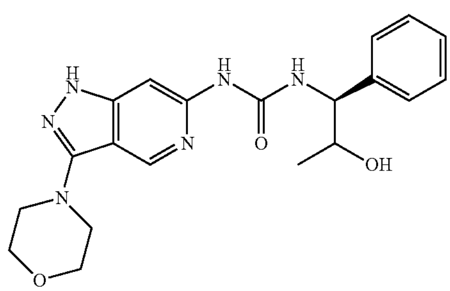 [SMILES: CC(O)[C@@H](NC(=O)Nc1cc2[nH]nc(N3CCOCC3)c2cn1)c1ccccc1] | 1-[(1S)-2-hydroxy-1-phenylpropyl]-3-(3-morpholin-4-yl-1H-pyrazolo[4,3-c]pyridin-6-yl)urea | Calc'd 397, found 397 | Scheme 1 |
| 456 | 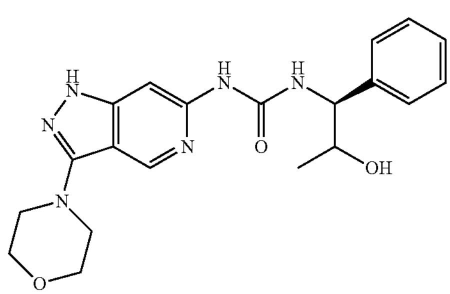 [SMILES: CC(O)[C@@H](NC(=O)Nc1cc2[nH]nc(N3CCOCC3)c2cn1)c1ccccc1] | 1-[(1S)-2-hydroxy-1-phenylpropyl]-3-(3-morpholin-4-yl-1H-pyrazolo[4,3-c]pyridin-6-yl)urea | Calc'd 397, found 397 | Scheme 1 |

| No. | Structure | IUPAC Name | Exact Mass [M + H]+ | Route Used |
|---|---|---|---|---|
| 457 | 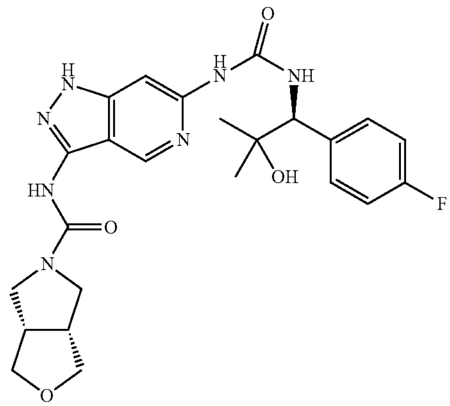 [SMILES: CC(C)(O)[C@@H](NC(=O)Nc1cc2[nH]nc(NC(=O)N3C[C@H]4COC[C@H]4C3)c2cn1)c1ccc(F)cc1] | (3aR,6aS)-N-(6-(3-((S)-1-(4-fluorophenyl)-2-hydroxy-2-methylpropyl)-ureido)-1H-pyrazolo[4,3-c]-pyridin-3-yl)-tetrahydro-1H-furo[3,4-c]pyrrole-5(3H)-carboxamide | Calc'd 498, found 498 | Following a similar procedure in Example 128 |
| 458 | 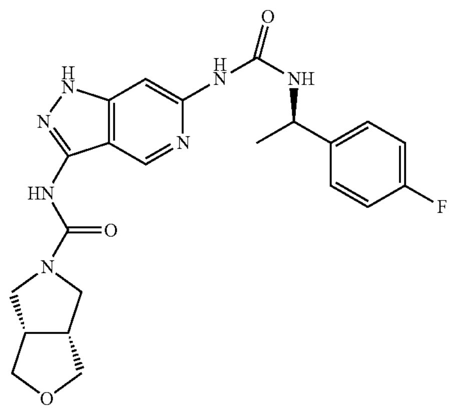 [SMILES: C[C@@H](NC(=O)Nc1cc2[nH]nc(NC(=O)N3C[C@H]4COC[C@H]4C3)c2cn1)c1ccc(F)cc1] | (3aR,6aS)-N-(6-(3-((R)-1-(4-fluorophenyl)ethyl)ureido)-1H-pyrazolo[4,3-c]pyridin-3-yl)tetrahydro-1H-furo[3,4-c]pyrrole-5(3H)-carboxamide | Calc'd 454, found 454 | Following a similar procedure in Example 128 |

Assays

Active Human ERK2 (hERK2) Activity Assay:

Activated ERK2 activity was determined in an IMAP-FP assay (Molecular Devices). Using this assay format, the potency ($IC_{50}$) of each compound was determined from a 10 point (1:3 serial dilution, 3 µM starting compound concentration) titration curve using the following outlined procedure. To each well of a black Corning 384-well plate (Corning Catalog #3575), 7.5 nL of compound (3333 fold dilution in final assay volume of 25 µL) was dispensed, followed by the addition of 15 µL of kinase buffer (tween containing kinase buffer, Molecular Devices) containing 0.0364 ng/mL (0.833 nM) of phosphorylated active hERK2 enzyme. Following a 15 minute compound & enzyme incubation, each reaction was initiated by the addition of 10 µL kinase buffer containing 2.45 µM ERK2 IMAP substrate peptides (2.25 µM-unlabeled IPTTPITTTYFFFK-COOH and 200 nM-labeled IPTTPITT-TYFFFK-SFAM (5-carboxyfluorescein)-COOH), and 75 µM ATP. The final reaction in each well of 25 µL consists of 0.5 nM hERK2, 900 nM unlabeled peptide, 80 nM labeled-peptide, and 30 µM ATP. Phosphorylation reactions were allowed to proceed for 60 minutes and were immediately quenched by the addition of 60 µL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer).

The AERK2 $IC_{50}$ in nanomolar (nM) for the compounds of Examples 1 to 60 is in Table 5.

TABLE 5

| Ex | $IC_{50}$ |
|---|---|
| 1 | 7.85 |
| 2 | 1.13 |
| 3 | 4.87 |
| 4 | 19.47 |
| 5 | 1.00 |
| 6 | 2295 |
| 7 | 341.6 |
| 8 | 255.2 |
| 9 | 104.6 |
| 10 | 42.11 |
| 11 | 30 |
| 12 | 51.6 |
| 13 | 27.99 |
| 14 | 21.83 |
| 15 | 17.29 |
| 16 | 20.6 |
| 17 | 11.8 |
| 18 | 15.19 |
| 19 | 13.81 |
| 20 | 13.63 |
| 21 | 10.4 |
| 22 | 8.75 |
| 23 | 8.69 |
| 24 | 4.80 |
| 25 | 4.78 |
| 26 | 3.29 |
| 27 | 1.20 |
| 28 | 1.00 |
| 29 | 0.82 |

TABLE 5-continued

| Ex | IC$_{50}$ |
|---|---|
| 30 | 0.40 |
| 31 | 0.40 |
| 32 | 0.37 |
| 33 | 0.67 |
| 34 | 0.61 |
| 35 | 0.67 |
| 36 | 5.25 |
| 37 | 80.9 |
| 38 | 13.94 |
| 39 | 1.45 |
| 40 | 0.63 |
| 41 | 20.18 |
| 42 | 0.20 |
| 43 | 1.07 |
| 44 | 2.81 |
| 45 | 1.67 |
| 46 | 1.79 |
| 47 | 0.66 |
| 48 | 1 |
| 49 | 0.56 |
| 50 | 320.8 |
| 51 | 651.6 |
| 52 | 914.1 |
| 53 | 424 |
| 54 | 810 |
| 55 | 88.75 |
| 56 | 191.1 |
| 57 | 3.05 |
| 58 | 6.43 |
| 59 | 6.47 |
| 60 | 38.82 |

The AERK2 IC$_{50}$ in nanomolar (nM) for the compounds of Examples 61 to 458 is in Table 6.

TABLE 6

| Ex | IC$_{50}$ (nM) |
|---|---|
| 61 | 8.8 |
| 62 | 14.7 |
| 63 | 5.8 |
| 64 | 5.6 |
| 65 | 365 |
| 66 | 31.6 |
| 67 | 0.7 |
| 68 | 0.5 |
| 69 | 1.5 |
| 70 | 0.6 |
| 71 | 4.4 |
| 72 | 106 |
| 73 | 39.2 |
| 74 | 1.7 |
| 75 | 0.8 |
| 76 | 1.3 |
| 77 | 2.1 |
| 78 | 7.4 |
| 79 | 9.7 |
| 80 | 5.5 |
| 81 | 8.5 |
| 82 | 3.7 |
| 83 | 2.7 |
| 84 | 4.4 |
| 85 | 0.8 |
| 86 | 4.7 |
| 87 | 13.4 |
| 88 | 3.6 |
| 89 | 9.1 |
| 90 | 14.9 |
| 91 | 52.0 |
| 92 | 27.3 |
| 93 | 9.9 |
| 94 | 25.4 |
| 95 | 14.0 |
| 96 | 0.3 |
| 97 | 0.2 |

TABLE 6-continued

| Ex | IC$_{50}$ (nM) |
|---|---|
| 98 | 0.2 |
| 99 | 0.6 |
| 100 | 1.1 |
| 101 | 0.9 |
| 102 | 2.7 |
| 103 | 1.1 |
| 104 | 1.6 |
| 105 | 2.8 |
| 106 | 0.5 |
| 107 | 0.3 |
| 108 | 0.4 |
| 109 | 0.3 |
| 110 | 1.3 |
| 111 | 0.5 |
| 112 | 0.5 |
| 113 | 1.6 |
| 114 | 0.8 |
| 115 | 0.8 |
| 116 | 94.2 |
| 117 | 18.0 |
| 118 | 57.2 |
| 119 | 60.1 |
| 120 | 27.2 |
| 121 | 24.5 |
| 122 | 8.4 |
| 123 | 0.4 |
| 124 | 0.3 |
| 125 | 0.4 |
| 126 | 0.2 |
| 127 | 0.3 |
| 128 | 3.4 |
| 129 | 0.4 |
| 130 | 0.5 |
| 131 | 1.5 |
| 132 | 4.9 |
| 133 | 2.4 |
| 134 | 8.6 |
| 135 | 382 |
| 136 | 12.2 |
| 137 | 1.3 |
| 138 | 5.9 |
| 139 | 5.5 |
| 140 | 111 |
| 141 | 15.4 |
| 142 | 1.2 |
| 143 | 167 |
| 144 | 2.0 |
| 145 | 2.1 |
| 146 | 115 |
| 147 | 246 |
| 148 | 0.8 |
| 149 | 0.6 |
| 150 | 359 |
| 151 | 315 |
| 152 | 0.9 |
| 153 | 0.7 |
| 154 | 435 |
| 155 | 495 |
| 156 | 0.7 |
| 157 | 93.2 |
| 158 | 1.1 |
| 159 | 1.8 |
| 160 | 279 |
| 161 | 2.3 |
| 162 | 165 |
| 163 | 0.6 |
| 164 | 30.2 |
| 165 | 50.2 |
| 166 | 1.7 |
| 167 | 4.2 |
| 168 | 31.7 |
| 169 | 50.2 |
| 170 | 2.7 |
| 171 | 4.1 |
| 172 | 31.2 |
| 173 | 5.8 |
| 174 | 4.4 |
| 175 | 33.8 |

TABLE 6-continued

| Ex | IC$_{50}$ (nM) |
|---|---|
| 176 | 38.2 |
| 177 | 12.0 |
| 178 | 4.6 |
| 179 | 1.0 |
| 180 | 17.9 |
| 181 | 4.3 |
| 182 | 2.6 |
| 183 | 3.6 |
| 184 | 102 |
| 185 | 1.5 |
| 186 | 2.3 |
| 187 | 6.8 |
| 188 | 146 |
| 189 | 1.7 |
| 190 | 9.3 |
| 191 | 64.3 |
| 192 | 79.8 |
| 193 | 14.0 |
| 194 | 28.4 |
| 195 | 10.2 |
| 196 | 27.9 |
| 197 | 3.1 |
| 198 | 0.5 |
| 199 | 1.1 |
| 200 | 1.1 |
| 201 | 0.5 |
| 202 | 0.6 |
| 203 | 3.6 |
| 204 | 5.9 |
| 205 | 1.2 |
| 206 | 0.5 |
| 207 | 4.6 |
| 208 | 27.8 |
| 209 | 1.6 |
| 210 | 2.8 |
| 211 | 3.1 |
| 212 | 11.7 |
| 213 | 2.2 |
| 214 | 2.9 |
| 215 | 3.9 |
| 216 | 12.0 |
| 217 | 47.7 |
| 218 | 25.1 |
| 219 | 32.5 |
| 220 | 354 |
| 221 | 6.6 |
| 222 | 3.6 |
| 223 | 12.4 |
| 224 | 355 |
| 225 | 39.8 |
| 226 | 17.0 |
| 227 | 11.3 |
| 228 | 3.5 |
| 229 | 1.2 |
| 230 | 11.7 |
| 231 | 57.0 |
| 232 | 18.6 |
| 233 | 28.0 |
| 234 | 52.0 |
| 235 | 334 |
| 236 | 0.7 |
| 237 | 8.3 |
| 238 | 9.6 |
| 239 | 27.4 |
| 240 | 14.7 |
| 241 | 11.8 |
| 242 | 2.4 |
| 243 | 1.7 |
| 244 | 10.8 |
| 245 | 6.7 |
| 246 | 2.4 |
| 247 | 2.2 |
| 248 | 3.2 |
| 249 | 12.0 |
| 250 | 32.0 |
| 251 | 3.2 |
| 252 | 2.0 |
| 253 | 1.0 |
| 254 | 57.7 |
| 255 | 18.1 |
| 256 | 37.5 |
| 257 | 37.1 |
| 258 | 103 |
| 259 | 325 |
| 260 | 0.4 |
| 261 | 6.0 |
| 262 | 20.7 |
| 263 | 127 |
| 264 | 940 |
| 265 | 24.5 |
| 266 | 13.8 |
| 267 | 5.3 |
| 268 | 10.7 |
| 269 | 3.3 |
| 270 | 3.2 |
| 271 | 17.3 |
| 272 | 5.6 |
| 273 | 2.6 |
| 274 | 32.4 |
| 275 | 4.6 |
| 276 | 2.3 |
| 277 | 3.2 |
| 278 | 21.8 |
| 279 | 63.4 |
| 280 | 143 |
| 281 | 98.3 |
| 282 | 34.2 |
| 283 | 44.4 |
| 284 | 33.0 |
| 285 | 1.1 |
| 286 | 5.2 |
| 287 | 1.0 |
| 288 | 0.6 |
| 289 | 0.9 |
| 290 | 0.6 |
| 291 | 1.0 |
| 292 | 19.7 |
| 293 | 5.8 |
| 294 | 26.4 |
| 295 | 55.0 |
| 296 | 2.5 |
| 297 | 2.0 |
| 298 | 1.2 |
| 299 | 1.6 |
| 300 | 2.9 |
| 301 | 1.4 |
| 302 | 0.7 |
| 303 | 3.1 |
| 304 | 3.4 |
| 305 | 7.3 |
| 306 | 1.5 |
| 307 | 1.7 |
| 308 | 461 |
| 309 | 3.6 |
| 310 | 2454 |
| 311 | 19.1 |
| 312 | 134 |
| 313 | 5.6 |
| 314 | 732 |
| 315 | 10.0 |
| 316 | 0.7 |
| 317 | 1.0 |
| 318 | 2.2 |
| 319 | 0.4 |
| 320 | 33.0 |
| 321 | 2.6 |
| 322 | 5.2 |
| 323 | 4.1 |
| 324 | 1.0 |
| 325 | 1.5 |
| 326 | 0.7 |
| 327 | 1.0 |
| 328 | 0.8 |
| 329 | 1.0 |
| 330 | 0.9 |
| 331 | 2.9 |

TABLE 6-continued

| Ex | IC$_{50}$ (nM) |
|---|---|
| 332 | 74.7 |
| 333 | 0.7 |
| 334 | 2.9 |
| 335 | 3.0 |
| 336 | 11.8 |
| 337 | 127 |
| 338 | 16.1 |
| 339 | 0.4 |
| 340 | 1.6 |
| 341 | 2.4 |
| 342 | 0.9 |
| 343 | 7.8 |
| 344 | 1021 |
| 345 | 13.8 |
| 346 | 0.4 |
| 347 | 18.3 |
| 348 | 3.1 |
| 349 | 484 |
| 350 | 33.3 |
| 351 | 88.0 |
| 352 | 1.2 |
| 353 | 0.6 |
| 354 | 2.2 |
| 355 | 2.9 |
| 356 | 54.1 |
| 357 | 1.4 |
| 358 | 0.8 |
| 359 | 1.2 |
| 360 | 2.6 |
| 361 | 385 |
| 362 | 1.3 |
| 363 | 52.2 |
| 364 | 0.3 |
| 365 | 0.9 |
| 366 | 0.4 |
| 367 | 0.6 |
| 368 | 1.1 |
| 369 | 0.4 |
| 370 | 19.7 |
| 371 | 0.7 |
| 372 | 14.7 |
| 373 | 1.1 |
| 374 | 2.8 |
| 375 | 2.5 |
| 376 | 13.8 |
| 377 | 2.3 |
| 378 | 62.3 |
| 379 | 127 |
| 380 | 15.5 |
| 381 | 367 |
| 382 | 72.1 |
| 383 | 2280 |
| 384 | 9.4 |
| 385 | 2.0 |
| 386 | 0.4 |
| 387 | 0.5 |
| 388 | 34.6 |
| 389 | 0.4 |
| 390 | 0.5 |
| 391 | 0.4 |
| 392 | 2.6 |
| 393 | 0.4 |
| 394 | 0.3 |
| 395 | 0.6 |
| 396 | 0.3 |
| 397 | 4.4 |
| 398 | 52.5 |
| 399 | 19.7 |
| 400 | 1.6 |
| 401 | 15.3 |
| 402 | 2.9 |
| 403 | 1.1 |
| 404 | 5.3 |
| 405 | 21.6 |
| 406 | 1.5 |
| 407 | 2.4 |
| 408 | 101 |
| 409 | 2.4 |
| 410 | 1.2 |
| 411 | 99.3 |
| 412 | 421 |
| 413 | 4.5 |
| 414 | 413 |
| 415 | 1.0 |
| 416 | 483 |
| 417 | 0.6 |
| 418 | 3.2 |
| 419 | 2.2 |
| 420 | 2.1 |
| 421 | 0.6 |
| 422 | 0.8 |
| 423 | 9.7 |
| 424 | 21.5 |
| 425 | 14.9 |
| 426 | 1.0 |
| 427 | 15.1 |
| 428 | 1.3 |
| 429 | 1.1 |
| 430 | 0.6 |
| 431 | 0.5 |
| 432 | 2.4 |
| 433 | 0.5 |
| 434 | 0.7 |
| 435 | 1.6 |
| 436 | 0.8 |
| 437 | 0.4 |
| 438 | 0.4 |
| 439 | 1.9 |
| 440 | 0.4 |
| 441 | 0.9 |
| 442 | 0.5 |
| 443 | 0.7 |
| 444 | 1.2 |
| 445 | 0.4 |
| 446 | 0.8 |
| 447 | 1.5 |
| 448 | 0.4 |
| 449 | 6.0 |
| 450 | 4.3 |
| 451 | 3.0 |
| 452 | 0.7 |
| 453 | 3.4 |
| 454 | 11.8 |
| 455 | 0.3 |
| 456 | 0.4 |
| 457 | 3.7 |
| 458 | 14.3 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

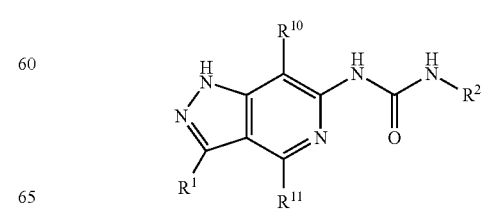

(1)

or a pharmaceutically acceptable salt, ester, solvate or prodrug thereof, wherein:

$R^1$ is —$NR^4R^5$;

$R^2$ is selected from the group consisting of: H, $(C_6-C_{10})$aryl-$(C_1-C_3$alkyl)-heterocycloalkyl-, —$(C_1-C_6$ alkyl), —$(C_1-C_6$alkyl)-O—$(C_1-C_6$alkyl), —$(C_1-C_6$ alkyl)-heterocycloalkyl-$(C_6-C_{10}$aryl), —$(C_1-C_4$alkyl)$(C_6-C_{10})$aryl, —$(C_1-C_4$alkyl)heteroaryl, —$(C_3-C_6$cycloalkyl)-$(C_6-C_{10}$ aryl), -heterocycloalkyl-$(C_6-C_{10}$aryl), —$(C_1-C_6$alkyl)-$(C_3-C_6$ cycloalkyl), —CH$(C_6-C_{10}$aryl)$(C_3-C_6$cycloalkyl), —CH$(C_6-C_{10}$aryl)$((C_1-C_6$alkyl)N$(R^{20})_2)$, —CH$(C_6-C_{10}$aryl)(heterocycloalkyl), —$(C_3-C_6$cycloalkyl-O—$(C_1-C_6$alkyl)), —CH$(C_6-C_{10}$aryl)C(O)N$(R^{21})_2$ wherein each $R^{21}$ is independently selected, and -fused (heterocycloalkyl)$(C_6-C_{10})$aryl wherein said heterocycloalkyl is a 5 to 8 membered ring (including the two atoms common with said aryl) comprising 1-3 heteroatoms selected from the group consisting of: O, S and N, and wherein the remaining atoms are carbon;

and wherein said aryl, heterocycloalkyl, heteroaryl, and cycloalkyl moieties of said $R^2$ groups are optionally substituted with 1-3 substituents independently selected from the group consisting of: CN, halo, —O—$(C_1-C_6$alkyl), —OH, —$CF_3$, —$(C_1-C_6$alkyl), —O(halo substituted$(C_1-C_6$alkyl)), —N$(R^{20})_2$, aryl and heteroaryl;

and wherein said alkyl moieties of said $R^2$ groups are optionally substituted with 1-3 substituents independently selected from the group consisting of: CN, halo, —O—$(C_1-C_6$alkyl), —OH and —$CF_3$, —O(halo substituted$(C_1-C_6$alkyl)) and —S$(C_1-C_6$alkyl);

$R^4$ and $R^5$ are each independently selected from the group consisting of: H, —$(C_1-C_6$alkyl), —$(C_1-C_6$alkyl)-O—$(C_1-C_6$alkyl), —C(O)$R^8$, —S(O)$_2R^9$, —$(C_1-C_6$alkyl) substituted with 1-3 substituents independently selected from the group consisting of: halo, —OH and —S(O)$_2$$(C_1-C_6$alkyl), —$(C_3-C_6$ cycloalkyl), —$(C_3-C_6$ cycloalkyl) substituted with 1-3 substituents independently selected from the group consisting of: halo, —$(C_1-C_6$alkyl), —$NH_2$, —NH$(C_1-C_6$alkyl), —N$(C_1-C_6$alkyl)$_2$ wherein each alkyl is independently selected, —$(C_3-C_6$ cycloalkenyl), —$(C_3-C_6$ oxocycloalkenyl), —$(C_6-C_{10}$aryl), —$(C_6-C_{10}$aryl) substituted with 1-3 substituents independently selected from the group consisting of: —CN, —O$(C_1-C_6$alkyl) and halo, —$(C_1-C_6$alkyl)$(C_6-C_{10}$aryl), —$(C_1-)$ $C_6$alkyl)C(O)N$(R^{20})_2$ wherein each $R^{20}$ is independently selected, heteroaryl, heteroaryl substituted with 1-3 substituents independently selected from the group consisting of: —CN, halo and —$(C_1-C_6$alkyl), —$(C_1-C_6$alkyl)(heteroaryl), —$(C_1-C_6$alkyl)(heteroaryl) substituted with 1-3 substitutents independently selected from the group consisting of: —$(C_1-C_6$alkyl), —$(C_1-C_6$alkyl)$(C_3-C_6$cycloalkyl), —$(C_1-C_6$alkyl)$(C_3-C_6$cycloalkyl) substituted with 1-3 substituents independently selected from the group consisting of: —O—$(C_1-C_6$alkyl), -(hydroxy$C_1-C_6$alkyl), —$(C_2-C_6$alkenyl), —$(C_1-C_6$alkyl)heterocycloalkyl,—C(O)(substituted $C_1-C_6$alkyl)NHC(O)O$(C_1-C_6$alkyl) wherein said substituted alkyl is substituted with a heterocycloalkyl, —C(O)$(C_1-C_6$alkyl)NHC(O)O$(C_1-C_6$alkyl), heterocycloalkyl, heterocycloalkyl substituted with 1-3 substituents independently selected from the group consisting of: —$(C_1-C_6$alkyl) and halo, —$(C_1-C_6$alkyl)heterocycloalkenyl, —$(C_1-C_6$alkyl)heterocycloalkenyl substituted with 1-3 substituents independently selected from the group consisting of: —$(C_1-C_6$alkyl); or $R^4$ and $R^5$ taken together with the nitrogen to which they are bonded to form a 4-6 membered heterocycloalkyl ring, said ring optionally comprising 1 or 2 additional heteroatoms independently selected from the group consisting of: O, S and N, and said heterocycloalkyl ring optionally comprising a 1-2 carbon bridge, and said ring is optionally substituted with 1-3 substituents independently selected from the group consisting of: —O$(C_1-C_6$alkyl) and —$(C_1-C_6$ alkyl), —OH, —$SCH_3$, halo, —$CF_3$, CN, —$(C_1-C_6$alkyl)-O—$(C_1-C_6$alkyl), —$(C_1-C_6$alkyl)-OH and —C(O)OH; or $R^4$ and $R^5$ taken together with the nitrogen to which they are bonded to form a spiro ring comprising two independently selected 4-6 membered heterocycloalkyl rings, wherein one of said rings comprises the nitrogen of the —$NR^4R^5$ group, and wherein the other ring of the spiro ring comprises one heteroatom selected from the group consisting of: O, N and S, and wherein each heterocycloalkyl ring optionally comprises 1 or 2 additional heteroatoms independently selected from the group consisting of: O, S and N, and wherein said spiro ring is optionally substituted with 1-3 substituents independently selected from the group consisting of: —OH, —$(C_1-C_6$alkyl)-O—$(C_1-C_6$alkyl), —$(C_1-C_6$alkyl)-OH, —O$(C_1-C_6$alkyl) and —$(C_1-C_6$ alkyl); or $R^4$ and $R^5$ taken together with the nitrogen to which they are bonded to form a fused bicyclic heterocycloalkyl ring, said ring optionally comprising 1 to 3 additional heteroatoms independently selected from the group consisting of: O, S and N, and said ring optionally comprising a —O— bridge between two ring carbons (i.e., an epoxy bridge), and said ring is optionally substituted with 1-3 substituents independently selected from the group consisting of: halogen, —O$(C_1-C_6$alkyl) and —$(C_1-C_6$ alkyl); or $R^4$ and $R^5$ taken together with the nitrogen to which they are bonded to form a fused bicyclic ring wherein one ring is a heterocycloalkyl ring, and one ring is a heteroaryl ring, said heterocycloalkyl ring optionally comprising 1 to 3 additional heteroatoms independently selected from the group consisting of: O, S and N, and said bicyclic ring is optionally substituted with 1-3 substituents independently selected from the group consisting of: halogen, —O$(C_1-C_6$alkyl) and —$(C_1-C_6$ alkyl); or $R^4$ and $R^{11}$ taken together form a 5-8 membered heterocycloalkyl ring, said ring optionally comprising 1 or 2 additional heteroatoms independently selected from the group consisting of: O, S, N, and —(C=O)—, and said ring is optionally substituted with 1-3 substituents independently selected from $R^{14}$ group;

$R^8$ and $R^9$ are each independently selected from the group consisting of: —$OR^{12}$, —$NHR^{12}$, —$NR^{12}R^{13}$, —$(C_1-C_6$alkyl), —$(C_1-C_6$alkyl)-O—$(C_1-C_6$alkyl), —$(C_3-C_6)$cycloalkyl, —$(C_1-C_6$alkyl)-$(C_3-C_6)$cycloalkyl, heterocycloalkyl, aryl, heteroaryl, —$(C_1-C_6$alkyl)$(C_6-C_{10}$aryl), and —$(C_1-C_6$alkyl)$(C_3-C_{10}$cycloalkyl), fused bicyclic heterocycloalkyl ring, and wherein said heterocycloalkyl is a 4-6 membered ring comprising 1-3 heteroatoms selected from the group consisting of: O, S and N and the remaining ring atoms are carbon, and wherein said aryl is a $C_6$ to $C_{10}$ aromatic ring, and wherein said heteroaryl is a 5 to 10 membered ring comprising 1-3 heteroatoms selected from the group consisting of: O, S and N and the remaining ring atoms are carbon, and wherein said $R^8$ heterocycloalkyl is optionally substituted with 1-3 substituents independently selected from the group consisting of: halo, —OH, and —($C_1$-$C_6$alkyl), and wherein said $R^8$ —($C_1$-$C_6$alkyl) is optionally substituted with 1-3 substituents independently selected from the group consisting of: halo, —NH($C_1$-$C_6$alkyl) and —N($C_1$-$C_6$alkyl)$_2$ wherein each alkyl is independently selected, and wherein said $R^8$ heteroaryl is optionally substituted with 1-3 substituents independently selected from the group consisting of: —($C_1$-$C_6$alkyl), and wherein said $R^8$ aryl is optionally substituted with 1-3 substituents independently selected from the group consisting of: halo; and $R^{10}$ is independently selected from the group consisting of: H, halo, CN, OH, NH$_2$, —CF$_3$, —O—($C_1$-$C_6$alkyl), —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, and —($C_1$-$C_6$alkyl)-heterocycloalkyl;

$R^{11}$ is independently selected from the group consisting of: H, halo, CN, OH, NH$_2$, aryl, heteroaryl, heterocycloalkyl, —NHR$^{12}$, —NR$^{12}$R$^{13}$, —NHC(O)R$^8$, —CF$_3$, —O—($C_1$-$C_6$alkyl), —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, —($C_1$-$C_6$alkyl)-heterocycloalkyl;

each $R^{12}$ is independently selected from the group consisting of: ($C_1$-$C_6$alkyl), ($C_3$-$C_6$cycloalkyl), (($C_3$-$C_6$cycloalkyl)($C_1$-$C_6$alkyl)-), ($C_3$-$C_6$cycloalkenyl), heterocycloalkyl, (heterocycloalkyl($C_1$-$C_6$alkyl))-, ($C_6$-$C_{10}$)aryl, (aryl($C_1$-$C_6$alkyl))-, heteroaryl, (heteroaryl ($C_1$-$C_6$alkyl))-, wherein each of said alkyl, cycloalkyl, cycloalkylalkyl, cycloalkenyl, heterocycloalkyl, heterocycloalkylalkyl, aryl, arylalkyl, heteroaryl, and heteroarylalkyl $R^{12}$ groups is optionally substituted with 1 to 3 independently selected $R^{14}$ groups;

each $R^{13}$ is independently selected from the group consisting of: ($C_1$-$C_6$alkyl), ($C_3$-$C_6$cycloalkyl), (($C_3$-$C_6$cycloalkyl)($C_1$-$C_6$alkyl)-), ($C_3$-$C_6$cycloalkenyl), heterocycloalkyl, (heterocycloalkyl($C_1$-$C_6$alkyl))-, ($C_6$-$C_{10}$)aryl, (aryl($C_1$-$C_6$ alkyl))-, heteroaryl, (heteroaryl ($C_1$-$C_6$alkyl))-, wherein each of said alkyl, cycloalkyl, cycloalkylalkyl, cycloalkenyl, heterocycloalkyl, heterocycloalkylalkyl, aryl, arylalkyl, heteroaryl, heteroarylalkyl $R^{13}$ groups is optionally substituted with 1 to 3 independently selected $R^{14}$ groups, or $R^{12}$ and $R^{13}$ taken together with the nitrogen to which they are bonded to form a 4-8 membered heterocycloalkyl ring, said ring optionally comprising 1 or 2 additional heteroatoms independently selected from the group consisting of: O, S and N, and said ring is optionally substituted with 1-3 substituents independently selected from $R^{14}$ group;

each $R^{14}$ group is independently selected from the group consisting of halo, —CF$_3$, —CN, OH, —OR$^{15}$, ($C_1$-$C_6$alkyl), ($C_3$-$C_6$cycloalkyl), ($C_3$-$C_6$cycloalkenyl), heterocycloalkyl, ($C_6$-$C_{10}$)aryl, heteroaryl and —C(O)($C_1$-$C_6$alkyl);

each $R^{15}$ is independently selected from the group consisting of: ($C_1$-$C_6$alkyl), ($C_3$-$C_6$cycloalkyl), (($C_3$-$C_6$cycloalkyl)($C_1$-$C_6$alkyl)-), ($C_3$-$C_6$cycloalkenyl), heterocycloalkyl, (heterocycloalkyl($C_1$-$C_6$alkyl))-, ($C_6$-$C_{10}$)aryl, (aryl($C_1$-$C_6$ alkyl))-, heteroaryl, (heteroaryl ($C_1$-$C_6$alkyl))- and —C(O)($C_1$-$C_6$alkyl);

$R^{20}$ is independently selected from the group consisting of H and ($C_1$-$C_6$alkyl); and $R^{21}$ is —($C_1$-$C_6$alkyl).

2. The compound of claim 1 wherein:

$R^2$ is selected from the group consisting of: H, ($C_6$-$C_{10}$) aryl-($C_1$-$C_3$alkyl)-heterocycloalkyl-, —($C_1$-$C_6$alkyl), —($C_1$-$C_6$alkyl)-O—($C_1$-$C_6$alkyl), —($C_1$-$C_6$ alkyl)-heterocycloalkyl-($C_6$-$C_{10}$aryl), —($C_1$-$C_4$alkyl)($C_6$-$C_{10}$) aryl, —($C_1$-$C_3$ alkyl)heteroaryl, —($C_3$-$C_6$cycloalkyl)-($C_6$-$C_{10}$aryl), -heterocycloalkyl($C_6$-$C_{10}$aryl); and wherein said aryl, heterocycloalkyl, heteroaryl, and cycloalkyl moieties of said $R^2$ groups are optionally substituted with 1-3 substituents independently selected from the group consisting of: halo, —O($C_1$-$C_6$alkyl), —OH, —CF$_3$, and —($C_1$-$C_6$alkyl); and wherein said alkyl moieties of said $R^2$ groups are optionally substituted with 1-3 substituents independently selected from the group consisting of: halo (e.g., F, Br, and Cl), —O—($C_1$-$C_6$alkyl), —OH and —CF$_3$;

$R^4$ and $R^5$ are each independently selected from the group consisting of: H, —($C_1$-$C_6$alkyl), ($C_1$-$C_6$alkyl)-O—($C_1$-$C_6$alkyl), —C(O)R$^8$, —S(O)$_2$R$^9$; or $R^4$ and $R^5$ taken together with the nitrogen to which they are bonded to form a 4-6 membered heterocycloalkyl ring, said ring optionally comprising 1 or 2 additional heteroatoms independently selected from the group consisting of: O, S and N, and said ring is optionally substituted with 1-3 substituents independently selected from the group consisting of: —O($C_1$-$C_6$alkyl) and —($C_1$-$C_6$ alkyl);

$R^8$ and $R^9$ are each independently selected from the group consisting of: ($C_1$-$C_6$alkyl), —($C_1$-$C_6$alkyl)-O—($C_1$-$C_6$alkyl), —($C_3$-$C_6$)cycloalkyl, ($C_1$-$C_6$alkyl)-($C_3$-$C_6$) cycloalkyl, heterocycloalkyl, aryl, and heteroaryl, and wherein said heterocycloalkyl is a 4-6 membered ring comprising 1-3 heteroatoms selected from the group consisting of: O, S and N and the remaining ring atoms are carbon, and wherein said aryl is a $C_6$ to $C_{10}$ aromatic ring, and wherein said heteroaryl is a 5 to 10 membered ring comprising 1-3 heteroatoms selected from the group consisting of: O, S and N and the remaining ring atoms are carbon; and $R^{10}$ and $R^{11}$ are each independently selected from the group consisting of: H, halo, —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N ($C_1$-$C_6$alkyl)$_2$ wherein each alkyl is independently selected, and —($C_1$-$C_6$alkyl)-heterocycloalkyl.

3. The compound of claim 1 wherein $R^1$ is selected from the group consisting of: A1 to A18.

4. The compound of claim 1 wherein $R^1$ is selected from the group consisting of: —NH$_2$, —NHCH$_3$, —NHCH$_2$CH$_3$, —NHCH(CH$_3$)$_2$, —NHC(O)CH$_3$, —NHC(O)NHCH$_2$CH$_3$, —NHC(O)cyclopropyl, —NHC(O)OCH$_3$, —NHC(O) OCH$_2$CHF, —NHC(O)CH(CH(CH$_3$)$_2$)NHC(O)OCH$_3$, —NH-teterahydrofuran, —NHC(D$_2$)CD$_3$ (wherein D represents deuterium), —NHC(O)CD$_3$, —NHCH$_2$cyclobutyl, —NH(CH$_2$cyclobutyl)$_2$, —NHCH$_2$cyclopropyl, —NH (CH$_2$cyclopropyl)$_2$, —NHC(O)CH(CH$_3$)$_2$, —NHCH$_2$phenyl, —NHCH(CH$_3$)CH$_2$C(CH$_3$)$_2$OH, —NHCH(CH$_3$)CH$_2$S(O)$_2$CH$_3$, —NHCH(CH$_3$)CH$_2$Cl, —NHC(O)CHCF$_3$, —NHC(O)cyclobutyl, —NHC(O) CH$_2$phenyl, —NHC(O)CH$_2$cyclohexyl, —NHC(O)cyclohexyl, —NHC(O)cyclopentyl, —NHC(O)CH$_2$N(CH$_3$)$_2$, —NHC(O)CH$_2$CH(CH$_3$)$_2$, —NHC(O)CH$_2$cyclopentyl, —NHC(O)C(CH$_3$)$_3$, —NHC(O)OC(CH$_3$)$_3$, —NHC(O) NHCH(CH$_3$)$_2$, —NHC(O)OCH$_2$CH(CH$_3$)$_2$, —NHC(O) OCH$_3$, —NHC(O)O(CH$_2$)$_2$OCH$_3$, —NHC(O)Ophenyl, —NHC(O)OCH(CH$_3$)$_2$, —NHC(O)OCH$_2$C(CH$_3$)$_3$, —NHC (O)OCH$_2$phenyl, —NHC(O)OCH$_2$CH$_3$, —NHC(O)cyclopropyl, —NHC(O)CH₂OCH₃, —NHtetrahydropyran, —NHcyclopropyl, —NHCH₂CF₃, —NHcyclobutyl, —NHCH₂C(O)N(CH₃)₂, —NH(CH₂)₂C(O)N(CH₃)₂, —N(CH₃)C(O)CH₃, —N(CH₂CH₃)C(O)CH₃, —NHC(CH₃)₃, —NHCH(CH₃)CHF₂, —NHC(CH₃)₂CH₂OCH₃, —NH(CH₂)₂OCH₃, —NHphenyl, —NHcyanopyridyl, —NHfluoropyridyl, —NHcyanophenyl, —NHcyclopentyl, —NHcyclohexyl, and A19 to A132.

5. The compound of claim 1 wherein R² is selected from the group consisting of: —(C₁-C₂alkyl)phenyl, —CH(phenyl)(C₁-C₂alkyl-O—C₁-C₂alkyl), —(C₁-C₂alkyl)pyridyl, -heterocycloalkyl-phenyl, and —(C₁-C₃alkyl)-O—C₁-C₂alkyl, and wherein said phenyl, pyridyl and heterocycloalkyl groups are optionally substituted with 1-3 substitutents independently selected from the group consisting of: —C₁-C₂alkyl, F, Cl, and wherein said heterocycloalkyl group is a 5-6 membered ring comprising 1 heteroatom selected from the group consisting of: N, O and S.

6. The compound of claim 1 wherein R² is selected from the group consisting of: —CH(CH₃)phenyl, —CH(phenyl)(CH₂—O—CH₃), —CH(CH₃)pyridyl, -pyrrolidinyl-phenyl, —(CH₂)₂—O—CH₃, —CH(CH₃)CH₂OCH₃, —N-methylpyrrolidinyl-phenyl, —CH(CH₃)(p-F-phenyl), —CH(p-F-phenyl)(CH₂—O—CH₃).

7. The compound of claim 1 wherein R⁴ and/or R⁵ is selected from the group consisting of: —(C₁-C₆alkyl), —C(O)R⁸ wherein R⁸ is —(C₁-C₆alkyl), —C(O)R⁸ wherein R⁸ is —OR¹² wherein R¹² is a —(C₁-C₆alkyl), —C(O)R⁸ wherein R⁸ is heterocycloalkyl, —C(O)R⁸ wherein R⁸ is a substituted -heterocycloalkyl.

8. The compound of claim 1 wherein: R⁴ and R⁵, taken together with the nitrogen to which they are bonded to, form a 4 to 6 membered heterocycloalkyl ring.

9. The compound of claim 1 wherein R⁴ and R⁵, taken together with the nitrogen to which they are bonded to, form a fused bicyclic ring wherein one ring is a heterocycloalkyl ring, and one ring is a heteroaryl ring.

10. The compound of claim 1 wherein R² is selected from the group consisting of: B1-B90.

11. The compound of claim 1 wherein R² is selected from the group consisting of: B100-B175.

12. The compound of claim 1 wherein R¹⁰ is selected from the group consisting of: H, Cl, F and —CF₃, and R¹¹ is selected from the group consisting of: H, Cl, —CH₃, —OCH₃, —CH₂OH, and —CH₂OCH₃.

13. The compound of claim 1 wherein R¹⁰ is selected from the group consisting of: H, F, Br, Cl, methyl and ethyl; and R¹¹ is selected from the group consisting of: H, F, Br, Cl, methyl and ethyl.

14. The compound of claim 1 wherein R¹⁰ is selected from the group consisting of: H, F and methyl, and R¹¹ is H.

15. The compound of claim 1 wherein said compound is selected from the group consisting of

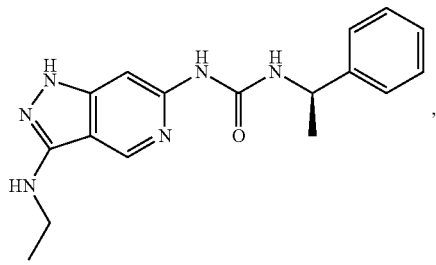

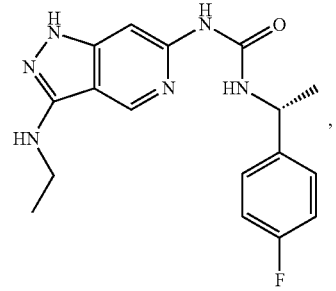

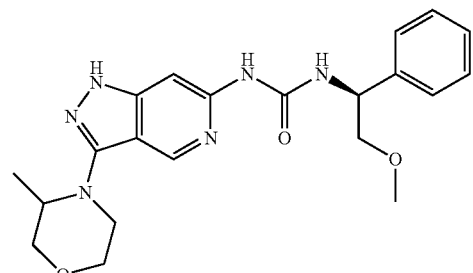

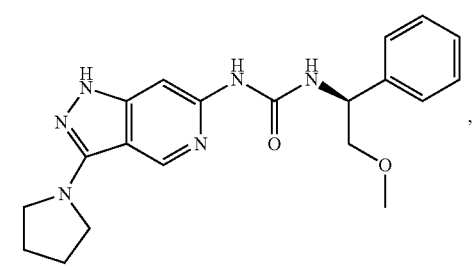

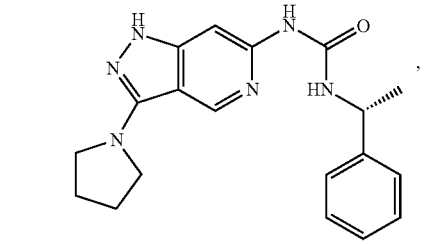

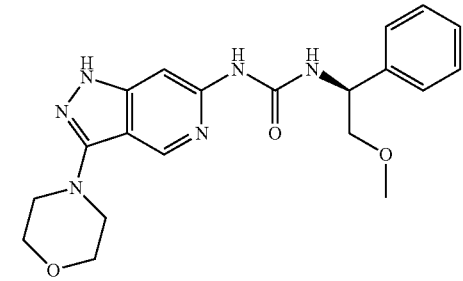

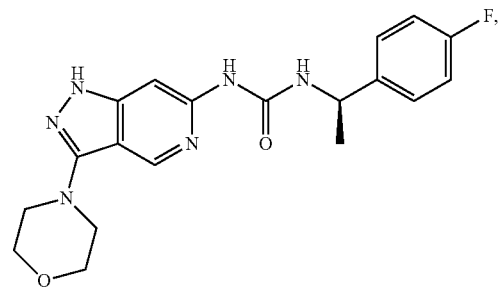

401 -continued

402 -continued

403
-continued
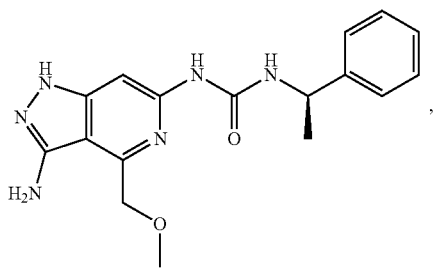
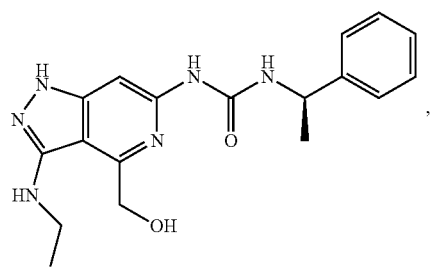
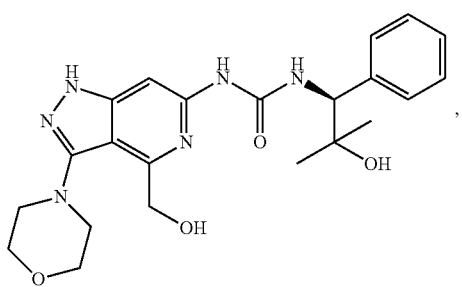
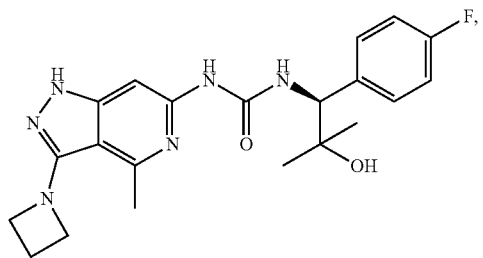
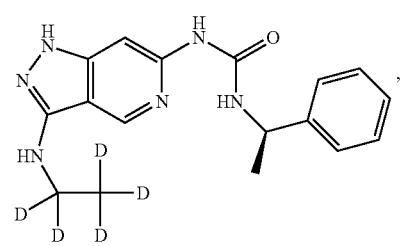
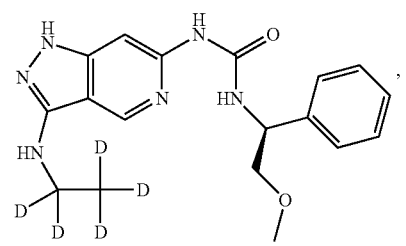
404
-continued
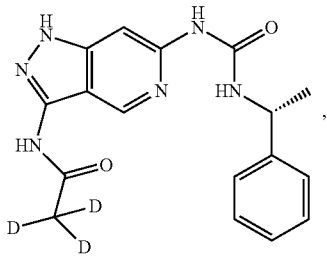
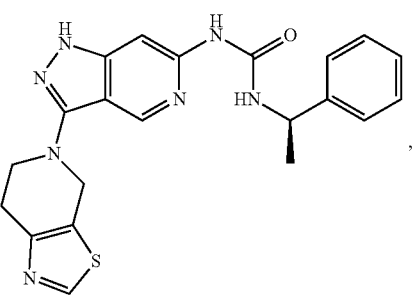
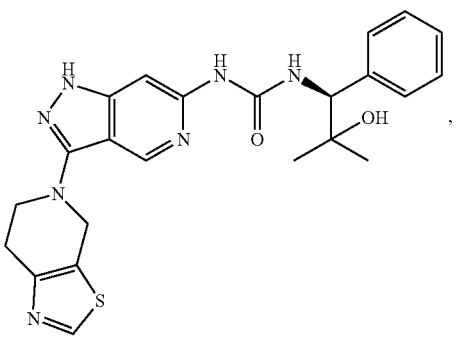
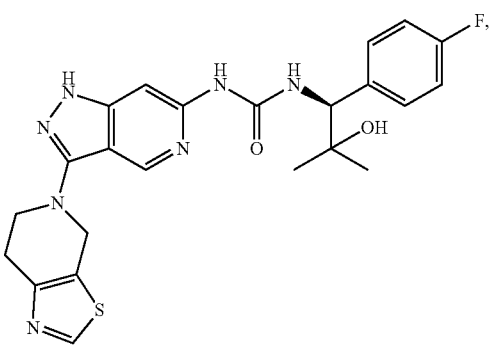
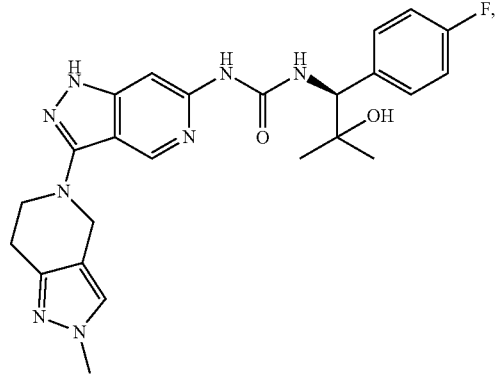

405
-continued
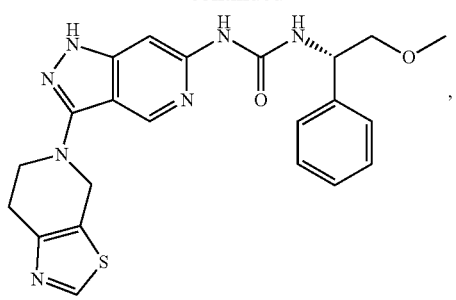
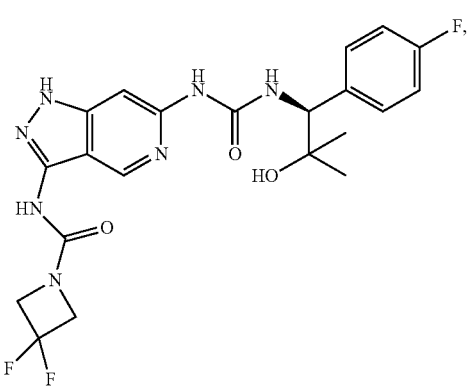
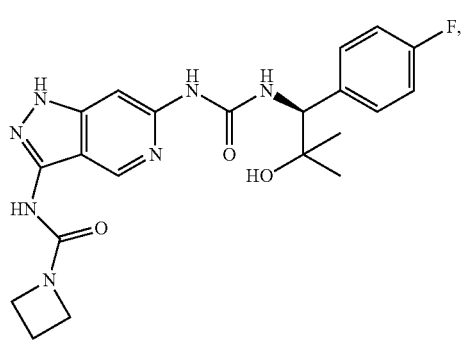
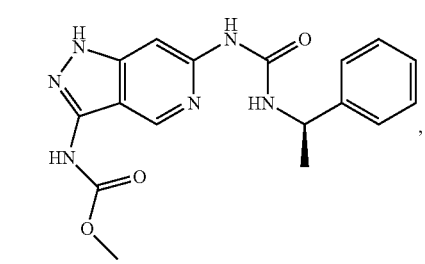
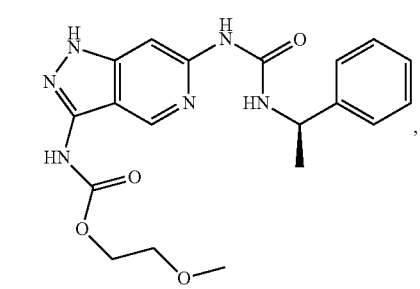
406
-continued
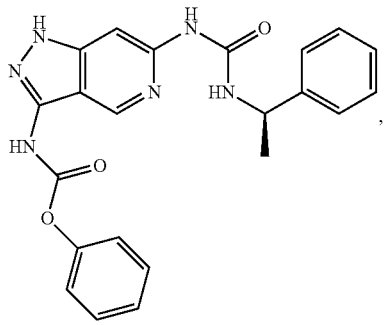
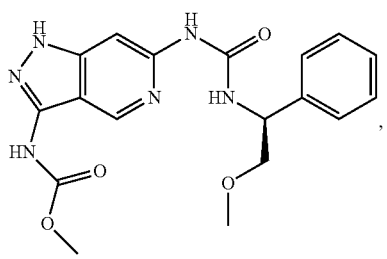
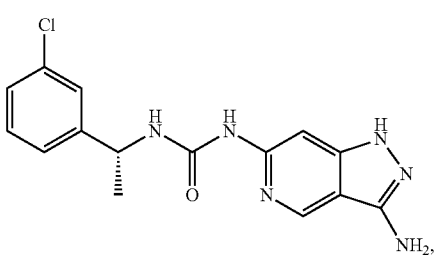
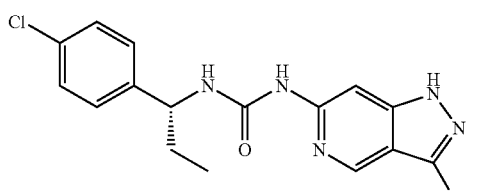
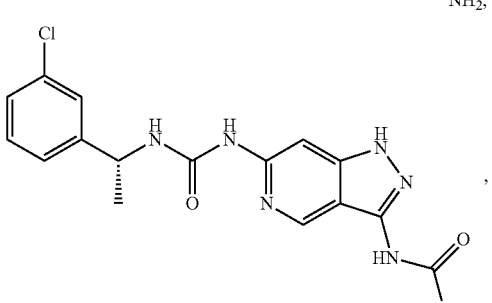
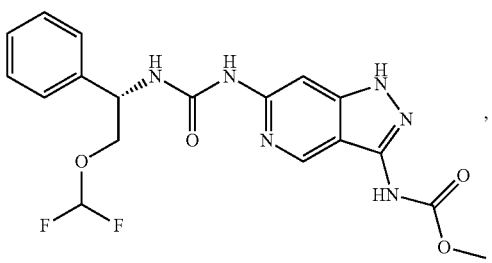

407
-continued
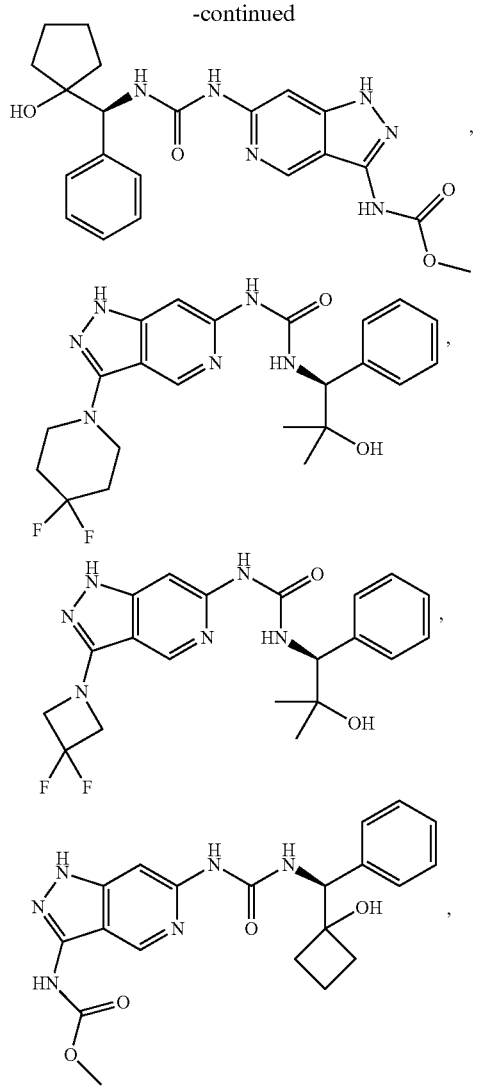
408
-continued
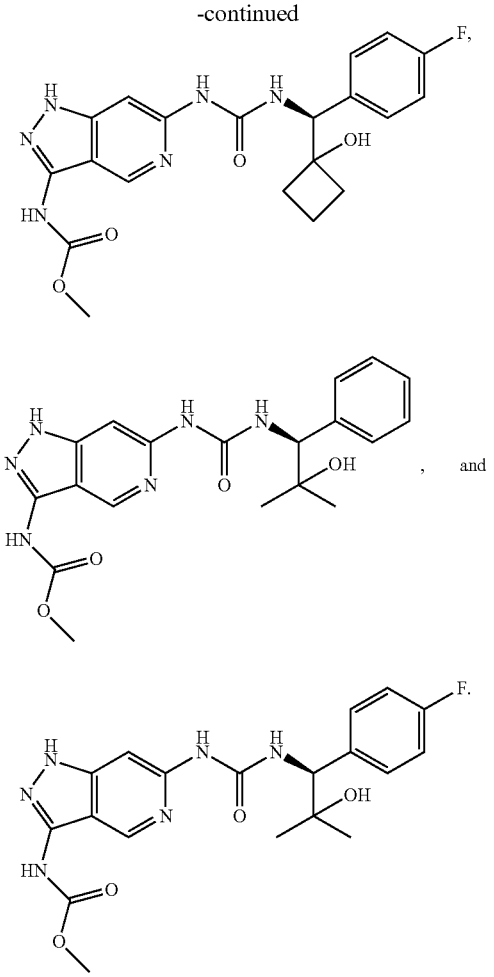
16. A pharmaceutical composition comprising a compound of claim 1 and a pharmaceutically acceptable carrier.
* * * * *